US008765410B2

(12) United States Patent
Glass et al.

(10) Patent No.: US 8,765,410 B2
(45) Date of Patent: Jul. 1, 2014

(54) METHODS AND COMPOSITIONS FOR IMPROVING SUGAR TRANSPORT, MIXED SUGAR FERMENTATION, AND PRODUCTION OF BIOFUELS

(71) Applicants: The Regents of the University of California, Oakland, CA (US); The Board of Trustees of the University of Illinois, Urbana, IL (US); BP Corporation North America Inc., Warrenville, IL (US)

(72) Inventors: N. Louise Glass, Berkeley, CA (US); Chaoguang Tian, Beijing (CN); William T. Beeson, IV, Oakland, CA (US); Huimin Zhao, Champaign, IL (US); Jing Du, Champaign, IL (US); Jin Ho Choi, Urbana, IL (US); James H. Doudna Cate, Berkeley, CA (US); Jonathan M. Galazka, Berkeley, CA (US); Suk-Jin Ha, Savoy, IL (US); Yong-Su Jin, Champaign, IL (US); Soo Rin Kim, Savoy, IL (US); Sijin Li, Urbana, IL (US); Xiaomin Yang, Albany, CA (US)

(73) Assignees: The Regents of the University of California, Oakland, CA (US); The Board of Trustees of the University of Illinois, Urbana, IL (US); BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 13/802,533

(22) Filed: Mar. 13, 2013

(65) Prior Publication Data

US 2013/0316437 A1 Nov. 28, 2013

Related U.S. Application Data

(62) Division of application No. 12/843,844, filed on Jul. 26, 2010, now Pat. No. 8,431,360.

(60) Provisional application No. 61/285,526, filed on Dec. 10, 2009, provisional application No. 61/271,833, filed on Jul. 24, 2009.

(51) Int. Cl.

| | |
|---|---|
| ***C12N 1/00*** | (2006.01) |
| ***C12P 21/04*** | (2006.01) |
| ***C12P 21/06*** | (2006.01) |

(52) U.S. Cl.
USPC .......................... 435/69.1; 435/71.1; 435/243

(58) Field of Classification Search
None
See application file for complete search history.

(56) References Cited

U.S. PATENT DOCUMENTS

| | | | |
|---|---|---|---|
| 5,100,791 A | 3/1992 | Spindler et al. |
| 6,207,436 B1 | 3/2001 | Bjornvad et al. |
| 7,344,876 B2 | 3/2008 | Levine |
| 2008/0280325 A1 | 11/2008 | Johansen et al. |
| 2009/0053784 A1 | 2/2009 | Travassos Leandro et al. |
| 2011/0177542 A1 | 7/2011 | Van zyl et al. |

OTHER PUBLICATIONS

Office Action recieved for Chinese Patent Application No. 201080039858.9, mailed on Feb. 5, 2013, 12 pages (5 pages of English Translation and 7 pages of Office Action).

Extended European Search Report and Search Opinion received for European Patent Application No. 10803022.2, mailed on Dec. 3, 2012, 7 pages.

Bluhm et al., "Involvement of ZFR1 of *Fusarium verticillioides* in Kernel Colonization and the Regulation of FST1, a Putative Sugar Transporter Gene Required for Fumonisin Biosynthesis on Maize Kernels", Molecular Plant Pathology, vol. 9, No. 2, 2008, pp. 203-211.

Galazka et al., "Cellodextrin Transport in Yeast for Improved Biofuel Production", Science, vol. 330, Oct. 1, 2010, pp. 84-86.

Karlyshev et al., "Analysis of *Campylobacter jejuni* Capsular Loci Reveals Multiple Mechanisms for the Generation of Structural Diversity and the Ability to Form Complex Heptoses", Molecular Microbiology, vol. 55, No. 1, 2005, pp. 90-103.

Mueckler et al., "Analysis of Transmembrane Segment 10 of the Glut1 Glucose Transporter by Cysteine-Scanning Mutagenesis and Substituted Cysteine Accessibility", The Journal of Biological Chemistry, vol. 277, No. 5, Feb. 1, 2002, pp. 3498-3503.

Hosaka et al., "A Dominant Mutation that Alters the Regulation of INO1 Expression in *Saccharomyces cerevisiae*" , J. Biochem., vol. 111, No. 3, 1992, pp. 352-358.

Jacobson et al., "*Neurospora* in Temperate Forests of Western North America", Mycologia, vol. 96, No. 1, 2004, pp. 66-74.

Jeffries et al., "Genome Sequence of the Lignoceliulose—Bioconverting and Xylose-Fermenting Yeast *Pichia stipitis*", Nature Biotechnology vol. 25, No. 3, Mar. 2007, pp. 319-326.

Kasuga et al., "Dissecting Colony Development of *Neurospora crassa* Using mRNA Profiling and Comparative Genomics Approaches", Eukaryotic Cell, vol. 7, No. 9, Sep. 2008, pp. 1549-1564.

(Continued)

*Primary Examiner* — Albert Navarro
(74) *Attorney, Agent, or Firm* — Morrison & Foerster LLP

(57) ABSTRACT

The present disclosure relates to host cells containing a recombinant polynucleotide encoding a polypeptide where the polypeptide transports cellodextrin into the cell. The present disclosure further relates to methods of increasing transport of cellodextrin into a cell, methods of increasing growth of a cell on a medium containing cellodextrin, methods of co-fermenting cellulose-derived and hemicellulose-derived sugars, and methods of making hydrocarbons or hydrocarbon derivatives by providing a host cell containing a recombinant polynucleotide encoding a polypeptide where the polypeptide transports cellodextrin into the cell. The present disclosure relates to host cells containing a recombinant polynucleotide encoding a polypeptide where the polypeptide transports a pentose into the cell, methods of increasing transport of a pentose into a cell, methods of increasing growth of a cell on a medium containing pentose sugars, and methods of making hydrocarbons or hydrocarbon derivatives by providing a host cell containing a recombinant polynucleotide encoding a polypeptide where the polypeptide transports a pentose into the cell.

17 Claims, 127 Drawing Sheets

(56) References Cited

OTHER PUBLICATIONS

Kasuga et al., "Long-Oligomer Microarray Profiling in *Neurospora crassa* Reveals the Transcriptional Program Underlying Biochemical and Physiological Events of Conidial Germination", Nucleic Acids Research, vol. 33, No. 20, Nov. 14, 2005, pp. 6469-6485.
Katahira et al., "Ethanol Fermentation from Lignocellulosic Hydrolysate by a Recombinant Xylose- and Cellooligosaccharide-Assimilating Yeast Strain", Appl Microbiol. Biotechnol, vol. 72, Mar. 31, 2006, pp. 1136-1143.
Katahira et al., "Improvement of Ethanol Productivity During Xylose and Glucose Co-Fermentation by Xylose-Assimilating *S. cerevisiae* via Expression of Glucose Transporter Sut1", Enzyme and Microbial Technology, vol. 43, 2008, pp. 115-119.
Koning et al., "Cellobiose Uptake in the Hyperthermophilic Archaeon *Pyrococcus furiosus* is Mediatied by an Inducibile, High-Affinity ABC Transporter", Journal of Bacteriology, vol. 183, No. 17, Sep. 2001, pp. 4979-4984.
Korkhin et al., "NADP-Dependent Bacterial Alcohol Dehydrogenases: Crystal Structure, Cofactor-Binding and Cofactor Specificity of the ADHs of *Clostridium beijerinckii* and *Thermoanaerobacter brockii*", J. Mol. Biol., vol. 278, 1998, pp. 967-981.
Kotaka et al., "Direct Ethanol Production from Barley Beta-Glucan by Sake Yeast Displaying *Aspergillus oryzae* Beta-Glucosidase and Endoglucanase", Journal of Bioscience and Bioengineering, vol. 105, No. 6, 2008, pp. 622-627.
Kotter et al., "Xylose Fermentation by *Saccharomyces cerevisiae*", Appl Microbiol. Biotechnol, vol. 38, 1993, pp. 776-783.
Kubicek et al., "Triggering of Cellulase Biosynthesis by Cellulose in *Trichoderma reesei*—Involvement of a Constitutive, Sophorose-Inducible, Glucose-Inhibited Beta-Diglucoside Permease", Journal of Biological Chemistry, vol. 268, No. 26, Sep. 15, 1993, pp. 19364-19368.
Kumar et al., "Bioconversion of Lignocellulosic Biomass : Biochemical and Molecular Perspectives", J Ind Microbiol Biotechnol, vol. 35, Mar. 13, 2008, pp. 377-391.
Kuyper et al., "High-level Functional Expression of a Fungal Xylose Isomerase: The Key to Efficient Ethanolic Fermentation of Xylose by *Saccharomyces cerevisiae*?", FEMS Yeast Research, vol. 4, May 13, 2003, pp. 69-78.
Lang et al., "Glucose Transport in a Kinaseless *Saccharomyces cerevisiae* Mutant", Journal of Bacteriology, vol. 169, No. 7, Jul. 1987, pp. 2932-2937.
Law et al., "Ins and Outs of Major Facilitator Superfamily Antiporters", NIH Public Access, Author Manuscript, Annu Rev Microbiol., vol. 62, 2008, pp. 289-305.
Leandro et al., "The Expression in *Saccharomyces cerevisiae* of a Glucose/Xylose Symporter from *Candida intermedia* is Affected by the Presence of a Glucose/Xylose Facilitator", Microbiology, vol. 154, 2008, pp. 1646-1655.
Leandro et al., "Two Glucose/Xylose Transporter Genes from the Yeast *Candida intermedia*: First Molecular Characterization of a Yeast Xylose/H+ Symporter", Biochemical Journal, Jan. 11, 2006, pp. 1-28.
Li et al., "Overcoming Glucose Repression in Mixed Sugar Fermentation by Co-expressing a Cellobiose Transporter and a β-glucosidase in *Saccharomyces cerevisiae*", Molecular BioSystems, vol. 6, 2010, pp. 2129-2132.
Linder et al., "The Cellulose-Binding Domain of the Major Cellobiohydrolase of *Trichoderma reesei* Exhibits True Reversibility and a High Exchange Rate on Crystalline Cellulose", Biochemistry, Proc. Natl. Acad. Sci. USA, vol. 93, Oct. 1996, pp. 12251-12255.
Lynd et al., "How Biotech Can Transform Biofuels", Nature Biotechnology, vol. 26, No. 2, Feb. 2008, pp. 169-172.
Lynd et al., "Microbial Cellulose Utilization: Fundamentals and Biotechnology", Microbiology and Molecular Biology Reviews, vol. 66, No. 3, Sep. 2002, pp. 506-577.
Madhavan et al., "Xylose Isomerase from Polycentric Fungus *Orpinomyces*: Gene Sequencing, Cloning, and Expression in *Saccharomyces cerevisiae* for Bioconversion of Xylose to Ethanol", Appl Microbiol Biotechnol, vol. 82, 2009, pp. 1067-1078.
Martin et al., "Perigord Black Truffle Genome Uncovers Evolutionary Origins and Mechanisms of Symbiosis", Nature Latters, vol. 464, Apr. 15, 2010, pp. 1033-1038.
Martinez et al., "Genome Sequence of the Lignocellulose Degrading Fungus *Phanerochaete chrysosporium* Strain RP78", Nature Biotechnology, vol. 22, No. 6, Jun. 2004, pp. 695-700.
Martinez et al., "Genome Sequencing and Analysis of the Biomass-Degrading *Trichoderma reesei* (Syn. *Hypocrea jecorina*)", Nature Biotechnology, vol. 26, No. 5, May 2008, pp. 553-560.
Martinez et al., "Genome, Transcriptome, and Secretome Analysis of Wood Decay Fungus *Postia placenta* Supports Unique Mechanisms of Lignocellulose Conversion", PNAS, vol. 106, No. 6, Feb. 10, 2009, pp. 1954-1959.
Matteucci et al., "The Synthesis of Oligodeoxypyrimidines on a Polymer Support", Tetrahedron Letters, vol. 21, 1980, pp. 719-722.
Matsushika et al., "Expression of Protein Engineered NADP+-Dependent Xylitol Dehydrogenase Increases Ethanol Production from Xylose in Recombinant *Saccharomyces cerevisiae*", Appl Microbiol Biotechnol, vol. 81, Aug. 27, 2008, pp. 243-255.
McCluskey, Kevin, "The Fungal Genetics Stock Center: from Molds to Molecules", Advances in Applied Microbiology, vol. 52, 2003, pp. 245-262.
Medve et al., "Hydrolysis of Microcrystalline Cellulose by Cellobiohydrolase I and Endoglucanase II from *Trichoderma reesei*: Adsorption, Sugar Production Pattern, and Synergism of the Enzymes", Biotechnology and Bioengineering, vol. 59, No. 5, Sep. 5, 1998, pp. 621-634.
Miyasaka, Hitoshi, "The Positive Relationship Between Codon Usage Bias and Translation Initiation AUG Context in *Saccharomyces cerevisiae*", Yeast, vol. 15, 1999, pp. 633-637.
Nair et al., "Biochemical Characterization of an L-Xylulose Reductase from *Neurospora crassa*", Applied and Environmental Microbiology, vol. 73, No. 6, Mar. 2007, pp. 2001-2004.
Nakamura et al., "Effective Xylose/Cellobiose Co-Fermentation and Ethanol Production by Xylose-Assimilating *S. cerevisiae* via Expression of Beta-Glucosidase on its Cell Surface", Enzyme and Microbial Technology, vol. 43, 2008, pp. 233-236.
Noguchi et al., "Genes Regulated by AoXlnR, the Xylanolytic and Cellulolytic Transcriptional Regulator, in *Aspergillus oryzae*", Appl Microbiol Biotechnol, vol. 85, Sep. 24, 2009, pp. 141-154.
Notredame et al., "T-Coffee: A Novel Method for Fast and Accurate Multiple Sequence Alignment", J. Mol. Biol., vol. 302, 2000, pp. 205-217.
Pace et al., "A Helix Propensity Scale Based on Experimental Studies of Peptides and Proteins" Biophysical Journal, vol. 75, Jul. 1998, pp. 422-427.
Pandit et al., "Life-History of *Neurospora intermedia* in a Sugar Cane Field" J. Biosci., vol. 21, No. 1, Mar. 1996, pp. 57-79.
Pao et al., "Major Facilitator Superfamily", Microbiology and Molecular Biology Reviews, vol. 62, No. 1, Mar. 1998, pp. 1-34.
Pauly et al., "X-Ray Crystallographic and Kinetic Studies of Human Sorbitol Dehydrogenase", Structure, vol. 11, Sep. 2003, pp. 1071-1085.
Pedelacq et al., "Engineering and Characterization of a Superfolder Green Fluorescent Protein", Nature Biotechnology, vol. 24, No. 1, Jan. 2006, pp. 79-88.
Perkins et al., "Strains of *Neurospora* Collected from Nature", Evolution, vol. 30, Jun. 1976, pp. 281-313.
Ramos et al., "Relationship Between Low- and High-Affinity Glucose Transport Systems of *Saccharomyces cerevisiae*" Journal of Bacteriology, vol. 170, No. 11, Nov. 1988, pp. 5375-5377.
Rawat et al., "Site and Significance of Cysteine Residues in Xylose Reductase from *Neurospora crassa* as Deduced by Fluorescence Studies", Biochemical and Biophysical Research Communications, Article No. RC977558, vol. 239, No. 3, 1997, pp. 789-793.
Reifenberger et al., "Kinetic Characterization of Individual Hexose Transporters of *Saccharomyces cerevisiae* and their Relation to the Triggering Mechanisms of Glucose Repression", Eur. J. Biochem., vol. 245, 1997, pp. 324-333.

(56) References Cited

OTHER PUBLICATIONS

Ren et al. "TransportDB: A Relational Database of Cellular Membrane Transport Systems", Nucleic Acids Research, vol. 32, Database Issue, 2004, pp. D284-D288.
Romero et al., "Cellulase Production by *Neurospora crassa* on Wheat Straw", Enzyme and MIcrobial Technology, vol. 25, 1999, pp. 244-250.
Rooyen et al., "Construction of Cellobiose—Growing and Fermenting *Saccharomyces cerevisiae* Strains", Journal of Biotechnology, vol. 120, 2005, pp. 284-295.
Roy et al., "I-Tasser: A Unified Platform for Automated Protein Structure and Function Prediction", Nature Protocols, vol. 5, No. 4, 2010, pp. 725-738.
Rubin, Edward M., "Genomics of Cellulosic Biofuels", Nature, vol. 454, Aug. 14, 2008, pp. 841-845.
Invitation to Pay Additional Fees recieved for PCT Patent Application No. PCT/US2010/043279, mailed on Apr. 26, 2011, 7 pages.
International Search Report and Written Opinion recieved for PCT Patent Application No. PCT/US2010/043279, mailed on Jul. 7, 2011, 16 pages.
International Preliminary Report on Patentability recieved for PCT Patent Application No. PCT/US2010/043279, mailed on Feb. 2, 2012, 10 pages.
Non Final Office Action recieved for U.S. Appl. No. 12/843,844, mailed on Jul. 2, 2012, 11 pages.
Notice of Allowance recieved for U.S. Appl. No. 12/843,844, mailed on Dec. 26, 2012, 7 pages.
Arendt et al., "Genetic Selection for a Highly Functional Cysteine-Less Membrane Protein Using Site Saturation Mutagenesis", Analytical Biochemistry, vol. 365, 2007, pp. 185-193.
Bai et al., "Ethanol Fermentation Techniques from Sugar and Starch Feedstocks", Biotechnology Advances, vol. 26, 2008, pp. 89-105.
Bailey et al., "Interlaboratory Testing of Methods for Assay of Xylanase Activity", Journal of Biotechnology, vol. 23, 1992, pp. 257-270.
Basso et al., "Yeast Selection for Fuel Ethanol Production in Brazil", FEMS Yeast Res, vol. 8, Aug. 22, 2008, pp. 1155-1163.
Becker et al., "Manipulation of Yeast Genes—Introduction of DNA into Yeast Cells", Current Protocols in Molecular Biology, Section III, Unit 13.7, 1993, pp. 13.7.1-13.7.10.
Bendtsen et al., "Improved Prediction of Signal Peptides: SignalP 3.0", J. Mol. Biol., 2004, pp. 1-22.
Bengsston et al., "Xylose Reductase from *Pichia stipitis* with Altered Coenzyme Preference Improves Ethanolic Xylose Fermentation by Recombinant *Saccharomyces cerevisiae*", Biotechnology for Biofuels, vol. 2, May 5, 2009, 10 pages.
Bhat et al., "*Sporotrichum thermophile* Growth, Cellulose Degradation, and Cellulase Activity", Applied and Environmental Microbiology, vol. 53, No. 9, Sep. 1987, pp. 2175-2182.
Bouffard et al., "Dependence of Lactose Metabolism upon Mutarotase Encoded in the Gal Operon in *Escherichia coli*", J. Mol. Biol., vol. 244, 1994, pp. 269-278.
Bouws et al., "Fungal Secretomes—Nature's Toolbox for White Biotechnology", Appl Microbiol Biotechnol, vol. 80, 2008, pp. 381-388.
Brat et al., "Functional Expression of a Bacterial Xylose Isomerase in *Saccharomyces cerevisiae*", Applied Environmental Microbiology, vol. 75, No. 8, Apr. 2009, pp. 2304-2311.
Canevascini, Giorgio, "Cellobiose Dehydrogenase from *Sporotrichum thermophile*", Methods in Enzymology, vol. 160, 1988, pp. 443-448.
Cantarel et al., "The Carbohydrate-Active EnZymes Database (CAZy): an Expert Resource for Glycogenomics", Nucleic Acids Research, vol. 37, Database issue, 2009, pp. D233-238.
Chauve et al., "Comparative Kinetic Analysis of Two Fungal Beta-Glucosidases", Biotechnology for Biofuels, vol. 3, No. 3, 2010, pp. 1-8.
Christakopoulos et al., "Enzymatic Synthesis of Trisaccharides and Alkyl Beta-D-Glucosides by the Transglycosylation Reaction of Beta-Glucosidase from *Fusarium oxysporum*", Int. J. Biol. Macromol., vol. 16, No. 6, 1994; pp. 331-334.
Christianson et al., "Multifunctional Yeast High-Copy-Number Shuttle Vectors", Gene, vol. 110, 1992, pp. 119-122.
Chu et al., "Genetic Improvement of *Saccharomyces cerevisiae* for Xylose Fermentation", Biotechnology Advances, vol. 25, Apr. 24, 2007, pp. 425-441.
Colot et al., "A High-Throughput Gene Knockout Procedure for *Neurospora* Reveals Functions for Multiple Transcription Factors", PNAS, vol. 103, No. 27, Jul. 5, 2006, pp. 10352-10357.
Cullen et al., "Sequence and Centromere Proximal Location of a Transformation Enhancing Fragment ans1from *Aspergillus nidulans*", Nucleic Acids Research, vol. 15, No. 22, 1987, pp. 9163-9175.
Davies et al., "Structure and Function of Humicola Insolens Family 6 Cellulases: Structure of the Endoglucanase, Cel6B, at 1.6 A Resolution", Biochem. J., vol. 348, 2000, pp. 201-207.
Davis et al., "Neurospora: a Model of Model Microbes", Timeline, Nature Reviews, Genetics, vol. 3, May 2002, pp. 7-13.
De Groot et al., "Metabolic Control Analysis of *Aspergillus niger* L-Arabinose Catabolism", Biotechnol. Prog., vol. 21, No. 6, Oct. 20, 2005, pp. 1610-1616.
Dementhon et al., "VIB-1 is Required for Expression of Genes Necessary for Programmed Cell Death in *Neurospora crassa*", Eukaryotic Cell, vol. 5, No. 12, Dec. 2006, pp. 2161-2173.
Doran-Peterson et al., "Simultaneous Saccharification and Fermentation and Partial Saccharification and Co-Fermentation of Lignocellulosic Biomass for Ethanol Production", Chapter 17, Methods in Molecular Biology, vol. 581, 2009, pp. 263-280.
Drissen et al., "Modelling Ethanol Production from Cellulose: Separate Hydrolysis and Fermentation Versus Simultaneous Saccharification and Fermentation", Biocatalysis and Biotransformation, vol. 27, No. 1, Jan.-Feb. 2009, pp. 27-35.
Dunlap et al., "Enabling a Community to Dissect an Organism: Overview of the *Neurospora* Functional Genomics Project", Advances in Genetics, vol. 57, 2007, pp. 49-96.
Du Preez et al., "The Fermentation of Hexose and Pentose Sugars by *Candida shehatae*and *Pichia stipitis*", Appl Microbial Biotechnol, vol. 23, 1986, pp. 228-233.
Eberhart et al., "Cellulase of *Neurospora crassa*", Journal of Bacteriology, vol. 139, vol. 1, Apr. 1977, p. 181-186.
Ellis et al., "Buffers of Constant Ionic Strength for Studying pH-Dependent Processes", Methods in Enzymology, vol. 87, 1982, pp. 405-426.
Espagne et al., "The Genome Sequence of the Model Ascomycete Fungus *Podospora anserina*", Genome Biology, vol. 9, No. 5, Article R77, May 6, 2008, pp. R77.1-R77.22.
Fonseca et al., "L-Arabinose Transport and Catabolism in Yeast", FEBS Journal, vol. 274, 2007, pp. 3589-3600.
Freer et al., "Transport of Glucose and Cellobiose by *Candida wickerhamii* and *Clavispora lusitaniae*", Journal of Biological Chemistry, vol. 265, No. 22, Aug. 5, 1990, pp. 12864-12868.
Freer, S. N., "Fermentation and Aerobic Metabolism of Cellodextrins by Yeasts" Applied and Environmental Microbiology, vol. 57, No. 3, Mar. 1991, pp. 655-659.
Galagan et al., "The Genome Sequence of the Filamentous Fungus *Neurospora crassa*", Nature, vol. 422, Apr. 24, 2003, pp. 859-868.
Galazka et al., "A New Diet for Yeast to Improve Biofuel Production", Bioengineered Bugs, vol. 2, No. 4, Jul./Aug. 2011, pp. 1-4.
Galazka et al., "Improving the Bioconversion of Plant Biomass to Biofuels: A Multidisciplinary Approach", Energy & Environmental Science, vol. 4, 2011, pp. 3329-3333.
Gems et al., "An Autonomously Replicating Plasmid Transforms *Aspergillus nidulans* at High Frequency", Gene, vol. 98, 1991, pp. 61-67.
Guindon et al., "A Simple, Fast, and Accurate Algorithm to Estimate Large Phylogenies by Maximum Likelihood", Systematic Biology, vol. 52, No. 5, 2003, pp. 696-704.
Ha et al., "Cofermentation of Cellobiose and Galactose by an Engineered *Saccharomyces cerevisiae* Strain", Applied and Environmental Microbiology, vol. 77, No. 16, Aug. 2011, pp. 5822-5825.

(56) References Cited

OTHER PUBLICATIONS

Ha et al., "Engineered *Saccharomyces cerevisiae* Capable of Simultaneous Cellobiose and Xylose Fermentation", Proceedings of the National Academy of Sciences, vol. 108, No. 2, Jan. 11, 2011, pp. 504-509.
Ha et al., "Xylitol Does Not Inhibit Xylose Fermentation by Eningineered *Saccharornyces cerevisiae* Expressing xylA as Severely as it inhibits Xylose Isomerase Reaction in Vitro", Applied Microbiology and Biotechnology, Jun. 8, 2011, 8 pages.
Hahn-Hagerdal et al., "Towards Industrial Pentose-Fermenting Yeast Strains", Appl Microbiol Biotechnol, vol. 74, Feb. 9, 2007, pp. 937-953.
Hamacher et al., "Characterization of the Xylose-Transporting Properties of Yeast Hexose Transporters and their Influence on Xylose Utilization", Microbiology, vol. 148, 2002, pp. 2783-2788.
Hector et al., "Expression of a Heterologous Xylose Transporter in a *Saccharomyces cerevisiae* Strain Engineered to Utilize Xylose Improves Aerobic Xylose Consumption", Appl Microbiol Biotechnol, vol. 80, Jul. 16, 2008, pp. 675-684.
Himmel et al. "Biomass Recalcitrance: Engineering plants and Enzymes for Biofuels Production" Science, vol. 315, Feb. 9, 2007, pp. 804-807.
Office Action received for New Zealand Patent Application No. 597001, issued on Jun. 28, 2013, 3 pages.
Ruepp et al., "The FunCat, a Functional Annotation Scheme for Systematic Classification of Proteins from Whole Genomes", Nucleic Acids Research, vol. 32, No. 18, Oct. 14, 2004, pp. 5539-5545.
Runquist et al. "Comparison of Heterologous Xylose Transporters in Recombinant *Saccharomyces cerevisiae*", Biotechnology for Biofuels, vol. 3, No. 5, 2010. pp. 1-7.
Runquist et al., "Expression of the Gxf1 Transporter from *Candida intermedia* Improves Fermentation Performance in Recombinant Xylose-Utilizing *Saccharomyces cerevisiae*", Appl Microbial Biotechnol, vol. 82, 2009, pp. 123-130.
Sadie et al., "Co-expression of a Cellobiose Phosphorylase and Lactose Permease Enables Intracellular Cellobiose Utilisation by *Saccharomyces cerevisiae*", Applied Microbiology and Biotechnology, Feb. 20, 2011, 8 pages.
Saha, Badal C., "Hemicellulose Bioconversion", J Ind Microbiol Biotechnol, vol. 30, 2003, pp. 279-291.
Saloheimo et al., "Xylose Transport Studies with Xylose-Utilizing *Saccharomyces cerevisiae* Strains Expressing Heterologous and Homologous Permeases", Appl Microbial Biotechnol, vol. 74. 2007, pp. 1041-1052.
Sarkar et al., "The "Megaprimer" Method of Site-Directed Mutagenesis", Biotechniques, vol. 8, No. 4, 1990, pp. 404-407.
Sauer, Uwe, "Evolutionary Engineering of Industrially important Microbial Phenotypes", Advances in Biochemical Engineering/ Biotechnology, vol. 73, 2001, pp. 129-169.
Scarborough, Gene A., "Transport in *Neurospora*", Int Rev Cytol, 1973, pp. 103-122.
Seiboth et al., "Role of Four Major Cellulases in Triggering of Cellulase Gene Expression by Cellulose in *Trichorderma reesei*", Journal of Bacteriology, vol. 179, No. 17, Sep. 1997, pp. 5318-5320.
Seidl et al., "The *Hypocrea jecorina*(*Trichoderma Reesei*) Hypercellulolytic Mutant RUT C30 Lacks a 85 kb (29 gene-encoding) Region of the Wild-type Genome", BMC Genomic, vol. 9, Jul. 11, 2008, 15 pages.
Shao et al., "DNA Assembler, an in vivo Genetic Method for Rapid Construction of Biochemical Pathways", Nucleic Acids Research, vol. 37, No. 2, 2009, e16, pp. 1-10.
Shill et al., "Ionic Liquid Pretreatment of Cellulosic Biomass: Enzymatic Hydrolysis and Ionic Liquid Recycle" Biotechnology and Bioengineering, vol. 108, No. 3, Mar. 2011, pp. 511-520.
Sikorski et al., "A System of Shuttle Vectors and Yeast Host Strains Designed for Efficient Manipulation of DNA in *Saccharomyces cerevisiae*", Genetics, vol. 122, May 1989, pp. 19-27.
Skory et al., "Expression and Secretion of the *Candida wickerhamii* Extracellular Beta-glucosidase Gene, bglB, in *Saccharomyces cerevisiae*.", Curr Genet, vol. 30, 1996, pp. 417-422.
Smith et al., "Vegetative Incompatibility in the Het-6 Region of *Neurospora crassa* is Mediated by Two Linked Genes," Genetics, vol. 155, Jul. 2000, pp. 1095-1104.
Spindler et al., "Evaluation of the Cellobiose—Fermenting Yeast *Brettanomyces custersii* in the Simultaneous Saccharification and Fermentation of Cellulose", Biotechnology Letters, vol. 15, No. 5, May 1992, pp. 403-407.
Spindler et al., "Simultaneous Saccharification and Fermentation of Pretreated Wheat Straw to Ethanol with Selected Yeast Strains and Beta-glucosidase Supplementation", Applied Biochemistry and Biotechnology, vol. 20/21, 1989, pp. 529-540.
Stambuk et al., "D-Xylose Transport by *Candida succiphila* and *Kluyveromyces marxianus*", Applied Biochemistry and Biotechnology, vol. 105-108, 2003, pp. 255-263.
Stephanopoulos, Gregory, "Challenges in Engineering Microbes for Biofuels Production", Science, vol. 315, Feb. 9, 2007, pp. 801-804.
Stricker et al., "Regulation of Transcription of Cellulases- and Hemicellulases Encoding Genes in *Aspergillus niger* and *Hypocrea jecorina*(*Trichoderma reesei*)", Appl Microbiol Biotechnol, vol. 78, 2008, pp. 211-220.
Stryer, Lubert, "Molecular Design of Life—Part 1", Biochemistry Fourth Edition, 1995, pp. 28-30.
Sullivan et al., "Cloning, Characterization, and Mutational Analysis of a Highly Active and Stable L-arabinitol 4-dehydrogenase from *Neurospora crassa*", Appl Microbiol Biotechnol, vol. 77, 2007, pp. 845-852.
Sun et al., "Hydrolysis of Lignocellulosic Materials for Ethanol Production: a Review", Bioresource Technology, vol. 83, 2002, pp. 1-11.
Suominen et al., "High Frequency One-Step Gene Replacement in *Trichoderma reesei*—II. Effects of Deletions of Individual Cellulase Genes", Mol Gen Genet, vol. 241, 1993, pp. 523-530.
Suzuki et al., "Cellotriose and Cellotetraose as Inducers of the Genes Encoding Cellobiohydrolases in the Basidiomycete *Phanerochaete chrysosporium*", Applied and Environmental Microbiology, vol. 76, No. 18, Sep. 2010, pp. 6164-6170.
Tian et al., "Systems Analysis of Plant Cell Wall Degradation by the Model Filamentous Fungus *Neurospora crassa*", PNAS Early Edition, 2009, pp. 1-6.
Tian et al., "Transcriptional Profiling of Cross Pathway Control in *Neurospora crassa* and Comparative analysis of the Gcn4 and CPC1 Regulons", Eukaryotic Cell, vol. 6, No. 6, Jun. 2007, pp. 1018-1029.
Townsend et al., "Bayesian Analysis of Gene Expression Levels: Statistical Quantification of Relative mRNA Level Across Multiple Strains or Treatments", Genome Biology, vol. 3, No. 12, Nov. 20, 2002, pp. 0071.1-0071.16.
Townsend, Jeffrey P., "Resolution of Large and Small Differences in Gene Expression Using Models For the Bayesian Analysis of Gene Expression Levels and Spotted DNA Microarrays", BMC Bioinformatics, vol. 5, May 5, 2004. 13 pages.
USDA, "The Economic Feasibility of Ethanol Production from Sugar in the United States", Jul. 2006, 78 pages.
Viklund et al., "Best α-Helical Transmembrane Protein Topology Predictions are Achieved using Hidden Markov Models and Evolutionary Information", Protein Science, vol. 13, 2004, pp. 1908-1917.
Vogel, H. J., "A Conventional Growth Medium for *Neurospora* (Mediun N)", Microbiol. Genet. Bull, vol. 13, Jan. 1956, pp. 42-45.
Wagner et al., "Rationalizing Membrane Protein Overexpression", Trends in Biotechnology, vol. 24, No. 8, Jul. 3, 2006, pp. 364-371.
Watanabe et al., "Complete Reversal of Coenzyme Specificity of Xylitol Dehydrogenase and Increase of Thermostability by the Introduction of Structural Zinc", The Journal of Biological Chemistry, vol. 280, No. 11, Mar. 18, 2005, pp. 10340-10349.
Watanabe et al., "Ethanol Production from Xylose by Recombinant *Saccharomyces cerevisiae* Expressing Protein-Engineered NADH-Preferring Xylose Reductase from *Pichia stipitis*", Microbiology, vol. 153, 2007, pp. 3044-3054.
Watanabe et al., "L-Arabinose 1-Dehydrogenase: A Novel Enzyme Involving in Bacterial L-Arabinose Metabilism", Nucleic Acids Symposium, vol. 49, 2005, pp. 309-310.

(56) References Cited

OTHER PUBLICATIONS

Weidemann et al., "Codon-Optimized Bacterial Genes Improve L-Arabinose Fermentation in Recombinant *Saccharomyces cerevisiae*", Appl Environ Microbiol, Feb. 8, 2008, 34 pages.
Wisselink et al., "Engineering of *Saccharomyces cerevisiae* for Efficient Anaerobic Alcoholic Fermentation of L-Arabinose", Applied and Environmental Microbiology, vol. 73, No. 15, Aug. 2007, pp. 4881-4891.
Wisselink et al., "Novel Evolutionary Engineering Approach for Accelerated Utilization of Glucose, Xylose, and Arabinose Mixtures by Engineered *Saccharomyces cerevisiae* Strains", Applied and Environmental Microbiology, vol. 75, No. 4, Feb. 2009, pp. 907-914.
Woodyer et al., "Heterologous Expression, Purification, and Characterization of a Highly Active Xylose Reductase from *Neurospora crassa*", Applied and Environmental Microbiology, vol. 71, No. 3, Mar. 2005, pp. 1642-1647.
Wymelenberg et al., "Transcriptome and Secretome Analyses of Phanerochaete Chrysosporium Reveal Complex Patterns of Gene Expression", Applied and Environmental Microbiology, vol. 75, No. 12, Jun. 2009, pp. 4058-4068.
Xin et al., "Acceleration of Ethanol Production from Paper Mill Waster Fiber by Supplementation with Beta-Glucosidase", Enzyme Micro. Technol., vol. 15, Jan. 1993, pp. 62-65.

Figure 5
A
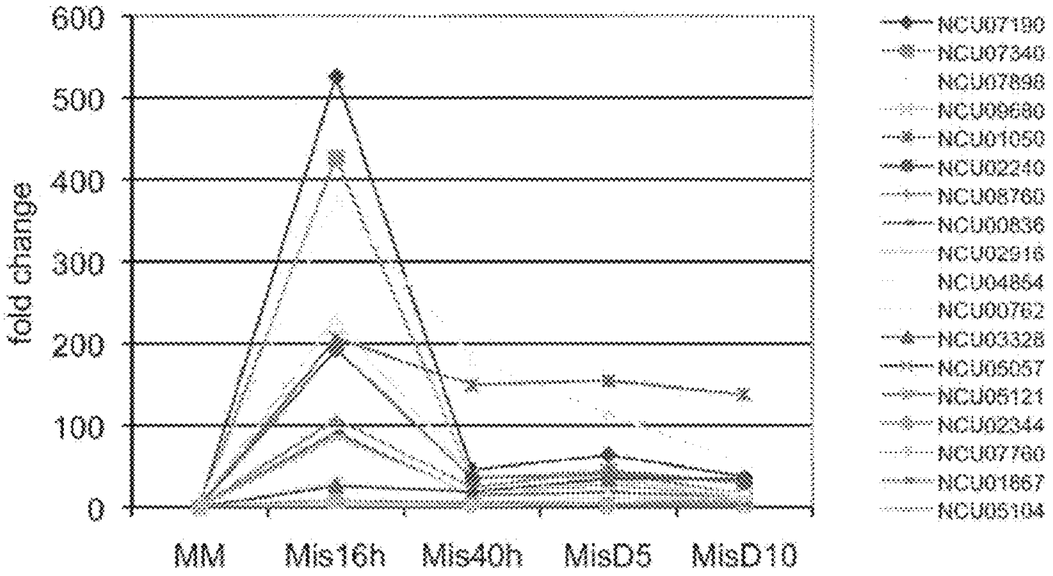
B
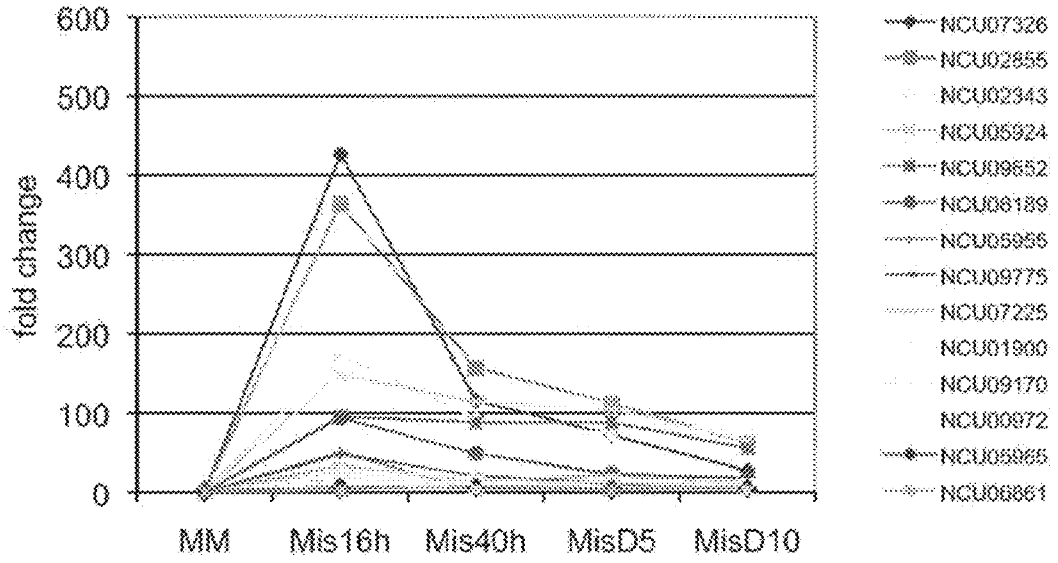

Figure 10-1

```
Query= NCU00801 |  neurospora_crassa hypothetical protein similar to MFS lactose
permease (580 nt)
         (579 letters)

Database: Spoth1_GeneModels_FilteredModels1_aa.fasta
           8806 sequences; 4,205,009 total letters

Searching..................................................done



                                                                 Score    E
Sequences producing significant alignments:                      (bits) Value

jgi|Spoth1|43941|e_gw1.2.4209.1                                     361   e-100

>jgi|Spoth1|43941|e_gw1.2.4209.1
          Length = 537

 Score =  361 bits (926), Expect = e-100,   Method: Compositional matrix adjust.
 Identities = 199/534 (37%), Positives = 284/534 (53%), Gaps = 29/534 (5%)

Query: 33  KGHGQTATHPGAQEEEVRHAALFAAIKE----SNIKPWSKESIHLYFAIFVAFCCACANG 89
            +   +I     A +  +E A L   +       +   PWS   I LY  + ++  C C NG
Sbjct: 5   KDEKETVVADHADDDALREADLAVQVAHDADGTVYSPWSLAMIRLYLVLSLSYLCGCLNG 64

Query: 89  YDGSLMTGIIAMDKFQNQFHTGDTGPKVSVIFSLYTVGAMVGAFFAAILSDRFGPKKGMF 148
            YDGSLM G+  M  +Q  FH    G     +IF++Y +G++     F   ++D FGR+ GMF
Sbjct: 65  YDGSLMGSLNGMISYQKYFHMSIAGSIIGLIFAMYNIGSVAAVFFIGPVNDIFGRPWGMF 124

Query: 149 IGSIFIIVGSLIVASGSKLAQFVVGRFVLGLGIAIMIVAAPAYSIEIAPFHWRGPCIGFY 208
            +G + +IVG+ + A  +    QF+ GRFVLG G++    V+AP Y  E+A P WRG  TG Y
Sbjct: 125 VGALLVIVGTCVQAFCTTRGQFLAGRFVLGFGVSFCCVSAPCYVSEMAHPKWRGTLTGLY 184

Query: 209 NCGWFGGSIPAACIIYGCYFIKSNWGWRIPLIIQAFICLIVMSSVPFLPESPRFLFANGR 268
            NC W+ GSI A+ + YGC +I +   +WRIP+  Q  T  +V   VP+LPESPR+L A  R
Sbjct: 185 NCTWYIGSIVASWVVYGCSYIDTLDAWKIPIWCQWVTSGLVCLGVFWLPESPRWLMRQDR 244

Query: 269 CAEAVAFLVKYHGNGDPNGKLVLLETEEMRGSIRTDGVDKVWWDYRPLFWTHSGRRRMAQ 328
              +A   L  YHG G   +  IV L+ +EM + I T+  DK W+DY   L+ THS R R+
Sbjct: 245 RGDAARVLAIYHGEGRADHRPIVKLQMQEMMNQISTEASDKRWYDYHELWNTHSAPKRLIC 304

Query: 329 VLMISIPGQFSGNGL-GYFNIVIFKNIGVIGISQQLAYNIINSVISAIGALIAVSMTDRM 387
            V+ +++FGQ SGN L  Y+    + R+ G+T    + LA N +N  +S +GA+     MID +
Sbjct: 305 VIGMAVFGQISGNGLGSYYLVNMLKGAGITEERRVLALNGVNPALGFLGAILGARMIDVV 364

Query: 388 FRRAVLIIIGTFMCAAALAINGGLSATLDKQIQRGTQINLNQGMNEQDARDNAYLRVDSNY 447
             RR +L+       +   A  +G S          R     N
Sbjct: 365 GRRPLLLYTIVFASVCFAVIIGSISKMAIDDPIKIAAAN---------------------- 402

Query: 448 AKGALAAYFLFNVIPGFTYTPLQGVIPTEALETTIRGKGLALSGPIVNAMGFINQFAGPI 507
                +A  F+F ++FGF +IPLQ +    E L T  R KG A+  F  +     I Q+A
Sbjct: 403 --ATIAFIFIFGIVFSFGWTFLQSMYIAEILPIATRAKGIAVGNFSSSVASIILQIASGP 460

Query: 508 ALHHIGYKYIFVFVGWDLIETVAWYFFGVESQGRTLEQLEWVYDQFNPVKASLK 561
            A   IGY +  VFV WDLIE     YF+  E++ RTLE+LE V+  PNPVK SL+
Sbjct: 461 AFEGIGYYFYLVFVFWDLIEGAIMYFYFFETKDRTLEELEEVFSAPNPVKKSLE 514
```

Figure 10-2

```
Query= NCU04963 |  neurospora_crassa hypothetical protein similar to
MFS monosaccharide transporter (523 nt)
         (527 letters)

Database: Spothl_GeneModels_FilteredModels1_aa.fasta
           9606 sequences; 4,205,009 total letters

Searching..................................................done



                                                                 Score    E
Sequences producing significant alignments:                      (bits) Value

jgi|Spoth1|62521|estExt_Genewise1.C_21757                           541   e-155

>jgi|Spoth1|62521|estExt_Genewise1.C_21757
          Length = 566

 Score =  541 bits (1395), Expect = e-155,   Method: Compositional matrix adjust.
 Identities = 263/508 (51%), Positives = 366/508 (72%), Gaps = 10/508 (1%)

Query: 6    KKPEGVPGKSWPAIVIGLFVAFGGVLFGYDIGTIGGILAMPYWQDLFSTGYRNPEHHLDV 65
            +KP+ V G S PAI++GLFVA GG+LFGYDIG I GILAM  +++ F+TGY + +    +
Sbjct: 9    QKPDNVAGSSAPAIMVGLFVAIGGLLFGYDIGAINGILAMDTFKKDFITGYTDKQGKPGL 68

Query: 66   TASQSATIVSILSAGTFFGALGAAPLADWAGRRLGLILSSFVFIFGVILQTAAVSIPLFL 125
             AS+ + IV++LSAGT  GAL +AP+ D  GRRL LI++  VF  G I+Q  A ++ + +
Sbjct: 69   YASEVSLIVAMLSAGTAIGALLSAPNSDKWGRRLSLIVAIGVFCVGSIIQVCAINVAMLV 128

Query: 126  AGRFFASLGVGLISATIPLYQSETAPKWIRSVIVGSYQLAITIGLLLASIVNNATHNMQN 185
             GR  AS+GVG++S  +PLYQSE APKWIR+ +V +YQL+IT GLL A+ VN  T+ +++
Sbjct: 129  VGRTLASIGVGVVSVLVPLYQSEMAPKWIRGTLVCAYQLSITAGLLAAATVNILTYKLKG 188

Query: 186  TGCYKIPIAVQFAWAIILIVGMIILPETPRFHIKPDNLPAATRSLAILPRLEQNHPAIIE 245
                YKIPI +Q  WA++L +G++ILPE PR+ +KR    AA  SL+ LRRL+  HPA+IE
Sbjct: 189  AAAYKIPIGLQLTWALVLALGLVILPESPRYLVKRGLKEAAALSLSRLRRLDITHPALIE 248

Query: 246  ELSEIQANHEFEKSLGKATYLDCLKG---NLLKRLLIGCFLQSLQQLTGINFIFYYGTQFF 303
            EL+EI+ANHE+E +LG  TY D + G  +L +R LIGC LQ LQQLTG+NFI YYGT FF
Sbjct: 249  ELAEIEANHEYEMALGPDTYKDIIFGEPHLGRRTLLGCGLQMLQQLTGVNFIMYYGTIFF 308

Query: 304  KNSGFSDSFLISLITNLVNVVSTLPGLYAIDKWGRRPVLLWGAVGMCVCQFIVAILGTTT 363
              +G  ++F +SLI  ++N+VST PGL+ ++ WGRR +L+ G+VGM +CQ ++A   T +
Sbjct: 309  YGAGIGNAFTVSLIMQVINLVSTFPGLFVVESWGRRKLLIVGSVGMAICQLLIASFATAS 368

Query: 364  TSQDASGMIIVHNLAAQKAAIAFICFYIFFFAASWGPVAWVVIGEIFPLKVRAKSLSITT 423
             + +              +  I F+  YIFFFAASWGPV WVVI EI+PLKVRAKS+SI+T
Sbjct: 369  GNDNKP--------TQNQILIIFVAIYIFFFAASWGPVVWVVISEIYPLKVRAKSMSIST 420

Query: 424  ASNWLLNWAIAYSIPYLVNYGPGNANLQSKIFFVWGGCCFICIAFVYFMIYETKGLTLEQ 483
            ASNW+LN+ IAY IPYLV+   G+ +L S++FFVWG  C + IAFV++M+YET  ++LEQ
Sbjct: 421  ASNWVLNFGIAYGIPYLVDTSDGSPDLGSRVFFVWGAFCILSIAFVWYMVYETSRISLEQ 480

Query: 484  VDELYEEVSDARKSIGWVPTIIFREIPE 511
            +DE+YE V+ A  S  + P+ +F+++R+
Sbjct: 481  IDEMYERVAHAWNSRSFEPSWSPQQMRD 503
```

Figure 10-3

```
Query= jgi|Spothl|48439|e_gw1.3.3367.1
         (512 letters)

Database: neurospora_crassa_7_proteins_no_asterisks.fas
           9822 sequences; 4,775,003 total letters

Searching..................................................done



                                                                 Score    E
Sequences producing significant alignments:                      (bits) Value

NCU01132 |  neurospora_crassa hypothetical protein similar to mo...   727   0.0

>NCU01132 |  neurospora_crassa hypothetical protein similar to
           monosaccharide transporter (554 nt)
          Length = 553

 Score =  727 bits (1876), Expect = 0.0,   Method: Compositional matrix adjust.
 Identities = 382/548 (69%), Positives = 431/548 (78%), Gaps = 42/548 (7%)

Query: 1    MKKFLGLRGQALNLAVGTIAGCDFLLFGYDQGVMGGILILKVFLDAFPMINPEAAGLSHD 60
            MK FLGLRGQ LNLAVG +AGCDFLLFGYDQGVMGGILTL  FL  F  INP+A GL+
Sbjct: 1    MKPFLGLRGQPLNLAVGSVAGCDFLLFGYDQGVMGGILTLFEFLGYFEQINPDAPSLTPH 60

Query: 61   ESSIRSTYQGIAVASYNLGCFLGAIITIFIGNPLGRKKVIMLGTSVMVIGAILQASSTTL 120
            ESS RSTYQGI+VASYNLGCF+GAIITIFIGNP GRK++I+LGTS+M++GAILQAS+TTL
Sbjct: 61   ESSMRSTYQGISVASYNLGCFIGAIITIFIGNPWGRKKIILLGTSIMIVGAILQASATTL 120

Query: 121  FQFIVGRIITGLGNGGNTSTVPTWQSETSKAHKRGKMIFF------CAIILAF------- 167
              FI+GRIITG+GNGGNTSTVPTWQSETSKAHKRGKM+            I+L++
Sbjct: 121  GHFIIGRIITGIGNGGNTSTVPTWQSETSKAHKRGKMVMIEGSLVTAGIMLSYWIDLGLS 180

Query: 168  -------------------------IPFLPESPRWLIILKGREDEAREVIAALEDIDISDR 202
                                    IPFLPESPRWL+ KGR+ EA+E++AAL D +  D
Sbjct: 181  FAPGSVAWRFPLAFQLIFCILILIFIPFLPESPRWLVFKGRDAEAKEILAALNDVELDDF 240

Query: 203  IVENEFLAIKETVLEMGKGTFFDLFTMDKNRNLHRILLAYFNQVFQQISGINLITYYAAV 262
            IV+ EF  I +TV+EMSKG+F+DLFTMDK+RN HRILLAY NQVFQQISGINLITYYAAV
Sbjct: 241  IVDTEFMFIHQTVVEMSKGSFKDLFTMDKDRNFHRILLAYLNQVFQQISGINLITYYAAV 300

Query: 263  IYKGLGMSDFLSRLLAALNGIEYFLASWFAVFLVERVGRRNLMLFGAVGQAATMAILAGV 322
            IY GLGMSDFL+RLLAALNGTEYF+ASWPAVFLVERVGRR LMLFGA+GQAATMAILAGV
Sbjct: 301  IYSGLGMSDFLARLLAALNGTEYFIASWPAVFLVERVGRRKLMLFGAIGQAATMAILAGV 360

Query: 323  NSR-QKIGFQIAGIVFLFVFNIFFAVGWLGMIWLYPAEIVPLRIRAPANALSTSANWIFN 381
            NSR  +  +QIAGIVFLFVFNI FAVGWLGM+WLYPAEIVPLRIRAPANALSTSANWIFN
Sbjct: 361  NSRPDDKPYQIAGIVFLFVFNIVFAVGWLGMSWLYPAEIVPLRIRAPANALSTSANWIFN 420

Query: 382  FLVVMITPVAFNNIGYQTYIIFAVINAFMVPCVYFFYPETAYRSLEEMDNIFHKVADGWK 441
            F+VVMITPVAFN I YQTYIIFAVINAF+VP VYFFYPETA RSLEEMD IFHKV DGWK
Sbjct: 421  FMVVMITPVAFNKIKYQTYIIFAVINAFIVPVVYFFYPETACRSLEEMDMIFHKV-DGWK 479

Query: 442  GVFTVVHQAKVEFRWYGKNGELL--VDYQQTEEHKRHLQQQESAVIASEKESVEKAGSGS 499
            G FTVVHQAKVEF+WY K+G+ +    D+++T  ++ H   +          K  VE   +
Sbjct: 480  GYFTVVHQAKVEFKWYDKDGQRIGGADFEETAGYQSHSIPESSGFEKPIKARVESPRADD 539
```

Figure 10-4

```
Query: 500 GSGDVKQD 507
           G      D
Sbjct: 540 GITSSSSD 547

Query= jgi|Spoth1|112305|estExt_fgenesh1_kg.C_50263
         (554 letters)

Database: neurospora_crassa_7_proteins_no_asterisks.fas
           9822 sequences; 4,775,003 total letters

Searching..................................................done


                                                                 Score    E
Sequences producing significant alignments:                      (bits) Value

NCU10021 |  neurospora_crassa high affinity glucose transporter ...   937   0.0

>NCU10021 |  neurospora_crassa high affinity glucose transporter
            (554 nt)
           Length = 553

 Score =  937 bits (2421), Expect = 0.0,   Method: Compositional matrix adjust.
 Identities = 474/542 (87%), Positives = 507/542 (93%), Gaps = 7/542 (1%)

Query: 1   MSSSEKEATGPVAAHVGNLAITQDVEKIEAPVTWKAYLICAFASFGGIFFGYDSGYINGV 60
           MSS+ ++ T P AAH+G LA TQDVE+IEAPVTWKAYLICAFASFGGIFFGYDSGYINGV
Sbjct: 1   MSSAHEKETAPTAAHIG-LAHTQDVERIEAPVTWKAYLICAFASFGGIFFGYDSGYINGV 59

Query: 61  LASKLFINAVEGAG--KDAISESHSSLIVSILSCGTFFGALIAGDLADFIGRKYTVILGC 118
           L S++FI+AVEG    +DA+SESH SL+VSILSCGTFFGALIAGDLAD IGRK+TVILGC
Sbjct: 60  LGSQIFIDAVEGTSPVRDALSESHQSLVVSILSCGTFFGALIAGDLADMIGRKWTVILGC 119

Query: 119 LIYIIGCVIQIITGLGNALGAIVAGRLIAGIGVGFESAIVILYMSEICPRKVRGALVAGY 178
           LIY+IGCVIQ+ITGLG+ALGAIVAGRLIAGIGVGFESA+VILYMSEICPRKVRGALVAGY
Sbjct: 120 LIYLIGCVIQMITGLGDALGAIVAGRLIAGIGVGFESAVVILYMSEICPRKVRGALVAGY 179

Query: 179 QFCIIIGLMLASCVVYSIQHRQDIGQYRIPIGIQFIWALILGGGLLCLPDSPRYFVKRGR 238
           QFCIIIGLMLASCVVY IQ+R DIG YRIPI IQFIWALIL GGL+CLPDSPRYFVK+G
Sbjct: 180 QFCIIIGLMLASCVVYAIQDRPDIGAYRIPIAIQFIWALILAGGLMCLPDSPRYFVKKGN 239

Query: 239 LADAISALSRLRGQPEDSEYIQVELAEIVANEEYERQLIPSTTWFGSWANCFKGSLFKAN 298
           LA AIS+LSRLRGQ  +SEYIQVELAEIVANEEYERQLIPSTTWFGSWANCFKGSL+KAN
Sbjct: 240 LAAAISELSRLRGQEPNSEYIQVELAEIVANEEYERQLIPSTTWFGSWANCFKGSLWKAN 299

Query: 299 SNLRKTILGTSLQMMQQWTGVNFIFYYSTPFLKSTGAIDDPFLMSMVFTIINVFSTPISF 358
           SNLRKTILGTSLQMMQQWTGVNFIFYYSTPFLKSTGAI + FL+SMVFTIINVFSTPISF
Sbjct: 300 SNLRKTILGTSLQMMQQWTGVNFIFYYSTPFLKSTGAISNTFLISMVFTIINVFSTPISF 359

Query: 359 YTVERFGRRTILFWGALGMLICQFLVAIVGVIVGFNHIHPAPTADDFEAILANNISAVNA 418
           +TVERFGRRTILFWGALGMLICQFLVAI+GVIVGFN IH  P  +     ++ANN+SAVNA
Sbjct: 360 WTVERFGRRTILFWGALGMLICQFLVAIIGVIVGFNKTHMGPDGS------SMANNVSAVNA 415

Query: 419 QIAFIAIFIFFFASIWGPGAWIVIGEIFPLPIRSRGVGLSTASNWLWNTIIAVITPYMVG 478
           QIAFIAIFIFFFASIWGPGAWI+IGEIFPLPIRSRGVGLSTASNWLWNTIIAVITPYMVG
Sbjct: 416 QIAFIAIFIFFFASIWGPGAWILIGEIFPLPIRSRGVGLSTASNWLWNTIIAVITPYMVG 475
```

Figure 10-5

```
Query: 479 EDRGNMKSSVFFVWGGLCICAFVYIYFLVPETKGLSLEQVDKMMEETTPRTSAKWKPTTT 538
           E RGN+KSSVFFVWGGLCICAF+YIYFLVPETKGLSLEQVDKMMEETTPRTSAKWKP TT
Sbjct: 476 EQRGNLKSSVFFVWGGLCICAFIYIYFLVPETKGLSLEQVDKMMEETIPRTSAKWKPETT 535

Query: 539 FA 540
           FA
Sbjct: 536 FA 537

Query= jgi|Spoth1|114107|estExt_fgenesh1_pm.C_20669
         (522 letters)

Database: neurospora_crassa_7_proteins_no_asterisks.fas
           9822 sequences; 4,776,003 total letters

Searching..................................................done


                                                                  Score    E
Sequences producing significant alignments:                       (bits) Value

NCU08114 |  neurospora_crassa hypothetical protein similar to MF...   832   0.0

>NCU08114 |  neurospora_crassa hypothetical protein similar to MFS
           hexose transporter (526 aa)
          Length = 525

 Score =  832 bits (2148), Expect = 0.0,   Method: Compositional matrix adjust.
 Identities = 397/523 (75%), Positives = 452/523 (86%), Gaps = 6/523 (1%)

Query: 1   MGIFAFNKQKFNAEATAVAQ--EEAPQFEKVDWKKDFGLRKLYFYAFVLCIASAITGYDG 58
           MGIF    +KF A+A  + Q  EEAPQFEKVDWK+DFGLRKLYFYAF+LCIASAITGYDG
Sbjct: 1   MGIF---NKKFVAQAVDLNQIQEEAPQFEKVDWKKDFGLRKLYFYAFILCIASAITGYDG 57

Query: 59  MFFNSVQNFEIWENYFNHPTGSKLGVLGALYQIGSLASIPLVPFIADRVGRKIPIAIGCV 118
           MFFNSVQNFEIW  YF  P GS+LG+LGALYQIGS+ SIP VP++ D  GRK PI IGCV
Sbjct: 58  MFFNSVQNFEIWIKYFGDPRGSELGLLGALYQIGSIGSIPFVPLLTDNFGRKTPIIIGCV 117

Query: 119 IMIVGAVLQAACENLGIFMGGRFLLGFGNSLAQLCSPMLLTELAHPQHRGRLITVYNCLW 178
           IMIVGAVLQA  +NL IFMGGR +LGFGNSLAQ+ SPMLLTELAHPQHR RLIT+YNCLW
Sbjct: 118 IMIVGAVLQATAENLDIFMSGRIMLGFGNSLAQIASPMLLTELAHPQHRARLITIYNCLW 177

Query: 179 NVGALVVAWVSFGIDYLKSDWSWRIPALIQAFPSVIQLLFIFWVPESPRYLMAKDKHEEA 238
           NVGALVV+W++FGI+Y+ +DWSWRIPAL+QAFPS+IQLL I+WVPESPR+L+AKDKH+ A
Sbjct: 178 NVGALVVSWLAFGINYINNDWSWRIPALLQAFPSIIQLLGIWWVPESPRFLIAKDKHDEA 237

Query: 239 LAILAKYHANGDANHPIVQFEYREIKETLRLEFEASKSSSYLDFVRTRGNRYRLAVLISL 298
           L ILAKYHANGD NHPIVQFE+REIKET+RLE E++R+SSYLDF ++RGNRYRLA+L+SL
Sbjct: 238 LHILAKYHANGDPNHPIVQFEFREIKETIRLEMESTRNSSYLDFFKGRGNRYRLAILLSL 297

Query: 299 GIFSQWSGNAIISNYSSKLYDTAGVIGSTQKLGLSAGQTGLSLIISVTMALIVDKFGRRP 358
           G FSQWSGNAIISNYSSKLY+TAGVI ST KLGLSAGQTGL+LI+SVTMALIVDK GRR
Sbjct: 298 GFFSQWSGNAIISNYSSKLYETAGVIGSTAKLGLSAGQTGLALIVSVTMALIVDKLGRRL 357

Query: 359 MFLTSTAGMFCIPIFWILISGLYEEHNADGARYAMILFIWIRGIFYSISWSGLLVGYAIE 418
            FL ST GM  IP+ WILI+GLI EH   GA  AMI FIW+ GIFYS++WSGLLVGYAIE
Sbjct: 358 AFLASTGGMCGIPVIWILIAGLIGEHRLKGADKAMIPFIWVPGIFYSLAWSGLLVGYAIE 417
```

Figure 10-6

```
Query: 419 VLPYKLHAKGLMIMNLTVQAALTLNTYANPVAFDAF-DGHSWKLYIIYTIWIFLELCFVW 477
           +LPY+LR KGLM+MN++VQ ALTLNTYANPVAFD F   HSWKLY+IYT WI  E  FV+
Sbjct: 418 ILPYRLRGKGLMVMNDMSVQCALTLNTYANPVAFDYFGPDHSWKLYLIYTCWIAAEFVFVF 477

Query: 478 EMYIETKGPTLEELAKIIDGDEAAVAHVDIKQVEKETHINEEK 520
            MY+ETKGPTLEELAK+IDGDEA VAH+DI QVEKE  I+E +
Sbjct: 478 FMYVETKGPTLEELAKVIDGDEAGVAHIGIHQVEKEVEIHEHE 520

Query= jgi|Spoth1|70023|estExt_Genewise1.C_53213
        (504 letters)

Database: neurospora_crassa_7_proteins_no_asterisks.fas
           9822 sequences; 4,778,003 total letters

Searching..............................................done


                                                                 Score    E
Sequences producing significant alignments:                      (bits) Value

NCU06138 |  neurospora_crassa hypothetical protein similar to MF...   263   6e-71

>NCU06138 |  neurospora_crassa hypothetical protein similar to MFS
           monosaccharide transporter (584 nt)
          Length = 583

 Score =  263 bits (673), Expect = 6e-71,   Method: Compositional matrix adjust.
 Identities = 159/488 (32%), Positives = 259/488 (53%), Gaps = 35/488 (7%)

Query: 10  FLVGVFASLGSLLYGYDLGVIAQVIASQSFKSRFSPSD--NEEAA-------VVSVFTGGA 61
           F +   FA +G +LYGY+ G+ + V+A  +F+        D  +E A+       + ++   GA
Sbjct: 39  FSIACFACIGGVLYGYNQGMFGSVLAMPAFQEHMGEYDPIDEGASQTKNGWLTAILELGA 98

Query: 62  FFGAMAAGPMGDKLGPKWTILCGALVPCLGGALQTGAQALSY--LYAGRSIAGLGVGVLC 119
           + G + +G M + L K++ +L   LVF LG  +Q  + +  +  + AGR I G+GVG L
Sbjct: 99  WLGTLLSGFMAEVLSRKYGVLVACLVFMLGVVIQATSISGGHETILAGRFITGMGVGSLA 158

Query: 120 MIVPMYQAELAHPSIRGRITALQQFMLGIGALAAAWISYGT-YVG---FAPINDGQWRIS 175
           MI+P+Y +E+A P +RG + ALQQ  +  G + + WI YGT Y+G       +D  W
Sbjct: 159 MIIPIYNSEVAPPEVRGALVALQQLAICFGIMVSFWIDYGTNYIGGTKLSTQSDAAWLVP 218

Query: 176 LGIQVIPAVFLAALIILLFPESPRWLIDHGRSEEGLRTLAQLHSHGDVDDAWVQAEYQQIR 235
           + +Q+ PA+ L   ++  P SPRWLI HGR  E  + L+ L       D   V+ E+ +I+
Sbjct: 219 VCLQLAPALIILFFGMMFMPFSPRWLIHHGREAEARKILSTLRGLPQ-DHELVELEFLEIK 277

Query: 236 ESVEFVRENEAKGYAEL-----------------------FRDRGCFPRLFLACAIQSGVQMTG 276
              F + + A+ + EL                       FR ++ FRP+ +A       Q +G
Sbjct: 278 AQSLFEKRSIAELFPELREQTAWNTFKLQFVAIEKLFRTKAMFRRVIVATVIMFFQQWSG 337

Query: 277 VGAIQYYSVTIYGLMGIEGDDT-LRYQAIGSIIALVAQALCILLIDRLGRRWTLIGGNLG 335
           ++AI YY+  I+  +G+ G+ T L     I+   +A    +L IDR+GR+  L  G LG
Sbjct: 338 INAILYYAPQIFKQLGLSGNTTGLLATGVVGIVMFIATVPAVLWIDHVGRKPVLTIGALG 397

Query: 336 NCVTFIIATVMLARYSPGTSSNKAAAWGFIVVTWVYNFSFSATCGPLSWIIPAEIFDTKT 395
              II  V++A+        ++KAA W  + + W++  F  + GP +WII AEI+   T
Sbjct: 398 MATCHIIIAVIVAKNVDQWETHKAAGWAAVAMVWLFVIHFGYSWGPCAWIIVAEIWPLST 457
```

Figure 10-7

```
Query: 396 RSKGVSIAIMISFALNIMISQVTGPAMKTVSYPFYLLFVVCNFTNALFFWAFLPETKKP 455
           R  GVS+    +++  N ++GQVT    +K + Y  Y++F +   +   A F W F+PET +
Sbjct: 458 RPYGVSLGASSNWMNNFIVGQVTPDMLKAIPYGIYIIFGLLIYMGAAFIWFFVPEIKRLI 517

Query: 456 LEEMNRLF 463
           LEEM+ +F
Sbjct: 518 LEEMDMIF 525

Query= jgi|Spoth1|102977|fgenesh1_pm.5_#_763
         (491 letters)

Database: neurospora_crassa_7_proteins_no_asterisks.fas
           9822 sequences; 4,775,003 total letters

Searching..................................................done


                                                                 Score    E
Sequences producing significant alignments:                      (bits) Value

NCU05897 |  neurospora_crassa hypothetical protein similar to l-...   713   0.0

>NCU05897 |  neurospora_crassa hypothetical protein similar to
           l-fucose permease (472 nt)
          Length = 471

 Score =  713 bits (1841), Expect = 0.0,   Method: Compositional matrix adjust.
 Identities = 347/447 (77%), Positives = 385/447 (86%), Gaps = 2/447 (0%)

Query: 1   MLSGSFWKPRSLRVPDNQKTKAAELTLRRSLYPLSLVTILFFLWGFSYGLLDTLNKHFQN 60
           M S  +WKRRSLRV D++ TKAAEL+LRESL PL LVTILFFLWGFSYGLLDTLNKHFQ
Sbjct: 1   MFSREWNKRRSLRVRDDKVTKAAELSLRESLLPLCLVTILFFLWGFSYGLLDTLNKHFQE 60

Query: 61  TLGITKTRSSGLQAAYFGAYPLASLGHAAWILRHYGYRAVFIWGLFLYGLGALLAIPSIN 120
           TL ITK RS+GLQAAYFGAYPLASLGHAA+ILR + YRAVFIWGLFLYGLGALLAIP I
Sbjct: 61  TLHITKAKSAGLQAAYFGAYPLASLGHAAYILRKFSYRAVFIWGLFLYGLGALLAIPCIK 120

Query: 121 KHSFAGFCVCIFIIGNGLGSLETAANPYITVCGPPKFSEIRINVAQAFNGIGTVVAPVLG 180
             SFAGFCVCIFIIGNGLGSLETAANPYITVCGPPK+SEIRIN AQAFNGIGTVVAPVLG
Sbjct: 121 AKSFAGFCVCIFIIGNGLGSLETAANPYITVCGPPKYSEIRINFAQAFNGIGTVVAPVLG 180

Query: 181 SYVFFTFDDQTALRNVQWVYLAIACFVFLLAGVFFLSVIPEITDADMAFQAAETHAGADD 240
           SYVFF FDD  AL+NVQWVYLAIA FV++LA VFFL  +PEITDADM  QAAETHAG  D
Sbjct: 181 SYVFFGFDDNLALQNVQWVYLAIAVFVYILAVVFFLIELPEITDADMQHQAAETHAGDAD 240

Query: 241 RPFHTQYRLFHAAFAQFCYTGAQVAIAGYFINYATETRPNTDSSLGSKFLAGSQAGFAVG 300
           +PF  QYRLFHA+F+QFCYTGAQ+AIAGYFINY IKIR NIDS+LG++FLAG+Q  FAVG
Sbjct: 241 QPFRKQYRLFHASFSQFCYTGAQIAIAGYFINYVTETRKNTDSALGAQFLAGAQCIFAVG 300

Query: 301 RFGGAAMMQFIKPRKVFALFMTMCIVFSAPAITQRGNAGLGMLYLVMFFESICFPTIIAL 360
           RF GAA+M F++PRKVF LF+T CI+F AP ITQR N G+S+LY+ +FFESICFPTI+AL
Sbjct: 301 RFAGAAIMHFVRPRKVFLLFLTACIIFVAPTITQPERTGMGLLYVTLFFESICFPTIMAL 360

Query: 361 GMRGLGRHTKRGSGWIVAGVLGGACVFPLMGAAADARGTGFGMLVPLCFFVAANTYALAV 420
           GMRGLGRHTKRGSG++VAGV GGA VFPLMGA AD   I  SM+VPL FF  ANTYALAV
Sbjct: 361 GMRSLGRHTKRGSGFLVAGVFGGAVVFPLMGAVADMHDIAMSMVVPLAFFAVANTYALAV 420
```

Figure 10-8

```
Query: 421 NFAPPYRSVVDAFSTTDVSLRERQPED 447
           NF P YR   DAF+T ++G+R+  RED
Sbjct: 421 NFWPWYRDTCDAFTTIAEIGVED--RED 445

Query= jgi|Spoth1|84164|estExt_Genewise1Plus.C_52100
         (546 letters)

Database: neurospora_crassa_7_proteins_no_asterisks.fas
           9822 sequences; 4,775,003 total letters

Searching..................................................done


                                                              Score    E
Sequences producing significant alignments:                   (bits) Value

NCU05853 |  neurospora_crassa conserved hypothetical protein (54...   586   e-168

>NCU05853 |  neurospora_crassa conserved hypothetical protein (542
           nt)
          Length = 541

 Score =  586 bits (1511), Expect = e-168,   Method: Compositional matrix adjust.
 Identities = 276/516 (53%), Positives = 369/516 (71%), Gaps = 11/516 (2%)

Query: 18  ADFIVTRLVQEDKIPWYKKPNLRRMYIFLPLCCMGVENTSGFDSQLINTLQYARTFHKYL 77
            +DP+++PL +ED IPWYKKPNLR +Y  LF  CMG+E+TSGFDSQ+IN LQ  E++ +Y
Sbjct: 11  SDFVISRLAKEDPIPWYKKPNLRFLYFWLFPTCMGIELTSGFDSQNINALQILESWIQYF 70

Query: 78  GNGRKDEDGNYAIEPGLLGPVNSCYQLGSIPAVPIAPWFAQPFGRRWSIMLGSLIMVSGA 137
             N +              L G +++ Y LG+I ++P+ P    RFGRRWSI LGS++M+ GA
Sbjct: 71  DNPQG-------------ALKGIIGAAYSLGAILSLPLVPIINDKFGRRWSIALGSIVMIVGA 120

Query: 138 IIQGFAQHVAMYIIARMILGMGILFCIISGAALIGELGHPKERAVLTSLFNDSYFIGQIL 197
            IIQGF+QHV MYI+ARMILG GI  CI+SG++LIGEL +PKER VLTSLFN SYF+GQI+
Sbjct: 121 IIQGFSQHVGMYIVARMILGFGIPTCIVSGSSLIGELAYPKERPVLTSLFNVSYFVGQIV 180

Query: 198 ADAITIGTTEMKTNWAWRLPSLLQICPSLLQIVTVFFLPESPRFLISKDRDDDAKEVLIK 257
            A+AI  GT  + +NW WR+PSLLQICPSLLQ+  VFF+PESPR+LI+KDR  +A ++L K
Sbjct: 181 AAAIVFGTNSIASNWGWRIPSLLQICPSLLQLAFVFFIPESPRWLIIKDRSQEAHDILKK 240

Query: 258 YHAEGDASSLLVQAEIVQIRETIRTEME-VSNQSWMELVSTYGMRRRLVITLFIGLFTQL 316
            YH E +      V AE  Q++  IR E E VS  SWM+L+ T GMR+RL+I+  +GLFTQ
Sbjct: 241 YHGEMERGEEFVAAEFAQMQAVIRLEYETVSKSSWMDLLRTPGMRKRLLISSMLGLFTQW 300

Query: 317 SGNTLLSYYSGKLFEMMGYTEASVKTRINVANACWSLLNATIIAFLVPYFRRPHMFNISA 376
            SGNTL+SY+ G L +M+G+T+++    +INV+ ACWSL     I++ LV   +RR M+M
Sbjct: 301 SGNTLISYFLGDLLKMIGFTDSTFIQKINVGIACWSLFCGVTVSLLVTRIRRRIMYMACT 360

Query: 377 LSMCAVFIAITVSLERTQAAQDAGFKNTAAGISGLFWIFAFAPCINWGNNALTYTILVEL 436
            +S+    +IA TVS+ER     +  G  N  A I+ LF+ + ++PCYNMG NALTYTY+VE+
Sbjct: 361 ISLLLCYIANTVSMERANIGKARGTPNNGANIATLFFIYNYSPCYNMGYNALTYTYVVEV 420

Query: 437 WPYSHRSRGIGVQQIFGNLSGFFSTNVNSIALDAIRWKYMAIYCGWIFFEFLIVFFLYPE 496
            WPY+ RSRGI V Q+FG+L GFF+T VN I L  + WKY+  YC W+ FE   V+F++PE
Sbjct: 421 WPYAERSRGIAVFQLFGRLAGFFTIFVNFIGLKNVGWKYLLGYCCWLAFEVCFVYFMFPE 480
```

Figure 10-9

```
Query: 497 TSGRTLEELAPLFEDASLNERAAAAVEKQIHYGDEK 532
           T GRTLEEL P+FE   L  +A AA EK +++ +
Sbjct: 481 TMGRTLEELTPMFEGEDLQPQANAAAERVVNHIEHD 516

Query= jgi|Spoth1|116270|estExt_fgenesh1_pm.C_30256
         (488 letters)

Database: neurospora_crassa_7_proteins_no_asterisks.fas
           9822 sequences; 4,775,003 total letters

Searching..................................................done



                                                                 Score    E
Sequences producing significant alignments:                      (bits) Value

NCU05519 |  neurospora_crassa hypothetical protein similar to Tn...   700   0.0


>NCU05519 |  neurospora_crassa hypothetical protein similar to Tna1
           (520 nt)
          Length = 519

 Score =  700 bits (1807), Expect = 0.0,   Method: Compositional matrix adjust.
 Identities = 338/512 (66%), Positives = 400/512 (78%), Gaps = 25/512 (4%)

Query: 1   MADEKRMSSSDSDKAAVQHSETLPGVSSTAAERGPAATDQNGQPIVQFDLKAEARLRRKL 60
           M  EKR  S           + E  PG +   AERG AATD +G P+V+ D  AE +LRRK+
Sbjct: 9   MTSEKPRQSLSESDIKEGYPERAPG-AHYRAERGQAATDIHGNPLVELDPVAETKLRRKI 67

Query: 61  DLPIVPTVSLLYLFCFIDRANIGNARIAGLEKDLNLTGYDYNALLSVFYIDYIVFEIPSN 120
           DL++VPTV++LYLFCFIDRANIGNAR+  LEKDL+L GYDYNALLSVFY+ YIVFEIP+N
Sbjct: 68  DLYVVPTVAILYLFCFIDRANIGNARLDKLEEDLDLHGYDYNALLSVFYVGYIVFEIPAN 127

Query: 121 IACKWIGPGWFIPAISLGFGVVSLATAFVDNFAQAAGVRFLLGVFEAGMMPGIAYYLSHW 180
           I CKW+GPGWF+P  SLGFG++S+  AFV+NF+QA GVRFLLGVFEAGM+PGIAYYLSRW
Sbjct: 128 IMCKWMGPGWFLPLTSLGFGIMSVCMAFVENFSQACGVRFLLGVFEAGMLPGIAYYLSRW 187

Query: 181 YRRAELIFRLSLYIVMAPMAGAFGGLLASGILSLDHVGGVIGWRMIFVVEGIITIGLSVI 240
           YRR+ELT RLSLYIVM+P+AGAFGGLLASGIL LDH G + GWRMIF +EGIIT+GLS+I
Sbjct: 188 YRRSELTLRLSLYIVMSPLAGAFGGLLASGILRLDHPGSLRGWRMIFGIEGIITVGLSLI 247

Query: 241 SFITLIDRPETARWLTQEERDLAIARVESERVATTEVLDPMDTEKLIQGILSPVTLATSF 300
            F+ILID P TA+WL+QEEKDLAIARVKSER+  TE++D+MD KKL +GI +PV   I F
Sbjct: 248 GFLTLTDHPATARWLSQEEKDLAIARVKSERIGQTEIIDKMDAKKLKRGIFNPVVFPTGF 307

Query: 301 MPLLNNIT------------------------QLFTVPPYVVGGFFTLALPLLSWILDRR 336
            FLLNNIT                        QL TVPPY+VGGFFT+ +PL+S +LDRR
Sbjct: 308 AFLLNNITVQGLAFFAPTVVATIIYPTKNIIQKQLLTVPPYIVGGFFTVLMPLISRWLDRR 367

Query: 337 QIIILLGIPLVIVGYSMFLGTTNPSARYGATFLLSSSLFAVGALSNSQVSANVVSDTARS 396
           QIII+    PLV+VGY MFL T N   RYGA FL+S+S+FA G L+NSQVSANVVSDTARS
Sbjct: 368 QIIIIACCPLVMVGYIMFLATENAHVRYGAAFLVSTSVFAAGPLTNSQVSANVVSDTARS 427

Query: 397 SAIGLNVMMGNVGGLIATWSYLPWDGPNYKIGNGLNLAACCTVLIILSAVTLLWMKWDNRR 456
           SAI  NVM+GNVGGL+ATWS+LP+D P Y IGNG+NLAA     LI++    L+WMK DN +
Sbjct: 428 SAIAYNVMLGNVGGLVATWSFLPFDAPKYRIGNGINLAASGGTLIIALCLLIWWKRDNNK 487
```

Figure 10-10

```
Query: 457 REGRNAEEELAGMSRQEIQDLDWRHPAFRWKP 488
           RE RNAEEEL GMS+QEIQDLD+KHP FRW+P
Sbjct: 488 RELRNAEEELTGMSQQEIQDLDIKHPGFRWKP 519

Query= jgi|Spoth1|79030|estExt_GenewiseIPlus.C_31624
         (519 letters)

Database: neurospora_crassa_7_proteins_no_asterisks.fas
           9822 sequences; 4,775,003 total letters

Searching..................................................done


                                                                 Score    E
Sequences producing significant alignments:                      (bits) Value

NC001291 |  neurospora_crassa hypothetical protein similar to ca...   834   0.0

>NC001281 |  neurospora_crassa hypothetical protein similar to
           carboxylic acid transport protein (520 nt)
          Length = 519

 Score =  834 bits (2154), Expect = 0.0,   Method: Compositional matrix adjust.
 Identities = 395/503 (78%), Positives = 441/503 (87%), Gaps = 1/503 (0%)

Query: 1    MESTHEPADPIAKGVLAIAKQSWHDLFIFKQRVVVINELGEISTEWARPVPLRNPISLLA 60
            MESTHEPADP+AKG+L IA+QSW DLFI+KQRVVVIN  GEI+TEWA+PVPL+NPISLLA
Sbjct: 1    MESTHEPADPVAKGILPIARQSWKDLFIWKQRVVVINVYGEIATEWAKPVPLKNPISLLA 60

Query: 61   QLSARNWLFFIVGFLAWVADAYDFHALSIQQVKLAKFYNTTKTDISTAITLTLLLRSVGA 120
            QLS R+W+ F+VGF AW ADA+DFHALSIQQVKLA +Y  +KT++STAITLTLLLRS+GA
Sbjct: 61   QLSGRDWICFLVGFCAWGADAPDFHALSIQQVKLAAYYGVSKTDVSTAITLTLLLRSIGA 120

Query: 121  AFFGLAGDKWGRKWPMVANMIVLGVLQIGTIYSVTPSQFLAVRALFGLFMGGVYGNAIAM 180
            A FGLAGD+WGRKWPMV NMIVLG+LQI TIYS T+S FL VRALFGLFMGGVYGNAIAM
Sbjct: 121  AAFGLAGDRWGRKWPMVVNMIVLGILQIATIYSSTYSQFLGVRALFGLFMGGVYGNAIAM 180

Query: 181  ALENSPPDARGLMSGILQQGYSLGYVIAACANLGVGGRDNSWKTVFWIGAGLSIGVGLVR 240
            ALENSP DARGLMSGILQQGY+ GYV AACANLGVGG  +SWKTVFWI AGLSIGVG++R
Sbjct: 181  ALENSPVDARGLMSGILQQGYAFGYVCAACANLGVGGDTDSWKTVFWIAAGLSIGVGIIR 240

Query: 241  CFFPESQQFLEARAAGKGQAGAGAPWKETNMMLAQEWKMCVYCIILMTWFNYYSHTSQDS 300
            CFFPES+QFLEAR  GK  A+ S FW+ETK+ML QEWKMCVYC ILMTWFNYYSHTSQD+
Sbjct: 241  CFFPESKQFLEARKEGKAHANPSQFWRETKVMLRQEWKMCVYCCILMTWFNYYSHTSQDN 300

Query: 301  YTTFMLTQKELDNDGASRASILMKVGACVGGTIIGYISQWFGRRRTIIVAALISGLIIPA 360
            YTTF+L  KE+DN  ASRASI+MK GACVGGTIIGY+SQ+FGRRRTIIV++LISG +IPA
Sbjct: 301  YTTFVLRAKEMDNSAASRASIIMKAGACVGGTIIGYLSQYFGRRRTIIVSSLISGCMIPA 360

Query: 361  WILPEGERSLSVTGFFMQFFVQGAWGVIPIHLNELSPPAFRSSFPGLTYQLGNMISSPSA 420
            WILP  ER+LS TGFFMQFFVQGAWGVIPIHLNEL+PPAFRSSFPG+TYQ+GNM+SSPSA
Sbjct: 361  WILPNGSEALSATGFFMQFFVQGAWGVIPIHLNELAPPAFRSSFPGITYQVGNMVSSPSA 420

Query: 421  QIVNAIAESHSVTSKSGKSVNAYGPTMGIATAIIATGIAVTTALGPEKRGREFEKTLPAG 480
            QIVNA++E   + S +GK V AYGPTMGIATAII  GI VTTA GPEKRGREFEK LPAG
Sbjct: 421  QIVNAVSEKIHIVGHIGKLVEAYGPTMSIATAIIVGSIVVTTAFGPEKRGREFEKALPAG 480
```

Figure 10-11

```
Query: 481 MNI-IQGGKAVDDLEKGDSRDEK 502
           MN+  Q GK VDDLE       EK
Sbjct: 481 MNLQKQRGKQVDDLEMETGHMEK 503


Query= jgi|Spoth1|108890|estExt_fgenesh1_pg.C_60848
         (533 letters)

Database: neurospora_crassa_7_proteins_no_asterisks.fas
           9822 sequences; 4,775,003 total letters

Searching..................................................done



                                                                 Score    E
Sequences producing significant alignments:                      (bits) Value

NCU00988 |  neurospora_crassa hypothetical protein similar to MF...   878   0.0

>NCU00988 |  neurospora_crassa hypothetical protein similar to MFS
           quinate transporter (538 nt)
          Length = 537

 Score =  878 bits (2269), Expect = 0.0,   Method: Compositional matrix adjust.
 Identities = 429/538 (79%), Positives = 471/538 (87%), Gaps = 10/538 (1%)

Query: 1   MGLS--TRILQKIVKNEAMASDPPEIYSWKVYLLACSACFGAMSFGWDSSVIGSVIVLPF 58
           MGLS   +IL+KIV+NEAMA DPPEIYSWKVYLLACSACFGAMSFGWDSSVIGSVI L F
Sbjct: 1   MGLSIGNRILRKIVKNEAMAEDPPEIYSWKVYLLACSACFGAMSFGWDSSVIGSVIELEF 60

Query: 59  FIRDFN-LGDPKSQASANLSANIVSTLQAGCFLGALVASPNIDRFGRKWCLIGVSLIIII 117
           F  DF  +G+ K  A ANL ANIVSTLQAGCFLGAL+ASP+IDRFGRKWCLI VSL++II
Sbjct: 61  FRHDFGFIGNDK--AKANLGANIVSTLQAGCFLGALIASPIIDRFGRKWCLIAVSLVVII 118

Query: 118 GIIMQAAASGRLGPNYAGRFIAGAGVGAASTINPIYVSENAPRAIRGLLTGLYQLFIVTG 177
           GIIMQAAASGRL PNY GRF+AG GVGAAS INP++VSENAPR+IRGLLTGLYQLFIVTG
Sbjct: 119 GIIMQAAASGRLAPNYIGRFVAGVGVGAASCINPVFVSENAPRSIRGLLTGLYQLFIVTG 178

Query: 178 GMIAFWINYSVSIHFPETKIMYVFPLAIQALPAALLCLCMLLCQESPRWLARRDRWEDTK 237
           GMIAFWINYSVS+HF + K MY+FPLAIQ LPA LLC+CMLLC ESPRWLARRDRWE+ K
Sbjct: 179 GMIAFWINYSVSLHF-KGKSMYIFPLAIQGLPAGLLCVCMLLCHESPRWLARRDRWEECK 237

Query: 238 RVLSRIRNLPFDHPYIQDEFQEIVAQLEHEERKLIGDASFWNLQREMWTIAGNRRRVLISI 297
            VL+RIRNLPFDHPYI DEF+EI  QLE EERKL GDA++W+L R+MWT+AGNR+R LISI
Sbjct: 238 SVLARIRNLPFDHPYIVDEFREIQDQLEQEERKLQGDATYWDLTRDMWTVAGNRKRALISI 297

Query: 298 ILMICQQMTGTNAINIYAPTIFKNLGLTGISTSLFSTGVYGIVKVTSCIIFLLPMADSLG 357
            LMICQQMTGTNAINIYAPTIFKNLG+TGISTSLFSTG+YGIVKV SC+IFLLP+ADSLG
Sbjct: 298 FLMICQQMTGTNAINIYAPTIFKNLGITGISTSLFSTGIYGIVKVVSCVIFLLPLADSLG 357

Query: 358 RRRSLLWTSIAQGLAMFYIGLYVRIAPPKEGESVPPASYFALVCIFLFAAFFQFGWGPAC 417
           RRRSLLWTSIAQGLAMFYIGLYVRI+PP +G+ VPPASY ALVCIFLFAAFFQFGWGPAC
Sbjct: 358 RRRSLLWTSIAQGLAMFYIGLYVRISPPIDGQPVPPASYVALVCIFLFAAFFQFGWGPAC 417

Query: 418 WIYASEIFAARLRSLNVAYAAATQWLFNFVVARTVPVMIVTMGEGGYGTYLLFGSFCFSM 477
           WIYASEIFAARLRSLNV+YAAATQWLFNFVVAR VP M+VT+G  GYGTYL+FGSFC SM
Sbjct: 418 WIYASEIFAARLRSLNVSYAAATQWLFNFVVARAVPTMLVTVGPHGYGTYLIFGSFCLSM 477
```

Figure 10-12

```
Query: 478 FVFVWFFVPETKGVSLEAMDKLFGVTD----ESSKSLTVDEDAKEKEKDGPHARQTEV 531
           FVFVWFFVPETKG+SLE MD+LFGVTD    E S     D+   E K    ++  EV
Sbjct: 478 FVFVWFFVPETKGISLEEMDELFGVTDGPAAEKSSVHGGDDVGSEMGKGDQKSKHVEV 535
```

Fig. 11
A
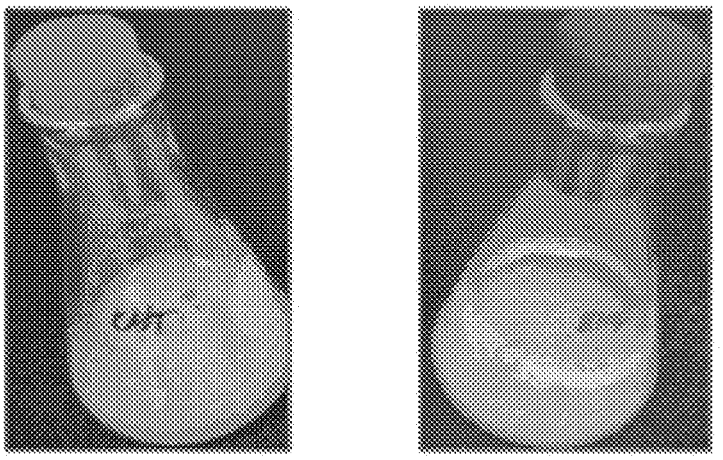
B
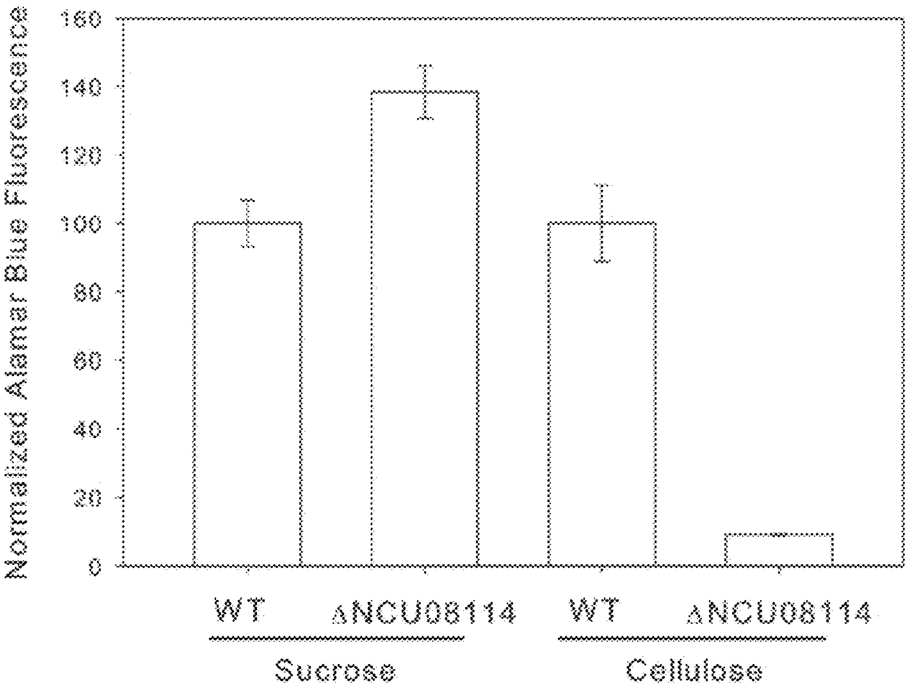

Fig. 12
A.
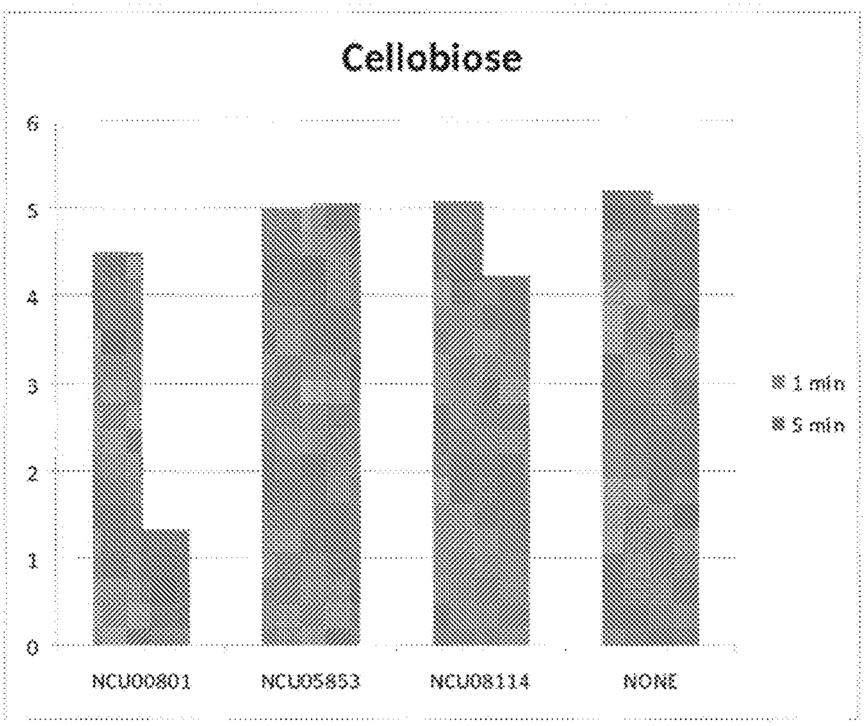
B.
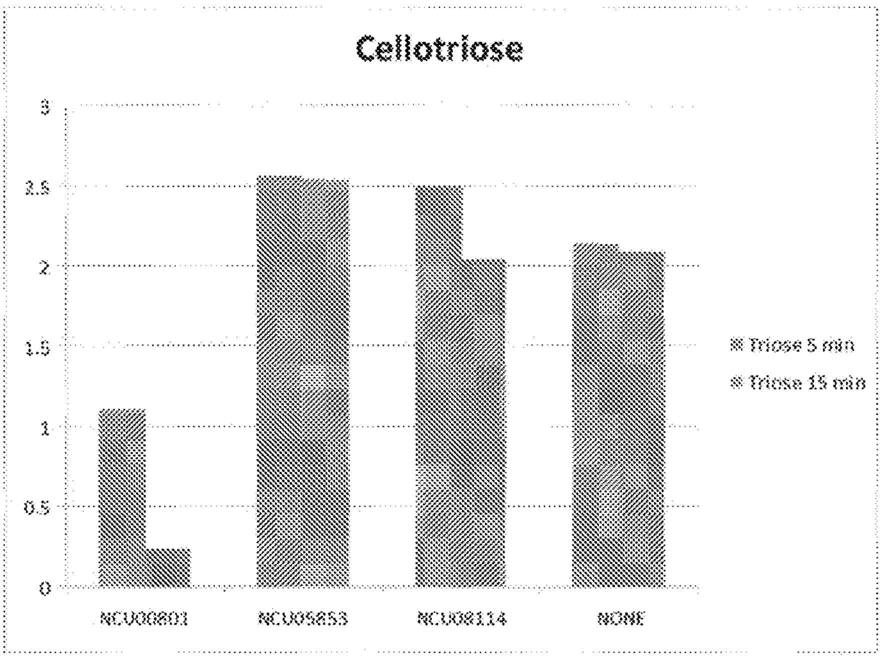

C.

D.

Figure 26 (a) (cont.)
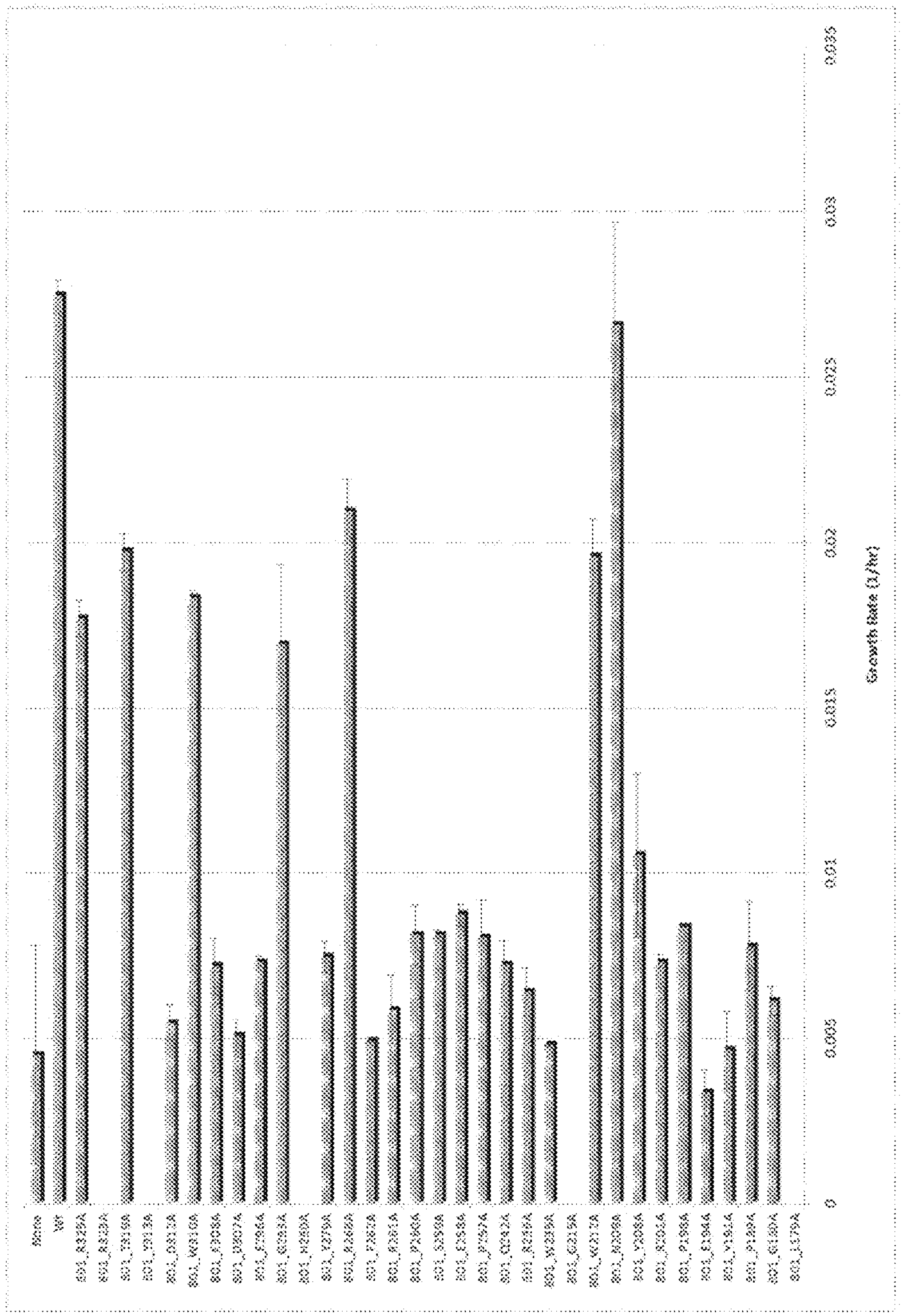

Figure 26 (a) (cont.)
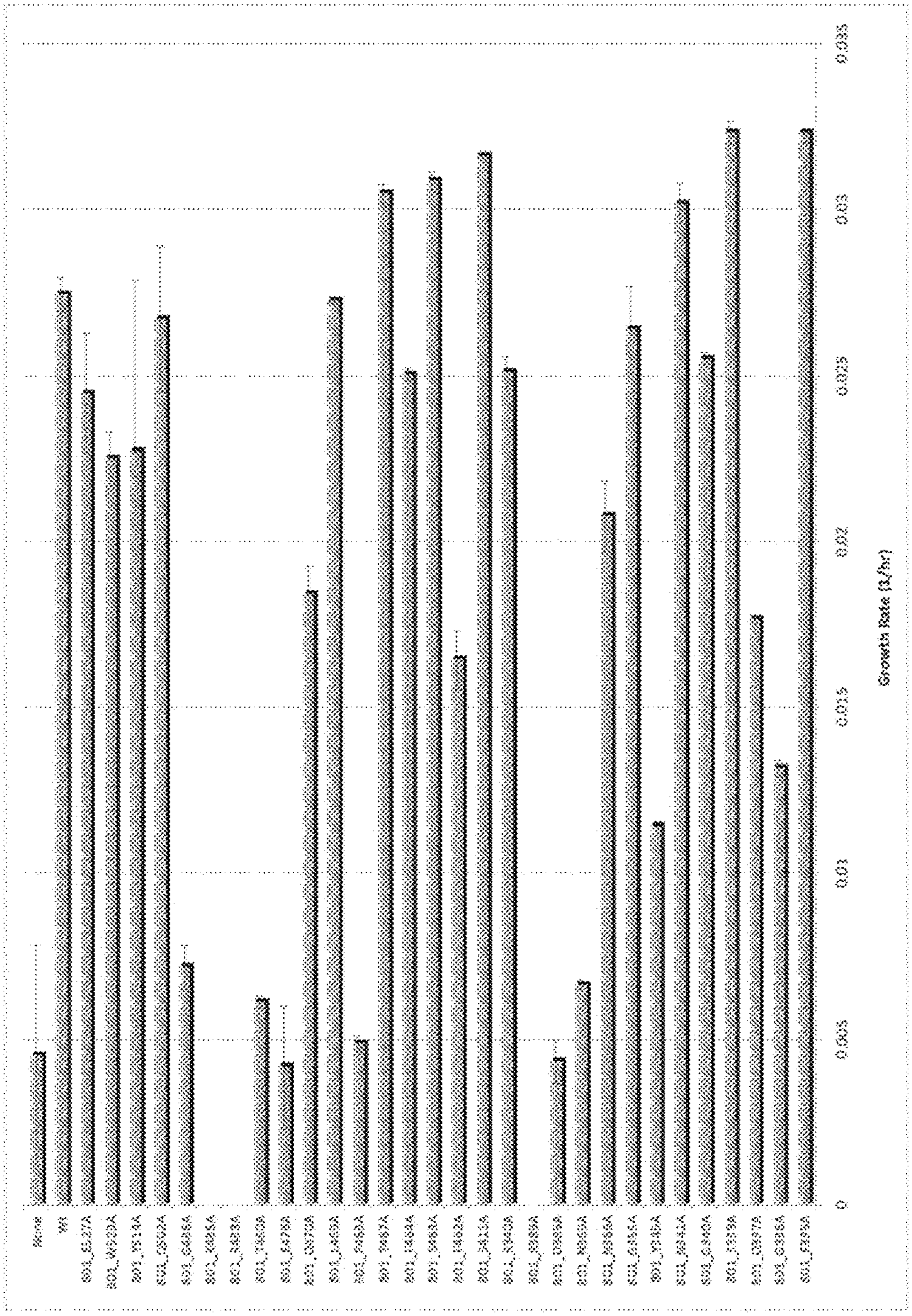

Polypeptide Sequence: NCU00801

MSSHGSHDGASTEKHLATHDIAPTHDAIKIVPKGHGQTATKPGAQEKEVR
NAALFAAIKESNIKPWSKESIHLYFAIFVAFCCACANGYDGSLMTGIIAM
DKFQNQFHTGDTGPKVSVIFSLYTVGAMVGAPFAAILSDRFGRKKGMFIG
GIFIIVGSIIVASSSKLAQFVVGRFVLGLGIAIMTVAAPAYSIEIAPPHW
RGRCTGFYNCGWFGGSIPAACITYGCYFIKSNWSWRIPLILQAFTCLIVM
SSVFFLPESPRFLFANGRDAEAVAFLVKYHGNGDPNSKLVLLETEEMRDG
IRTDGVDKVWWDYRPLFMTHSGRWRMAQVLMISIFGQFSGNGLGYFNTVI
FKNIGVTSTSQQLAYNILNSVISAIGALTAVSMTDRMPRRAVLIIGTFMC
AAALATNSGLSATLDKQTQRGTQINLNQGMNEQDAKDNAYLHVDSNYAKG
ALAAYFLFNVIFSFTYTPLQGVIPTEALETTIRGKGLALSGFIVNAMGFI
NQFAGPIALHNIGYKYIFVFVGWDLIETVAWYFFGVESQGRTLEQLEWVY
DQPNFVKASLKVEKVVVQADGHVSEAIVA

Italicized: All transporters
Double-underlined: β-linked transporters
Capped: NCU00801 clade
Bold: Essential in *S. cerevisiae* Hxt1/Hxt3
Underlined: functionally important according to alanine scanning experiment

Polypeptide Sequence: NCU08114

MGIFNKKPVAQAVDLNQIQEEAPQFERVDWKKDPGLRKLYFYAFILCIAS
AITGYDGMFFNSVQNFETWIKYFGDPRGSELGLLGALYQIGSIGSIPFVP
LLTDNFGRKTPIIIGCVIMIVGAVLQATAKNLDTFMGGRTMLGFGNSLAQ
IASPMLLTELAHPQHRARLTTIYNCLWNVGALVVSWLAFGTNYINNDWSW
RIPALLQAFPSIIQLLGIWWVPESPRFLIAKDKHDEALHILAKYHANGDP
NHPTVQFEFREIKETIRLEMESTKNSSYLDFFKSRGNRYRLAILLSLGFF
SQWSGNAIISNYSSKLYETAGVTDSTAKLGLSAGQTGLALIVSVTMALLV
DKLGRRLAFLASTGGMCGTFVIWTLTAGLYGEHRLKGADKAMIFFIWVFG
IFYSLAWSGLLVGYAIEILPYRLRGKGLMVMNMSVQCALTLNTYANPVAF
DYFGPDHSWKLYLIYTCWIAAEFVFVFFMYVETKGPTLEELAKVIDGDEA
DVAHIDIHQVEKEVEIHEHEGKSVA

Italicized: All transporters
Double-underlined: β-linked transporters
Capped: NCU08114 clade
Bold: Essential in *S. cerevisiae* Hxt1/Hxt3
Underlined: functionally important according to alanine scanning experiment (a)

Underlined: LYF-PESPR-KYH motifs

Capped: strictly conserved residues, critical to function (Ala-scan results)

```
NCU00801       ---------------------MGSRGSHD-----GASTEKR-LATRDIAPTHDA---IKIVPKGRG
NCU008114      ------------------------------------------------------------------MG
LAC2           ---------------------MGTNSLNDSYNPSSTKEKD-IVVQSEALADVA---I----------
C_parasiti     MILQDVQTTVFKRIDLIMGASKTDF-----VVDKSNH-EISADV------Q--YPVVAESTG
A_clavatus     ---------------------MGSTDE-----------KHGISVHHDSFGSDADFKPAVAAGQG
A_nidulans     ---------------------MGKD-------------------------TFTLA--G--------
S_thermo_1     ---------------------MSSKGS-D-----RIGDEKR-PVSPEIATAAVP--V--------S
S_thermo_i     ------------------------------------------------------------------MG

NCU00801       QIA-TK-FSAQEKEVRNAALFA--------AIKEGNIKPWSKESIH-LYFAIFVAFCCACAN
NCU008114      IPN-KK-FVAQAVDLNQIQEEA--------PQFERVDWEKDPGLRK-LYFYAFILCIASATT
LAC2           ETAFET-DG-YKK---------------IPQEHPVPEWTKLPLS-IYFTCLVIYLVSTIN
C_parasiti     KTL-DISAGAKAREVHNAELFA-------AVQESHIEEWGKDSGIQ-LYFAVFIAFCCACAN
A_clavatus     EIA-KV-GGAKIRQVHNAELYA-------AITETPIEKWGKESLH-MYFAIFVAFCCACAN
A_nidulans     R-EWP-------------------------------KVEWWEMRGMRSVYLTLGAAMVTSATN
S_thermo_1     HIP-KV-QG-KEKKVHNAELYA------AILEAKIEPWSRTSIH-LYFSIFIAFCCACAN
S_thermo_i     IP---------AFNKQKPNAEATAVAQEEAFQFEEVDWKEDPGLRK-LYFYAFVLCIASATT
                                                            :*:          : :.

NCU00801       GYDGSLMTGIIAMDKFQNQFHIGDTGPKVGVIFSLYTVGAMVGAPFAAILSDRFGRKKGM
NCU008114      GYDGMFFNSVQNFETWIKYFGDP-RGSELGLLGALYQIGSIGSIPFVPLLTDNFGRKTPI
LAC2           GYDGSLLSGLITMPEFISHLNIK-SASGIGIVFAIFQVGQMVATLFV-WLGDFIGRRNAI
C_parasiti     GYDGSLIGGIIAMKPFMDTFNSELTGTKVSIISGLYSVGTIVTGPLAAMLSDRFGRKWGM
A_clavatus     GYDGSLMGAILAMDHFQNTFHTSMDGPKVSLVTSLYTVGSIAATPFSAVLSDKLGRKKGM
A_nidulans     GYDGSLMNGLEALDDWKESYRHP-EGATLGLLAASMSIGSILAIPVVPYVADLFGRRFGV
S_thermo_1     GYDGSLMTSIIAMPHFQQTFDVGKVGTGAAVVFSLYVVGAMVGSPFAATLSDKFGRRKSM
S_thermo_i     GYDGMFFNSVQNFETWENYFNHP-TGSKLGVLGALYQIGSLASIPLVPIIADRVGRKIPI
               **** :: .: : :                  .. .:: :  :* :    .   : * .**:  :

NCU00801       FIGGIFIIVGSIIVASSGKLAQFVVGRFVLGLGIAIMTVAAPAYSIEIAPPHWRGRCIGF
NCU008114      IIGCVIMIVGAVLQATAKNLDTFMGGRIMLGFGNSLAQIASPMLLTELAHPQHRAKLTTI
LAC2           FIGSVIVCLGAIITSIANNTSTFIGGRFLLSFGGGISCALSTTYLLEITSPDERSALCAI
C_parasiti     FIGGWVIIVGSVIACSSSTVAQIIVGRFILGGGISIMTVAAPAYSIEIAPAHWRGRCTGF
A_clavatus     FVGAWVIIAGSIIIATANHLEQFIVGRVVLGFSIQIMVVSAPAYAVEIAPPHWRGRAVGF
A_nidulans     VLGCMIMIGGVAMVSIGYKIALFVVGRIILGFGLGIAQECSPLLVTELVHPQHRAIYSTI
S_thermo_1     FAGGLTIIIGMILVSTAHRLFQFVVGRFVLGLGIAIMTVAAPAYAIEVAPPHWRGRCIGF
S_thermo_i     AIGCVIMIVGAVLQAACDNLGTFMGGRFLLGFGNSLAQLCSPMLLTELAHPQHRGRLTTV
                  *   :  *  : .           :  ** :*. *  :      :.     *:. .. *.    .

NCU00801       YNCGWFGGSIPAACITYGCY---FIK-SNWGWRIPLILQAF-TCLIVM-SSVFFLPESPRF
NCU008114      YNCLWNVGALVVSWLAFGTN---YIN-NDWGWRIPALLQAF-PSIIQL-LGIWWVPESPRF
LAC2           YNSLYYIGSIIATWSSYATSISYAN-SVLSFRIPIMLQILCPALVVIGLLVGVAPESPRF
```

Fig. 28 (a) (cont.)

```
C_parasiti       YNCGWFGGSIPAAFVIFGCG--YMT-GNWAWRLPLLLQCF-ACFIVI-ASVWFLPESPRF
A_clavatus       YNCGWFGGSIPAAAVTYGTN--FTD-NDFGWRIPFILQCF-ACVIVI-FAVWFIPESPRW
A_nidulans       YNGLWYVGSLIGACVALGTN--NIKGNDWSWRVPCLLQGV-PGVCQL-IFIWFVPESPRW
S_thermo_1       YNCGWFGGAIPAAIITFGCN--YMD-NDYGWRVPLIFQAF-ACLIVM-VAVFFIPESPRF
S_thermo_i       YNCLWNVGALVVAWVGFGTD--YLR-GDWSWRIPALIQAF-PGVIQL-LFIFWVPESPRY
                 **.  :    *:)   :   :  .           .   ::*:*   :* . ..,    :     :    *****:

NCU00801         LFANGRDAEAVAFLVKYRGNGDPNSKLVLLEIEEMRDGIRTDGV-DKV-WWDYRPLFMTH
NCU008114        LIAKDKRDEALHILAKYHANGDPNHPTVQFEFREIKETIRLEMR-STK-NSSYLDFFKSR
LAC2             YYLTGQPDKARAFFCKYHANGDEKHPIVEYEMAQLELSLLEVPKLRVRDYFDARILFKTK
C_parasiti       LMANGREEEAVAFLVKYHGNGDPSSRLVLLEIEEMRENIRQDGQ-DKV-WWDYRPMFLTH
A_clavatus       QMAHGQDEAALAFLIRYRGNGDPNARLVRLEIEEMREGIRIDGI-DKR-WWDYRPFFFTH
A_nidulans       LISKGKSEKAKKILAYVHAQGDEDDELVNVEFDEIQQTIALEKQLEGS-GWS--ELWGTP
S_thermo_1       LMANGRDDEALAFLIKYRGNGDPNSRLVRLEYEEMKEGIRQDGI-DKV-WWDYRPFLLSH
S_thermo_i       LMAKDKREKALAILAKYHANGDANHPTVQFEYREIKETLRLEFE-ASK-SSSYLDFVRTR
                     .:      *    ::      *.:**  .     *     *   ::.  :                   .    :   :

NCU00801         SGRWRMAQVLMISIFGQFSGNGL-GYFNTVIFKNIGVTSTSQQLAYNILNSVISAIGALT
NCU008114        GNRYRLAILLSLGFFSQWSGNAIISNYSSKLYETAGVTDSTAKLGLSAGQTGLALIVSVT
LAC2             SRIYRSLVCIAHSAFGQLSGNAVVGYYITNIFLELGITRPTTRLLLRGVNSILGFIFAMS
C_parasiti       NGKWRFGQIIMISVFGQFSGNGL-GYFNAAIFGLIGVKSTAQQLGFNVLNSVLSAIGAGF
A_clavatus       SGRWKFLQVMMISVFGQWSGNGL-GYFNATIIYQRLGYTSSMQLLMRLVNSIVSAIGALT
A_nidulans       GNRHRSIILISIGFFSQWSGNGIVSYFLPKVLELIGIIDSHKVLTINSVLNAVNVVGATG
S_thermo_1       SGRWKIAQVLMISIFGQFSGNGL-GYFNTTIFENLGVTSVFQQLGYNILNQVLSAIGALT
S_thermo_i       GNKYRLAVLISLGIFSQWSGNAIISNYSSKLYDTAGVTGSTQKLGLSAGQTGLSLIISVT
                 .     *       :   .   *.*  ***.:  .  :  .  :       *  ..       *   .           :   :  :

NCU00801         AVSMTDRMFRRAVLIIGTFMCAAALATNSGLSATLDKQTQRSTQINLNQSMNEQDAKDNA
NCU008114        MALLVDKLGRRLAFLASTGGMCGTFVIWTLTAGLYGEHR-L-------------------
LAC2             GSILVGKIGRRPILLYSTTGFVISFTIIAACIAAYTNNN-----N---------------
C_parasiti       GVSLSDKMNRKIVLVYGTFICACLLAVNGGTSTGLKKYETTDSSGNLNISA----D----
A_clavatus       AVALTDRMFRRKVLVWGTLACAIAMAINAGVSEPNIKQAETFAGIN--------------
A_nidulans       ICFFVDKLGRRKLFLISVICMLLCFISTTIALARFPHSP-----GGAD------------
S_thermo_1       AVSLTDKMPRRPVLVFGIFMCAAALATNSGLSAVLDEQTQRG------------------
S_thermo_i       MALLVDKFGRRPMFLTSIAGMPCTFIFWTLTSGLYEEHN-A-------------------
                     : .:: **   :: ..           :                 .

NCU00801         YLRVDSNYAKGALAAYFLF-NVIFSFTYTPLQGVIPTEALETTIRGKGLALSGFIVNAMG
NCU008114        -----KGADKAMIFFIWVF-GIFYSLAWSGLLVGYAIEILPYRLRGKGLMVMNMSVQCAL
LAC2             -----QVAAKVGIAFIYIFNNVFFSFGYTPLQPLYPAEILSSEMRAKGMALFQITQGTAS
C_parasiti       -----GKSLAQAALAFYFLF-HIIYSFTYTPLQGIIPAEALDTNLRAKGLAASGMIVGLFG
A_clavatus       -----RTFGQTAVAFYYLF-NIIFSFTYTPLQGVIPAEALETTTRAKGLALSGLMVSGIG
A_nidulans       -----DHAGNAVIVFIFLY-YISYRIGFSGLLVSYSSEILPYRLRAKGLTLMFFCVALSL
S_thermo_1       --QIDLSYGRGALASYFLF-NIIFSFTYTPLQGAIPTEALETTTRAKGLALSAFIVNGMG
S_thermo_i       -----DGARYAMILFIWIS-GIFYSISWSGLLVGYAIEVLPYKLRAKGLMIMNLTVQAAL
                                :    ::.  : :.: :: *      . * *      *.**:      :
```

Fig. 28 (a) (cont.)

```
NCU00801      FINQFAGPIALRNI----GYKYIFVFVGWDLIETVAWYFFGVESQGRTLEQLEWVYDQPN
NCU08114      TINTYANPVAFDYFGPDHSWKLYLIYTCWIAAEFVFVFFMYVETKGPTLEELAKVIDGDE
LAC2          FINTYAAPVAMQNI----KYWYYVFFVFWDIFEVIIIYLYFVETKNLTLEEIELIFESAT
C_parasiti    FINQFAGPIALANI----NINYVYVFVAWDVIESILWWIFGVESQGRTLEQLEWVYNQPK
A_clavatus    FVSQYASPIGLRNI----STHYFWIFVGWDLFEALCWYLFGVESQGRTLEELEWVYQQPN
A_nidulans    LFNQYVNPIALLDI----GWKYYIVYCVWLLFELFVVWKYYVETKNTPLEEIVKFFDGDQ
S_thermo_l    FINQFAGPIALERI----GYKYIYVFVAWDCIEALAWYLFGVESQGRTIEQLEWVYNQPN
S_thermo_i    TINTYANPVAFDAFE-GRSWKLYIIYTIWIFLELCFVWKMYIETKGPTLEELAKIIDGDE
                .: :. *:.: :        .: *  *   :   :*::. .:*::  . :

NCU00801      PVKASLKV----EKVVVQA----------DGHVSEA-IV----A
NCU08114      ADVAHIDI----HQVEKEV----------EIHEHEGKSV----A
LAC2          FVKISMII-----SKPGHAANEEKL-ELANLKLGKN-YVA----
C_parasiti    FVQASIKV----DKVVVQA----------DGKVTEK-IVADAAS
A_clavatus    PVKASLQV----DKVVVQA----------DGQVTEK-IT-D--A
A_nidulans    AVLGGAAATEKIHELVT--VQARSAEETLGEKGPA-VSAEAR-
S_thermo_l    FVKASLKV----DKVILTD----------DGKVAEK-IV----A
S_thermo_i    AAVAHVDI----KQV--EK----------ETHIHEE-KS----V
              .           :                 .
```

Fig.28 (b)

```
NCU00801      MSSHGSHDGASTEKR~LATHDIAPTHDA~~IKIVPKGHGQTATKPGAQEKEVRNAALFAA
NCU08114      ~~~~~~~~~~~~~~~~~~~~~~~~~~~~~~~~~~~~~~~~MGIFNKKFVAQAVDLNQIQEEAP
LAC2          MST--------NSLNDSYNPSSTEEKDIVVQSEALADVAIETAFEIDGYE-----------KI
A_clavatus    MSS--------TDEKHGISVHHDSPGSDADFKPAVAAGQSETAKVGGAKTRQVHNAELYAA
                                                                    *

NCU00801      IKESNIKPWSKESIHLYFAIFVAFCCACANGYDGSLMTGIIAMDRFQRQFHTGDTGPKVS
NCU08114      QFERVDWKKDPGLRKLYFYAFILCIASATTGYDGMFFNSVQNFEIWIKYFSD-PRGSELG
LAC2          FQEHPVFRWTKLRLSIYFICLVIYLVSTTNGYDGSLLSSLITMPEFISHLNI~KSASGTG
A_clavatus    ITETPIEEWSKESLHMYFAIFVAFCCACANGYDGSLMGAILAMDRFQRTFHIGNDGPKVS
                *              :**  ::    : :.****  ::  .:   :   :  .  :       ..  .

NCU00801      VIFSLYTVGAMVGAPFAAILSDRFGRKKGMFIGGIFIIVGSIIVASSSKLAQFVVGRFVL
NCU08114      LLGALYQIGSIGSIPFVPLLTDNFGRKTPIIIGCVIMIVGAVLQATAKNLDTFMGGRTML
LAC2          IVFAIFQVGQMVATLF-VWLSDFIGRPNAIFIGSVIVCLGAIITSIANNTSTFIGGRFLL
A_clavatus    LVTSLYTVGSIAATPFSAVLSDKLGRKKCMFVGAWVIIAGSIIIATAKHLEQFYVGRVVL
              :: ::: :* : .  *    * * :**:. ::*  .:   *::: : :.:    *  ** :*

NCU00801      GLGIAIMTVAAPAYSIEIAPPHWRGRCIGFYNCGWFGGSIPAACITYGC---YFIKSNWSW
NCU08114      GFGNSLAQIASFMLLTELAHPQHRARLTTIYNCLWNVGALVVGWLAFGT---NYINNDWGW
LAC2          SFGSGISCALSTTYLLEITSPDERSALCAIYNSLYYIGSIIATWSSYATSISYANSVLSF
A_clavatus    GFGIQIMVVGAPAYAVEIAPPHWRGRAVGFYNCGWFGGSIPAAAVTYGT---NFIQNDFSW
              .:*  :     :.     *:: *. *.     :**. :  *:: .:  ::.      : ..  *:

NCU00801      RIPLIIQAFT~CLIVM~SSVFFLPESPRFLFANGRDAEAVAFLVKYHGNGDPNSKLVLLE
NCU08114      RIPALLQAFF-SIIQL-LGIWWVPESPKFLIAKDKHDEALHILAKYHANSDPNHPTVQFE
LAC2          RIPLWLQILCPALVVIGLLVGVAFEGPRFYYLTGQPDKARAFFCKYHANGDEKHPIVEYE
A_clavatus    RIPFILQCFA~CVIVI~FAVWFIPESPRWQMAHGQDEAALAFLTRYHGNGDPNARLVRLE
              ***  ** :  .:: :    :    *****:      .:   *  :: :**.*** :   *  *

NCU00801      IEEMRDGI~RIDGVDKV~WWDYRPLFMTHSGRWRMAQVIMISIFGQFSGNGL~GYFNTVI
NCU08114      FREIKETI~RLEMESTK~NSSYLDFFKSRGNRYRLAILLSLGFFSQWSGNAIISNYSSKL
LAC2          MAQLELSLLEVPKLPVRDYFDARILFKTKSRIYRSLVCIARSAFGQLSGNAVVSYYINI
A_clavatus    IEEMREGI~RIDGIDKR~WWDIKPFFFTHSGRWRFLQVMMISVFGQWSGNGL~GYFNATI
                :: .  : .                .    :* ::.  :*     :  . *.* ***.: . : : :

NCU00801      FKHISVIGTSQQLAYNILNSVISAIGALTAVSMTDKMPRRAVLIIGTFMCAAALATNSGL
NCU08114      YETAGVTDSTAKLSLGAGQTGLALIVSVIMALLVDKLGRRLAFLASTGGMLGTFVIWT---
LAC2          FLELGITNPTTRLLLNGVNSILGFIFAMSGSILVGRIGRRPILLYSTIGFVISFTIIAAC
A_clavatus    YQRLGYTSSSMQLLMNLVNSIVSAIGALTAVALIDRMPRRKVLVWGILACAIAMAINAGV
              :    * *..: :*  .   ::  :. * ::    :..:: **  :: .*      ::.  :

NCU00801      SATLDKQTQRGIQINLNQGMNEQDAKDNAYLHVDSNYAKGALAAYFLF~NVIFSFTYTPL
NCU08114      --------------------LTAGLYGR----------HRLKGADKAMIFFIWVF~GIFYGLAWSGL
LAC2          I---------AAYTN----------------------------NNNQVAAKVGIAFIYIFNNVFFGFGYIPL
A_clavatus    SEPMINQAKIPAGIN----------------------KIFGQTAVAFYYLF~NIIFSFTYTPL
                                                      .   :   :   ::* .:::*: :: *

NCU00801      QGVIPTEALETTIKGKGLALSGFIVNAMGFINQFAGPIALKNIG------YKYIFVFVGWDL
NCU08114      LVGYAIEILPYRLRGKGLMVMNMSVQCALTLNTYANPVAFDYFGPDHSWKLYLIYICWIA
LAC2          QPLYPAEILSSEMRAKGMALFQITQGTASFINTYAAPVAMQNIK----YWIYVFFVFWDT
A_clavatus    QGVIPAEALETTIRAKGLALSGLMVSGIGFVSQYASPIGLRNIS------THYPWIFVGWDL
                   . * *    *.**: :  :           :. :* *:.:   :          .:. *

NCU00801      IETVAWYFFGVESQGRILEQLEWVYDQPNPVKASLEVEK-------VVVQADGHVSEAIV-
NCU08114      AEFVFVEFMYVETKGPTLEELAKVIDGDEADVAHIDIHQ--------VERVEIHEHEGKSV
LAC2          FEVIIIYLYFVETKNLTLEEIELIFESAIPVKTGMIISKFGHAANEEKLELANLKIGENY
A_clavatus    FEALCWYLFGVESQGRILEELEWVYQQPNPVKASLQVDK------VVVQADGQVTEKIID
               * :  ::  **::. ***::  : :    .  : : : :                :

NCU00801      ~A
NCU08114      ~A
LAC2          VA
A_clavatus    ~A
               *
```

Fig. 28 (c)

BLASTP 2.2.24+
Reference: Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

Reference for compositional score matrix adjustment: Stephen F. Altschul, John C. Wootton, E. Michael Gertz, Richa Agarwala, Aleksandr Morgulis, Alejandro A. Schaffer, and Yi-Kuo Yu (2005) "Protein database searches using compositionally adjusted substitution matrices", FEBS J. 272:5101-5109.

RID: 4HJKWKG311R

Query= NCU00801
Length=579

```
                                                          Score
E
Sequences producing significant alignments:               (Bits)
Value

lcl|47823  NCU08114                                         238
4e-67

ALIGNMENTS
>lcl|47823 NCU08114
Length=525

 Score =  238 bits (608),  Expect = 4e-67, Method: Compositional matrix
adjust.
 Identities = 152/518 (29%), Positives = 257/518 (49%), Gaps = 35/518 (6%)

Query  66   WSKES--IHLYFAIFVAFCCACANGYDGSLMTGIIAMDKFQNQFHTGD-TGPKVSVIFSL  122
            W K+     LYF  F+    +   GYDG     +   + +    F  GD  G ++ ++ +L
Sbjct  30   WKKDPGLRKLYFYAFILCIASATTGYDGMFFNSVQNFETWIKYF--GDPRGSELGLLGAL  87

Query  123  YTVGAMVGAPFAAILSDRFGRKKGMFIGGIFIIVGSIIVASSSKLAQFVVGRFVLGLGIA  182
            Y +G++    PF  +L+D FGRK  + IG + +IVG+++ A++  L  F+ GR +LG G +
Sbjct  88   YQIGSIGSIPFVPLLTDNFGRKTPIIIGCVIMIVGAVLQATAKNLDTFMGGRTMLGFGNS  147

Query  183  IMTVAAPAYSIEIAPPHWRGRCTGFYNCGWFGGSIPAACITYGCYFIKSNWSWRIPLILQ  242
            +  +A+P     E+A P  R R T  YNC W  G++  + + +G  +I ++WSWRIP +LQ
Sbjct  148  LAQIASPMLLTELAHPQHRARLTTIYNCLWNVGALVVSWLAFGTNYINNDWSWRIPALLQ  207

Query  243  AFTCLIVMSSVFFLPESPRFLFANGRDAEAVAFLVKYHGNGDPNSKLVLLETEEMRDGIR  302
            AF  +I +  ++++PESPRFL A  +  EA+  L KYH NGDPN   V  E  E+++ IR
Sbjct  208  AFPSIIQLLGIWWVPESPRFLIAKDKHDEALHILAKYHANGDPNHPTVQFEFREIKETIR  267

Query  303  TDGVDKVWWDYRPLFMTHSGRWRMAQVLMISIFGQFSGNG-LGYFNTVIFKNIGVTSTSQ  361
             +         Y   F +   R+R+A +L +  F Q+SGN  +  +++ +++  GVT ++
Sbjct  268  LEMESTKNSSYLDFFKSRGNRYRLAILLSLGFFSQWSGNAIISNYSSKLYETAGVTDSTA  327

Query  362  QLAYNILNSVISAIGALTAVSMTDRMPRRAVLIIGTFMCAAALATNSGLSATLDKQTQRG  421
            +L  +   + ++ I ++T   + D++ RR          A LA+  G+  T   T
Sbjct  328  KLGLSAGQTGLALIVSVTMALLVDKLGRR----------LAFLASTGGMCGTFVIWT---  374
```

Fig. 28 (c) (cont.)

```
Query  422  TQINLNQGMNEQDAKDNAYLHVDSNYAKGALAAYFLFNVIFSFTYTPLQGVIPTEALETT  481
                L  G+  +        H      K  +   ++F + +S  ++  L      E L
Sbjct  375  ----LTAGLYGE--------HRLKGADKAMIFFIWVFGIFYSLAWSGLLVGYAIEILPYR  422

Query  482  IRGKGLALSGFIVNAMGFINQFAGPIALHNIG----YKYIFVFVGWDLIETVAWYFFGVE  537
            +RGKGL +    V     +N +A P+A    G    +K  ++   W   E V  +F  VE
Sbjct  423  LRGKGLMVMNMSVQCALTLNTYANPVAFDYFGPDHSWKLYLIYTCWIAAEFVFVFFMYVE  482

Query  538  SQGRTLEQLEWVYDQPNPVKASLKVEKVVVQADGHVSE  575
            ++G TLE+L  V D      A + + +V  + + H  E
Sbjct  483  TKGPTLEELAKVIDGDEADVAHIDIHQVEKEVEIHEHE  520
```

Fig. 29
(a)
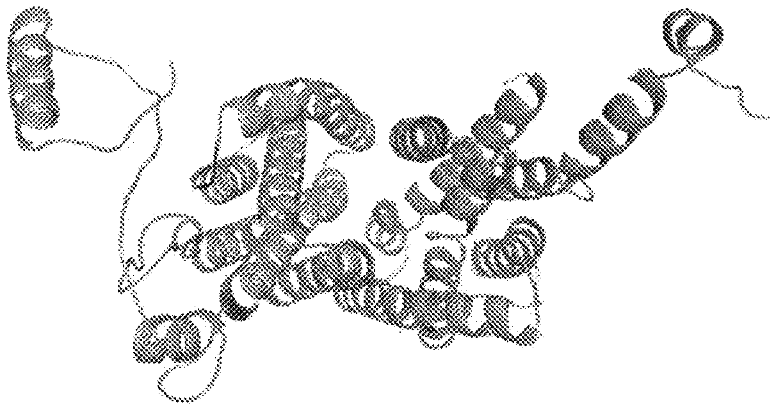
I.
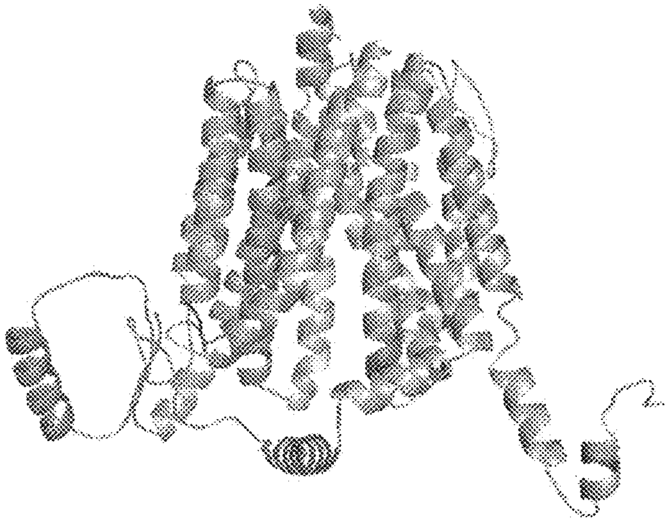
II.
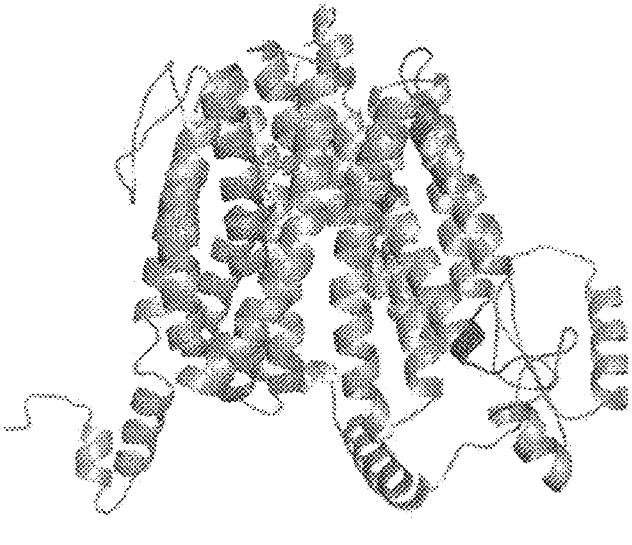
III.

Fig. 29 (cont.)
(b)
I.
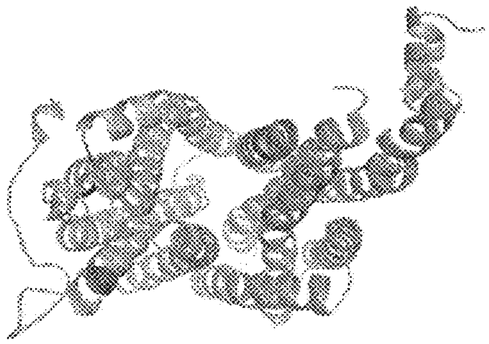
II.
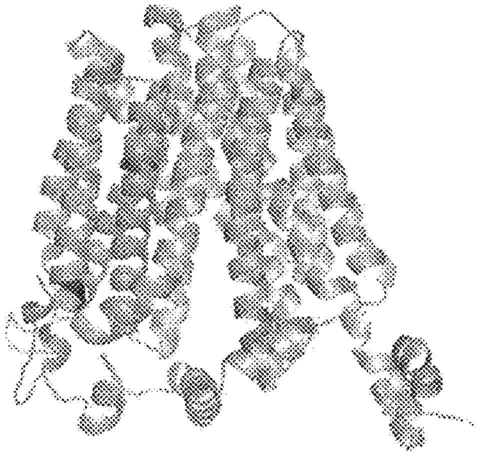
III.
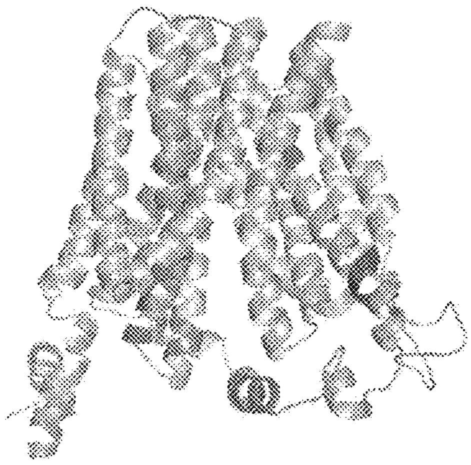

Figure 33
A
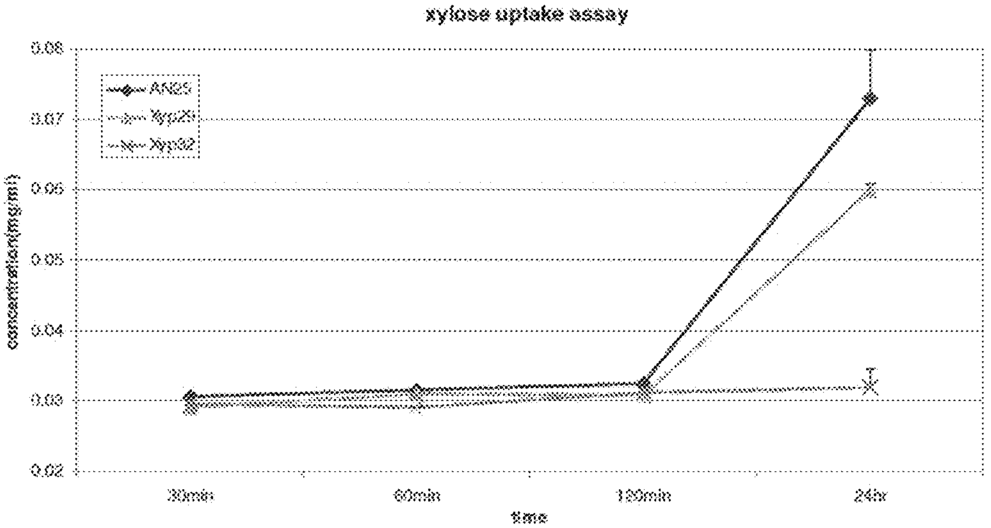
B
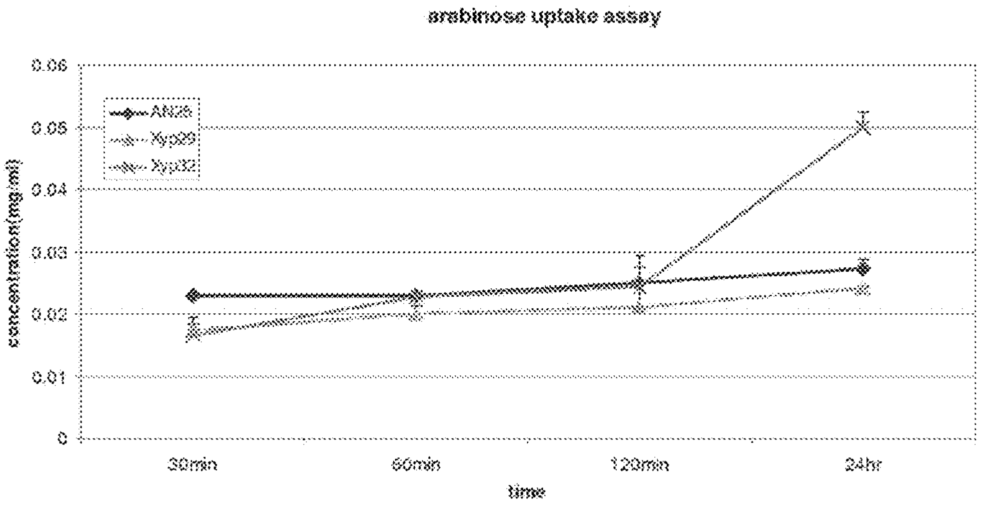

Figure 37 (cont.)
D
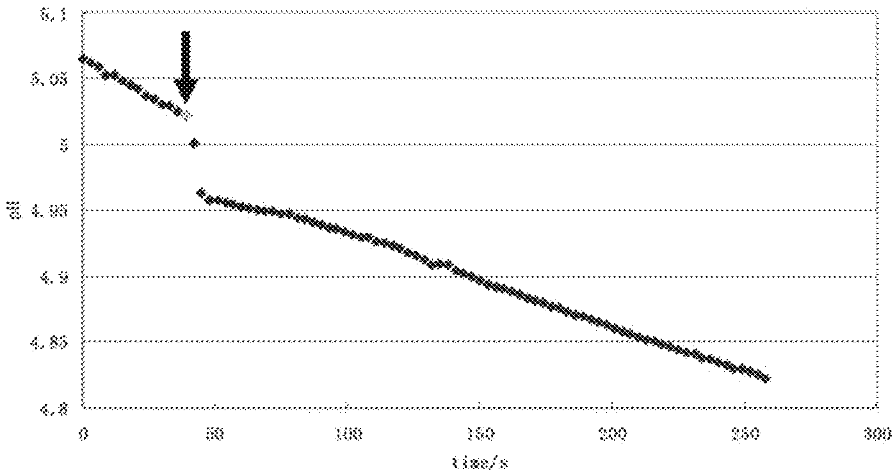
E
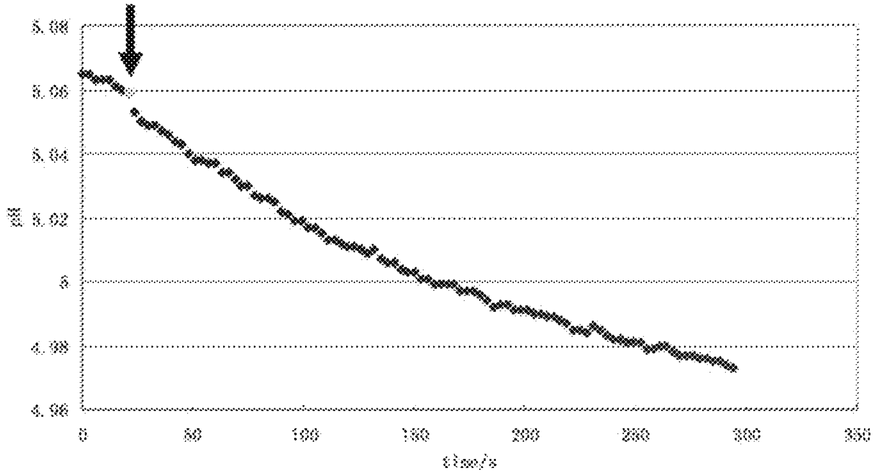
F
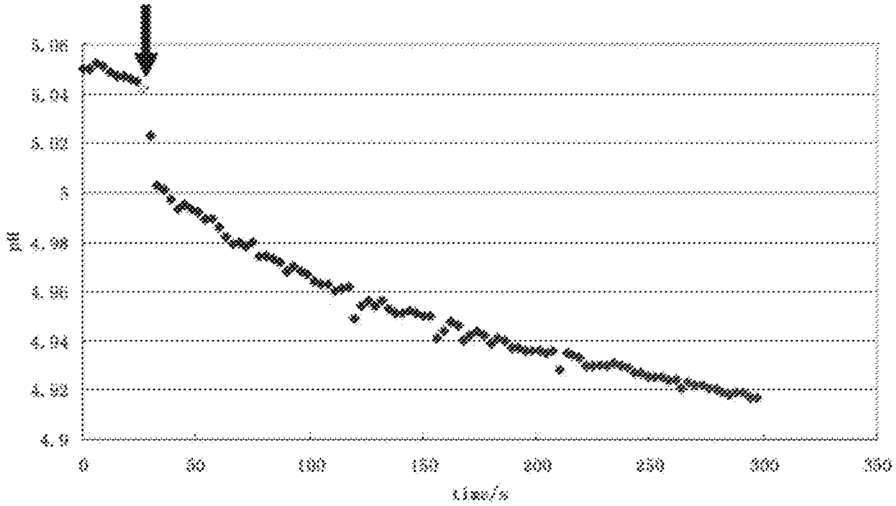

Figure 39 (cont.)
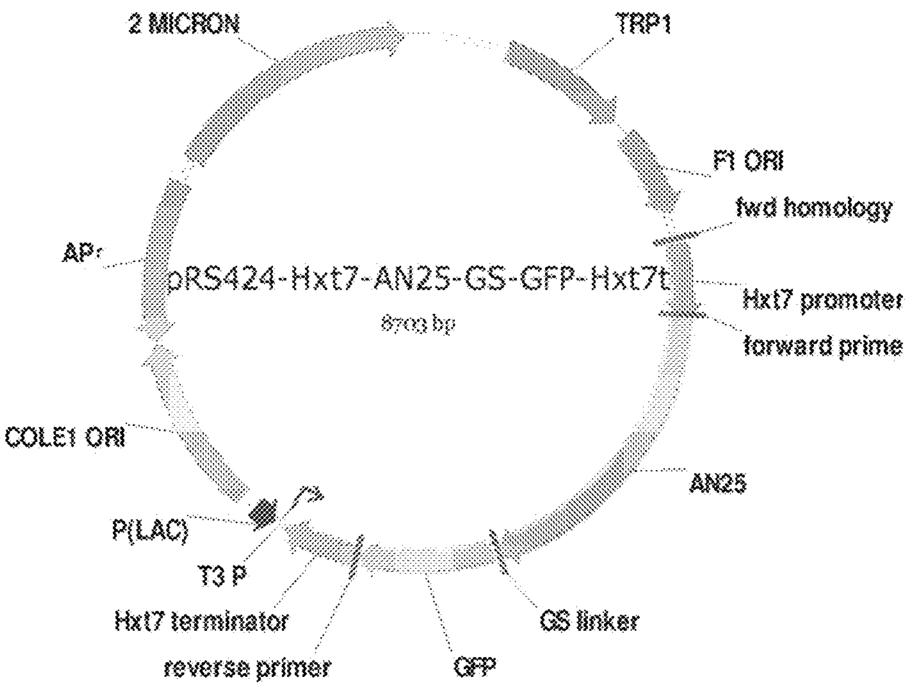
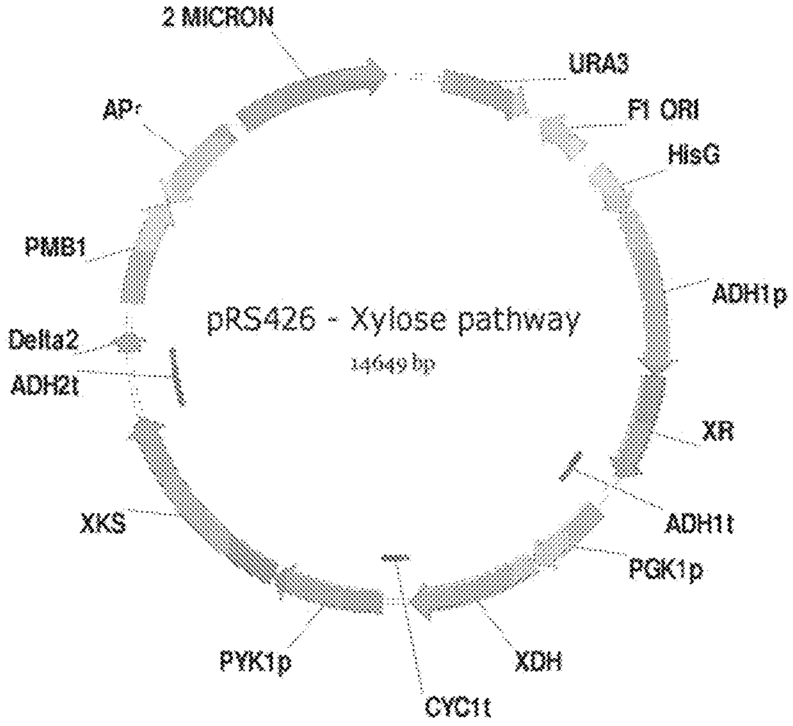

Figure 41

Consensus key

* - single, fully conserved residue

: - conservation of strong groups

. - conservation of weak groups

- no consensus

CLUSTAL W (1.81) multiple sequence alignment

(a)

```
NCU00821          ------------------------MAPPKFLGLSGRPLSLAVSTVATTGPLLFGYDQGVM
XP_002488227.1    ------------------------MAVPQFAGMSGAKLSWSISTIATLGPLLFGYDQGVM
XP_002382573.1    -------------------------MAPTFAGLSGRPLSLAVST----------------
XUT6              MEFSSYEKSAETASYTSQVSASGSAKTNSYLGLRGHKLNPAVSCPAGVGFLLFGYDQGVM
                                              : *: *: *.  ::*

NCU00821          SGIITAPAFNNFFTPTKD--NSTMQGLITAIYEIGCLIGAMFVLWTGDLLGRKRNIMVGA
XP_002488227.1    SGIISAKPFNTVFKATED--DSTMQGTVTAIYEIGCLFGAMFILWFGDWLGRKKSVMLGA
XP_002382573.1    ------------------------------------------------------------
XUT6              GSLLTLPSFENTFPAMKASNNATLQGAVIALYEIGCMSSSLATIYLGDRLGRLKIMFIGC

NCU00821          FIMALGVIIQVTCQAGSNPFAQLFVGRVVMGIGNGMNTSTIPTYQAECSKTSNRGLLICI
XP_002488227.1    AIMILGVVIQVTAYTGHVPLAQFIVGRVVTGVGNGINTSTIPTYQAECSRTTNRGLLICI
XP_002382573.1    ------------------------------------------------AECSKTSNRGLLICI
XUT6              VIVCIGAALQASAFT------IAHLTVARIITGLGTGFIISTVPVYQSECSPAKKRGQLIMM
                                                                  :*** :.:** ** :

NCU00821          EGGVIAFGTLIAYWIDYGASYGPDD-------LVWRFPIAFQLLFAIFICVPMFYLPESPRW
XP_002488227.1    EGGVIAFGTLIAYWIDFGASYGPDD-------LTWRFPIAFQIVFGLGIIAGMFFLPESPRW
XP_002382573.1    EGGVIAIGTAIAYWIDFGAHYGPDD-------LVWRFPIAFQIVFGVIIIVGMFFLPDSPRY
XUT6              EGSLIALGTAISYWIDFGFYFLRNDGLHSSASWRAPIALQCVFAVLLISTVFFTPESPRW
                  **.:**:*  *:****:*   :  :*        ** ***:* :*.: :    :*::*:***:

NCU00821          LLSHGRTEEADKVIAALRGYEIDGPETIQERNLIVDSLRA--------------------SG
XP_002488227.1    LFMREKYQEGEAVIAALLNEETNSHHVQLQKTLVLDSIRA--------------------SG
XP_002382573.1    LISKDRIQEGEYVLAALGGYEVHDQETQTQKNLVIDSIRAYVCCLEVLPNKSVTNLDNSS
XUT6              LLNKGRTEEAREVFSALYDLPADSEKISIQIEEIQAAIDL--------------------ER
                  *: : * :*.  *::** .    ..  .     :    :  ::                 .
```

Figure 41 (cont.)

```
NCU00821        GFCQKSTPPKALFTGGKTGFFERLLGSSSQFWQFGGCNAVIYYPPILPQSIGESHNM
XP_002488227.1  QAG-KSTPLSAFTGGKTGFFERSMIGASSQFWQIGGCNAVIYYPPILPENSIGQIHTM
XP_002382573.1  GAG-ATTRYRELTGGRSGFLERLLIGSSSQLTQQLSGCNAVIYYLPVLLKQSLRQSNDE
XUT6            QAG-EGFVLKELFTQLPAKSLGRVALSCWSQIMQQITGINITYVAGTIPLSYIGWSPFM
                    *       :*  *     *:  ::  **:;**:  *   *  :::.  :  :

NCU00821        SMLGGINMIVYSIPATVSMPAIERVGRERLFLIGTVGQMLSMV-IVPACLIPDD--PMK
XP_002488227.1  SMLGGVNMIVYSIPATNSMPLIERVGREKLFLNGTIGQCGSMI-LTPACLIPGT--PGP
XP_002382573.1  ALLGGINMIVYAIPATFSMPFLEKIGREKLFLGGSITQTTAMV-ITPACLIPDD--TQV
XUT6            SRLAALNGTEYFLVSLIAPYTVRSLGRERFLLFWGALAMALYRAGLTVTVKLAGEGNTHA
                : ::,  *  *  ,  : ::: :**;**  *::  *::         *   :::  ::  .

NCU00821        ARGAAYGLFTYIAFPLATWLPLPWLYPAEVNPIKTRGKANAVSTCSWMFNFLIVWVIPI
XP_002488227.1  ARGAAYGLFTYIASPLATWLPLPWLYPABISPIKTRAKANAISTCIMWLFNFLIVWVFPY
XP_002382573.1  SKGAVFGLPLYMAAPSAAWLPLPWLYPABLSPIKTRAKANASTCSWLFNFTVVMLTPV
XUT6            GVGAAVLLPAFNSFPDYSWLGGSWLLPPBLLSLKLRAPGAALSTASWAFNFMVVMLTPV
                . **  **  *  :  :  ***   *** *,*: ::  *:  * :*:,*** *** :***:*** :

NCU00821        MVDKIGRGTYLPPAVRNGCPLPLIYFFYPETANKSLRRIDIIPAKG-FVENMSYTAAKE
XP_002488227.1  MISNIKRGTYLPPAIVNACFLPVIYWFYPETARKSLRRIDIIPAKG-YTENISYVRAAKE
XP_002382573.1  MIAHICRGTYLPPAALNALFIPIIWLFYPETANKSLRRIDIIPAKG-YTENISYVKASKD
XUT6            GFQSIGSYTVLIPAAINLLWAPVIYPLYPEIRGESLRRIDIFPNQCPVWPFWKVYQIAKD
                .  *  **  *** :*  : *:;  *** *****,****    *  ,*   :::

NCU00821        LPIETAIEIESYANKYGLVDRDSNGEGGNHHDEEKTRDRPDQSDSDSPAIIVEIDVVDERG
XP_002488227.1  LPYLSDEDVERMAIQYGFGPAEVPSESG-----------EKASAHSEEFAETTGTPKQG
XP_002382573.1  LPKLNDLETEQKANEYGFGNSTEDPEK-----------ATAAEYSPSTSE--------
XUT6            LPIMMSEVLDHERNVTIKKSRIEHVN-----------IS-----------
                **  ; *  ::               :                   *

NCU00821        VESGPGDGINTKETR
XP_002488227.1  EEH--------VSKMV-
XP_002382573.1  --------------
XUT6            --------------
```

```
EEQ43601.1      MSKGDLEELDIQKLIVEKRLEQENGSGFATMKRNKRALGTCLFVSLGGILYGYNQGMFGQ
XUT1            -MEGGGIGNDITEIIAARRLQIAGKSGVAGLVANSRIFFIAVFASLGGLVYGYNQGMFGQ
                  :*.  :   **  ::*.  :**:  :.  **.* :    *.*::   . :*.*****:**********

EEQ43601.1      VSSMESFGETVGIGKIQDNFTLQGLLTSILELGAWVGVLMNGYVADALGRKASVVIGCIL
XUT1            ISGMYSFSKAIGVEKIQDNFTLQGLLTSILELGAWVGVLMNGYIADRLGRKKSVVVGVFF
                :*.*:**. ::.:*: ****************************:** ***: ***:*  ::

EEQ43601.1      FNIGVIIQAVARDADYGYILGGRFVIGLGVGVLSMVVPLYNSEISRAEIRGANTAIYQLS
XUT1            FFIGVIVQAVARGGKYDYILGGRFVVGIGVGILSMVVPLYNAEISPPEIRGSLVALQQLA
                * ****:*****. . :*.********:*:***:**********:***  .****: .*:  **:

EEQ43601.1      TIFGIMISYWITYGTNFIGGTGDNQSQASWLVPMCIQAAPAIILAVFIYSFPESPRWLIN
XUT1            ITFGIMISYWITYGTNYIGGTGSGQSKASWLVPICIQLVPALLLGVGIFFMPESPRWLMN
                ****************:*****.. **:******:***  .**: :*.* *:  :*******:*

EEQ43601.1      VGQEDKALEVLAWLRETEQENVGLQIEFLEMKAQKIFEQTLETEAYPHLQEGTKMSKFKI
XUT1            EDREDECLSVLSNLRSLSKEDTLVQMEFLEMKAQKLFERELSAKYFPHLQDGSAKSNFLI
                 . :**:.*.**: **.  . :*:.  :*:**********:**: *. :: :******:   *:* *

EEQ43601.1      NLNQYKSMVTHLFTIPKRVSVACLTMVFQQWTGAYNFILYYAPFIFASLGLSGNTTSLLAS
XUT1            GFNQYKSMIIRYFIPKRVAVACLIMTFQQWTG-VNFILYYAPFIFSSLGLSGNTTSLLAS
                . :******:** ******:**** *.******   *************:********* *****

EEQ43601.1      GVVGIVNFLCTIPAVNWVDKVGRKPLLISGALVMGLCHFVVAGILGGYSDNIGSHKAACW
XUT1            GVVGIVMFLATIPAVLWVDRLGRKPVLISGAIIMGICHFVVAAILGQFGGSFVNESGACW
                *********.*****:***::*****:*****::**:*******.***  :. .*:  .*. .***

EEQ43601.1      VAVVPIWIFAGAPGYSWGPCAWVIVAEVFPLGMRAKGVSLGSSFNWLMNFSVAISTPKFV
XUT1            VAVVFVWIFAIGPGYSWGPCAWVLVAEVFPLGLRAKGVSIGASSNWLNNFAVAQSTPDFV
                ****:****  .***********:*********:*******:*:* *** **:**:***.**

EEQ43601.1      ANAKYGAYIFLGLMCYIGSMYVYFMVPETKNKTLDELDEVFGDPIGTSKKESELSKKILK
XUT1            AKAKFGAYIFLGLMCIFGAAYVQFFCPETKGRTLEEIDELFGDTSGTSKMEKETHEQKLK
                *:**:**********:*:  ** *:  ****.:**:*:**:***  :**** *.*::*:  **
```

Figure 41 (cont.)

```
EEQ43601.1    QVGLVDLLVGSDKELDSFKSKPEVEYKEREAISE
XUT1          EVGLLQLLG-EENASLSENSKADVYHVEK-----
              :***::**  .::  :* .**.:* : **
```

```
NCU00821          ------------------------MAPPKFLGLSGKPLSLAVSTVATTGFLLFGYDQGVM
XP_002488227.1    ------------------------MAVPQFAGMSGKKLSWSISTIATLGFLLFGYDQGVM
XP_002382573.1    ------------------------MAPTFAGLSGKPLSLAVST-----------------
XUT6              MEFSSVEKSAETASYTSQVSASGSAKTNSYLGLRGHKLNFAVSCFAGVGFLLFGYDQGVM
EEQ43601.1        --MSKGDLEELDIQKLIVEKRLEQSNGSGFATWKRNKRALGTCLFVSLGGILYGYNQGMF
XUT1              ----MHGGGDGNDITEIIAARRLQIAGKSGVAGLVANSRSFFIAVFASLGGLVYGYNQGMF
                                                   :  .       .

NCU00821          SGIITTAPAFNNFFTPTKD--NSTMQGLITAIYEIGCLIGAMFVLWTGDLLGRRRNIMVGA
XP_002488227.1    SGIISAKPFNTVFKATED--DSTMQGTVTAIYEIGCLFGAMFILWPGDWLGRRKSVMLGA
XP_002382573.1    ------------------------------------------------------------
XUT6              GSLLTLPSFENTFPAMKASNNATLQGAVIALYEIGCMSSSLATIYLGDRLGRLKIMFIGC
EEQ43601.1        GQVSSMIESFGETVGIGKIQDNPTLQGLLTSILELGAWVGVLMNGYVADALGRRASVVIGC
XUT1              GQISGMYSPSKAIGVEKIQDNPTLQGLLTSILELGAWVGVLMNGYIADRLGRKKSVVVGV

NCU00821          FIMALGVIIQVTCQAGSNPPAQLFVGRVVMGIGNGMNTSTIPTYQAECSKTSNRGLLICI
XP_002488227.1    AIMILGVVIQVTAYTGHVPLAQFIVGRVVTGVGNGINTSTIPTYQAECSKITNRGLLICI
XP_002382573.1    ----------------------------------------------AECSKTSNRGLLICI
XUT6              VIVCIGAALQASAFT------IAHLTVARIITGLGTGFITSTVPVYQSECSPAKKRGQLIMM
EEQ43601.1        ILFNIGVIIQAVARDAD--YGYILGGRFVIGLGVGVLSMVVPLYNSEISRAEIRGANTAI
XUT1              FFFFIGVIVQAVARGGN--YDYILGGRFVVGIGVGILSMVVPLYNAEISPPEIRGSLVAL
                                                             :* * .    **      :

NCU00821          EGGVIAFGTLIAYWIDYGASYGPDD-------LVWRFPIAFQLLFAIFICVPMFYLPESPR
XP_002488227.1    EGGVIAFGTLIAYWIDFGASYGPDD---------LTWRFPIAFQIVFGLGIIAGMFFLPESPR
XP_002382573.1    EGGVIAIGTAIAYWIDFGAHYGPDD-------LVWRFPIAFQIVPGVIIIVGMFFLPESPR
XUT6              EGSLIALGIAISYWIDFGPYFLRNDGL--HSSASWRAPIALQCVFAVLLISTVFFFPESPR
EEQ43601.1        YQLSITFGIMISYWITYGTNFIGGTGDNQSQASWLVPWCIQAAPAIILAVFIYSFPESPR
XUT1              QQLAITFGIMISYWITYGTNYIGGTGSGQSKASWLVPICIQLVPALLLGVGIFFMPESPR
                      *::*  *:*** :*  :  .          *  *:.:*   .: :    :: :*:***

NCU00821          WLLSHGRTQEADKVIAALRGYEIDGPETIQERNLIVDSLRA--------------------------S
XP_002488227.1    WLFMREKYQEGEAVIAALLNEETNSHHVQLQKTLVLDSIRA-------------------------S
XP_002382573.1    YLISKDPIQEGEYVLAALGGYEVHDQETQTQKNLVIDSIRAYVCCLEVLPNKSVTNLDNS
XUT6              WLLNKGRTEEAREVFSALYDLPADSEKISIQIEEIQAAIDL----------------------E
EEQ43601.1        WLINVGQEEKALEVLAWLRETEQENVGLQIEFLEMKAQKIFEQTLETEAYP----------H
XUT1              WLMNEDREDECLSVISNLRSLSKEDTLVQMEFLEMKAQKLFERELSAKYFP-----------H
                  :*:    : ::    *:: *       ..         :    :
```

Figure 41 (cont.)

```
NCU00821          GGFGQKSTPFKALFTGGK------TQIFRRLLLGSSSQFMQVGG-CNAVIYYFPILFQDS
XP_002488227.1    GQMG-KSTPLSAVFTGGK------TQIFRRMLGASSQFMQIGG-CNAVIYYFPILFENS
XP_002382573.1    SGAG-ATTRYRDLLTGGR------SQILRRMLIGSSSQIFQGLSG-CNAVIYYLPVLLKQS
XUT6              RQAG-EGFVLKELFTQGP------ARNLGRVALSCWSQIMQQITG-INIITYYAGTIFESY
EEQ43601.1        LQDGTKMSKFKINLNQYKSMVTHLPTFKRYSVACLTMVFQQWTGAYNFILYYAPFIFASL
XUT1              LQDGSAKSNFLIGFNQYKSMITHYPTFKRYAVACLIMTFQQWTG-VNFILYYAPFIFSSL
                     *        :.             ::*: :,.     :**  *  * : **   :: .

NCU00821          IGESHNMSMLLGGINMIVYSIFATVSWFAILERVGRRRLFLIGTVGQMLSMV-IVFACLIP
XP_002488227.1    IGQTHTMSMLLGGVNMIVYSIFATMSWFLIERVGRRKLFLWGTIGQCGSMI-LTFACLIP
XP_002382573.1    LHQSNDEALLIGGINMIVYAIFATPSWFFIERIGRRKLFLGGSIIQTIAMV-ITFACLIP
XUT6              IGMSPFMSRILAALNGTEYFLVSLIAFYTYERLGRRPLLFWGAIAMALVMAGLTVTVKLA
EEQ43601.1        GLSGNTTSLLASGVVGIVMFLCTIPAVMWYDKVGRRPLLISGALVMGLCHFVVAGILGGY
XUT1              GLSGNTISLLASGVVGIVMFLATIPAVLWYDRLGRRPYLISGAIIMGICHFVVAAILGQF
                          : : ..:       : :  :   :::**: ::: *::          :.

NCU00821          DD--PMKARG----AAVGLFTYIAFFGATWLPLPWLYPAEVNPIRTRGKANAVSTCSNWMF
XP_002488227.1    GT--PGPAKG----AAVGLFTYIASFGATWLPLPWLYPAEISPIKTRAKANALSTCTNWLF
XP_002382573.1    DD--TQVSKG----AVFGLFLYMAAFGAAWLPLPWLYPAELSPIKTRAKANAVSTCSNWLF
XUT6              GEGNTHAGVG----AAVLLFAFNSFFGVSWLGGSWLLPFELLSLKLRAPGAALSTASNWAF
EEQ43601.1        SDNIGSHKAAGWVAVYFIWIFAGAFGYSWGPCAWIVAAEVFPLGMRAKGVSLGSSFNWLM
XUT1              GGNFVNHSGAGWVAVVFVWIFAIGFGYSWGPCAWVLVAEVFPLGLRAKGVSIGASSNWLN
                  .          .    *.. :: :    ** :*    .*:  .*: .:  *. , ::.:. **

NCU00821          NFLIVMVTPIMVDKIGWGTYLFFAVMNGCFLPIIYFFYPETANRSLEEIDIIFAKG-PVE
XP_002488227.1    NFLIVMVTPVMISNIKWGTYLFFAIVNACFLPVIYFWYPETARRSLEEIDIIFAKG-YTE
XP_002382573.1    NFTVVMITPVMIAHIGWGTYLFFAALNALFIPIIWLFYPETANRSLEEIDIIFAKG-YTE
XUT6              NFMVVMITPVGFQSIGSYTYLIFAAINLLMAPVIYFLYPETKGRSLEEMDIIFNQCPVWE
EEQ43601.1        NFSVAISTPKFVANAKYGAYIFLGLMCVIGSMYVYFMVPETKNKTLDELDEVFG--------
XUT1              NFAVAMSTPDFVAKAKFGAYIFLGLMCTFGAAYVQFFCPETKGRTLEEIDELFG--------
                  ** :.: **  .        :*:::. :          : :  ***  ::*:*:* :*

NCU00821          NMSYVTAAEELPHLTAEEIESYANKYGLVDRDSNGEGGNRHDEEKTRDRPDQSDSDSPAH
XP_002488227.1    NISYVRAAEELPYLSDEDYERMAIQYGFGPAEVPSDSG--------------EKASAHSEEF
XP_002382573.1    NISYVKASKDLPKLNDEEIEQKANEYGFGNSTEDPEK---------------ATAAEYSPST
XUT6              PWEVVQIAKDLPIMHSEVLDHEKNVIIKKSRIEHVEN------------------------TS-----
EEQ43601.1        --DFTGTSKKESELREKILKQVGLVDLLVGSDKELDSF------------------RSKPE
XUT1              --DTSGTSSMEKEIHEQKLKEVGLLQLLG-EENASESE----------------------NSKAD
                    .      ::     :  :  :.                  :                  *
```

Figure 41 (cont.)

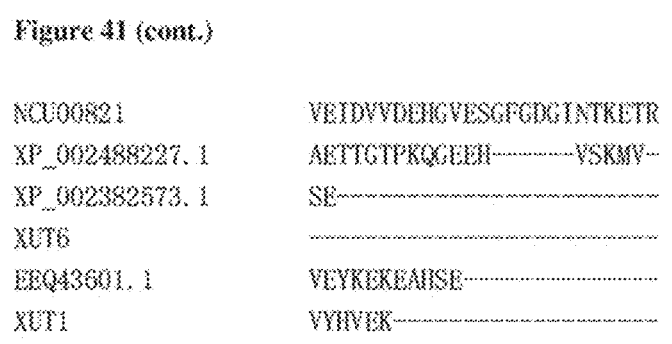

```
NCU00821          VEIDVVDEHGVESGFGDGINTKETR
XP_002488227.1    AETTGTPKQGEEH------VSKMV-
XP_002382573.1    SE-----------------------
XUT6              -------------------------
EEQ43601.1        VEYKEKEAHSE--------------
XUT1              VYHVEK-------------------
```

Strain backgrounds vs. xylose fermentation

- Construction of engineered strains using an identical construct and different laboratory strains Identical expression cassette under different strain backgrounds Figure 44 Three different laboratorial strains Figure 45 (a) (b) (c)

(a)

(b)

Hypothesis and experimental design

| WT | Parental xylose-fermenting strain | Integration vector | Overexpression levels of *XYL2* |
|---|---|---|---|
| L2612 | YSX3 (TDHp-*XYL1*, TDHp-*XYL2*, and native-XYL3) | | + |
| | | p404 TDHp-*XYL2* | ++ |
| | | p404 PGKp-*XYL2* | +++ |

**Additional *XYL2* integration improves xylose fermenting ability**

Negligible amounts of xylitol were accumulated after additional overexpression of *XYL2-XYL3*

FOA selection + *XYL2* ↑ + *XYL2* ↑ and *XYL*

| XDH activity | ++ | ++ | ++++ | ++++ / X ↑ |
|---|---|---|---|---|

Construction of engineered strains exhibiting different XR activities

Strong *XYL1* with *XYL2/XYL3* caused xylitol accumulation

Two equivalent engineered strains expressing *XYL1* and *GRE3* were constructed

Xylose fermentation with high OD (OD=10) inoculations

80 g/L of xylose fermentation with high OD (OD=15) inoculations

Figure 56

```
Score = 299 bits (765), Expect = 3e-79, Method: Compositional matrix
adjust.
Identities = 169/365 (46%), Positives = 222/365 (60%), Gaps = 22/365
(6%)

psXDH ANFSLVLNKIDDISFETYDAPEISEPTDVLVQVKKTGICGSDIHFYAHGRIGNFVLTKPM 62
      +N S VLNK  D+ F+     P+I+ P DVLV V  TGICGSD+H++ HG IG+FV+  PM
ncXDH SNLSFVLNKPLDVCFQDKPVPKINSPHDVLVAVNYTGICGSDVHYWLHGAIGHFVVKDPM 66

psXDH VLGHESAGTVVQVGKGVISLKVGDNVAIEPGIPSRFSDEYKSGHYNLCPHMAFAATPNSK 122
      VLGHESAGT+V VG  V +L VGD VA+EPG P R        SGHYNLCP M FAATP
ncXDH VLGHESAGTIVAVGDAVKTLSVGDRVALEPGYPCRRCVHCLSGHYNLCPEMRFAATPPYD 126

psXDH EGEFNPPGTLCKYFKSPEDFLVKLPDHVSLELGALVEPLSVGVHASKLGSVAFGDYVAVF 182
             GTL  ++ +P DF  KLP+ VSL+ GAL+EPL+V VH +K    +  G  V V
ncXDH -------GTLTGFWTAPADFCYKLPETVSLQEGALIEPLAVAVHITKQAKIQPGQIVVVM 179

psXDH GAGPVGLLAAAVAKTFGAKGVIVVDIFDNKLKMAKDIGAATHTFNSKTGGSEE-----LI 237
      GAGPVGLL AAVAK +GA  V+ VDI  +KL+ AK   AATHT+ S+     EE     +
ncXDH GAGPVGLLCAAVAKAYGASKVVSVDIVPSKLEEAKSF-AATHTYLSQRVSPEENARNIIA 236

psXDH KAFGGNVPNVVLECTGAEPCIKLGVDAIAPGGRFVQVGNAAGPVSFPITVFAMKELTLFG 297
       A  G     +V++ +GAEP I+ +    +  GG +VQ G      ++FPI     +KE+T  G
ncXDH AADLGEGADAVIDASGAEPSIQAALHVVRQGGHYVQGGMGKDNITFPIMALCIKEVTASG 298

psXDH SFRYGFNDYKTAVGIFDTNYQNGKENAPIDFEQLITHRYKFKDAIEAYDLVRAGKGAVKC 357
      SFRYG  DY+ A+ +            E    +D ++L+      FK+A EA+  V+ G+  +K
ncXDH SFRYGEGDYRLAIQLV--------EQGKVDVKKLVNGVVPFKNAEEAFKKVKEGE-VIKI 349

psXDH LIDGP 362
      LI GP
ncXDH LIAGP 354
```

| | Plasmid (L2612) | | Integration (D452-2) | |
|---|---|---|---|---|
| | OD 48 | OD 96 | OD 51 | OD 96 |
| Ethanol (g/L) | 4.92 | 5.15 | 7.67 | 7.88 |
| Yield (EtOH) | 0.35 | 0.34 | 0.40 | 0.40 |
| Productivity (g/L-hr) | 0.04 | 0.04 | 0.05 | 0.06 |
| Xylitol (g/L) | 3.62 | 3.61 | 2.80 | 2.74 |
| Yield (Xt) | 0.26 | 0.24 | 0.15 | 0.14 |

| | DBtXI | DBtXI-X2 | DBtXI-X3 | DBtXI-X2X3 |
|---|---|---|---|---|
| $Y_{EtOH}$ | 0.34 | 0.15 | 0.41 | 0.37 |
| $Y_{XOH}$ | 0.18 | 0.50 | 0.14 | 0.12 |

Cell growth on xylulose

| | OD ($A_{600}$) | Ethanol (g/L) | $Y_{EtOH}$ (g/g) | $P_{EtOH}$ (g/L-hr) |
|---|---|---|---|---|
| galM-Ec | 20.4 | 30.3 | 0.40 | 0.88 |
| GAL10-Sc | 19.5 | 34.9 | 0.45 | 1.01 |
| GAL10-Ps | 20.5 | 31.7 | 0.41 | 0.92 |
| YHR210C-Sc | 20.0 | 34.7 | 0.45 | 1.01 |
| YNR071C-Sc | 20.0 | 34.6 | 0.45 | 1.00 |
| Control-423 | 21.8 | 32.0 | 0.42 | 0.93 |

| | |
|---|---|
| OD | 23.0 |
| Ethanol (g/L) | 40.1 |
| $Y_{EtOH}$(g/g) | 0.34 |
| $P_{EtOH}$(g/L-h) | 0.83 |

Fig. 76

NCU00010.2
NCU00026.2
NCU00060.2
NCU00073.2
NCU00102.2
NCU00111.2
NCU00122.2
NCU00124.2
NCU00130.2
NCU00173.2
NCU00292.2
NCU00299.2
NCU00304.2
NCU00305.2
NCU00378.2
NCU00379.2
NCU00591.2
NCU00606.2
NCU00611.2
NCU00642.2
NCU00643.2
NCU00663.2
NCU00673.2
NCU00695.2
NCU00709.2
NCU00809.2
NCU00810.2
NCU00821.2
NCU00864.2
NCU00870.2
NCU00884.2
NCU00888.2b
NCU00890.2
NCU00891.2
NCU00892.2
NCU00937.2
NCU00972.1
NCU00988.2
NCU00992.2
NCU00999.1
NCU01045.2
NCU01068.2
NCU01107.2
NCU01132.2
NCU01140.2
NCU01145.2
NCU01181.2
NCU01230.2
NCU01231.2
NCU01233.2
NCU01240.2
NCU01258.2
NCU01275.2
NCU01320.2
NCU01328.2
NCU01417.2
NCU01419.2
NCU01420.2
NCU01424.2
NCU01430.2
NCU01436.2
NCU01555.2
NCU01701.2
NCU01704.2
NCU01740.2
NCU01798.2
NCU01815.2
NCU01847.1
NCU01866.2
NCU01900.2
NCU01904.2
NCU01905.2
NCU01906.2
NCU01940.2
NCU01970.2
NCU01983.2
NCU02018.2
NCU02027.2
NCU02097.2
NCU02124.2
NCU02136.2
NCU02179.2
NCU02188.2
NCU02238.2
NCU02307.2
NCU02318.2
NCU02342.2
NCU02343.2
NCU02361.2
NCU02397.2
NCU02453.1
NCU02455.2
NCU02512.2
NCU02582.2
NCU02583.2
NCU02598.2
NCU02605.2
NCU02637.2
NCU02653.2
NCU02654.2
NCU02701.2
NCU02730.2
NCU02887.2
NCU03013.2
NCU03043.2
NCU03086.2
NCU03198.2
NCU03216.2
NCU03222.2
NCU03253.2
NCU03263.2
NCU03281.2
NCU03322.2
NCU03323.2
NCU03350.2
NCU03358.2
NCU03388.2
NCU03398.2
NCU03415.2
NCU03523.2
NCU03606.2
NCU03637.2
NCU03639.2
NCU03731.2
NCU03749.2
NCU03753.2
NCU03779.2
NCU03803.2
NCU03813.2
NCU03893.2
NCU03949.2
NCU03965.2
NCU04109.2
NCU04133.2
NCU04264.2
NCU04265.2
NCU04266.2
NCU04272.2
NCU04287.2
NCU04295.2
NCU04298.2
NCU04349.2a
NCU04369.2
NCU04371.2
NCU04373.2
NCU04388.2
NCU04394.2
NCU04400.2
NCU04401.2
NCU04415.2
NCU04417.2
NCU04460.2
NCU04475.2
NCU04491.2b
NCU04510.2
NCU04521.2
NCU04605.2
NCU04623.2
NCU04674.2
NCU04675.2
NCU04676.2
NCU04791.2
NCU04801.2
NCU04815.2
NCU04905.2
NCU04906.2
NCU04908.2a
NCU04908.2b
NCU04909.2
NCU04910.2
NCU04918.2
NCU04930.2
NCU04963.2
NCU05134.2
NCU05137.2
NCU05143.2
NCU05148.2
NCU05159.2
NCU05164.2
NCU05170.2
NCU05318.2
NCU05395.2
NCU05493.2
NCU05498.2
NCU05627.2
NCU05751.2
NCU05795.2
NCU05770.2
NCU05832.2
NCU05837.2
NCU05850.2
NCU05853.2
NCU05897.2
NCU05924.2
NCU05965.2
NCU05977.2
NCU05994.2
NCU06005.2
NCU06043.2
NCU06123.2
NCU06125.2
NCU06138.2
NCU06143.2
NCU06255.2
NCU06261.2
NCU06265.2
NCU06277.2
NCU06305.2
NCU06358.2
NCU06364.2
NCU06380.2
NCU06490.2
NCU06597.2
NCU06603.2
NCU06650.2
NCU06653.2
NCU06656.2
NCU06681.2
NCU06707.2
NCU06752.2
NCU06800.2
NCU06977.2
NCU06999.2
NCU07027.2
NCU07063.2
NCU07064.2b
NCU07133.2
NCU07143.2
NCU07158.2
NCU07225.2
NCU07267.2
NCU07273.2
NCU07286.2
NCU07287.2b
NCU07310.2
NCU07311.2
NCU07313.2b
NCU07392.2
NCU07453.2
NCU07624.2
NCU07705.2
NCU07706.2
NCU07723.2
NCU07771.2
NCU07798.2
NCU07883.2
NCU07890.2a
NCU07941.2
NCU07987.2
NCU08017.2
NCU08076.2
NCU08092.2
NCU08114.2
NCU08130.2
NCU08131.2
NCU08189.2
NCU08190.2
NCU08224.2
NCU08273.2
NCU08282.2
NCU08330.2
NCU08331.2
NCU08333.2
NCU08351.2
NCU08356.2
NCU08384.2
NCU08428.2
NCU08457.2
NCU08516.2
NCU08541.2
NCU08549.2
NCU08554.2
NCU08577.2
NCU08657.2
NCU08750.2
NCU08752.2
NCU08755.2
NCU08771.2
NCU08779.2
NCU08943.2
NCU08949.2
NCU08977.2
NCU09010.2
NCU09013.2
NCU09027.2
NCU09034.2
NCU09041.2
NCU09043.2
NCU09051.2b
NCU09115.2
NCU09133.2
NCU09138.2
NCU09169.2
NCU09175.2
NCU09209.2
NCU09210.2
NCU09266.2
NCU09267.2
NCU09285.2
NCU09316.2
NCU09427.2
NCU09491.2
NCU09532.2
NCU09533.2
NCU09552.2
NCU09682.2
NCU09705.2
NCU09763.2b
NCU09783.2
NCU09821.2
NCU09886.2
NCU09923.2
NCU09924.2
NCU10020.2
NCU10021.2
NCU10040.2
NCU10045.2
NCU10107.2a
NCU10398.2a
NCU10398.2b
NCU10547.2a
NCU10656.2c
NCU10733.2a
NCU10986.2a
NCU10986.2b
NCU10987.2a
xnc066_080
NCU00132.2
NCU00157.2
NCU00442.2
NCU00987.2
NCU01517.2
NCU02042.2
NCU02138.2
NCU03156.2
NCU03284.2
NCU03518.2b
NCU03636.2
NCU04053.2
NCU04197.2
NCU04525.2
NCU04626.2
NCU05303.2
NCU06081.1
NCU06961.2
NCU07190.2
NCU07215.2
NCU07325.2
NCU09161.2
NCU09689.2
NCU09698.2
NCU09777.2
NCU09792.2
NCU09883.2
NCU09906.2

A

| | Bradford | CMC-activity |
|---|---|---|
| Wt-1 | 0.57 | 0.50 |
| Wt-2 | 0.58 | 0.53 |
| Ko-1 | 0.89 | 0.76 |
| Ko-2 | 0.89 | 0.65 |
| GFP | 0.56 | 0.54 |
| GFP | 0.60 | 0.58 |

B

M, wt,wt, ko,ko, gfp1,gfp1

METHODS AND COMPOSITIONS FOR IMPROVING SUGAR TRANSPORT, MIXED SUGAR FERMENTATION, AND PRODUCTION OF BIOFUELS

CROSS-REFERENCE TO RELATED APPLICATIONS

This application is a divisional of U.S. application Ser. No. 12/843,844, filed Jul. 26, 2010, which claims the benefit of U.S. Provisional Application No. 61/285,526, filed Dec. 10, 2009, and U.S. Provisional Application No. 61/271,833, filed Jul. 24, 2009, all of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 677792000110SeqList.txt, date recorded: Mar. 13, 2013, size: 104 KB).

FIELD OF THE INVENTION

The present disclosure relates to methods and compositions for increasing the transport of sugars into cells, for increasing growth of cells, for increasing synthesis of hydrocarbons and hydrocarbon derivatives, and for co-fermenting cellulose-derived and hemicellulose-derived sugars.

BACKGROUND OF THE INVENTION

Biofuels are under intensive investigation due to the increasing concerns about energy security, sustainability, and global climate change (Lynd et al., 1991). Bioconversion of plant-derived lignocellulosic materials into biofuels has been regarded as an attractive alternative to chemical production of fossil fuels (Lynd et al. 2008; Hahn-Hagerdal et al. 2006). Lignocellulosic biomass is composed of cellulose, hemicellulose, and lignin.

The engineering of microorganisms to perform the conversion of lignocellulosic biomass to ethanol efficiently remains a major goal of the biofuels field. Much research has been focused on genetically manipulating microorganisms that naturally ferment simple sugars to alcohol to express cellulases and other enzymes that would allow them to degrade lignocellulosic biomass polymers and generate ethanol within one cell. However, an area that has been less well studied is that of sugar transporters. An understanding of the regulation of sugar transport and the genetic engineering of microorganisms to have improved sugar-uptake ability will greatly improve efficiency (Stephanopoulos 2007). Furthermore, other types of proteins involved in the regulation of cellulase expression and activity remain to be fully explored.

*Saccharomyces cerevisiae*, also known as baker's yeast, has been used for bioconversion of hexose sugars into ethanol for thousands of years. It is also the most widely used microorganism for large scale industrial fermentation of D-glucose into ethanol. *S. cerevisiae* is a very suitable candidate for bioconversion of lignocellulosic biomass into biofuels (van Maris et al., 2006). It has a well-studied genetic and physiological background, ample genetic tools, and high tolerance to high ethanol concentration and inhibitors presented in lignocellulosic hydrolysates (Jeffries 2006). The low fermentation pH of *S. cerevisiae* can also prevent bacterial contamination during fermentation.

Unfortunately, wild type *S. cerevisiae* cannot utilize pentose sugars (Hector et al., 2008). To overcome this limitation, pentose utilization pathways from pentose-assimilating organisms have been introduced into *S. cerevisiae*, allowing fermentation of D-xylose and L-arabinose (Hahn-Hagerdal et al., 2007; Brat et al., 2009; Wisselink et al., 2007, 2009; Wiedemann and Boles 2008; Karhumma et al., 2006). However, efficient conversion of pentose sugars into biofuels is limited by multiple issues including cellular redox imbalance, low influx of pentose phosphate pathway, and lack of efficient pentose transport into the cell (Hector et al., 2008).

In addition, both natural and engineered microorganisms show reduced ethanol tolerance during xylose fermentation as compared to glucose fermentation (Jeffries and Jin 2000). Combined with the lower fermentation rate, the reduced ethanol tolerance during xylose fermentation poses a significant problem in fermentation of sugar mixtures containing the high concentrations of glucose (~70-100 g/L) and xylose (~40-60 g/L) present in cellulosic hydrolysates. Since microorganisms utilize glucose preferentially, at the time of glucose depletion (when cells begin to use xylose), the ethanol concentration is already high enough (~35-45 g/L) to further reduce the xylose fermentation rate. As a result, sequential utilization of xylose after glucose depletion because of "glucose repression" is a significant challenge to be overcome in order to successfully utilize mixed sugars in cellulosic hydrolysates.

Thus, a need exists for the identification of additional genes that are critical for the degradation of lignocellulose and for their use in the engineering of microorganisms for improved growth on lignocellulose and uptake of compounds resulting from lignocellulose degradation. A further need exists for improved methods of efficient conversion of pentose sugars into biofuels and of mixed sugar fermentation for the production of biofuels.

BRIEF SUMMARY OF THE INVENTION

In order to meet these needs, the invention described herein provides methods of increasing transport of cellodextrin into a cell, methods of increasing growth of a cell on a medium containing cellodextrin, methods of co-fermenting cellulose-derived and hemicellulose-derived sugars, and methods of making hydrocarbons or hydrocarbon derivatives by providing a host cell containing a recombinant polynucleotide encoding a polypeptide where the polypeptide transports cellodextrin into the cell. Further described are host cells containing a recombinant polynucleotide encoding a polypeptide where the polypeptide transports cellodextrin into the cell. Further described herein are host cells containing a recombinant polynucleotide encoding a polypeptide where the polypeptide transports a pentose into the cell, methods of increasing transport of a pentose into a cell, methods of increasing growth of a cell on a medium containing pentose sugars, and methods of making hydrocarbons or hydrocarbon derivatives by providing a host cell containing a recombinant polynucleotide encoding a polypeptide where the polypeptide transports a pentose into the cell.

As used herein, cellodextrin refers to glucose polymers of varying length and includes, without limitation, cellobiose (2 glucose monomers), cellotriose (3 glucose monomers), cellotetraose (4 glucose monomers), cellopentaose (5 glucose monomers), and cellohexaose (6 glucose monomers).

Thus one aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 1 contains SEQ ID NO: 1, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 2 contains SEQ ID NO: 2, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and a loop connecting transmembrane α-helix 2 and transmembrane α-helix 3 contains SEQ ID NO: 3, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 5 contains SEQ ID NO: 4, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 6 contains SEQ ID NO: 5, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and sequence between transmembrane α-helix 6 and transmembrane α-helix 7 contains SEQ ID NO: 6, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 7 contains SEQ ID NO: 7, and culturing the cell in a medium such that the recombinant polynucleotide is expressed, where expression of the recombinant polynucleotide results in increased transport of cellodextrin into the cell compared with a cell that does not contain the recombinant polynucleotide.

Another aspect includes methods of increasing transport of cellodextrin into a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 10 and transmembrane α-helix 11 and the sequence between them contains SEQ ID NO: 8, and culturing the cell in a medium such that the recombinant polynucleotide is expressed, where expression of the recombinant polynucleotide results in increased transport of cellodextrin into the cell compared with a cell that does not contain the recombinant polynucleotide.

In certain embodiments that may be combined with any of the preceding aspects, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments that may be combined with any of the preceding embodiments, the host cell contains a second recombinant polynucleotide encoding at least a catalytic domain of a β-glucosidase. In certain embodiments that may be combined with the preceding embodiments having a host cell containing a second recombinant polynucleotide encoding at least a catalytic domain of a β-glucosidase, the β-glucosidase is from *Neurospora crassa*. In certain embodiments that may be combined with the preceding embodiments having a host cell containing a second recombinant polynucleotide encoding at least a catalytic domain of a β-glucosidase from *Neurospora crassa*, the β-glucosidase is encoded by NCU00130. In certain embodiments that may be combined with any of the preceding embodiments, the host cell further contains one or more recombinant polynucleotides where the one or more polynucleotides encode one or more enzymes involved in pentose utilization. In certain embodiments that may be combined with the preceding embodiments having a host cell further containing one or more recombinant polynucleotides where the one or more polynucleotides encode one or more enzymes involved in pentose utilization, the one or more enzymes are selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase. In certain embodiments that may be combined with any of the preceding embodiments, the host cell further contains a third recombinant polynucleotide where the third recombinant polynucleotide encodes a pentose transporter. In certain embodiments that may be combined with the preceding embodiments having the host cell further containing a third recombinant polynucleotide where the third recombinant polynucleotide encodes a pentose transporter, the pentose transporter is selected from the group consisting of NCU00821, NCU04963, NCU06138, STL12/XUT6, SUT2, SUT3, XUT1, and XUT3.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 1 contains SEQ ID NO: 1, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 2 contains SEQ ID NO: 2, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and a loop connecting transmembrane α-helix 2 and transmembrane α-helix 3 contains SEQ ID NO: 3, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 5 contains SEQ ID NO: 4, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 6 contains SEQ ID NO: 5, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and sequence between transmembrane α-helix 6 and transmembrane α-helix 7 contains SEQ ID NO: 6, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 7 contains SEQ ID NO: 7, and the polypeptide is a cellodextrin transporter, and culturing the host cell in a medium containing cellodextrin, where the host cell grows at a faster rate in the medium than a cell that does not contain the recombinant polynucleotide.

Another aspect includes methods of increasing growth of a cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 10 and transmembrane α-helix 11 and the sequence between them contain SEQ ID NO: 8, and the polypeptide is a cellodextrin transporter, and culturing the host cell in a medium containing cellodextrin, where the host cell grows at a faster rate in the medium than a cell that does not contain the recombinant polynucleotide.

In certain embodiments that may be combined with any of the preceding aspects of increasing growth of cells, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments that may be combined with any of the preceding embodiments, the host cell contains an endogenous or a second recombinant polynucleotide where the polynucleotide encodes at least a catalytic domain of a β-glucosidase. In certain embodiments that may be combined with the preceding embodiments having a host cell containing an endogenous or a second recombinant polynucleotide where the polynucleotide encodes at least a catalytic domain of a β-glucosidase, the β-glucosidase is from *Neurospora crassa*. In certain embodiments that may be combined with the preceding embodiments having a host cell containing an endogenous or a second recombinant polynucleotide where the polynucleotide encodes at least a catalytic domain of a β-glucosidase from *Neurospora crassa*, the β-glucosidase is encoded by NCU00130.

Another aspect includes methods of co-fermenting cellulose-derived and hemicellulose-derived sugars, containing providing a host cell, where the host cell contains a first recombinant polynucleotide encoding a cellodextrin transporter and a second recombinant polynucleotide encoding a catalytic domain of a β-glucosidase, and culturing the host cell in a medium containing a cellulose-derived sugar and a hemicellulose-derived sugar, where expression of the recombinant polynucleotides enables co-fermentation of the cellulose-derived sugar and the hemicellulose-derived sugar. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 1 contains SEQ ID NO: 1. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 2 contains SEQ ID NO: 2. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and a loop connecting transmembrane α-helix 2 and transmembrane α-helix 3 contains SEQ ID NO: 3. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 5 contains SEQ ID NO: 4. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 6 contains SEQ ID NO: 5. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and sequence between transmembrane α-helix 6 and transmembrane α-helix 7 contains SEQ ID NO: 6. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 7 contains SEQ ID NO: 7. In certain embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 10 and transmembrane α-helix 11 and the sequence between them contain SEQ ID NO: 8. In certain embodiments that may be combined with any of the preceding embodiments, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments that may be combined with any of the preceding embodiments, the β-glucosidase is from *Neurospora crassa*. In certain embodiments that may be combined with the preceding embodiments having a host cell containing a second recombinant polynucleotide encoding a catalytic domain of a β-glucosidase from *Neurospora crassa*, the β-glucosidase is encoded by NCU00130. In certain embodiments that may be combined with any of the preceding embodiments, the host cell further contains one or more recombinant polynucleotides where the one or more polynucleotides encode one or more enzymes involved in pentose utilization. In certain embodiments that may be combined with the preceding embodiments having a host cell further containing one or more recombinant polynucleotides where the one or more polynucleotides encode one or more enzymes involved in pentose utilization, the one or more enzymes are selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase. In certain embodiments that may be combined with any of the preceding embodiments, the host cell further contains a third recombinant polynucleotide where the third recombinant polynucleotide encodes a pentose transporter. In certain embodiments that may be combined with the preceding embodiments having the host cell further containing a third recombinant polynucleotide where the third recombinant polynucleotide encodes a pentose transporter, the pentose transporter is selected from the group consisting of NCU00821, NCU04963, NCU06138, STL12/XUT6, SUT2, SUT3, XUT1, and XUT3. In certain embodiments that may be combined with any of the preceding embodiments, the cellulose-derived sugar is selected from the group consisting of cellobiose, cellotriose, and celltetraose, and the hemicellulose-derived sugar is xylose.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 1 contains SEQ ID NO: 1, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, containing providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 2 contains SEQ ID NO: 2, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and a loop connecting transmembrane α-helix 2 and transmembrane α-helix 3 contains SEQ ID NO: 3, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 5 contains SEQ ID NO: 4, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 6 contains SEQ ID NO: 5, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and sequence between transmembrane α-helix 6 and transmembrane α-helix 7 contains SEQ ID NO: 6, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 7 contains SEQ ID NO: 7, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 10 and transmembrane α-helix 11 and the sequence between them contain SEQ ID NO: 8, and the polypeptide transports cellodextrin into the host cell for the synthesis of hydrocarbons or hydrocarbon derivatives, and culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide.

In certain embodiments that may be combined with any of the preceding aspects increasing the synthesis of hydrocarbons or hydrocarbon derivatives, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments that may be combined with any of the preceding embodiments, the host cell further contains a second recombinant polynucleotide where the polynucleotide encodes at least a catalytic domain of a β-glucosidase. In certain embodiments that may be combined with preceding embodiments having the host cell further containing a second recombinant polynucleotide where the polynucleotide encodes at least a catalytic domain of a β-glucosidase, the β-glucosidase is from *Neurospora crassa*. In certain embodiments that may be combined with preceding embodiments having the host cell further containing a second recombinant polynucleotide where the polynucleotide encodes at least a catalytic domain of a β-glucosidase from *Neurospora crassa*, the β-glucosidase is encoded by NCU00130. In certain embodiments that may be combined with any of the preceding embodiments, the source of the cellodextrin contains cellulose. In certain embodiments that may be combined with any of the preceding embodiments, the hydrocarbons or hydrocarbon derivatives can be used as fuel. In certain embodiments that may be combined with the preceding embodiments having the hydrocarbons or hydrocarbon derivatives used as fuel, the hydrocarbons or hydrocarbon derivatives contain ethanol. In certain embodiments that may be combined with the preceding embodiments having the hydrocarbons or hydrocarbon derivatives used as fuel, the hydrocarbons or hydrocarbon derivatives contain butanol.

In certain embodiments that may be combined with any of the preceding aspects, the medium contains a cellulase-containing enzyme mixture from an altered organism, where the cellulase-containing mixture has reduced β-glucosidase activity compared to a cellulase-containing mixture from an unaltered organism. In certain embodiments that may be combined with any of the preceding aspects, the host cell is selected from the group consisting of *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, and *Bacillus subtilis*. In certain embodiments that may be combined with any of the preceding aspects, cellodextrin is selected from one or more of the group consisting of cellobiose, cellotriose, and cellotetraose.

Another aspect includes host cells containing a recombinant polynucleotide encoding a polypeptide having transmembrane α-helix 1, α-helix 2, α-helix 3, α-helix 4, α-helix 5, α-helix 6, α-helix 7, α-helix 8, α-helix 9, α-helix 10, α-helix 11, α-helix 12, an intracellular N-terminus, an intracellular C-terminus, and a sequence selected from the group consisting of SEQ ID NO: 1 in transmembrane α-helix 1, SEQ ID NO: 2 in transmembrane α-helix 2, SEQ ID NO: 3 in a loop connecting transmembrane α-helix 2 and transmembrane α-helix 3, SEQ ID NO: 4 in transmembrane α-helix 5, SEQ ID NO: 5 in transmembrane α-helix 6, SEQ ID NO: 6 in the sequence between transmembrane α-helix 6 and transmembrane α-helix 7, SEQ ID NO: 7 in transmembrane α-helix 7, and SEQ ID NO: 8 in transmembrane α-helix 10 and transmembrane α-helix 11 and the sequence between them, where the polypeptide is a cellodextrin transporter. In certain embodiments, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments that may be combined with either of the preceding embodiments, the host cell further contains a second recombinant polynucleotide where the second recombinant polynucleotide encodes a catalytic domain of a β-glucosidase. In certain embodiments that may be combined with preceding embodiments having the host cell further containing a second recombinant polynucleotide where the second recombinant polynucleotide encodes a catalytic domain of a β-glucosidase, the β-glucosidase is from *Neurospora crassa*. In certain embodiments that may be combined with the preceding embodiments having the host cell further containing a second recombinant polynucleotide where the second recombinant polynucleotide encodes a catalytic domain of a β-glucosidase from *Neurospora crassa*, the β-glucosidase is encoded by NCU00130. In certain embodiments that may be combined with any of the preceding embodiments, the host cell further contains one or more recombinant polynucleotides where the one or more polynucleotides encode one or more enzymes involved in pentose utilization. In certain embodiments that may be combined with the preceding embodiments having the host cell further containing one or more recombinant polynucleotides where the one or more polynucleotides encode one or more enzymes involved in pentose utilization, the one or more enzymes are selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase. In certain embodiments that may be combined with any of the preceding embodiments, the host cell further contains a third recombinant polynucleotide where the third recombinant polynucleotide encodes a pentose transporter. In certain embodiments that may be combined with the preceding embodiment having the host cell further containing a third recombinant polynucleotide where the third recombinant polynucleotide encodes a pentose transporter, the pentose transporter is selected from the group consisting of NCU00821, NCU04963, NCU06138, STL12/XUT6, SUT2, SUT3, XUT1, and XUT3.

In certain embodiments that may be combined with any of the preceding aspects, the host cell further contains one or more inducible promoters operably linked to the one or more recombinant polynucleotides.

Another aspect includes a host cell containing a recombinant polynucleotide encoding a polypeptide selected from the group consisting of NCU00821 and STL12/XUT6, where the polypeptide transports xylose into the cell.

Another aspect includes a host cell containing a recombinant polynucleotide encoding a XUT1 polypeptide, where the polypeptide transports arabinose into the cell.

Another aspect includes a host cell containing a recombinant polynucleotide encoding an NCU06138 polypeptide, where the polypeptide transports arabinose and glucose into the cell.

Another aspect includes a host cell containing a recombinant polynucleotide encoding a polypeptide selected from the group consisting of SUT2, SUT3, and XUT3, where the polypeptide transports xylose and glucose into the cell.

Another aspect includes a host cell containing a recombinant polynucleotide encoding an NCU04963 polypeptide, where the polypeptide transports xylose, arabinose, and glucose into the cell.

In certain embodiments that may be combined with any of the preceding aspects having a host cell containing a recombinant polynucleotide encoding a pentose transporter, the host cell further contains one or more recombinant polynucleotides where the one or more polynucleotides encode one or more enzymes involved in pentose utilization. In certain embodiments that may be combined with the preceding embodiment having the host cell further containing one or more recombinant polynucleotides where the one or more polynucleotides encode one or more enzymes involved in pentose utilization, the one or more enzymes are selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase.

Another aspect includes methods of increasing transport of xylose into a cell, including providing a host cell, where the host cell contains a recombinant polynucleotide encoding a polypeptide selected from the group consisting of NCU00821 and STL12/XUT6, and culturing the cell such that the recombinant polynucleotide is expressed, where expression of the recombinant polynucleotide results in increased transport of xylose into the cell compared with a cell that does not contain the recombinant polynucleotide.

Another aspect includes methods of increasing transport of arabinose into a cell, including providing a host cell, where the host cell contains a recombinant polynucleotide encoding a XUT1 polypeptide, and culturing the cell such that the recombinant polynucleotide is expressed, where expression of the recombinant polynucleotide results in increased transport of arabinose into the cell compared with a cell that does not contain the recombinant polynucleotide.

Another aspect includes methods of increasing transport of arabinose or glucose into a cell, including providing a host cell, where the host cell contains a recombinant polynucleotide encoding a NCU06138 polypeptide, and culturing the cell such that the recombinant polynucleotide is expressed, where expression of the recombinant polynucleotide results in increased transport of arabinose or glucose into the cell compared with a cell that does not contain the recombinant polynucleotide.

Another aspect includes methods of increasing transport of xylose or glucose into a cell, including providing a host cell, where the host cell contains a recombinant polynucleotide encoding a polypeptide selected from the group consisting of SUT2, SUT3, and XUT3, and culturing the cell such that the recombinant polynucleotide is expressed, where expression of the recombinant polynucleotide results in increased transport of xylose or glucose into the cell compared with a cell that does not contain the recombinant polynucleotide.

Another aspect includes methods of increasing transport of xylose, arabinose, or glucose into a cell, including providing a host cell, where the host cell contains a recombinant polynucleotide encoding a NCU04963 polypeptide, and culturing the cell such that the recombinant polynucleotide is expressed, where expression of the recombinant polynucleotide results in increased transport of xylose, arabinose, or glucose into the cell compared with a cell that does not contain the recombinant polynucleotide.

In certain embodiments that may be combined with any of the preceding aspects of increasing transport of xylose, arabinose, or glucose into cells, the method further includes one or more recombinant polynucleotides where the one or more polynucleotides encode one or more enzymes involved in pentose utilization. In certain embodiments that may be combined with the preceding embodiments having the method further including one or more recombinant polynucleotides where the one or more polynucleotides encode one or more enzymes involved in pentose utilization, the one or more enzymes are selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase.

Another aspect includes methods of increasing growth of a cell, including providing a host cell, where the host cell contains a recombinant polynucleotide where the polynucleotide encodes a polypeptide selected from the group consisting of NCU00821 and STL12/XUT6, and the polypeptide transports xylose, and culturing the host cell in a medium containing xylose, where the host cell grows at a faster rate in the medium than a cell that does not contain the recombinant polynucleotide.

Another aspect includes methods of increasing growth of a cell, including providing a host cell, where the host cell contains a recombinant polynucleotide where the polynucleotide encodes a XUT1 polypeptide, and the polypeptide transports arabinose, and culturing the host cell in a medium containing arabinose, where the host cell grows at a faster rate in the medium than a cell that does not contain the recombinant polynucleotide.

Another aspect includes method of increasing growth of a cell, including providing a host cell, where the host cell contains a recombinant polynucleotide where the polynucleotide encodes an NCU06138 polypeptide, and the polypeptide transports arabinose and glucose, and culturing the host cell in a medium containing arabinose or glucose, where the host cell grows at a faster rate in the medium than a cell that does not contain the recombinant polynucleotide.

Another aspect includes methods of increasing growth of a cell, including providing a host cell, where the host cell contains a recombinant polynucleotide where the polynucleotide encodes a polypeptide selected from the group consisting of SUT2, SUT3, and XUT3, and the polypeptide transports xylose and glucose, and culturing the host cell in a medium including xylose or glucose, where the host cell grows at a faster rate in the medium than a cell that does not contain the recombinant polynucleotide.

Another aspect includes methods of increasing growth of a cell, including providing a host cell, where the host cell contains a recombinant polynucleotide where the polynucleotide encodes a NCU04963 polypeptide, and the polypeptide transports xylose, arabinose, and glucose, and culturing the host cell in a medium containing xylose, arabinose, or glucose, where the host cell grows at a faster rate in the medium than a cell that does not contain the recombinant polynucleotide.

In certain embodiments that may be combined with the preceding aspects of increasing growth of cells by culturing a host cell containing a recombinant polynucleotide encoding a polypeptide that transports xylose and/or arabinose and/or glucose, the host cell further contains one or more endogenous or recombinant polynucleotides encoding one or more enzymes involved in pentose utilization. In certain embodiments that may be combined with the preceding embodiments having the host cell further containing one or more endogenous or recombinant polynucleotides encoding one or more enzymes involved in pentose utilization, the one or more enzymes are selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase.

Another aspect includes methods of increasing the synthesis of hydrocarbons or hydrocarbon derivatives by a host cell, including providing a host cell, where the host cell contains a recombinant polynucleotide encoding a polypeptide selected from the group consisting of NCU00821 and STL12/XUT6, where the polypeptide transports xylose into the host cell for the synthesis of hydrocarbons or hydrocarbon derivatives, and culturing the host cell in a medium containing xylose or a source of xylose to increase the synthesis of hydrocarbons or hydrocarbon derivatives by the host cell, where transport of xylose into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding a XUT1 polypeptide, where the polypeptide transports arabinose into the host cell for the synthesis of hydrocarbons or hydrocarbon derivatives, and culturing the host cell in a medium containing arabinose or a source of arabinose to increase the synthesis of hydrocarbons or hydrocarbon derivatives by the host cell, where transport of arabinose into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding an NCU06138 polypeptide, where the polypeptide transports arabinose or glucose into the host cell for the synthesis of hydrocarbons or hydrocarbon derivatives, and culturing the host cell in a medium containing arabinose or glucose or a source of arabinose or glucose to increase the synthesis of hydrocarbons or hydrocarbon derivatives by the host cell, where transport of arabinose or glucose into the cell is increased upon expression of the recombinant polynucleotide.

Another aspect includes method of increasing the synthesis of hydrocarbons or hydrocarbon derivatives by a host cell, including providing a host cell, where the host cell contains a recombinant polynucleotide encoding a polypeptide selected from the group consisting of SUT2, SUT3, and XUT3, where the polypeptide transports xylose or glucose into the host cell for the synthesis of hydrocarbons or hydrocarbon derivatives, and culturing the host cell in a medium containing xylose or glucose or a source of xylose or glucose to increase the synthesis of hydrocarbons or hydrocarbon derivatives by the host cell, where transport of xylose or glucose into the cell is increased upon expression of the recombinant polynucleotide.

Another aspect includes methods of increasing the synthesis of hydrocarbons or hydrocarbon derivatives by a host cell, including providing a host cell, where the host cell contains a recombinant polynucleotide encoding an NCU04963 polypeptide, where the polypeptide transports xylose, arabinose, or glucose into the host cell for the synthesis of hydrocarbons or hydrocarbon derivatives, and culturing the host cell in a medium containing xylose, arabinose, or glucose or a source of xylose, arabinose, or glucose to increase the synthesis of hydrocarbons or hydrocarbon derivatives by the host cell, where transport of xylose, arabinose, or glucose into the cell is increased upon expression of the recombinant polynucleotide.

In certain embodiments that may combine any of the preceding aspects of increasing the synthesis of hydrocarbons or hydrocarbon derivatives by culturing a host cell containing a recombinant polynucleotide encoding a polypeptide that transports glucose, the source of glucose contains cellulose. In certain embodiments that may combine any of the preceding embodiments, the source of xylose or arabinose contains hemicellulose. In certain embodiments that may combine any of the preceding embodiments, the hydrocarbons or hydrocarbon derivatives can be used as fuel. In certain embodiments that may combine the preceding embodiment having the hydrocarbons or hydrocarbon derivatives used as fuel, the hydrocarbons or hydrocarbon derivatives contain ethanol. In certain embodiments that may combine the preceding embodiment having the hydrocarbons or hydrocarbon derivatives used as fuel, the hydrocarbons or hydrocarbon derivatives contain butanol.

In certain embodiments that may combine any of the preceding embodiments, the host cell is selected from the group consisting of *Saccharomyces* sp., *Saccharomyces cerevisiae, Saccharomyces* monacensis, *Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, and *Bacillus subtilis.*

Another aspect includes methods of increasing growth of a cell, including providing a host cell, where the host cell contains a recombinant polynucleotide where the polynucleotide encodes a NCU07705 polypeptide, and culturing the cell in a medium containing cellulose, where the host cell grows at a faster rate in the medium than a cell that does not contain the recombinant polynucleotide. In certain embodiments, the host cell is selected from the group consisting of *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, and *Bacillus subtilis.* In certain embodiments, the host cell further contains an inducible promoter operably linked to the recombinant polynucleotide. In certain embodiments, expression of cellulases is increased in the host cell upon expression of the recombinant polynucleotide.

Another aspect includes methods of increasing growth of a cell on a biomass polymer, including providing a host cell, where the host cell contains an endogenous polynucleotide where the polynucleotide encodes an NCU05137 polypeptide, inhibiting expression of the endogenous polynucleotide, and culturing the cell in a medium containing the biomass polymer, where the host cell grows at a faster rate in the medium than a cell in which expression of the endogenous polynucleotide is not inhibited. In certain embodiments, the host cell is selected from the group consisting of *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, and *Bacillus subtilis*. In certain embodiments, cellulase activity of the host cell is increased upon inhibiting expression of the endogenous polynucleotide. In certain embodiments, hemicellulase activity of the host cell is increased upon inhibiting expression of the endogenous polynucleotide. In certain embodiments, inhibiting expression of the endogenous polynucleotide contains mutating or deleting a gene containing the endogenous polynucleotide. In certain embodiments, the biomass polymer is cellulose. In certain embodiments, the biomass polymer is hemicellulose.

Another aspect includes methods of increasing growth of a cell, including providing a host cell, where the host cell contains a recombinant polynucleotide where the polynucleotide encodes a polypeptide selected from the group consisting of NCU01517, NCU09133, and NCU10040, and culturing the cell in a medium containing hemicellulose, where the host cell grows at a faster rate in the medium than a cell that does not contain the recombinant polynucleotide. In certain embodiments, the host cell is selected from the group consisting of *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, and *Bacillus subtilis*. In certain embodiments, the host cell further contains an inducible promoter operably linked to the recombinant polynucleotide. In certain embodiments, hemicellulase activity of the host cell is increased upon expression of the recombinant polynucleotide.

Another aspect includes methods of degrading cellulose, including providing a composition containing cellulose, and contacting the composition with a cellulase-containing enzyme mixture from an altered organism, where the cellulase-containing mixture has reduced β-glucosidase activity compared to a cellulase-containing mixture from an unaltered organism, and where the cellulose is degraded by the cellulase-containing mixture. In certain embodiments, the organism is altered by mutation of a gene encoding a β-glucosidase. In certain embodiments, the organism is altered by reducing the expression of a β-glucosidase. In certain embodiments that may be combined with any of the preceding embodiments, the organism is selected from the group consisting of a fungus and a bacterium. In certain embodiments that may be combined with any of the preceding embodiments having the organism selected from the group consisting of a fungus and a bacterium, the organism is a filamentous fungus. In certain embodiments that may be combined with any of the preceding embodiments, the cellulose is from plant material. In certain embodiments that may be combined with the preceding embodiments having the cellulose from plant material, the plant material is selected from the group consisting of switchgrass, *Miscanthus*, rice hulls, bagasse, flax, bamboo, sisal, abaca, straw, leaves, grass clippings, corn stover, corn cobs, distillers grains, legume plants, sorghum, sugar cane, sugar beet pulp, wood chips, sawdust, and biomass crops.

Yet another aspect includes methods of increasing the synthesis of hydrocarbons or hydrocarbon derivatives by a host cell comprising providing a host cell, wherein the host cell comprises a recombinant polynucleotide wherein the polynucleotide encodes a polypeptide encoded by a sequence selected from the group consisting of NCU00801, NCU00988, NCU01231, NCU04963, NCU05519, NCU05853, NCU05897, NCU06138, NCU00809, NCU08114, NCU10021, and any of the genes listed in Table 15 and culturing the host cell in a medium comprising a source of a compound to increase the synthesis of hydrocarbons or hydrocarbon derivatives by the host cell, wherein the compound is a substrate for the synthesis of the hydrocarbons or hydrocarbon derivatives, and wherein transport of the compound into the cell is increased upon expression of the recombinant polynucleotide. In certain embodiments, the host cell is selected from the group consisting of *Saccharomyces cerevisiae, Escherichia coli, Zymomonas mobilis, Neurospora crassa, Candida shehatae, Clostridium* sp., *Clostridium phytofermentans, Clostridium thermocellum, Moorella thermocetica, Thermoanaerobacterium saccharolyticum, Klebsiella oxytoca*, and *Pichia stipitis*. In certain embodiments, the host cell further comprises an inducible promoter operably linked to the recombinant polynucleotide. In certain embodiments, the recombinant polynucleotide encodes a polypeptide having at least 50% amino acid identity to the polypeptide encoded by a sequence selected from the group consisting of NCU00801, NCU00988, NCU01231, NCU04963, NCU05519, NCU05853, NCU05897, NCU06138, NCU00809, NCU08114, NCU10021, and any of the genes listed in Table 15. In some embodiments, the hydrocarbons or hydrocarbon derivatives can be used as fuel. In certain embodiments, the medium comprises cellulose. In other embodiments, the medium comprises hemicellulose. In certain embodiments, the compound is a sugar. In certain embodiments that may be combined with the preceding embodiments, the sugar is a pentose. In certain embodiments that may be combined with the preceding embodiments, the sugar is a hexose. In certain embodiments that may be combined with the preceding embodiments, the sugar is a disaccharide. In certain embodiments that may be combined with the preceding embodiments, the sugar is an oligosaccharide. In other embodiments, the compound is a plant phenol. In certain embodiments that may be combined with the preceding embodiments, the plant phenol is quinic acid. In certain embodiments that may be combined with the preceding embodiments, the plant phenol is nicotinamide. In other embodiments, the compound is pyruvate or lactate.

Another aspect includes methods of increasing growth of a cell on a biomass polymer comprising providing a host cell, wherein the host cell comprises a recombinant polynucleotide wherein the polynucleotide encodes a polypeptide encoded by any of the *Neurospora* or *Pichia stipitis* genes listed in Table 10, in Supplemental Data, Dataset S1, page 3 in Tian et al., *PNAS*, 2009, vol. 106, no. 52, 22157-22162, the disclosure of which is hereby incorporated by reference, in Table 15, or NCU01517, NCU09133, or NCU10040 and culturing the cell in a medium comprising the biomass polymer, wherein the host cell grows at a faster rate in the medium than a cell that does not comprise the recombinant polynucleotide. In certain embodiments, the polynucleotide encodes a polypeptide encoded by any of the sequences NCU00130.2, NCU00248.2, NCU00326.2, NCU00762.2, NCU00810.2, NCU00890.2, NCU03328.2, NCU03415.2, NCU03731.2, NCU03753.2, NCU04197.2, NCU04249.2, NCU04287.2, NCU04349.2, NCU04475.2, NCU04997.2, NCU05057.2, NCU05159.2, NCU05493.2, NCU05751.2, NCU05770.2, NCU05932.2, NCU06009.2, NCU06490.2, NCU07340.2, NCU07853.2, NCU07997.2, NCU08744.2, NCU08746.2, NCU08760.2, NCU09108.2, NCU09495.2, NCU09680.2, or NCU10045.2. In certain embodiments, the polynucleotide encodes a polypeptide encoded by NCU07705. In certain embodiments, the recombinant polynucleotide encodes a polypeptide having at least 50% amino acid identity to the polypeptide encoded by any of the *Neurospora* or *Pichia stipitis* genes listed in Table 10, in Supplemental Data, Dataset S1, page 3 in Tian et al., 2009, or in Table 15. In certain embodiments, the polynucleotide encodes a polypeptide having at least 50% amino acid identity to the polypeptide encoded by any of the sequences NCU00130.2, NCU00248.2, NCU00326.2, NCU00762.2, NCU00810.2, NCU00890.2, NCU03328.2, NCU03415.2, NCU03731.2, NCU03753.2, NCU04197.2, NCU04249.2, NCU04287.2, NCU04349.2, NCU04475.2, NCU04997.2, NCU05057.2, NCU05159.2, NCU05493.2, NCU05751.2, NCU05770.2, NCU05932.2, NCU06009.2, NCU06490.2, NCU07340.2, NCU07853.2, NCU07997.2, NCU08744.2, NCU08746.2, NCU08760.2, NCU09108.2, NCU09495.2, NCU09680.2, or NCU10045.2. In certain embodiments, the recombinant polynucleotide encodes a polypeptide having at least 50% amino acid identity to the polypeptide encoded by NCU07705. In certain embodiments, the biomass polymer is cellulose. In other embodiments, the biomass polymer is hemicellulose. In certain embodiments, the host cell is selected from the group consisting of *Saccharomyces cerevisiae, Escherichia coli, Zymomonas mobilis, Neurospora crassa, Candida shehatae, Clostridium* sp., *Clostridium phytofermentans, Clostridium thermocellum, Moorella thermocetica, Thermoanaerobacterium saccharolyticum, Klebsiella oxytoca*, and *Pichia stipitis*. In certain embodiments, the host cell further comprises an inducible promoter operably linked to the recombinant polynucleotide. In certain embodiments, expression of cellulases is increased in the host cell upon expression of the recombinant polynucleotide. In other embodiments, expression of hemicellulases is increased in the host cell upon expression of the recombinant polynucleotide.

Yet another aspect includes methods of increasing growth of a cell on a biomass polymer comprising providing a host cell, wherein the host cell comprises an endogenous polynucleotide wherein the polynucleotide encodes a polypeptide encoded by any of the *Neurospora* or *Pichia stipitis* genes listed in Table 10, in Supplemental Data, Dataset S1, page 3 in Tian et al., 2009, or in Table 15, or, inhibiting expression of the endogenous polynucleotide, and culturing the cell in a medium comprising the biomass polymer, wherein the host cell grows at a faster rate in the medium than a cell in which expression of the endogenous polynucleotide is not inhibited. In certain embodiments, the endogenous polynucleotide encodes a polypeptide encoded by any of the sequences NCU00130.2, NCU00248.2, NCU00326.2, NCU00762.2, NCU00810.2, NCU00890.2, NCU03328.2, NCU03415.2, NCU03731.2, NCU03753.2, NCU04197.2, NCU04249.2, NCU04287.2, NCU04349.2, NCU04475.2, NCU04997.2, NCU05057.2, NCU05159.2, NCU05493.2, NCU05751.2, NCU05770.2, NCU05932.2, NCU06009.2, NCU06490.2, NCU07340.2, NCU07853.2, NCU07997.2, NCU08744.2, NCU08746.2, NCU08760.2, NCU09108.2, NCU09495.2, NCU09680.2, or NCU10045.2. In certain embodiments, the endogenous polynucleotide encodes a polypeptide encoded by NCU05137. In certain embodiments, the endogenous polynucleotide encodes a polypeptide having at least 50% amino acid identity to the polypeptide encoded by any of the *Neurospora* or *Pichia stipitis* genes listed in Table 10, in Supplemental Data, Dataset S1, page 3 in Tian et al., 2009, or in Table 15. In certain embodiments, the endogenous polynucleotide encodes a polypeptide having at least 50% amino acid identity to the polypeptide encoded by any of the sequences NCU00130.2, NCU00248.2, NCU00326.2, NCU00762.2, NCU00810.2, NCU00890.2, NCU03328.2, NCU03415.2, NCU03731.2, NCU03753.2, NCU04197.2, NCU04249.2, NCU04287.2, NCU04349.2, NCU04475.2, NCU04997.2, NCU05057.2, NCU05159.2, NCU05493.2, NCU05751.2, NCU05770.2, NCU05932.2, NCU06009.2, NCU06490.2, NCU07340.2, NCU07853.2, NCU07997.2, NCU08744.2, NCU08746.2, NCU08760.2, NCU09108.2, NCU09495.2, NCU09680.2, or NCU10045.2. In certain embodiments, the endogenous polynucleotide encodes a polypeptide having at least 50% amino acid identity to the polypeptide encoded by NCU05137. In certain embodiments, the host cell is selected from the group consisting of *Saccharomyces cerevisiae, Escherichia coli, Zymomonas mobilis, Neurospora crassa, Candida shehatae, Clostridium* sp., *Clostridium phytofermentans, Clostridium thermocellum, Moorella thermocetica, Thermoanaerobacterium saccharolyticum, Klebsiella oxytoca*, and *Pichia stipitis*. In certain embodiments, the biomass polymer is cellulose. In other embodiments, the biomass polymer is hemicellulose. In certain embodiments, cellulase activity of the host cell is increased upon inhibiting expression of the endogenous polynucleotide. In other embodiments, hemicellulase activity of the host cell is increased upon inhibiting expression of the endogenous polynucleotide. In certain embodiments, inhibiting expression of the endogenous polynucleotide comprises mutating or deleting a gene comprising the endogenous polynucleotide.

BRIEF DESCRIPTION OF THE DRAWINGS

FIG. 4A shows hierarchical clustering analysis of 769 genes showing expression differences in *Miscanthus* culture. Dark shading indicates higher relative expression and light shading indicates lower relative expression. Lane 1: Expression profile of a 16 hr Vogel's minimal medium *N. crassa* culture (Vogel 1956). Lane 2: Expression profile of a culture grown on *Miscanthus* as a sole carbon source for 16 hrs. Lanes 3, 4, 5: Expression profiles from cultures grown on *Miscanthus* for 40 hrs, 5 days, and 10 days. The three clusters are shown as C1, C2, and C3. The cluster that showed increased expression levels of most of the cellulase and hemicellulase genes is boxed (C3 cluster). FIG. 4B shows analysis of the overlap in expression profiles between the *N. crassa Miscanthus* versus Avicel grown cultures (Top). Analysis and overlap of proteins detected in the culture filtrates of *N. crassa* grown on *Miscanthus* and Avicel by tandem mass spectrometry (Bottom). FIG. 4C shows functional category (FunCat) enrichment analysis (Ruepp 2004) of the 231 genes that showed an increase in relative expression levels in *Miscanthus* cultures. Functional categories that showed significant enrichment ($p<0.001$), including the unclassified group are shown.

FIG. 5 shows the relative expression levels of *N. crassa* genes encoding cellulases (A) and hemicellulases (B) during growth on minimal medium (MM) and during growth on *Miscanthus* for 16 hr, 40 hr, 5 days and 10 days. FIG. 5A shows cellulases. FIG. 5B shows hemicellulases.

FIG. 6A shows SDS-PAGE of proteins present in the culture filtrates of 16 deletion strains as compared to wild type when grown on Avicel for 7 days. Deletion strains were chosen based on identification of the protein by mass spectrometry in both *Miscanthus* and Avicel culture filtrates. Strains are ordered based on gene NCU number, the wild-type strain is FGSC 2489. Missing protein bands that correspond to the deleted genes are marked with boxes. FIG. 6B shows the total secreted protein, azo-CMCase, and β-glucosidase activity assays (see Example 5) performed on 16 deletion strains and the wild-type parental strain (FGSC 2489) using the same sample from FIG. 6A. Activities and protein concentrations were normalized compared to wild type levels and represent the average of triplicate biological measurements. FIG. 6C show cellulase activity of the culture filtrates from the 16 deletion strains using the same samples as in FIG. 6A. Culture filtrates were diluted 10 fold and mixed with 5 mg/mL Avicel (see Example 5) to assess Avicelase activity. Glucose (black) and cellobiose (white) were measured after 8 hours of incubation at 40° C.

FIG. 8A shows SDS-PAGE of total secreted proteins in WT, ΔNCU04952, and ΔNCU05137. Cultures were grown on Avicel from conidia, and harvested at 30 hrs, two days (48 hrs) and three days (72 hrs) (see Example 5). Lanes 1-3, 20× concentrated culture filtrates after 30 hrs of growth on Avicel from WT, ΔNCU04952, and ΔNCU05137 strains, respectively. Lanes 4-6, unconcentrated culture filtrates after two days of growth from WT, ΔNCU04952, and ΔNCU05137 strains, respectively. Lane 7-9, unconcentrated culture filtrates after three days of growth from WT and ΔNCU04952 and ΔNCU05137 strains, respectively. FIG. 8B shows RT-PCR of cbh-1 (NCU07340; CBHI) and gh6-2 (NCU09680; CBHII) in the WT, ΔNCU04952, and ΔNCU05137 strains during growth on Avicel. The WT and deletion strains were grown on Avicel from conidia, and harvested at 48 hrs and 72 hrs (see Example 5). The minimal medium (MM) culture, with sucrose as a sole carbon source (Vogel 1956), was grown for 16 hrs (similar developmental time point). The fold induction of cbh-1 and gh6-2 were relative to the expression of these genes under MM conditions, with actin gene expression used as the control in all samples.

FIG. 10-1, FIG. 10-2, FIG. 10-3, FIG. 10-4, FIG. 10-5, FIG. 10-6, FIG. 10-7, FIG. 10-8, FIG. 10-9, FIG. 10-10, FIG. 10-11, and FIG. 10-12 show BLAST results from searching the sequences of *N. crassa* putative transporters against a database of *S. thermophile* protein sequences or from searching the sequences of *S. thermophile* putative transporters against a database of *N. crassa* protein sequences.

FIG. 11 shows the growth phenotype of a *N. crassa* strain lacking NCU08114. FIG. 11A shows shaker flasks of WT (left) and ΔNCU08114 (right) *N. crassa* strains after 3 days of growth with crystalline cellulose as a carbon source. FIG. 11B shows the mean Alamar Blue© fluorescence from *N. crassa* cultures grown with either sucrose or crystalline cellulose as a carbon source for 16 or 28 hours, respectively. Fluorescence was normalized by setting WT to 100%. Error bars were the standard deviation between measurements from three biological replicates. *N. crassa* lacking NCU00801 did not have an obvious phenotype. *N. crassa* secreted β-glucosidases (Tian et al., 2009) that hydrolyzed cellodextrins to glucose, which was subsequently taken up by monosaccharide transporters (Scarborough 1973). This alternate route of consumption led to an underestimate of the cellodextrin transport defect in these deletion lines.

FIG. 12 shows (A) cellobiose consumption for *S. cerevisiae* strains expressing NCU00801, NCU05853, or NCU08114 along with NCU00130; (B) cellotriose consumption for *S. cerevisiae* strains expressing NCU00801, NCU05853, or NCU08114 along with NCU00130; (C) cellotetraose consumption for *S. cerevisiae* strains expressing NCU00801, NCU05853, or NCU08114 along with NCU00130; and (D) cellohexaose consumption for *S. cerevisiae* strains expressing NCU00801, NCU05853, or NCU08114 along with NCU00130. FIG. 12A shows cellobiose consumption. FIG. 12B shows cellotriose consumption. FIG. 12C shows cellotetraose consumption. FIG. 12D shows cellohexaose consumption.

FIG. 15A shows images of *S. cerevisiae* strains expressing cbt1 (left), or cbt2 (right), fused to GFP at their C-terminus. FIG. 15B shows GFP fluorescence of yeast strains without a cellobiose transporter, or expressing cbt1 or cbt2 fused to GFP at their C-terminus. Values were the mean from three biological replicates, and error bars represent the standard deviation between these replicates.

FIG. 16A shows cellobiose-mediated growth of yeast strains expressing the gene NCU00801 (named cbt1, ○), NCU08114 (named cbt2, ▼), or no transporter (●). All strains also expressed the intracellular β-glucosidase, NCU00130. A representative experiment is shown. Growth rates from three independent experiments were as follows: cbt1, 0.0341±0.0010 $hr^{-1}$; cbt2, 0.0131±0.0008 $hr^{-1}$; no transporter, 0.0026±0.0001 $hr^{-1}$. FIG. 16B shows growth of yeast strains on cellotriose and cellotetraose. Strains expressing the intracellular β-glucosidase, NCU00130, as well as the transporters listed in the legend, were grown with 0.5% (w/v) of cellotriose (G3) or cellotetraose (G4) serving as the sole carbon source. A representative experiment is shown. Growth rates from three independent experiments were as follows: cbt1 cellotriose, 0.0332±0.0004 $hr^{-1}$; cbt1 cellotetraose 0.0263±0.0020 $hr^{-1}$; no transporter cellotriose, 0.0043±0.0015 $hr^{-1}$; cbt2 cellotriose, 0.0178±0.0005 $hr^{-1}$; cbt2 cellotetraose 0.0041±0.0003 $hr^{-1}$; no transporter cellotetraose, 0.0031±0.0008 $hr^{-1}$. FIG. 16C shows glucose produced from cellobiose (G2), cellotriose (G3), and cellotetraose (G4) hydrolysis by purified NCU00130. The mean and standard deviation of three independent measurements are shown. Residual glucose in incubations without enzyme (2 nmol) was subtracted from the values shown.

FIG. 24A shows cellobiose fermentation to ethanol. Ethanol produced by yeast strains with CBT1 (●), or without CBT1 (○). Cellobiose concentration during the fermentation reaction using yeast strains with CBT1 (▼), or without CBT1 (Δ). FIG. 24B shows SSF using yeast strains with and without CBT1. Cellobiose (●) and glucose (▼) concentrations in the presence of a strain with CBT1, and cellobiose (○) and glucose (Δ) concentrations in the presence of a strain lacking CBT1. Note, 0.1 mg/mL cellobiose=292 μM. FIG. 24C shows ethanol produced during SSF using a strain with CBT1 (●), or without CBT1 (○). In all panels, values are the mean of 3 biological replicates. Error bars were the standard deviation between these replicates. All strains also expressed the intracellular β-glucosidase, NCU00130.

FIG. 26A shows Ala-scan of cbt1/NCU00801. FIG. 26B shows polypeptide sequence (important residues marked) of cbt1/NCU00801. FIG. 26C shows polypeptide sequence (important residues marked) of cbt2/NCU08114.

FIG. 27A shows cell growth of *S. cerevisiae* strains expressing β-glucosidase and orthologs of cellobiose transporters NCU00801, NCU08114, and NCU05853. FIG. 27B shows a comparison of cellobiose transporters from *P. stipitis*: cell growth of *S. cerevisiae* strains expressing β-glucosidase and cellobiose transporters. FIG. 27C shows a comparison of cellobiose transporters from *P. stipitis*: xylose consumption and ethanol production by *S. cerevisiae* strains expressing β-glucosidase and cellobiose transporters.

FIG. 28 shows alignments of cellobiose transporter orthologs. FIG. 28A shows alignment of cellobiose transporter orthologs including ones that did not appear to have transporter function under the conditions tested. FIG. 28B shows alignment of cellobiose transporter orthologs that had transport function. FIG. 28C shows alignment of NCU00801 and NCU08114.

FIG. 29 shows functionally important motifs marked in homology models of NCU00801 and NCU08114. FIG. 29A shows location of cellobiose transporters motifs on NCU00801 homology model. Motif [LIVM]-Y-[FL]-x(13)-[YF]-D (SEQ ID NO: 1) is shown in red. Motif [YF]-x(2)-G-x(5)-[PVF]-x(6)-[DQ] (SEQ ID NO: 2) is shown in light green. Motif G-R-[RK] (SEQ ID NO: 3) is shown in dark blue. Motif R-x(6)-[YF]-N (SEQ ID NO: 4) is shown in yellow. Motif WR-[IVLA]-P-x(3)-Q (SEQ ID NO: 5) is shown in magenta. Motif P-E-S-P-R-x-L-x(8)-A-x(3)-L-x(2)-Y-H (SEQ ID NO: 6) is shown in cyan. Motif F-[GST]-Q-x-S-G-N-x-[LIV] (SEQ ID NO: 7) is shown in orange. Motif L-x(3)-[YIV]-x(2)-E-x-L-x(4)-R-[GA]-K-G (SEQ ID NO: 8) is shown in dark green. I. View of NCU00801 from the cytoplasmic side looking into the putative cellobiose binding pore. Note that in this image, some of the residues connecting transmembrane helices 6 and 7 have been removed for clarity as they occlude the pore. II. View of one side of NCU00801. III. View of the side opposite to that shown in II. FIG. 29B shows location of cellobiose transporters motifs on NCU08114 homology model. Motif [LIVM]-Y-[FL]-x(13)-[YF]-D (SEQ ID NO: 1) is shown in red. Motif [YF]-x(2)-G-x(5)-[PVF]-x(6)-[DQ] (SEQ ID NO: 2) is shown in light green. Motif G-R-[RK] (SEQ ID NO: 3) is shown in dark blue. Motif R-x(6)-[YF]-N (SEQ ID NO: 4) is shown in yellow. Motif WR-[IVLA]-P-x(3)-Q (SEQ ID NO: 5) is shown in magenta. Motif P-E-S-P-R-x-L-x(8)-A-x(3)-L-x(2)-Y-H (SEQ ID NO: 6) is shown in cyan. Motif F-[GST]-Q-x-S-G-N-x-[LIV] (SEQ ID NO: 7) is shown in oranges. Motif L-x(3)-[YIV]-x(2)-E-x-L-x(4)-R-[GA]-K-G (SEQ ID NO: 8) is shown in dark green. I. View of NCU08114 from the cytoplasmic side looking into the putative cellobiose binding pore. Note that in this image, some of the residues connecting transmembrane helices 6 and 7 have been removed for clarity as they occlude the pore. II. View of one side of NCU08114. III. View of the side opposite to that shown in II. FIG. 29C shows predicted secondary structures in NCU00801 and NCU08114.

FIG. 29*b* shows transporter-GFP fusion proteins.

FIG. 33 shows pentose uptake of NCU00821 (AN25), STL12/XUT6 (Xyp29), and XUT1 (Xyp32). FIG. 33A shows xylose uptake. FIG. 33B shows arabinose uptake.

FIG. 36A shows NCU00821 (AN25). FIG. 36B shows STL12/XUT6 (Xyp29). FIG. 36C shows XUT1 (Xyp32).

FIG. 37A shows NCU00821 for xylose. FIG. 37B shows NCU00821 for arabinose. FIG. 37C shows XUT1 for arabinose. FIG. 37D shows XUT1 for xylose. FIG. 37E shows STL12/XUT6 for arabinose. FIG. 37F shows STL12/XUT6 for xylose. The black arrows the time points when maltose was added.

FIG. 38 shows phenotypic analyses of transporter overexpression.

FIG. 41 shows sequence alignments of the pentose transporter orthologs by Clustal W (1.81).

FIG. 41A shows alignment of the xylose transporter orthologs. FIG. 41B shows alignment of the arabinose transporters. FIG. 41B shows alignment of xylose and arabinose transporters. Consensus key: *—single, fully conserved residue; :—conservation of strong groups; .—conservation of weak groups.

FIG. 45A shows 40 g/L xylose in a shaker flask. FIG. 45B shows 80 g/L xylose in a shaker flask. FIG. 45C shows 80 g/L xylose in a bioreactor. Symbols: xylose (■), ethanol (♦), and $OD_{600}$ (●).

FIG. 46A shows *S. cerevisiae* DA24. FIG. 46B shows *P. stipitis.*

FIG. 55A shows temperature-dependent catalytic activities. FIG. 55B shows thermal inactivation at 50° C. over time. FIG. 55C shows pH-dependent catalytic activities. Error bars indicate standard error of the mean (n=3).

FIG. 56 shows an alignment of XDH from *N. crassa* (ncXDH) and *P. stipitis* (psXDH).

FIG. 62 shows the effect of over-expression of NCU09705 homologs in *E. coli, S. cerevisiae*, and *P. stipitis* on fermentation parameters. Over-expression of galM, GAL10-Sc, GAL10-Ps, YHR210C, and YNR071C on (A) cellobiose consumption, growth, and ethanol production; and on (B) ethanol yield and productivity.

FIG. 63 shows the experimental design enabling simultaneous co-fermentation of cellobiose and xylose without glucose repression through integration of a cellodextrin assimilation pathway from filamentous fungi (*N. crassa*) and modified xylose metabolic pathway from the xylose-fermenting yeast *P. stipitis* into *S. cerevisiae*.

FIG. 65A shows SL01. FIG. 65B shows SL04. FIG. 65C shows SL02. FIG. 65D shows SL05. FIG. 65E shows SL03. FIG. 65F shows SL06. FIG. 65G shows SL00.

FIG. 66 shows the change in concentrations of cellobiose (■), glucose (●), D-xylose (▲), ethanol (▼), and biomass (□) in *S. cerevisiae* strains SL01 (a, c) and SL00 (b, d) grown in cellobiose-xylose mixtures in shake-flasks (a, b) or bioreactors (c, d) plotted as a function of time.

FIG. 67 shows the change in concentrations of cellobiose (■), glucose (●), D-xylose (▲), ethanol (▼), and biomass (□) in *S. cerevisiae* strains SL01 (a, c) and SL00 (b, d) grown in media containing 5 g/L glucose-40 g/L cellobiose-50 g/L xylose mixture (a, b) or 10 g/L glucose-40 g/L cellobiose-50 g/L xylose mixture (c, d) in bioreactors, plotted as a function of time.

FIG. 68 shows a comparison of cellobiose utilizations by β-glucosidase (NCU00130)-containing *S. cerevisiae* strain expressing (a) NCU00801, (b) NCU00809, and (c) NCU08114. Symbols: cellobiose (■), ethanol (♦), and $OD_{600}$ (●).

FIG. 69 shows co-fermentation of cellobiose and xylose by the *S. cerevisiae* strain DA24-16BT3 grown in mixtures containing various concentrations of the two sugars: (a) 20 g/L (each) of cellobiose and xylose, (b) 30 g/L (each) of cellobiose and xylose, and (c) 40 g/L (each) of cellobiose and xylose. Symbols: cellobiose (▲), xylose (■), ethanol (♦), and $OD_{600}$ (●).

FIG. 70 shows the synergistic effects of co-fermentation of cellobiose and xylose by the *S. cerevisiae* strain DA24-16BT3. Symbols: cellobiose (▲), xylose (■), ethanol (♦), and $OD_{600}$ (●).

FIG. 71 shows co-fermentation of glucose, cellobiose, and xylose by the *S. cerevisiae* strain DA24-16BT3 and the wild-type *P. stipitis* strain. Symbols: cellobiose (▲), xylose (■), ethanol (♦), $OD_{600}$ (●), and glucose (▼).

FIG. 74 shows a comparison of sugar utilization by *S. cerevisiae* transformants expressing (a) an integrated copy of NCU00801 and (b) NCU00801 on a multi-copy plasmid, during co-fermentation of 40 g/L (each) of cellobiose and xylose. Symbols: cellobiose (▲), xylose (■), ethanol (♦), and $OD_{600}$ (●).

FIG. 75 shows ethanol production by cultivation of two different yeast strains.

FIG. 76 shows a listing of 354 xylan-induced genes in *N. crassa.*

DETAILED DESCRIPTION OF THE INVENTION

Figure 1:
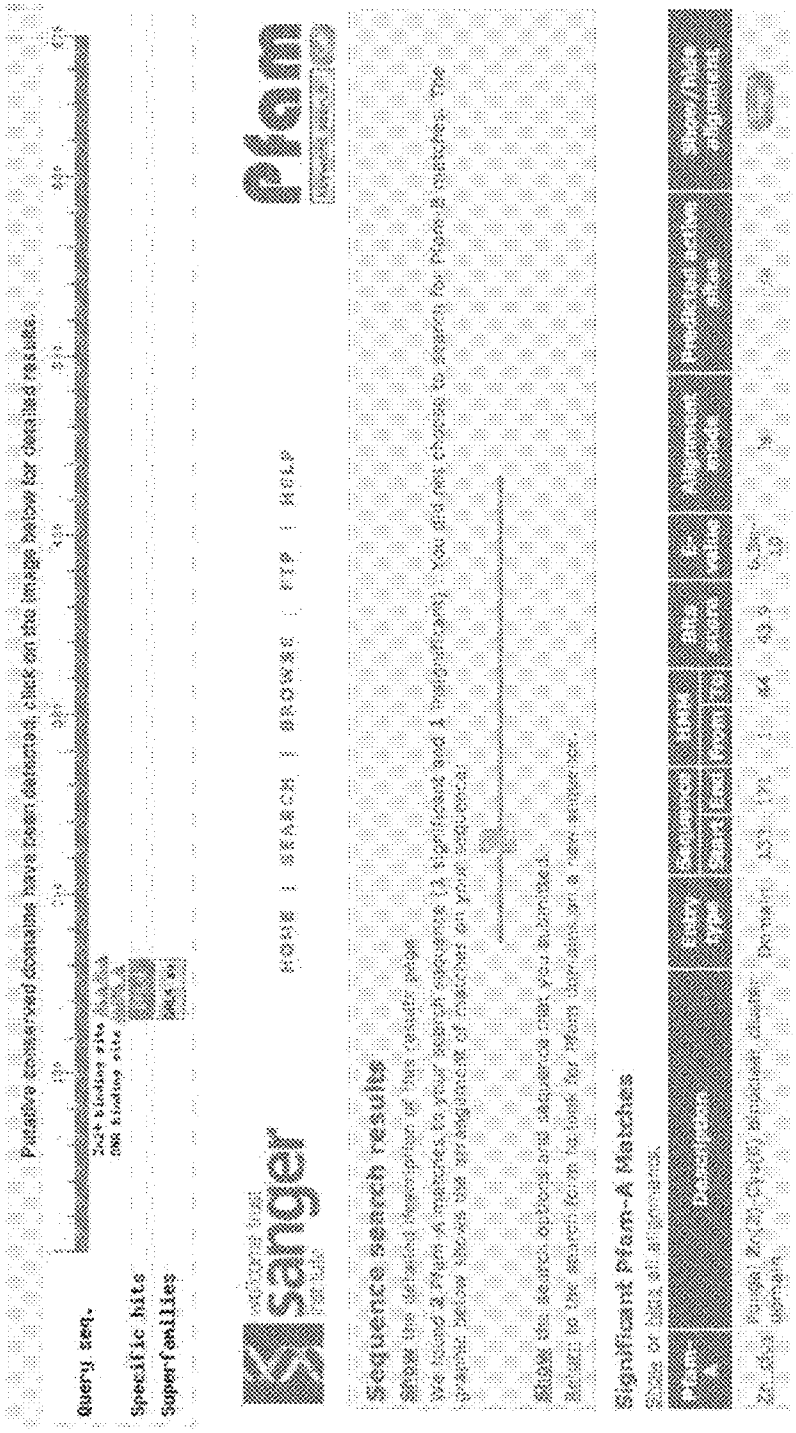
FIG. 1 shows the domain structure of the polypeptide encoded by NCU07705.

The present disclosure relates to host cells containing a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, and α-helix 12, where one or more of the following is true: transmembrane α-helix 1 comprises SEQ ID NO: 1, transmembrane α-helix 2 comprises SEQ ID NO: 2, the loop connecting transmembrane α-helix 2 and transmembrane α-helix 3 comprises SEQ ID NO: 3, transmembrane α-helix 5 comprises SEQ ID NO: 4, transmembrane α-helix 6 comprises SEQ ID NO: 5, sequence between transmembrane α-helix 6 and transmembrane α-helix 7 comprises SEQ ID NO: 6, transmembrane α-helix 7 comprises SEQ ID NO: 7, and transmembrane α-helix 10 and transmembrane α-helix 11 and the sequence between them comprise SEQ ID NO: 8, and where the polypeptide transports cellodextrin into the cell. Further described herein are methods of increasing transport of cellodextrin into a cell, methods of increasing growth of a cell on a medium containing cellodextrin, methods of co-fermenting cellulose-derived and hemicellulose-derived sugars, and methods of making hydrocarbons or hydrocarbon derivatives using the host cells. Further described herein are host cells containing a recombinant polynucleotide encoding a polypeptide where the polypeptide transports a pentose into the cell, methods of increasing transport of a pentose into a cell, methods of increasing growth of a cell on a medium containing pentose sugars, and methods of making hydrocarbons or hydrocarbon derivatives by providing a host cell containing a recombinant polynucleotide encoding a polypeptide where the polypeptide transports a pentose into the cell.

As used herein, cellodextrin refers to glucose polymers of varying length and includes, without limitation, cellobiose (2 glucose monomers), cellotriose (3 glucose monomers), cellotetraose (4 glucose monomers), cellopentaose (5 glucose monomers), and cellohexaose (6 glucose monomers).

As used herein, sugar refers to monosaccharides (e.g., glucose, fructose, galactose, xylose, arabinose), disaccharides (e.g., cellobiose, sucrose, lactose, maltose), and oligosaccharides (typically containing 3 to 10 component monosaccharides).

Polynucleotides of the Invention

The invention herein relates to host cells and methods of using such host cells where the host cells comprise recombinant polynucleotides encoding polypeptides capable of transporting various sugars.

As used herein, the terms "polynucleotide," "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; inter-nucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (Biochem. 9:4022, 1970).

As used herein, a "polypeptide" is an amino acid sequence comprising a plurality of consecutive polymerized amino acid residues (e.g., at least about 15 consecutive polymerized amino acid residues, optionally at least about 30 consecutive polymerized amino acid residues, at least about 50 consecutive polymerized amino acid residues). In many instances, a polypeptide comprises a polymerized amino acid residue sequence that is a transporter, a transcription factor, a predicted protein of unknown function, or a domain or portion or fragment thereof. A transporter is involved in the movement of ions, small molecules, or macromolecules, such as a carbohydrate, across a biological membrane. A transcription factor can regulate gene expression and may increase or decrease gene expression in a host cell. The polypeptide optionally comprises modified amino acid residues, naturally occurring amino acid residues not encoded by a codon, and non-naturally occurring amino acid residues.

As used herein, "protein" refers to an amino acid sequence, oligopeptide, peptide, polypeptide, or portions thereof whether naturally occurring or synthetic.

Recombinant polynucleotides of the invention include any polynucleotides that encode a polypeptide encoded by any of the genes listed in Table 10, in Supplemental Data, Dataset S1, page 3 in Tian et al., 2009; in Tables 14, 15, 16, 29; or in FIG. 76. In preferred embodiments, polynucleotides of the invention include any polynucleotides that encode a polypeptide encoded by any of the sequences NCU00801, NCU00809, NCU08114, NCU00130, NCU00821, NCU04963, NCU06138, STL12/XUT6, SUT2, SUT3, XUT1, XUT3, NCU07705, NCU05137, NCU01517, NCU09133, or NCU10040.

Table 1 shows polynucleotides of the invention including sequences listed below or sequences encoding polypeptides listed below.

| Gene Name/Locus | Alternate Name | NCBI Reference Sequence/GenBank Accession Number | Organism |
|---|---|---|---|
| NCU00801 | cbt1 | XP_963801.1/EAA34565 | *N. crassa* |
| NCU00809 | | XP_964302.1/EAA35116.1 | *N. crassa* |
| NCU00821 | AN25 | XP_964364.2/EAA35128.2 | *N. crassa* |
| NCU00988 | Xy33 | XP_963898.1/EAA34662.1 | *N. crassa* |
| NCU01231 | | XP_961597.2/EAA32361.2 | *N. crassa* |
| NCU01494 | AN49 | XP_955927.2/EAA26691.2 | *N. crassa* |
| NCU02188 | AN28-3 | XP_959582.2/EAA30346.2 | *N. crassa* |
| NCU04537 | Xy50 | XP_955977.1/EAA26741.1 | *N. crassa* |
| NCU04963 | AN29-2 | XP_959411.2/EAA30175.2 | *N. crassa* |
| NCU05519 | | XP_960481.1/EAA31245.1 | *N. crassa* |
| NCU05853 | | XP_959844.1/EAA30608.1 | *N. crassa* |
| NCU05897 | | XP_959888.1/EAA30652.1 | *N. crassa* |
| NCU06138 | Xy31 | XP_960000.1/EAA30764.1 | *N. crassa* |
| NCU08114 | cbt2 | XP_963873.1/EAA34637.1 | *N. crassa* |
| NCU09287 | AN41 | XP_958139.1/EAA28903.1 | *N. crassa* |
| NCU10021 | | XP_958069.2/EAA28833.2 | *N. crassa* |
| XP_001387242 | Ap26 | XP_001387242 | *P. stipitis* |
| HGT3 | Xyp30-1 | XP_001386715.1/ABN68686.1 | *P. stipitis* |
| STL1 | Xyp30 | XP_001383774.1/ABN65745.1 | *P. stipitis* |
| STL12/XUT6 | Xyp29 | XP_001386589.1/ABN68560.1 | *P. stipitis* |
| SUT2 | Ap31 | XP_001384295.2/ABN66266.2 | *P. stipitis* |
| SUT3 | Xyp37 | XP_001386019.2/ABN67990.2 | *P. stipitis* |
| XUT1 | Xyp32 | XP_001385583.1/ABN67554.1 | *P. stipitis* |
| XUT2 | Xyp31 | XP_001387242.1/EAZ63219.2 | *P. stipitis* |
| XUT3 | Xyp33 | XP_001387138.1/EAZ63115.1 | *P. stipitis* |
| XUT7 | Xyp28 | XP_001387067.1/EAZ63044.1 | *P. stipitis* |
| NCU07705 | cdr-1 | XP_962291.1/EAA33055 | *N. crassa* |
| NCU05137 | | XP_956635.1/EAA27399 | *N. crassa* |
| NCU01517 | | XP_956966.1/EAA27730 | *N. crassa* |
| NCU09133 | | XP_958905.1/EAA29669 | *N. crassa* |
| NCU10040 | | | *N. crassa* |

In certain embodiments, the recombinant polynucleotides of the invention encode polypeptides having at least about 20%, or at least about 29%, or at least about 30%, or at least about 40%, or at least about 50%, or at least about 55%, or at least about 60%, or at least about 65%, or at least about 70%, or at least about 75%, or at least about 80%, or at least about 85%, or at least about 90%, or at least about 92%, or at least about 94%, or at least about 96%, or at least about 98%, or at least about 99%, or at least about 100% amino acid residue sequence identity to a polypeptide encoded by any of the genes listed in genes listed in Table 10, in Supplemental Data, Dataset S1, page 3 in Tian et al., 2009; in Tables 14, 15, 16, 29; or in FIG. 76. In preferred embodiments, the polynucleotides of the invention encode polypeptides having at least about 20%, or at least about 29%, or at least about 30%, or at least about 40%, or at least about 50%, or at least about 55%, or at least about 60%, or at least about 65%, or at least about 70%, or at least about 75%, or at least about 80%, or at least about 85%, or at least about 90%, or at least about 92%, or at least about 94%, or at least about 96%, or at least about 98%, or at least about 99%, or at least about 100% amino acid residue sequence identity to a polypeptide encoded by any of the sequences NCU00801, NCU00809, NCU08114, NCU00130, NCU00821, NCU04963, NCU06138, STL12/XUT6, SUT2, SUT3, XUT1, XUT3, NCU07705, NCU05137, NCU01517, NCU09133, or NCU10040.

Polynucleotides of the invention further include polynucleotides that encode conservatively modified variants of polypeptides encoded by the genes listed above. "Conservatively modified variants" as used herein include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Polynucleotides of the invention further include polynucleotides that encode homologs or orthologs of polypeptides encoded by any of the genes listed in Table 10, in Supplemental Data, Dataset S1, page 3 in Tian et al., 2009; in Tables 14, 15, 16, 29; or in FIG. 76. "Homology" as used herein refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity. "Orthology" as used herein refers to genes in different species that derive from a common ancestor gene.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8):2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17):3389-3402 and Altschul et al. (1990) J. Mol Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22):10915-10919] alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

As described herein, polynucleotides of the invention include members of the Major Facilitator Superfamily sugar transporter family, including NCU00988, NCU10021, NCU04963, NCU06138, NCU00801, NCU08114, and NCU05853. Members of the Major Facilitator Superfamily (MFS) (Transporter Classification #2.A.1) of transporters almost always consist of 12 transmembrane α-helices, with an intracellular N- and C-terminus (S. S. Pao, I. T. Paulsen, M. H. Saier, Jr., *Microbiol Mol Biol Rev* 62, 1 (March, 1998)). While the primary sequence of MFS transporters varies widely, all are thought to share the tertiary structure of the *E. coli* lactose permease (LacY) (J. Abramson et al., *Science* 301, 610 (Aug. 1, 2003)), and the *E. coli* Pi/glycerol-3-phospate (GlpT) (Y. Huang, M. J. Lemieux, J. Song, M. Auer, D. N. Wang, *Science* 301, 616 (Aug. 1, 2003)). In these examples the six N- and C-terminal helices form two distinct domains connected by a long cytoplasmic loop between helices 6 and 7. This symmetry corresponds to a duplication event thought to have given rise to the MFS. Substrate binds within a hydrophilic cavity formed by helices 1, 2, 4, and 5 of the N-terminal domain, and helices 7, 8, 10, and 11 of the C-terminal domain. This cavity is stabilized by helices 3, 6, 9, and 12.

The Sugar Transporter family of the MFS (Transporter Classification #2.A.1.1) is defined by motifs found in transmembrane helices 6 and 12 (PESPR (SEQ ID NO: 9)/PETK (SEQ ID NO: 10)), and loops 2 and 8 (GRR/GRK) (M. C. Maiden, E. O. Davis, S. A. Baldwin, D. C. Moore, P. J. Henderson, Nature 325, 641 (Feb. 12-18, 1987)). The entire Hidden Markov Model (HMM) for this family can be viewed at pfam.janelia.org/family/PF00083#tabview=tab3. PROSITE (N. Hulo et al., *Nucleic Acids Res* 34, D227 (Jan. 1, 2006)) uses two motifs to identify members of this family. The first is [LIVMSTAG]-[LIVMFSAG]-{SH}-{RDE}-[LIVMSA]-[DE]-{TD}-[LIVMFYWA]-G-R-[RK]-x(4,6)-[GSTA] (SEQ ID NO: 11). The second is [LIVMF]-x-G-[LIVMFA]-{V}-x-G-{KP}-x(7)-[LIFY]-x(2)-[EQ]-x(6)-[RK] (SEQ ID NO: 12). As an example of how to read a PROSITE motif, the following motif, [AC]-x-V-x(4)-{ED}, is translated as: [Ala or Cys]-any-Val-any-any-any-any-{any but Glu or Asp} (SEQ ID NO: 13).

As described herein, NCU00801, NCU00809, NCU08114, XP_001268541.1, and LAC2 were discovered to encode polypeptides that transport cellodextrins. Further, alanine scanning experiments and sequence analyses were used to determine that a recombinant polypeptide containing 12 transmembrane α-helices, and one or more of the sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 encodes a polypeptide that transports cellodextrin.

Thus, in one aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 1 comprises SEQ ID NO: 1. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 2 comprises SEQ ID NO: 2. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and a loop connecting transmembrane α-helix 2 and transmembrane α-helix 3 comprises SEQ ID NO: 3. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 5 comprises SEQ ID NO: 4. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 6 comprises SEQ ID NO: 5. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and sequence between transmembrane α-helix 6 and transmembrane α-helix 7 comprises SEQ ID NO: 6. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 7 comprises SEQ ID NO: 7. In another aspect, the invention provides a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, and transmembrane α-helix 10 and transmembrane α-helix 11 and the sequence between them comprise SEQ ID NO: 8.

Each of the above described aspects may be combined in any number of combinations. A polynucleotide according to any of these aspects may encode a polypeptide containing 1, 2, 3, 4, 5, 6, or 7 of any of SEQ ID NOs: 1-8, or the polypeptide may contain all of SEQ ID NOs: 1-8. For example, a polynucleotide may encode a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 1 comprises SEQ ID NO: 1, a loop connecting transmembrane α-helix 2 and transmembrane α-helix 3 comprises SEQ ID NO: 3, and transmembrane α-helix 7 comprises SEQ ID NO: 7. Or, in another example, a polynucleotide may encode a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 2 comprises SEQ ID NO: 2, transmembrane α-helix 3 comprises SEQ ID NO: 3, transmembrane α-helix 6 comprises SEQ ID NO: 5, and transmembrane α-helix 10 and transmembrane α-helix 11 and the sequence between them comprise SEQ ID NO: 8.

In certain embodiments of the above described aspects, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114.

As further described herein, NCU08221 and STL12/XUT6 were discovered to encode polypeptides that transport xylose. XUT1 was discovered to encode a polypeptide that transports arabinose. NCU06138 was discovered to encode a polypeptide that transports arabinose or glucose. SUT2, SUT3, and XUT3 were discovered to encode polypeptides that transport xylose or glucose. NCU04963 was discovered to encode a polypeptide that transports xylose, arabinose, or glucose. In preferred embodiments, polynucleotides of the invention include recombinant polynucleotides encoding a NCU08221 or STL12/XUT6 polypeptide, where the polypeptide transports xylose. In other preferred embodiments, polynucleotides of the invention include recombinant polynucleotides encoding a XUT1 polypeptide, where the polypeptide transports arabinose. In other preferred embodiments, polynucleotides of the invention include recombinant polynucleotides encoding a NCU06138 polypeptide, where the polypeptide transports arabinose or glucose. In other preferred embodiments, polynucleotides of the invention include recombinant polynucleotides encoding a SUT2, SUT3, or XUT3 polypeptide, where the polypeptide transports xylose or glucose. In other preferred embodiments, polynucleotides of the invention include recombinant polynucleotides encoding a NCU04963 polypeptide, where the polypeptide transports xylose, arabinose, or glucose.

The polynucleotides of the invention that encode polypeptides encoded by NCU07705 are predicted by FunCat (Ruepp, 2004; webpage broad.mit.edu/annotation/genome/neurospora/Home.html) to encode an unclassified protein. However, BLAST analysis of the polypeptide encoded by NCU07705 revealed that the polypeptide has high similarity to many C6 zinc finger domain containing transcription factors (see FIG. 1; a list of exemplary homologs can be found in FIG. 23 of related U.S. Appl. No. 61/271,833). Polynucleotides of the invention include polynucleotides that encode these homologs of the polypeptide encoded by NCU07705 or any other homologs identified with any methods known in the art.

In another aspect of the invention, polynucleotides of the invention include those polynucleotides that encode polypeptides encoded by NCU05137. FunCat classifies the polypeptide encoded by NCU05137 to be an unclassified protein. However, NCU05137 is highly conserved in the genomes of a number of filamentous ascomycete fungi (see FIG. 2). Polynucleotides of the invention include polynucleotides that encode these homologs of the polypeptide encoded by NCU05137 or any other homologs identified with any methods known in the art.

In another aspect of the invention, polynucleotides of the invention include those polynucleotides that encode polypeptides encoded by NCU01517, NCU09133, or NCU10040. FunCat classifies the polypeptide encoded by NCU01517 to be a glucoamylase precursor. FunCat classifies the polypeptides encoded by NCU09133 and NCU10040 to be unclassified proteins. Polynucleotides of the invention include polynucleotides that encode these homologs of the polypeptide encoded by NCU01517, NCU09133, or NCU10040 or any other homologs identified with any methods known in the art.

Predicted functions of these polypeptides can be confirmed by performing functional analyses of the polynucleotide and its encoded protein. These analyses may include, for example, phenotypic analysis of strains containing deletions of the polynucleotide, genetic complementation experiments, phenotypic analysis of strains over expressing a wild-type copy of the polynucleotide, expression and purification of a recombinant form of the polypeptide, and subsequent characterization of the biochemical properties and activity of the recombinant polypeptide.

Sequences of the polynucleotides of the invention are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature [e.g., in Matteucci et al., (1980) Tetrahedron Lett 21:719-722; U.S. Pat. Nos. 4,500,707; 5,436,327; and 5,700,637]. In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each polynucleotide of the invention can be incorporated into an expression vector. "Expression vector" or "vector" refers to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

Incorporation of the individual polynucleotides may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a polynucleotide having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired polynucleotide are often cleaved with the same restriction enzyme, thereby assuring that the ends of the expression vector and the ends of the polynucleotide are complementary to each other. In addition, DNA linkers maybe used to facilitate linking of nucleic acids sequences into an expression vector.

A series of individual polynucleotides can also be combined by utilizing methods that are known to those having ordinary skill in the art (e.g., U.S. Pat. No. 4,683,195).

For example, each of the desired polynucleotides can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual polynucleotides may be "spliced" together and subsequently transduced into a host cell simultaneously. Thus, expression of each of the plurality of polynucleotides is affected.

Individual polynucleotides, or "spliced" polynucleotides, are then incorporated into an expression vector. The invention is not limited with respect to the process by which the polynucleotide is incorporated into the expression vector. Those of ordinary skill in the art are familiar with the necessary steps for incorporating a polynucleotide into an expression vector. A typical expression vector contains the desired polynucleotide preceded by one or more regulatory regions, along with a ribosome binding site, e.g., a nucleotide sequence that is 3-9 nucleotides in length and located 3-11 nucleotides upstream of the initiation codon in *E. coli*. See Shine and Dalgarno (1975) Nature 254(5495):34-38 and Steitz (1979) Biological Regulation and Development (ed. Goldberger, R. F.), 1:349-399 (Plenum, New York).

The term "operably linked" as used herein refers to a configuration in which a control sequence is placed at an appropriate position relative to the coding sequence of the DNA sequence or polynucleotide such that the control sequence directs the expression of a polypeptide.

Regulatory regions include, for example, those regions that contain a promoter and an operator. A promoter is operably linked to the desired polynucleotide, thereby initiating transcription of the polynucleotide via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (Lad repressor protein changes conformation when contacted with lactose, thereby preventing the Lad repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter (see de Boer et al., (1983) Proc Natl Acad Sci USA 80(1):21-25). As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSClOl, pBR322, pBBRlMCS-3, pUR, pEX, pMRlOO, pCR4, pBAD24, pUC19; bacteriophages, such as Ml 3 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Host Cells of the Invention

The invention herein relates to host cells containing recombinant polynucleotides encoding polypeptides where the polypeptides transport cellodextrin or a pentose into the cell. Further described herein are methods of increasing transport of cellodextrin into a host cell, methods of increasing growth of a host cell on a medium containing cellodextrin, methods of co-fermenting cellulose-derived and hemicellulose-derived sugars, and methods of making hydrocarbons or hydrocarbon derivatives by providing a host cell containing a recombinant polynucleotide encoding a polypeptide where the polypeptide transports cellodextrin into the cell. Further described herein are methods of increasing transport of a pentose into a host cell, methods of increasing growth of a host cell on a medium containing pentose sugars, and methods of making hydrocarbons or hydrocarbon derivatives by providing a host cell containing a recombinant polynucleotide encoding a polypeptide where the polypeptide transports a pentose into the cell.

"Host cell" and "host microorganism" are used interchangeably herein to refer to a living biological cell that can be transformed via insertion of recombinant DNA or RNA. Such recombinant DNA or RNA can be in an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

Any prokaryotic or eukaryotic host cell may be used in the present invention so long as it remains viable after being transformed with a sequence of nucleic acids. Preferably, the host cell is not adversely affected by the transduction of the necessary nucleic acid sequences, the subsequent expression of the proteins (e.g., transporters), or the resulting intermediates. Suitable eukaryotic cells include, but are not limited to, fungal, plant, insect or mammalian cells.

In preferred embodiments, the host is a fungal strain. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In particular embodiments, the fungal host is a yeast strain. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In a more preferred embodiment, the yeast host is a *Candida, Hansenula, Kluyveromyces, Pichia, Saccharomyces, Schizosaccharomyces*, or *Yarrowia* strain.

In certain embodiments, the yeast host is a *Saccharomyces carlsbergensis* (Todkar, 2010), *Saccharomyces cerevisiae* (Duarte et al., 2009), *Saccharomyces diastaticus, Saccharomyces douglasii, Saccharomyces kluyveri, Saccharomyces norbensis, Saccharomyces* monacensis (GB-Analysts Reports, 2008), *Saccharomyces bayanus* (Kristen Publicover, 2010), *Saccharomyces pastorianus* (Nakao et al., 2007), *Saccharomyces pombe* (Mousdale, 2008), or *Saccharomyces oviformis* strain. In other preferred embodiments, the yeast host is *Kluyveromyces lactis* (O. W. Merten, 2001), *Kluyveromyces fragilis* (Pestal et al., 2006; Siso, 1996), *Kluyveromyces marxiamus* (K. Kourkoutas et al., 2008), *Pichia stipitis* (Almeida et al., 2008), *Candida shehatae* (Ayhan Demirbas, 2003), or *Candida tropicalis* (Jamai et al., 2006). In other embodiments, the yeast host may be *Yarrowia lipolytica* (Biryukova E. N., 2009), *Brettanomyces custersii* (Spindler D. D. et al., 1992), or *Zygosaccharomyces roux* (Chaabane et al., 2006).

In another particular embodiment, the fungal host is a filamentous fungal strain. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In preferred embodiments, the filamentous fungal host is, but not limited to, an *Acremonium, Aspergillus, Fusarium, Humicola, Mucor, Myceliophthora, Neurospora, Penicillium, Scytalidium, Thielavia, Tolypocladium*, or *Trichoderma* strain.

In certain embodiments, the filamentous fungal host is an *Aspergillus awamori, Aspergillus foetidus, Aspergillus japonicus, Aspergillus nidulans, Aspergillus niger*, or *Aspergillus oryzae* strain. In other embodiments, the filamentous fungal host is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* strain. In yet other preferred embodiments, the filamentous fungal host is a *Humicola insolens, Humicola lanuginosa, Mucor miehei, Myceliophthora thermophila, Neurospora crassa, Penicillium purpurogenum, Scytalidium thermophilum, Sporotrichum thermophile* (Topakas et al., 2003), or *Thielavia terrestris* strain. In a further embodiment, the filamentous fungal host is a *Trichoderma harzianum, Trichoderma koningii, Trichoderma longibrachiatum, Trichoderma reesei*, or *Trichoderma viride* strain.

In other preferred embodiments, the host cell is prokaryotic, and in certain embodiments, the prokaryotes are *E. coli* (Dien, B. S. et al., 2003; Yomano, L. P. et al., 1998; Moniruzzaman et al., 1996), *Bacillus subtilis* (Susana Romero et al., 2007), *Zymomonas mobilis* (B. S. Dien et al, 2003; Weuster Botz, 1993; Alterthum and Ingram, 1989), *Clostridium* sp. (Zeikus, 1980; Lynd et al., 2002; Demain et al., 2005), *Clostridium phytofermentans* (Leschine S., 2010), *Clostridium thermocellum* (Lynd et al., 2002), *Clostridium beijerinckii* (Giles Clark, 2008), *Clostridium acetobutylicum* (Moorella thermoacetica) (Huang W. C. et al., 2004; Dominik et al., 2007), *Thermoanaerobacterium saccharolyticum* (Marietta Smith, 2009), or *Klebsiella oxytoca* (Dien, B. S. et al., 2003; Zhou et al., 2001; Brooks and Ingram, 1995). In other embodiments, the prokaryotic host cells are *Carboxydocella* sp. (Dominik et al., 2007), *Corynebacterium glutamicum* (Masayuki Inui, et al., 2004), *Enterobacteriaceae* (Ingram et al., 1995), *Erwinia chrysanthemi* (Zhou and Ingram, 2000; Zhou et al., 2001), *Lactobacillus* sp. (McCaskey, T. A., et al., 1994), *Pediococcus acidilactici* (Zhou, S. et al., 2003), *Rhodopseudomonas capsulata* (X. Y. Shi et al., 2004), *Streptococcus lactis* (J. C. Tang et al., 1988), *Vibrio furnissii* (L. P. Wackett, 2010), *Vibrio furnissii* M1 (Park et al, 2001), *Caldicellulosiruptor saccharolyticus* (Z. Kadar et al., 2004), or *Xanthomonas campestris* (S. T. Yang et al., 1987). In other embodiments, the host cells are cyanobacteria. Additional examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis*, and *Paracoccus* taxonomical classes.

In especially preferred embodiments of the invention, the host cell is *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, or *Bacillus subtilis. Saccharomyces* sp. may include Industrial *Saccharomyces* strains. Argueso et al. discuss the genome structure of an Industrial *Saccharomyces* strain commonly used in bioethanol production as well as specific gene polymorphisms that are important for bioethanol production (Genome Research, 19: 2258-2270, 2009).

The host cells of the present invention may be genetically modified in that recombinant nucleic acids have been introduced into the host cells, and as such the genetically modified host cells do not occur in nature. The suitable host cell is one capable of expressing one or more nucleic acid constructs encoding one or more proteins for different functions.

"Recombinant nucleic acid" or "heterologous nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid. Specifically, the present invention describes the introduction of an expression vector into a host cell, wherein the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant.

In some embodiments, the host cell naturally produces any of the proteins encoded by the polynucleotides of the invention. The genes encoding the desired proteins may be heterologous to the host cell or these genes may be endogenous to the host cell but are operatively linked to heterologous promoters and/or control regions which result in the higher expression of the gene(s) in the host cell. In other embodiments, the host cell does not naturally produce the desired proteins, and comprises heterologous nucleic acid constructs capable of expressing one or more genes necessary for producing those molecules.

"Endogenous" as used herein with reference to a nucleic acid molecule or polypeptide and a particular cell or microorganism refers to a nucleic acid sequence or peptide that is in the cell and was not introduced into the cell using recombinant engineering techniques; for example, a gene that was present in the cell when the cell was originally isolated from nature.

"Genetically engineered" or "genetically modified" refer to any recombinant DNA or RNA method used to create a prokaryotic or eukaryotic host cell that expresses a protein at elevated levels, at lowered levels, or in a mutated form. In other words, the host cell has been transfected, transformed, or transduced with a recombinant polynucleotide molecule, and thereby been altered so as to cause the cell to alter expression of a desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetically engineering techniques include but are not limited to expression vectors, targeted homologous recombination and gene activation (see, for example, U.S. Pat. No. 5,272,071 to Chappel) and transactivation by engineered transcription factors (see, for example, Segal et al., (1999) Proc Natl Acad Sci USA 96(6): 2758-2763).

Genetic modifications that result in an increase in gene expression or function can be referred to as amplification, overproduction, overexpression, activation, enhancement, addition, or up-regulation of a gene. More specifically, reference to increasing the action (or activity) of enzymes or other proteins discussed herein generally refers to any genetic modification of the host cell in question which results in increased expression and/or functionality (biological activity) of the enzymes or proteins and includes higher activity or action of the proteins (e.g., specific activity or in vivo enzymatic activity), reduced inhibition or degradation of the proteins, and overexpression of the proteins. For example, gene copy number can be increased, expression levels can be increased by use of a promoter that gives higher levels of expression than that of the native promoter, or a gene can be altered by genetic engineering or classical mutagenesis to increase the biological activity of an enzyme or action of a protein. Combinations of some of these modifications are also possible.

Genetic modifications which result in a decrease in gene expression, in the function of the gene, or in the function of the gene product (i.e., the protein encoded by the gene) can be referred to as inactivation (complete or partial), deletion, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action of proteins discussed herein generally refers to any genetic modification in the host cell in question, which results in decreased expression and/or functionality (biological activity) of the proteins and includes decreased activity of the proteins (e.g., decreased transport), increased inhibition or degradation of the proteins as well as a reduction or elimination of expression of the proteins. For example, the action or activity of a protein of the present invention can be decreased by blocking or reducing the production of the protein, reducing protein action, or inhibiting the action of the protein. Combinations of some of these modifications are also possible. Blocking or reducing the production of a protein can include placing the gene encoding the protein under the control of a promoter that requires the presence of an inducing compound in the growth medium. By establishing conditions such that the inducer becomes depleted from the medium, the expression of the gene encoding the protein (and therefore, of protein synthesis) could be turned off. Blocking or reducing the action of a protein could also include using an excision technology approach similar to that described in U.S. Pat. No. 4,743,546, incorporated herein by reference. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In general, according to the present invention, an increase or a decrease in a given characteristic of a mutant or modified protein (e.g., enzyme activity, ability to transport compounds) is made with reference to the same characteristic of a wild-type (i.e., normal, not modified) protein that is derived from the same organism (from the same source or parent sequence), which is measured or established under the same or equivalent conditions. Similarly, an increase or decrease in a characteristic of a genetically modified host cell (e.g., expression and/or biological activity of a protein, or production of a product) is made with reference to the same characteristic of a wild-type host cell of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the host cell is measured, as well as the type of assay used, the host cell that is evaluated, etc. As discussed above, equivalent conditions are conditions (e.g., culture conditions) which are similar, but not necessarily identical (e.g., some conservative changes in conditions can be tolerated), and which do not substantially change the effect on cell growth or enzyme expression or biological activity as compared to a comparison made under the same conditions.

Preferably, a genetically modified host cell that has a genetic modification that increases or decreases the activity of a given protein (e.g., a transporter, an enzyme) has an increase or decrease, respectively, in the activity or action (e.g., expression, production and/or biological activity) of the protein, as compared to the activity of the wild-type protein in a wild-type host cell, of at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, or any percentage, in whole integers between 5% and 100% (e.g., 6%, 7%, 8%, etc.). The same differences are preferred when comparing an isolated modified nucleic acid molecule or protein directly to the isolated wild-type nucleic acid molecule or protein (e.g., if the comparison is done in vitro as compared to in vivo).

In another aspect of the invention, a genetically modified host cell that has a genetic modification that increases or decreases the activity of a given protein (e.g., a transporter, an enzyme) has an increase or decrease, respectively, in the activity or action (e.g., expression, production and/or biological activity) of the protein, as compared to the activity of the wild-type protein in a wild-type host cell, of at least about 2-fold, and more preferably at least about 5-fold, and more preferably at least about 10-fold, and more preferably about 20-fold, and more preferably at least about 30-fold, and more preferably at least about 40-fold, and more preferably at least about 50-fold, and more preferably at least about 75-fold, and more preferably at least about 100-fold, and more preferably at least about 125-fold, and more preferably at least about 150-fold, or any whole integer increment starting from at least about 2-fold (e.g., 3-fold, 4-fold, 5-fold, 6-fold, etc.).

Host Cell Components

In one aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 1 comprises SEQ ID NO: 1. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 2 comprises SEQ ID NO: 2. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where the loop connecting transmembrane α-helix 2 and transmembrane α-helix 3 comprises SEQ ID NO: 3. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 5 comprises SEQ ID NO: 4. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 6 comprises SEQ ID NO: 5. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where sequence between transmembrane α-helix 6 and transmembrane α-helix 7 comprises SEQ ID NO: 6. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 7 comprises SEQ ID NO: 7. In another aspect, host cells of the invention contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 10 and transmembrane α-helix 11 and the sequence between them comprise SEQ ID NO: 8.

Each of the above described aspects may be combined in any number of combinations. A host cell may contain a polynucleotide encoding a polypeptide containing 1, 2, 3, 4, 5, 6, or 7 of any of SEQ ID NOs: 1-8, or the polypeptide may contain all of SEQ ID NOs: 1-8. For example, a host cell may contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 1 comprises SEQ ID NO: 1, a loop connecting transmembrane α-helix 2 and transmembrane α-helix 3 comprises SEQ ID NO: 3, and transmembrane α-helix 7 comprises SEQ ID NO: 7. Or, in another example, a host cell may contain a polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, α-helix 12, where transmembrane α-helix 2 comprises SEQ ID NO: 2, transmembrane α-helix 3 comprises SEQ ID NO: 3, transmembrane α-helix 6 comprises SEQ ID NO: 5, and transmembrane α-helix 10 and transmembrane α-helix 11 and the sequence between them comprise SEQ ID NO: 8.

In certain embodiments of the above described aspects, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114.

In preferred embodiments, the host cells further contain a polynucleotide, where the polynucleotide encodes a catalytic domain of a β-glucosidase. As used herein, β-glucosidase refers to a 13-D-glucoside glucohydrolase (E.C. 3.2.1.21), which catalyzes the hydrolysis of terminal non-reducing β-D-glucose residues with the release of β-D-glucose. A catalytic domain of β-glucosidase has β-glucosidase activity as determined, for example, according to the basic procedure described by Venturi et al., 2002. A catalytic domain of a β-glucosidase is any domain that catalyzes the hydrolysis of terminal non-reducing residues in β-D-glucosides with release of glucose. In preferred embodiments, the β-glucosidase is a glycosyl hydrolase family 1 member. Members of this group can be identified by the motif, [LIVMFSTC]-[LIVFYS]-[LIV]-[LIVMST]-E-N-G-[LIVMFAR]-[CSAGN] (SEQ ID NO: 14). Here, E is the catalytic glutamate (webpage expasy.org/cgi-bin/prosite-search-ac?PD0000495). In certain embodiments, the polynucleotide encoding a catalytic domain of β-glucosidase is heterologous to the host cell. In preferred embodiments, the catalytic domain of β-glucosidase is located intracellularly in the host cell. In preferred embodiments, the β-glucosidase is from *N. crassa*, and in particularly preferred embodiments, the β-glucosidase is NCU00130. In certain embodiments, the β-glucosidase may be an ortholog of NCU00130. Examples of orthologs of NCU00130 include, without limitation, *T. melanosporum*, CAZ82985.1; *A. oryzae*, BAE57671.1; *P. placenta*, EED81359.1; *P. chrysosporium*, BAE87009.1; *Kluyveromyces lactis*, CAG99696.1; *Laccaria bicolor*, EDR09330; *Clavispora lusitaniae*, EEQ37997.1; and *Pichia stipitis*, ABN67130.1. Other β-glucosidases could be used include those from the glycosyl hydrolase family 3. These β-glucosidases can be identified by the following motif according to PROSITE: [LIVM](2)-[KR]-x-[EQKRD]-x(4)-G-[LIVMFTC]-[LIVT]-[LIVMF]-[ST]-D-x(2)-[SGADNIT] (SEQ ID NO: 15). Here D is the catalytic aspartate. Typically, any β-glucosidase may be used that contains the conserved domain of β-glucosidase/6-phospho-β-glucosidase/β-galactosidase found in NCBI sequence COG2723. Catalytic domains from specific β-glucosidases may be preferred depending on the cellodextrin transporter contained in the host cell.

In certain embodiments, the host cell contains one or more polynucleotides, where the one or more polynucleotides encode one or more enzymes involved in pentose utilization. The one or more polynucleotides may be endogenous or heterologous to the host cell. Pentose, as used herein, refers to any monosaccharide with five carbon atoms. Examples of pentoses include, without limitation, xylose, arabinose, mannose, galactose, and rhamnose. The one or more enzymes involved in pentose utilization may include, for example, L-arabinose isomerase, L-ribulokinase, L-ribulose-5-P 4 epimerase, xylose isomerase, xylulokinase, aldose reductase, L-arabitinol 4-dehydrogenase, L-xylulose reductase, and xylitol dehydrogenase in any combination. These enzymes may come from any organism that naturally metabolizes pentose sugars. Examples of such organisms include, for example, *Kluyveromyces* sp., *Zymomonas* sp., *E. coli*, *Clostridium* sp., and *Pichia* sp.

Examples 12-15 describe ways in which the pentose utilization pathway in the host cell may be improved or made to be more efficient. Strain background of a host cell can affect the efficiency of its pentose utilization pathway. In embodiments of the invention where the host cell is a *Saccharomyces* sp., preferred pentose utilizing strains include DA24-16 (see Example 13) and L2612 (see Example 16). Other host cells containing polynucleotides encoding enzymes involved in pentose utilization include a DuPont *Zymomonas* strain (WO 2009/058927) and a *Saccharomyces* strain (U.S. Pat. No. 5,789,210).

In certain embodiments of the invention, the host cell contains a recombinant polynucleotide encoding a pentose transporter. In certain embodiments, pentose transporters include those transporters discovered and described herein, including NCU00821, NCU04963, NCU06138, STL12/XUT6, SUT2, SUT3, XUT1, and XUT3 (see Example 11). In other embodiments, pentose transporters may include Gxs1 from *C. intermedia*, Aut1 from *P. stipitis*, Xylhp from *D. hansenii* (Nobre et al., 1999), xylose transporter from *K. marxianus* (Stambuk et al., 2003), LAT1 and LAT2 from *Ambrosiozyma monospora* (EMBL AY923868 and AY923869, respectively, R. Verho et al.), ART1 from *C. arabinofermentans* (Fonseca et al., 2007), KmLAT1 from *K. marxiamus* (Knoshaug et al., 2007), PgLAT2 from *P. guilliermondii* (Knoshaug et al., 2007), and araT from *P. stipitis* (Boles & Keller, 2008).

Methods of Producing and Culturing Host Cells of the Invention

The invention herein relates to host cells containing recombinant polynucleotides encoding polypeptides where the polypeptide transports cellodextrin or a pentose into the cell. Further described herein are methods of increasing transport of cellodextrin into a host cell, methods of increasing growth of a host cell on a medium containing cellodextrin, methods of co-fermenting cellulose-derived and hemicellulose-derived sugars, and methods of making hydrocarbons or hydrocarbon derivatives by providing a host cell containing a recombinant polynucleotide encoding a polypeptide where the polypeptide transports cellodextrin into the cell. Further described herein are methods of increasing transport of a pentose into a host cell, methods of increasing growth of a host cell on a medium containing pentose sugars, and methods of making hydrocarbons or hydrocarbon derivatives by providing a host cell containing a recombinant polynucleotide encoding a polypeptide where the polypeptide transports a pentose into the cell.

Methods of producing and culturing host cells of the invention may include the introduction or transfer of expression vectors containing the recombinant polynucleotides of the invention into the host cell. Such methods for transferring expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids which together contain the total DNA to be introduced into the genome of the host, or a transposon may be used.

The vectors preferably contain one or more selectable markers which permit easy selection of transformed hosts. A selectable marker is a gene the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, and hyg genes.

Suitable markers for yeast hosts are, for example, ADE2, HIS3, LEU2, LYS2, MET3, TRP1, and URA3. Selectable markers for use in a filamentous fungal host include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in *Aspergillus* are the amdS and pyrG genes of *Aspergillus nidulans* or *Aspergillus oryzae* and the bar gene of *Streptomyces hygroscopicus*. Preferred for use in *Trichoderma* are bar and amdS.

The vectors preferably contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further comprise an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo. Examples of origins of replication for use in a yeast host are the 2 micron origin of replication, ARS1, ARS4, the combination of ARS1 and CEN3, and the combination of ARS4 and CEN6. Examples of origins of replication useful in a filamentous fungal cell are AMA1 and ANS1 (Gems et al., 1991; Cullen et al., 1987; WO 00/24883). Isolation of the AMA1 gene and construction of plasmids or vectors comprising the gene can be accomplished according to the methods disclosed in WO 00/24883.

For other hosts, transformation procedures may be found, for example, in Jeremiah D. Read, et al., *Applied and Environmental Microbiology*, August 2007, p. 5088-5096, for *Kluyveromyces*, in Osvaldo Delgado, et al., *FEMS Microbiology Letters* 132, 1995, 23-26, for *Zymomonas*, in U.S. Pat. No. 7,501,275 for *Pichia stipitis*, and in WO 2008/040387 for *Clostridium*.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. Methods of the invention may include culturing the host cell such that recombinant nucleic acids in the cell are expressed. For microbial hosts, this process entails culturing the cells in a suitable medium. Typically cells are grown at 35° C. in appropriate media. Preferred growth media in the present invention include, for example, common commercially prepared media such as Luria Bertani (LB) broth, Sabouraud Dextrose (SD) broth or Yeast medium (YM) broth. Other defined or synthetic growth media may also be used and the appropriate medium for growth of the particular host cell will be known by someone skilled in the art of microbiology or fermentation science. Temperature ranges and other conditions suitable for growth are known in the art (see, e.g., Bailey and 011 is 1986).

According to some aspects of the invention, the culture media contains a carbon source for the host cell. Such a "carbon source" generally refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, etc. These include, for example, various monosaccharides such as glucose, oligosaccharides, polysaccharides, a biomass polymer such as cellulose or hemicellulose, xylose, arabinose, disaccharides, such as sucrose, saturated or unsaturated fatty acids, succinate, lactate, acetate, ethanol, etc., or mixtures thereof. The carbon source can additionally be a product of photosynthesis, including, but not limited to glucose.

In preferred embodiments, the carbon source is a biomass polymer such as cellulose or hemicellulose. "A biomass polymer" as described herein is any polymer contained in biological material. The biological material may be living or dead. A biomass polymer includes, for example, cellulose, xylan, xylose, hemicellulose, lignin, mannan, and other materials commonly found in biomass. Non-limiting examples of sources of a biomass polymer include grasses (e.g., switchgrass, *Miscanthus*), rice hulls, bagasse, cotton, jute, hemp, flax, bamboo, sisal, abaca, straw, leaves, grass clippings, corn stover, corn cobs, distillers grains, legume plants, sorghum, sugar cane, sugar beet pulp, wood chips, sawdust, and biomass crops (e.g., *Crambe*).

In addition to an appropriate carbon source, media must contain suitable minerals, salts, cofactors, buffers and other components, known to those skilled in the art, suitable for the growth of the cultures and promotion of the enzymatic pathways necessary for the fermentation of various sugars and the production of hydrocarbons and hydrocarbon derivatives. Reactions may be performed under aerobic or anaerobic conditions where aerobic, anoxic, or anaerobic conditions are preferred based on the requirements of the microorganism. As the host cell grows and/or multiplies, expression of the enzymes, transporters, or other proteins necessary for growth on various sugars or biomass polymers, sugar fermentation, or synthesis of hydrocarbons or hydrocarbon derivatives is affected.

Methods of Increasing Transport of a Sugar into a Cell

The present invention provides methods of increasing transport of a sugar into a cell. In one aspect, the invention provides a method of transporting cellodextrin into a cell, including a first step of providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, and α-helix 12, where one or more of the following is true: transmembrane α-helix 1 comprises SEQ ID NO: 1, transmembrane α-helix 2 comprises SEQ ID NO: 2, the loop connecting transmembrane α-helix 2 and transmembrane α-helix 3 comprises SEQ ID NO: 3, transmembrane α-helix 5 comprises SEQ ID NO: 4, transmembrane α-helix 6 comprises SEQ ID NO: 5, sequence between transmembrane α-helix 6 and transmembrane α-helix 7 comprises SEQ ID NO: 6, transmembrane α-helix 7 comprises SEQ ID NO: 7, and transmembrane α-helix 10 and transmembrane α-helix 11 and the sequence between them comprise SEQ ID NO: 8. The method includes a second step of culturing the cell such that the recombinant polynucleotide is expressed, where expression of the recombinant polynucleotide results in increased transport of cellodextrin into the cell compared with a cell that does not contain the recombinant polynucleotide. Transport of cellodextrin into a cell may be measured by any method known to one of skill in the art, including those methods described in Example 9 such as measuring uptake of [$^3$H]-cellobiose into cells or measuring the ability of an *S. cerevisiae* host cell to grow when cellobiose is the sole carbon source. Typically, the host cell containing the recombinant polynucleotide and the host cell that does not contain the recombinant polynucleotide will otherwise be identical in genetic background.

In certain embodiments, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments, the host cell also contains a recombinant polynucleotide encoding a catalytic domain of a β-glucosidase. Such embodiments are useful for host cells lacking the endogenous ability to utilize cellodextrins. Preferably, the catalytic domain of the β-glucosidase is intracellular. In preferred embodiments, the β-glucosidase is from *Neurospora crassa*. In particularly preferred embodiments, the β-glucosidase is encoded by NCU00130.

In methods of increasing transport of cellodextrin into a cell, the cell may be cultured in a medium containing a cellulase-containing enzyme mixture from an altered organism, where the mixture has reduced β-glucosidase activity compared to a cellulase-containing mixture from an unaltered organism. The organism may be altered to reduce the expression of β-glucosidase, such as by mutation of a gene encoding β-glucosidase or by targeted RNA interference or the like.

In another aspect, the invention provides a method of increasing transport of xylose into a cell, including the steps of providing a host cell, where the host cell contains a recombinant polynucleotide encoding a NCU00821 or STL12/XUT6 polypeptide, and culturing the cell such that the recombinant polynucleotide is expressed, where expression of the recombinant polynucleotide results in increased transport of xylose into the cell compared with a cell that does not contain the recombinant polynucleotide. In another aspect, the invention provides a method of increasing transport of arabinose into a cell, including the steps of providing a host cell, where the host cell contains a recombinant polynucleotide encoding a XUT1 polypeptide, and culturing the cell such that the recombinant polynucleotide is expressed, where expression of the recombinant polynucleotide results in increased transport of arabinose into the cell compared with a cell that does not contain the recombinant polynucleotide. In yet another aspect, the invention provides a method of increasing transport of arabinose or glucose into a cell, including the steps of providing a host cell, where the host cell contains a recombinant polynucleotide encoding a NCU06138 polypeptide, and culturing the cell such that the recombinant polynucleotide is expressed, where expression of the recombinant polynucleotide results in increased transport of arabinose or glucose into the cell compared with a cell that does not contain the recombinant polynucleotide. In yet another aspect the invention provides a method of increasing transport of xylose or glucose into a cell, including the steps of providing a host cell, where the host cell comprises a recombinant polynucleotide encoding a SUT2, SUT3, or XUT3 polypeptide, and culturing the cell such that the recombinant polynucleotide is expressed, where expression of the recombinant polynucleotide results in increased transport of xylose or glucose into the cell compared with a cell that does not contain the recombinant polynucleotide. In another aspect, the invention provides a method of increasing transport of xylose, arabinose, or glucose into a cell, including the steps of providing a host cell, where the host cell contains a recombinant polynucleotide encoding a NCU04963 polypeptide, and culturing the cell such that the recombinant polynucleotide is expressed, where expression of the recombinant polynucleotide results in increased transport of xylose, arabinose, or glucose into the cell compared with a cell that does not contain the recombinant polynucleotide.

Transport of xylose, arabinose, or glucose into a cell may be measured by any method known to one of skill in the art, including those methods described in Example 11. These methods include, for example, measuring D-xylose or L-arabinose transport by extracting accumulated D-xylose and xylitol or L-arabinose and arabinitol from the host cell using osmosis and analyzing it using high performance liquid chromatography and measuring glucose transport by using host cells lacking the ability to grow on glucose as a sole carbon source. Typically, the host cell containing the recombinant polynucleotide and the host cell that does not contain the recombinant polynucleotide will otherwise be identical in genetic background.

In certain embodiments, the host cell also contains one or more recombinant polynucleotides where the one or more polynucleotides encode one or more enzymes involved in pentose utilization. The one or more enzymes may be, for example, L-arabinose isomerase, L-ribulokinase, L-ribulose-5-P 4 epimerase, xylose isomerase, xylulokinase, aldose reductase, L-arabitinol 4-dehydrogenase, L-xylulose reductase, xylitol dehydrogenase, or any other pentose utilization enzymes known in the art.

Methods of Increasing Growth of a Cell

The present invention further provides methods of increasing the growth of a cell. In one aspect the invention provides methods of increasing growth of a cell, including a first step of providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, and α-helix 12, where one or more of the following is true: transmembrane α-helix 1 comprises SEQ ID NO: 1, transmembrane α-helix 2 comprises SEQ ID NO: 2, the loop connecting transmembrane α-helix 2 and transmembrane α-helix 3 comprises SEQ ID NO: 3, transmembrane α-helix 5 comprises SEQ ID NO: 4, transmembrane α-helix 6 comprises SEQ ID NO: 5, sequence between transmembrane α-helix 6 and transmembrane α-helix 7 comprises SEQ ID NO: 6, transmembrane α-helix 7 comprises SEQ ID NO: 7, and transmembrane α-helix 10 and transmembrane α-helix 11 and the sequence between them comprise SEQ ID NO: 8, and the polypeptide transports cellodextrin. The method includes a second step of culturing the host cell in a medium containing cellodextrin, where the host cell grows at a faster rate in the medium than a cell that does not contain the recombinant polynucleotide. The growth rate of a host cell may be measured by any method known to one of skill in the art. Typically, growth rate of a cell will be measured by evaluating cell concentration in suspension by optical density. Preferably, the host cell containing the recombinant polynucleotide and the host cell that does not contain the recombinant polynucleotide will otherwise be identical in genetic background. Media containing cellodextrins may have resulted from enzymatic treatment of biomass polymers such as cellulose.

In certain embodiments, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments, the host cell also contains a recombinant polynucleotide encoding a catalytic domain of a β-glucosidase. Such embodiments are useful for host cells lacking the endogenous ability to utilize cellodextrins. Preferably, the catalytic domain of the β-glucosidase is intracellular. In preferred embodiments, the β-glucosidase is from *Neurospora crassa*. In particularly preferred embodiments, the β-glucosidase is encoded by NCU00130.

In methods of increasing growth of a cell, the culturing medium may contain a cellulase-containing enzyme mixture from an altered organism, where the mixture has reduced β-glucosidase activity compared to a cellulase-containing mixture from an unaltered organism. The organism may be altered to reduce the expression of β-glucosidase, such as by mutation of a gene encoding β-glucosidase or by targeted RNA interference or the like.

In another aspect, the invention provides a method of increasing growth of a cell, including the steps of providing a host cell, where the host cell contains a recombinant polynucleotide where the polynucleotide encodes a NCU00821 or STL12/XUT6 polypeptide, and the polypeptide transports xylose, and culturing the host cell in a medium containing xylose, where the host cell grows at a faster rate in the medium than a cell that does not contain the recombinant polynucleotide. In another aspect the invention provides a method of increasing growth of a cell, including the steps of providing a host cell, where the host cell contains a recombinant polynucleotide where the polynucleotide encodes a XUT1 polypeptide, and the polypeptide transports arabinose, and culturing the host cell in a medium containing arabinose, where the host cell grows at a faster rate in the medium than a cell that does not contain the recombinant polynucleotide. In yet another aspect, the invention provides a method of increasing growth of a cell, including the steps of providing a host cell, where the host cell contains a recombinant polynucleotide where the polynucleotide encodes a NCU06138 polypeptide, and the polypeptide transports arabinose and glucose, and culturing the host cell in a medium containing arabinose or glucose, where the host cell grows at a faster rate in the medium than a cell that does not contain the recombinant polynucleotide. In another aspect, the invention provides a method of increasing growth of a cell, including the steps of providing a host cell, where the host cell contains a recombinant polynucleotide where the polynucleotide encodes a SUT2, SUT3, or XUT3 polypeptide, and the polypeptide transports xylose and glucose, and culturing the host cell in a medium containing xylose or glucose, where the host cell grows at a faster rate in the medium than a cell that does not contain the recombinant polynucleotide. In yet another aspect, the invention provides a method of increasing growth of a cell, including the steps of providing a host cell, where the host cell contains a recombinant polynucleotide where the polynucleotide encodes a NCU04963 polypeptide, and the polypeptide transports xylose, arabinose, and glucose, and culturing the host cell in a medium containing xylose, arabinose, or glucose, where the host cell grows at a faster rate in the medium than a cell that does not contain the recombinant polynucleotide.

The growth rate of a host cell may be measured by any method known to one of skill in the art. Typically, growth rate of a cell will be measured by evaluating cell concentration in suspension by optical density. Preferably, the host cell containing the recombinant polynucleotide and the host cell that does not contain the recombinant polynucleotide will otherwise be identical in genetic background. Media containing xylose or arabinose may have resulted from acid treatment of biomass polymers such as hemicellulose. Media containing glucose may have resulted from enzymatic treatment of biomass polymers such as cellulose.

In certain embodiments, the host cell also contains one or more recombinant polynucleotides where the one or more polynucleotides encode one or more enzymes involved in pentose utilization. The one or more enzymes may be, for example, L-arabinose isomerase, L-ribulokinase, L-ribulose-5-P 4 epimerase, xylose isomerase, xylulokinase, aldose reductase, L-arabitinol 4-dehydrogenase, L-xylulose reductase, xylitol dehydrogenase, or any other pentose utilization enzymes known in the art.

In one aspect, the invention provides methods of increasing growth of a cell on a biomass polymer. In preferred embodiments, the biomass polymer is cellulose. In other preferred embodiments, the biomass polymer is hemicellulose. According to one aspect of the invention, the method includes providing a host cell comprising a recombinant polynucleotide that encodes a NCU07705 polypeptide. According to another aspect of the invention, the method includes culturing the cell in a medium comprising the biomass polymer wherein the host cell grows at a faster rate in the medium than a cell that does not comprise the recombinant polynucleotide.

In another aspect of the invention, the invention provides a method of increasing growth of a cell, including the steps of providing a host cell, where the host cell contains a recombinant polynucleotide where the polynucleotide encodes a NCU01517, NCU09133, or NCU10040 polypeptide, and culturing the cell in a medium containing hemicellulose, where the host cell grows at a faster rate in the medium than a cell that does not contain the recombinant polynucleotide.

According to another aspect of the invention, the method includes providing a host cell comprising an endogenous polynucleotide that encodes a NCU05137 polypeptide. According to another aspect of the invention, the method includes inhibiting expression of the endogenous polynucleotide and culturing the cell in a medium comprising a biomass polymer wherein the host cell grows at a faster rate in the medium than a cell in which expression of the endogenous polynucleotide is not inhibited.

Methods of the invention may include culturing the host cell such that recombinant nucleic acids in the cell are expressed. For microbial hosts, this process entails culturing the cells in a suitable medium. Typically cells are grown at 35° C. in appropriate media. Preferred growth media in the present invention include, for example, common commercially prepared media such as Luria Bertani (LB) broth, Sabouraud Dextrose (SD) broth, or Yeast medium (YM) broth. Other defined or synthetic growth media may also be used and the appropriate medium for growth of the particular host cell will be known by someone skilled in the art of microbiology or fermentation science. Temperature ranges and other conditions suitable for growth are known in the art (see, e.g., Bailey and Ollis 1986).

The source of the biomass polymer in the medium may include, for example, grasses (e.g., switchgrass, *Miscanthus*), rice hulls, bagasse, cotton, jute, hemp, flax, bamboo, sisal, abaca, straw, leaves, grass clippings, corn stover, corn cobs, distillers grains, legume plants, sorghum, sugar cane, sugar beet pulp, wood chips, sawdust, and biomass crops (e.g., *Crambe*). In addition to a biomass polymer, the medium must contain suitable minerals, salts, cofactors, buffers and other components, known to those skilled in the art, suitable for the growth of the cultures. The rate of growth of the host cell may be measured by any methods known to one of skill in the art.

In certain embodiments of the invention, the expression of cellulases is increased in the host cell upon expression of a recombinant polynucleotide. "Cellulase" as used herein refers to a category of enzymes capable of hydrolyzing cellulose polymers to shorter cello-oligosaccharide oligomers, cellobiose, and/or glucose. Cellulases include, without limitation, exoglucanases, exocellobiohydrolases, endoglucanases, and glucosidases. Expression of cellulases may be measured by RT-PCR or other methods known in the art.

In certain embodiments of the invention, the expression of hemicellulases is increased in the host cell upon expression of a recombinant polynucleotide. "Hemicellulase" as used herein refers to a category of enzymes capable of hydrolyzing hemicellulose polymers. Hemicellulases include, without limitation, xylanases, mannanases, arabinases (both endo and exo kinds) and their corresponding glycosidases. Expression of hemicellulases may be measured by RT-PCR or other methods known in the art.

Inhibition of expression of the endogenous polynucleotide may be achieved, for example, by genetic modifications which result in a decrease in gene expression, in the function of the gene, or in the function of the gene product (i.e., the protein encoded by the gene) and can be referred to as inactivation (complete or partial), deletion, interruption, blockage, silencing, or down-regulation, or attenuation of expression of a gene. For example, a genetic modification in a gene which results in a decrease in the function of the protein encoded by such a gene can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action of proteins discussed herein generally refers to any genetic modification in the host cell in question which results in decreased expression and/or functionality (biological activity) of the proteins and includes decreased activity of the proteins (e.g., decreased transport), increased inhibition or degradation of the proteins, as well as a reduction or elimination of expression of the proteins. For example, the action or activity of a protein of the present invention can be decreased by blocking or reducing the production of the protein, reducing protein action, or inhibiting the action of the protein. Combinations of some of these modifications are also possible. Blocking or reducing the production of a protein can include placing the gene encoding the protein under the control of a promoter that requires the presence of an inducing compound in the growth medium. By establishing conditions such that the inducer becomes depleted from the medium, the expression of the gene encoding the protein (and therefore, of protein synthesis) could be turned off. Blocking or reducing the action of a protein could also include using an excision technology approach similar to that described in U.S. Pat. No. 4,743,546. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In certain embodiments of the invention, cellulase activity of the host cell is increased upon inhibiting expression of an endogenous polynucleotide. Cellulase activity may be measured as described in Example 5 and by any other methods known in the art.

In certain embodiments of the invention, hemicellulase activity of the host cell is increased upon inhibiting expression of an endogenous polynucleotide. Hemicellulase activity may be measured as described in Example 17 and by any other methods known in the art.

Methods of Co-Fermentation

One aspect of the present invention provides methods of co-fermenting cellulose-derived and hemicellulose-derived sugars. As used herein, co-fermentation refers to simultaneous utilization by a host cell of more than one sugar in the same vessel. The method includes the steps of providing a host cell, where the host cell contains a first recombinant polynucleotide encoding a cellodextrin transporter and a second recombinant polynucleotide encoding a catalytic domain of a β-glucosidase, and culturing the host cell in a medium containing a cellulose-derived sugar and a hemicellulose-derived sugar, where expression of the recombinant polynucleotides enables co-fermentation of the cellulose-derived sugar and the hemicellulose-derived sugar.

The first recombinant polynucleotide may encode any polypeptide that is capable of transporting cellodextrin into a cell. Cellodextrin transport may be measured by any method known to one of skill in the art, including the methods discussed in Example 9. In preferred embodiments, the first recombinant polynucleotide encodes a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, and α-helix 12, where one or more of the following is true: transmembrane α-helix 1 comprises SEQ ID NO: 1, transmembrane α-helix 2 comprises SEQ ID NO: 2, the loop connecting transmembrane α-helix 2 and transmembrane α-helix 3 comprises SEQ ID NO: 3, transmembrane α-helix 5 comprises SEQ ID NO: 4, transmembrane α-helix 6 comprises SEQ ID NO: 5, sequence between transmembrane α-helix 6 and transmembrane α-helix 7 comprises SEQ ID NO: 6, transmembrane α-helix 7 comprises SEQ ID NO: 7, and transmembrane α-helix 10 and transmembrane α-helix 11 and the sequence between them comprise SEQ ID NO: 8. Examples of such polypeptides include NCU00801, NCU00809, NCU08114, XP_001268541.1, and LAC2. In preferred embodiments, the first recombinant polypeptide encodes NCU00801.

The second recombinant polynucleotide may encode any catalytic domain capable of catalyzing the hydrolysis of terminal non-reducing residues in β-D-glucosides with release of glucose. Preferably, the β-glucosidase catalytic domain is located intracellularly in the host cell. In certain embodiments the source of the β-glucosidase domain is a *N. crassa* β-glucosidase. In preferred embodiments the source of the β-glucosidase domain is NCU00130. Catalytic domains from different sources may work best with different cellodextrin transporters.

In certain embodiments, the host cell also contains one or more recombinant polynucleotides where the one or more polynucleotides encode one or more enzymes involved in pentose utilization. Alternatively, one or more polynucleotides encoding one or more enzymes involved in pentose utilization may be endogenous to the host cell. The one or more enzymes may include, for example, L-arabinose isomerase, L-ribulokinase, L-ribulose-5-P 4 epimerase, xylose isomerase, xylulokinase, aldose reductase, L-arabitinol 4-dehydrogenase, L-xylulose reductase, xylitol dehydrogenase, or any other pentose-utilizing enzymes known to one of skill in the art.

In certain embodiments, the host cell contains a third recombinant polynucleotide where the polynucleotide encodes a pentose transporter. Alternatively, the host cell may contain an endogenous polynucleotide encoding a pentose transporter. In preferred embodiments, the pentose transporter transports xylose and/or arabinose into the cell. In certain embodiments, the third recombinant polynucleotide encodes a polypeptide such as NCU00821, NCU04963, NCU06138, STL12/XUT6, SUT2, SUT3, XUT1, or XUT3. The expression of a pentose transporter in the host cell may enhance the efficiency of co-fermentation if glucose is present along with a pentose sugar is the growth medium.

In methods of co-fermentation as described herein, cellulose-derived sugars preferably include cellobiose, cellotriose, and celltetraose, and hemicellulose-derived sugars preferably include xylose and arabinose. Typically, in order to prepare the cellulose-derived sugars and hemicellulose-derived sugars for co-fermentation by a host cell, lignocellulosic biomass is first pretreated to alter its structure and allow for better enzymatic hydrolysis of cellulose. Pretreatment may include physical or chemical methods, including, for example, ammonia fiber/freeze explosion, the lime method based on calcium or sodium hydroxide, and steam explosion with or without an acid catalyst. Acid treatment will release xylose and arabinose from the hemicellulose component of the lignocellulosic biomass. Next, preferably, the cellulose component of the pretreated biomass is hydrolyzed by a mixture of cellulases. Examples of commercially available cellulase mixtures include Celluclast 1.5L® (Novozymes), Spezyme CP® (Genencor) (Scott W. Pryor, 2010, *Appl Biochem Biotechnol*), and Cellulyve 50L (Lyven).

Cellulase mixtures typically contain endoglucanases, exoglucanases, and β-glucosidases. In methods of co-fermentation as described herein, the amount of β-glucosidase activity in the cellulase mixture should be minimized as much as possible. For example, the culturing medium may contain a cellulase-containing enzyme mixture from an altered organism, where the mixture has reduced β-glucosidase activity compared to a cellulase-containing mixture from an unaltered organism. The organism may be altered to reduce the expression of β-glucosidase, such as by mutation of a gene encoding β-glucosidase or by targeted RNA interference or the like.

Surprisingly, as described in Example 17, co-fermentation of cellobiose and xylose by the methods of the invention resulted in a synergistic effect on sugar consumption and ethanol production by the host cell.

Methods of Synthesis of Hydrocarbons or Hydrocarbon Derivatives

One aspect of the present invention provides methods for increasing the synthesis of hydrocarbons or hydrocarbon derivatives by a host cell.

"Hydrocarbons" as used herein are organic compounds consisting entirely of hydrogen and carbon. Hydrocarbons include, without limitation, methane, ethane, ethene, ethyne, propane, propene, propyne, cyclopropane, allene, butane, isobutene, butene, butyne, cyclobutane, methylcyclopropane, butadiene, pentane, isopentane, neopentane, pentene, pentyne, cyclopentane, methylcyclobutane, ethylcyclopropane, pentadiene, isoprene, hexane, hexene, hexyne, cyclohexane, methylcyclopentane, ethylcyclobutane, propylcyclopropane, hexadiene, heptane, heptene, heptyne, cycloheptane, methylcyclohexane. heptadiene, octane, octene, octyne, cyclooctane, octadiene, nonane, nonene, nonyne, cyclononane, nonadiene, decane, decene, decyne, cyclodecane, and decadiene.

"Hydrocarbon derivatives" as used herein are organic compounds of carbon and at least one other element that is not hydrogen. Hydrocarbon derivatives include, without limitation, alcohols (e.g., arabinitol, butanol, ethanol, glycerol, methanol, 1,3-propanediol, sorbitol, and xylitol); organic acids (e.g., acetic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); esters; ketones (e.g., acetone); aldehydes (e.g., furfural); amino acids (e.g., aspartic acid, glutamic acid, glycine, lysine, serine, and threonine); and gases (e.g., carbon dioxide and carbon monoxide).

In preferred embodiments, the hydrocarbon or hydrocarbon derivative can be used as fuel. In particularly preferred embodiments, the hydrocarbon or hydrocarbon derivative is ethanol or butanol.

According to one aspect of the invention, a method of increasing the synthesis of hydrocarbons or hydrocarbon derivatives by a host cell includes a first step of providing a host cell, where the host cell contains a recombinant polynucleotide encoding a polypeptide containing transmembrane α-helix 1, α-helix 2, α-helix 3, α-helix 4, α-helix 5, α-helix 6, α-helix 7, α-helix 8, α-helix 9, α-helix 10, α-helix 11, and α-helix 12, where one or more of the following is true: transmembrane α-helix 1 comprises SEQ ID NO: 1, transmembrane α-helix 2 comprises SEQ ID NO: 2, the loop connecting transmembrane α-helix 2 and transmembrane α-helix 3 comprises SEQ ID NO: 3, transmembrane α-helix 5 comprises SEQ ID NO: 4, transmembrane α-helix 6 comprises SEQ ID NO: 5, sequence between transmembrane α-helix 6 and transmembrane α-helix 7 comprises SEQ ID NO: 6, transmembrane α-helix 7 comprises SEQ ID NO: 7, and transmembrane α-helix 10 and transmembrane α-helix 11 and the sequence between them comprise SEQ ID NO: 8, and where the polypeptide transports cellodextrin into the host cell for the synthesis of hydrocarbons or hydrocarbon derivatives. The method includes a second step of culturing the host cell in a medium containing cellodextrin or a source of cellodextrin to increase the synthesis of hydrocarbons or hydrocarbon derivatives by the host cell, where transport of cellodextrin into the cell is increased upon expression of the recombinant polynucleotide. In certain embodiments, the polypeptide has at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114. In certain embodiments, the host cell also contains a recombinant polynucleotide encoding a catalytic domain of a β-glucosidase. Such embodiments are useful for host cells lacking the endogenous ability to utilize cellodextrins. Preferably, the catalytic domain of the β-glucosidase is intracellular. In preferred embodiments, the β-glucosidase is from *Neurospora crassa*. In particularly preferred embodiments, the β-glucosidase is encoded by NCU00130. Transport of cellodextrin into the cell may be measured by any methods known to one of skill in the art, including the methods described in Example 9. Typically, the source of the cellodextrin is cellulose.

The culturing medium may contain a cellulase-containing enzyme mixture from an altered organism, where the mixture has reduced β-glucosidase activity compared to a cellulase-containing mixture from an unaltered organism. The organism may be altered to reduce the expression of β-glucosidase, such as by mutation of a gene encoding β-glucosidase or by targeted RNA interference or the like.

According to another aspect of the invention, a method of increasing the synthesis of hydrocarbons or hydrocarbon derivatives by a host cell includes the steps of providing a host cell, where the host cell contains a recombinant polynucleotide encoding a NCU00821 or STL12/XUT6 polypeptide, where the polypeptide transports xylose into the host cell for the synthesis of hydrocarbons or hydrocarbon derivatives, and culturing the host cell in a medium containing xylose or a source of xylose to increase the synthesis of hydrocarbons or hydrocarbon derivatives by the host cell, where transport of xylose into the cell is increased upon expression of the recombinant polynucleotide.

According to another aspect, a method of increasing the synthesis of hydrocarbons or hydrocarbon derivatives by a host cell includes the steps of providing a host cell, where the host cell contains a recombinant polynucleotide encoding a XUT1 polypeptide, where the polypeptide transports arabinose into the host cell for the synthesis of hydrocarbons or hydrocarbon derivatives, and culturing the host cell in a medium containing arabinose or a source of arabinose to increase the synthesis of hydrocarbons or hydrocarbon derivatives by the host cell, where transport of arabinose into the cell is increased upon expression of the recombinant polynucleotide.

According to yet another aspect, a method of increasing the synthesis of hydrocarbons or hydrocarbon derivatives by a host cell includes the steps of providing a host cell, where the host cell contains a recombinant polynucleotide encoding a NCU06138 polypeptide, where the polypeptide transports arabinose or glucose into the host cell for the synthesis of hydrocarbons or hydrocarbon derivatives, and culturing the host cell in a medium comprising arabinose or glucose or a source of arabinose or glucose to increase the synthesis of hydrocarbons or hydrocarbon derivatives by the host cell, where transport of arabinose or glucose into the cell is increased upon expression of the recombinant polynucleotide.

According to yet another aspect, a method of increasing the synthesis of hydrocarbons or hydrocarbon derivatives by a host cell includes the steps of providing a host cell, where the host cell contains a recombinant polynucleotide encoding a SUT2, SUT3, or XUT3 polypeptide, where the polypeptide transports xylose or glucose into the host cell for the synthesis of hydrocarbons or hydrocarbon derivatives, and culturing the host cell in a medium containing xylose or glucose or a source of xylose or glucose to increase the synthesis of hydrocarbons or hydrocarbon derivatives by the host cell, where transport of xylose or glucose into the cell is increased upon expression of the recombinant polynucleotide.

According to another aspect, a method of increasing the synthesis of hydrocarbons or hydrocarbon derivatives by a host cell includes the steps of providing a host cell, where the host cell contains a recombinant polynucleotide encoding a NCU04963 polypeptide, where the polypeptide transports xylose, arabinose, or glucose into the host cell for the synthesis of hydrocarbons or hydrocarbon derivatives, and culturing the host cell in a medium comprising xylose, arabinose, or glucose or a source of xylose, arabinose, or glucose to increase the synthesis of hydrocarbons or hydrocarbon derivatives by the host cell, where transport of xylose, arabinose, or glucose into the cell is increased upon expression of the recombinant polynucleotide.

Transport of xylose, arabinose, or glucose into the cell may by measured by any methods known to one of skill in the art, including the methods described in Example 11. Typically, the source of glucose is cellulose, and the source of xylose and arabinose is hemicellulose.

Methods of Degrading Cellulose

One aspect of the present invention provides methods of degrading cellulose. The methods include a first step of providing a composition comprising cellulose. The cellulose is preferably from plant material, such as switchgrass, *Miscanthus*, rice hulls, bagasse, flax, bamboo, sisal, abaca, straw, leaves, grass clippings, corn stover, corn cobs, distillers grains, legume plants, sorghum, sugar cane, sugar beet pulp, wood chips, sawdust, and biomass crops.

The methods include a second step of contacting the composition with a cellulase-containing enzyme mixture from an altered organism, where the cellulase-containing mixture has reduced β-glucosidase activity compared to a cellulase-containing mixture from an unaltered organism. The cellulose is degraded by the cellulase-containing mixture. The organism may be altered by mutation of a gene encoding a β-glucosidase or by reducing the expression of a β-glucosidase with a technique such as RNA interference. The organism may be a fungus or a bacterium. In preferred embodiments, the organism is a filamentous fungus such as *T. reesei.*

Alternatively, the methods include a second step of contacting the composition with a cellulase-containing enzyme mixture that has been altered to reduce its β-glucosidase activity. For example, the cellulase-containing enzyme mixture may be altered by affinity chromatography where β-glucosidase enzymes are captured during the chromatography, and thus removed from the mixture. In another example, the cellulase-containing enzyme mixture is altered by inactivation of β-glucosidase enzymes in the mixtures with an inhibitor. Examples of commercially available cellulase mixtures include Celluclast 1.5L® (Novozymes), Spezyme CP® (Genencor) (Scott W. Pryor, 2010, *Appl Biochem Biotechnol*), and Cellulite 50L (Lyven).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

The invention having been described, the following examples are offered to illustrate the subject invention by way of illustration, not by way of limitation.

EXAMPLES

Example 1

Transcriptome Analysis of *N. crassa* Grown on *Miscanthus* and Avicel

Figure 3:
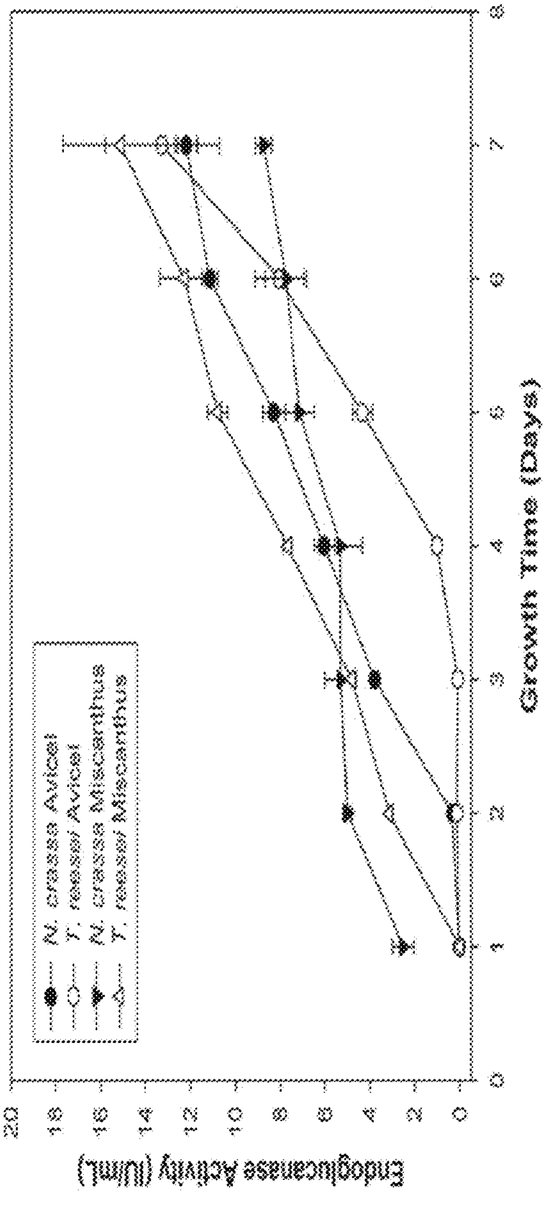
FIG. 3 shows an analysis of *N. crassa* FGSC2489 and *T. reesei* QM9414 endoglucanase activity when grown on *Miscanthus* and Avicel as a sole carbon source. Endoglucanase activity in culture filtrates of *N. crassa* WT strain FGSC2489 and *T. reesei* QM9414. *N. crassa* was grown on Vogel's minimal medium containing 2% of either Avicel or *Miscanthus* powder as a sole carbon source at 25° C. *T. reesei* strain was inoculated in MA medium with either 1% Avicel or *Miscanthus* powder as sole carbon source at 25° C. Both strains were inoculated with the same amount of conidia ($1\times10^6$/mL in 100 mL culture). The endoglucanase activity in the cultures at different time points were measured at pH 4.5 using Azo-CM-cellulose as a substrate according to the manufacturer's instructions (Megazyme, Ireland).
Figure 4:
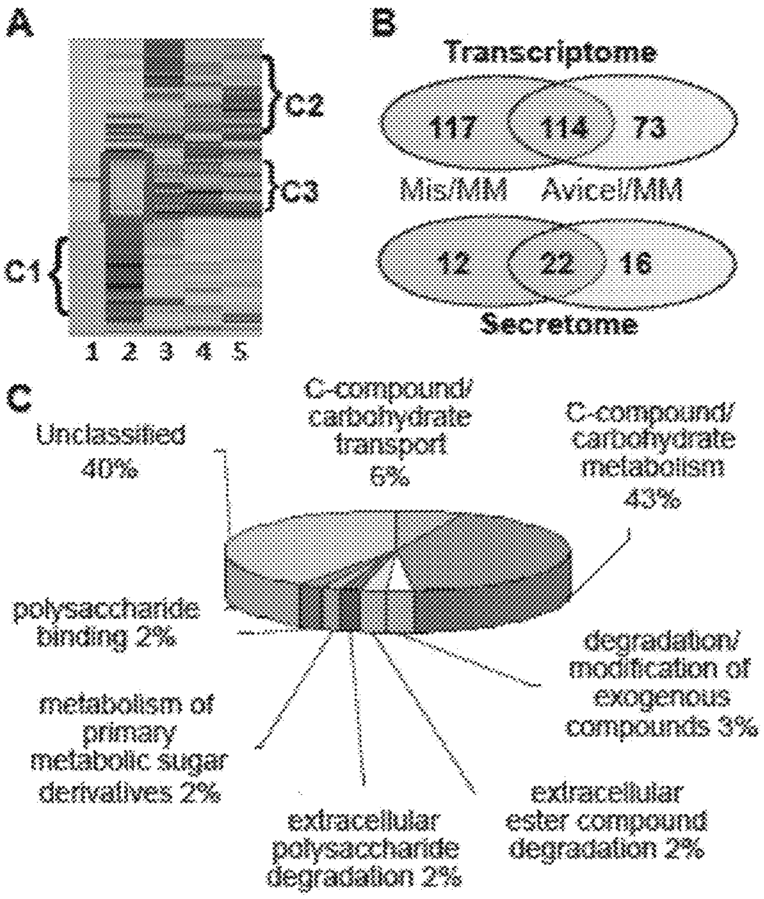
FIG. 4 shows transcriptional profiling of *N. crassa* grown on *Miscanthus* and Avicel.

In this example, the expression profile of the *N. crassa* genome was examined during growth on *Miscanthus* or Avicel. Growth and cellulase activity of *N. crassa* (FGSC 2489) cultured on Vogel's minimal media with crystalline cellulose (Avicel) as the sole carbon source was similar to that of *T. reesei* (QM9414) (FIG. 3); *N. crassa* completely degraded Avicel in approximately 4 days. *N. crassa* also grew rapidly on ground *Miscanthus* stems, suggesting functional cellulase and hemicellulase degradative capacity. To determine the transcriptome associated with plant cell wall deconstruction in *N. crassa*, we used full genome microarrays (Kasuga and Glass 2008; Tian et al., 2007; Kasuga et al., 2005) to monitor gene expression profiles during growth of *N. crassa* on ground *Miscanthus* stems. RNA was sampled after 16 hrs of growth on sucrose and compared to RNA isolated from *N. crassa* grown on *Miscanthus* medium at 16 and 40 hrs, 5 days and 10 days (FIG. 4; also see Supplemental Data, Dataset S1, page 1 in Tian et al., 2009; data can also be found at bioinfo-.townsend.yale.edu/browse.jsp, Experiment IDs 52 and 53).

A total of 769 *N. crassa* genes showed a statistically significant difference in relative expression level among the four *Miscanthus* samples as compared to the sucrose sample (see Supplemental Data, Dataset S1, page 3 in Tian et al., 2009). Hierarchical clustering showed that these genes fell into three main clusters (FIG. 4A). The first cluster of genes (C1; 300 genes) showed the highest expression levels in minimal medium with sucrose as a carbon source. Functional category (FunCat) analysis (Ruepp 2004) of these genes showed an enrichment for ribosomal proteins and other functional categories associated with primary metabolism, such as respiration, electron transport and amino acid metabolism (see Supplemental Data, Dataset S1, page 4 in Tian et al., 2009). The second cluster (C2) included 327 genes that showed the highest expression levels in *Miscanthus* cultures at later time points (40 hrs to 10 days; FIG. 4A). Within this group were 89 genes that showed a high relative expression level in *Miscanthus* cultures at all time points. For further analyses, these 89 genes were added to the cluster of genes that showed the highest expression levels from the 16 hr *Miscanthus* cultures (C3 cluster, see below). FunCat analysis (Ruepp 2004) of the remaining 238 genes showed one functional category (C-compound and carbohydrate metabolism) was slightly enriched (see Supplemental Data, Dataset S1, page 5 in Tian et al., 2009).

A third cluster of 142 genes showed the highest relative expression level after 16 hrs of growth of *N. crassa* on *Miscanthus* (C3, FIG. 4A). FunCat analysis (Ruepp 2004) of these 142 genes plus the 89 genes that showed high expression levels in *Miscanthus* cultures at all time points (C3+ cluster; total 231 genes) showed an enrichment for proteins involved with carbon metabolism, including predicted cellulases and hemicellulases (FIG. 4C; also see Supplemental Data, Dataset S1, page 6 in Tian et al., 2009). Of the 23 predicted cellulase genes in the *N. crassa* genome, 18 showed significant increases in expression levels during growth on *Miscanthus* (see Table 1 in Tian et al., 2009), particularly at the 16 hr time point (FIG. 5). Five genes showed an increase in expression level over 200-fold (cbh-1 (CBH(I); NCU07340, gh6-2 (CBH(II)-like gene; NCU09680), gh6-3 (NCU07190) and two GH61 genes (gh61-4; NCU01050 and NCU07898))).

Plant cell walls are complex structures composed of cellulose microfibrils, hemicellulose, lignin, pectin, cutin, and protein. Thus, we compared expression profiles of *N. crassa* grown on *Miscanthus* to expression profiles of *N. crassa* grown on Avicel, a pure form of crystalline cellulose (see Tian et al., 2009, Supplemental Data, Dataset S1, page 2; data can also be found at bioinfo.townsend.yale.edu/browse.jsp, Experiment IDs 52 and 53). Over 187 genes showed a significant increase in relative expression level during growth of *N. crassa* on Avicel. Of these genes, 114 overlapped with the 231 genes in the C3+ cluster (FIG. 4B). FunCat analysis of the 114-overlap gene set showed a clear enrichment for genes predicted to be involved in carbon metabolism (see Supplemental Data, Dataset S1, page 6 in Tian et al., *PNAS,* 2009). Within this gene set, there was a further enrichment for secreted proteins; 53 of the 114 gene products were predicted to be secreted. Of these 53 genes, 32 encode predicted proteins that have annotation suggesting a role in plant cell wall degradation, while 16 encode putative or hypothetical proteins that lack any functional prediction. The remaining 61 genes encode predicted intracellular proteins, including ten predicted major facilitator superfamily transporters (NCU00801, NCU00988, NCU01231, NCU04963, NCU05519, NCU05853, NCU05897, NCU06138, NCU08114 and NCU10021) and 23 putative or hypothetical proteins.

Of the 117 genes within the *Miscanthus*-specific cluster (FIG. 4B), 37 encode proteins predicted to be secreted. Nine predicted hemicellulases or enzymes related to the degradation of hemicellulose were identified (NCU00710, NCU04265, NCU04870, NCU05751, NCU05965, NCU09170, NCU09775, NCU09923 and NCU09976) (Tian et al., 2009—Table 2). The remaining 80 *Miscanthus*-specific genes encode predicted intracellular proteins, including genes involved in the metabolism of pentose sugars (for example, NCU00891, xylitol dehydrogenase and NCU00643, a predicted arabinitol dehydrogenase), a predicted sugar transporter (NCU01132), and 48 proteins of unknown function.

Example 2

Secretome Analysis of *N. crassa* Grown on *Miscanthus* and Avicel

Lignocellulose degradation by fungi takes place extracellularly and requires the secretion of proteins associated with depolymerization of cell wall constituents (Lynd et al., 2002). To compare with transcriptional profiling data, which showed that genes encoding predicted cellulases, hemicellulases, and other secreted proteins increased in expression levels when *N. crassa* was grown on *Miscanthus* or Avicel, we analyzed the secretome of *N. crassa* using a shotgun proteomics approach (FIG. 4B). Supernatants from seven day old *Miscanthus* and Avicel cultures were digested with trypsin and analyzed by liquid chromatography nano-electrospray ionization tandem mass spectrometry (MS; see Example 5). Secreted proteins that bound to phosphoric acid swollen cellulose (PASC) were enriched and also analyzed by MS.

A total of 50 proteins were identified with confidence by tandem MS (Tables 2 and 3). There were 34 proteins detected in the *Miscanthus* grown *N. crassa* cultures, while 38 proteins were identified from Avicel grown cultures; twenty-two proteins were detected in both samples. Of these 22 proteins, 21 were predicted to be secreted based on computational analyses and 19 showed increased expression levels in both the *Miscanthus* and Avicel grown cultures (Table 2). The overlap dataset included eight of the 23 predicted cellulases in *N. crassa* (Table 3). There were also five predicted hemicellulases, a predicted β-glucosidase (gh3-4; NCU04952), five proteins with predicted activity on carbohydrates, and two proteins with unknown function (NCU07143 and NCU05137) (Table 4-5).

For Table 2, the annotation was generated by the Broad Institute at webpage broad.mit.edu/annotation/genome/neurospora/Home.html. The "sample detected" was the sample in which peptides were detected for a particular protein. Peptides were validated by manual inspection. A protein was determined to be present if at least 1 peptide was detected in each biological repeat. "TOTAL" refers to peptides detected from a tryptic digest of all extracellular proteins. "PASC BOUND" refers to peptides detected after enrichment for proteins that bind to phosphoric acid swollen cellulose. "UNBOUND" refers to proteins remaining in solution after removal of PASC bound proteins.

TABLE 2

Proteins identified by LC-MS/MS In the culture filtrates of Avicel grown *Neurospora crassa*

| GENE ID | ANNOTATION | SAMPLE DETECTED |
|---|---|---|
| NCU00206 | *Neurospora crassa* hypothetical protein similar to cellobiose dehydrogenase 830 nt | TOTAL |
| NCU00762 | *Neurospora crassa* endoglucanase 3 precursor 391 nt | TOTAL |
| NCU01050 | *Neurospora crassa* hypothetical protein similar to endoglucanase II 239 nt | TOTAL |
| NCU02343 | *Neurospora crassa* hypothetical protein similar to alpha L arabinofuranosidase A 668 nt | TOTAL |
| NCU04870 | *Neurospora crassa* hypothetical protein similar to acetyl xylan esterase 313 nt | TOTAL |
| NCU04952 | *Neurospora crassa* hypothetical protein similar to beta D glucoside glucohydrolase 736 nt | TOTAL |
| NCU05137 | *Neurospora crassa* conserved hypothetical protein 692 nt | TOTAL |
| NCU05159 | *Neurospora crassa* acetylxylan esterase precursor 301 nt | TOTAL |
| NCU05924 | *Neurospora crassa* endo 1 4 beta xylanase 330 nt | TOTAL |
| NCU07143 | *Neurospora crassa* predicted protein 391 nt | TOTAL |
| NCU07190 | *Neurospora crassa* conserved hypothetical protein 384 nt | TOTAL |
| NCU07225 | *Neurospora crassa* endo 1 4 beta xylanase 2 precursor 255 nt | TOTAL |
| NCU07326 | *Neurospora crassa* predicted protein 327 nt | TOTAL |
| NCU07340 | *Neurospora crassa* exoglucanase 1 precursor 522 nt | TOTAL |
| NCU07898 | *Neurospora crassa* predicted protein 242 nt | TOTAL |
| NCU08189 | *Neurospora crassa* hypothetical protein similar to endo 1 4 beta xylanase 385 nt | TOTAL |
| NCU08398 | *Neurospora crassa* conserved hypothetical protein 391 nt | TOTAL |
| NCU08760 | *Neurospora crassa* predicted protein 343 nt | TOTAL |
| NCU08785 | *Neurospora crassa* conserved hypothetical protein 291 nt | TOTAL |
| NCU09491 | *Neurospora crassa* feruloyl esterase B precursor 293 nt | TOTAL |
| NCU09680 | *Neurospora crassa* exoglucanase 2 precursor 485 nt | TOTAL |
| NCU09923 | *Neurospora crassa* hypothetical protein similar to beta xylosidase 775 nt | TOTAL |
| NCU00206 | *Neurospora crassa* hypothetical protein similar to cellobiose dehydrogenase 830 nt | PASC BOUND |
| NCU00762 | *Neurospora crassa* endoglucanase 3 precursor 391 nt | PASC BOUND |
| NCU05159 | *Neurospora crassa* acetylxylan esterase precursor 301 nt | PASC BOUND |
| NCU05955 | *Neurospora crassa* hypothetical protein similar to Cel74a 862 nt | PASC BOUND |
| NCU07225 | *Neurospora crassa* endo 1 4 beta xylanase 2 precursor 255 nt | PASC BOUND |
| NCU07340 | *Neurospora crassa* exoglucanase 1 precursor 522 nt | PASC BOUND |
| NCU08760 | *Neurospora crassa* predicted protein 343 nt | PASC BOUND |
| NCU09680 | *Neurospora crassa* exoglucanase 2 precursor 485 nt | PASC BOUND |
| NCU09708 | *Neurospora crassa* conserved hypothetical protein 465 nt | PASC BOUND |
| NCU00762 | *Neurospora crassa* endoglucanase 3 precursor 391 nt | UNBOUND |
| NCU01651 | *Neurospora crassa* conserved hypothetical protein 783 nt | UNBOUND |
| NCU02343 | *Neurospora crassa* hypothetical protein similar to alpha L arabinofuranosidase A 668 nt | UNBOUND |
| NCU04202 | *Neurospora crassa* nucleoside diphosphate kinase 1 153 nt | UNBOUND |
| NCU04870 | *Neurospora crassa* hypothetical protein similar to acetyl xylan esterase 313 nt | UNBOUND |
| NCU04952 | *Neurospora crassa* hypothetical protein similar to beta D glucoside glucohydrolase 736 nt | UNBOUND |
| NCU05057 | *Neurospora crassa* endoglucanase EG 1 precursor 439 nt | UNBOUND |
| NCU05137 | *Neurospora crassa* conserved hypothetical protein 692 nt | UNBOUND |
| NCU05751 | *Neurospora crassa* conserved hypothetical protein 242 nt | UNBOUND |
| NCU05924 | *Neurospora crassa* endo 1 4 beta xylanase 330 nt | UNBOUND |
| NCU06239 | *Neurospora crassa* conserved hypothetical protein 514 nt | UNBOUND |
| NCU07143 | *Neurospora crassa* predicted protein 391 nt | UNBOUND |
| NCU07190 | *Neurospora crassa* conserved hypothetical protein 384 nt | UNBOUND |
| NCU07225 | *Neurospora crassa* endo 1 4 beta xylanase 2 precursor 255 nt | UNBOUND |
| NCU07326 | *Neurospora crassa* predicted protein 327 nt | UNBOUND |
| NCU07898 | *Neurospora crassa* predicted protein 242 nt | UNBOUND |
| NCU08189 | *Neurospora crassa* hypothetical protein similar to endo 1 4 beta xylanase 385 nt | UNBOUND |
| NCU08398 | *Neurospora crassa* conserved hypothetical protein 391 nt | UNBOUND |
| NCU08412 | *Neurospora crassa* conserved hypothetical protein 401 nt | UNBOUND |
| NCU08760 | *Neurospora crassa* predicted protein 343 nt | UNBOUND |
| NCU08785 | *Neurospora crassa* conserved hypothetical protein 291 nt | UNBOUND |
| NCU09024 | *Neurospora crassa* conserved hypothetical protein 625 nt | UNBOUND |
| NCU09175 | *Neurospora crassa* conserved hypothetical protein 411 nt | UNBOUND |
| NCU09267 | *Neurospora crassa* conserved hypothetical protein 1048 nt | UNBOUND |
| NCU09491 | *Neurospora crassa* feruloyl esterase B precursor 293 nt | UNBOUND |
| NCU09775 | *Neurospora crassa* hypothetical protein similar to alpha L arabinofuranosidase 343 nt | UNBOUND |
| NCU09923 | *Neurospora crassa* hypothetical protein similar to beta xylosidase 775 nt | UNBOUND |

TABLE 3

| 22 secreted proteins detected in both *Miscanthus* and Avicel cultures | | | | | |
|---|---|---|---|---|---|
| Gene name | Gene annotation | Profiling | kos | CBM1 | Signal P |
| NCU00206.2 | CBDH | both | heter | yes | yes |
| NCU00762.2 | probable cellulase precursor | both | 16747 | yes | yes |
| NCU01050.2 | related to cel1 protein precursor | both | 16543 | no | yes |
| NCU04952.2 | probable beta-D-glucoside glucohydrolase | both | 13732 | no | yes |
| NCU05057.2 | probable endo-1,4-beta-glucanase | both | 13343 | no | yes |
| NCU05137.2 | conserved hypothetical protein | both | 11682 | no | yes |
| NCU05924.2 | probable endo-beta-1,4-D-xylanase | both | 15626 | no | yes |
| NCU05955.2 | probable endoglucanase C | both | 13535 | yes | yes |
| NCU07143.2 | hypothetical | both | No | no | yes |
| NCU07190.2 | CBHII homolog | both | 19315 | no | yes |
| NCU07225.2 | probable endo-1,4-beta-xylanase B precursor | both | heter | yes | yes |
| NCU07326.2 | related to putative arabinase | both | 19534 | no | yes |
| NCU07340.2 | CBHI | both | 15630 | yes | yes |
| NCU07898.2 | related to cel1 protein precursor | both | 19600 | no | yes |
| NCU08189.2 | similar to endo-1,4-beta xylanase | both | 19861 | no | yes |
| NCU08398.2 | related to aldose 1-epimerase | both | 20310 | no | yes |
| NCU08412.2 | hypothetical protein 401 nt | none | No | no | no |
| NCU08760.2 | related to family 61 endoglucanase | both | 15664 | yes | yes |
| NCU09024.2 | hypothetical protein 625 nt | none | No | no | yes |
| NCU09175.2 | glucan 1,3-beta-glucosidase precursor | both | 11750 | no | yes |
| NCU09491.2 | feruloyl esterase B precursor | mis | No | no | yes |
| NCU09680.2 | CBHII | both | 15633 | yes | yes |

Table 4 shows predicted cellulase genes in *Neurospora crassa*

| Gene | GH[1] Family | CBM1[2] | SP[3] | MS[4] | EL[5] *Miscanthus* | EL[5] Avicel |
|---|---|---|---|---|---|---|
| NCU00762 | 5 | yes | yes | both | 29.6 | 31.5 |
| NCU03996 | 6 | no | no | ND6 | ND | ND |
| NCU07190 | 6 | no | yes | both | 526.0 | 119 |
| NCU09680 | 6 | yes | yes | both | 230.9 | 251.3 |
| NCU04854 | 7 | no | yes | ND | 32.9 | 10.8 |
| NCU05057 | 7 | no | yes | both | 8.7 | 7.4 |
| NCU05104 | 7 | no | yes | ND | 11.6 | NC7 |
| NCU07340 | 7 | yes | yes | both | 426.4 | 382.2 |
| NCU05121 | 45 | yes | yes | avi | 8.6 | 17.2 |
| NCU00836 | 61 | yes | yes | ND | 91.2 | 31 |
| NCU01050 | 61 | no | yes | both | 206.7 | 382.1 |
| NCU01867 | 61 | yes | yes | ND | 2.2 | NC |
| NCU02240 | 61 | yes | yes | avi | 193.5 | 84 |
| NCU02344 | 61 | no | yes | ND | 8.1 | 4.1 |
| NCU02916 | 61 | yes | yes | ND | 85.2 | 17.7 |
| NCU03000 | 61 | no | yes | ND | NC | ND |
| NCU03328 | 61 | no | yes | ND | 26.4 | 23.8 |
| NCU05969 | 61 | no | yes | ND | ND | 12.7 |
| NCU07520 | 61 | no | yes | ND | ND | ND |
| NCU07760 | 61 | yes | yes | ND | 3.7 | NC |
| NCU07898 | 61 | no | yes | both | 376.3 | 230 |
| NCU07974 | 61 | no | yes | ND | NC | NC |
| NCU08760 | 61 | yes | yes | both | 107.5 | 44.7 |

[1]Glucoside Hydrolase;
[2]CBM1, carbohydrate binding module;
[3]Signal peptide prediction (signalP = webpage cbs.dtu.dk/services/SignalP/);
[4]MS, mass spectrometry analysis;
[5]EL, relative expression level;
6ND, not detected;
7NC, no change in expression level versus minimal media.

TABLE 5

| Cellulases and Hemicellulases identified by LC-MS/MS | | | | | |
|---|---|---|---|---|---|
| Gene ID | GH Family | AV MS | MIS MS | AV ARRAY | MIS ARRAY |
| Predicted cellulases in the genome of *Neurospora crassa* | | | | | |
| NCU00762 | 5 | + | + | 31.5 | 29.6 |
| NCU00836 | 61 | – | – | 31 | 91.2 |

TABLE 5-continued

| Cellulases and Hemicellulases identified by LC-MS/MS | | | | | |
|---|---|---|---|---|---|
| Gene ID | GH Family | AV MS | MIS MS | AV ARRAY | MIS ARRAY |
| NCU01050 | 61 | + | + | 382.1 | 206.7 |
| NCU01867 | 61 | – | – | 1 | 1 |
| NCU02240 | 61 | + | – | 84 | 193.5 |
| NCU02344 | 61 | – | – | 4.1 | 8.1 |
| NCU02916 | 61 | – | – | 17.7 | 85.2 |
| NCU03000 | 61 | – | – | 1 | 1 |
| NCU03328 | 61 | – | – | 23.8 | 26.4 |
| NCU03996 | 6 | – | – | 2.5 | 6.3 |
| NCU04854 | 7 | – | – | 10.8 | 32.9 |
| NCU05057 | 7 | + | + | 7.4 | 8.7 |
| NCU05104 | 7 | – | – | 1 | 1 |
| NCU05121 | 45 | + | – | 17.2 | 8.6 |
| NCU05969 | 61 | – | – | 12.7 | 12.3 |
| NCU07190 | 6 | + | + | 119 | 526 |
| NCU07340 | 7 | + | + | 382.2 | 426.4 |
| NCU07520 | 61 | – | – | 1 | 1 |
| NCU07760 | 61 | – | – | 1 | 3.4 |
| NCU07898 | 61 | + | + | 230.5 | 376.3 |
| NCU07974 | 61 | – | – | 1 | 1 |
| NCU08760 | 61 | + | + | 44.7 | 107.5 |
| NCU09680 | 6 | + | + | 251.3 | 230.9 |
| Predicted hemicellulases in the genome of *Neurospora crassa* | | | | | |
| NCU00852 | 43 | – | – | 1 | 1 |
| NCU00972 | 53 | – | – | 9.03 | 15.6 |
| NCU01900 | 43 | – | – | 10.03 | 26 |
| NCU02343 | 51 | – | + | 6.63 | 174.6 |
| NCU02855 | 11 | + | – | 10.2 | 364 |
| NCU04997 | 10 | – | – | 1 | 25.6 |
| NCU05924 | 10 | + | + | 55.9 | 149.3 |
| NCU05955 | 74 | + | + | 19.9 | 50.5 |
| NCU05965 | 43 | – | – | 1 | 5.4 |
| NCU06861 | 43 | – | – | 1 | 1 |
| NCU07130 | 10 | – | – | 1 | 1 |
| NCU07225 | 11 | + | + | 11.43 | 33.5 |
| NCU07326 | 43 | + | + | 104.5 | 426.6 |
| NCU07351 | 67 | – | – | 1 | 1 |
| NCU08087 | 26 | – | – | 1 | 1 |
| NCU08189 | 10 | + | + | 39.8 | 94.4 |

TABLE 5-continued

| Cellulases and Hemicellulases identified by LC-MS/MS | | | | | |
|---|---|---|---|---|---|
| Gene ID | GH Family | AV MS | MIS MS | AV ARRAY | MIS ARRAY |
| NCU09170 | 43 | – | – | 1 | 16.7 |
| NCU09652 | 43 | – | – | 12.2 | 95.4 |
| NCU09775 | 54 | – | + | 1 | 48.3 |

GH Family - Glycosyl Hydrolase Family;
AV MS - Protein detected by LC-MS/MS in the culture filtrates of Avicel grown *Neurospora crassa*. (+) detected, (–) not detected;
MIS MS - Protein detected by LC-MS/MS in the culture filtrates of *Miscanthus* grown *Neurospora crassa*. (+) detected, (–) not detected;
AV ARRAY - Fold upregulation after 30 hours of growth on Avicel relative to 16 hours of growth on sucrose from profiling data;
MIS ARRAY - Fold upregulation after 16 hours of growth on *Miscanthus* relative to 16 hours of growth on sucrose from profiling data, peptides detected only in Miscanthus culture filtrates.

There were 16 proteins identified with confidence only in the Avicel culture and 14 of these were predicted to be secreted (Table 6) including two predicted cellulases (gh61-1; NCU02240 and gh45-1; NCU05121), one xylanase (gh11-1; NCU02855), one predicted protease (NCU04205), three other proteins with predicted activity on carbohydrates (NCU08909, NCU05974 and gh30-1 (NCU04395)), three *Neurospora*-specific proteins of unknown function, and four conserved hypothetical proteins, including one protein with a cellulose binding domain (NCU09764). Twelve proteins were specific for culture filtrates of *Miscanthus* cultures and seven of these were predicted to be secreted (Table 3). Three of the five predicted intracellular proteins were conserved hypothetical proteins. The remaining two included a predicted glyoxal oxidase (NCU09267, identified from the *N. crassa Miscanthus* transcriptome) and a nucleoside diphosphate kinase (ndk-1; NCU04202, not identified in the *N. crassa* transcriptome). The seven proteins predicted to be secreted included three predicted esterases (NCU04870, NCU05159, and NCU08785), two predicted xylanases (GH51; NCU02343 and GH54; NCU09775), a predicted β-xylosidase (gh3-7; NCU09923) and a conserved hypothetical protein (NCU05751).

TABLE 6

| Proteins identified by LC-MS/MS In the culture filtrates of Avicel grown *Neurospora crassa* | | |
|---|---|---|
| GENE ID | ANNOTATION | SAMPLE DETECTED |
| NCU00206 | *Neurospora crassa* hypothetical protein similar to cellobiose dehydrogenase 830 nt | TOTAL |
| NCU00762 | *Neurospora crassa* endoglucanase 3 precursor 391 nt | TOTAL |
| NCU00798 | *Neurospora crassa* predicted protein 313 nt | TOTAL |
| NCU01050 | *Neurospora crassa* hypothetical protein similar to endoglucanase II 239 nt | TOTAL |
| NCU01595 | *Neurospora crassa* protein SOF1 446 nt | TOTAL |
| NCU02240 | *Neurospora crassa* hypothetical protein similar to endoglucanase II 323 nt | TOTAL |
| NCU02696 | *Neurospora crassa* hypothetical protein similar to DEAD DEAH box RNA helicase 1195 nt | TOTAL |
| NCU02855 | *Neurospora crassa* endo 1 4 beta xylanase A precursor 221 nt | TOTAL |
| NCU04952 | *Neurospora crassa* hypothetical protein similar to beta D glucoside glucohydrolase 736 nt | TOTAL |
| NCU05057 | *Neurospora crassa* endoglucanase EG 1 precursor 439 nt | TOTAL |
| NCU05137 | *Neurospora crassa* conserved hypothetical protein 692 nt | TOTAL |
| NCU05924 | *Neurospora crassa* endo 1 4 beta xylanase 330 nt | TOTAL |
| NCU05955 | *Neurospora crassa* hypothetical protein similar to Cel74a 862 nt | TOTAL |
| NCU07143 | *Neurospora crassa* predicted protein 391 nt | TOTAL |
| NCU07190 | *Neurospora crassa* conserved hypothetical protein 384 nt | TOTAL |
| NCU07225 | *Neurospora crassa* endo 1 4 beta xylanase 2 precursor 255 nt | TOTAL |
| NCU07326 | *Neurospora crassa* predicted protein 327 nt | TOTAL |
| NCU07340 | *Neurospora crassa* exoglucanase 1 precursor 522 nt | TOTAL |
| NCU07898 | *Neurospora crassa* predicted protein 242 nt | TOTAL |
| NCU08171 | *Neurospora crassa* predicted protein 382 nt | TOTAL |
| NCU08412 | *Neurospora crassa* conserved hypothetical protein 401 nt | TOTAL |
| NCU08760 | *Neurospora crassa* predicted protein 343 nt | TOTAL |
| NCU09491 | *Neurospora crassa* feruloyl esterase B precursor 293 nt | TOTAL |
| NCU09680 | *Neurospora crassa* exoglucanase 2 precursor 485 nt | TOTAL |
| NCU09764 | *Neurospora crassa* conserved hypothetical protein 406 nt | TOTAL |
| NCU00206 | *Neurospora crassa* hypothetical protein similar to cellobiose dehydrogenase 830 nt | PASC BOUND |
| NCU00762 | *Neurospora crassa* endoglucanase 3 precursor 391 nt | PASC BOUND |
| NCU05121 | *Neurospora crassa* endoglucanase V 294 nt | PASC BOUND |
| NCU05955 | *Neurospora crassa* hypothetical protein similar to Cel74a 862 nt | PASC BOUND |
| NCU07225 | *Neurospora crassa* endo 1 4 beta xylanase 2 precursor 255 nt | PASC BOUND |
| NCU07340 | *Neurospora crassa* exoglucanase 1 precursor 522 nt | PASC BOUND |
| NCU08760 | *Neurospora crassa* predicted protein 343 nt | PASC BOUND |
| NCU09680 | *Neurospora crassa* exoglucanase 2 precursor 485 nt | PASC BOUND |
| NCU00206 | *Neurospora crassa* hypothetical protein similar to cellobiose dehydrogenase 830 nt | UNBOUND |
| NCU00762 | *Neurospora crassa* endoglucanase 3 precursor 391 nt | UNBOUND |
| NCU00798 | *Neurospora crassa* predicted protein 313 nt | UNBOUND |
| NCU01050 | *Neurospora crassa* hypothetical protein similar to endoglucanase II 239 nt | UNBOUND |
| NCU04205 | *Neurospora crassa* predicted protein 346 nt | UNBOUND |
| NCU04395 | *Neurospora crassa* endo 1 6 beta D glucanase precursor 481 nt | UNBOUND |
| NCU04952 | *Neurospora crassa* hypothetical protein similar to beta D glucoside glucohydrolase 736 nt | UNBOUND |
| NCU05057 | *Neurospora crassa* endoglucanase EG 1 precursor 439 nt | UNBOUND |
| NCU05134 | *Neurospora crassa* hypothetical protein 124 nt | UNBOUND |
| NCU05137 | *Neurospora crassa* conserved hypothetical protein 692 nt | UNBOUND |
| NCU05852 | *Neurospora crassa* conserved hypothetical protein 254 nt | UNBOUND |
| NCU05924 | *Neurospora crassa* endo 1 4 beta xylanase 330 nt | UNBOUND |
| NCU05974 | *Neurospora crassa* hypothetical protein similar to cell wall glucanosyltransferase Mwg1 365 nt | UNBOUND |

TABLE 6-continued

| Proteins identified by LC-MS/MS In the culture filtrates of Avicel grown *Neurospora crassa* | | |
|---|---|---|
| GENE ID | ANNOTATION | SAMPLE DETECTED |
| NCU07143 | *Neurospora crassa* predicted protein 391 nt | UNBOUND |
| NCU07190 | *Neurospora crassa* conserved hypothetical protein 384 nt | UNBOUND |
| NCU07225 | *Neurospora crassa* endo 1 4 beta xylanase 2 precursor 255 nt | UNBOUND |
| NCU07326 | *Neurospora crassa* predicted protein 327 nt | UNBOUND |
| NCU07340 | *Neurospora crassa* exoglucanase 1 precursor 522 nt | UNBOUND |
| NCU07898 | *Neurospora crassa* predicted protein 242 nt | UNBOUND |
| NCU08171 | *Neurospora crassa* predicted protein 382 nt | UNBOUND |
| NCU08189 | *Neurospora crassa* hypothetical protein similar to endo 1 4 beta xylanase 385 nt | UNBOUND |
| NCU08398 | *Neurospora crassa* conserved hypothetical protein 391 nt | UNBOUND |
| NCU08412 | *Neurospora crassa* conserved hypothetical protein 401 nt | UNBOUND |
| NCU08760 | *Neurospora crassa* predicted protein 343 nt | UNBOUND |
| NCU08909 | *Neurospora crassa* hypothetical protein similar to beta 1 3 glucanosyltransferase 543 nt | UNBOUND |
| NCU08936 | *Neurospora crassa* clock controlled gene 15 412 nt | UNBOUND |
| NCU09024 | *Neurospora crassa* conserved hypothetical protein 625 nt | UNBOUND |
| NCU09046 | *Neurospora crassa* predicted protein 187 nt | UNBOUND |
| NCU09175 | *Neurospora crassa* conserved hypothetical protein 411 nt | UNBOUND |
| NCU09491 | *Neurospora crassa* feruloyl esterase B precursor 293 nt | UNBOUND |

ANNOTATION - Generated by the Broad Institute (webpage at broad.mit.edu/annotation/genome/neurospora/Home.html);
SAMPLE DETECTED - Sample in which peptides were detected for a particular protein. Peptides were validated by manual inspection. A protein was determined to be present if at least 1 peptide was detected in each biological repeat.
TOTAL, peptides detected from a tryptic digest of all extracellular proteins;
PASC BOUND, peptides detected after enrichment for proteins that bind to phosphoric acid swollen cellulose;
UNBOUND, proteins remaining in solution after removal of PASC bound proteins.

Many plant cell wall degrading enzymes contain a cellulose-binding module (CBM), which aids in attachment of the enzyme to the substrate (Linder and Teeri 1996). Within the *N. crassa* genome, proteins encoded by 19 genes are predicted to contain a CBM1 domain (Cantarel et al., 2009). Of these 19 genes, 16 showed an increase in relative gene expression in *Miscanthus*-grown cultures (Table 7).

TABLE 7

| Effect of *Miscanthus* and Avicel on *N. crassa* gene expression | | | | | |
|---|---|---|---|---|---|
| Gene name | CBM prediction | Annotation | Mis Array | Avicel array | MS |
| NCU00206 | cazy and mips | probable cellobiose dehydrogenase | 164 | 12 | both |
| NCU00710 | cazy and mips | acetylxylan esterase | 30 | no detect | none |
| NCU00762 | cazy and mips | EG2 | 29 | 31 | both |
| NCU00836 | cazy and mips | EG, GH61 | 91 | 30 | none |
| NCU01867 | cazy and mips | EG, GH61 | 2.2-d10 | no difference | none |
| NCU02240 | cazy and mips | EG, GH61 | 193 | 84 | avi |
| NCU02916 | cazy and mips | EG, GH61 | 85 | 17 | none |
| NCU04500 | cazy and mips | similar to chitinase 4 | no detect | no detect | none |
| NCU04997 | cazy and mips | similar to xylanase | no detect | no detect | none |
| NCU05121 | cazy and mips | EG, GH45 | 8.5 | 17 | avi |
| NCU05159 | cazy and mips | acetylxylan esterase precursor | 34 | 10 | mis |
| NCU05955 | cazy and mips | GH74 | 50 | 19 | both |
| NCU07225 | cazy and mips | xylanase | 33 | 11 | both |
| NCU07340 | cazy and mips | CBH1 | 426 | 382 | both |
| NCU07760 | cazy and mips | EG, GH61 | 3.7 | no difference | none |
| NCU08760 | cazy and mips | EG, GH61 | 107 | 44 | both |
| NCU09416 | cazy and mips | hypothetical | no detect | 27 | none |
| NCU09680 | cazy and mips | CBH2 | 230 | 251 | both |
| NCU09764 | cazy and mips | hypothetical | 18 | 16.6 | avi |

From the 50 proteins identified by MS, 11 contained a CBM1 domain. PASC was used to enrich for proteins that bind to cellulose (see Example 4 for methods). Nine proteins were identified by MS that bound to PASC from the supernatant of *Miscanthus*-grown *N. crassa* cultures, while eight proteins from the Avicel supernatants were identified; seven cellulose binding proteins were identified in both (Tables 2, 3, 8). These included NCU00206, a predicted cellobiose dehydrogenase; gh5-1 (NCU00762), a predicted endoglucanase; NCU05955, a predicted GH74 xyloglucanase; gh11-2 (NCU07225), a predicted endoxylanase; cbh-1 (NCU07340); gh61-5 (NCU08760), a predicted endoglucanase; and gh6-2 (NCU09680), a predicted cellobiohydrolase 2 precursor.

TABLE 8

Proteins identified by LC-MS/MS in the culture filtrates of Avicel-grown *Neurospora crassa*

| GENE ID | ANNOTATION | CULTURE |
|---|---|---|
| NCU00206 | *Neurospora crassa* hypothetical protein similar to cellobiose dehydrogenase 830 nt | BOTH |
| NCU00762 | *Neurospora crassa* endoglucanase 3 precursor 391 nt | BOTH |
| NCU01050 | *Neurospora crassa* hypothetical protein similar to endoglucanase II 239 nt | BOTH |
| NCU04952 | *Neurospora crassa* hypothetical protein similar to beta D glucoside glucohydrolase 736 nt | BOTH |
| NCU05057 | *Neurospora crassa* endoglucanase EG 1 precursor 439 nt | BOTH |
| NCU05137 | *Neurospora crassa* conserved hypothetical protein 692 nt | BOTH |
| NCU05924 | *Neurospora crassa* endo 1 4 beta xylanase 330 nt | BOTH |
| NCU05955 | *Neurospora crassa* hypothetical protein similar to Cel74a 862 nt | BOTH |
| NCU07143 | *Neurospora crassa* predicted protein 391 nt | BOTH |
| NCU07190 | *Neurospora crassa* conserved hypothetical protein 384 nt | BOTH |
| NCU07225 | *Neurospora crassa* endo 1 4 beta xylanase 2 precursor 255 nt | BOTH |
| NCU07326 | *Neurospora crassa* predicted protein 327 nt | BOTH |
| NCU07340 | *Neurospora crassa* exoglucanase 1 precursor 522 nt | BOTH |
| NCU07898 | *Neurospora crassa* predicted protein 242 nt | BOTH |
| NCU08189 | *Neurospora crassa* hypothetical protein similar to endo 1 4 beta xylanase 385 nt | BOTH |
| NCU08398 | *Neurospora crassa* conserved hypothetical protein 391 nt | BOTH |
| NCU08412 | *Neurospora crassa* conserved hypothetical protein 401 nt | BOTH |
| NCU08760 | *Neurospora crassa* predicted protein 343 nt | BOTH |
| NCU09024 | *Neurospora crassa* conserved hypothetical protein 625 nt | BOTH |
| NCU09175 | *Neurospora crassa* conserved hypothetical protein 411 nt | BOTH |
| NCU09491 | *Neurospora crassa* feruloyl esterase B precursor 293 nt | BOTH |
| NCU09680 | *Neurospora crassa* exoglucanase 2 precursor 485 nt | BOTH |
| NCU00798 | *Neurospora crassa* predicted protein 313 nt | AV |
| NCU01595 | *Neurospora crassa* protein SOF1 446 nt | AV |
| NCU02240 | *Neurospora crassa* hypothetical protein similar to endoglucanase II 323 nt | AV |
| NCU02696 | *Neurospora crassa* hypothetical protein similar to DEAD DEAH box RNA helicase 1195 nt | AV |
| NCU02855 | *Neurospora crassa* endo 1 4 beta xylanase A precursor 221 nt | AV |
| NCU04205 | *Neurospora crassa* predicted protein 346 nt | AV |
| NCU04395 | *Neurospora crassa* endo 1 6 beta D glucanase precursor 481 nt | AV |
| NCU05121 | *Neurospora crassa* endoglucanase V 294 nt | AV |
| NCU05134 | *Neurospora crassa* hypothetical protein 124 nt | AV |
| NCU05852 | *Neurospora crassa* conserved hypothetical protein 254 nt | AV |
| NCU05974 | *Neurospora crassa* hypothetical protein similar to cell wall glucanosyltransferase Mwg1 365 nt | AV |
| NCU08171 | *Neurospora crassa* predicted protein 382 nt | AV |
| NCU08909 | *Neurospora crassa* hypothetical protein similar to beta 1 3 glucanosyltransferase 543 nt | AV |
| NCU08936 | *Neurospora crassa* clock controlled gene 15 412 nt | AV |
| NCU09046 | *Neurospora crassa* predicted protein 187 nt | AV |
| NCU09764 | *Neurospora crassa* conserved hypothetical protein 406 nt | AV |
| NCU01651 | *Neurospora crassa* conserved hypothetical protein 783 nt | MIS |
| NCU02343 | *Neurospora crassa* hypothetical protein similar to alpha L arabinofuranosidase A 668 nt | MIS |
| NCU04202 | *Neurospora crassa* nucleoside diphosphate kinase 1 153 nt | MIS |
| NCU04870 | *Neurospora crassa* hypothetical protein similar to acetyl xylan esterase 313 nt | MIS |
| NCU05159 | *Neurospora crassa* acetylxylan esterase precursor 301 nt | MIS |
| NCU05751 | *Neurospora crassa* conserved hypothetical protein 242 nt | MIS |
| NCU06239 | *Neurospora crassa* conserved hypothetical protein 514 nt | MIS |
| NCU08785 | *Neurospora crassa* conserved hypothetical protein 291 nt | MIS |
| NCU09267 | *Neurospora crassa* conserved hypothetical protein 1048 nt | MIS |
| NCU09708 | *Neurospora crassa* conserved hypothetical protein 465 nt | MIS |
| NCU09775 | *Neurospora crassa* hypothetical protein similar to alpha L arabinofuranosidase 343 nt | MIS |
| NCU09923 | *Neurospora crassa* hypothetical protein similar to beta xylosidase 775 nt | MIS |

ANNOTATION - Generated by the Broad Institute (webpage broad.mit.edu/annotation/genome/neurospora/Home.html);

CULTURE - Culture in which peptides were detected for a particular protein.

BOTH, peptides detected in both Avicel and *Miscanthus* culture filtrates;

AV, peptides detected only in Avicel culture filtrates;

MIS, peptides detected only in *Miscanthus* culture filtrates.

Example 3

Figure 6:
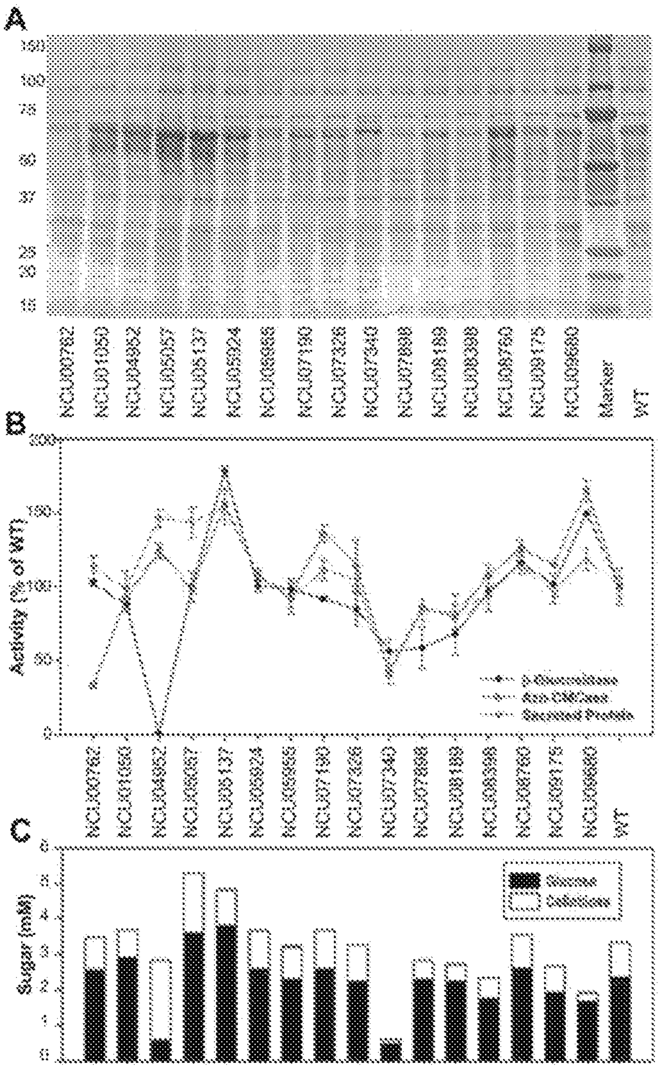
FIG. 6 shows the protein profile and enzymatic activity of culture supernatants from strains containing deletions of genes encoding secreted proteins identified by MS.

Characterization of Extracellular Proteins and Cellulase Activity in Strains Containing Deletions in Genes Identified in the Overlap of the Transcriptome/Secretome Datasets Of the 22 extracellular proteins detected in both the *Miscanthus* and Avicel grown cultures, homokaryotic strains containing deletions in genes encoding 16 of these extracellular proteins were available to the public (Dunlap et al., 2007). None of these 16 deletion strains had been previously characterized with respect to their influence on plant cell wall or cellulose degradation in *N. crassa*. The 16 deletion strains were grown both on media containing sucrose or Avicel as a preferred carbon source. All strains showed a wild type growth phenotype on sucrose. On medium containing Avicel, the bulk growth of the 16 deletion strains was monitored for a 7-day period. After seven days, the total secreted protein, endoglucanase activity, β-glucosidase activity, and aggregate Avicelase activity of the culture filtrates was measured and compared with the wild-type strain from which all the mutants were derived (FIG. 6). SDS-PAGE was also done on unconcentrated culture supernatants to investigate the relative abundance of secreted proteins.

Figure 7:
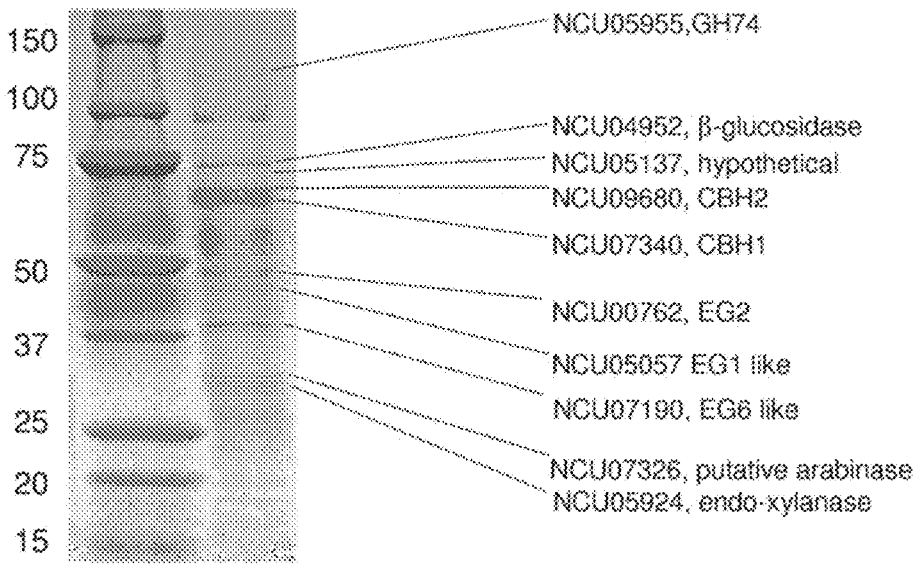
FIG. 7 shows the identity of *N. crassa* secreted proteins based on mutant analysis from a culture grown on Avicel as a sole carbon source. SDS-PAGE of secreted proteins from WT *N. crassa* (FGSC 2489) grown on 2% Avicel in 100 mL shake flasks for 7 days at 25° C. 15 μL of unconcentrated culture filtrate was loaded onto Criterion 4-15% 26-well gel. Proto Blue Safe (Coomassie) from National Diagnostics was used to stain the gel. The protein bands were identified in this study as shown in FIG. 6A based on analysis of secreted proteins in deletion strains.

There were growth deficiencies on Avicel for strains containing deletions of two predicted exoglucanases (cbh-1; NCU07340 and gh6-2; NCU09680) and a predicted β-glucosidase (gh3-4; NCU04952). The cbh-1 mutant was the most severe; after seven days much of the Avicel remained, while in the wild-type strain all of the Avicel was degraded by this time. For 10 of the 16 deletion strains, SDS-PAGE analysis of the secreted proteins showed an altered extracellular protein profile where a single band disappeared, thus allowing assignment of a particular protein band to a predicted gene (FIG. 6A, boxes; FIG. 7). These included NCU00762 (gh5-1), NCU04952 (gh3-4), NCU05057 (gh7-1), NCU05137, NCU05924 (gh10-1), NCU05955, NCU07190 (gh6-3), NCU07326, NCU07340 (cbh-1), and NCU09680 (gh6-2).

For the majority of the deletion strains, the total secreted protein, endoglucanase, β-glucosidase, and Avicelase activities of the culture supernatants were similar to wild type (FIG. 6B, C and Table 9).

Deviations from this trend were seen with the Δgh5-1 (NCU00762), Δgh3-4 (NCU04952), ΔNCU05137, Δcbh-1 (NCU07340), and Δgh6-2 (NCU09680) mutants. In Δgh5-1 (NCU00762), Δgh3-4 (NCU04952), and Δcbh-1 (NCU07340), Avicelase, endoglucanase or Δ-glucosidase activities were lower than the corresponding wild-type activities. In particular, the deletion of NCU04952 eliminated all β-glucosidase activity from the culture supernatant, as evidenced by PNPGase activity and by higher levels of cellobiose and lower levels of glucose in the Avicelase enzyme assays (FIG. 6B, C). Despite lowering endoglucanase activity, the culture filtrate from Δgh5-1 (NCU00762) showed no significant deficiency in Avicelase activity relative to the wild-type strain (FIG. 6C). As expected, mutations in cbh-1 (NCU07340) resulted in lower endoglucanase and Avicelase activity, due to poor growth. A strain containing a deletion of NCU09680, encoding a CBH(II)-like protein (gh6-2), also showed reduced cellobiose accumulation, as observed with Δcbh-1 mutant (FIG. 6C).

Figure 2:
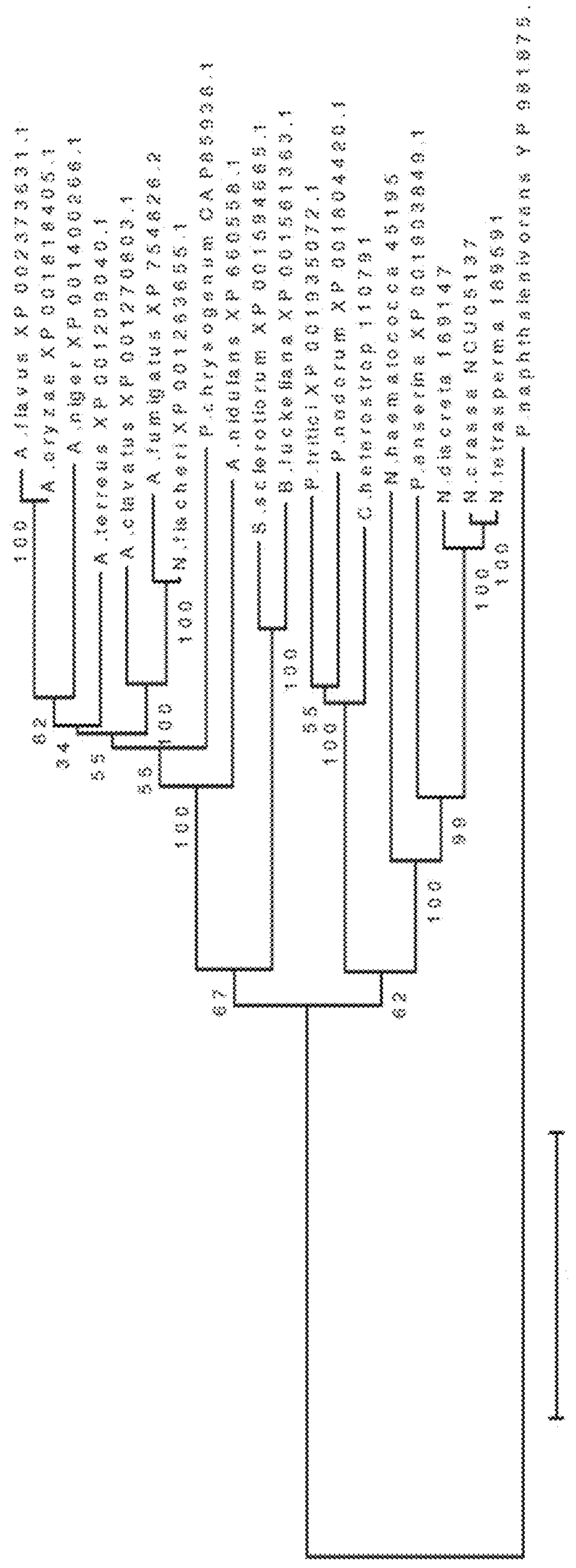
FIG. 2 shows the phylogenetic analysis of NCU05137. The predicted orthologs of *N. crassa* NCU05137 were retrieved from NCBI and JGI based on amino acid sequences showing significant similarity by BLAST. All identified filamentous fungal orthologs are shown; NCBI E values were 0.0 except for *B. fuckeliana*, which was 9e-175. Homologs of NCU05137 were also identified in a number of bacteria (E value~e-30). YP 981875 from *Polaromonas naphthalenivorans* (a beta-proteobacterium) was used as an outgroup. A.=*Aspergillus*; N.=*Neosartorya; P. chyrosogenum=Penicillium*; S.=*Sclerotinia*; B.=*Botryotinia*; P.=*Pyrenophora*; C.=*Cochliobolus; N. haematococca=Nectria; P. anserina=Podospora*; N.=*Neurospora*. The tree was made by MEGA3, NJ. Bar=0.2 substitutions per amino acid site.
Figure 8:
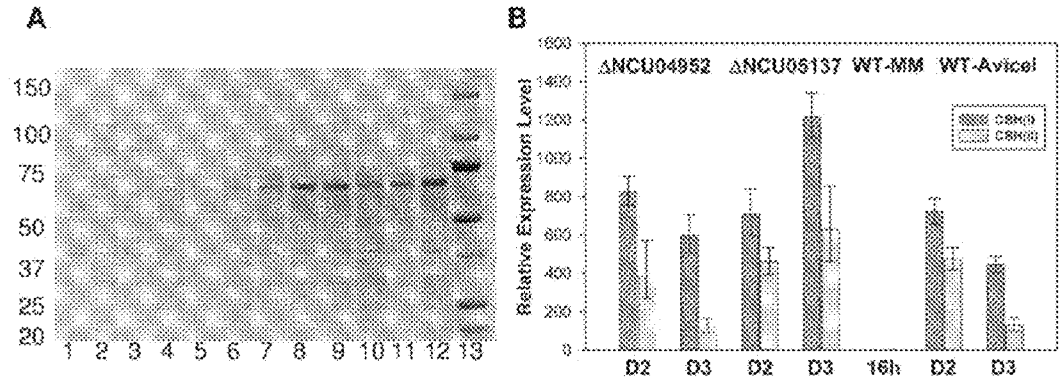
FIG. 8 shows the profile of secreted proteins and expression of cbh-1 (NCU07340) and gh6-2 (NCU09680; CBHII) in ΔNCU04952 and ΔNCU05137.

Mutations in three strains resulted in an increased level of secreted proteins, especially CBH(I) (FIG. 6A); gh3-4 (NCU04952), gh7-1 (NCU05057) and a hypothetical protein gene (NCU05137). In addition to increased levels of secreted proteins, the ΔNCU05137 mutant showed increased endoglucanase, β-glucosidase, and Avicelase activity (FIG. 6B, C). NCU05137 is highly conserved in the genomes of a number of filamentous ascomycete fungi, including other cellulolytic fungi, but notably does not have an ortholog in *T. reesei* (FIG. 2). It is possible that the increase in CBH(I) levels observed in Δgh3-4, Δgh7-1, and ΔNCU05137 could be due to either increased secretion, protein stability or, alternatively, feedback that results in an increase in expression of cbh-1. To differentiate these possibilities, the profile of extracellular proteins produced by ΔNCU05137 and Δgh3-4 (NCU04952) was compared with gene expression levels of cbh-1 (NCU07340) and gh6-2 (CBH(II); NCU09680) as assayed by quantitative RT-PCR (FIG. 8). The strains ΔNCU05137 and Δgh3-4 showed a higher level of CBH(I) protein as early as two days in an Avicel-grown culture. Quantitative RT-PCR of cbh-1 and gh6-2 from Avicel-grown cultures showed that both genes exhibited high expression levels in wild type and the ΔNCU05137 and Δgh3-4 mutants after two days of growth. However, although expression of both of these genes

TABLE 9

Enzyme Activity of Deletion Strains

| Gene Name | Growth on Avicel | [Secreted Protein] (% of WT) | Azo-CMCase (% of WT) | Bgl (% of WT) | [CB] (mM) | [GLC] (mM) |
|---|---|---|---|---|---|---|
| NCU00762 | * * * | 113 ± 8 | 33 ± 2 | 102 ± 2 | 0.9 ± 0.0 | 2.6 ± 0.1 |
| NCU01050 | * * * | 98 ± 12 | 92 ± 8 | 88 ± 5 | 0.8 ± 0.2 | 2.9 ± 0.3 |
| NCU04952 | * * * | 146 ± 6 | 124 ± 5 | 1 ± 0.3 | 2.24 ± 0.2 | 0.6 ± 0.0 |
| NCU05057 | * * * | 143 ± 10 | 98 ± 3 | 100 ± 10 | 1.7 ± 0.1 | 3.6 ± 0.1 |
| NCU05137 | * * * | 154 ± 12 | 156 ± 10 | 178 ± 3 | 1.0 ± 0.0 | 3.8 ± 0.1 |
| NCU05924 | * * * | 108 ± 3 | 108 ± 5 | 101 ± 4 | 1.1 ± 0.1 | 2.6 ± 0.2 |
| NCU05955 | * * * | 92 ± 10 | 94 ± 8 | 98 ± 7 | 0.9 ± 0.1 | 2.3 ± 0.1 |
| NCU07190 | * * * | 111 ± 7 | 136 ± 6 | 92 ± 1 | 1.1 ± 0.0 | 2.6 ± 0.0 |
| NCU07326 | * * * | 105 ± 4 | 114 ± 17 | 85 ± 11 | 1.0 ± 0.0 | 2.3 ± 0.0 |
| NCU07340 | * | 41 ± 2.2 | 43 ± 9 | 56 ± 9 | 0.1 ± 0.0 | 0.5 ± 0.1 |
| NCU07898 | * * * | 84 ± 7 | 86 ± 1.5 | 59 ± 15 | 0.5 ± 0.3 | 2.3 ± 0.5 |
| NCU08189 | * * * | 83 ± 12 | 80 ± 8 | 69 ± 15 | 0.5 ± 0.1 | 2.3 ± 0.4 |
| NCU08398 | * * * | 95 ± 11 | 107 ± 7 | 97 ± 3 | 0.6 ± 0.1 | 1.8 ± 0.0 |
| NCU08760 | * * * | 115 ± 3 | 126 ± 6 | 115 ± 8 | 0.9 ± 0.1 | 2.6 ± 0.1 |
| NCU09175 | * * * | 96 ± 7 | 115 ± 0 | 101 ± 8 | 0.7 ± 0.0 | 1.9 ± 0.1 |
| NCU09680 | * * | 118 ± 7 | 165 ± 7 | 150 ± 1 | 0.23 ± 0.1 | 1.7 ± 0.1 |
| WT | * * * | 100 ± 7 | 100 ± 12 | 100 ± 6 | 0.97 ± 0.0 | 2.4 ± 0.1 |

decreased significantly on day three in the wild-type strain, both cbh-1 and gh6-2 expression levels increased in the ΔNCU05137 mutant, and decreased less than wild type in Δgh3-4 (FIG. 8). Sustained expression of cbh-1 and gh6-2 genes in the ΔNCU05137 and Δgh3-4 mutants could be responsible for the observed increase in CBH(I) and CBH(II) protein levels.

Example 4

Materials and Methods for Transcriptome and Secretome Studies

Strains

All *Neurospora crassa* strains were obtained from the Fungal Genetics Stock Center (FGSC; webpage fgsc.net) (Supplemental Data, Dataset S1, page 1 in Tian et al., 2009). Gene deletion strains were from the *N. crassa* functional genomics project (Dunlap et al., 2007). *Trichoderma reesei* QM9414 was a gift from Dr. Monika Schmoll (Vienna University of Technology). Strains were grown on Vogel's salts (Vogel 1956) with 2% (w/v) carbon source (*Miscanthus*, sucrose or Avicel (Sigma)). *Miscanthus*×*giganteus* (milled stem to ~0.1 mm) was a gift from the University of Illinois.

Enzyme Activity Measurements

Total extracellular protein content was determined using a Bio-Rad DC Protein Assay kit (Bio-Rad). Endoglucanase activity in culture supernatants was measured with an azo-CMC kit (Megazyme SCMCL). β-glucosidase activity was measured by mixing 10-fold diluted culture supernatant with 500 μM 4-nitrophenyl β-D-glucopyranoside in 50 mM sodium acetate buffer, pH 5.0, for 10 minutes at 40° C. The reaction was quenched with 5% w/v sodium carbonate, and the absorbance at 400 nm was measured. Avicelase activity was measured by mixing 2-fold diluted culture supernatant with 50 mM sodium acetate, pH 5.0, and 5 mg/mL Avicel at 40° C. Supernatants were analyzed for glucose content using a coupled enzyme assay with glucose oxidase/peroxidase. Fifty μL of the avicelase reaction was transferred to 150 μL of glucose detection reagent containing 100 mM sodium acetate pH 5.0, 10 U/mL horseradish peroxidase, 10 U/mL glucose oxidase, and 1 mM o-dianisidine. After 30 minutes absorption was measured at 540 nm. Cellobiose concentrations were determined using a coupled enzyme assay with cellobiose dehydrogenase (CDH) from *Sporotrichum thermophile*. CDH was isolated from *S. thermophile* similar to previous reports (Canevascini 1988). Fifty μL of the avicelase reaction was transferred to 250 μL of cellobiose detection reagent containing 125 mM sodium acetate pH 5.0, 250 μM dichlorophenol indophenol, and 0.03 mg/mL CDH. After 10 minutes absorption was measured at 530 nm.

RNA Isolation, Microarray Analysis, and Signal Peptide Predictions

Mycelia were harvested by filtration and flash frozen in liquid nitrogen. Total RNA was isolated using trizol (Tian et al., 2007; Kasuga et al., 2005). Microarray hybridization and data analysis were as previously described (Tian et al., 2007). Normalized expression values were analyzed using BAGEL (Bayesian analysis of gene expression levels) (Townsend 2004; Townsend and Hartl 2002), which infers relative gene expression levels and credible intervals for each gene at each experimental time point. Signal peptides were predicted using the N-terminal 70 amino acid region of each predicted protein with the signalP3 program (webpage cbs.dtu.dk/services/SignalP-3.0/). Original profiling data is obtainable at (webpage yale.edu/townsend/Links/ffdatabase/).

Protein Gel Electrophoresis

Except where otherwise noted, unconcentrated culture supernatants were treated with 5×SDS loading dye and boiled for 5 minutes before loading onto Criterion 4-15% Tris-HCl polyacrylamide gels. Coomassie dye was used for staining.

Preparation of Tryptic Peptides for Secretome Analysis

Culture supernatants were concentrated with 10 kDa MWCO PES spin concentrators. Cellulose binding proteins were isolated from the culture supernatant by addition of phosphoric acid swollen cellulose (PASC). Five mL of a suspension of 10 mg/mL PASC was added to 10 mL of culture supernatant. After incubation at 4° C. for 5 minutes, the mixture was centrifuged and the pelleted PASC was then washed with 20 pellet volumes of 100 mM sodium acetate pH 5.0. The supernatant after treatment with PASC was saved as the unbound fraction and concentrated. 36 mg of urea, 5 μL of 1M Tris PH 8.5, and 5 μL of 100 mM DTT were then added to 100 μL of concentrated culture supernatant or protein-bound PASC and the mixture was heated at 60° C. for 1 hour. After heating 700 μL of 25 mM ammonium bicarbonate and 140 μL of methanol were added to the solution followed by treatment with 50 μL of 100 μg/mL trypsin in 50 mM sodium acetate pH 5.0. For the PASC bound proteins, the PASC was removed by centrifugation after heating, and the supernatant was then treated with trypsin. The trypsin was left to react overnight at 37° C. After digestion the volume was reduced by speedvac and washed with MilliQ water three times. Residual salts in the sample were removed by using OMIX microextraction pipette tips according to the manufacturer's instructions.

Liquid Chromatography of Tryptic Peptides

Trypsin-digested proteins were analyzed using a tandem mass spectrometer that was connected in-line with ultraperformance liquid chromatography (UPLC). Peptides were separated using a nanoAcquity UPLC (Waters, Milford, Mass.) equipped with C18 trapping (180 μm×20 mm) and analytical (100 μm×100 mm) columns and a 10 μL sample loop. Solvent A was 0.1% formic acid/99.9% water and solvent B was 0.1% formic acid/99.9% acetonitrile (v/v). Sample solutions contained in 0.3 mL polypropylene snap-top vials sealed with septa caps (Wheaton Science, Millville, N.J.) were loaded into the nanoAcquity autosampler prior to analysis. Following sample injection (2 μL, partial loop), trapping was performed for 5 min with 100% A at a flow rate of 3 μL/min. The injection needle was washed with 750 μL each of solvents A and B after injection to avoid cross-contamination between samples. The elution program consisted of a linear gradient from 25% to 30% B over 55 min, a linear gradient to 40% B over 20 min, a linear gradient to 95% B over 0.33 min, isocratic conditions at 95% B for 11.67 min, a linear gradient to 1% B over 0.33 min, and isocratic conditions at 1% B for 11.67 min, at a flow rate of 500 nL/min. The analytical column and sample compartment were maintained at 35° C. and 8° C., respectively.

Mass Spectrometry

The column was connected to a NanoEase nanoelectrospray ionization (nanoESI) emitter mounted in the nanoflow ion source of a quadrupole time-of-flight mass spectrometer (Q-Tof Premier, Waters). The nanoESI source parameters were as follows: nanoESI capillary voltage 2.3 kV, nebulizing gas (nitrogen) pressure 0.15 mbar, sample cone voltage 30 V, extraction cone voltage 5 V, ion guide voltage 3 V, and source block temperature 80° C. No cone gas was used. The collision cell contained argon gas at a pressure of 8×10-3 mbar. The T of analyzer was operated in "V" mode. Under these conditions, a mass resolving power 1 of 1.0×104 (measured at m/z=771) was routinely achieved, which is sufficient to resolve the isotopic distributions of the singly and multiply charged peptide ions measured in this study. Thus, an ion's mass and charge could be determined independently, i.e., the ion charge was determined from the reciprocal of the spacing between adjacent isotope peaks in the m/z spectrum. External mass calibration was performed immediately prior to analysis, using solutions of sodium formate. Survey scans were acquired in the positive ion mode over the range m/z=450-1800 using a 0.95 s scan integration and a 0.05 s interscan delay. In the data-dependent mode, up to five precursor ions exceeding an intensity threshold of 35 counts/second (cps) were selected from each survey scan for tandem mass spectrometry (MS/MS) analysis. Real-time deisotoping and charge state recognition were used to select 2+, 3+, 4+, 5+, and 6+ charge state precursor ions for MS/MS. Collision energies for collisionally activated dissociation (CAD) were automatically selected based on the mass and charge state of a given precursor ion. MS/MS spectra were acquired over the range m/z=50-2500 using a 0.95 s scan integration and a 0.05 s interscan delay. Ions were fragmented to achieve a minimum total ion current (TIC) of 30,000 cps in the cumulative MS/MS spectrum for a maximum of 3 s. To avoid the occurrence of redundant MS/MS measurements, real time exclusion was used to preclude re-selection of previously analyzed precursor ions over an exclusion width of ±0.25 m/z unit for a period of 180 s.

Mass Spectrometry Data Analysis

The data resulting from LC-MS/MS analysis of trypsin-digested proteins were processed using ProteinLynx Global Server software (version 2.3, Waters), which performed background subtraction (threshold 35% and fifth order polynomial), smoothing (Savitzky-Golay2 10 times, over three channels), and centroiding (top 80% of each peak and minimum peak width at half height four channels) of the mass spectra and MS/MS spectra. The processed data were searched against the *N. crassa* database (Broad Institute) using the following criteria: tryptic fragments with up to five missed cleavages, precursor ion mass tolerance 50 ppm, fragment ion mass tolerance 0.1 Da, and the following variable post-translational modifications: carbamylation of N-terminus and Lys side chains, Met oxidation, and Ser/Thr dehydration. The identification of at least three consecutive fragment ions from the same series, i.e., b or y-type fragment ions, was required for assignment of a peptide to an MS/MS spectrum. The MS/MS spectra were manually inspected to verify the presence of the fragment ions that uniquely identify the peptides.

Quantitative RT-PCR

The RT-PCR was performed in an ABI7300 with reagents from Qiagen (SYBR-green RT-PCR kit (Cat No. 204243)). The primers for CBHI (NCU07340) were: forward 5'-ATCTGGGAAGCGAACAAAG-3' (SEQ ID NO: 16) and reverse 5'-TAGCGGTCGTCGGAATAG-3' (SEQ ID NO: 17). The primers for CBHII (NCU09680) were: forward 5'-CCCATCACCACTACTACC-3' (SEQ ID NO: 18) and reverse 5'-CCAGCCCTGAACACCAAG-3' (SEQ ID NO: 19). Actin was used as a control for normalization. The primers for actin were: forward 5'-TGA TCT TAC CGA CTA CCT-3' (SEQ ID NO: 20) and reverse 5'-CAG AGC TTC TCC TTG ATG-3' (SEQ ID NO: 21). Quantitative RT-PCR was performed according to Dementhon et al., (2006).

Example 5

Discussion of Transcriptome and Secretome Studies

Figure 9:
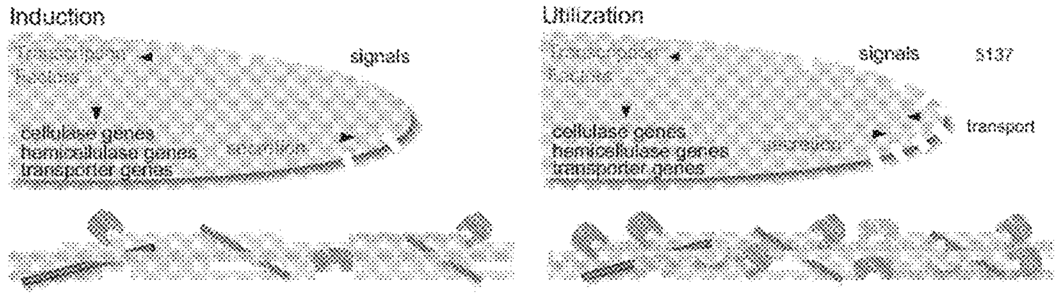
FIG. 9 shows a model of plant cell wall deconstruction in *N. crassa*. Induction: Extracellular enzymes expressed at low levels generate secondary metabolites that signal *N. crassa* to dramatically increase the expression level of genes encoding plant cell wall degrading enzymes, most of which are secreted. Utilization: Extracellular enzymes and transporters specific for translocation of cell wall degradation products enable *N. crassa* to utilize plant cell material for growth. Some extracellular proteins (NCU05137, NCU05057, and NCU04952) may generate metabolites that modulate gene expression of cellulases and hemicellulase during the utilization phase; double hexagon (cellobiose), double pentagon (xylobiose), hexagon (glucose), and pentagon (xylose). The depicted plant cell wall-degrading enzymes include CBH(I), CBH(II), EG2, EG1, EG6, and xylanase. Additional cellulolytic enzymes are not shown. Thickness of arrows indicates relative strength of response.

Degradation of plant biomass requires the production of many different enzymatic activities, which are regulated by the type and complexity of the available plant material (FIG. 9) (Bouws et al., 2008). The first systematic analyses of plant cell wall degradation by a cellulolytic fungus are described here, which include transcriptome, secretome, and mutant analyses. Profiling data showed that *N. crassa* coordinately expresses a host of extracellular and intracellular proteins when challenged by growth on *Miscanthus* or Avicel (FIG. 9). Many of the most highly expressed genes during growth on cellulosic substrates encode proteins predicted to be involved in the metabolism of plant cell wall polysaccharides, many of which were identified by MS analyses. Genome comparisons of filamentous fungi show a large number of glycosyl hydrolases (~200) with varying numbers of predicted cellulases, from 10 in *T. reesei* (Martinez et al., 2008) to 60 in *Podospora anserina* (Espagne et al., 2008), a dung-degrading species closely related to *N. crassa*. A comparison between these results and a recent transcriptome/secretome study on the white rot basidiomycete fungus, *Phanerochaete chrysosporium*, (Wymelenberg et al., 2009) showed little overlap in regulated genes (18 genes) and secreted proteins (2 proteins) when both species were grown on pure cellulose. These data suggest that different fungi may utilize different gene sets for plant cell wall degradation. However, one aspect that both studies had in common was the high number of uncharacterized genes/proteins associated with cellulose degradation. Other cellulolytic fungi, including *P. chrysosporium*, do not have the genetic and molecular tools that are readily available with *N. crassa*. Using the functional genomic tools available with *N. crassa*, both the function and redundancy of plant cell wall degrading enzyme systems can be addressed to create optimal enzyme mixtures for industrial production of liquid fuels from lignocellulose biomass.

In this study, it was found that cellobiohydrolase(I) (CBHI) in *N. crassa* is the most highly produced extracellular protein during growth on Avicel or *Miscanthus*, and deletion of this gene caused the most severe growth deficiencies on cellulosic substrates. These results are similar to those reported in *T. reesei* (Suominen et al., 1993, Seiboth et al., 1997). Deletion of cellobiohydrolase(II) also caused growth deficiencies on cellulosic substrates, but to a much lesser extent than CBH(I), suggesting that exoglucanase activity in *N. crassa* is predominantly from CBH(I) and that cellulases and other CBHs do not compensate for the loss of CBH(I). Here, it was shown that the three most highly produced endoglucanases during growth on cellulosic substrates are the proteins encoded by NCU05057, NCU00762, and NCU07190. These proteins have homology to endoglucanases EG1, EG2, and EG6, respectively. Deletion of these genes did not affect growth on Avicel, although differences in the secreted protein levels and endoglucanase activity were observed. Unexpectedly, in the ΔNCU05057 strain, extracellular protein levels were much higher, especially CBH(I), suggesting that to maintain the wild-type growth phenotype on crystalline cellulose the mutant was forced to increase production of other cellulases or that the products of NCU05057 catalysis may repress cellulase production. It was concluded that no one endoglucanase in *N. crassa* is required for growth on crystalline cellulose and that the different endoglucanases have overlapping substrate specificities.

The glycoside hydrolase family 61 enzymes are greatly expanded in *N. crassa* compared to *T. reesei* (Martinez et al., 2008). These enzymes have poorly defined biological function, but their general conservation and abundance in cellulolytic fungi suggests an important role in plant cell wall metabolism. Here, genes for 10 of the 14 GH61 enzymes were identified in the *N. crassa* transcriptome, suggesting that these enzymes are utilized during growth on cellulosic biomass. The four GH61 deletion strains tested showed only small differences compared to wild type in the secreted protein levels, endoglucanase, and total cellulase activities. However, analyses of additional GH61 mutants and the capacity to create strains containing multiple mutations in *N. crassa* via sexual crosses will address redundancy and expedite functional analysis of this family.

In addition to predicted cellulase genes, genes encoding hemicellulases, carbohydrate esterases, β-glucosidases, β-xylosidases, and other proteins predicted to have activity on carbohydrates were identified in the *N. crassa* transcriptome from both *Miscanthus* and Avicel. The fact that Avicel contains no hemicellulose components suggests that cellulose is probably the primary inducer of genes encoding plant cell wall degrading enzymes in *N. crassa*. However, genes encoding some hemicellulases and carbohydrate esterases were only expressed during growth on *Miscanthus*. Similarly, in other cellulolytic fungi such as *T. reesei* and *Aspergillus niger*, genes encoding some cellulases and hemicellulases are coordinately regulated, while others are differentially regulated (Stricker et al., 2008). As expected, deletions of non-cellulase genes had little effect on growth on Avicel or cellulase activity, with the exception of NCU05137 and gh3-4. The ΔNCU05137 strain secreted more protein, had higher cellulase activity, and showed higher expression of cbh-1 (CBH (I)) and gh6-2 (CBH(II)) than wild type. NCU05137 encodes a secreted hypothetical protein that has no homology to proteins of known function, but is highly conserved in other cellulolytic fungi (FIG. 2; E value 0.0). NCU05137 also has more distant homologs, but also of unknown function, in a number of bacterial species. The protein product of NCU05137 may interfere with signaling processes associated with induction of cellulase gene expression *N. crassa* (FIG. 9). Similarly, mutations in gh3-4 (NCU04952) also increased CBH(I) activity. Deletion of this gene completely removed PNPGase activity and cellobiose accumulated in in vitro cellulase assays using Δgh3-4 culture filtrates. All the data together suggested that NCU04952 encodes the primary extracellular β-glucosidase in *N. crassa*. These data were consistent with catabolite repression of cellulase production by glucose.

Extracellular degradation of cellulose and hemicellulose results in the formation of soluble carbohydrates that are subsequently transported into the cell (FIG. 9). In this study, 10 genes encoding permeases/transporters were identified which showed significantly increased expression when *N. crassa* was grown on *Miscanthus* or Avicel, suggesting their involvement in transport of plant cell wall degradation products into the cell. The major degradation products by cellulases and hemicellulases in vitro are cellobiose, glucose, xylobiose, and xylose. Some of these transporters may be functionally redundant or capable of transporting oligosaccharides. The function of these putative transporters was further explored (see Examples 7-9). Construction of downstream processing strains capable of transporting oligosaccharides by heterologous expression of *N. crassa* transporters may improve industrial fermentation of biomass hydrolysis products. None of these transporters or what they may transport has been characterized at the molecular or functional level in any filamentous fungi.

Many genes that showed increased expression levels during growth on *Miscanthus* and Avicel encode proteins of unknown function that are conserved in other cellulolytic fungi. By assessing the phenotype of only 16 strains, a mutant in a gene encoding a protein of unknown function that significantly affects cellulase activity was identified. The well-understood genetics and availability of functional genomic resources in *N. crassa* make it an ideal model organism to determine the biological function of these proteins, as well as regulatory aspects of cellulase and hemicellulase production, and to dissect redundancies and synergies between extracellular enzymes involved in the degradation of plant cell walls.

Example 6

Screening of Mutants of Genes Upregulated During Growth on *Miscanthus*

In order to analyze additional genes identified in the transcriptional profiling experiment, the phenotypes of mutants of 188 genes that were upregulated in *Neurospora* grown on *Miscanthus* for 16 hours were analyzed (see Example 1). A knockout mutant of each gene was grown on minimal Vogel's medium for 10-14 days. Conidia were harvested with 2 mL dd$H_2O$ and inoculated into 100 mL media in 250 mL flasks at a concentration of $10^6$ conidia per mL. One of three different carbon sources was added to each flask: 2% sucrose, 2% Avicel, or 2% *Miscanthus* (1 mm particles from Calvin Laboratory, University of California, Berkeley, Calif.). Cultures were grown at 25° C. with 220 rpm of shaking for 4 days.

Table 10 lists the phenotypes of the mutants that showed a significant difference in cellulase activity and growth on Avicel or *Miscanthus* compared to wild-type. Growth on Avicel or *Miscanthus* was evaluated by eye with a "+" scoring system. Wild-type growth was set at "++". Total protein in the culture supernatant was measured by Bradford assay (100 μl supernatant to 900 μl Bradford dye). Endoglucanase activity was measured with the Azo-CMC kit from Megazyme and indicated in Table 10 as the percentage of endoglucanase activity in the mutant compared to wild type. Total cellulase activity was measured by detecting cellobiose levels in the supernatant as described in Example 4. Results are indicated in Table 10 as a percentage of wild-type.

Table 10 Shows Mutant Screening Data

| NCU# | FGSC # | Broad Annotation (Domains) | Pfam* | Up-Regulation | Growth (Avi, Mis) | % WT Bradford (Avi) |
|---|---|---|---|---|---|---|
| NCU00130.2 | FGSC 11823 | beta-glucosidase (GH1) | Glycosyl Hydrolase 1 (2.5e−196) | 394.6 | ++, ++ | 203.2477947 |
| NCU00248.2 | FGSC 12214 | Predicted Protein | no significant hit | 9.74 | +, ++ | 86.96013289 |
| NCU00326.2 | FGSC 15868 | Conserved Hypothetical (SMP-30/ gluconolactonase) | SMP-30/ Gluconolaconase/ LRE-like region (3.5e−82) | 7.7 | +, ++ | 33.02879291 |

-continued

| | | | | | | |
|---|---|---|---|---|---|---|
| NCU00762.2 | FGSC 16747 | Endoglucanase-3 precursor (GH5, CBD1) | Cellulase (1.4e−69), Fungal cellulose binding domain (9.2e−14) | 29.6 | ++, ++ | 104.3504411 |
| NCU00810.2 | FGSC 11285 | Similar to Glycosyl Hydrolase (GH2, beta-galactosidase) | Glycosyl hydrolases family 2 (1.7e−145) | 5.3 | ++, ++ | 163.805047 |
| NCU00890.2 | FGSC 16749 | Similar to beta-manosidase (GH2) | Glycosyl hydrolases family 2 (4.1e−06) | 20.45 | +, + | 47.57417803 |
| NCU03328.2 | FGSC 16589 | Conserved Hypothetical (GH61) | Glycosyl hydrolase family 61 (2.3e−10) | 26.4 | ++, ++ | 100.1752848 |
| NCU03415.2 | FGSC 12922 | Aldehyde Dehydrogenase | Aldehyde dehydrogenase family (2.5e−267) | 9.8 | ++, ++ | 104.2278204 |
| NCU03731.2 | FGSC 18653 | Similar to HAD Superfamily Hydrolase | haloacid dehalogenase-like hydrolase (9.2e−21) | 2.7 | ++, ++ | 131.3691128 |
| NCU03753.2 | FGSC 16379 | ccg-1 (clock controlled gene) | no significant hit | 10.5 | ++, ++ | 107.6792892 |
| NCU04197.2 | FGSC 17499 | Conserved Hypothetical | no significant hit | 5.04 | ++, ++ | 103.0668127 |
| NCU04249.2 | FGSC 18628 | Hypothetical Protein | no significant hit | 5.3 | ++, ++ | 93.29682366 |
| NCU04287.2 | FGSC 14573 | Predicted Protein | no significant hit | 4.7 | ++, ++ | 115.5157859 |
| NCU04349.2 | FGSC 18634 | Similar to mitochondrial pyruvate dehydrogenase kinase | BCDHK_A dom3 (4.7e−78), Histidine ATPase_c (6.9e−14) | 2.9 | ++, ++ | 87.87776465 |
| NCU04475.2 | FGSC 15386 | Predicted Protein | no significant hit | 76.7 | +++, ++ | 98.10205352 |
| NCU04997.2 | FGSC 15623 | Similar to xylanase (GH10, CBD1) | Glycosyl hydrolase family 10 (3.3e−148), Fungal cellulose binding domain (2.1e−16) | 25.6 | ++, ++ | 105.3520176 |
| NCU05057.2 | FGSC 13342 | Endoglucanase EG-1 precursor (GH7) | Glycosyl hydrolase family 7 (3.3e−189) | 8.7 | ++, ++ | 137.5316563 |
| NCU05159.2 | FGSC 13439 | acetylxylan esterase precursor (Cutinase, CBD1) | Cutinase (3.4e−110), Fungal cellulose binding domain (7.4e−14) | 34.8 | +++, ++ | 86.18543871 |
| NCU05493.2 | FGSC 14625 | Predicted Protein | no significant hit | 4.5 | +, ++ | 73.25266013 |
| NCU05519.2 | FGSC 19924 | Similar to Tna1 (MFS transporter) | Major Facilitator Superfamily (3.7e−40) | 2.8 | ++ ,++ | 85.31191321 |
| NCU05751.2 | FGSC 15757 | Conserved Hypothetical (GDSL-like lipase) | GDSL-like Lipase/ Acylhydrolase (1.3e−11) | 3.9 | +, ++ | 97.01648237 |
| NCU05770.2 | FGSC 11532 | Peroxidase/ Catalase 2 | Peroxidase (9.4e−195) | 11.9 | ++, ++ | 109.8630989 |
| NCU05853 | FGSC 13771 | Sugar Transporter | Sugar Transporter | 130.7 | + | 40.27924687 |
| NCU05897.2 | FGSC 13717 | Similar to l-fucose permease (MFS transporter) | Major Facilitator Superfamily (3.8e−16) | 20.9 | +, ++ | 33.78464142 |
| NCU05932.2 | FGSC 19952 | Predicted Protein | no significant hit | 38.2 | ++, ++ | 70.89826428 |

-continued

| | | | | | | |
|---|---|---|---|---|---|---|
| NCU06009.2 | FGSC 14922 | Similar to aldo/keto reductase | Aldo/keto reductase family (4.8e−63) | 6.9 | +, ++ | 148.6633726 |
| NCU06490.2 | FGSC 15539 | Conserved Hypothetical | no significant hit | 13.8 | +, ++ | 77.46104143 |
| NCU07340.2 | FGSC 15630 | Exoglucanase-1 precursor, CBH1 (GH7) | Glycosyl hydrolase family 7 (1e−999), Fungal cellulose binding domain (4.9e−18) | 426.4 | +, ++ | 21.09634551 |
| NCU07853.2 | FGSC 19036 | Uricase | Uricase (1.7e−119) | 4.3 | +++, ++ | n/a |
| NCU07997.2 | FGSC 18273 | Predicted Protein | no significant hit | 4.5 | ++, ++ | n/a |
| NCU08114.2 | FGSC 17869 | Similar to MFS hexose transporter (MFS transporter) | Sugar (and other) transporter (5.1e−88), Major Facilitator Superfamily (3.8e−24) | 6.7 | +, ++ | 81.69263905 |
| NCU08744.2 | FGSC 11387 | Predicted Protein, possible TF (basic region leucine zipper) | no significant hit | 2.3 | ++, ++ | n/a |
| NCU08746.2 | FGSC 18358 | Conserved Hypothetical (starch binding domain) | Starch binding domain (5.36-54) | 6 | ++, ++ | 98.69504624 |
| NCU08760.2 | FGSC 15664 | Predicted Protein (CBD1) | Fungal cellulose binding domain (1.9e−11), Glycosyl hydrolase family 61 (1.3e−9) | 107.5 | ++, ++ | 158.1395349 |
| NCU09108.2 | FGSC 19207 | Conserved Hypothetical | no significant hit | 4.1 | ++, ++ | n/a |
| NCU09495.2 | FGSC 12411 | set-6, histone methyltransferase | SET domain (6.9e−5) | 26.2 | ++, ++ | 109.3300111 |
| NCU09680.2 | FGSC 15633 | Exoglucanase-2 precursor, CBH2 (GH6, CBD1) | Glycosyl hydrolases family 6 (1.1e−152), Fungal cellulose binding domain (1.2e−13) | 230.9 | +, ++ | 102.7131783 |
| NCU10045.2 | FGSC 18480 | pectinesterase precursor | Pectinesterase (4.4e−22) | 10.9 | +, ++ | 105.3085012 |

| NCU# | % WT Bradford (Mis) | % WT endo (Avi) | % WT endo (Mis) | % WT cellobiose (Avi) | % WT cellobiose (Mis) |
|---|---|---|---|---|---|
| NCU00130.2 | 118.3987972 | 152.2858578 | 129.3547494 | n/a | n/a |
| NCU00248.2 | 86.04471858 | 30.39187506 | 156.5050144 | 93.05143946 | 89.27698219 |
| NCU00326.2 | 144.1210486 | 39.91568458 | 227.0366809 | 89.76872415 | 79.05154639 |
| NCU00762.2 | 84.57056944 | 26.92790756 | 39.26890058 | n/a | n/a |
| NCU00810.2 | 123.5564757 | 161.2908993 | 159.4983744 | 102.2745211 | 91.73345664 |
| NCU00890.2 | 101.5974441 | 43.25546345 | 164.0819718 | n/a | n/a |
| NCU03328.2 | 109.9667248 | 142.6962073 | 167.0075481 | n/a | n/a |
| NCU03415.2 | 96.61435373 | 96.4633125 | 63.45523329 | 76.96643943 | 103.1273983 |
| NCU03731.2 | 110.5801446 | 145.0235135 | 134.627995 | 230.1450412 | 100.4172375 |
| NCU03753.2 | 111.3481086 | 74.42402278 | 129.2196777 | n/a | n/a |
| NCU04197.2 | 99.08305414 | 108.9737808 | 89.86128625 | 75.17285531 | 96.05075054 |
| NCU04249.2 | 106.1012167 | 79.0053469 | 84.16141236 | 64.07989522 | 100.124185 |
| NCU04287.2 | 102.2361065 | 125.5086234 | 127.9282577 | 202.516129 | 183.8679245 |
| NCU04349.2 | 89.36205196 | 71.41381803 | 145.2415813 | 208.4329349 | 101.2993763 |
| NCU04475.2 | 122.2034851 | 156.3643221 | 127.0676692 | n/a | n/a |
| NCU04997.2 | 114.5840184 | 123.3295466 | 231.6983895 | 136.4189483 | 102.5403983 |
| NCU05057.2 | 95.69220651 | 133.5226686 | 174.2679356 | 182.023775 | 97.81330657 |
| NCU05159.2 | 39.51658235 | 92.2873845 | 67.11779449 | n/a | n/a |
| NCU05493.2 | 104.4102564 | 102.3841739 | 116.8954593 | 70.37185126 | 99.42837929 |

-continued

| | | | | | |
|---|---|---|---|---|---|
| NCU05519.2 | 101.0666667 | 118.8447721 | 87.77719113 | 51.6886931 | 97.87501655 |
| NCU05751.2 | 111.4051282 | 114.7202911 | 136.3780359 | 87.71492649 | 105.5920583 |
| NCU05770.2 | 86.73412029 | 69.1872525 | 146.2155388 | n/a | n/a |
| NCU05853 | 24.41259790 | n/a | n/a | n/a | n/a |
| NCU05897.2 | 34.72754541 | 26.3266891 | 86.25954198 | n/a | n/a |
| NCU05932.2 | 76.87132044 | 80.78910753 | 117.9596823 | 58.07431478 | 96.7108463 |
| NCU06009.2 | 74.06784413 | 120.602266 | 99.48075748 | 70.89513625 | 97.00573241 |
| NCU06490.2 | 80.26352677 | 76.95289207 | 79.38301772 | 59.91109168 | 99.99371385 |
| NCU07340.2 | 95.21973786 | 35.54661301 | 96.99134496 | 93.62619808 | 78.44902553 |
| NCU07853.2 | n/a | 120.9286562 | 168.2340648 | 65.7599456 | 99.14659177 |
| NCU07997.2 | n/a | 148.127436 | 98.11912226 | 60.65548063 | 93.78704271 |
| NCU08114.2 | 79.22624054 | 85.18187239 | 92.97495418 | 58.83068556 | 93.1432252 |
| NCU08744.2 | n/a | 168.8527368 | 110.7628004 | 136.2451567 | 97.44134197 |
| NCU08746.2 | 79.11410149 | 111.0713576 | 120.2504582 | 447.2796518 | 100.5753667 |
| NCU08760.2 | 86.17964534 | 208.2590783 | 81.00013738 | 97.32646961 | 84.34251774 |
| NCU09108.2 | n/a | 93.22148788 | 111.8077325 | 60.89420655 | 97.24517906 |
| NCU09495.2 | 122.5327679 | 129.9223915 | 130.8971013 | 152.7495439 | 92.25216554 |
| NCU09680.2 | 95.20046261 | 89.54680464 | 102.6789394 | 94.61873756 | 83.87661343 |
| NCU10045.2 | 101.5138772 | 109.8886901 | 132.5290165 | 83.25906421 | 103.6151641 |

*Note:
All sequences were searched against Pfam ls models and hits were accepted with an e-value < .0001

Example 7

Further Analyses of Transporter Genes

As described in Example 1, ten genes encoding predicted sugar transporter proteins showed increased expression levels when *Neurospora* was grown on *Miscanthus* and Avicel: NCU00801, NCU00988, NCU01231, NCU04963, NCU05519, NCU05853, NCU05897, NCU06138, NCU08114 and NCU10021. Deletion strains for nine of these genes were available from the Fungal Genetics Stock Center. A deletion strain of NCU10021 was not available.

Deletion mutations of NCU05853, NCU05897, or NCU08114 resulted in strains that showed a growth defect on *Miscanthus* or Avicel and/or had a cellulase enzyme defect (see Example 6; Table 10). ΔNCU05853 showed reduced growth on Avicel and reduced endoglucanase activity compared to wild-type. ΔNCU05897 showed reduced growth on Avicel and reduced endoglucanase activity compared to wild-type, and ΔNCU08114 showed reduced growth on Avicel and reduced cellobiose levels compared to wild-type. Notably, in a comparison with expression analysis of Sporotrichum thermophile, another filamentous fungus, the homologs of NCU05853 (ST8454) and NCU08114 (ST5194) were also upregulated when *S. thermophile* was grown on Avicel compared to glucose (see Example 8, Table 11), further indicating their importance in cellulose utilization.

Table 11 Shows *S. thermophile* Expression Data

| Gene Name | Like NCU# | Gene Length | Glu | Avi | Cot | Glu_norm | Avi_norm | Cot_norm | Avi/Glu | Cot/Glu |
|---|---|---|---|---|---|---|---|---|---|---|
| jgi\|Spoth1\|108890\|estExt_fgenesh1_pg.C_60848 | NCU00988 | 1937 | 322 | 370 | 293 | 42.97830583 | 60.2250594 | 48.07756207 | 1.149068 | 0.9099379 |
| jgi\|Spoth1\|-48439\|e_gw1.3.3367.1 | NCU01132 | 1539 | 113 | 59 | 56 | 15.08244894 | 9.60345542 | 9.188885583 | 0.522124 | 0.4955752 |
| jgi\|Spoth1\|79030\|estExt_Genewise1Plus.C_31624 | NCU01231 | 1776 | 1171 | 1206 | 469 | 156.2968824 | 196.30114 | 76.95691676 | 1.029889 | 0.4005124 |
| jgi\|Spoth1\|116270\|estExt_fgenesh1_pm.C_50266 | NCU05519 | 1680 | 103 | 78 | 54 | 13.74771895 | 12.6960936 | 8.860711098 | 0.757282 | 0.5242718 |
| jgi\|Spoth1\|84164\|estExt_Genewise1Plus.C_62100 | NCU05853 | 1706 | 2703 | 20760 | 14284 | 360.7775176 | 3379.11414 | 2343.822173 | 7.680355 | 5.2844987 |
| jgi\|Spoth1\|102977\|fgenesh1_pm.5_#_763 | NCU05897 | 1446 | 1510 | 546 | 322 | 201.5442292 | 88.8726553 | 52.8360921 | 0.361589 | 0.213245 |
| jgi\|Spoth1\|84305\|estExt_Genewise1Plus.C_70023 | NCU06138 | 1605 | 1131 | 1330 | 2376 | 150.9579624 | 216.484673 | 389.8712883 | 1.17595 | 2.1007958 |
| jgi\|Spoth1\|114107\|estExt_fgenesh1_pm.C_20669 | NCU08114 | 1945 | 2246 | 22423 | 10779 | 299.7803568 | 3649.80137 | 1768.696388 | 9.983526 | 4.7991986 |

-continued

| Gene Name | Like NCU# | Gene Length | Glu | Avi | Cot | Glu_norm | Avi_norm | Cot_norm | Avi/Glu | Cot/Glu |
|---|---|---|---|---|---|---|---|---|---|---|
| jgi\|Spoth1\|112305\|estExt_fgenesh1_kg.C_60263 | NCU10021 | 2026 | 6204 | 5287 | 5619 | 828.0664888 | 860.567268 | 922.006216 | 0.852192 | 0.905706 |
| jgi\|Spoth1\|43941\|e_gw1.2.4209.1 | NCU00801 | 1614 | 41 | 71 | 159 | 5.472392979 | 11.5567006 | 26.08987157 | 1.731707 | 3.8780488 |
| jgi\|Spoth1\|62521\|estExt_Genewise1.C_21757 | NCU04963 | 2204 | 799 | 1548 | 641 | 106.6449266 | 251.968627 | 105.1799225 | 1.937422 | 0.8022528 |

In order to narrow down the identity of each predicted transporter's substrate, strains containing deletion mutations of NCU05853 or NCU08114 were cultured on glucose, xylose, cellobiose, xylan and Avicel (Table 12). The culturing medium contained Vogel's medium plus 2% of the carbon source. Both mutants showed greatly reduced growth on Avicel but not on xylan, glucose, xylose, or cellobiose.

Table 12 Shows Growth of Deletion Mutants on Different Sugars

| Gene Name | Growth on Sucrose | Growth on Avicel | Growth on Mis | Growth on Xylan | Growth on Glucose | Growth on Xylose | Growth on Cellobiose |
|---|---|---|---|---|---|---|---|
| NCU00801 | * * * | * * * | * * * | | | | |
| NCU00988 | * * * | * * * | * * * | | | | |
| NCU01231 | * * * | * * * | * * * | | | | |
| NCU04963 | * * * | * * * | * * * | | | | |
| NCU05519 | * * * | * * * | * * * | | | | |
| NCU05853 | * * * | * | * * | * * * | * * * | * * * | * * * |
| NCU05897 | * * * | * | * * | | | | |
| NCU06138 | * * * | * * * | * * * | | | | |
| NCU08114 | * * * | * | * * | * * * | * * * | * * * | * * * |
| NCU10021 | No deletion strain | | | | | | |
| wt | * * * | * * * | * * * | * * * | * * * | * * * | * * * |

To investigate the role of these transporters in utilization of hemicellulose, the expression of the ten transporter genes was examined when *Neurospora* was grown on xylan. Methods were used as described in Example 4, except that strains were grown on Vogel's salts with 2% (w/v) xylan. Expression of all ten transporters was upregulated during growth on xylan (Table 13), suggesting that they can transport sugars derived from hemicellulose degradation (e.g., xylobiose, xylose, arabinose, xylo-oligosaccharides) as well as from cellulose degradation (e.g., cellobiose, glucose, cello-oligosaccharides). The mutant growth results and expression analyses suggested that at least two of the predicted transporters, NCU05853 and NCU08114, can transport disaccharides (cellobiose, xylobiose) and/or oligosaccharides (cellodextrins).

Table 13 Shows Expression Analysis of Transporter Genes

| Gene Name | wt-Xylan 4 h | Fold change in St-Avicel-4 h/Glucose-4 h |
|---|---|---|
| NCU00801 | ~6 | 10 |
| NCU00988.2 | 31.1 | NO CHANGE |
| NCU01231.2 | 732.1 | NO CHANGE |
| NCU04963.2 | 96.5 | NO DETECT |
| NCU05519.2 | 3.9 | NO CHANGE |
| NCU05853.2 | 71.2 | 8.5 |
| NCU05897.2 | 122.3 | NO CHANGE |

-continued

| Gene Name | wt-Xylan 4 h | Fold change in St-Avicel-4 h/Glucose-4 h |
|---|---|---|
| NCU06138.2 | 141.0 | NO CHANGE |
| NCU08114.2 | 10.0 | 11 |
| NCU10021.2 | 44.7 | NO CHANGE |

Example 8

Expression Analysis of *Sporotrichum Thermophile* Homologs of *N. Crassa* Transporters During Growth on Various Carbon Sources In order to compare the expression of homologous genes from a different filamentous fungus, the expression profile of *Sporotrichum thermophile* was analyzed from cultures grown on glucose, Avicel, or cotton. cDNA was isolated from cultures grown on minimal media with a carbon source of glucose, Avicel, or cotton for 16-30 hours.

First, in order to identify homologs of *Neurospora* transporter proteins in the *S. thermophile* genome, each *Neurospora* sequence was compared against a database of *S. thermophile* proteins with BLAST. The sequences of *S. thermophile* proteins found by this method were then compared to a database of *Neurospora* proteins with BLAST. These results are listed in FIG. 10. The amino acid sequences for all of the *S. thermophile* homologs of putative *Neurospora* transporters that were identified can be found in SEQ ID NOs: 22-32.

Next, the expression profile of the *S. thermophile* homologs was examined. The data is presented in Table 11. The first column contains the *S. thermophile* gene name from the Joint Genome Institute *S. thermophile* assembly. The second column contains the NCU number for the most closely related putative transporter in *Neurospora*. The third column contains the gene length of the *S. thermophile* gene in nucleotides. The fourth to sixth columns contain the expression level (number of reads, comparable to absolute expression level) during growth on Vogel's minimal media supplemented with 2% of glucose, Avicel, or cotton balls as the carbon source. The seventh to ninth columns contain the normalized expression data (the # of reads divided by the total reads in the dataset). The final two columns contain the relative expression level data for each gene as a ratio of Avicel/glucose or cotton/glucose. Homologs of NCU5853, NCU8114, and NCU0801 were upregulated when grown on both Avicel and cotton. The homolog of NCU6138 was upregulated when grown on cotton, and the homolog of NCU4963 was upregulated when grown on Avicel. These data provided further support that putative transporters NCU5853, NCU8114, NCU0801, NCU6138, and NCU4963 are important for the utilization of cellulose.

Example 9

Identification and Analysis of Cellodextrin Transporters

Figure 12:
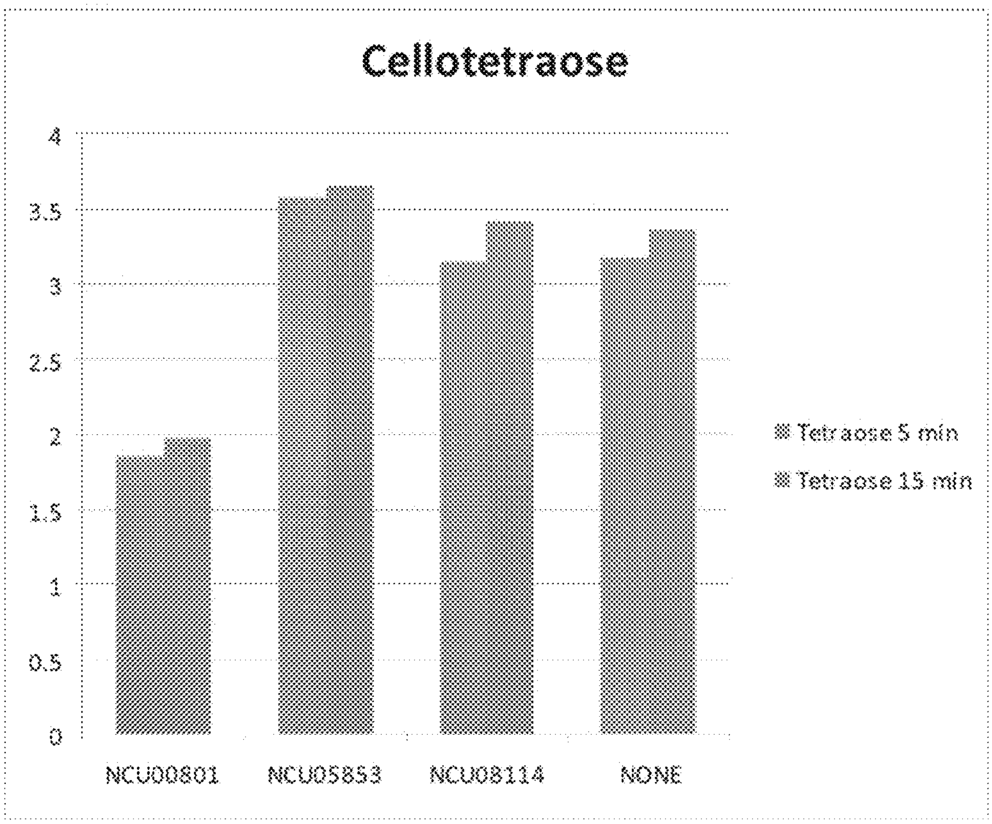
Figure 12:
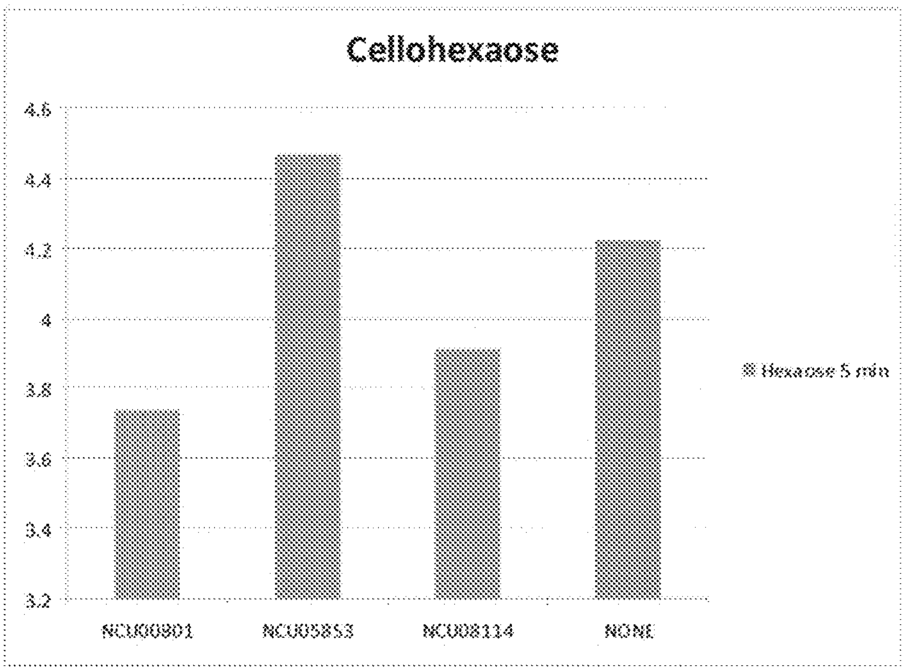
Figure 13:
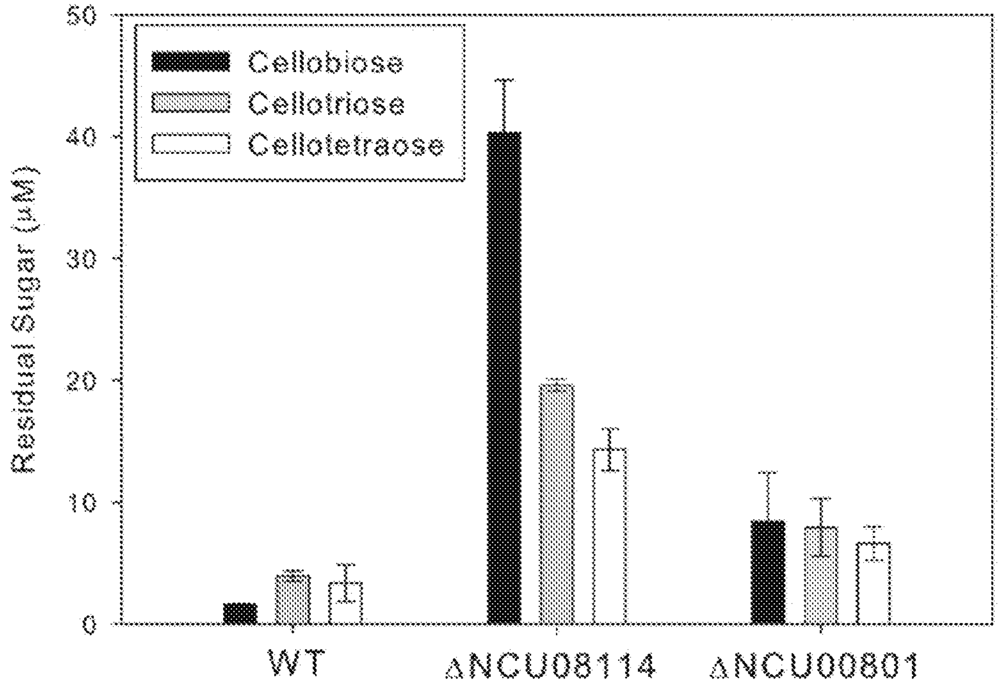
FIG. 13 shows cellodextrin consumption by *N. crassa* strains lacking NCU008114 or NCU00801. The indicated *N. crassa* strains were incubated with 90 μM of the respective sugars for 15 minutes. Bars represent the mean concentration of sugars remaining in the supernatant following the incubation from two independent experiments. Error bars were the standard deviation between these experiments.

When grown on pure cellulose, *N. crassa* was shown to increase transcription of seven Major Facilitator Superfamily sugar transporters as well as an intracellular β-glucosidase (Ex. 1; also see Supplemental Data, Dataset S1, page 6 in Tian et al., PNAS, 2009). Notably, knockout strains lacking individual transporters from this set grew more slowly on crystalline cellulose, suggesting that they may play a direct role in cello-oligosaccharide uptake under cellulolytic conditions (Ex. 7; Tables 10, 12). For example, deletion of NCU08114 resulted in severely retarded *N. crassa* growth (FIG. 11), and reduced *N. crassa* consumption of cellobiose (FIGS. 12-13). In this example, transporter genes NCU00801/cbt1 and NCU08114/cbt2 were further analyzed and identified to encode transporters of cellodextrin.

Figure 14:
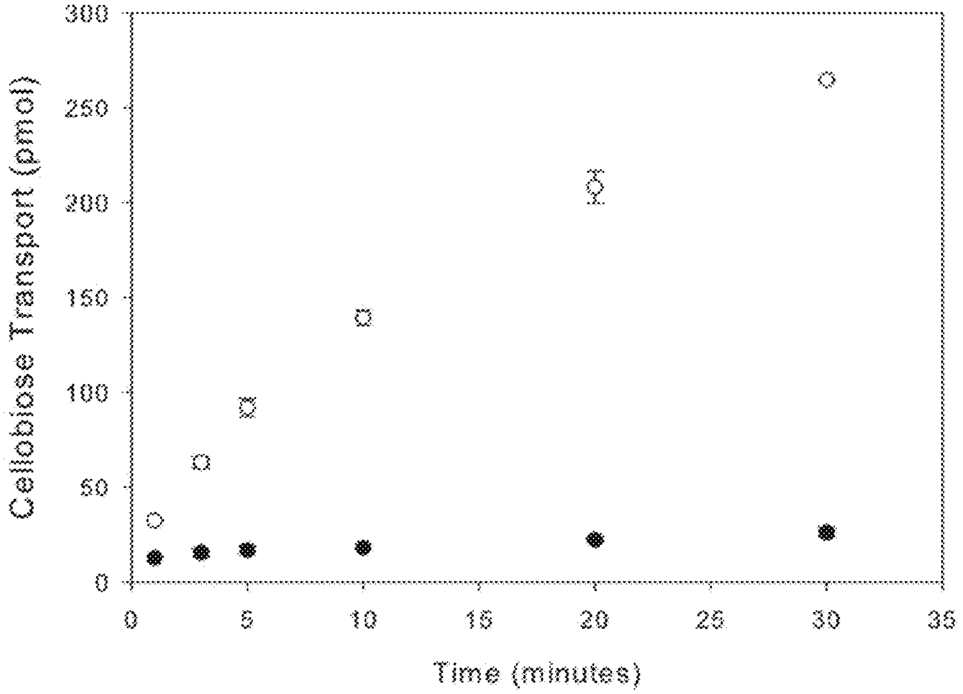
FIG. 14 shows cellobiose transport by a *S. cerevisiae* strain expressing NCU00801/cbt1. Shown is cellobiose transport by yeast with (○) or without (●) CBT1. Both strains expressed the intracellular β-glucosidase, NCU00130. The initial concentration of cellobiose was 50 μM. All values were the mean between two measurements, with error bars representing the standard deviation between these measurements.
Figure 15:
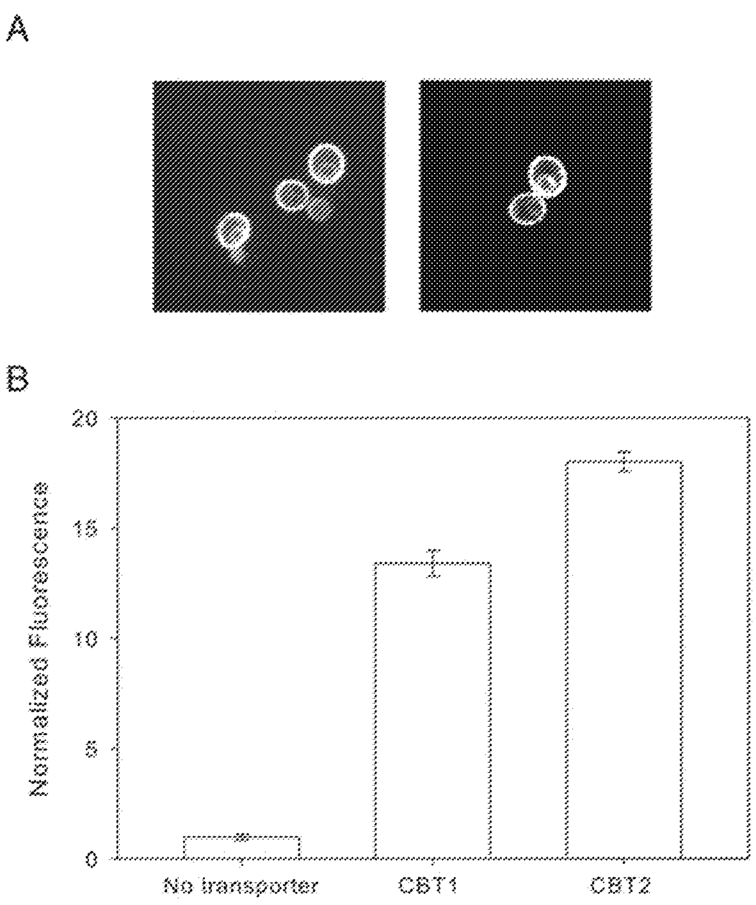
FIG. 15 shows localization and quantification of GFP fused to CBT1 and CBT2.
Figure 16:
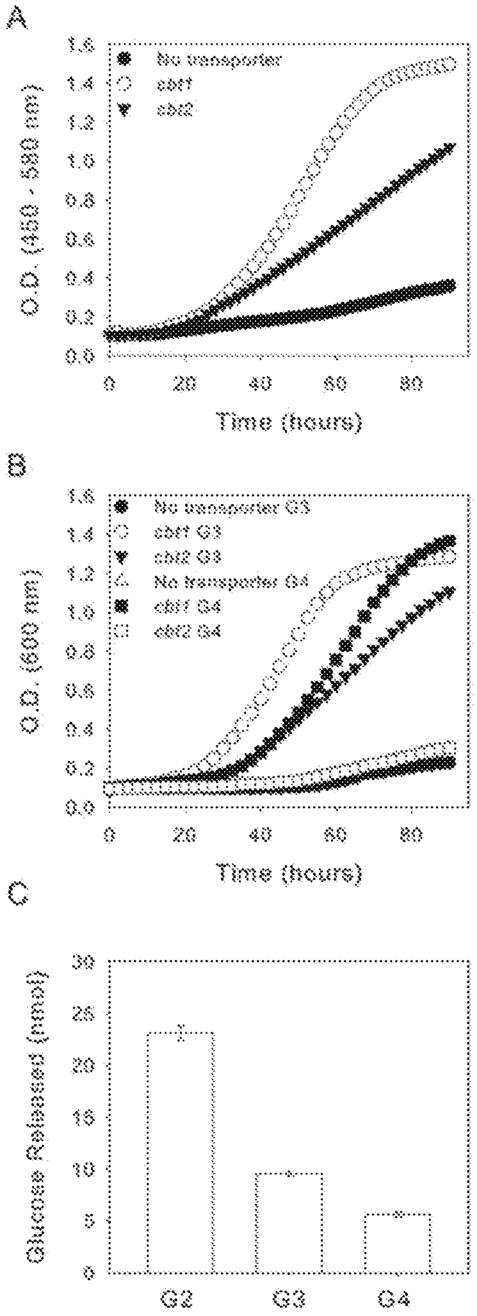
FIG. 16 shows cellodextrin transport by *N. crassa* transport systems expressed in *S. cerevisiae*.
Figure 17:
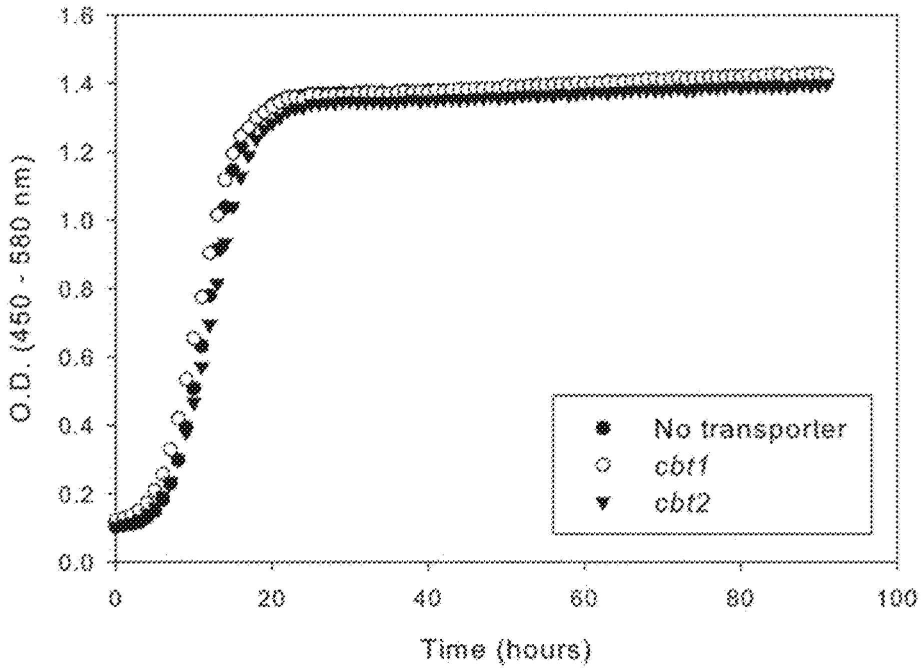
FIG. 17 shows growth of *S. cerevisiae* strains expressing cbt1 (○), cbt2 (▼), or no transporter (●) on glucose. All strains expressed the β-glucosidase, NCU00130. A representative experiment is shown.
Figure 18:
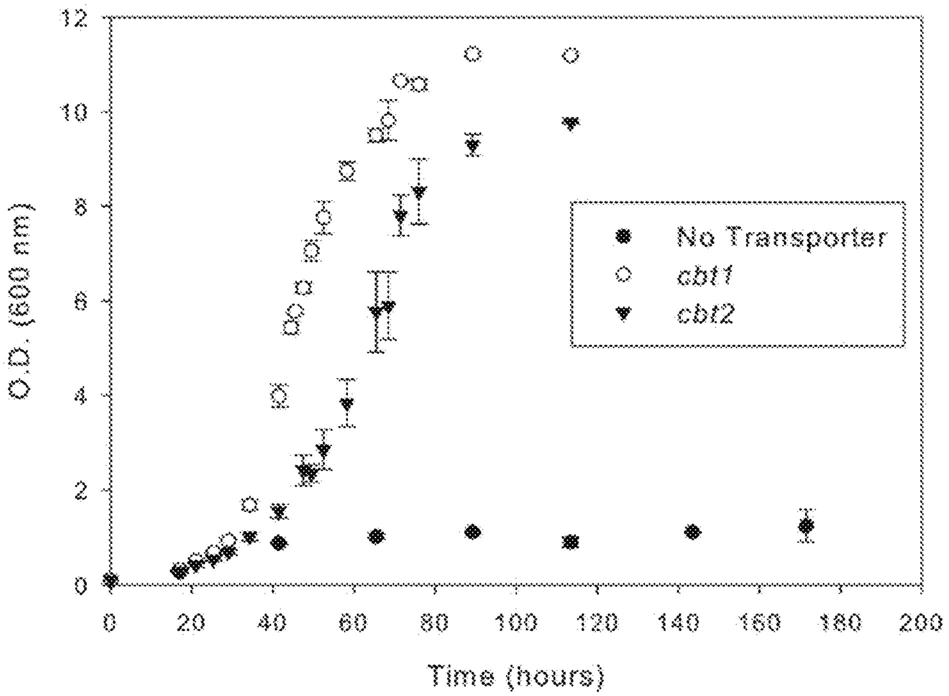
FIG. 18 shows cellobiose-mediated growth of *S. cerevisiae* strains in 250 mL flasks. Values represent the mean OD between two replicate cultures of yeast strains expressing the β-glucosidase, NCU00130, cbt1 or cbt2, or a strain expression NCU00130, but lacking any transporters. Error bars represent the standard deviation between replicates.

To assay the function of each transporter individually, the fact that cellobiose is not catabolized by *S. cerevisiae* and is not accumulated in its cytoplasm was exploited (FIG. 14). It was reasoned that expression of a functional cellobiose transporter in conjunction with an intracellular β-glucosidase would allow *S. cerevisiae* to grow when cellobiose is presented as the sole carbon source. Yeast strains were engineered to express the transporters NCU00801 or NCU08114 fused to Green Fluorescent Protein (GFP), and the putative intracellular β-glucosidase, NCU00130. Both transporters were expressed and localized correctly to the plasma membrane (FIG. 15). The strains expressing NCU00801 or NCU08114 allowed yeast to grow with specific growth rates of 0.0341 $hr^{-1}$ and 0.0131 $hr^{-1}$, respectively (FIG. 16A). These growth rates correspond to 30% and 12% of the growth rate on glucose, respectively (FIG. 17). Growth could not be explained by the extracellular hydrolysis of cellobiose to glucose followed by transport, as a strain expressing only the putative intracellular β-glucosidase grew at a rate of 0.0026 $hr^{-1}$ (FIG. 16A), and did not grow in large-scale cultures (FIG. 18). Based on these observations, NCU00801 and NCU08114, which were named CBT1 and CBT2, were determined to function as cellobiose transporters.

Figure 19:
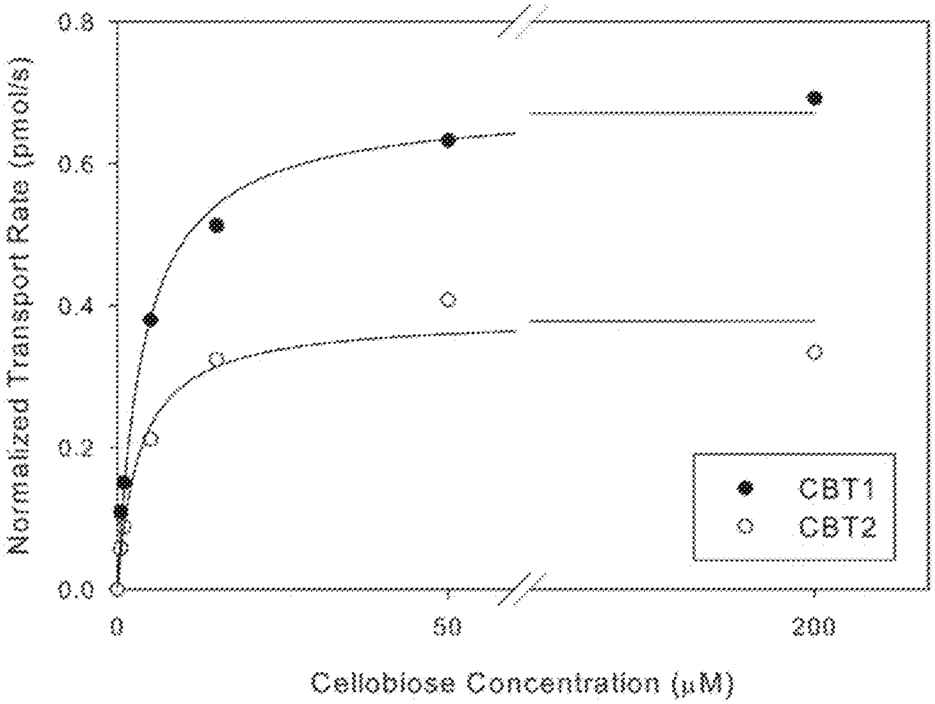
FIG. 19 shows kinetics of cellobiose transport by CBT1 and CBT2. The rate of cellobiose transport was determined as a function of cellobiose concentration by yeast strains expressing either cbt1 or cbt2. The transport rate was normalized for transporter abundance.
Figure 20:
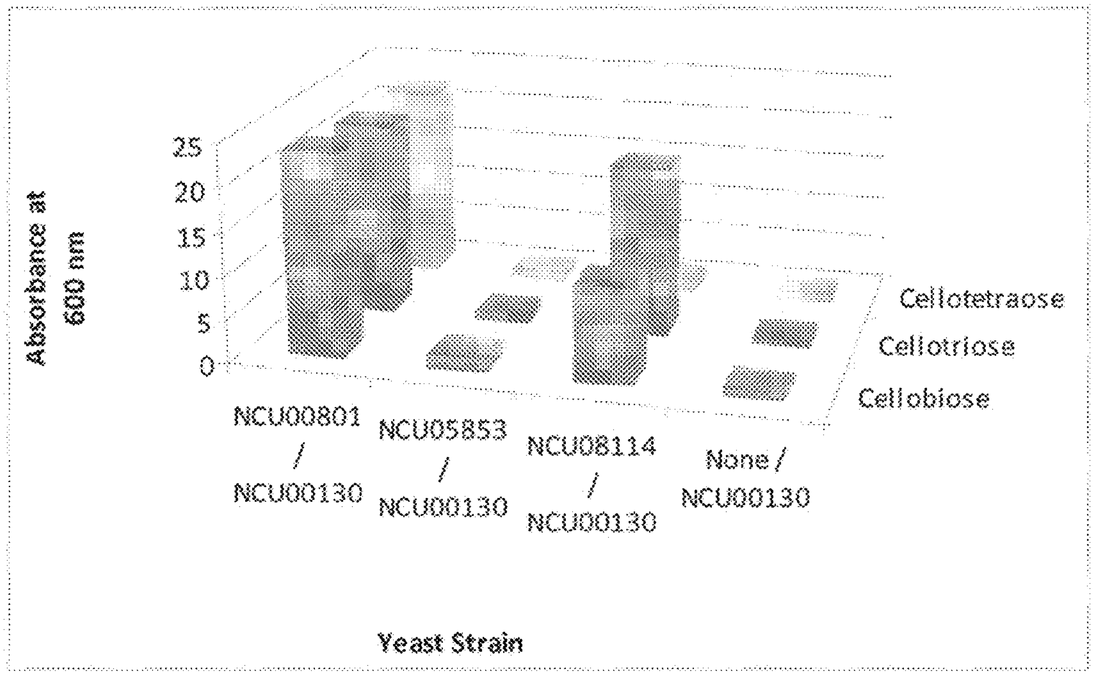
FIG. 20 shows the ability of *S. cerevisiae* expressing the combinations of *Neurospora* genes shown on the x-axis to grow on cellobiose, cellotriose, or cellotetraose.
Figure 21:
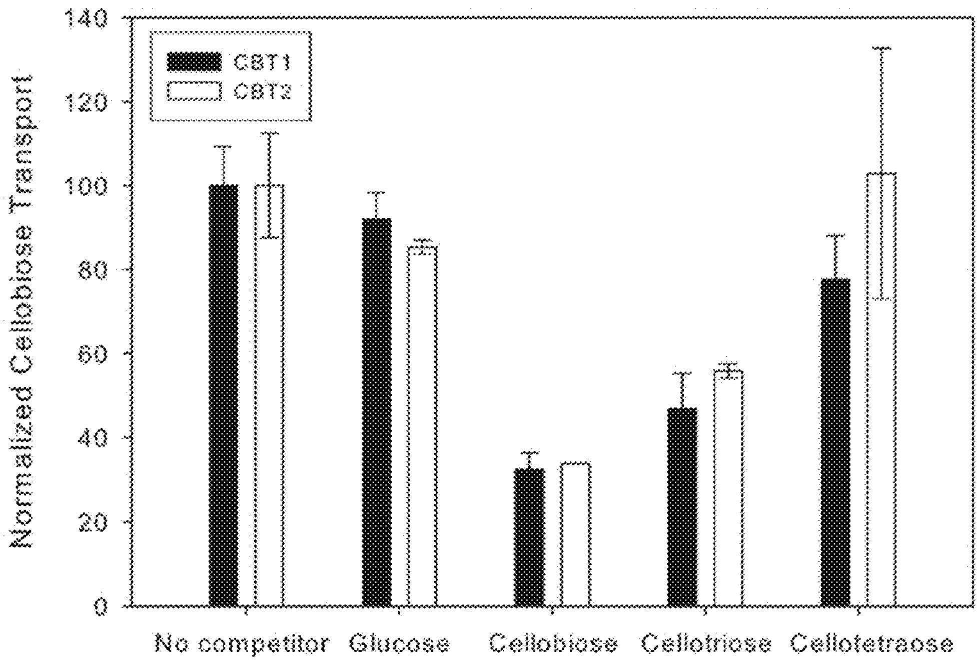
FIG. 21 shows competition by cellodextrins for cellobiose transport in strains carrying cbt1 or cbt2. A 5-fold excess of the respective unlabeled sugar was included during assays of [$^3$H]-cellobiose transport. Substrates of CBT1 or CBT2 would decrease the [$^3$H]-cellobiose transport rate by competing for binding. Bars represent the mean from three replicates. Error bars represent the standard deviation between these replicates. Values were normalized by setting the rate of [$^3$H]-cellobiose transport without a competing sugar to 100.
Figure 22:
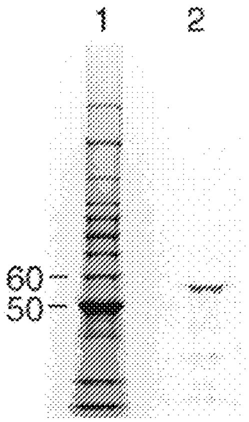
FIG. 22 shows the SDS-PAGE gel of purified NCU00130. Lane 1, Protein molecular weight standards, in kDa. Lane 2, NCU00130 after purification over nickel-NTA resin. Molecular weights in kDa are shown to the left.

To directly assay transporter function, the uptake of [$^3$H]-cellobiose into yeast cells was measured. Both CBT1 and CBT2 were found to be high-affinity cellobiose transporters, with $K_m$ values of 4.0±0.3 μM and 3.2±0.2 μM, respectively (FIG. 19). The expression-normalized $V_{max}$ of CBT1 was 2.2 times that of CBT2, a fact that explained differences seen in the yeast growth assays. Notably, cellodextrin molecules longer than cellobiose supported the growth of yeast expressing cbt1 and cbt2 (FIG. 20; FIG. 16B), suggesting that cellodextrin molecules are transported by CBT1 and CBT2. In agreement, cellobiose transport by CBT1 and CBT2 was inhibited by excess cellotriose, and CBT1 activity was also inhibited by cellotetraose (FIG. 21). Furthermore, upon purification, the β-glucosidase, NCU00130 (FIG. 22), was found to hydrolyze cellobiose, cellotriose, and cellotetraose (FIG. 16C).

Figure 23:
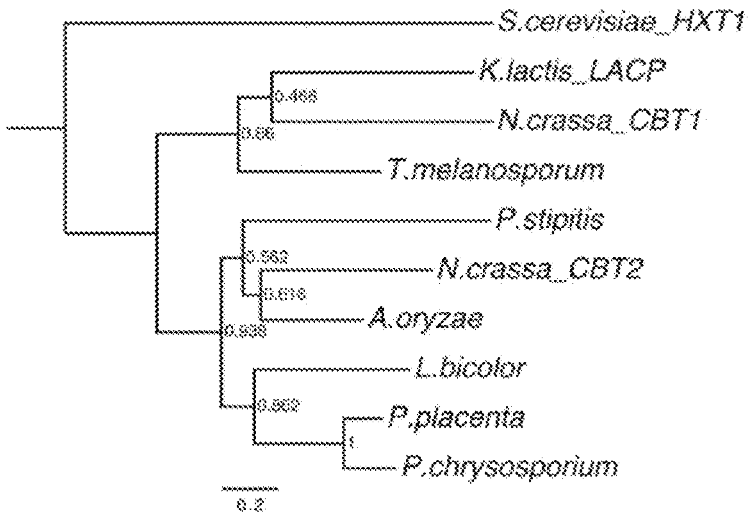
FIG. 23 shows maximum likelihood phylogenetic analysis of the cellobiose transporters NCU08114 and NCU00801. With the exception of *S. cerevisiae* HXT1 and *K. lactis* LACP, all genes encoding proteins shown are reported to increases in expression level when the fungus comes into contact with plant cell wall material or cellobiose (Tian et al., 2009; Noguchi et al., 2009; Wymelenberg et al., 2010; Martin et al., 2010). *S. cerevisiae* HXT1, a low affinity glucose transporter (Reifenberger et al., 1997), was used as an outgroup.

Orthologs of cbt1 and cbt2 were identified and found to be widely distributed in the fungal kingdom (FIG. 23). Recent expression data shows their importance to various interactions between fungi and plants. For example, when the ascomycete, *Tuber melanosporum*, or the basidiomycete, *Laccaria bicolor*, interacts symbiotically with root tips to form ectomycorrihzas, the ortholog of cbt1 is upregulated in both (Martin et al., 2010). Likewise, the saprophytes, *Aspergillus oryzae* (Noguchi et al., 2009), *Postia placenta* (Vanden Wymelenberg et al., 2010), and *Phanerochaete chrysosporium* (Vanden Wymelenberg et al., 2010), upregulate orthologs of cbt2 when in contact with plant wall material. Certain yeasts, such as *Kluveromyces lactis* and *Pichia stipitis* grow on cellobiose (Freer, 1991; Preez et al., 1986), and cellobiose transport has been reported in *Clavispora lusitaniae* (Freer and Greene 1990). It was determined in this study that all of these yeasts contain orthologs of cbt1, cbt2, or both (see below for methods). Cellobiose transport has been observed in *Hypocrea jecorina* (*Trichoderma reesei*), but since the transporter was not identified, it is not clear if this activity can be ascribed to orthologs of cbt1 or cbt2 (Kubicek et al., 1993).

Figure 24:
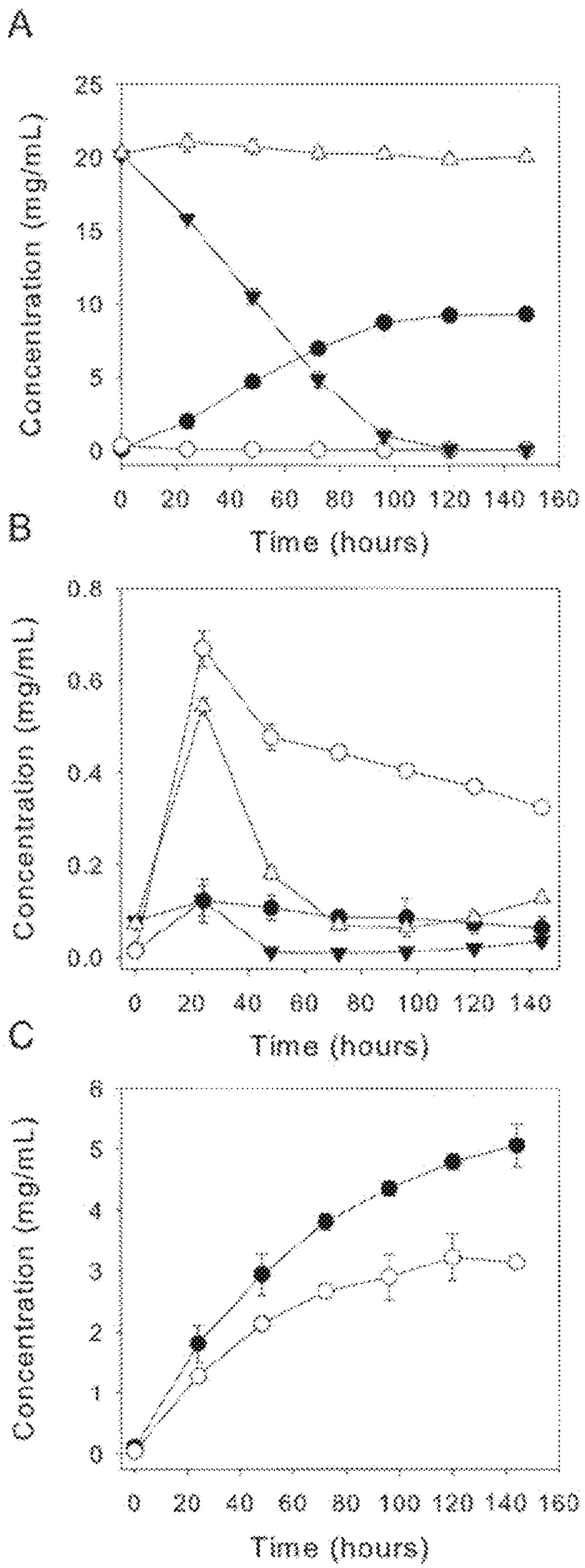
FIG. 24 shows cellobiose fermentation, and simultaneous saccharification and fermentation of cellulose, by *S. cerevisiae* expressing the cellobiose transport system from *N. crassa*.

The use of cellobiose transporters by cellulolytic fungi suggests that they are essential for their optimal growth on cellulose. To test whether cellobiose catabolism could improve yeast ethanol production, the yeast strains constructed above were grown under fermentation conditions. With little optimization, yeast with a complete cellobiose catabolism pathway ported from *N. crassa* were shown to ferment cellobiose to ethanol efficiently (FIG. 24A), with an ethanol yield of 0.47, 86% of the theoretical value (Bai et al., 2008). This was comparable to industrial yields from glucose of 90-93% (Basso et al., 2008). The high affinity of CBT1 and CBT2 for cellobiose compared to the hexose transporters of *S. cerevisiae* (Reifenberger et al., 1997), and reported extracellular β-glucosidases (Chauve et al., 2010), suggested that a cellobiose/cellodextrin transport system would be particularly useful during SSF. For example, cellobiose/celldextrin transport would lower the requirement for full hydrolysis of cellulose to glucose, decrease cellobiose-mediated inhibition of cellulolytic enzymes, and reduce the risk of contamination by glucose-dependent organisms. Indeed, yeasts expressing a cellobiose/cellodextrin transport system markedly improved the efficiency of SSF reactions by reducing the steady state concentration of both cellobiose and glucose, and increasing the ethanol production rate (FIG. 24B, C).

Figure 25:
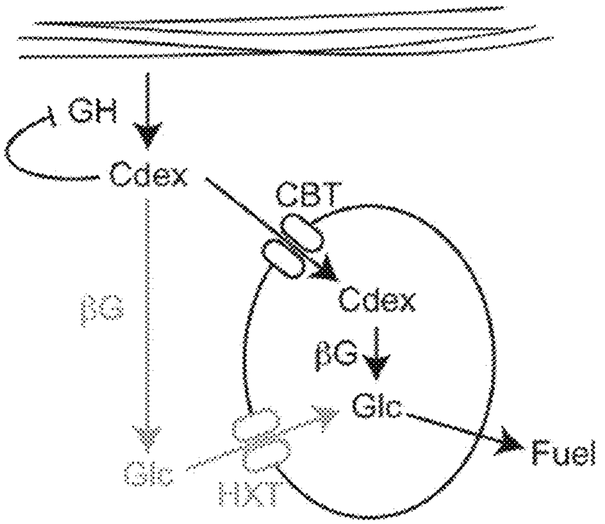
FIG. 25 shows use of cellodextrin transport pathways from filamentous fungi during simultaneous saccharification and fermentation of cellulose by yeast. The cellodextrin (Cdex) transport pathway (black) includes a cellodextrin transporter (CBT) and intracellular β-glucosidase (βG). The sugar catabolism pathway presented in standard yeast includes hexose transporters (HXT). In SSF, both cellulases (GH) and extracellular β-glucosidase (βG) could be used.

Biofuel production from cellulose requires efficient and economical depolymerization of plant biomass to sugars coordinated with fuel production by improved host strains (Kumar et al., 2008). Here it was shown that cellulolytic fungi use cello-oligosaccharide transport pathways for optimal growth on plant biomass. Furthermore, reconstitution of these pathways in yeast revealed that they can be ported in a modular fashion to improve cellobiose catabolism, with a minimal pathway composed of a transporter and an intracellular cello-oligosaccharide hydrolase (FIG. 25). The use of cellodextrin transport in biofuel-producing strains of yeast and other organisms is critical for making cellulosic biofuel processes more economically viable.

Transporter and β-Glucosidase Orthologs

GenBank accession numbers or Joint Genome Institute (JGI) protein ID (PID) numbers for cellodextrin transporters are as follows: *Tuber melanosporum*, CAZ81962.1; *Pichia stipitis*, ABN65648.2; *Laccaria bicolor*, EDR07962; *Aspergillus oryzae*, BAE58341.1; *Phanerochaete chrysosporium*, PID 136620 (JGI) (Martinez et al., 2004); *Postia placenta*, PID 115604 (JGI) (Martinez et al., 2009). The GenBank accession number for *Saccharomyces cerevisiae* HXT1 and *Kluyveromyces lactis* LACP are DAA06789.1 and CAA30053.1, respectively. The *P. chrysosporium* and *P. placenta* genomes can be accessed at genome.jgi-psf.org/Phchr1/Phchr1.home.html and genome.jgi-psf.org/Posp11/Posp11.home.html, respectively.

GenBank accession numbers for cellodextrin hydrolases that are orthologs of NCU00130 are as follows: *T. melanosporum*, CAZ82985.1; *A. oryzae*, BAE57671.1; *P. placenta*, EED81359.1; and *P. chrysosporium*, BAE87009.1. The other organisms that contain cellodextrin transporter orthologs contain genes in the GH3 family predicted to be intracellular β-glucosidases (Bendtsen et al., 2004; Cantarel et al., 2009), as follows: *Kluyveromyces lactis*, CAG99696.1; *Laccaria bicolor*, EDR09330; *Clavispora lusitaniae*, EEQ37997.1; and *Pichia stipitis*, ABN67130.1.

Strains and Media

The yeast strain used in this study was YPH499 (Sikorski et al., 1989), which has the genotype: MATa ura3-52 lys2-801_amber ade2-101_ochre trp1-Δ63 his3-Δ200 leu2-Δ1. It was grown in YPD media supplemented to 100 mg/L adenine hemisulfate. Transformed strains (Becker et al., 2001) were grown in the appropriate complete minimal dropout media, supplemented to 100 mg/L adenine hemisulfate. *Neurospora crassa* stains used in this study were obtained from the Fungal Genetics Stock Center (McCluskey 2004) and include WT (FGSC 2489) and two cellobiose transporter deletion strains (FGSC 16575, ΔNCU00801.2 and FGSC 17868, ΔNCU08114.2 (Colot et al., 2006)).

Plasmids and Cloning

Transporters were cloned into the 2μ plasmid, pRS426, which was modified to include the *S. cerevisiae* PGK1 promoter inserted between SacI and SpeI using the primers, ATATAT GAGCTCGTGAGTAAGGAAAGAGTGAGGAACTATC (SEQ ID NO: 53) and ATATAT ACTAGTTGTTTTATATTTGTTGTAAAAAGTAGAT AATTACTTCC (SEQ ID NO: 54). (In all primers above and below, restriction sites are underlined). NCU00801 with a C-terminal Myc-tag and optimized Kozak sequence (Miyasaka 1999) was then inserted between BamHI and EcoRI using the primers, ATGGATCCAAAAATGTCGT CTCACGGCTCC (SEQ ID NO: 55) and AT GAATTCCTACAAATCTT CTTCAGAAATCAATTTTT GTTCAGCAACGATAGCTTCGGAC (SEQ ID NO: 56), and NCU08114 with a C-terminal Myc-tag and optimized Kozak sequence was inserted between SpeI and ClaI using the primers, AT ACTAGTAAAAATGGGCATCTTCAACAAGAAGC (SEQ ID NO: 57) and GCATATCGATCTACAAATCTTC TTCA-GAAATCAATT TTTGTTCAGCAACAGACTTGCCCT-CATG (SEQ ID NO: 58). To make GFP fusions, superfolder GFP (Pedelacq et al., 2006) with an N-terminal linker of Gly-Ser-Gly-Ser was first inserted between the ClaI and SalI sited of the PGK1 promoter-containing pRS426 plasmid with the primers, TATTAA ATCGATGGTAGTGGTAGTGTGAGCAAGGGC GAG-GAG (SEQ ID NO: 59) and TATTAA GTCGACCTACTTGTACAGCTCGTCCATGCC (SEQ ID NO: 60). Transporters were then fused to GFP as follows: NCU00801 was inserted between BamHI and EcoRI using the primers, GCATGGATCCATGTCGTCTCACGGCTCC (SEQ ID NO: 61) and TATAAT GAATTCAGCAACGATAGCTTCGGAC (SEQ ID NO: 62), and NCU08114 was inserted between SpeI and EcoRI using the primers, TATTAAACTAGTATGGGCATCTTCA ACAAGAAGC (SEQ ID NO: 63) and TTATAA GAATTCAGCAACAGACTTG CCCTCATG (SEQ ID NO: 64).

The β-glucosidase, NCU00130, was cloned into the 2μ plasmid, pRS425, modified to include the PGK1 promoter described above. NCU00130 with an optimized Kozak sequence and a C-terminal 6xHis tag was inserted between SpeI and PstI using the primers, GCAT ACTAGTAAAAATGTCTCTTCCTAAGGATTTCCTCT (SEQ ID NO: 65) and ATA CTGCAGTTAATGATGATGATGATGATGGTCCTTCT TGATCAAAGAGTCAAAG (SEQ ID NO: 66). All constructs included the Cyc transcriptional terminator between XhoI and KpnI. All *N. crassa* genes were amplified by PCR from cDNA synthesized from mRNA isolated from *N. crassa* (FGSC 2489) cultured on minimal media with pure cellulose (Avicel) as the sole carbon source.

Yeast Growth Assays

To monitor growth on cello-oligosaccharides, engineered strains were grown in 5 mL of complete minimal media with appropriate dropouts overnight. These starter cultures were washed three times with 25 mL of ddH$_2$O, and resuspended to an OD (at 600 nm) of 0.1 in Yeast Nitrogen Base (YNB) plus the appropriate Complete Supplemental Media (CSM) and 1% (w/v) of cellobiose, or 0.5% (w/v) of either cellotriose or cellotetraose. Assays were performed in a Bioscreen C™ with constant shaking at maximum amplitude at 30° C. and a final assay volume of 0.4 mL. The change in OD was measured either at 600 nm or using a wideband filter from 450-580 nm. Growth rates were taken from the linear portion of each growth curve, and are reported as the mean of three independent experiments±the standard deviation between these experiments. Cellotriose and cellotetraose were obtained from Seikagaku Biobusiness Corporation (Tokyo, Japan).

Purification of NCU00130 and Assay of its Activity

A 1 L culture of *S. cerevisiae* expressing cbt1 and NCU00130 was grown to an OD of 2.0 in complete minimal media. Cells were harvested by centrifugation and resuspended in 30 mL of lysis buffer (50 mM NaH$_2$PO$_4$ [pH 8.0], 300 mM NaCl, 10 mM imidazole, 2 mM β-ME, Complete™ Mini, EDTA free protease inhibitor cocktail). Cells were lysed by sonication, and the lysate was cleared by centrifugation at 15,000 g for 30 minutes. The lysate was bound to 1 mL of nickel-NTA resin by gravity flow, and washed three times with 25 mL wash buffer (identical to lysis buffer but with 20 mM imidazole). NCU00130 was eluted with 5 mL of elution buffer (identical to lysis buffer but with 250 mM imidazole), and the appropriate fractions were pooled, exchanged into storage buffer (Phosphate Buffered Saline (PBS), 2 mM DTT, 10% glycerol), aliquoted, frozen in liquid nitrogen, and stored at −80° C. Purity was determined by SDS-PAGE (FIG. 22), and protein concentration was determined from the absorbance at 280 nm, using an extinction coefficient of 108,750 M$^{-1}$cm$^{-1}$.

Purified NCU00130 was assayed from hydrolysis activity with different cellodextrin substrates. Activity was measured by incubating 5 pmol of enzyme with 500 μM of each sugar in 150 μL PBS plus 3 mM DTT. Reactions proceeded for 40 minutes at 30° C. before 100 μL was removed and quenched in 400 μL of 0.1 M NaOH. The results were analyzed by ion chromatography with a Dionex ICS-3000, with CarboPac PA200 column. Peaks were detected with an electrochemical detector.

Phylogenetic Analysis of Transporter Orthologs

Amino acid sequences of orthologs of CBT1 and CBT2 were obtained from online databases. Multiple sequence alignments were performed using T-Coffee (Notredame et al., 2000). A maximum likelihood phylogeny was determined using PhyML version 3.0 (Guindon and Gascuel 2003) with 100 Bootstraps. Both programs were accessed through Phylogeny.fr (webpage phylogeny.fr/). The resulting tree was visualized with FigTree v.1.2.1 (webpage tree.bio.ed.ac.uk/).

Fermentation and SSF

In fermentation and SSF experiments, comparisons were made between yeast expressing NCU00130 and either Myc-tagged cbt1, or no transporter. These strains were grown aerobically overnight in complete minimal media, washed three times with 25 mL water, and resuspended to a final OD of 2.0 in 50 mL YNB plus the appropriate CSM, and either 2% (w/v) cellobiose or 3% (w/v) pure cellulose (Avicel), in sealed serum flasks. The SSF reactions also included 50 Filter Paper Units/g cellulose of filter-sterilized Celluclast (Sigma C2730), without β-glucosidase supplementation. Reactions were carried out anaerobically at 30° C. with shaking. At indicated time points, 1 mL samples were removed and filtered through a 0.2 μm syringe filter. The ethanol, glucose, and cellobiose concentration in the filtrate was determined by HPLC with an Aminex HPX-87H column and refractive index detection.

*N. crassa* Growth and Alamar Blue® Assays

WT *N. crassa* (FGSC 2489), and the homokaryotic NCU08114 (FGSC 17868) (Colot et al., 2006) were acquired from the Fungal Genetics Research Center (McCluskey 2003), and grown at 25° C. in 50 mL of Vogel's salts plus 2% of either sucrose or pure cellulose (Avicel) in a 250 mL unbaffled flask. After 16 or 28 hours, respectively, 100 μL of Alamar Blue® was added, and cultures were incubated at room temperature for 20 minutes. At this time, 1 mL samples were removed, debris pelleted, and the fluorescence of 100 μL of the supernatant determined with excitation/emission wavelengths of 535/595 nm in a Beckman Coulter Paradigm plate reader.

*N. crassa* Cellobiose Transport Assays

WT *N. crassa* (FGSC 2489), and homokaryotic deletion lines (Colot et al., 2006) of NCU00801 (FGSC 16575) and NCU08114 (FGSC 17868) were acquired from the Fungal Genetics Stock Center (McCluskey 2003), and grown for 16 hours in 50 mL of Vogel's salts plus 2% (w/v) sucrose at 25° C., starting with an inoculum of $10^6$ conidia/mL. Mycelia were harvested by centrifugation, washed three times with Vogel's salts, and transferred to Vogel's salts plus 0.5% (w/v) pure cellulose (Avicel) for 4 hours to induce the transporter expression. Ten mL of the culture was harvested by centrifugation, washed three times with Vogel's salts, and resuspended in 1 mL $ddH_2O$ plus cycloheximide (100 μg/mL) and 90 μM of the respective cellodextrin (cellobiose, cellotriose, or cellotetraose). To measure cellodextrin consumption, 100 μL was removed after 15 minutes, clarified by centrifugation, and transferred into 900 μL of 0.1 M NaOH. The amount of sugar remaining in the supernatant was determined by HPLC with a Dionex ICS-3000, using a CarboPac PA200 column. Peaks were detected with an electrochemical detector.

GFP Fluorescence and Confocal Fluorescence Microscopy

Bulk-cell GFP fluorescence measurements were made in a Beckman Coulter Paradigm plate reader with excitation/emission wavelengths of 485/535 nm. Confocal fluorescence microscopy was performed with cells at an OD (at 600 nm) of 0.8-1.2, using a 100×1.4 NA oil immersion objective on a Leica SD6000 microscope attached to a Yokogawa CSU-X1 spinning disc head with a 488 nm laser and controlled by Metamorph software. Z series were recorded with a 200 nm step size and analyzed using ImageJ.

[$^3$H] Cellobiose Transport Assays and Kinetic Parameters

Transport assays were performed using a modification of the oil-stop method (Arendt et al., 2007). Yeast strains expressing either cbt1 or cbt2 fused to GFP were grown to an OD (at 600 nm of 1.5-3.0 in selective media, washed three times with ice cold assay buffer (30 mM MES-NaOH [pH 5.6] and 50 mM ethanol), and resuspended to an OD of 20. To start transport reactions, 50 μL of cells were added to 50 μL of [$^3$H] cellobiose layered over 100 μL of silicone oil (Sigma 85419). Reactions were stopped by spinning cells through oil for 1 minute at 17,000 g, tubes were frozen in ethanol/dry ice, and tube-bottoms containing the cell-pellets were clipped off into 1 mL of 0.5 M NaOH. The pellets were solubilized overnight, 5 mL of Ultima Gold scintillation fluid added, and CPM determined in a Tri-Carb 2900TR scintillation counter. [$^3$H] cellobiose was purchased from Moravek Biochemicals, Inc. and had a specific activity of 4 Ci/mmol and a purity of >99%. Kinetic parameters were determined by measuring the linear rate of [$^3$H] cellobiose uptake over 3 minutes for a range of cellobiose concentrations. $V_{max}$ and $K_m$ values were determined by fitting a single rectangular, 2-parameter hyperbolic function to a plot of rates vs. cellobiose concentration by non-linear regression in SigmaPlot®. $V_{max}$ values were normalized for differences in transporter abundance by measuring the GFP fluorescence from 100 μL of cells at OD 20 immediately before beginning transport assays. Kinetic parameters reported in the text are mean±the standard deviation from three separate experiments. Competition assays were performed by measuring transport of 50 μM [$^3$H]-cellobiose over 20 seconds in the percent of 250 μM of the respective competitors.

Large Scale Yeast Growth

To monitor growth on different carbon sources, engineered strains were grown in 5 mL of complete minimal media with appropriate dropouts overnight. These starter cultures were washed three times with 25 mL of ddH2O and resuspended to an OD (at 600 nm) of 0.1 in 50 mL Yeast Nitrogen Base (YNB) plus the appropriate Complete Supplemental Media (CSM) and 2% (w/v) cellobiose. Cultures were grown in 250 mL unbaffled flasks at 30° C., with shaking at 200 rpm. The change in OD (at 600 nm) was monitored by periodically removing samples.

Example 10

Identification of Critical Residues for Cellodextrin Transporter Function

In this example, sequence analysis and mutagenesis studies were used to identify conserved and functionally important residues in the cellodextrin transporters. In addition, additional cellodextrin transporters were identified.

The growth rates of yeast strains expressing various mutants of the cellodextrin transporter NCU00801 (cbt1) or NCU08114 (cbt2) and the wild-type β-glucosidase NCU00130 were grown with cellobiose as the sole carbon source. Amino acid residues at 96 positions of NCU00801 and at 96 positions of NCU08114 were individually mutated to alanine using QuickChange® II Site-directed Mutagenesis Kit (Stratagene, La Jolla, Calif.) as per the manufacturer's instructions. Strains were grown in synthetic defined media-ura-leu 100 mg/L adenine with 2% cellobiose. Cultures were started from two independent colonies.

Figure 26:
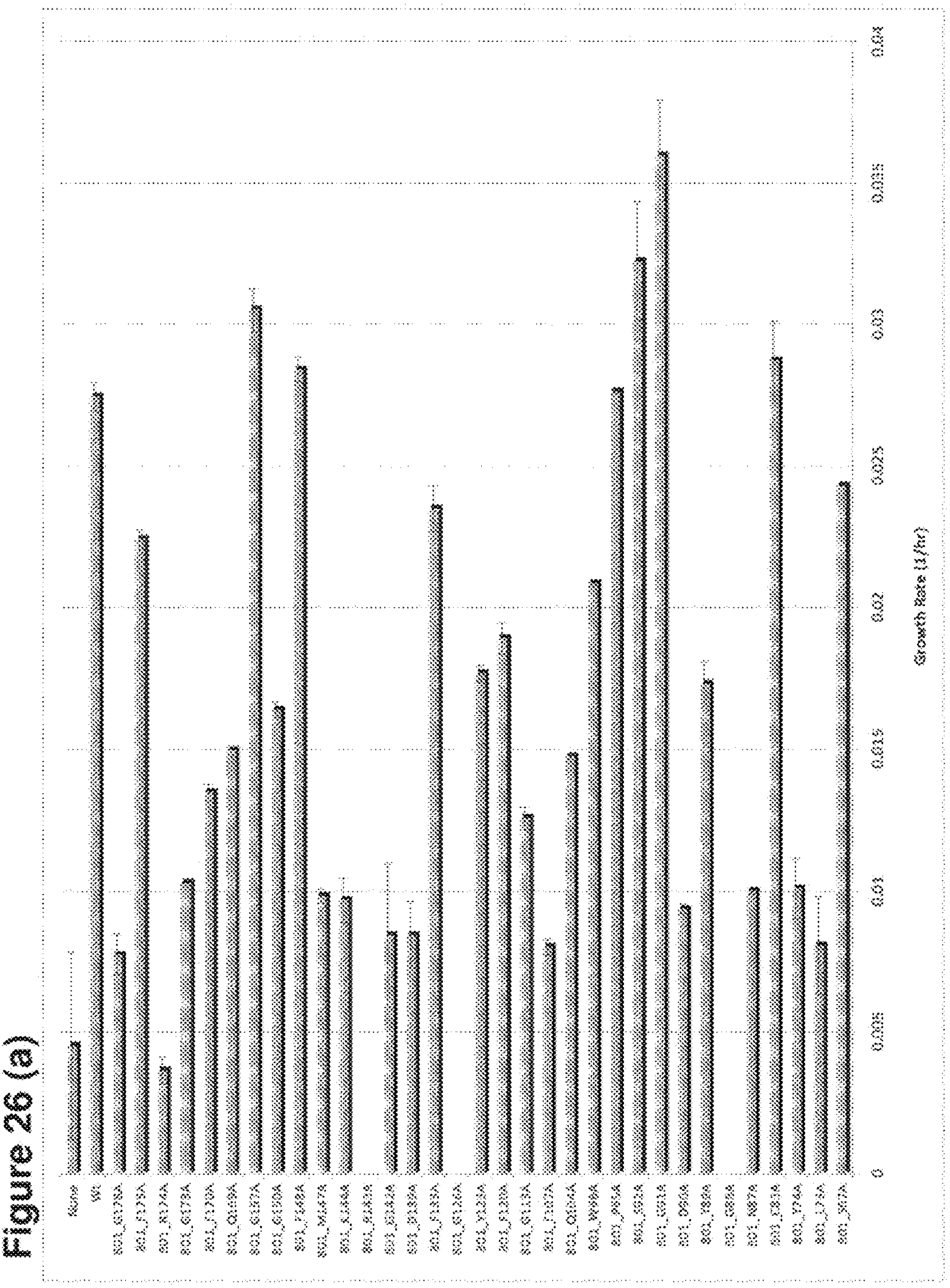
FIG. 26 shows residues in NCU00801 and NCU08114 that are critical for function.

As the results shown in FIG. 26 (*a, b*) indicate, mutant strains that expressed NCU00801 with substitutions at W66, L73, Y74, N87, Y89, D90, Q 104, F107, G113, F120, Y123, D139, G142, K144, M147, G150, Q169, F170, G173, R174, G178, G180, P189, Y191, E194, P198, R201, Y208, W235, R236, Q242, $^{257}$PESPRF$^{262}$ (SEQ ID NO: 67), Y279, G283, E296, D307, K308, W310, D312, R325, G336, Y345, N369, D385, F462, P468, E476, T480, or G486 showed at least a 25% growth defect compared to wild-type strain.

The alanine scanning experiment on NCU08114 indicated the following residues as being functionally important: L38, Y39, G54, D56, F73, G91, P100, D104, G107, R108, M118, R139, F144, Q150, P154, E159, P163, H165, R166, Y173, N174, W199, Q214, $^{222}$PESP$^{225}$ (SEQ ID NO: 68), Y244, H245, D249, E258, E268, Q302, W303, S304, N306, Y312, F359, L360, F402, Y403, S404, Y414, E417, P420, Y421, K426, N442, N446, P447, W459, K460, E482, T483, L488, E489, E490, D496, and G497 (FIG. 26*b*).

In particular, the motifs $^{73}$LYF$^{75}$, $^{257}$PESP$^{260}$ (SEQ ID NO: 69), and $^{278}$KYH$^{280}$ (residue numbering of NCU00801) appeared to be functionally important in both transporters (residues $^{257}$PESP$^{260}$ (SEQ ID NO: 69) of NCU00801 and residues $^{222}$PESP$^{225}$ (SEQ ID NO: 68) of NCU08114), which have an amino acid sequence identity of 29% (FIG. 26*b, c*). Several residues that are conserved in transporters in general (italicized in FIG. 26*b, c*), or in β-linked transporters in particular (double-underlined), were experimentally shown to be important for transporter function (underlined), e.g., D90 (NCU00801) and D56 (NCU08114), and L73 (NCU00801) and L38 (NCU08114). Results of the mutagenesis experiment also implicated residues conserved in the NCU00801/NCU08114 Glade (capped) as being functionally important, e.g., Q168 (NCU00801) and Q214 (NCU08114). Moreover, multiple residues determined to be functionally important in this experiment were previously shown to be conserved in the *S. cerevisiae* sugar transporters (Hxt1/Hxt3), e.g., L73 (NCU00801) and L38 (NCU08114).

Figure 27:
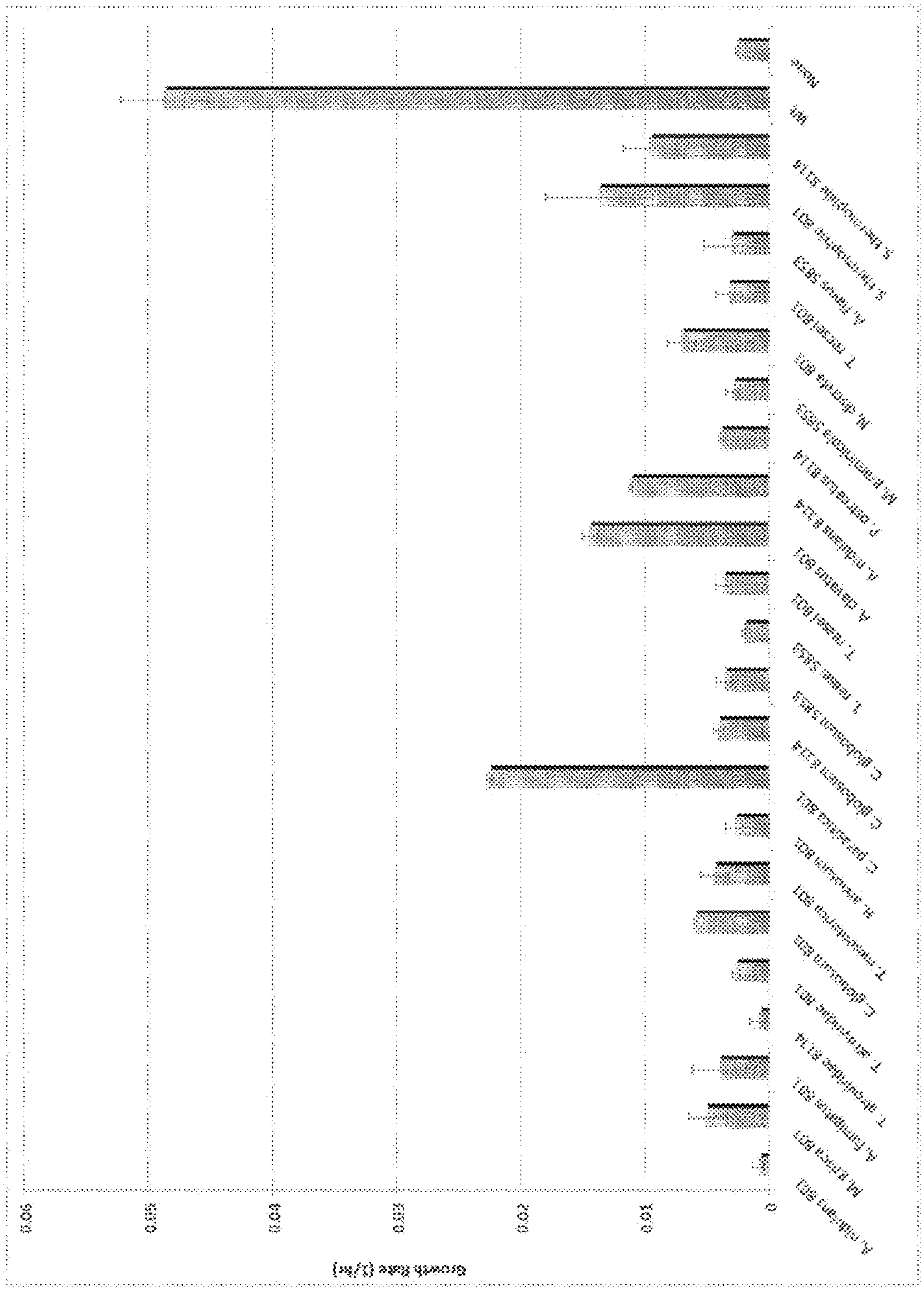
FIG. 27 shows a comparison of *S. cerevisiae* strains expressing cellobiose transporters from *P. stipitis*.
Figure 27:
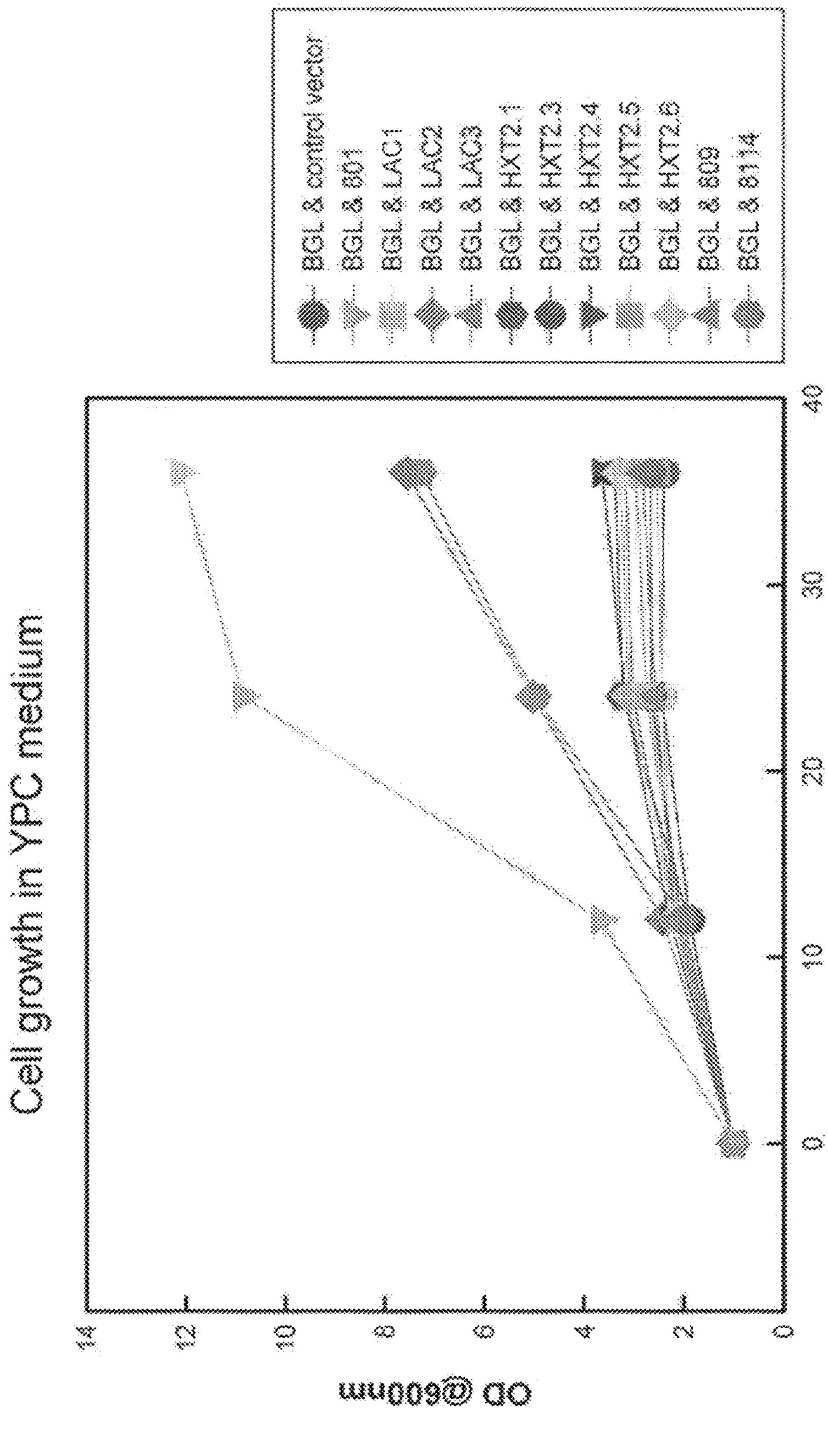
Figure 27:
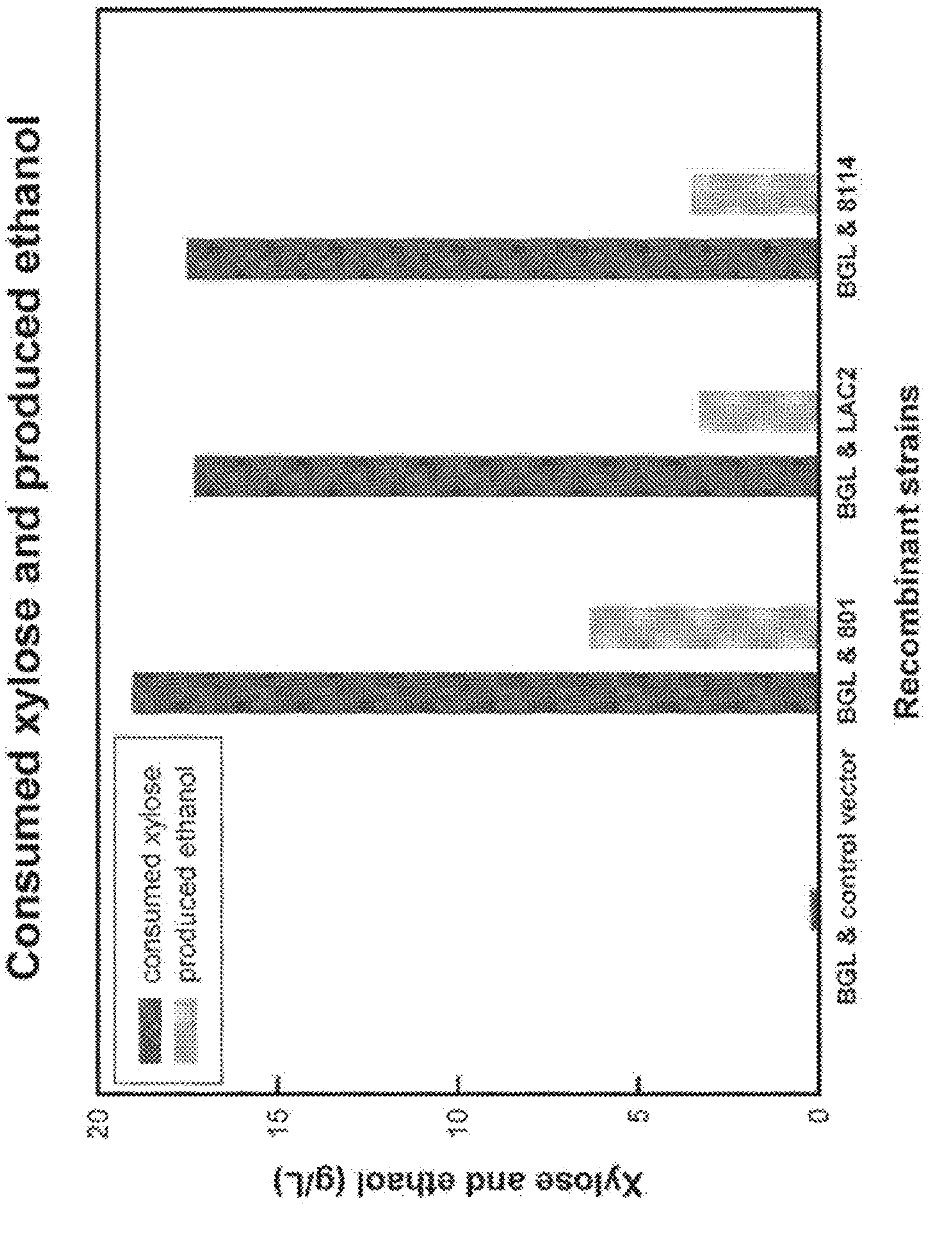

Orthologs of *N. crassa* cellodextrin transporters from different organisms were also studied (FIG. 27). Representative orthologs were synthesized by Genescript and cloned into the expression vector, pRS426 containing the Cup1 promoter using the sites BamHI and HindIII. These constructs were transformed into the yeast strain, YPH499 along with the intracellular β-glucosidase, NCU00130. Transporter activity was determined by measuring the growth rates of these strains when cellobiose was present as the sole carbon source.

Alternatively, different fungal strains containing putative orthologs were cultivated in rich media supplemented with cellobiose. Total RNA was isolated and reverse transcribed into cDNA. Polymerase chain reaction (PCR) was used to amplify the putative transporter genes directly from cDNA. However, because the regulation mechanism and expression pattern were unknown for cellodextrin transporters in fungal species, cDNAs encoding the putative transporters were not always obtainable despite alteration of cultivation condition. In this case, primers were designed according to the corresponding cDNA sequences from GenBank and used to amplify the exons using genomic DNA as a template. Overlap-extension PCR was then used to assemble the exons into the full-length genes. The resulting PCR products were cloned into the pRS424 shuttle vector containing a HXT7 promoter and a HXT7 terminator using the DNA assembler method. Yeast plasmids isolated from transformants were retransformed into *E. coli* DH5α, and isolated *E. coli* plasmids were first checked by diagnostic PCR using the primers used to amplify the original transporter genes. The entire open reading frames were submitted for sequencing to confirm the correct construction of the plasmids. In the orthologs LAC2, LAC3, HXT2.1, and HXT2.6 from *P. stipitis*, one or more alternative codons (CUG) substitute Ser for Leu. Most of the cloning work was carried out using the yeast homologous recombination mediated DNA assembler method. pRS424-HXT7-GFP plasmid was used for cloning of putative cellodextrin transporters. In this plasmid, the HXT7 promoter, the GFP gene flanked with the EcoRI sites at both ends, and the HXT7 terminator were assembled into the pRS424 shuttle vector (New England Biolabs) linearized by ClaI and BamHI. PCR products of the putative transporters flanked with DNA fragments sharing sequence identity to the HXT7 promoter and terminator were co-transferred into CEN.PK2-1C with EcoRI digested pRS424-HXT7-GFP using the standard lithium acetate method. The resulting transformation mixture was plated on SC-Trp plates supplemented with 2% D-glucose to recover transformants. Yeast expressing putative cellodextrin transporter orthologs and NCU00130 were tested for growth on cellobiose as the sole carbon source.

A listing of the putative cellodextrin transporter orthologs and results obtained from the study are shown in Table 14.

TABLE 14

Listing of putative cellodextrin transporter orthologs and summary of results.

| *N. crassa* ortholog | Species | NCBI Reference Sequence/ NCBI GI Number/JGI number ¥ | Aver. Growth Rate | Growth Rate error | Seq results* |
|---|---|---|---|---|---|
| NCU00809 | *Chaetomium globusom* CBS148.51 | XP_001220480 | — | — | OK |
| NCU00809 | *Podospora anserina* | XP_001912722 | — | — | — |
| NCU00809 | *Nectria haematococca* mpVI77-13-4 | EEU41662 | — | — | — |
| NCU00809 | *Aspergillus nidulans* FGSC A4 | XP_660803 | — | — | 1 intron and 50 bp insertion |
| NCU00809 | *Aspergillus terreus* NIH2624 | XP_001218592 | — | — | — |

TABLE 14-continued

Listing of putative cellodextrin transporter orthologs and summary of results.

| *N. crassa* ortholog | Species | NCBI Reference Sequence/ NCBI GI Number/JGI number ¥ | Aver. Growth Rate | Growth Rate error | Seq results* |
|---|---|---|---|---|---|
| NCU00809 | *Talaromyces stipitatus* ATCC 10500 | XP_002341594 | — | — | — |
| NCU00809 | *Aspergillus niger* | XP_001395979 | — | — | Ala > Val |
| NCU00809 | *Aspergillus fumigatus* Af293 | XP_747891 | — | — | — |
| NCU00809 | *Aspergillus terreus* NIH2624 | XP_00120996 | — | — | — |
| NCU00809 | *Aspergillus oryzae* RIB40 | XP_001817400 | — | — | OK |
| NCU08114 | *Podospora anserina* | XP_001908539 | — | — | N/A |
| NCU08114 | *Penicillium chrysogenum* Wisconsin 54-1255 | XP_002568019 | — | — | N/A |
| NCU08114 | *Aspergillus terreus* NIH2624 | XP_001209810 | — | — | Wrong |
| NCU08114 | *Aspergillus oryzae* RIB40 | XP_001820343 | — | — | OK |
| NCU08114 | *Aspergillus terreus* NIH2624 | XP_001210859 | — | — | N/A |
| NCU08114 | *Neurospora crassa* OR74A | XP_001728155 | — | — | N/A |
| NCU08114 | *Aspergillus oryzae* RIB40 | XP_001826848 | — | — | N/A |
| NCU08114 | *Aspergillus nidulans* FGSC A4 | XP_657617 | — | — | OK |
| NCU08114 | *Talaromyces stipitatus* ATCC 10500 | XP_002487579 | — | — | N/A |
| NCU08114 | *Chaetomium globosum* CBS 148.51 | XP_001227497 | — | — | Wrong |
| NCU08114 | *Trichoderma atroviridae* | 215408 | 0.000836364 | 0.00064871 | I, D |
| NCU08114 | *Chaetomium globosum* | XP_001220290.1 | 0.004036364 | 0.00047168 | OK |
| NCU08114 | *Aspergillus nidulans* | ANID_08347 | 0.011109091 | 0.000072727 | Other |
| NCU08114 | *Pleurotus ostreatus* | 51322 | 0.00390303 | 0.00018212 | — |
| NCU08114 | *Sporotrichum thermophile* | 114107 | 0.009569697 | 0.00216366 | — |
| NCU00801 | *Aspergillus nidulans* | XP_660418.1 | 0.000860606 | 0.000438 | P |
| NCU00801 | *Magnaporthe grisea* | XP_364883.1 | 005090909 | 0.00138313 | OK |
| NCU00801 | *Aspergillus fumigatus* | XP_753099.1 | 0.003975758 | 0.00211951 | OK |
| NCU00801 | *Trichoderma atroviridae* | 211304 | 0.002678788 | 0.00031193 | D |
| NCU00801 | *Chaetomium globosum* | XP_001220469.1 | 0.005890909 | 0.00010285 | OK |
| NCU00801 | *Tremella mesenterica* | 63529 | 0.004381818 | 0.00115751 | D |
| NCU00801 | *Heterobasidion. annosum* | 105952 | 0.002751515 | 0.00068763 | D |
| NCU00801 | *Cryphonectria parasitica* | 252427 | 0.02250303 | 0.00021692 | D |
| NCU00801 | *Trichoderma ressei* | 67752 | 0.003672727 | 0.00066233 | D |
| NCU00801 | *Aspergillus clavatus* | XP_001268541.1 | 0.014381818 | 0.00059613 | OK |
| NCU00801 | *Neurospora discreta* | 77429 | 0.007060606 | 0.00110566 | D |
| NCU00801 | *Trichoderma reesei* | 3405 | 0.003264646 | 0.001033998 | D |
| NCU00801 | *Sporotrichum thermophile* | 43941 | 0.013654545 | 0.00431534 | — |
| NCU00801 | *Neurospora crassa* | XP_963801.1 | 0.048754872 | 0.00354017 | — |
| NCU05853 | *Chaetomium globosum* | XP_001226269.1 | 0.003593939 | 0.00062306 | OK |
| NCU05853 | *Trichoderma reesei* | 46819 | 0.002042424 | 0.000085924 | D |
| NCU05853 | *Mycosphaerella graminicola* | 68287 | 0.00290101 | 0.00060123 | D |
| NCU05853 | *Aspergillus flavus* | AFLA_000820A | 0.003078788 | 0.00209132 | — |
| — | None | — | 0.0026 | 0.0001 | — |
| NCU00809 | *Pichia stipitis* CBS6054 (LAC1) | XP_001383110.1/ GI: 126133170 | See FIG. 27 | — | — |
| NCU00809 | *Pichia stipitis* CBS6054 (LAC2) | XP_001387231.1/ GI: 126276337 | See FIG. 27 | — | — |
| NCU00809 | *Pichia stipitis* CBS6054 (LAC3) | XP_001383677.2/ GI: 150864727 | See FIG. 27 | — | — |
| NCU08114 | *Pichia stipitis* CBS6054 (HXT2.1) | XP_001386873.1/ GI: 126275571 | See FIG. 27 | — | — |
| NCU05853 | *Pichia stipitis* CBS6054 (HXT2.3) | XP_001382754.1/ GI: 126132458 | See FIG. 27 | — | — |
| NCU08114 | *Pichia stipitis* CBS6054 (HXT2.4) | XP_001387757.1/ GI: 126273939 | See FIG. 27 | — | — |
| NCU08114 | *Pichia stipitis* CBS6054 (HXT2.5) | XP_001385684.1/ GI: 126138322 | See FIG. 27 | — | — |

TABLE 14-continued

Listing of putative cellodextrin transporter orthologs and summary of results.

| N. crassa ortholog | Species | NCBI Reference Sequence/ NCBI GI Number/JGI number ¥ | Aver. Growth Rate | Growth Rate error | Seq results* |
|---|---|---|---|---|---|
| NCU08114 | *Pichia stipitis* CBS6054 (HXT2.6) | XP_001384653.2/ GI: 15086543 | See FIG. 27 | — | — |

*Wrong = difference between tested sequence and sequence in NCBI or JGI databases; I = insertion in tested sequence; D = deletion in tested sequence; P = point mutation in tested sequence; OK = no difference between tested sequence and sequence deposited in NCBI or JGI databases; Other = other problems in sequencing, excluding insertion, deletion, and point mutations in tested sequence; "—" = results not yet available (study in progress).

¥ When accession numbers were not available, the JGI number was used. The JGI number allows access to the gene sequence via the JGI genome portal for this organism (accessible from the following page: genome.jgi-psf.org/programs/fungi/index.jsf). The *A. flavus* and *A. nidulans* identifiers allow access to the genes through their genome portals at webpage cadre-genomes.org.uk/ and webpage broadinstitute.org/annotation/genome/aspergillus_group/MultiHome.html, respectively.

In certain cases, the sequences of the cloned orthologs were determined to be correct, and the yeast expressing those clones were able to utilize cellobiose. Thus, these clones, LAC2 from *Pichia stipitis* and XP_001268541.1 from *Aspergillus clavatus* were confirmed to be functional cellobiose transporters. Testing of the cellobiose transporting function of other clones is still in progress. Cloned orthologs with sequences different from the published sequences in databases (e.g., ones with insertions, deletions, etc.) (Table 14) will be re-cloned, re-sequences, and similarly tested for cellobiose transport activity by expressing them in *S. cerevisiae* and monitoring growth rates.

An alignment of NCU00801, NUC08114, and functional orthologs of these transporters is shown in FIG. 28. The alignment in FIG. 28*a* includes both putative and confirmed cellodextrin transporters, whereas the alignment in FIG. 28*b* includes only confirmed cellodextrin transporters. In addition, FIG. 28*c* shows an alignment of NCU00801 and NCU08114. The two transporters share 29% amino acid sequence identity.

Motifs critical for cellodextrin transporter function were identified by visual inspection of multiple sequence alignments between sugar transporters. Specifically, motifs common to cellodextrin transporters were identified from multiple sequence alignments produced in T-COFFEE between putative cellodextrin transporter orthologs and confirmed cellodextrin transporters. To ensure that these motifs were largely unique to cellodextrin transporters, their absence was confirmed from a multiple sequence alignment between the hexose transporters of *S. cerevisiae*, the human glucose transporter, Glut1, and two *N. crassa* monosaccharide transporters produced in T-COFFEE.

The identified motifs are described below. In the motifs, residues that were found to be critical to the function of NCU00801 are underlined. The residues that were critical for the function of NCU08114 are marked with the superscript "†". The residues that were critical to the function of both transporters are marked with the superscript "*". All motifs were defined using PROSITE notation. As an example of how to read a PROSITE motif, the following motif, [AC]-x-V-x (4)-{ED}, is translated as: [Ala or Cys]-any-Val-any-any-any-any-{any but Glu or Asp} (SEQ ID NO: 13)

Cellodextrin transporters, like all sugar transporters, have 12 transmembrane α-helices. The N- and C-terminus of cellodextrin transporters are both intracellular.

The sequence before transmembrane helix 1 had no distinguishing features.

Transmembrane helix 1 contained the motif, [L*IVM]-Y*-[FL]-x(13)-[YF]-D* (SEQ ID NO: 1).

Transmembrane helix 2 contained the motif, [YF]-x(2)-G$^{\dagger}$-x(5)-[PVF]-x(6)-[DQ]* (SEQ ID NO: 2).

The loop connecting transmembrane helix 2 and transmembrane helix 3 contained the motif, G*-R$^{\dagger}$-[RK]* (SEQ ID NO: 3).

Transmembrane helix 3 had no distinguishing features.

Transmembrane helix 4 had no distinguishing features.

Transmembrane helix 5 contained the motif, R*-x(6)-[YF]*-N$^{\dagger}$ (SEQ ID NO: 4).

Transmembrane helix 6 contained the motif, W*R-[IVLA]-P-x(3)-Q (SEQ ID NO: 5).

The sequence between transmembrane helix 6 and transmembrane helix 7 contained the motif, P*-E*-S*-P*-R-x-L-x(8)-A-x(3)-L-x(2)-Y*-H$^{\dagger}$ (SEQ ID NO: 6).

Transmembrane helix 7 contained the motif, F$^{\dagger}$[GST]-Q*-x-S$^{\dagger}$-G-N$^{\dagger}$-x-[LIV] (SEQ ID NO: 7).

Transmembrane helix 8 had no distinguishing features.

Transmembrane helix 9 had no distinguishing features.

Transmembrane helix 10 and transmembrane helix 11 and the sequence between them contained the motif, L-x(3)-[YIV]$^{\dagger}$-x(2)-E*-x-L-x(4)-R-[GA]-K$^{\dagger}$-G (SEQ ID NO: 8).

Transmembrane helix 12 had no distinguishing features.

The sequence after transmembrane helix 12 had no distinguishing features.

Homology models of NCU00801 and NCU08114 were produced from the primary amino acid sequences of NCU00801 and NCU08114 using the I-TASSER server at: zhanglab.ccmb.med.umich.edu/I-TASSER/ (Roy et al., 2010). The top structural models produced by I-TASSER were visualized in PYMOL (webpage pymol.org/). Mapping of the motifs was also performed in PYMOL. The homology models of NCU00801 and NCU08114 with the cellodextrin transporter motifs marked are shown in FIG. 29 (*a, b*). FIG. 29 (*c*) shows the predicted secondary structures of NCU00801 and NCU08114.

Example 11

Characterization of Novel Pentose-Specific Transporters from *Neurospora crassa* and *Pichia stipitis* in *Saccharomyces cerevisiae*

In this example, a bioinformatics approach was taken to identify novel pentose-specific transporters in *N. crassa* and *P. stipitis.*

Genome Mining of Pentose-Specific Transporters

Bioinformatics Study

To discover novel D-xylose-specific transporters, the genes encoding the D-glucose/D-xylose symporter Gxs1 from *C. intermedia* (Leandro et al., 2006) and the uncharacterized putative L-arabinose-proton symporter Aut1 from *P. stipitis* (locus tag PICST_87108) were used as probes in BLAST searches (webpage ncbi.nlm.nih.gov/) against the sequenced genomes of two efficient xylose-utilizing species, *N. crassa* and *P. stipitis* (Galagan et al., 2003; Jeffries et al., 2007). Any proteins with known D-glucose transport activity or activity other than sugar transport were eliminated from the analyses. Using a cut-off of 25% minimal sequence identity, 17 putative pentose transporter genes were identified (Table 15), in addition to AUT1 from *P. stipitis*. These putative pentose transporter genes shared 25-50% identity with either GXS1 from *C. intermedia* or AUT1 from *P. stipitis*. All 17 putative pentose transporters were annotated as either sugar-transport proteins or hypothetical proteins with unknown activity. The D-glucose transporter genes SUT1 and SUT2 from *P. stipitis* were also cloned for comparison.

Table 15 shows the putative pentose transporters obtained from BLAST using (a) AUT1 from *P. stipitis* as a probe and (b) GSX1 from *C. intermedia* as a probe.

a. BLAST search results using AUT1 as a probe.

| Name | Origin | % identity with AUT1 | Annotation from NCBT | Length (cDNA) | Locus Tag |
|---|---|---|---|---|---|
| Ap31/SUT2 | *P. stipitis* | 31 | sugar uptake (tentative) | 1653 | ABN66266 |
| Ap26/XP_001387242 | *P. stipitis* | 26 | sugar transporter | 1404 | XP001387242 |
| AN49/NCU01494 | *N. crassa* | 49 | hypothetical protein NCU01494, similar to MFS sugar transporter | 2025 | EAA2669I |
| AN41/NCU09287 | *N. crassa* | 41 | hypothetical protein NCU09287, similar to galactose-proton symporter | 1968 | EAA28903 |
| AN29-2/NCU04963 | *N. crassa* | 29 | hypothetical protein NCU04963, similar to MFS monosaccharide transporter | 1584 | EAA30175 |
| AN28-3/NCU02188 | *N. crassa* | 28 | hypothetical protein NCU02188, conserved hypothetical protein | 1458 | EAA30346 |
| AN25/NCU00821 | *N. crassa* | 25 | sugar transporter | 1689 | EAA35128 |

b. BLAST search results using GSX1 as a probe.

| Name | Origin | % identity with GSX1 | Annotation from NCBI | Length (cDNA) | Locus Tag |
|---|---|---|---|---|---|
| Xy50/NCU04537 | *N. crassa* | 50 | hypothetical protein NCU04537 similar to monosaccharide transporter | 1626 | EAA26741 |
| Xy31/NCU06138 | *N. crassa* | 31 | hypothetical protein NCU06138, similar to MFS monosaccharide transporter | 1757 | EAA30764 |
| Xy33/NCU00988 | *N. crassa* | 33 | hypothetical protein NCU00988, similar to MFS quinate transporter | 1614 | EAA34662 |
| Xyp37/SUT3 | *P. stipitis* | 37 | sugar uptake (tentative) | 1653 | ABN67990 |
| Xyp33/XUT3 | *P. stipitis* | 33 | sugar transporter, putative xylose uptake (tentative); predicted transporter (major facilitator superfamily) | 1656 | EAZ63115 |
| Xyp32/XUT1 | *P. stipitis* | 32 | sugar transporter, high affinity, putative; xylose uptake (tentative) | 1701 | ABN67554 |
| Xyp30/STL1 | *P. stipitis* | 30 | sugar transporter, strongly conserved | 1590 | ABN65745 |
| Xyp31/XUT2 | *P. stipitis* | 31 | sugar transporter, xylose transporter (tentative) similarly to GXSI (STL1) | 1407 | AAVQOIOOOO02 |
| Xyp29/STL12/XUT6 | *P. stipitis* | 29 | sugar transporter, putative (STL12); .xylose uptake (tentative) | 1641 | ABN68560 |
| Xyp30-1/HGT3 | *P. stipitis* | 30 | high affinity xylose transporter (putative), xylose uptake (tentative) | 1587 | ABN68686 |
| Xyp28/XUT7 | *P. stipitis* | 28 | xylose transporter, high affinity, putative similarity to STL13, high affinity sugar transporters | 1257 | EAZ63044 |

Cloning of Putative Pentose Transporters

Figure 30A:
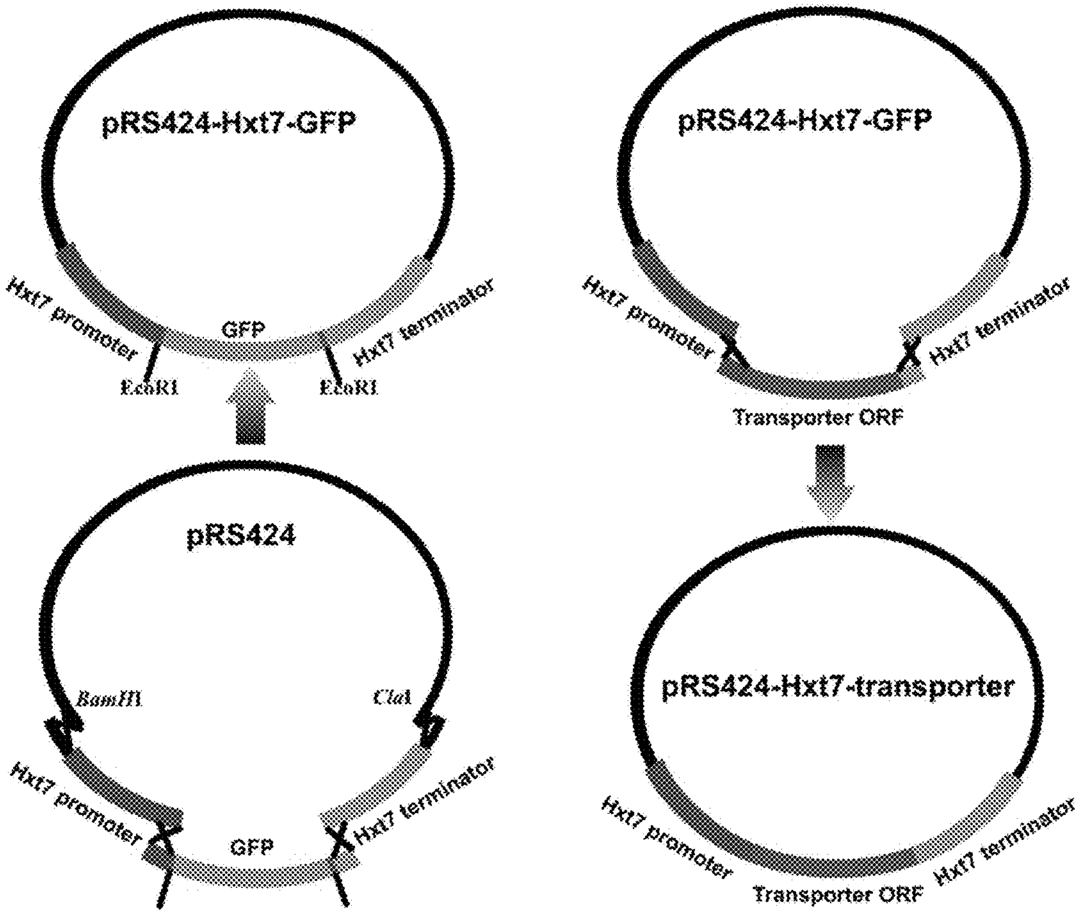
FIG. 30A shows putative transporters.

*N. crassa* and *P. stipitis* were cultivated in rich media supplemented with either D-xylose or L-arabinose as carbon sources. Total RNA was isolated and reverse transcribed into cDNA. Polymerase chain reaction (PCR) was used to amplify the putative transporter genes directly from cDNA. However, because the regulatory mechanism and expression patterns of pentose transporters in fungal species were unknown, cDNAs encoding the putative pentose transporters were not always obtainable despite alteration of cultivation conditions. In those cases, primers were designed according to the corresponding cDNA sequences from GenBank and used to amplify the exons with genomic DNA as templates. Overlap-extension PCR was then used to assemble the exons into full length genes. The resulting PCR products were cloned into the pRS424-HXT7-GFP shuttle vector using the yeast homologous recombination-mediated DNA assembler method (Shao et al., 2009). In this plasmid, an HXT7 promoter, a GFP gene flanked with the EcoRI sites at both ends, and an HXT7 terminator were assembled into the pRS424 shuttle vector (New England Biolabs) linearized by ClaI and BamHI. PCR products of the putative pentose transporters flanked with DNA fragments, sharing sequence identity with the HXT7 promoter and terminator (FIG. 30*a*) were co-transferred into *S. cerevisiae* CEN.PK2-1C strain (MATα leu2-3, 112 ura3-52, trp1-289, his3-Δ1 MAL2-8c) purchased from Euroscarf (Frankfurt, Germany) with EcoRI digested pRS424-HXT7-GFP using the standard lithium acetate method. The resulting transformation mixture was plated on SC-Trp plates supplemented with 2% D-glucose.

Yeast plasmids isolated from transformants using Zymoprep Yeast Plasmid Miniprep II (Zymo Research, Orange, Calif.) were re-transferred into *Escherichia coli* DH5α cells (Cell Media Facility, University of Illinois at Urbana-Champaign, Urbana, Ill.). The plasmids were isolated using the QIAprep Spin Miniprep Kit (QIAGEN, Valencia, Calif.) and then checked by diagnostic PCR with the primers used to amplify the original transporter genes. The entire open reading frames were also submitted for DNA sequencing to confirm correct construction (Core Sequencing Facility, University of Illinois at Urbana-Champaign, Urbana, Ill.). The DNA sequencing results were compared to gene sequences in databases using Sequencher 4.7 (Gene Codes Corporation, Ann Arbor, Mich.). All sequences of cloned putative transporters are listed in SEQ ID NOs: 33-52.

Yeast strains were cultivated in synthetic dropout media to maintain plasmids (0.17% Difco yeast nitrogen base without amino acids and ammonium sulfate, 0.5% ammonium sulfate, 0.05% amino acid drop out mix). YPA media supplemented with 2% of sugar was used to grow yeast strains harboring no plasmids (1% yeast extract, 2% peptone, 0.01% adenine hemisulfate). *S. cerevisiae* strains were cultured at 30° C. and 250 rpm for aerobic growth and at 30° C. and 100 rpm for oxygen-limited conditions. Yeast strains were grown under aerobic conditions for cell manipulation unless specified otherwise. *E. coli* strains were cultured at 37° C. and 250 rpm in Luria broth (LB) (Fisher Scientific, Pittsburgh, Pa.). All restriction enzymes were purchased from New England Biolabs (Ipswich, Mass.). All chemicals were purchased from Sigma Aldrich (St. Louis, Mo.) or Fisher Scientific.

Transporter Activity Assay for Cloned Putative Transporters

Intracellular Accumulation of Pentose Sugars

The cloned putative pentose transporters were over-expressed in an *S. cerevisiae* sugar transporter deletion strain, and uptake of pentose sugars was measured. The D-xylose-uptake ability of putative pentose transporters was determined by summation of intracellular D-xylose and xylitol concentrations. D-xylose accumulated within *S. cerevisiae* cells can be partially converted to xylitol due to the presence of endogenous aldose reductase. Both D-xylose and xylitol were extracted using osmosis and analyzed using high performance liquid chromatography (HPLC).

The sugar transporter knock-out *S. cerevisiae* strain EBY.VW4000 (CEN.PK2-1c Δhxt1-17, Δstl1, Δagt1, Δydl247w, Δyjr160c, Δgal2), which was a gift from Professor E. Boles' laboratory (Institut für Mikrobiologie, Heinrich-Heine-Universität, Universitätsstr. 1, Geb. 26.12.01, D-40225 Düsseldorf, Germany), had concurrent knock-outs of more than 20 sugar transporters and sensors including HXT1-17 and GAL2. Growth on D-glucose as the sole carbon source was completely abolished in this strain, whereas uptake of maltose through a different sugar transport system was retained. The EBY.VW4000 strain also exhibited minimal pentose-uptake under HPLC assay conditions, which made it a suitable host for testing recombinant D-xylose uptake. Plasmids over-expressing the cloned putative pentose transporter genes were transferred into the EBY.VW4000 strain using the standard lithium acetate method, and single colonies were used for measuring sugar uptake activity.

Cells were first cultured in 2 mL SC-Trp medium supplemented with 2% maltose. Seed culture was then used to inoculate a 50 mL culture in a 250 mL flask. The cells were harvested by centrifugation after 24 hours of growth and re-suspended in YPA medium supplemented with 2% D-xylose or L-arabinose to a final $OD_{600}$ of 10. At 30 min, 60 min, 120 min, and 24 hours, 5 mL cultures were taken for measuring intracellular sugar concentrations. Culture samples were washed twice with ice-cold water and re-suspended in 3 mL of deionized water. Cell suspensions were incubated at 37° C. with 250 rpm agitation for 2 days to extract intracellular sugars. The resulting cell suspension was filtered through a 0.22 μm PES filter (Corning, Lowell, Mass.) before HPLC analysis. The concentrations of sugar and corresponding sugar alcohol (discussed below) were determined using Shimadzu HPLC equipped with a BioRad HPX-87C column (BioRad Laboratories, Hercules, Calif.) and Shimadzu ELSD-LTII low temperature-evaporative light scattering detector (Shimadzu) following the manufacturer's protocol. The sugar-uptake activity was calculated as mg of sugar extracted through osmosis per mL of cell culture at OD~10.

Several putative pentose transporters were identified to be active in uptake of D-glucose or D-xylose or both. Since D-glucose can be metabolized once inside yeast, the D-glucose transport activity could not be determined by measuring intracellular D-glucose concentration. However, because the EBY.VW4000 strain normally cannot grow on media containing D-glucose as the sole carbon source, growth of the strain transformed with a putative pentose transporter on D-glucose indicated that the putative transporter has D-glucose transport activity.

Figure 31:
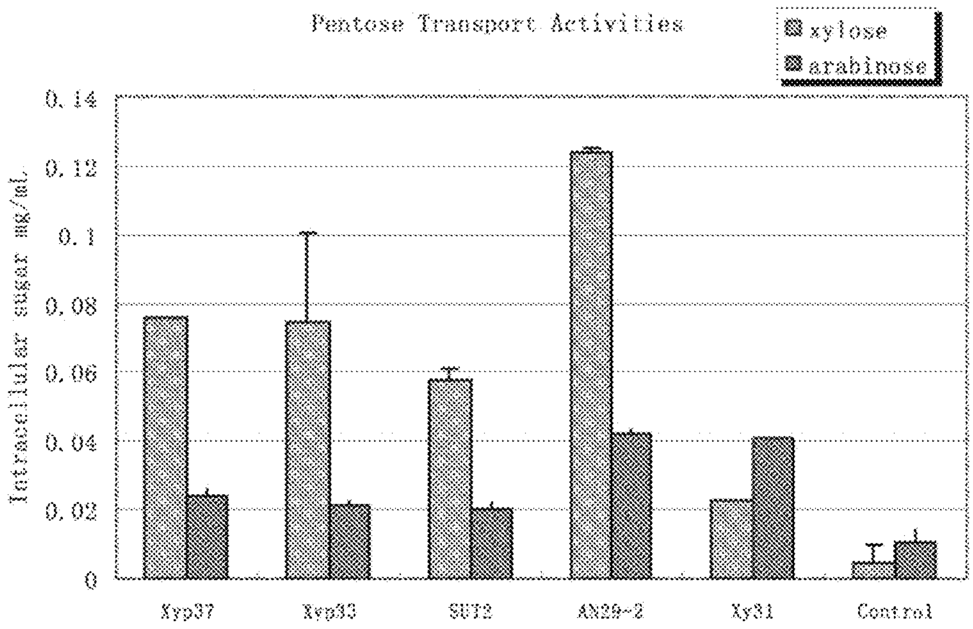
FIG. 31 shows pentose transport activity of putative transporters identified to have glucose-uptake activity.
Figure 32:
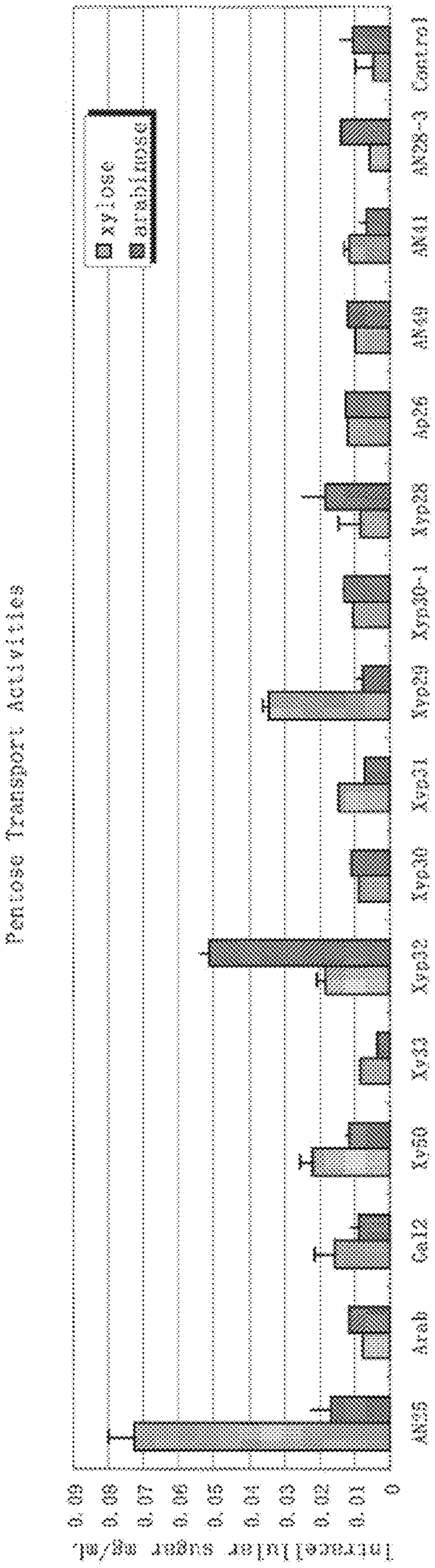
FIG. 32 shows pentose transport activity of putative transporters identified to not have glucose-uptake activity.

Introduction of SUT3 (Xyp37), XUT3 (Xyp33), SUT2 (Ap31), NCU04963 (An29-2), and NCU06138 (Xy31) restored growth of the EBY.VW4000 strain on D-glucose and, thus, enabled glucose transport activity. SUT3, XUT3, SUT2, and NCU04963 also had xylose transport activity, whereas NCU04963 and NCU06138 showed arabinose transport activity (FIG. 31). The rest of the putative transporters failed to enable growth on D-glucose, and most of them also did not show any pentose transport activity. However, NCU00821 and STL12/XUT6 showed xylose transport activity, and XUT1 exhibited arabinose transport activity, indicating they may be sugar transporters specific for pentoses (FIG. 32).

To further confirm that STL12/XUT6 and XUT1 from *P. stipitis* and NCU00821 from *N. crassa* were actually pentose-specific transporters with no D-glucose-uptake activity, the sugar-uptake assay was performed using $^{14}C$-labeled D-glucose, D-xylose, and L-arabinose as substrates. It was found that D-glucose- and L-arabinose-uptake activities of the EBY.VW4000 strain over-expressing only STL12/XUT6 and NCU00821 were too low to be measured under assay conditions used to determine D-xylose-uptake kinetics of both transporters.

$^{14}C$-labeled D-glucose, L-arabinose, and D-xylose were purchased from American Radiolabeled Chemicals (St. Louis, Mo.) as solutions in 90% ethanol. Radiolabeled sugars were first dried in a chemical hood and then re-suspended in water. Sugar solutions at concentrations of 1.33 M and 1 M with specific radioactivity of approximately 40,000 dpm/μL, and at concentrations of 500 mM, 350 mM, 250 mM, 100 mM, and 50 mM with specific radioactivity of about 20,000 dpm/μL were used for the sugar-uptake assay. Cell culture at the exponential phase was harvested and washed twice with ice-cold water and re-suspended to about 60 mg dry cell weight (DCW) per mL in 100 mM Tris-citrate buffer at pH 5. Three aliquots of 160 μL cell suspension were dried at 65° C. for 24 hours to determine the DCW. The rest of the cell suspension was kept on ice before use. For the sugar-uptake assay, cell suspension was equilibrated at 30° C. for 5 min before the assay. In a 50 mL conical tube, 160 μL of cell suspension was mixed with 40 μL of radio-labeled sugar solution for 40 or 60 seconds (accurately timed). The reaction was stopped by adding 10 mL of ice-cold water delivered by a syringe. The zero-time-point sample was obtained by adding ice-cold water and cell suspension simultaneously in a culture tube containing the radio-labeled solution. The mixture was then filtered immediately through a Whatman GF/C filter (Whatman, Florham Park, N.J.) pre-soaked in 40% sugar solution and washed with 15 mL of ice-cold water. The filter was placed in 3 mL of Econo I scintillation cocktail (Fisher Scientific) and counted using a Beckman LS6500 scintillation counter (Beckman Coulter, Brea, Calif.) for 1 min. All data points were measured in three independent experiments. The sugar-uptake rate was calculated as mmol sugar transported per hour per gram of dry cell weight.

Intracellular accumulation of both D-xylose and L-arabinose in EBY.VW4000 strains over-expressing STL12/XUT6, NCU00821, or XUT1 was also measured using HPLC. Cell cultures incubated with pentose sugars for 30 min, 60 min, 120 min, and 24 hours were analyzed by HPLC. The EBY.VW4000 strains over-expressing STL12/XUT6 or NCU00821 exhibited D-xylose uptake activity, whereas the strain over-expressing XUT1 exhibited L-arabinose-uptake activity after a 24-hour incubation (FIG. 33).

The $^{14}C$-labeled sugar uptake assay together with HPLC analysis of intracellular sugar accumulations confirmed that among the three most abundant monosaccharides in lignocellulosic hydrolysates, D-glucose, D-xylose, and L-arabinose, STL12/XUT6 and NCU00821 were responsible for D-xylose uptake and XUT1 was responsible for L-arabinose uptake. Of note, most sugar transporters studied in yeast for D-xylose uptake have higher uptake activity towards D-glucose than towards D-xylose. Only Trxlt1 from *Trichoderma reesei* after adaptive evolution exhibited D-xylose-specific uptake activity (Saloheimo et al., 2007). This data indicated that STL12/XUT6 from *P. stipitis*, NCU00821 from *N. crassa* are the first two experimentally confirmed naturally-occurring D-xylose-specific transporters introduced into *S. cerevisiae*. Similarly, XUT1 from *P. stipitis* is the first experimentally confirmed naturally-occurring L-arabinose-specific transporter introduced into *S. cerevisiae*.

Kinetic Parameters

Figure 34:
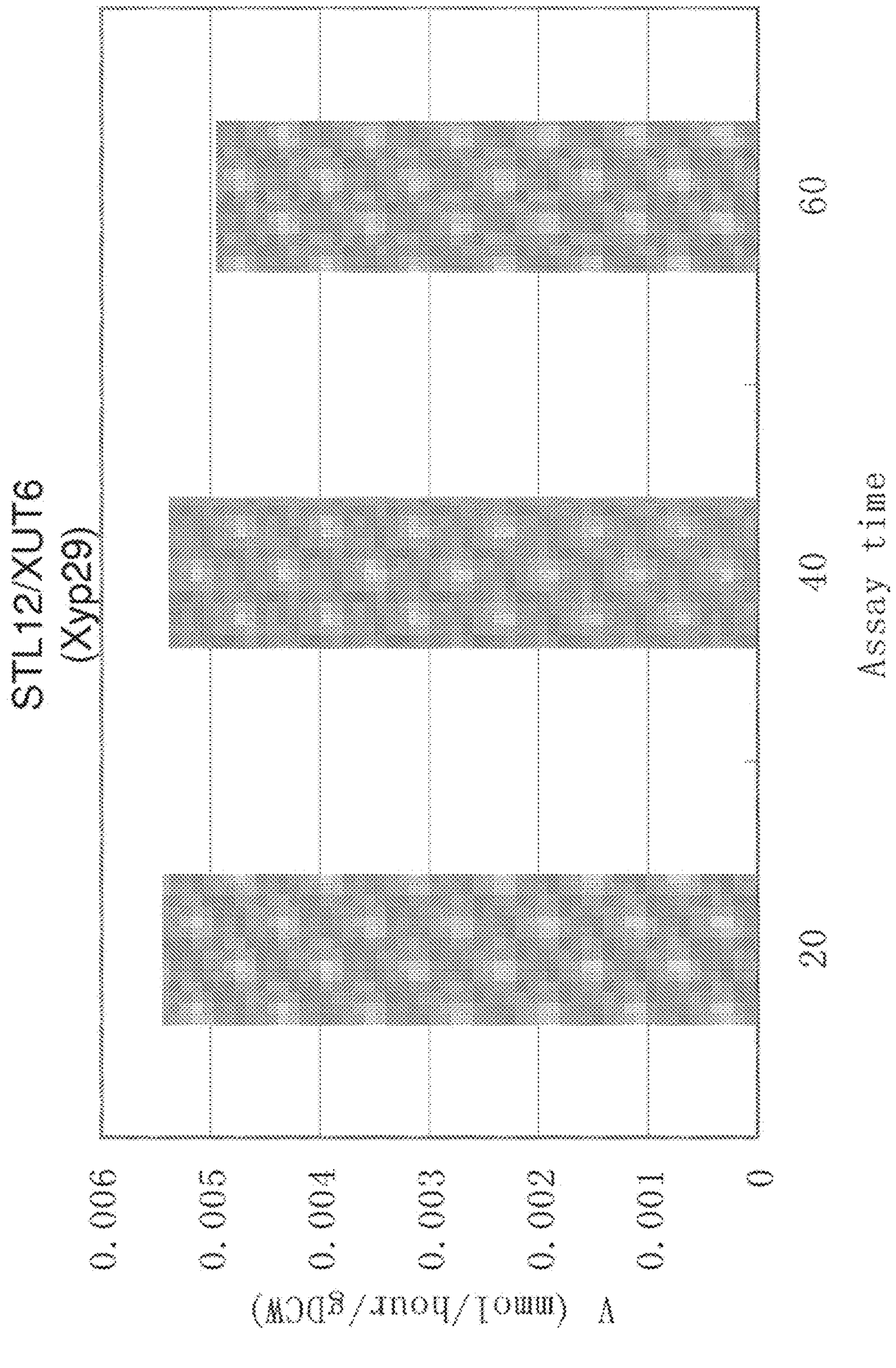
FIG. 34 shows $^{14}C$-labeled sugar uptake by *S. cerevisiae* expressing STL12/XUT6 (Xyp29).

Using the $^{14}C$-labeled sugar-uptake assay, kinetic parameters of D-xylose transport through NCU00921, STL12/XUT6, and XUT1 were determined. It was observed that under the assay conditions, sugar uptake was within a linear range for the first 60 seconds (FIG. 34). The EBY.VW4000 strains over-expressing NCU00821, STL12/XUT6, or XUT1 were incubated with labeled D-xylose or L-arabinose for 40 or 60 seconds followed by addition of ice-cold water to stop further sugar uptake. The reaction mixture was then filtered and washed before measurement using a liquid scintillation counter. The sugar-uptake rates and substrate concentrations were fitted into a Michaelis-Menten equation by non-linear regression using the Origin software (OriginLab Corporation, Northampton, Mass.). The $K_m$ values for D-xylose uptake by the EBY.VW4000 strain harboring only NCU00821 or STL12/XUT6 were 175.7±21.4 mM and 56.0±9.4 mM, respectively. The corresponding $V_{max}$ values were 36.7±2.9 and 41.5±2.3 μmol/h/gram DCW, respectively. Similarly, the $K_m$ and $V_{max}$ values for L-arabinose uptake by the EBY.VW4000 strain harboring XUT1 were 48.0±13.2 mM and 5.6±1.6 μmol/h/gram DCW respectively.

In naturally-occurring D-xylose-assimilating fungal species, both the high affinity D-xylose-proton symport system and the low affinity D-xylose facilitated diffusion system are present. The $K_m$ values of these two systems were determined to be 0.4-4 mM for the symport system and around 140 mM for the facilitated diffusion system (Leandro et al., 2006; Stambuk et al., 2003). These values are close to the affinity of the D-glucose-uptake system in *S. cerevisiae*, which has a $K_m$ of 1.5 mM for the high affinity system and 20 mM for the low affinity system (Lang and Cirillo 1987; Ramos et al., 1988). Unfortunately, the D-xylose uptake affinity of wild-type *S. cerevisiae* is two orders of magnitude lower than its affinity for D-glucose. The $K_m$ values for D-xylose uptake in *S. cerevisiae* are only 190 mM for the high affinity system and 1.5 M for the low affinity system (Kötter and Ciriacy, 1993). The affinities of the newly discovered D-xylose-specific transporters were lower when compared to the high affinity D-xylose-uptake system in naturally occurring D-xylose-assimilating yeasts. However, compared to the D-xylose-uptake system in wild-type *S. cerevisiae*, NCU00821 and STL12/XUT6 showed higher affinity towards D-xylose. In particular, the $K_m$ of D-xylose uptake by STL12/XUT6 and XUT1 were only one-fourth of the $K_m$ of xylose uptake by the transporter in wild-type *S. cerevisiae*. The $K_m$ values of the D-xylose-specific transporters were also close to those of Gxfl ($K_m$ 88 mM) and Sut1 ($K_m$ 145 mM), which have been shown to improve D-xylose fermentation in recombinant *S. cerevisiae* (Runquist et al., 2009; Katahira et al., 2008). Thus, D-xylose fermentation may be improved by introducing these newly discovered D-xylose-specific transporters into *S. cerevisiae*.

Cellular Localization of Sugar Transporters

Sugar transporters are transmembrane proteins, and correct folding and localization in the cell membrane is required for them to be functional. Since no signal peptide was specifically added when the putative pentose transporters were cloned, it was important to ensure that the D-xylose-specific transporters were correctly localized to the cell membrane. This was particularly true for putative pentose transporters like NCU00821 cloned from the filamentous fungi *N. crassa*, which exhibits a very different physiology compared to *S. cerevisiae*. To study the cellular localization of D-xylose-specific transporters in *S. cerevisiae*, NCU00821, STL12/

XUT6, and XUT1 were fused with Green Fluorescent Protein (GFP) at the C-termini via linkers, and their localization was monitored by fluorescent imaging.

Figure 30B:
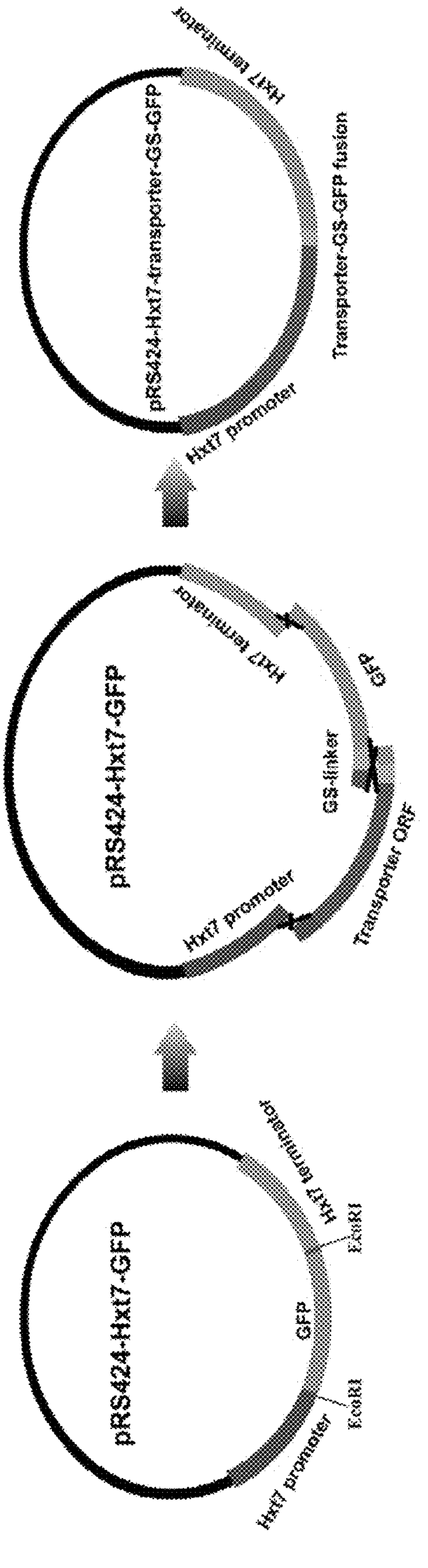
FIG. 30 shows the cloning process used in the construction of plasmid expressing: (A) putative transporters and (B) transporter-GFP fusion proteins.

The fusion proteins of the pentose-specific transporters with the GFP at the C-terminus were constructed for the transporter localization study. A GS-linker (Gly-Gly-Gly-Gly-Ser-Gly-Gly-Gly-Gly-Ser (SEQ ID NO: 70)) was introduced between the transporter and the GFP. The GS-linker was added to the N-terminus of the GFP open reading frame by a PCR primer, resulting in a PCR product of GS-linker-GFP flanked with nucleotide sequence homologous to the transporters at the 5'-end and the HXT7 terminator at the 3'-end. Transporter genes were amplified from the original pRS424-HXT7-transporter constructs to generate DNA fragments of the transporters flanked with nucleotide sequence identical to the HXT7 promoter at the 5'-end and GS-linker-GFP at the 3'-end. These two fragments were then co-transferred into the *S. cerevisiae* strain CEN.PK2-1C with pRS424-HXT7-GFP digested with EcoRI (FIG. 30*b*). The resulting transformation mixture was plated on SC-Trp plates supplemented with 2% D-glucose.

Single colonies were inoculated into 2 mL of SC-Trp liquid medium supplemented with 2% maltose. Cell culture was harvested at the exponential phase. In a centrifuge tube, 250 μL of cell culture was stained with 10 μL Hoechst 33342 nuclei dye (Invitrogen, Carlsbad, Calif.) for 10 minutes at room temperature. A small droplet of cell culture was then transferred onto a piece of cover glass and fluorescent images were taken using an Andor Technology Revolution System Spinning Disk Confocal Microscope (Core facilities, Institute for Genomic Biology, University of Illinois at Urbana-Champaign, Urbana, Ill.). Images were processed using Imaris image analysis and visualization software (Bitplane, Saint Paul, Minn.).

Figure 35:
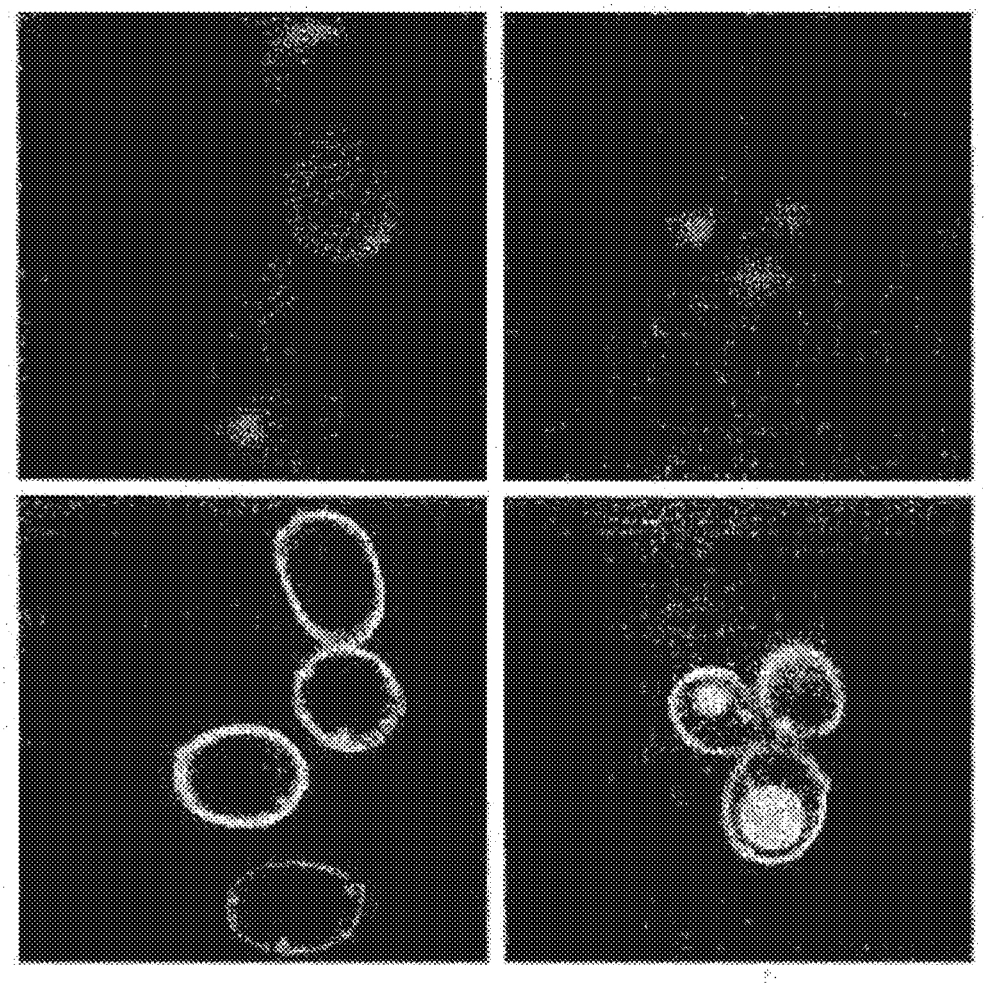
FIG. 35 shows localizations of transporters expressed in *S. cerevisiae* cells as monitored by GFP fluorescence. First row from left to right: NCU00821-GFP fluorescence, NCU00821 nuclei; second row from left to right: STL12/XUT6-GFP fluorescence, STL12/XUT6 nuclei.

Yeast strains over-expressing pentose-specific transporters showed a distinctive fluorescent halo at the cell periphery (FIG. 35). For NCU00821 and XUT1, almost all the GFP fluorescence appeared in the cell membrane, while a large portion of fluorescence in STL12/XUT6-over-expressing cells remained in the cytoplasm. This could indicate inefficient export of the STL12/XUT6 transporter due to elevated expression of the membrane protein. It was also noticed that not all the cells showed fluorescence, indicating that expression of the transporter was not optimal. Further improvements of transporter expression can be achieved through altering the expression level and/or integrating the transporter genes into the genome of recombinant *S. cerevisiae.*

Determination of the Type of Pentose Transporters

There are two types of sugar transporters in *S. cerevisiae*, symporters and facilitators. For symporters, sugar uptake is coupled to proton uptake. Sugar symporters usually exhibit high affinity towards sugar. Meanwhile, sugar uptake through facilitators is not coupled to proton transport, and facilitators usually exhibit low sugar-uptake affinities (Leandro et al., 2006). Symporter assays were performed for NCU00821, STL12/XUT6, and XUT1 expressed in the EBY.VW4000 strain.

To determine the type of transporters, pH change of the EBY.VW4000 over-expressing pentose-specific transporters was measured in un-buffered cell suspension containing D-xylose, L-arabinose, or maltose using a Seven Multi pH meter equipped with an USB communication module and Direct pH software (Mettler Toledo, Columbus, Ohio). Plasmids encoding pentose-specific transporters were transferred into EBY.VW4000 strain followed by plating on the SC-Trp plates supplemented with 2% maltose. Single colonies were inoculated in 2 mL SC-Trp medium supplemented with 2% maltose. Seed culture was then used to inoculate a 400 mL culture in 2 L flasks. The culture was harvested at OD~1 and washed twice with ice-cold water. Cell pellets were re-suspended in 4 mL of water and kept on ice before use. For the symporter assay, the pH electrode was immersed in a water-jacketed beaker of 50 mL capacity kept at 25° C. and provided with magnetic stirring. To the beaker, 23 mL of deionized water and 1 mL of cell suspension equilibrated at 25° C. was added. The pH was adjusted to 5, and a base line was obtained. The pH change was recorded with addition of 1 mL of 50% sugar solution at pH 5.

Figure 36:
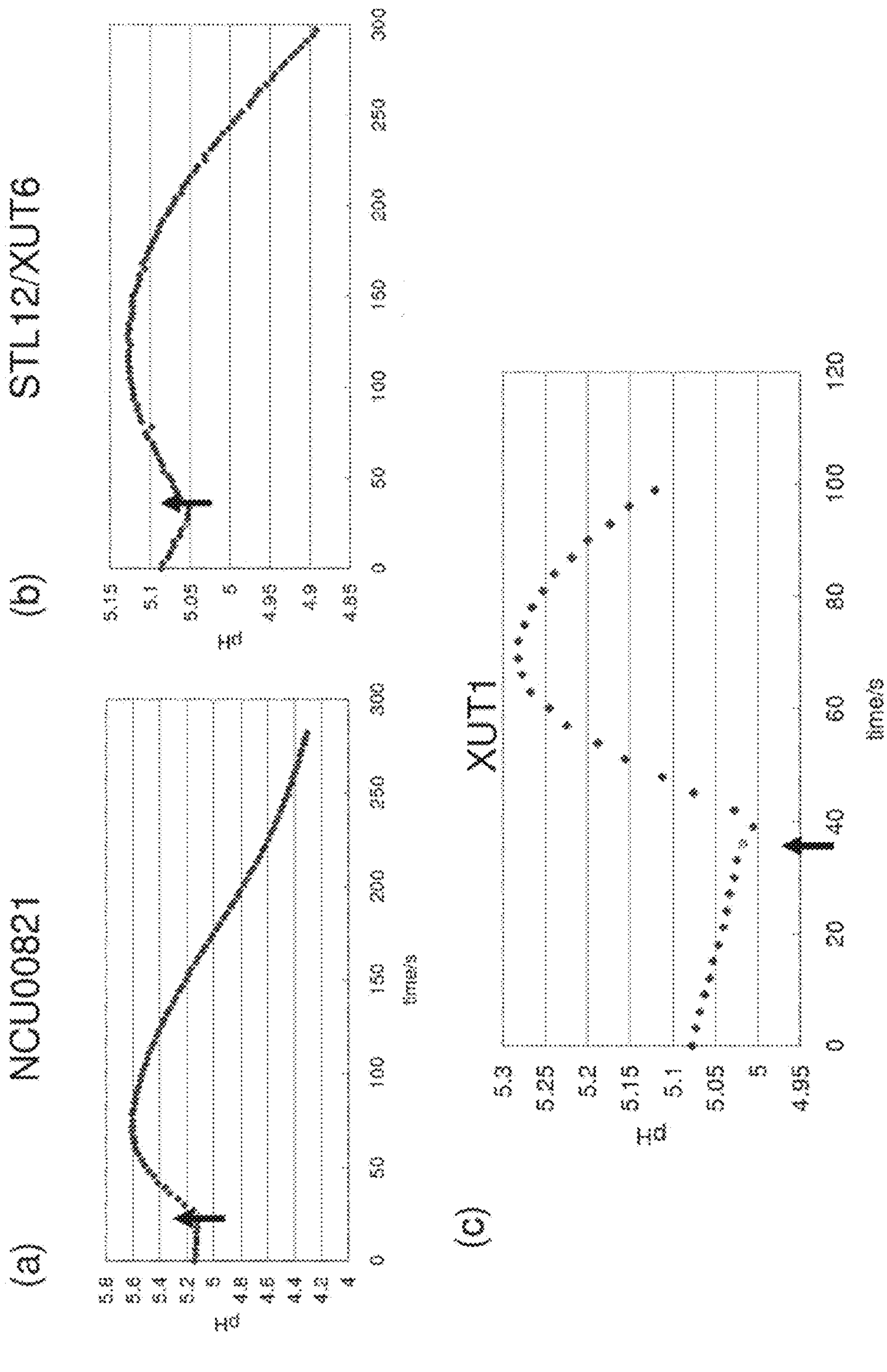
FIG. 36 shows the effect on pH upon addition of maltose to un-buffered cell suspension expressing: (a) NCU00821 (AN25), (b) STL12/XUT6 (Xyp29), and (c) XUT1 (Xyp32). The black arrows indicate the time points when maltose was added.

FIG. 36 shows pH changes in un-buffered cell suspension after the addition of maltose. As was reported, pH in un-buffered *S. cerevisiae* cell suspension went up with the addition of maltose. One mL of 50% maltose solution was added to the un-buffered cell suspension to ensure that the pH recording system was functional. The pH elevations observed in all samples indicated that the pH recording system could monitor transient pH changes in the experimental setting.

Figure 37:
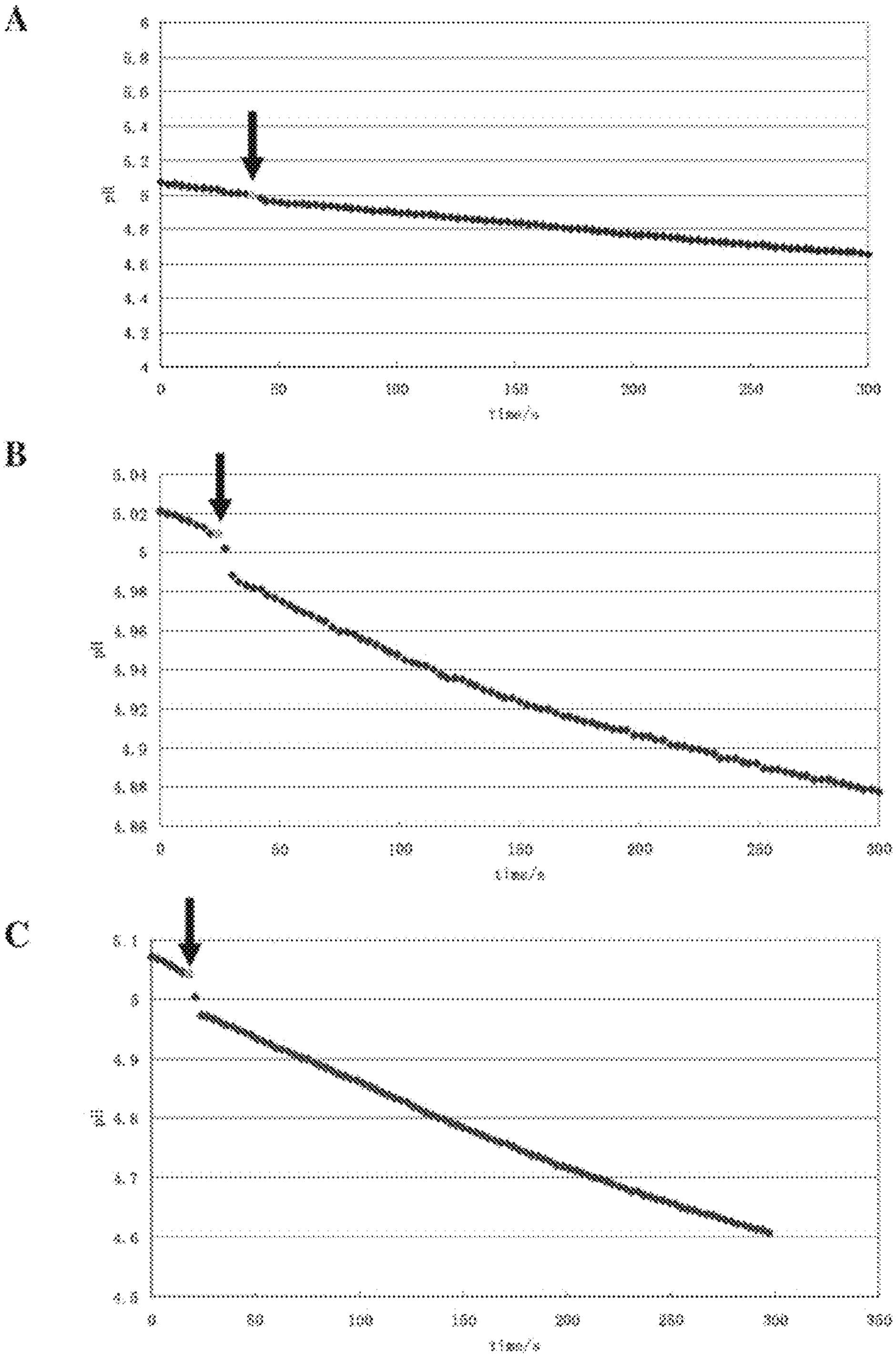
FIG. 37 shows results of a symporter assay of NCU00821, STL12/XUT6, and XUT1.
Figure 38A:
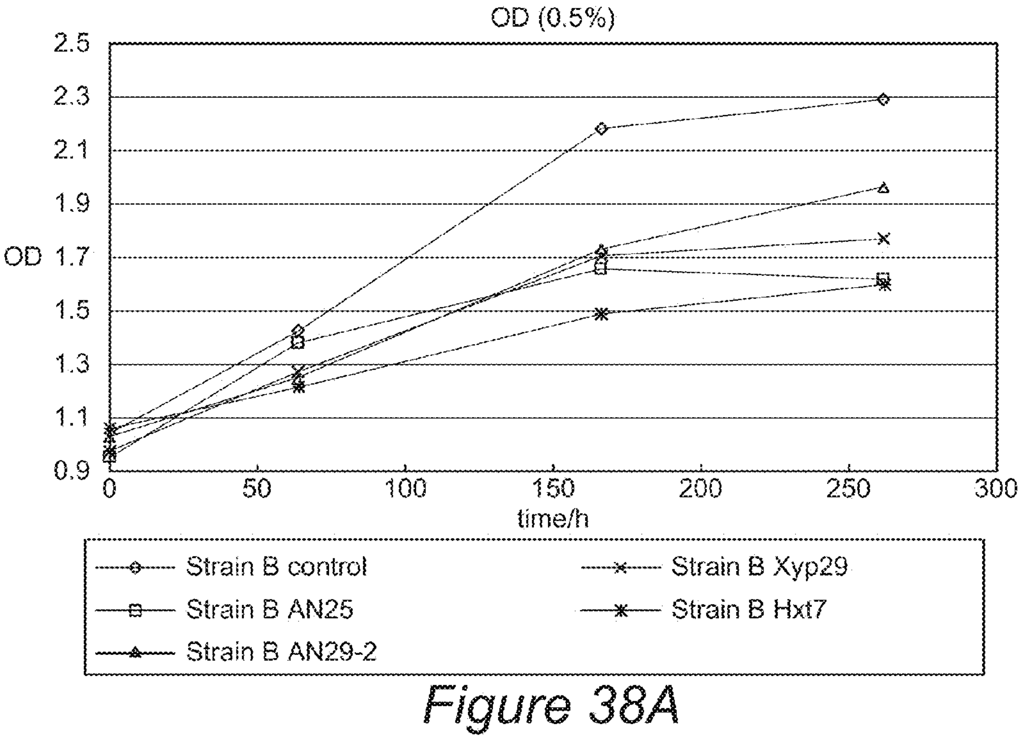
FIG. 38A shows OD.
Figure 38B:
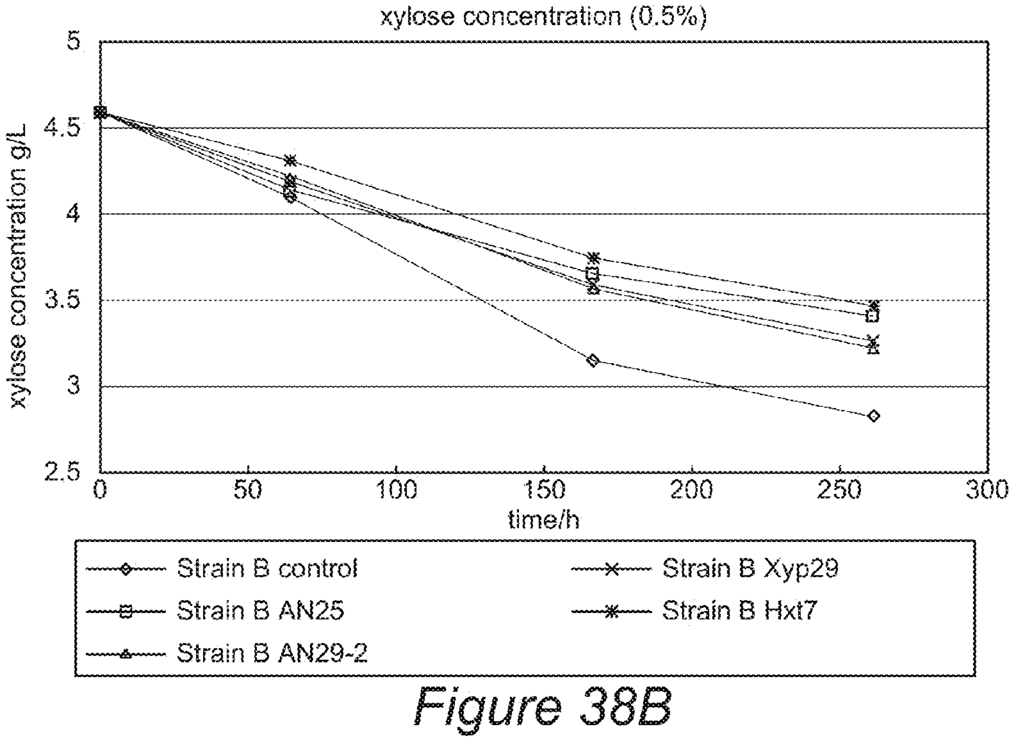
FIG. 38B shows xylose concentration.
Figure 38C:
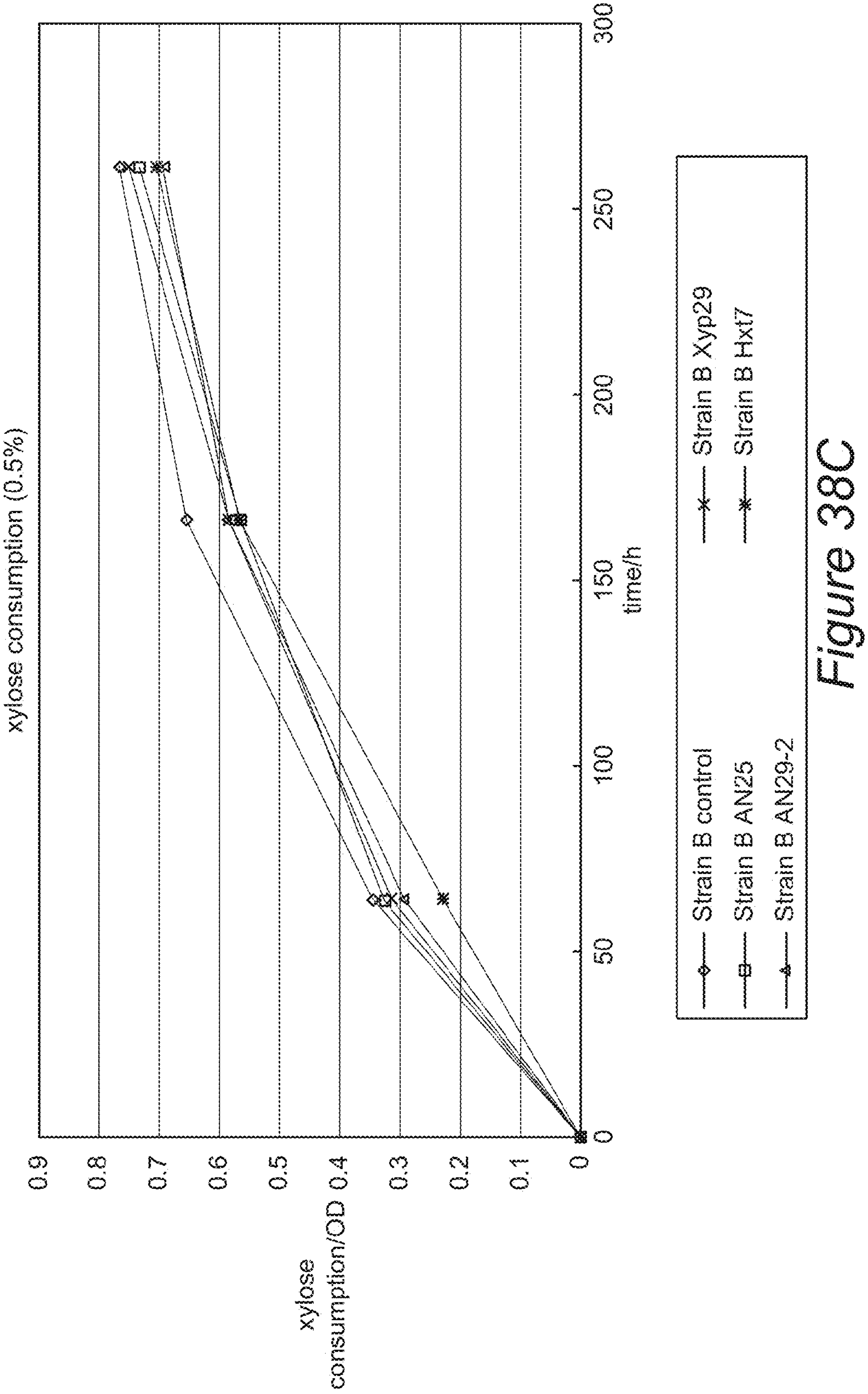
FIG. 38C shows xylose consumption in 0.5% xylose-containing media.
Figure 38D:
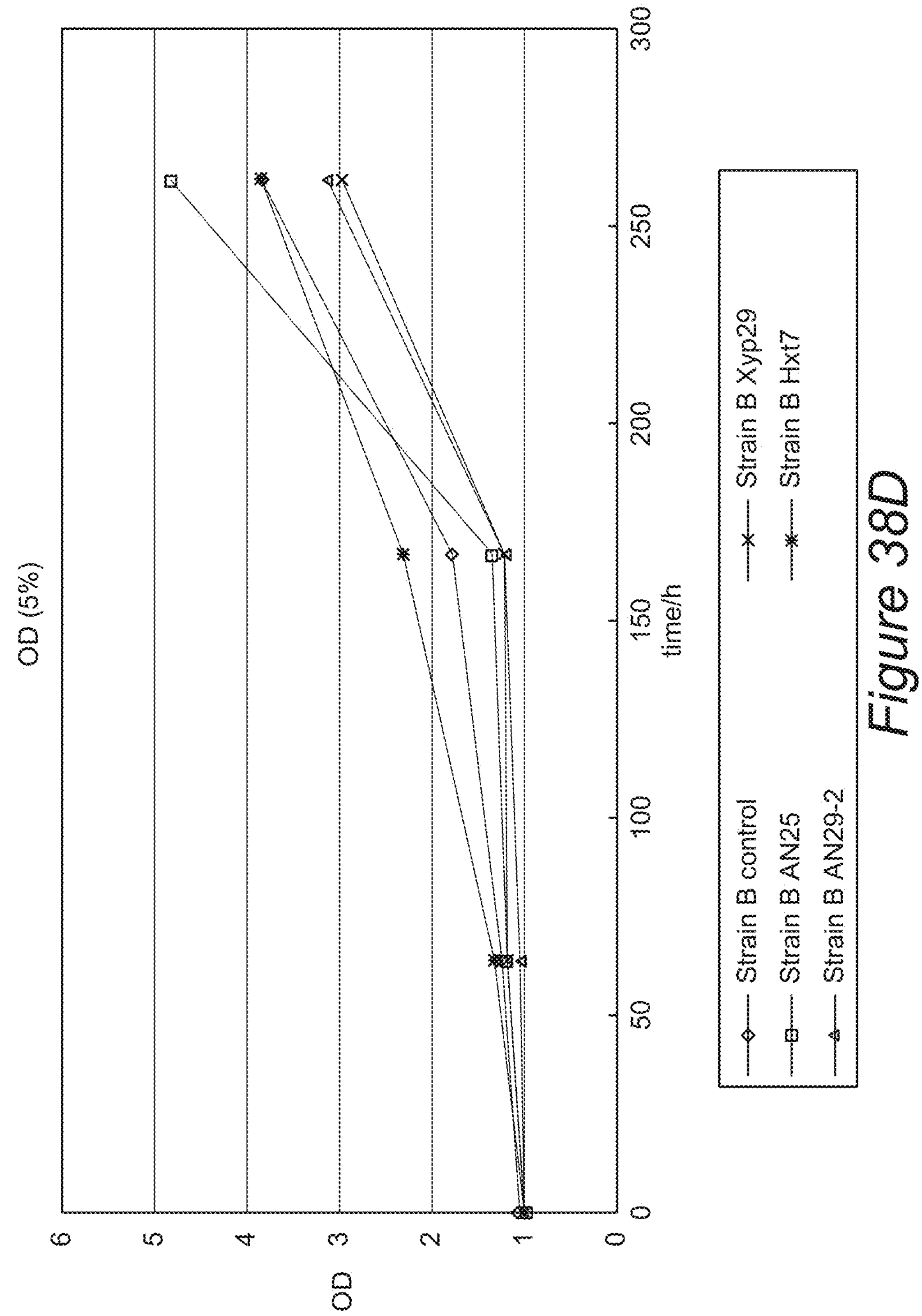
FIG. 38D shows OD.
Figure 38E:
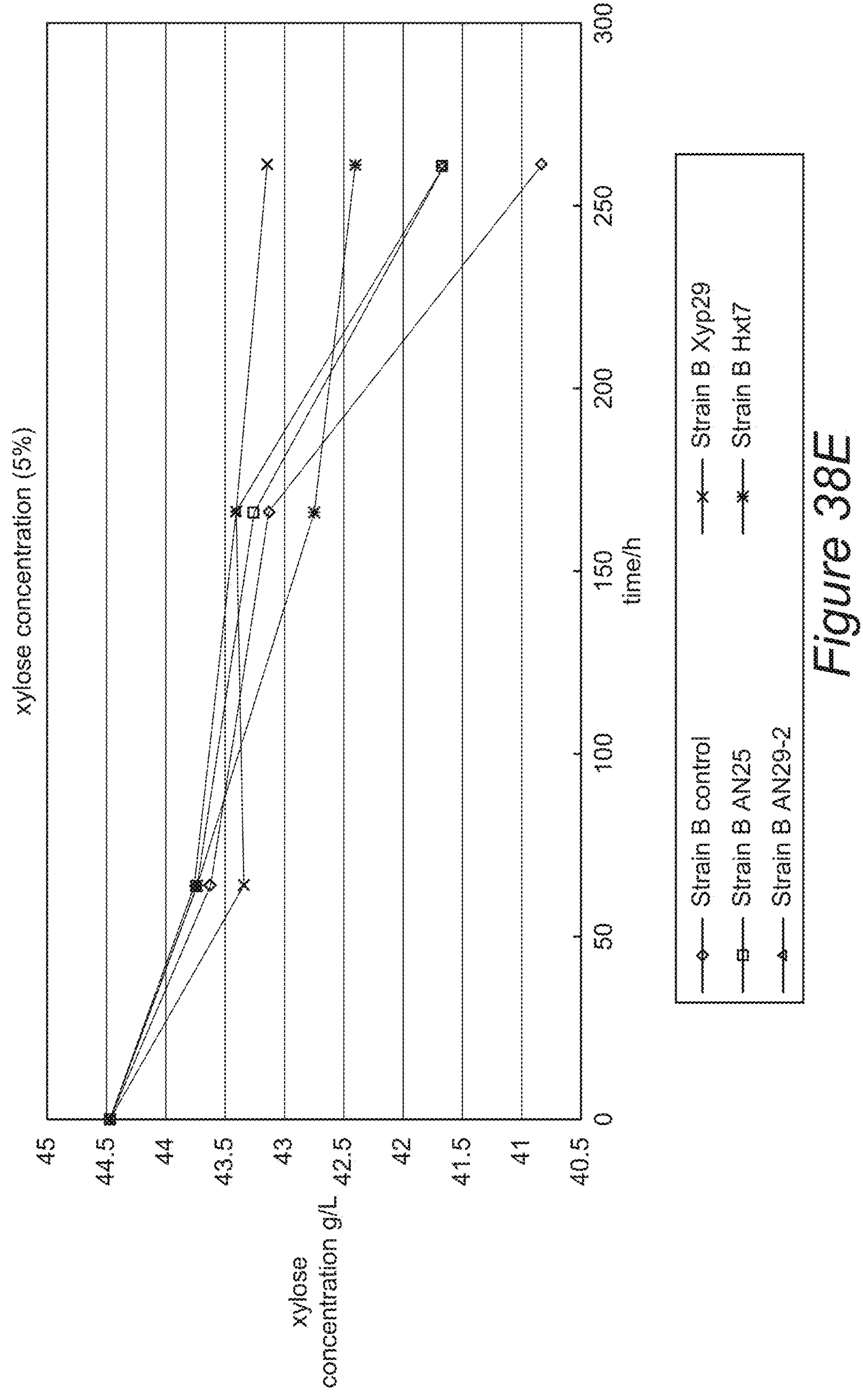
FIG. 38E shows xylose concentration.
Figure 38F:
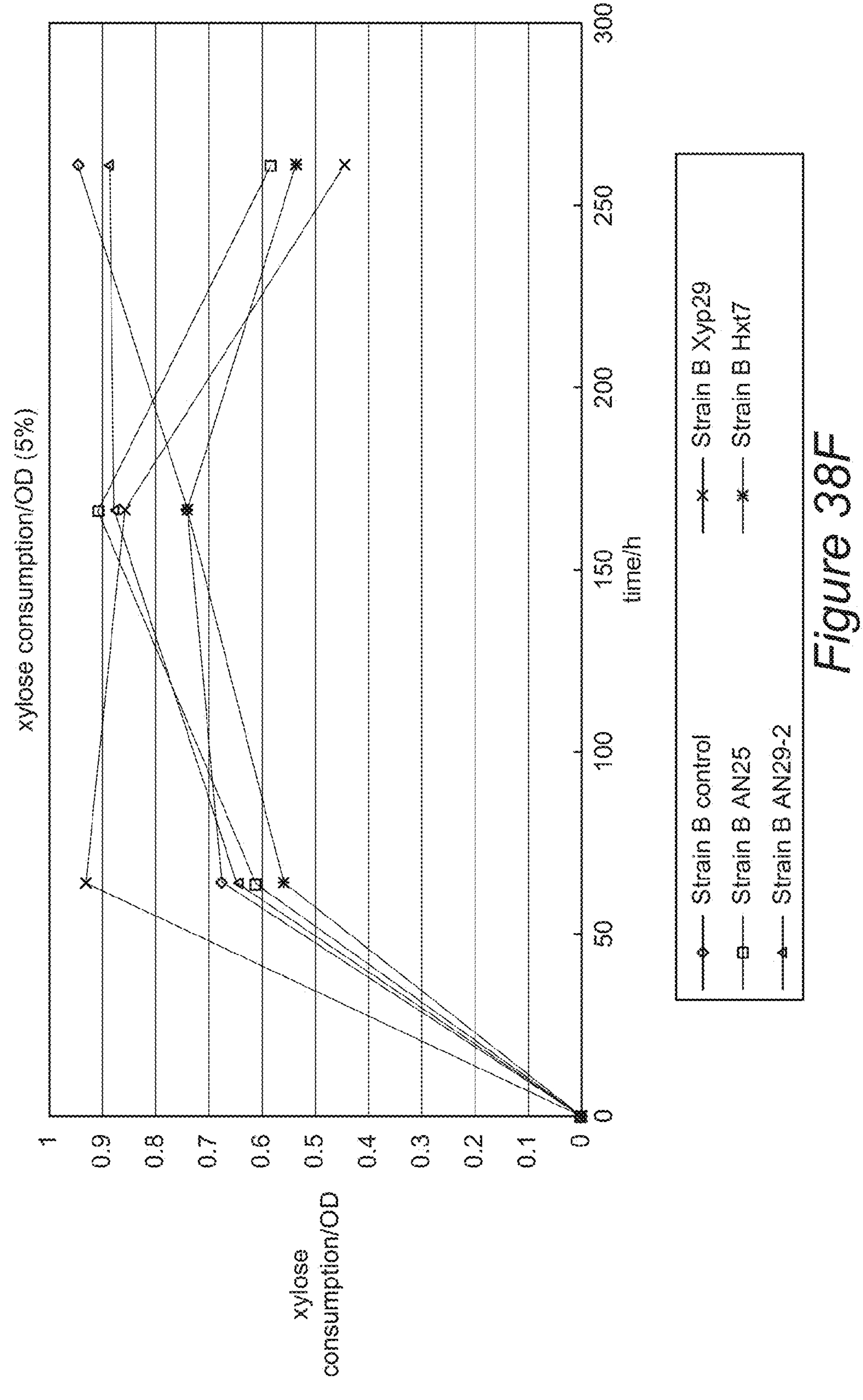
FIG. 38F shows xylose consumption in 5% xylose-containing media.
Figure 38G:
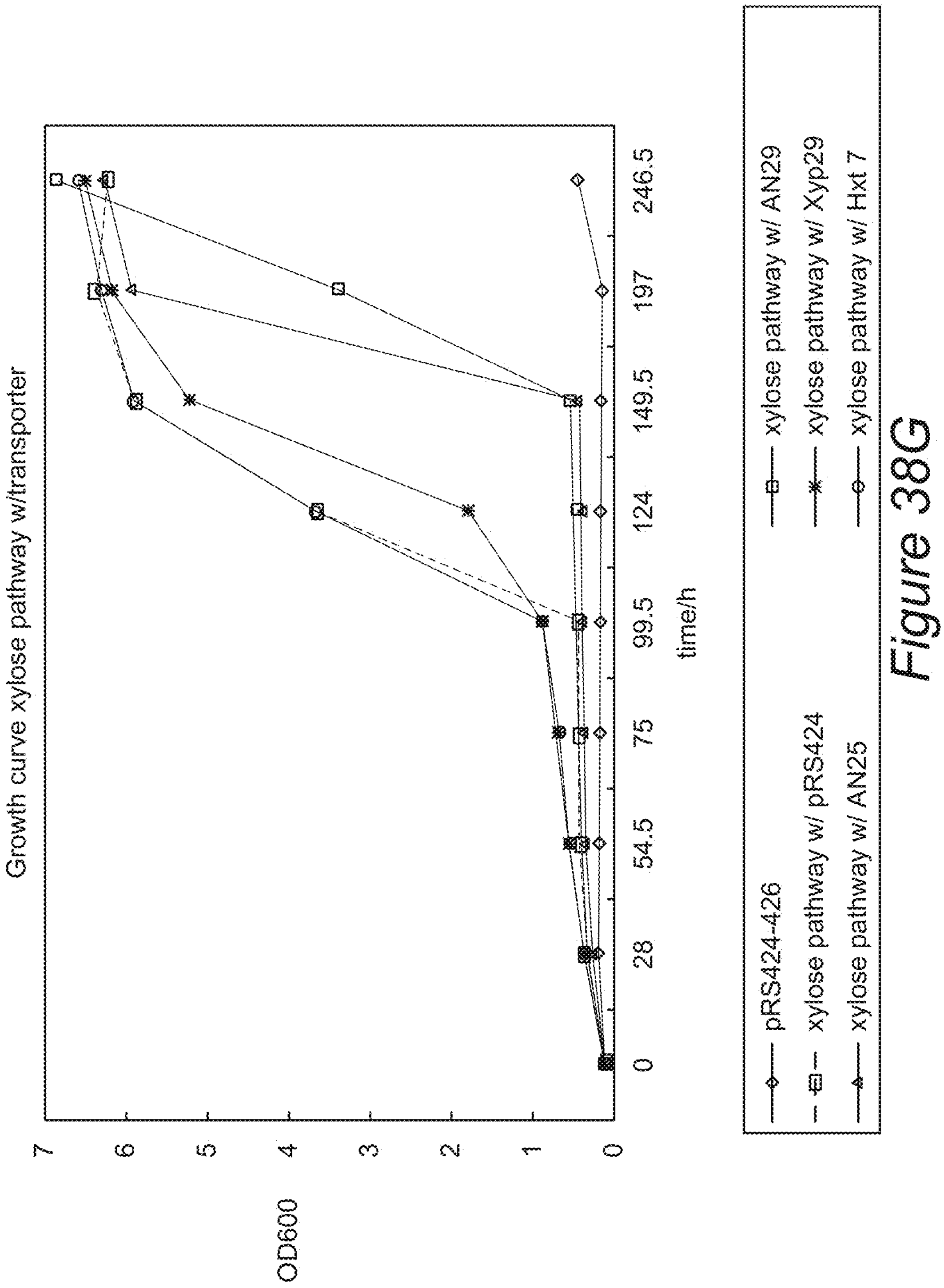
FIG. 38G shows the growth curve of *S. cerevisiae* containing pentose transporters introduced on pRS424, a multicopy plasmid.

No elevation of pH in un-buffered cell suspensions was observed for any of the pentose-specific transporters, indicating that pentose uptake through these transporters is not coupled with proton transport (FIG. 37). Thus, NCU00821, STL12/XUT6, and XUT1 were determined to be pentose facilitators.

This result was consistent with the fact that the kinetic parameters of NCU00821 and STL12/XUT6 were similar to those of the low affinity D-xylose facilitated diffusion system in naturally-occurring D-xylose-assimilating yeasts. Despite the fact that symporters have higher affinities towards D-xylose, over-expression of symporters may not always facilitate sugar utilization by D-xylose-assimilating strains due to the ATP requirement to create the proton gradient. In fact, most of the transporters shown to be beneficial for D-xylose fermentation are facilitators (Runquist et al., 2009; Katahira et al., 2008).

Heterologous Over-Expression of D-Xylose-Specific Transporters

The over-expression of active heterologous D-xylose-specific transporters in *S. cerevisiae* strains containing the D-xylose utilization pathway was also investigated to determine whether their over-expression could improve xylose utilization. Xylose utilization was studied using a shake-flask under aerobic conditions. Plasmids expressing the xylose transporters NCU00821, NCU04963, XUT1, STL12/XUT6, and Hxt7 were introduced into strain HZE63 (CEN.PK2 ura3::xylose utilization pathway). This strain had a xylose utilization pathway integrated into the URA3 site onto the chromosome. It was constructed using a plasmid from previous work that contained xylulose reductase (XR) and xylitol dehydrogenase (XDH) from *N. crassa* and xylulokinase (XKS) from *P. stipitis*. This plasmid was digested with ApaI and transformed into yeast strain CEN.PK2 to yield the strain HZE63.

The HZE63 strain transformed with the xylose transporter-encoding plasmids was selected by plating on SC-Ura plates supplemented with 2% glucose. The transformed strain was pre-cultured in SC-Trp-Ura with 2% glucose and then inoculated into SC-Trp-Ura supplemented with 0.5% or 5% of xylose to an initial $OD_{600}$=1.0. Cell cultures were grown in a 125 mL shake-flask containing 50 mL of culture at 30° C. and 250 rpm (FIG. 38).

Figure 39:
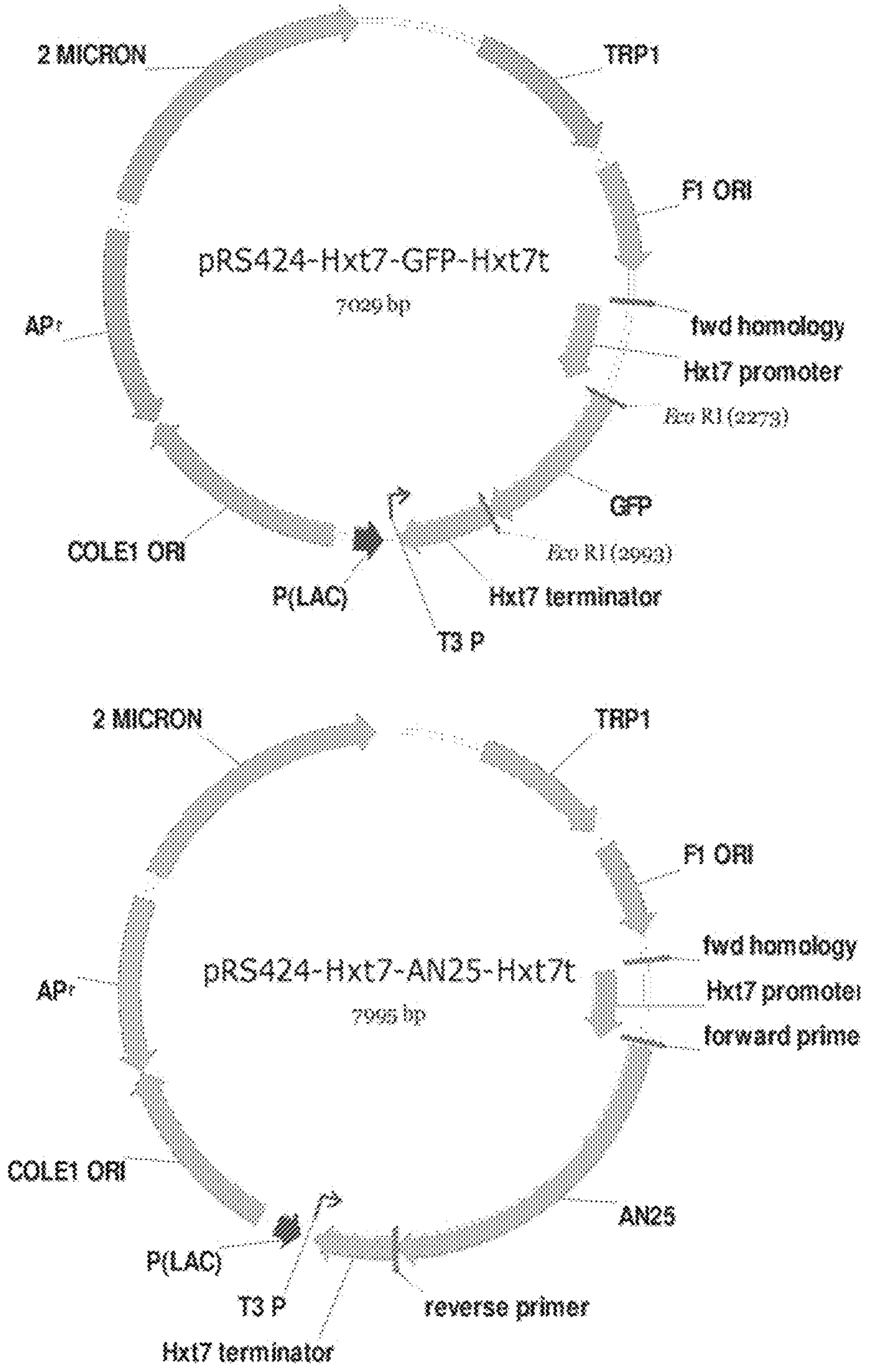
FIG. 39 shows maps of the plasmids used for cloning of heterologous transporters.

Yeast plasmids of transformants were transformed into *E. coli* DH5α cells. The plasmids were then isolated and checked by diagnostic PCR and submitted for sequencing to confirm correct construction. Plasmid maps can be found in FIG. 39.

Unfortunately, the advantage of pentose-specific transporter over-expression could not be observed despite alteration of expression strategies, cultivation conditions, and choice of the D-xylose utilization pathway. There are several possible reasons. Firstly, the over-expression of membrane proteins, such as sugar transporters, could affect the integrity of the cell membrane and consequently hamper cell growth (Wagner et al., 2006). It was observed that transporter over-expression strains displayed a slower growth rate even when D-glucose was used as a carbon source. The final OD of 2-day cultures of strains carrying transporters grown in glucose-containing SC-ura media was only 4, whereas the OD of the negative control was around 6. Secondly, the D-xylose-uptake activity of the wild-type *S. cerevisiae* through hexose transporters is much higher than the D-xylose-uptake activity of a certain D-xylose transporter over-expressed in a hexose transporter knockout strain. The low sugar transport activity of newly discovered D-xylose-specific transporters may make it hard to observe the improvement of sugar uptake ability. Thirdly, even if the introduction of new D-xylose-specific transporters could improve the uptake of D-xylose into *S. cerevisiae* cells, the benefit of D-xylose utilization can only be observed when the D-xylose utilization pathway is efficient enough to make sugar-uptake the limiting step. It was shown that the effect of over-expression of sugar transporters depends on the strain background and cultivation conditions (Runquist et al., 2010). Examples 12-15 below describe the optimization of the xylose utilization pathway in yeast.

Cloning of Additional Pentose-Specific Transporters

Orthologs of NCU00821, STL12/XUT6, and XUT1 were cloned and tested for pentose uptake. Different fungal strains were cultivated in rich media supplemented with glucose or pentoses. Total RNA was isolated and reverse transcribed into cDNA. Polymerase chain reaction (PCR) was used to amplify the putative transporter genes directly from cDNA. However, because the regulation mechanism and expression pattern were unknown for pentose transporters in fungal species, cDNAs encoding the putative pentose transporters were not always obtainable despite alteration of cultivation condition. In this case, primers were designed according to the corresponding cDNA sequences from GenBank and used to amplify the exons using genomic DNA as a template. Overlap-extension PCR was then used to assemble the exons into the full-length genes. The resulting PCR products were cloned into the pRS424 shuttle vector containing a HXT7 promoter and a HXT7 terminator using the DNA assembler method. Yeast plasmids isolated from transformants were retransformed into *E. coli* DH5α, and isolated *E. coli* plasmids were first checked by diagnostic PCR using the primers used to amplify the original transporter genes. The entire open reading frames were submitted for sequencing to confirm the correct construction of the plasmids.

Most of the cloning work was carried out using the yeast homologous recombination mediated DNA assembler method. pRS424-HXT7-GFP plasmid was used for cloning of putative pentose transporters. In this plasmid, the HXT7 promoter, the GFP gene flanked with the EcoRI sites at both ends, and the HXT7 terminator were assembled into the pRS424 shuttle vector (New England Biolabs) linearized by ClaI and BamHI. PCR products of the putative pentose transporters flanked with DNA fragments sharing sequence identity to the HXT7 promoter and terminator were co-transferred into CEN.PK2-1C with EcoRI digested pRS424-HXT7-GFP using the standard lithium acetate method. The resulting transformation mixture was plated on SC-Trp plates supplemented with 2% D-glucose. Transformants were then tested for pentose transport activity.

Figure 40:
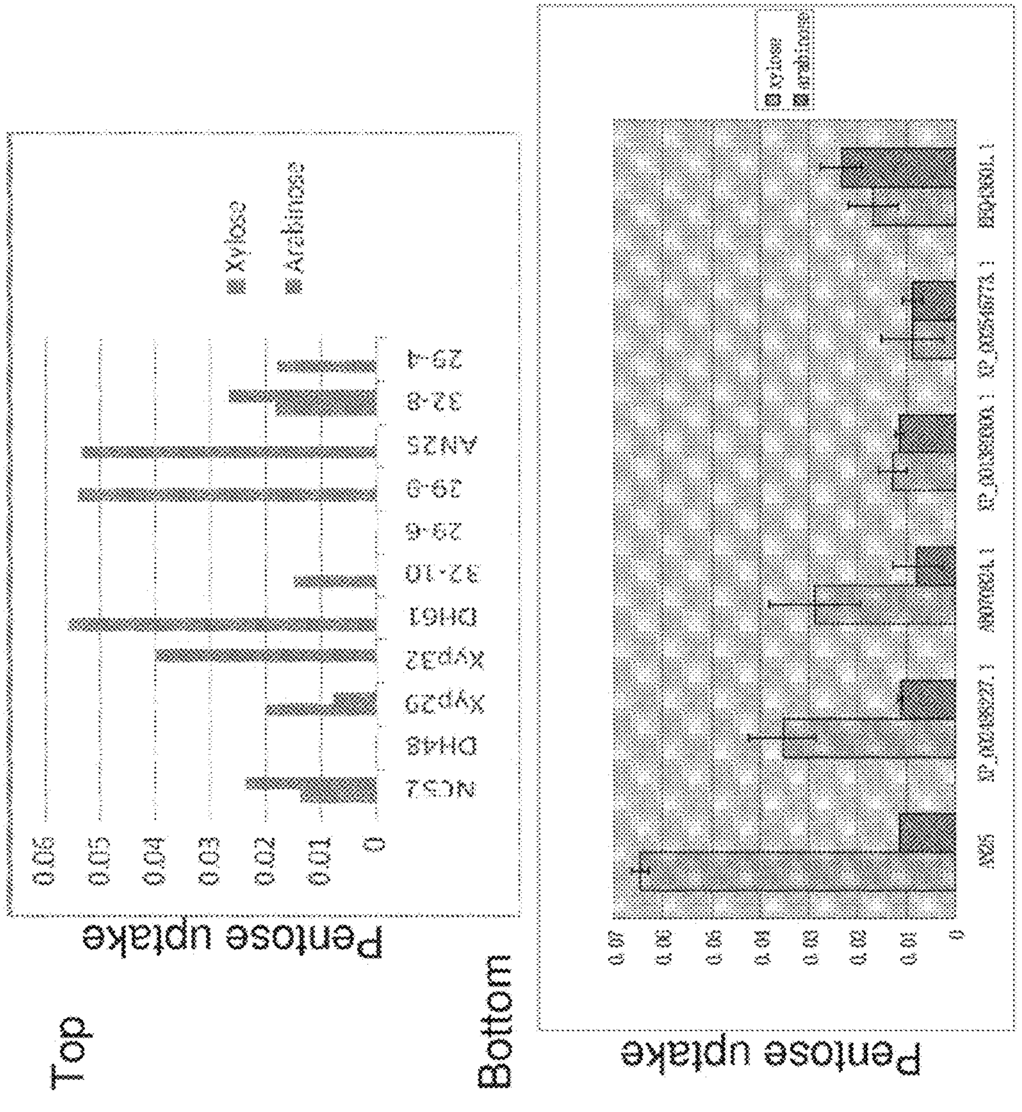
FIG. 40 shows results of the sugar-uptake assay by *S. cerevisiae* strains expressing pentose transporter orthologs.

The results are shown below in FIG. 40 and Table 16. Among the eight putative pentose specific transporters [XP_960000 (NC52), CAG88709 (DH48), XP_457508 (DH61), XP_681669 (32-10), XP_001487429 (29-6), XP_001727326 (29-9), XP_657854 (32-8), XP_720384 (29-4)], only NC52 enabled cell growth on a glucose plate, which suggested that the other seven transporters may be pentose-specific or inactive. Using the HPLC-based pentose uptake assay, four xylose-specific transporters were found, including XP_457508 (DH61), XP_001727326 (29-9), XP_720384 (29-4), and XP_681669 (32-10). In addition, one arabinose-specific transporter, XP_657854 (32-8) was identified (FIG. 40; Top). Five additional putative pentose specific transporters (XP_002488227, AB070824.1, XP_001389300, XP_002488227, EEQ43601.1) were also tested, none of which enabled cell growth in a glucose plate. Further pentose uptake assays indicated that XP_002488227 and AB070824.1 were xylose specific transporters (FIG. 40; Bottom). The summary of these results are shown in Table 16D.

TABLE 16A

Cloning of xylose-specific transporter NCU00821 orthologs

| NCBI Reference Sequence | Origin | Sequence Results* | Uptake Assay | Status |
|---|---|---|---|---|
| XP_002488227 | *Talaromyces stipitatus* | Correct | Yes | Cloned |
| XP_001400900 | *Aspergillus niger* | Correct | Yes | Cloned |
| XP_001220481 | *Chaetomium globosum* CBS 148.51 | No | No | Sequenced, one intron |
| XP_001912725 | *Podospora anserina* | No | No | OE-PCR, no PCR product |
| XP_660079 | *Aspergillus nidulans* FGSC A4 | Correct | Yes | Cloned |
| AAL89823 | *Aspergillus niger* | Correct | Yes | Cloned |
| XP_002382573 | *Aspergillus flavus* NRRL3357 | Wrong | Yes | Cloned |
| XP_459386 | *Debaryomyces hansenii* CBS767 | No | No | Genomic DNA, no PCR product |
| XP_001825132 | *Aspergillus oryzae* RIB40 | Correct | Yes | Cloned |
| XP_001389300 | *Aspergillus niger* | Correct | Yes | Cloned |

*"Correct" = Sequence of clone matched sequence in database(s); "Wrong" = Sequence of clone did not match sequence in database(s); "No" = Results not available (work in progress)

TABLE 16B

Cloning of xylose-specific transporter STL12/XUT6 orthologs

| NCBI Reference Sequence | Origin | Sequence Results* | Uptake Assay | Status |
|---|---|---|---|---|
| XP_457508 (DH61) | *Debaryomyces hansenii* CBS767 | Correct | No | Cloned |
| XP_002551364 | *Candida tropicalis* MYA-3404 | Wrong | No | No |
| XP_001523322 | *Lodderomyces elongisporus* NRRL | Wrong | No | No |
| XP_720384 (29-4) | *Candida albicans* SC5314 | Correct | No | Cloned |
| XP_456868 | *Debaryomyces hansenii* CBS767 | Wrong | No | No |
| XP_001487429 (29-6) | *Pichia guilliermondii* ATCC 6260 | Wrong | No | Cloned |
| XP_961039 | *Neurospora crassa* | Wrong | No | No |
| CAG88709 (DH48) | *Debaryomyces hansenii* CBS767 | Correct | No | Cloned |
| XP_001727326 (29-9) | *Aspergillus oryzae* | Correct | No | Cloned |
| XP_001816757 | *Aspergillus oryzae* | Correct | No | Cloned |

*"Correct" = Sequence of clone matched sequence in database(s); "Wrong" = Sequence of clone did not match sequence in database(s); "No" = Results not available (work in progress)

TABLE 16C

Cloning of arabinose-specific transporter XUT1 orthologs

| NCBI Reference Sequence | Origin | Sequence Results* | Uptake Assay | Status |
|---|---|---|---|---|
| XP_002545773 | *Candida tropicalis* MYA-3404 | Correct | Yes | Cloned |
| EEQ43601 | *Candida albicans* WO-1 | Correct | Yes | Cloned |
| XP_001818631 | *Aspergillus oryzae* RIB40 | No | No | No PCR product |
| XP_002558275 | *Penicillium chrysogenum* Wisconsin 54-1255 | Wrong | Yes | Cloned |
| XP_001390883 | *Aspergillus niger* | No | No | No PCR product |
| XP_750103 | *Aspergillus fumigatus* Af293 | Wrong | No | No |
| XP_960000 (NC52) | *Neurospora crassa* OR74A | Wrong | No | Cloned |
| XP_657854 (32-8) | *Aspergillus nidulans* FGSC A4 | Correct | No | Cloned |
| XP_001825068 | *Aspergillus oryzae* RIB40 | Correct | No | Cloned |
| XP_681669 (32-10) | *Aspergillus nidulans* FGSC | Correct | No | Cloned |

*"Correct" = Sequence of clone matched sequence in database(s); "Wrong" = Sequence of clone did not match sequence in database(s) (e.g., because of mutation in clone) "No" = Results not available (work in progress)

TABLE 16D

Listing of new xylose-specific transporters and one arabinose-specific transporter.

| NCBI Reference Sequence | Origin | Xylose-specific | Arabinose-specific |
|---|---|---|---|
| XP_457508 (DH61) | *Debaryomyces hansenii* CBS767 | Yes | |
| XP_001727326 (29-9) | *Aspergillus oryzae* | Yes | |
| XP_720384 (29-4) | *Candida albicans* SC5314 | Yes | |
| XP_681669 (32-10) | *Aspergillus nidulans* FGSC A4 | Yes | |
| XP_657854 (32-8) | *Aspergillus nidulans* L FGSC A4 | | Yes |

TABLE 16D-continued

Listing of new xylose-specific transporters and one arabinose-specific transporter.

| NCBI Reference Sequence | Origin | Xylose-specific | Arabinose-specific |
|---|---|---|---|
| XP_002488227 | *Talaromyces stipitatus* | Yes | |
| AB070824.1 | *Aspergillus oryzae* | Yes | |

The orthologs with sequences inconsistent with the sequences in databases (e.g., ones with mutations) will be re-cloned, sequenced, expressed in yeast strains, and tested for sugar uptake function. Similarly, the orthologs for which there is no sequencing results will also be tested for transporter function.

Figure 41:
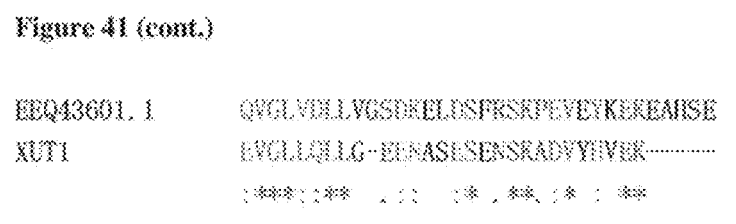

Sequence alignments of the pentose transporter orthologs were analyzed to identify conserved residues, which could have potential roles in transporter function. Alignments of a sample of xylose transporters (NCU0821, STL12/XUT6, XP_002488227.1, and XP_002382573.1) and arabinose transporters (XUT1 and EEQ43601.1) are shown in FIG. 41 (*a, b*) respectively. Several residues are specifically conserved in xylose transporters whereas others are specifically conserved in the arabinose transporters. These residues may have critical roles in transporting the specific pentose. An overall comparison of the sequences of the xylose and arabinose transporters (FIG. 41*c*) shows that there are also residues that are conserved in both types of pentose transporters, indicating functional roles in uptake of pentoses in general.

Examples 12-15 relate to optimization of the xylose utilization pathway in yeast.

Example 12

Engineering Pentose-Utilizing *S. cerevisiae* Strain

An efficient xylose metabolic pathway was reconstituted by exploiting the concept of isoenzymes. Isoenzymes catalyze the same chemical reaction with different kinetic or regulatory properties, and are known to confer fine-tuned control of metabolic fluxes in response to dynamic changes in the cytosolic environment. However, no prior metabolic engineering approaches had employed isoenzymes to increase fluxes of interest. This study demonstrated that simultaneous expression of both wild-type and mutant xylulose reductase (XR) isozymes could decrease xylitol accumulation and increase the overall xylose fermentation rate.

Inspired by the prevalence of isoenzymes in living systems, wild type XR and mutant XR (R276H) were co-expressed in *S. cerevisiae* along with xylitol dehydrogenase (XDH) and xylulokinase (XK) in order to construct a functional xylose metabolic pathway in *S. cerevisiae*. The XR mutant had been reported to exhibit much lower preference for NADPH over NADH whereas wild type XR showed 116 two-fold higher preference for NADPH over NADH (Watanabe et al., 2007).

The xylose-metabolizing genes (wild-type XYL1, 2, and 3 and mutant XYL1) from *P. stipitis* were PCR-amplified and placed under the control of constitutive promoters (PGK1 and TDH3) to construct expression cassettes. These integration cassettes were integrated into the genome of the D452-2 strain.

Transformation of expression cassettes for constructing xylose metabolic pathways was performed using the yeast EZ-Transformation kit (BIO 101, Vista, Calif.). To select transformants using an amino acid auxotrophic marker, yeast synthetic complete (YSC) medium was used, which contained 6.7 g/liter yeast nitrogen base plus 20 g/liter glucose, 20 g/liter agar, and CSM-Leu-Trp-Ura (BIO 101), which supplied appropriate nucleotides and amino acids. Yeast strains were routinely cultivated at 30° C. in YP medium 234 (10 g/liter yeast extract, 20 g/liter Bacto peptone) with 20 g/liter glucose.

Figure 42:
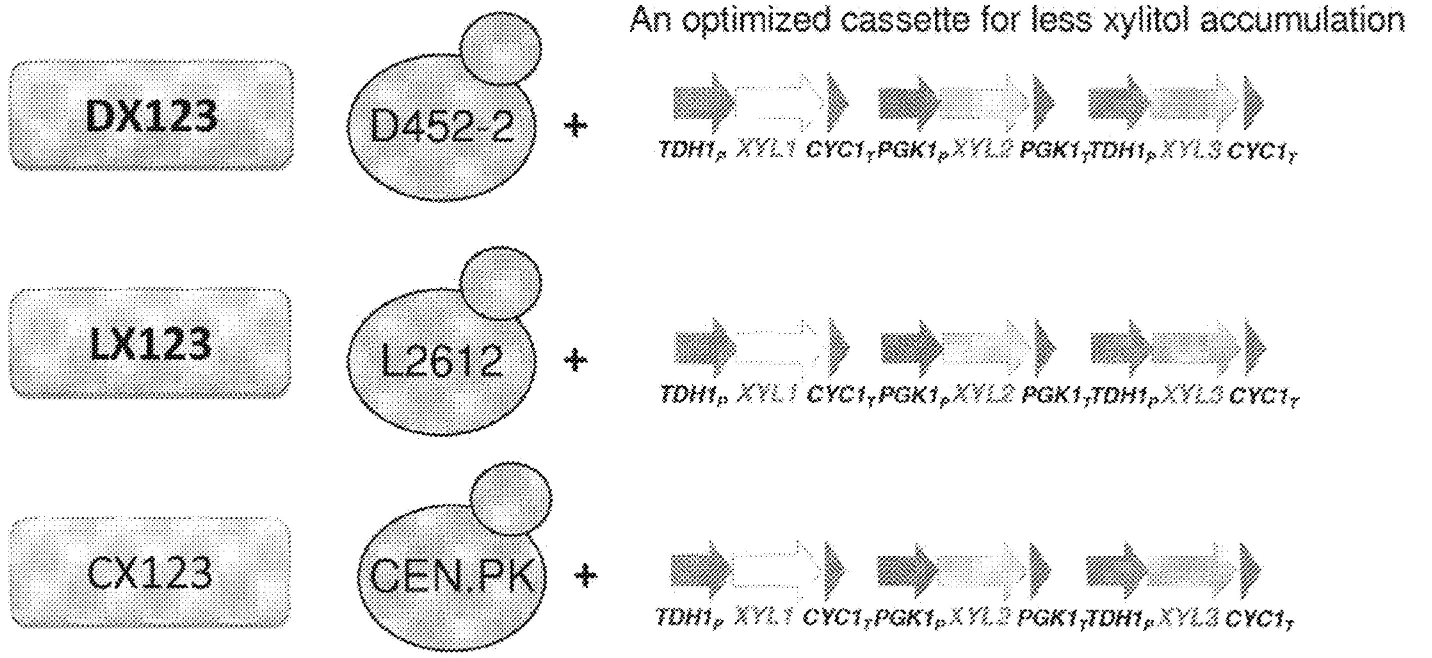
FIG. 42 describes the different *S. cerevisiae* strains engineered to express xylose-utilizing enzymes.
Figure 43:
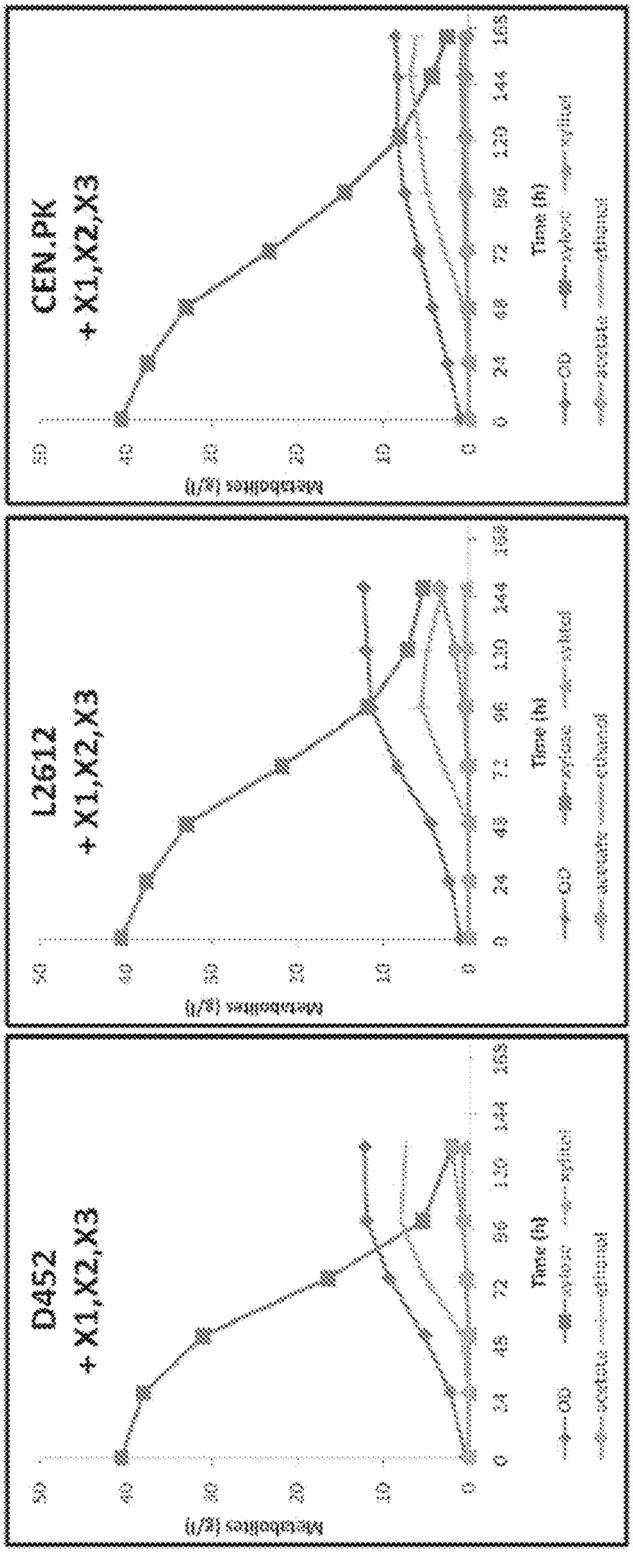
FIG. 43 shows xylose metabolism (as monitored by xylose consumption, ethanol production, etc.) of three *S. cerevisiae* strains of different backgrounds expressing identical cassettes containing xylose utilization pathway enzymes.
Figure 44:
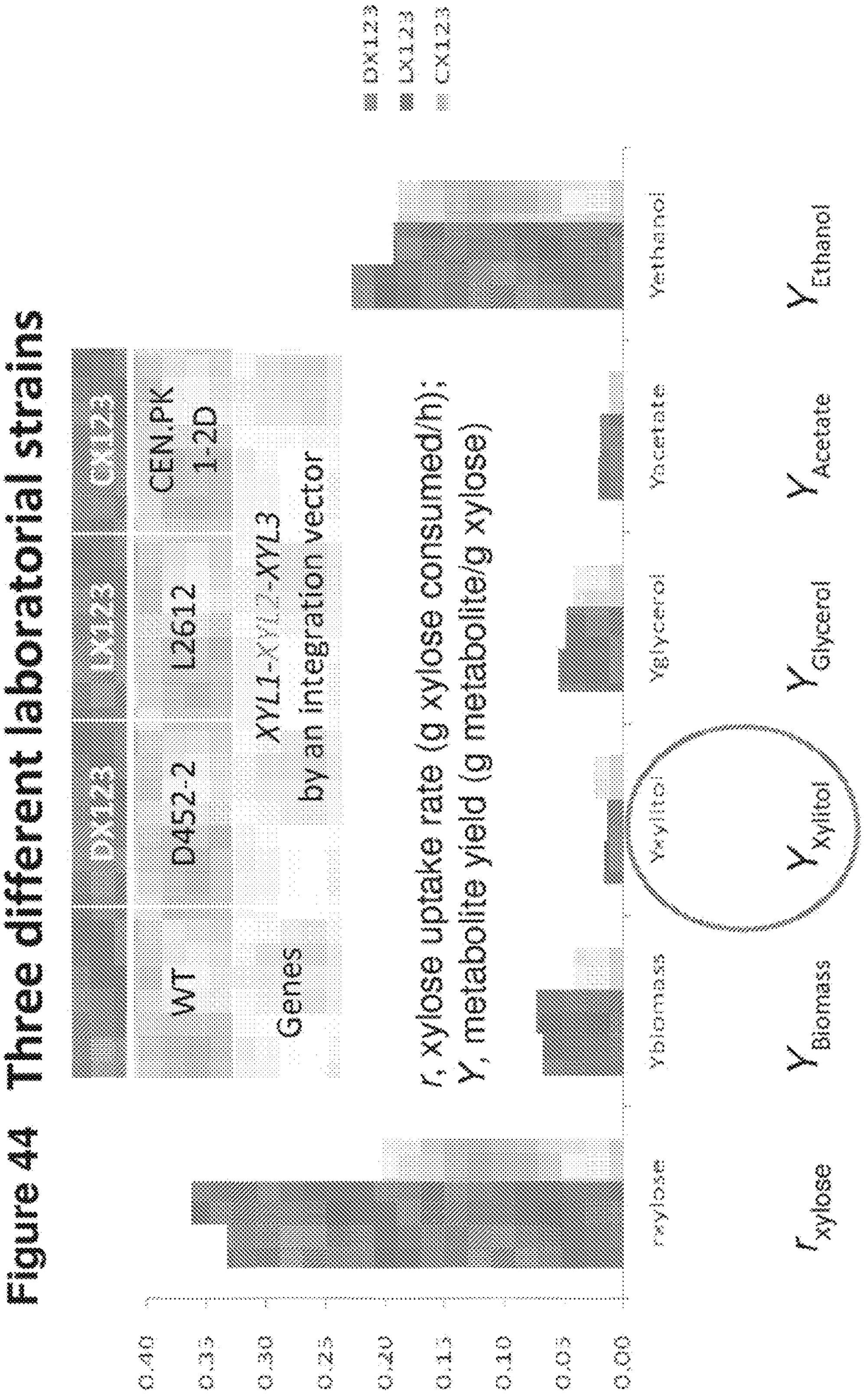
FIG. 44 shows xylose-uptake rates and metabolite yields of three *S. cerevisiae* strains of different backgrounds expressing identical cassettes containing xylose utilization pathway enzymes.

The effect of *S. cerevisiae* strain background on xylose-metabolizing efficiency was also tested by expressing identical constructs containing optimized xylose utilization pathway enzymes in several different yeast strains. The three laboratory strains used were D452-2 (MATα, leu2, his3, ura3, can1), L2612 (MATa, leu2-3, leu2-112, ura3-52, trp1-298, can1, cyn1, gal+), and CEN.PK. Production of xylitol, acetate, and ethanol was monitored together with use of xylose and $OD_{600}$. The results indicated that the D452-2 strain was the best amongst the three tested strains (FIG. 42-44). *S. cerevisiae* D452-2 was used for engineering of the xylose-metabolizing enzymes in yeast. Strains and plasmids used in this study are described in Table 17.

TABLE 17

Strain and plasmids used in study

| Strain or plasmid | Description | Reference |
|---|---|---|
| Strain | | |
| D452-2 | MATa, leu2, his3, ura3, can1 | Hosaka et al., (1992) |
| D801-130 | D452-2 expressing β-glucosidase (NCU00130) and cbt1 (NCU00801) | In this study |
| D809-130 | D452-2 expressing β-glucosidase (NCU00130) and NCU00809 | In this study |
| D8114-130 | D452-2 expressing β-glucosidase (NCU00130) and cbt2 (NCU08114) | In this study |
| DA24 | D452-2 expressing XYL1, mXYL1, XYL2, and XKS1 (Isogenic of D452-2 except for leu2::TDH3P-XYL1-TDH3T, ura3::URA3-PGKP-mXYL1-PGKT-PGKP-XYL2-PGKT, Ty3::neo-TDHP-XKS1-TDHT) | In this study |
| DA24-16 | Evolved strain of DA24 in xylose containing media | In this study |
| DA24-16BT3 | DA24-16 expressing β-glucosidase (NCU00130) in a multi-copy plasmid and cbt1 (NCU00801) though single-copy integration | In this study |
| DA24-16BT-M | DA24-16 expressing β-glucosidase (NCU00130) and cbt1 (NCU00801) in multi-copy plasmids | In this study |
| Plasmid | | |
| pRS425 | LEU2, a multi copy plasmid | Christianson et al., (1992) |
| pRS426 | URA3, a multi copy plasmid | Christianson et al., (1992) |
| pRS403 | HIS3, an integrative plasmid | Sikorski et al., (1989) |
| pRS405 | URA3, an integrative plasmid | Sikorski et al., (1989) |
| pRS425-β-glucosidase | β-glucosidase (NCU00130) under the control of PGK promoter in pRS425 | Submitted |
| pRS426-cbt1 | cbt1 under the control of PGK promoter in pRS426 | Submitted |
| pRS426-cbt2 | cbt2 under the control of PGK promoter in pRS426 | Submitted |
| pRS426-NCU00809 | NCU00809 under the control of PGK promoter in pRS426 | Submitted |
| pRS403-cbt1 | cbt1 under the control of PGK promoter in pRS403 | In this study |

Figure 45:
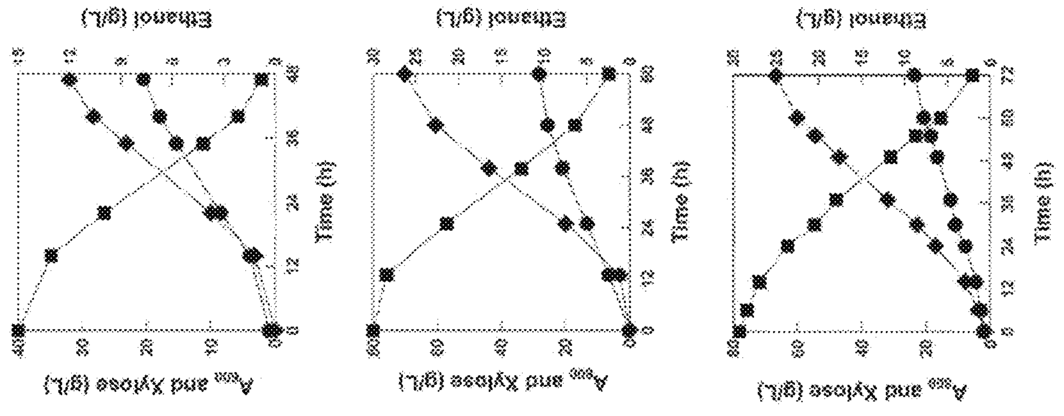
FIG. 45 shows xylose fermentation by the *S. cerevisiae* strain DA24 under various conditions.

The engineered xylose-fermenting *S. cerevisiae* strain (DA24) consumed xylose and produced ethanol with negligible amounts of xylitol accumulation. When 40 and 80 g/L of xylose were used as a sole carbon source, the DA24 strain produced ethanol with consistent yields ($Y_{Ethanol/Xylose}$=0.31~0.32 g/g) in both shaker-flask and bioreactor fermentation experiments (FIG. 45). However, the DA24 strain consumed xylose slower than the naturally existing xylose-fermenting yeast, *P. stipitis*. Xylose fermentation capability of DA24 was further improved using an evolutionary engineering approach (Sauer 2001). One of the strains (DA24-16) isolated after repeated sub-cultures of the DA24 on xylose-containing medium showed much faster xylose fermentation rates as compared to the parental strain under various culture conditions (Table 18).

Table 18 shows the comparison of fermentation parameters of the two *S. cerevisiae* strains DA24 and DA24-16 under different sugar conditions.

| Carbon source | Strains | Produced Ethanol (g/L) | Sugar consumption rate (g/L/h) | Yield (g/g) | Productivity (g/L · h) |
|---|---|---|---|---|---|
| Xylose | DA24 | 24 | 1.16 | 0.34 | 0.40 |
| (80 g/L) | DA24-16 | 28 | 1.32 | 0.35 | 0.47 |
| Glucose | DA24 | 34 | 1.45 | 0.39 | 0.74 |
| (70 g/L) and xylose (40 g/L) | DA24-16 | 45 | 1.78 | 0.42 | 0.96 |

Figure 46:
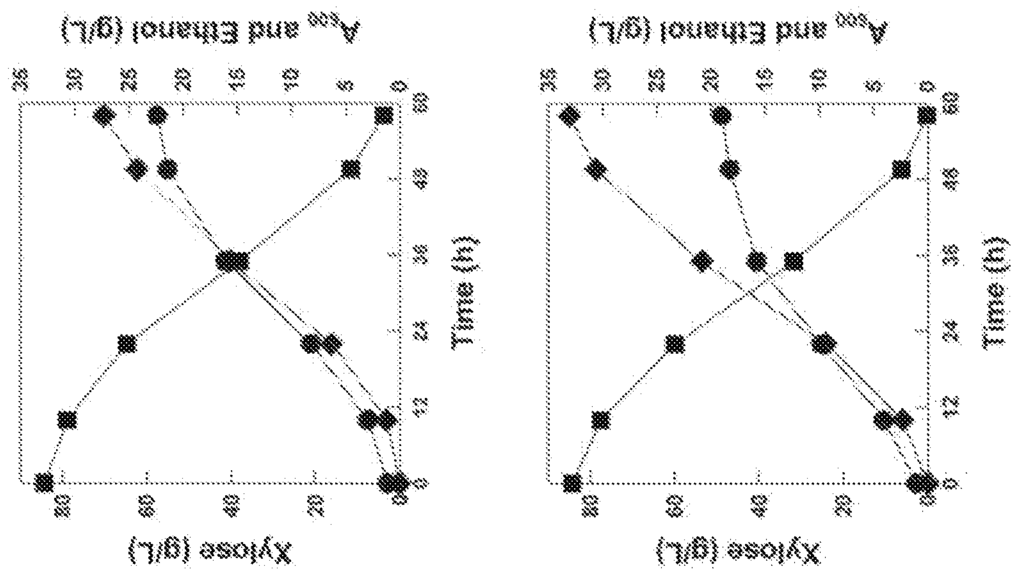
FIG. 46 shows a comparison of xylose consumption and ethanol production between (a) *S. cerevisiae* DA24 and (b) *P. stipitis*. Symbols: xylose (■), ethanol (♦), and $OD_{600}$ (●).

Interestingly, the DA24-16 strain consumed xylose as fast as *P. stipitis*, the fastest xylose-fermenting yeast known. However, ethanol yield by DA24-16 was slightly lower than that by *P. stipitis* (FIG. 46).

A screen was set up using *S. cerevisiae* strain L2612 expressing the xylose-utilizing enzymes (strain YSX3) transformed with a genomic library. Transformation was followed by serial culture transfer in 40 g/L xylose under oxygen-limiting conditions to enrich for strains that are efficient in utilizing xylose. Fermentations were performed in 50 mL YPX media under oxygen-limited conditions and 0.1% (50 μL) of a fully grown cell culture was transferred to the next serial culture when $OD_{600}$=10 was reached. After 10 serial cultures, cells were spread with serial dilution on YPX (40 g/L) agar media. Through fermentation experiments using 5 mL of YPX media, colonies were screened for low xylitol and high ethanol formation. DNA sequencing revealed that the two most efficient strains contained integrated copies of XYL2, which was then cloned into a multi-copy plasmid through homologous recombination and transformed into YSX3 cells.

Figure 47:
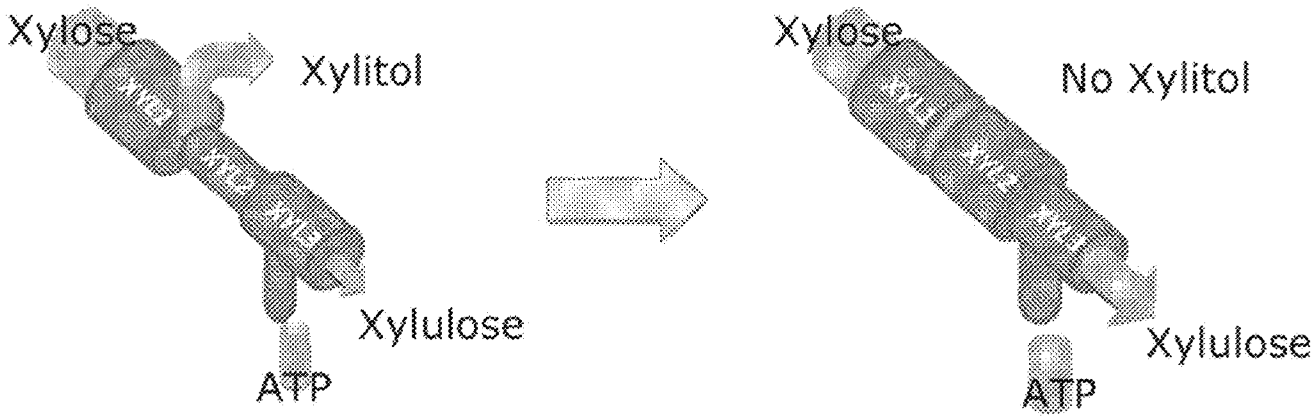
FIG. 47 describes the experimental design used to test the effect of XYL2 over-expression levels on xylose metabolism in engineered *S. cerevisiae.*
Figure 48:
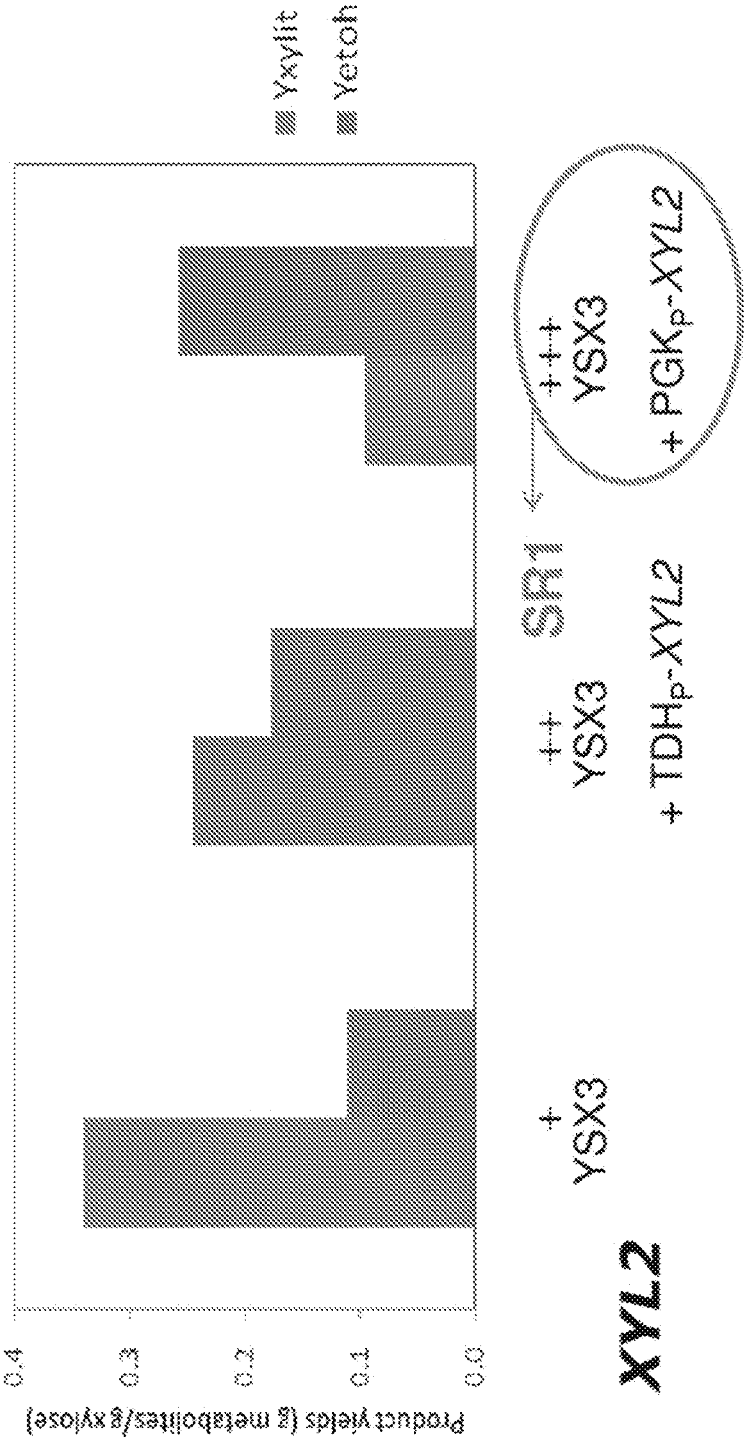
FIG. 48 shows the effect of additional XYL2 integration (i.e. increased XYL2 expression level) into the genome of engineered xylose-fermenting *S. cerevisiae.*
Figure 49:
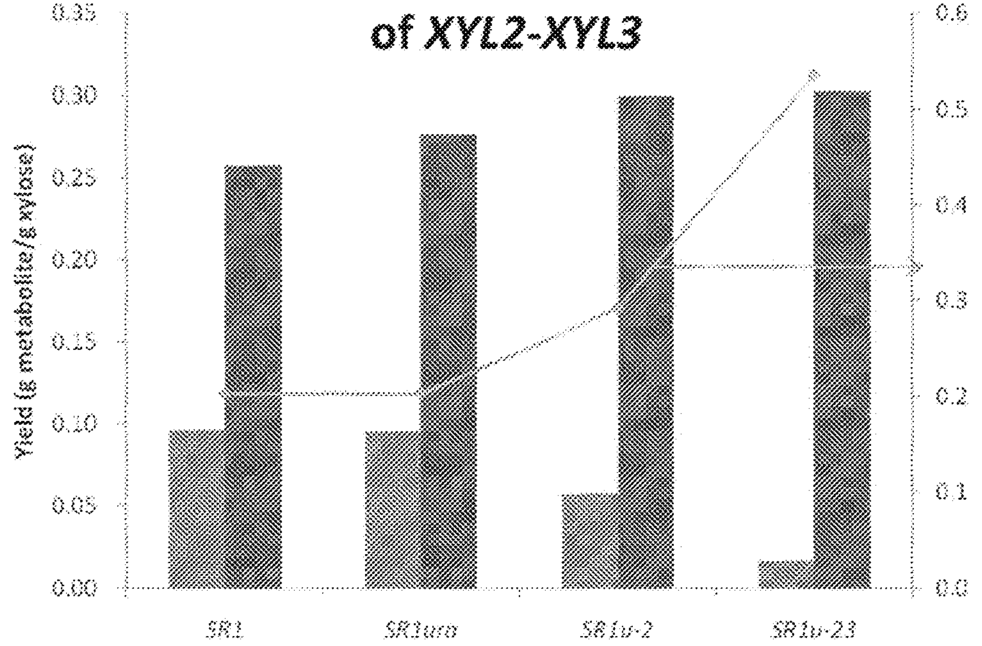
FIG. 49 shows the effect of additional simultaneous over-expression of XYL2 and XYL3 on xylose fermentation by engineered *S. cerevisiae.*
Figure 50:
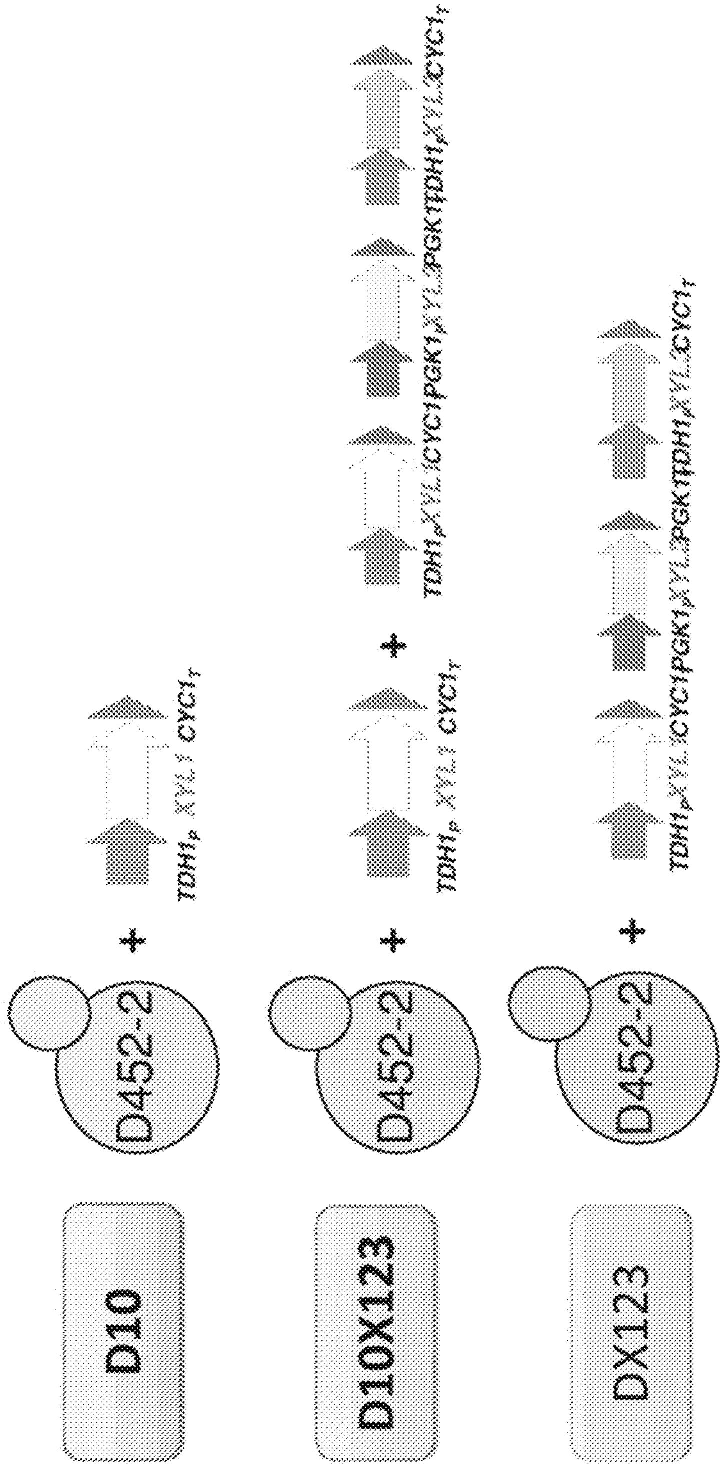
FIG. 50 describes *S. cerevisiae* strains expressing different levels of xylose-fermenting enzymes.
Figure 51:
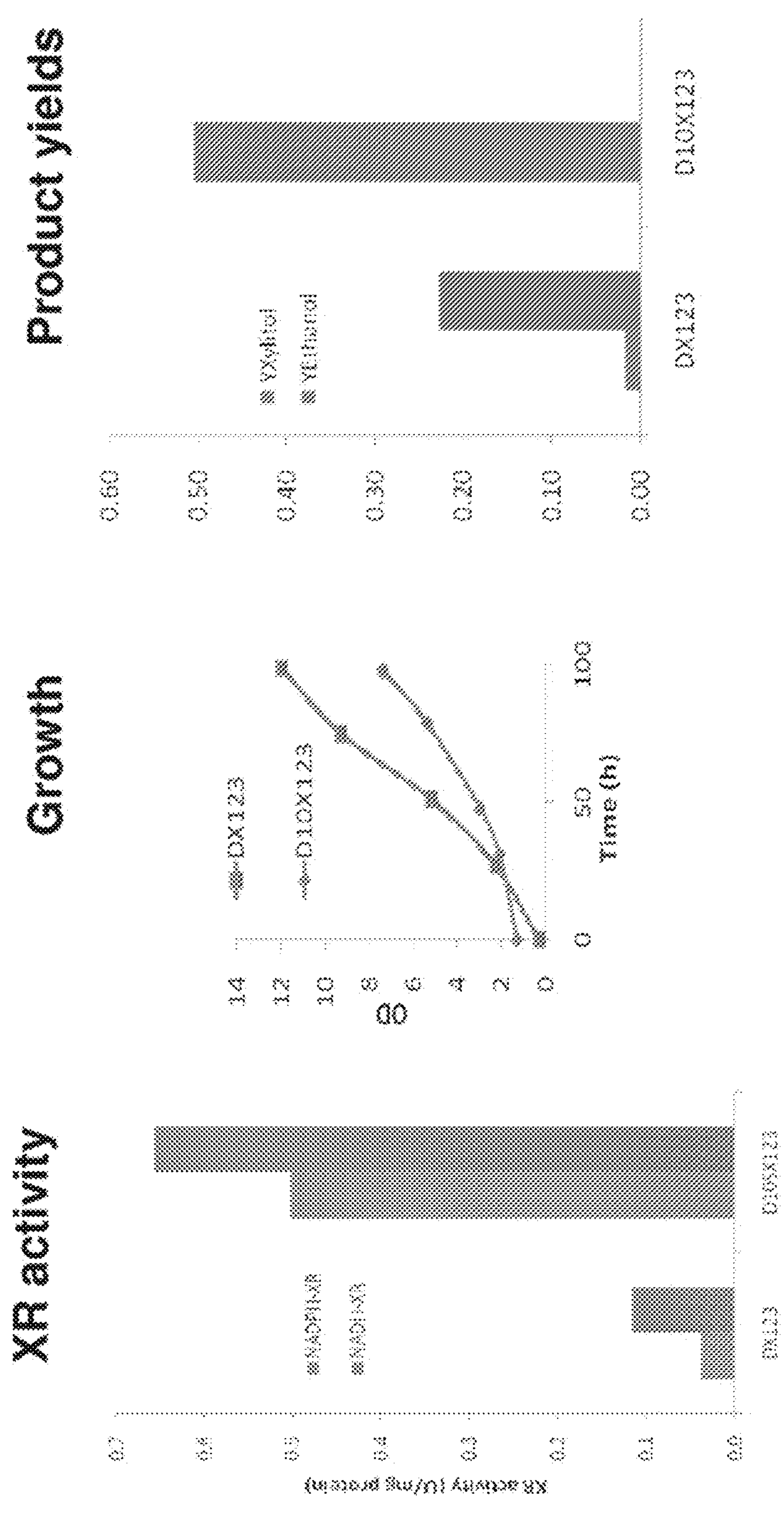
FIG. 51 shows the effect of differential XYL1 expression of fermentation by engineered *S. cerevisiae.*

The XYL2 gene was placed in integration vectors under the control of promoters of different strength, e.g., TDHp or PGKp, and transformed into YSX3 cells (FIG. 47). Studies were conducted to monitor the effect of these plasmids on xylitol and ethanol formation in the transformed yeast cells. The results indicated that the YSX3 cells expressing higher levels of XYL2 (under the PGKp) were more efficient at ethanol production and in addition, produced lower amounts of xylitol (FIG. 48). When additional XYL3 was expressed in these cells (termed SR1 strain), the amount of xylitol produced was further decreased in the resulting strain SRu-23 (FIG. 49). Therefore, it appeared that XYL2 expression level in engineered *S. cerevisiae* strains is a key factor for implementing xylose fermentation, and when expression is under a strong promoter, the strain has less xylitol accumulation as well as high ethanol yield. Simultaneous over-expression of XYL2 and XYL3 can further decrease the amount of xylitol accumulation. However, when XYL1 was further over-expressed in a strain over-expressing XYL2 and XYL3, there was considerable xylitol accumulation and consequently decreased xylose fermentation (FIGS. 50-51). Therefore, it appeared that there was an optimal level of XYL1 for efficient xylose fermentation.

Figure 52:
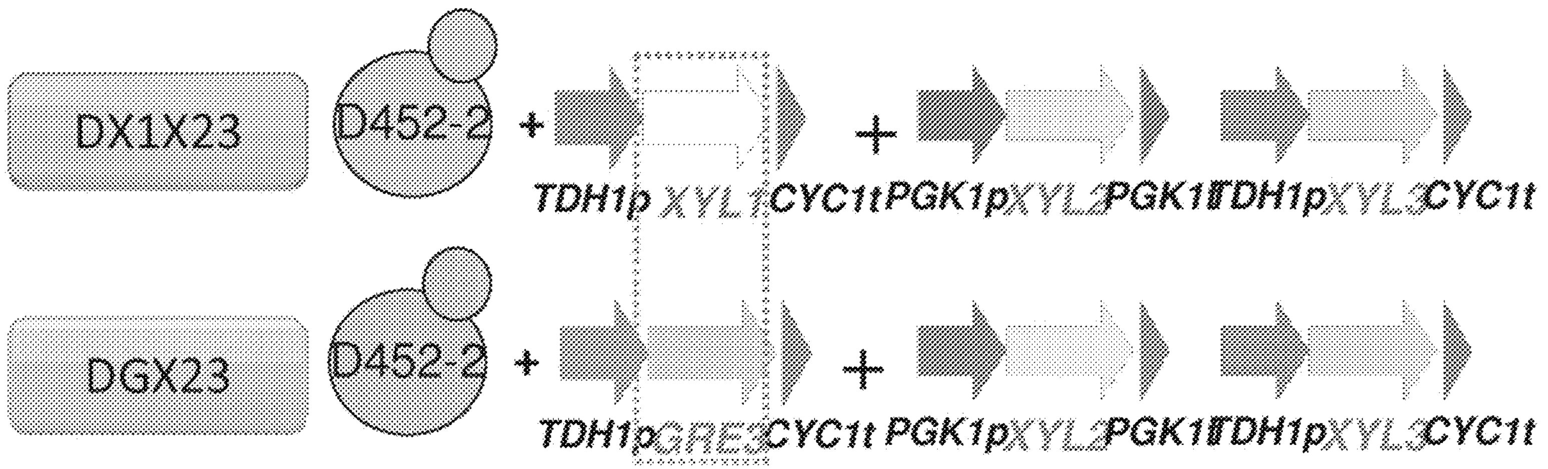
FIG. 52 describes *S. cerevisiae* strains engineered to over-express identical XYL2 and XYL3 but different reductases (XYL1 vs. GRE3).
Figure 53:
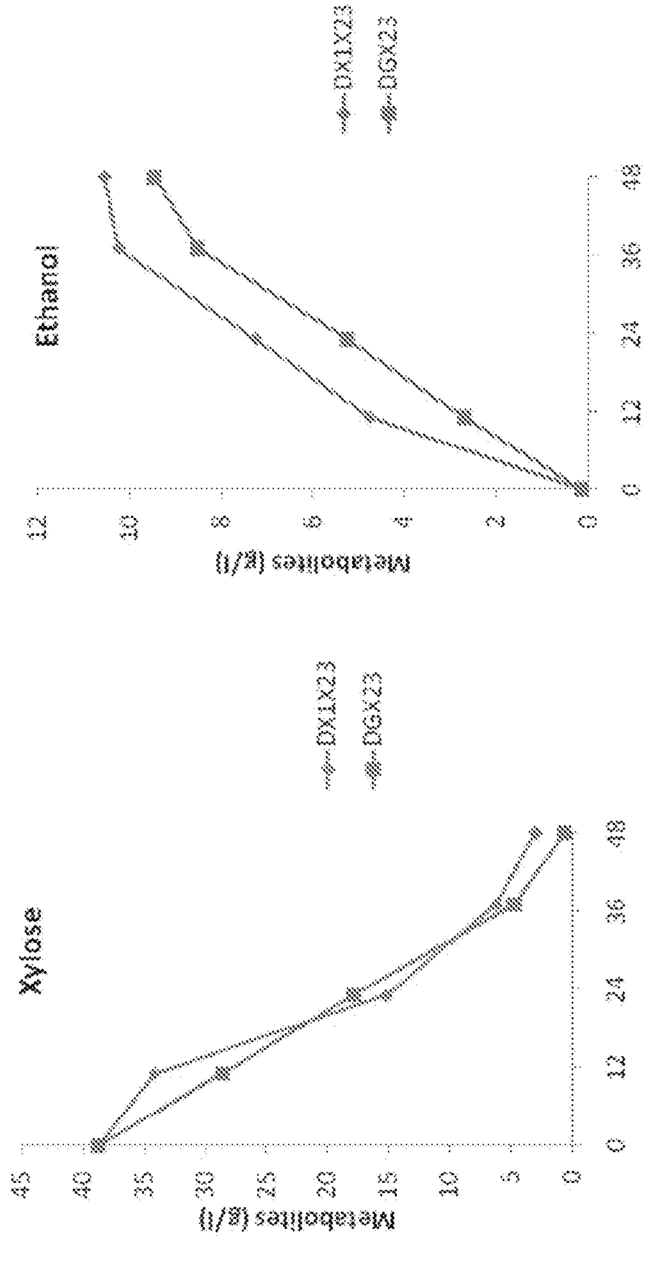
FIG. 53 shows the effect of over-expressing XYL1 versus GRE3 on xylose fermentation by engineered *S. cerevisiae* grown in 40 g/L xylose.
Figure 54:
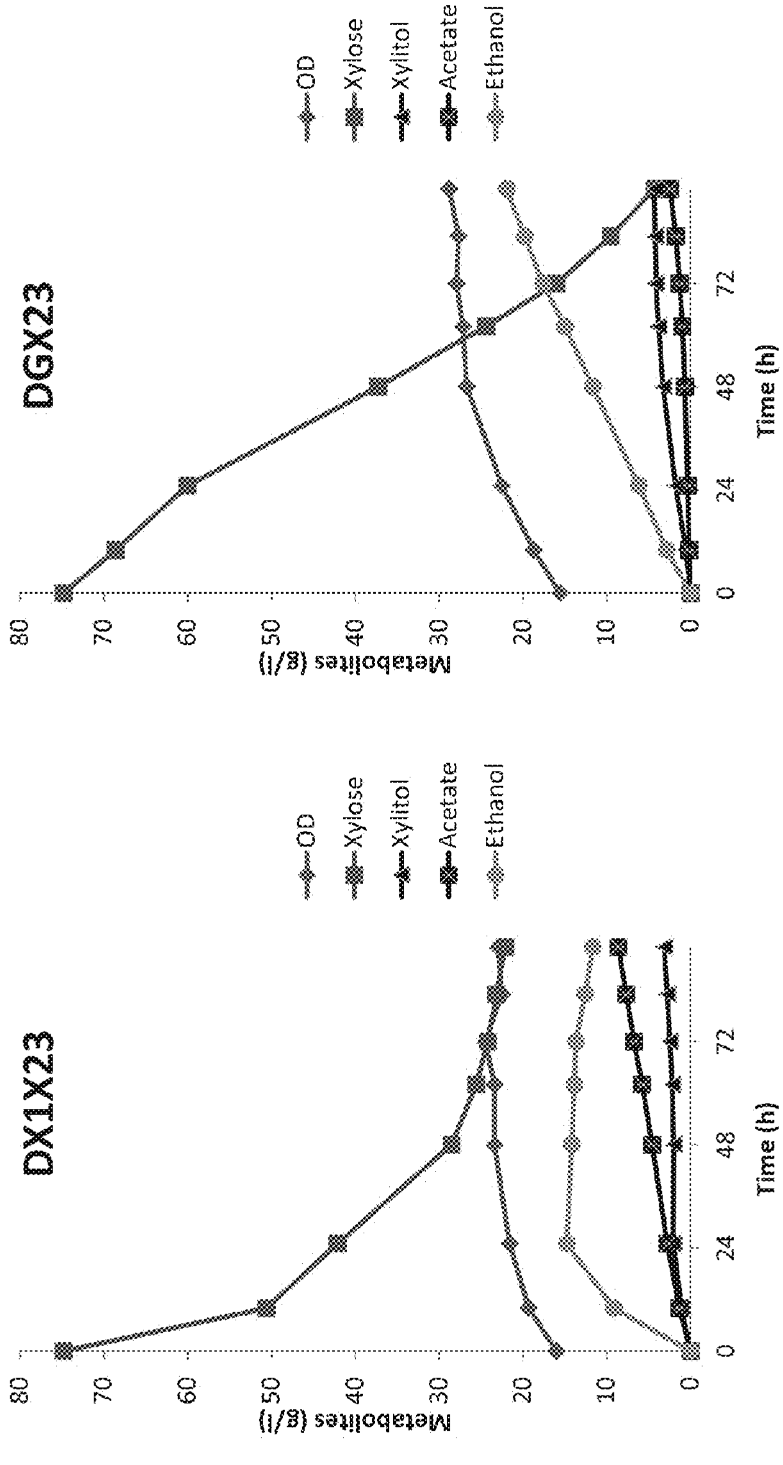
FIG. 54 shows the effect of over-expressing XYL1 versus GRE3 on xylose fermentation by engineered *S. cerevisiae* grown in 80 g/L xylose.

Experiments were also carried out to test if over-expression of endogenous GRE3 in *S. cerevisiae* expressing XYL2 and XYL3 could facilitate xylose fermentation. For the construction of pRS403-GRE3, GRE3 gene was amplified from *S. cerevisiae* D452-2 and inserted into pR403 vector with TDH3 promoter and CYC terminator. After linearization of pRS403-GRE3, it was integrated into the genome of D452-2. The xylose-utilizing genes were introduced into the yeast strain D452-2 (FIG. 52), and xylose fermentation parameters were monitored. The results indicated that over-expression of GRE3 was as effective as the over-expression of XYL1 in ethanol production and xylitol accumulation, particularly when cells were grown in 80 g/L of xylose at high OD inoculations (FIGS. 53-54).

Example 13

Engineering LAD and XDH

L-arabinitol and xylitol accumulation, thought to be caused by cofactor imbalance between NADPH-dependent XR and NAD$^+$-dependent XDH and LAD, has been regarded as a major bottleneck during xylose fermentation in engineered *S. cerevisiae* expressing the pentose-utilizing enzymes. While the imbalance between XR and XDH has been corrected by engineering enzymes with reversed cofactor preferences (Watanabe et al., 2007; Matsushika et al., 2008; Bengtsson et al., 2009), this approach resulted in reduced flux, as the modified enzymes had reduced specific activities. The *P. stipitis* XR mutant had been reported to exhibit much lower preference for NADPH over NADH whereas wild type psXR showed two-fold higher preference for NADPH (Watanabe et al., 2007).

In this study, similar studies were done on L-arabinitol 4-dehydrogenase (LAD) and XDH from *N. crassa* to alter cofactor specificity and hence improve xylose fermentation in engineered *S. cerevisiae*.

Identification of Putative LAD-Encoding Genes

Methods of identifying putative LAD-encoding genes and of cloning LAD-encoding and putative LAD-encoding genes are described.

Identification of Putative LAD-Encoding Genes

From a protein BLAST search using ncLAD (EAA36547.1) as a probe, two putative genes were identified in *P. chrysogenum* (XP_002569286.1) and *P. guilliermondii* (EDK37120.2), respectively. The amino acid sequence identities of these two proteins with ncLAD were 71% and 46%, respectively.

Cloning LAD-Encoding and Putative LAD-Encoding Genes

*A. niger* (NRRL 326), *P. guilliermondii* (NRRL Y2075), and *P. chrysogenum* (NRRL 807) were obtained from the United States Department of Agriculture Agricultural Research Service Culture Collection (Peoria, Ill.). *T. longibrachiatum* (*T. reesei*, YSM 768) was obtained from the German Resource Centre for Biological Material (DSMZ).

*A. niger, T. longibrachiatum, P. chrysogenum,* and *P. guilliermondii* were grown in liquid media or on agar plates containing 1% yeast extract, 2% peptone, and 2% L-arabinose. Cells were frozen in liquid nitrogen for the isolation of total RNA or genomic DNA. Reverse transcription-PCR (RT-PCR) was performed on mRNAs isolated from *T. longibrachiatum, P. chrysogenum,* and *P. guilliermondii* to obtain cDNA, and PCR was used to obtain the genes encoding (putative) LADs. For *A. niger*, the putative LAD gene could not be amplified from cDNA due to unknown reasons. Thus, overlap extension-PCR (OE-PCR) was used to clone this intron-containing gene from the isolated genomic DNA. Note that all primer sequences used to clone these genes are listed in Table 19.

TABLE 19

Primers used for the cloning of wild type LADs.
Restriction enzyme sites are in bold and italicized.

| | Restriction Enzyme | Primer | Sequence |
|---|---|---|---|
| anLAD | NdeI | Fwd-fragment1[a] | 5'-GACATCGATGA*CATATG*GCTACCGCAAC-3' SEQ ID NO: 71 |
| | | Rev-fragment1 | 5'-GTGCACGTCGGACCCGCAGATTCC-3' SEQ ID NO: 72 |
| | BamHI | Fwd-fragment2[b] | 5'-GGAATCTGCGGGTCCGACGTGCAC-3' SEQ ID NO: 73 |
| | | Rev-fragment2 | 5'-CAGAAGATTTAA*GGATCC*TGAACGTAGA-3' SEQ ID NO: 74 |
| tlLAD | NdeI | Fwd | 5'-GACATCAGTGA*CATATG*TCGCCTTCC-3' SEQ ID NO: 75 |
| | BamHI | Rev | 5'-CCTGGATTGA*GGATCC*TGAACGTATA-3' SEQ ID NO: 76 |
| pcLAD | NdeI | For | 5'-GACATCGATGA*CATATG*GCTTCCGCAAC-3' SEQ ID NO: 77 |
| | EcoRI | Rev | 5'-CCAGAAGTATTGA*GAATTC*TGAACGTAGA-3' SEQ ID NO: 78 |
| pgLAD | NdeI | Fwd | 5'-GACATCGATGA*CATATG*GCGACTCTGC-3' SEQ ID NO: 79 |
| | BamHI | Rev | 5'-GGATACAGAATGA*GGATCC*TGAACGTAGA-3' SEQ ID NO: 80 |

[a, b]Fragment 1 and 2 indicate the upstream and downstream exons flanking the intron.
[c]Sequences in bold (italicized) indicate restriction enzyme sites.

PCR products were subcloned into pET-28a vector and the constructs were used to transform into two *E. coli* strains, DH5α and BL21 (DE3), by electroporation for cloning and expression, respectively. NdeI/BamHI restriction sites were used for the subcloning of the predicted genes from *A. niger, T. longibrachiatum*, and *P. guilliermondii*, and NdeI/EcoRI sites were used for *P. chrysogenum*. The constructs encoded (putative) LADs as N-terminal $His_6$-tagged fusions. Plasmids were sequenced using BIGDYE™ Terminator sequencing method and analyzed with 3730×L Genetic Analyzer (Applied Biosystems, Foster City, Calif.) at the Biotechnology Center at the University of Illinois at Urbana-Champaign (Urbana, Ill.).

Protein Expression and Purification

Genes encoding pcLAD (XP_002569286.1), pgLAD (EDK37120.2), anLAD (CAH69383.1), and tlLAD (AAL08944.1) were cloned into the pET-28a vector and expressed in *E. coli* BL21 (DE3). *E. coli* BL21 (DE3) containing the LAD genes were grown overnight at 30° C. on a rotary shaker at 250 rpm. Overnight culture (50 μL) was used to inoculate a fresh culture (5 mL), which was grown at 30° C. with shaking at 250 rpm until the optical density at 600 nm ($OD_{600}$) reached 0.6-1.0. The cultures were then induced with 0.3 mM IPTG at 30° C. for 3-4 hrs or at 18° C. for 20 hrs.

The induced cells (1 mL) were lysed by re-suspending them in 1 mL of 50 mM potassium phosphate buffer (pH 7.0) with 1 mg/mL lysozyme and shaking at 30° C. and 250 rpm for 30 min. Cells were kept at −80° C. overnight and thawed at room temperature. The resulting cell lysates were centrifuged at 13,200 rpm for 15 min, and the supernatant and precipitate were analyzed for protein expression by sodium dodecyl sulfate-polyacrylamide gel electrophoresis (SDS-PAGE).

For protein purification, the induced cells (400 mL) were treated with 15 mL of Buffer A (20 mM Tris, 0.5 M NaCl, 20% glycerol, pH 7.6) with 1 mg/mL lysozyme and shaken at 30° C. and 250 rpm for 30 min. After a freeze-thaw cycle, the resulting product was further lysed by sonication followed by centrifugation for 20 min at 12,000 rpm to remove cell debris. The supernatants were applied to a column packed with $Co^{2+}$-immobilized metal affinity chromatography resin to purify $His_6$-tagged proteins following the manufacturer's instructions. The purified proteins were desalted by ultrafiltration (Amicon Ultra, Millipore, Billerica, Mass.) and washed with HEPES buffer (pH 7.0) containing 150 mM NaCl and 15% glycerol and kept at −20° C. Protein concentrations were determined by the Bradford method (Bradford 1976) according to the manufacturer's protocol.

Characterization of LAD Proteins

The steady-state kinetics, molecular weight, quaternary structure, temperature dependence, pH dependence, L-arabinitol dehydrogenase activity, and metal content of LAD enzymes were analyzed.

L-Arabinitol Dehydrogenase Activity

Lysates were prepared from host cells expressing LAD from *P. chrysogenum, P. guilliermondii, A. niger*, and *T. longibrachiatum*. Ten microliters of cell lysate were used for an activity assay with 200 mM L-arabinitol and 2 mM $NAD^+$ as the substrates in 50 mM potassium phosphate buffer (pH 7.0). NADH production was monitored by measuring absorbance at 340 nm ($\epsilon$=6.22 $mM^{-1}cm^{-1}$) using a Cary 300 Bio UV-vis spectrophotometer (Varian, Cary, N.C.).

Steady-State Kinetics

Kinetic parameters of different LAD enzymes were determined. Initial rates were determined by measuring the absorbance change at 340 nm using a UV-vis spectrophotomer at room temperature in 50 mM potassium phosphate buffer (pH 7.0). Initial rates were measured at various concentrations of the substrate (L-arabinitol) and cofactors ($NAD^+$/$NADP^+$) (5 to 320 mM for L-arabinitol, 0.5 to 3.2 mM for cofactors). Enzyme kinetics for the substrate and cofactors were analyzed using Michaelis-Menten kinetics, and kinetic parameters were determined by fitting data to the Lineweaver-Burk plot. The parameters for substrate were determined by measuring initial rates at saturated cofactor concentrations (3.2 mM) and those for cofactors were determined at saturated substrate concentrations (320 mM). Assays were performed in triplicate.

The cloned LADs showed different binding affinities and catalytic activities for L-arabinitol: $K_m$ differed by two fold and $k_{cat}$ by about three fold amongst the LADs. For L-arabinitol, the $K_m$ values of anLAD, tlLAD, and pcLAD were 25±1, 18±1, and 37±2 mM, and the $k_{cat}$ values were 507±22, 346±41, and 1085±71 $min^{-1}$, respectively (Table 20) The tlLAD enzyme had the lowest $K_m$ while pcLAD showed the highest catalytic activity ($k_{cat}$) and efficiency ($k_{cat}/K_m$) despite having the highest $K_m$ (Table 20). For cofactor $NAD^+$ kinetics, the cloned LADs showed $K_m$ values in the range of 0.2-0.3 mM and catalytic efficiencies in the range of 2526 to 3460 $mM^{-1}\cdot min^{-1}$ (Table 21). All cloned LADs showed minimal activities toward $NADP^+$ (Tables 20, 21). The initial rates were not saturated at highest substrate and cofactor concentration (320 mM for L-arabinitol and 3.2 mM for $NADP^+$) due to the large $K_m$. Therefore, only the catalytic efficiency of the enzyme was determined using 0.1 or 0.2 mM for $NADP^+$ and 10 or 20 mM for L-arabinitol ($K_m$>>[S]) (Tables 20, 21).

TABLE 20

Kinetic parameters of LADs for L-arabinitol at saturated cofactor concentrations.

| | | Specific activity (U/mg protein) | $K_m$ (mM) | $k_{cat}$ ($min^{-1}$) | $k_{cat}/K_m$ ($mM^{-1}\cdot min^{-1}$) |
|---|---|---|---|---|---|
| anLAD | $NAD^+$ | 11.7 ± 0.3[a] | 25 ± 1 | 507 ± 22 | 20.0 ± 0.8 |
| | $NADP^+$ | —[b] | — | — | 0.04 ± 0.01 |
| tlLAD | $NAD^+$ | 8.7 ± 0.1 | 18 ± 1 | 346 ± 41 | 19.0 ± 0.8 |
| | $NADP^+$ | — | — | — | 0.13 ± 0.02 |
| pcLAD | $NAD^+$ | 25.3 ± 1.4 | 37 ± 2 | 1085 ± 71 | 29 ± 1 |
| | $NADP^+$ | — | — | — | 0.04 ± 0.02 |

[a]Error indicates standard deviation from the mean, n = 3

[b]Dash indicates not determined due to high $K_m$ for indicated cofactor

TABLE 21

Kinetic parameters of LADs for $NAD^+$ and $NADP^+$ at saturated L-arabinitol concentration.

| | | $K_m$ (mM) | $k_{cat}$ ($min^{-1}$) | $k_{cat}/K_m$ ($mM^{-1}\cdot min^{-1}$) |
|---|---|---|---|---|
| anLAD | $NAD^+$ | 0.20 ± 0.01[a] | 494 ± 11 | 2526 ± 83 |
| | $NADP^+$ | —[b] | — | 20 ± 9 |
| tlLAD | $NAD^+$ | 0.2 ± 0.1 | 436 ± 96 | 2689 ± 646 |
| | $NADP^+$ | — | — | 17 ± 9 |
| pcLAD | $NAD^+$ | 0.3 ± 0.1 | 1039 ± 165 | 3460 ± 505 |
| | $NADP^+$ | — | — | 15 ± 4 |

[a]Error indicates standard deviation from the mean, n = 3

[b]Dash indicates not determined due to high $K_m$ for indicated cofactor

Molecular Weight and Quaternary Structure

Calculated molecular weights of the subunits of the four proteins were 43 kDa (anLAD), 41 kDa (tlLAD), 42 kDa (pcLAD), and 42 kDa (pgLAD). The molecular weights of the proteins were determined using a Bio-Sil SEC-250 column (300×7.8 mm, Bio-Rad, Hercules, Calif.) on a Shimadzu HPLC system (Shimadzu, Kyoto, Japan). The mobile phase consisted of 50 mM $Na_2HPO_4$, 50 mM $NaH_2PO_4$, 150 mM NaCl, and 10 mM $NaN_3$ (pH 6.8) and the flow rate was 1.0 mL/min. The molecular weights were calculated by comparing the retention times with those of protein molecular weight standard.

The quaternary structures were determined based on the molecular weights observed by HPLC and the molecular weights of monomeric subunits which were determined by SDS-PAGE analysis. Molecular weights of an-, tl-, and pcLAD were determined to be 178, 194, and 173 kDa, respectively. Comparing to the molecular weights of the subunits determined by SDS-PAGE, results suggested that the LADs were non-covalently linked tetramers in their native forms.

Temperature and pH Dependence

The optimal temperatures of the proteins were determined by assaying enzyme activities at temperatures ranging from 10 to 70° C. Thermal inactivation was determined by measuring enzyme activity after various incubation times at 50° C. in phosphate buffer. Enzyme activity was measured with 2 mM $NAD^+$ and 200 mM L-arabinitol. Half-life of enzyme activity was determined using a first-order exponential decay function. Temperature was controlled by a Cary temperature controller connected to the UV-vis spectrophotometer (Varian, Cary, N.C.). pH-dependent enzyme activity was determined by measuring activity at pH between 5.0 and 11.0 at saturated concentrations of NAD (2 mM) and L-arabinitol (200 mM) in a universal buffer (50 mM morpholineethanesulfonic acid/50 mM Tris/50 mM glycine) (Ellis and Morrison 1982).

Figure 55:
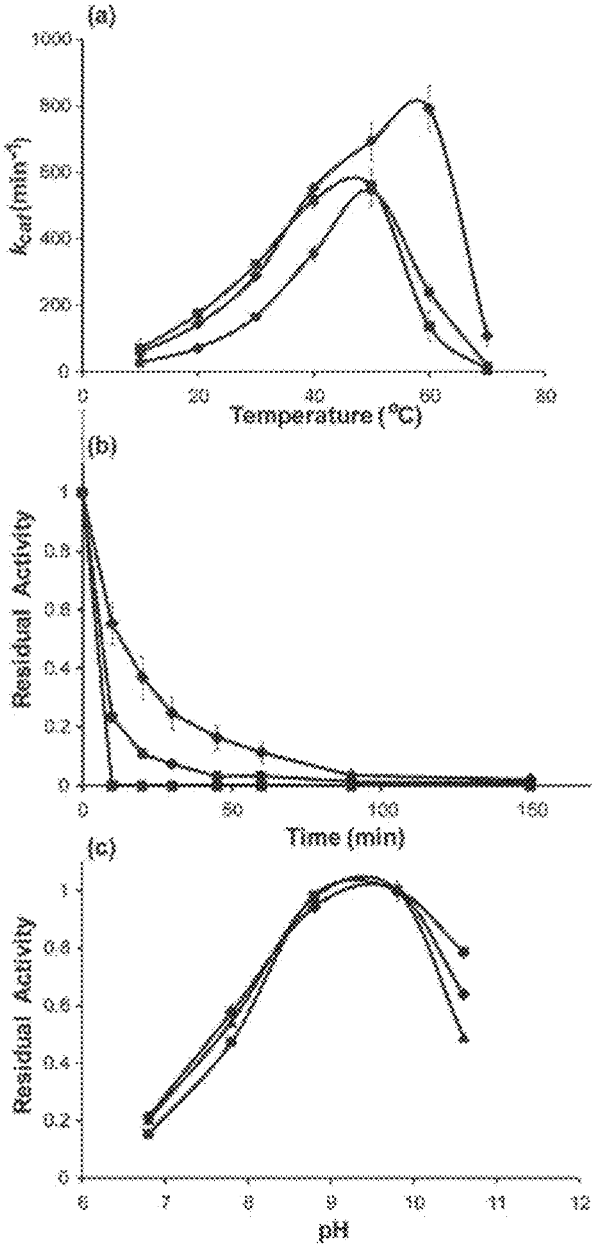
FIG. 55 shows the thermal and pH-dependent properties of different wild-type LAD enzymes: anLAD (■), tlLAD (♦), and pcLAD (●).

The optimal temperatures of anLAD and pcLAD were between 40 and 50° C., whereas tlLAD showed higher optimal temperature between 55 and 65° C. (FIG. 55*a*). Catalytic activities of the LADs exponentially decreased with the length of incubation time at 50° C. and were almost completely deactivated after 100 min (FIG. 55*b*). tlLAD was the most thermally stable with a half-life of 20 min at 50° C., and anLAD was least stable with a half-life of less than 5 min at 50° C. All characterized LADs showed activity in the pH range of 7 to 11 with maximum activity around pH 9.4 (FIG. 55*c*). In the pH range outside of 9 to 10, activity was significantly reduced and approximately 20% of activity remained at pH 7.0 (FIG. 55*c*). No activity was detected at or below pH 5.0.

Metal Analysis

Duplicate samples for metal analysis were prepared in phosphate buffered saline (PBS) by buffer exchange and lyophilization. Each sample contained 1-2 mg of protein in 1 mL buffer solution. The identity and content of the metal were analyzed by inductively coupled plasma atomic emission spectrometry (OES Optima 2000 DV, Perkin Elmer, Boston, Mass.) in the Microanalytical Laboratory at the University of Illinois at Urbana-Champaign (Urbana, Ill.).

Measured weight percentages of $Zn^{2+}$ were close to those calculated based on the 1:1 molar ratio (Table 22).

TABLE 22

Calculated and measured $Zn^{2+}$ contents.

| | Calculated Weight[a] (%) | Measured weight (%) |
|---|---|---|
| anLAD | 0.027 | 0.027 ± 0.003[b] |
| tlLAD | 0.047 | 0.048 ± 0.003 |
| pcLAD | 0.048 | 0.061 ± 0.013 |

[a]Calculated molecular weights were determined based on the buffer composition, protein concentration, and 1:1 molar ratio of LAD monomer subunit and $Zn^{2+}$. Buffer solution (1 L) contained NaCl (8 g), KCl (0.2 g), $Na_2HPO_4$ (1.44 g), and $KH_2PO_4$ (0.24 g).

[b]All samples were analyzed in duplicate and errors were standard deviations.

Engineering of LAD Enzymes with Altered Cofactor Specificity

Methods of altering the cofactor specificity of LADs were determined, and mutated LADs were analyzed for altered cofactor specificity and other characteristics.

Development of LADs with Altered Cofactor Specificity

Site-directed mutagenesis was performed to alter the cofactor specificity of anLAD, tlLAD, and pcLAD from $NAD^+$ to $NADP^+$. Amino acid numbers 224, 225, and 362 of naturally occurring tlLAD were substituted with serine, arginine, and threonine, respectively, to generate the tlLAD with altered cofactor specificity. The amino acid sequences of cloned anLAD and pcLAD were aligned with the *T. longibrachiatum* LAD (tlLAD) sequence, and the amino acids that correspond to tlLAD amino acid numbers 224, 225, and 362 were mutated. For all of the LADs with altered cofactor specificity, two amino acid residues within the β-α-β motif of the coenzyme binding domain were replaced with serine and arginine, respectively: D213 and 1214 for anLAD, D224 and 1225 for tlLAD, and D212 and 1213 for pcLAD (Korkhin et al., 1998; Pauly et al., 2003; Watanabe et al., 2005), and the third mutation was introduced at A359 for anLAD, A362 for tlLAD, and 5358 for pcLAD and replaced with threonine (For primer sequences, see Table 23). Megaprimer PCR method was used to introduce site-specific mutations using wild type LAD constructs as the templates (Sarkar and Sommer 1990). Correct mutations were confirmed by DNA sequence analysis.

TABLE 23

Primers used for site directed mutagenesis by the megaprimer PCR method.[a]

| | | |
|---|---|---|
| | Fwd-T7-pro | 5'-TAATACGACTCACTATAGGG-3' SEQ ID NO: 81 |
| | Rev-T7-term | 5'-GCTAGTTATTGCTCAGCGG-3' SEQ ID NO: 82 |
| anLAD | Fwd-D213S/I214R | 5'-CCTATCGTCATTACCTCACGT[b]GACGAGGGGCGGCTG-3' SEQ ID NO: 83 |
| | Rev-D213S/I214R | 5'-CAGCCGCCCCTCGTCACGTGAGGTAATGACGATAGG-3' SEQ ID NO: 84 |
| | Fwd-A359T | 5'-CCT TCGAAACGGCTACAAACCCCAAGACG -3 SEQ ID NO: 85 |

TABLE 23 -continued

| Primers used for site directed mutagenesis by the megaprimer PCR method.[a] | | |
|---|---|---|
| tlLAD | Fwd-D214S/I215R | 5'-GCTTGTCATCACATCACGTTCAGAGAGCCGTCTG-3' SEQ ID NO: 86 |
| | Rev-D214S/I215R | 5'-CAGACGGCTCTCTGAACGTGATGTGATGACAAGC-3' SEQ ID NO: 87 |
| | Fwd-S362T | 5'-GCATTTGAGACGTCAACAGATCCCAAGAGC-3' SEQ ID NO: 88 |
| pcLAD | Fwd-D212S/I213R | 5'-CCTATTGTCATCACTTCACGTGACGAGGGCCGCTTG-3' SEQ ID NO: 89 |
| | Rev-D212S/I213R | 5'-CAAGCGGCCCTCGTCACGTGAAGTGATGACAATAGG-3' SEQ ID NO: 90 |
| | Fwd-S358T | 5'-CCTTTGAGACTGCCACAAACCCTAAGACCGGTG-3' SEQ ID NO: 91 |

[a]To create mutant LADs, fragments 1 and 2 were amplified using Fwd-T7-pro and Rev-D213S/I214R and Fwd-A359T and Rev-T7-term primers, respectively. Fragment 3 was amplified using Fwd-D123S/I214R and fragment 2 (Rev megaprimer). Full mutant genes were amplified by overlap extension of fragment 1 and 3. Template DNA was pET-28a plasmid.
[b]Sequences underlined were the mutation sites.

Kinetic Analysis of LADs with Altered Cofactor Specificity

In this example, "tlLAD mutant" is defined as tlLAD with the mutations D224S/1225R/A362T; "anLAD mutant" is defined as anLAD with the mutations D213S/1214R/A359T; and "pcLAD mutant" is defined as pcLAD with the mutations D212S/I213R/S358T. The tlLAD mutant showed significantly altered cofactor specificity from NAD to $NADP^+$. It also demonstrated the highest catalytic activity. The $K_m$ and $k_{cat}$ of the tlLAD mutant for L-arabinitol with $NADP^+$ were 46±4 mM and 170±9 $min^{-1}$, respectively (Table 24). In all assays including the tlLAD mutant with saturated $NAD^+$, a plateau of reaction rate was not observed in the tested concentration range, so catalytic efficiencies were determined at 0.8 mM for $NAD^+$ and 80 mM for L-arabinitol (Tables 24, 25). For cofactors, anLAD and tlLAD mutants showed significantly higher preference for $NADP^+$ over $NAD^+$ (Table 25). The $K_m$ values of the anLAD and tlLAD mutants were 0.46±0.09 and 0.10±0.01 mM, and the $k_{cat}$ values were 55.7±6.4 and 90.5±9.2 $min^{-1}$, respectively (Table 25). The catalytic efficiencies of anLAD and tlLAD mutants were 130±32 and 934±72 $mM^{-1}\cdot min^{-1}$, and the ratios of the catalytic efficiencies with $NADP^+$ to $NAD^+$ were 100 and 161, respectively. For the tlLAD mutant, the ratio of catalytic efficiency for $NADP^+$ to $NAD^+$ was increased by $2.5\times10^4$ fold (Tables 21, 25). The pcLAD mutant showed no activity with $NAD^+$.

Table 24 shows kinetic parameters of LAD mutants for L-arabinitol at saturated cofactor concentrations.

| | | Specific activity (U/mg protein) | $K_m$ (mM) | $k_{cat}$ ($min^{-1}$) | $k_{cat}/K_m$ ($mM^{-1}\cdot min^{-1}$) |
|---|---|---|---|---|---|
| anLAD | $NAD^+$ | —[a] | — | — | 0.010 ± 0.002[b] |
| mutant | $NADP^+$ | — | — | — | 0.45 ± 0.20 |
| tlLAD | $NAD^+$ | — | — | — | 0.050 ± 0.007 |
| mutant | $NADP^+$ | 3.9 ± 0.2 | 46 ± 4 | 170 ± 9 | 3.7 ± 0.2 |
| pcLAD | $NAD^+$ | — | — | — | — |
| mutant | $NADP^+$ | — | — | — | 0.02 ± 0.02 |

[a]Dash indicates not determined due to high $K_m$ for indicated cofactor
[b]Error indicates standard deviation from the mean, n = 3

Table 25 shows kinetic parameters of LAD mutants for $NAD^+$ and $NADP^+$ at saturated L-arabinitol concentration.

| | | $K_m$ (mM) | $k_{cat}$ ($min^{-1}$) | $k_{cat}/K_m$ ($mM^{-1}\cdot min^{-1}$) |
|---|---|---|---|---|
| anLAD mutant | $NAD^+$ | —[a] | — | 1.3 ± 0.3[b] |
| | $NADP^+$ | 0.46 ± 0.09 | 55.7 ± 6.4 | 130 ± 32 |
| tlLAD mutant | $NAD^+$ | — | — | 5.8 ± 0.8 |
| | $NADP^+$ | 0.097 ± 0.011 | 90.5 ± 9.2 | 934 ± 72 |
| pcLAD mutant | $NAD^+$ | — | — | — |
| | $NADP^+$ | — | — | 3.6 ± 1.0 |

[a]Dash indicates not determined due to high $K_m$ for indicated cofactor
[b]Error indicates standard deviation from the mean, n = 3

Engineering of *N. crassa* XDH (ncXDH) with Altered Cofactor Specificity

Cloning and Characterization of Putative ncXDH

A putative *N. crassa* xylitol dehydrogenase (ncXDH) sequence was found using a protein BLAST search on the National Center for Biotechnology Information website (webpage ncbi.nlm.nih.gov) using the *P. stipitis* xylitol dehydrogenase (psXDH) enzyme as a query sequence. The two enzymes were aligned fully using a ClustalW algorithm and found to share 44% identity and 60% similarity (FIG. 56). The whole-genome sequence of *Neurospora crassa* has been published (Galagan et al., 2003) and it was utilized to design primers for cloning of the putative xylitol dehydrogenase (XDH) gene.

RT-PCR performed on total RNA isolated from D-xylose-induced *N. crassa* 10333 showed the expected size of gene product (~1.1 kb). The RT-PCR product was cloned into the pET-28a vector using NdeI and SacI restriction sites and was transformed into *E. coli* BL21 (DE3). This construct (pET-28a ncXDH) expressed ncXDH as an N-terminal His6-tagged fusion with a thrombin cleavage site. Cell lysates of IPTG-induced cultures of these cells were prepared, analyzed by SDS-PAGE, and assayed for XDH activities. The XDH was then purified by immobilized metal ion affinity chromatography (IMAC) using Talon® Co2+ Superflow resin (Clontech, Mountain View, Calif.) according to manufacturer's protocol. The purified protein was desalted by ultrafiltration with several washes of 50 mM 4-(2-hydroxyethyl)piperazine-1-ethanesulfonic acid (HEPES) buffer (pH 7.25)+15% glycerol and stored frozen at −80° C. Protein concentrations were determined by the Bradford method (Bradford 1976).

ncXDH is a strictly $NAD^+$-preferring enzyme. ncXDH also displays high stability (half-life of ~200 min at 50° C.)

and expression. Previous work by Watanabe et al. (2005b) was aimed at reversing the cofactor specificity of psXDH.

Development of ncXDH with Altered Cofactor Specificity

Through sequence alignment, residues D204, I205, and V206 of ncXDH were targeted for site-directed mutagenesis to alanine, arginine, and serine, respectively, to create ncXDH-ARS. Table 26 shows that ncXDH-ARS has completely reversed cofactor specificity, now preferring $NADP^+$. The affinity for substrate xylitol did not suffer very much from the affinity-change for the co-factor.

Table 26 shows kinetic parameters for *N. crassa* and *P. stipitis* XDH and XDH-ARS with nicotinamide cofactors $NAD^+$ and $NADP^+$ at saturated xylitol concentrations.

| | $NAD^+$ | | | $NADP^+$ | | | |
|---|---|---|---|---|---|---|---|
| Enzyme | $k_{cat}$ ($min^{-1}$) | $K_m$ (mM) | $k_{cat}/K_m$ ($mM^{-1}$ $min^{-1}$) | $k_{cat}$ ($min^{-1}$) | $K_m$ (mM) | $k_{cat}/K_m$ ($mM^{-1}$ $min^{-1}$) | Source |
| ncXDH-wt | 2160 | 0.127 | 17000 | —a | ~5.6 | ~68 | This work |
| ncXDH-ARS | —a | ~3.5 | ~165 | 2080 | 0.325 | 6400 | This work |
| psXDH | 1050 | 0.381 | 2760 | 110 | 170 | 0.65 | Watanabe et al. (2005b) |
| psXDH-ARS | 240 | 1.3 | 181 | 2500 | 0.897 | 2790 | Watanabe et al. (2005b) |

aNot determined, cofactor saturation not reached.
All assays were performed at 25° C. in 50 mM Tris, pH 8.0.

Kinetic Analysis of ncXDH Mutant

The mutant ncXDH had a dramatic reversal of cofactor specificity. The $K_m$ of the mutant ncXDH for $NADP^+$ was only about 2.5-fold higher than the $K_m$ of wild-type ncXDH for NAD whereas the $k_{cat}$ values were similar (Table 27).

Table 27 shows kinetic parameters of ncXDH mutants for substrate xylitol.

Figure 57:
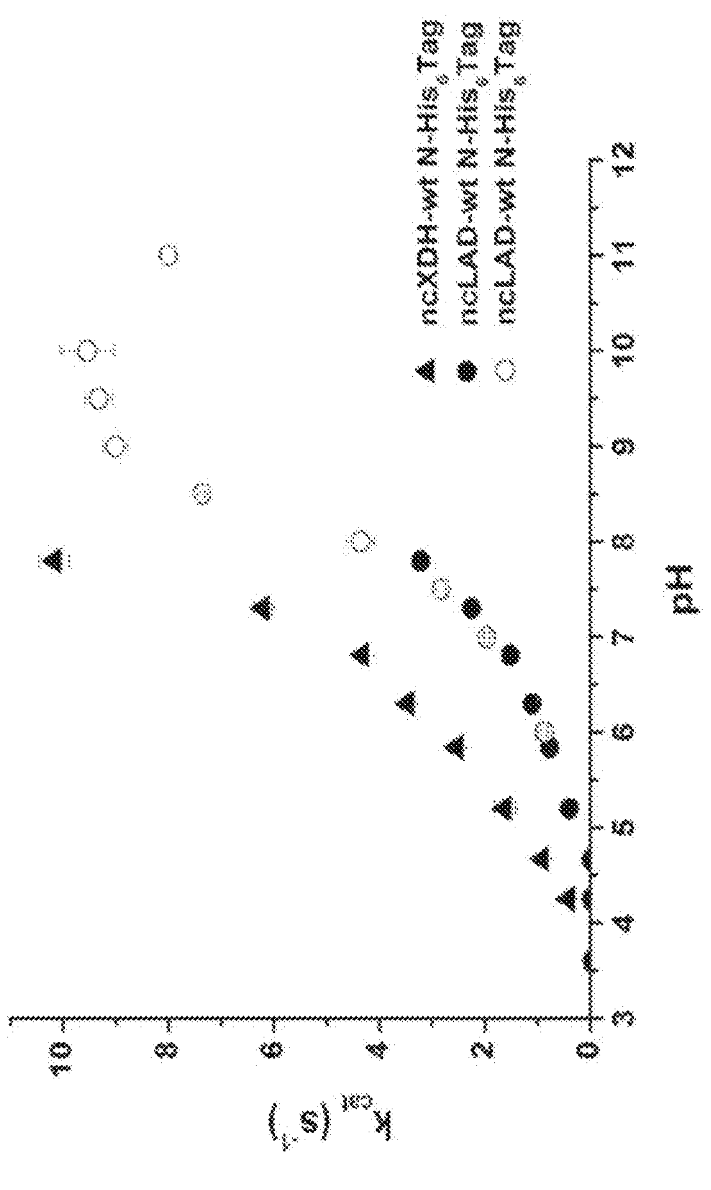
FIG. 57 show a comparison of pH rate profiles of *N. crassa* LAD and XDH. Data taken from the characterization of LAD was performed in universal buffer MES/Tris/glycine, and overlapped with data for ncXDH (closed triangles) and ncLAD (closed circles) performed in universal buffer acetic acid/MES/Tris for lower pH values.

| Enzyme | $k_{cat}$ ($min^{-1}$) | $K_m$ (mM) | $k_{cat}/K_m$ ($mM^{-1}$ $min^{-1}$) |
|---|---|---|---|
| ncXDH-wt | 2170 ± 135 | 6.6 ± 2.0 | 330 |
| ncXDH-ARS | 2090 ± 35 | 4.3 ± 0.3 | 490 |

a Not determined, cofactor saturation not reached.
All assays were performed at 25° C. in 50 mM Tris, pH 8.0.
All enzymes were purified and characterized with N-$His_6$-tag As shown in FIG. 57, XDH activity exhibits a higher tolerance to more acidic conditions with activity extending down to pH 4.0, whereas LAD activity is abolished at pH 5.0 in the in vitro activity assay.

Example 14

Expression of Xylose Isomerase from *Bacteroides* Stercoris in *S. Cerevisiae*

Bacterial xylose isomerase (XI) is involved in converting xylose into xylulose. Recently, three successful cases of expressing active XI from two species of anaerobic fungi (*Piromyces* sp. and *Orpinomyces* sp.) and from the anaerobic bacteria (*Clostridium phytofermentans*) have been reported. A fungal XYLA gene from *Piromyces* sp. E2 was functionally expressed in *S. cerevisiae* and a maximum 1.1 U/mg-protein of XI activity was obtained at 30° C. (Kuyper et al., 2003). The second fungal XYLA gene from *Orpinomyces*, which has 94% identity with that from *Piromyces* sp., was also functionally expressed in *S. cerevisiae* (Madhavan et al., 2009). Recently, the first prokaryotic xylA gene from *Clostridium phytofermentans* was functionally expressed in *S. cerevisiae* (Brat et al., 2009).

Figure 58:
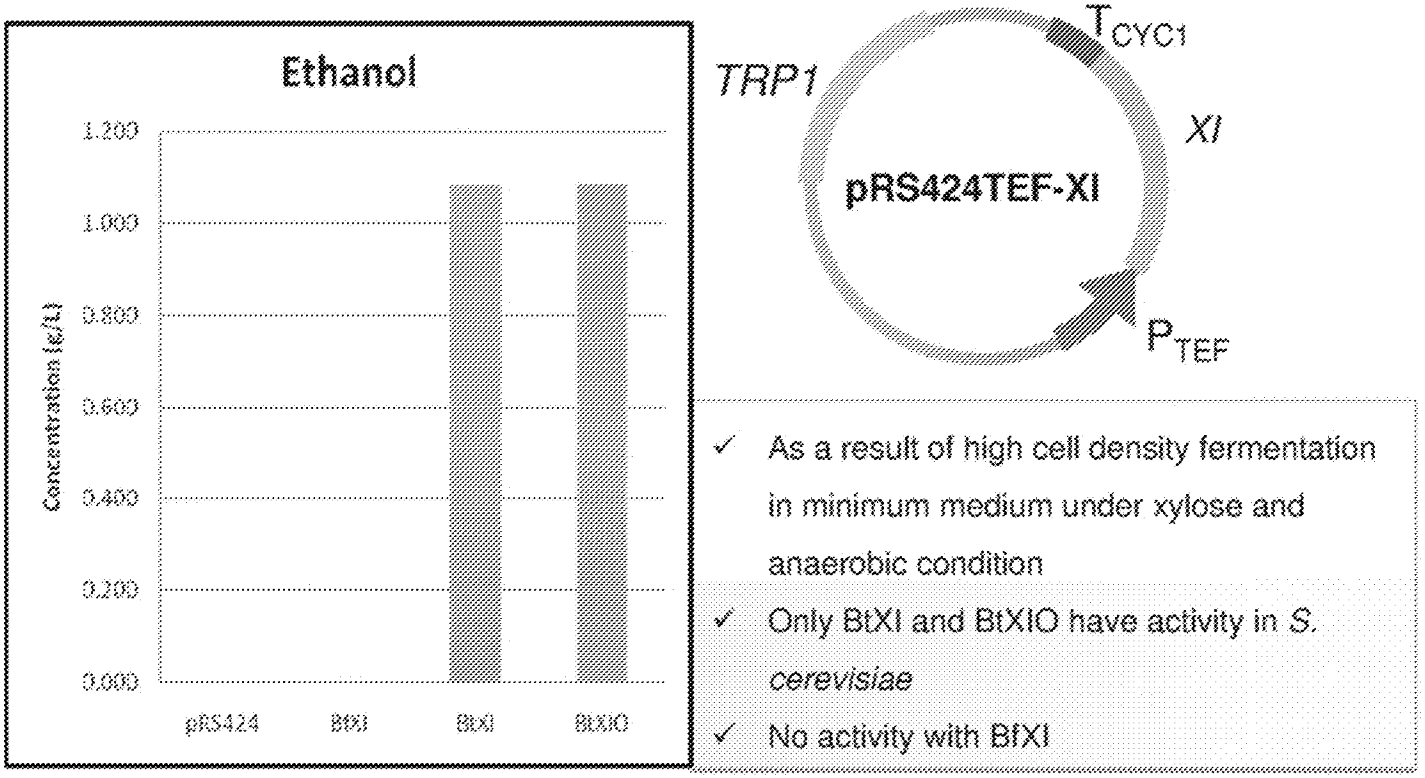
FIG. 58 shows ethanol production by *S. cerevisiae* strain L2612 transformed with xylose isomerase enzyme from *Bacteroids stercoris* (BtXI), *Bifidobacterium longum* (BfXI), and BtXIO coding for codon-optimized BtXI. The XI gene was cloned into the pRs424TEF vector.
Figure 59:
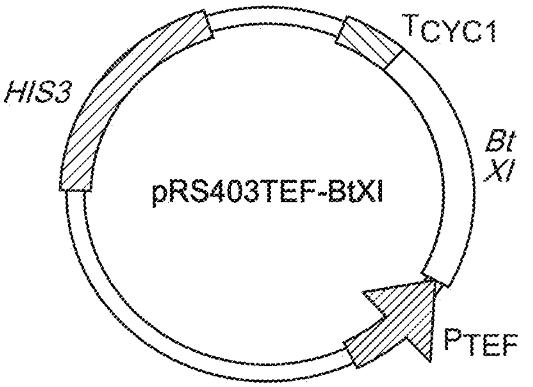
FIG. 59 shows xylose consumption and ethanol production by *S. cerevisiae* strain D452-2, which had BtXI integrated into its genome by the vector pRS403TEF. Comparison is also made to xylose-fermentation by *S. cerevisiae* strain L2612, which expresses BtXI from a plasmid
Figure 59:
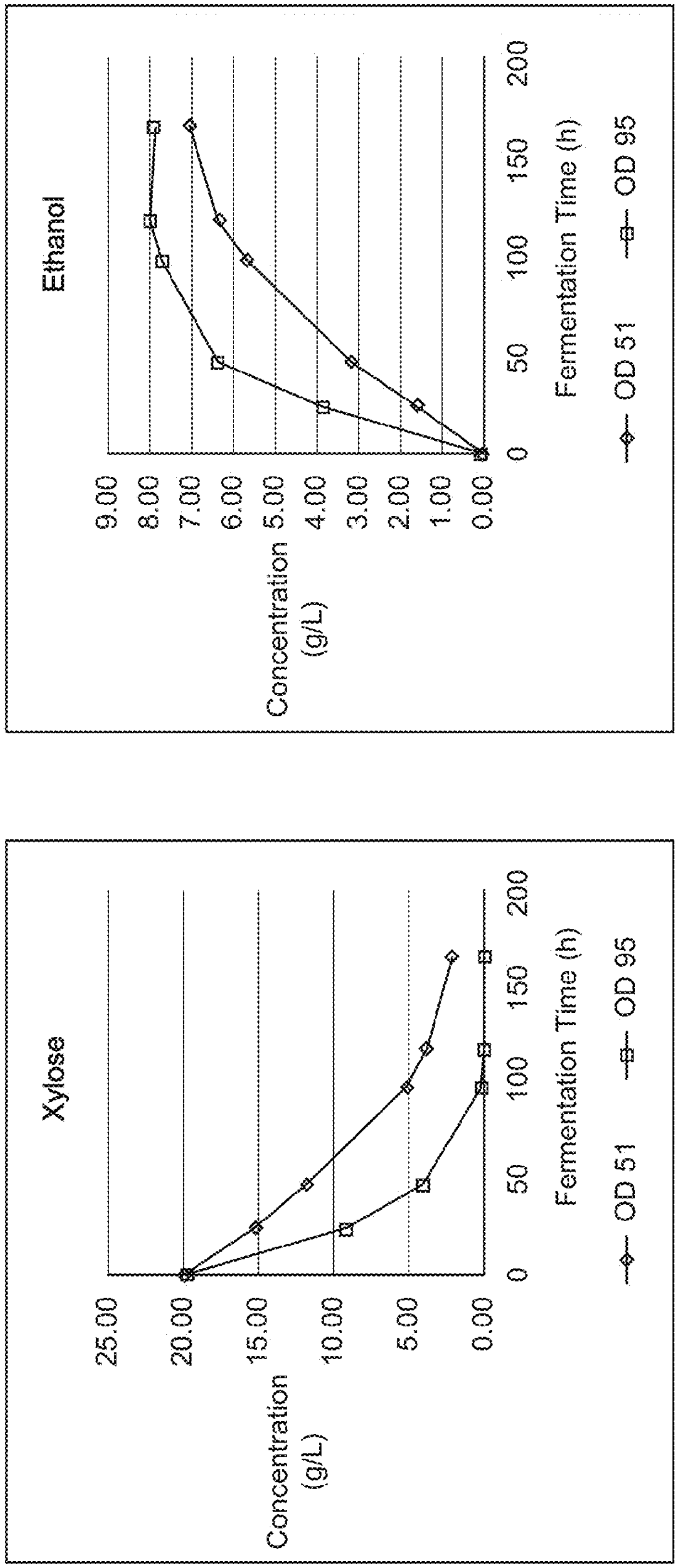

The isomerase gene xylA from the anaerobic bacteria *Bacteroides stercoris* (BtXI) shares high sequence identity with the isomerase gene from *Piromyces* sp. (82%). BtXI was cloned into the pRS424TEF vector and transformed into the *S. cerevisiae* L2612 strain. The gene was also integrated into the *S. cerevisiae* D452-2 strain by using the pRS403TEF vector. Ethanol production was observed in both strains expressing BtXI (5 g/L in L2612 and 7.8 g/L in D452-2) (FIG. 58-59). However, rates of production were relatively low compared to that of engineered strains expressing the XYL genes.

Figure 60:
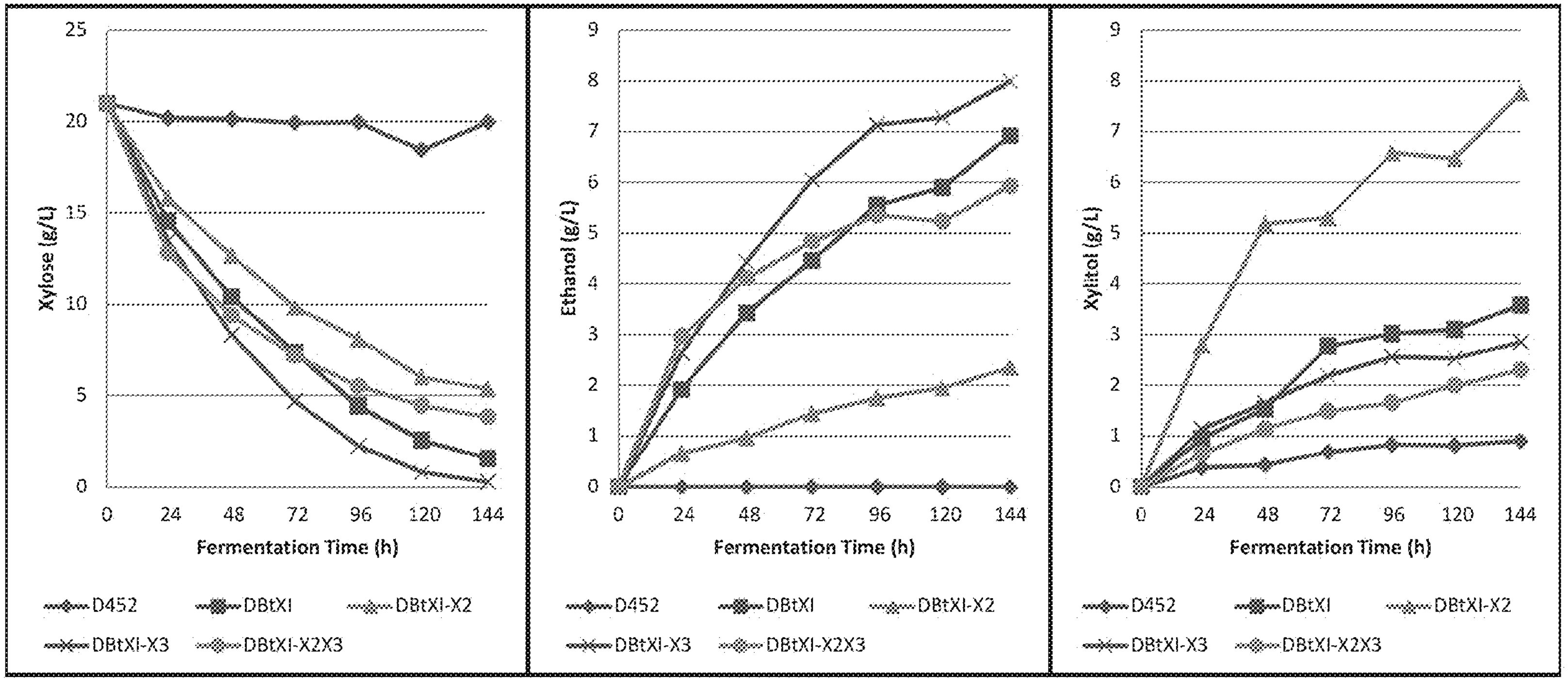
FIG. 60 shows xylose fermentation by *S. cerevisiae* strain, containing integrated BtXI and expressing XYL2 or XYL3 or XYL2 and XYL3.

The low ethanol production could be attributed to the inhibitory effect of any accumulated xylitol (formed from xylose by endogenous yeast aldose reductase). To decrease xylitol accumulation, XDH and XK were expressed in BTXI-expressing yeast strain (DBtXI). The resulting strain had slightly improved ethanol yield and decreased xylitol production (FIG. 60). Co-expression of these two XYL genes in DBtXI resulted in ethanol production even under aerobic conditions.

Example 15

Over-Expression of Enzymes in Pentose Phosphate Pathway (PPP)

The PPP enzymes glucose-6-phosphate dehydrogenase (ZWF1), 6-phosphogluconate dehydrogenase (GDN1), transaldolase (TALI), and transketolase (TKT1) from *P. stipitis* were cloned into an integration vector (pRS406) under the control of a strong promoter ($P_{GPD}$). The plasmid was linearized by the enzyme StuI and integrated into the chromosome of *S. cerevisiae.*

Figure 61:
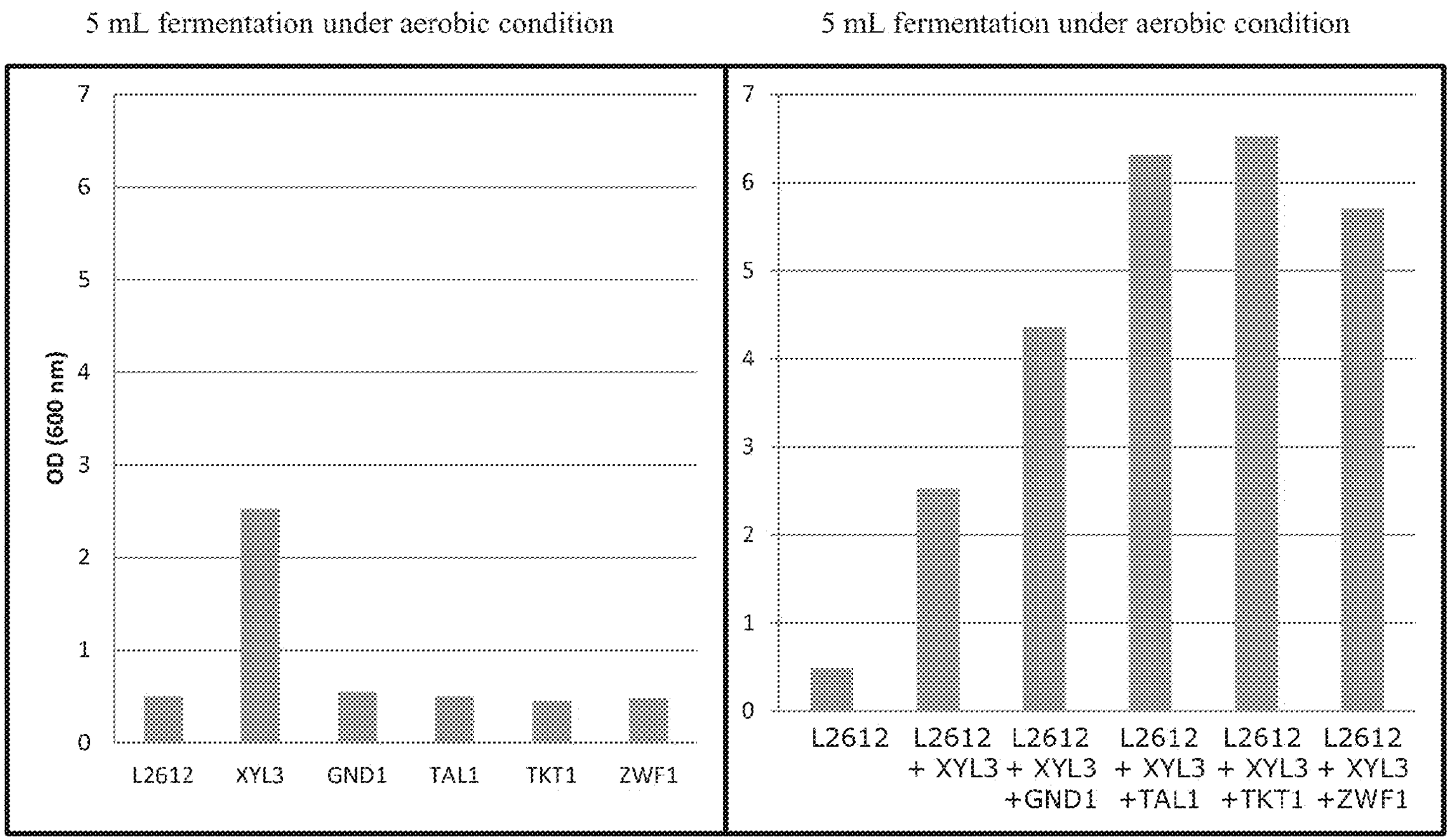
FIG. 61 shows the necessity of XYL3 expression in *S. cerevisiae* engineered to over-express enzymes, such as GND1, involved in the pentose phosphate pathway in order to efficiently metabolize xylose.

However, to get the beneficial effects of over-expressing the PPP enzymes, there also had to be over-expression of XYL3 (XK) (FIG. 61). Expression of XYL3 and the PPP enzymes also improved ethanol production in YP-xylulose media.

Example 16

Expression of Aldose-1-Epimerase

Hydrolysis of cellobiose by β-glucosidase releases β-D-glucose. However, yeast hexokinases prefer (or exclusively use) α-D-glucose, and the rate of mutaroation of β-D-glucose to α-D-glucose could effectively slow down metabolic rate.

Figure 62A:
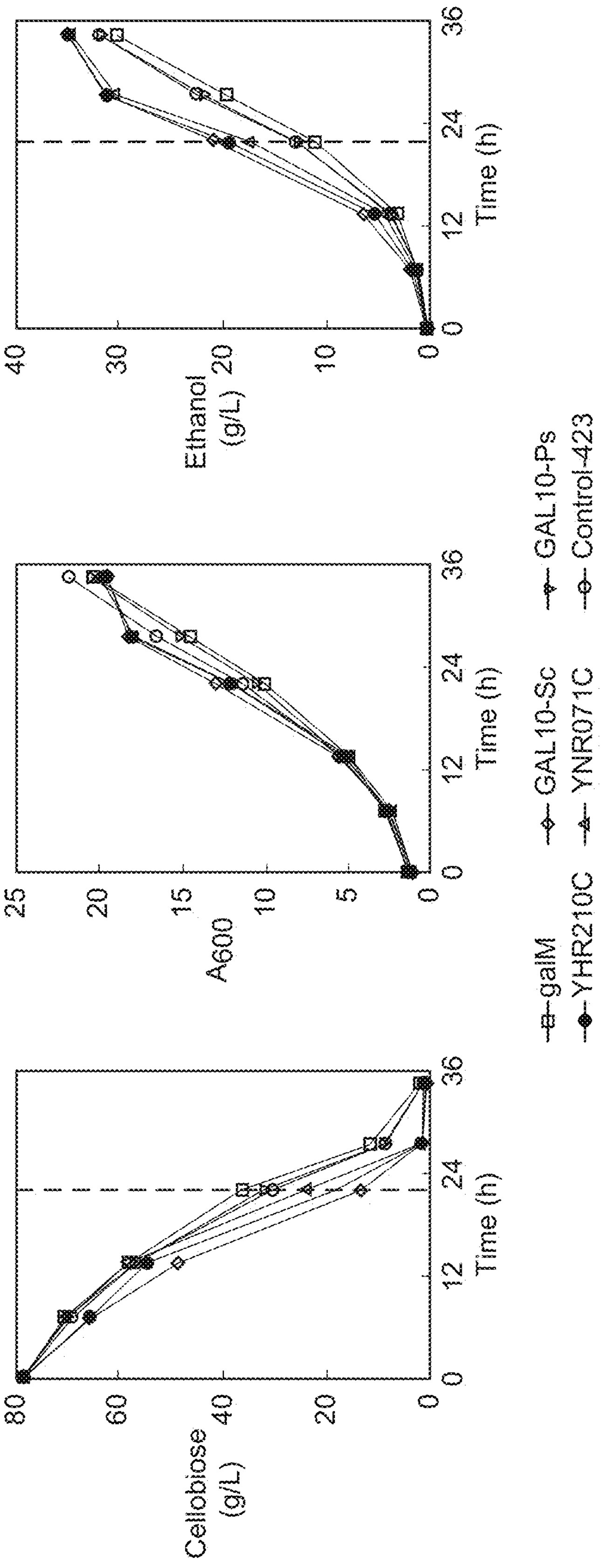
FIG. 62A shows cellobiose consumption, growth, and ethanol production.
Figures 62A, 62B:
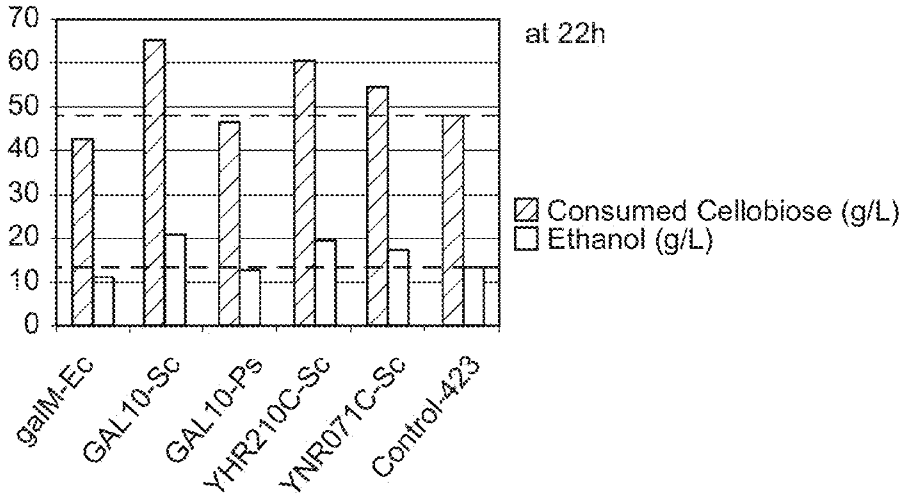
FIG. 62B shows ethanol yield and productivity.

One way of enhancing the conversion was to over-express the predicted aldose-1-epimerase NCU09705. This hypothesis was tested by over-expressing NCU09705 homologs: galM in *E. coli*; GAL10, YHR210C, and YNR071C in *S. cerevisiae*; and GAL 10 in *P. stipitis*. The strains were then tested for cellobiose consumption and ethanol production (FIG. 62). The results indicated that over-expression of the homologs in *S. cerevisiae* caused a slight increase in cellobiose consumption and ethanol production.

Example 17

Co-Fermentation of Xylose and Cellobiose

Figure 63A:
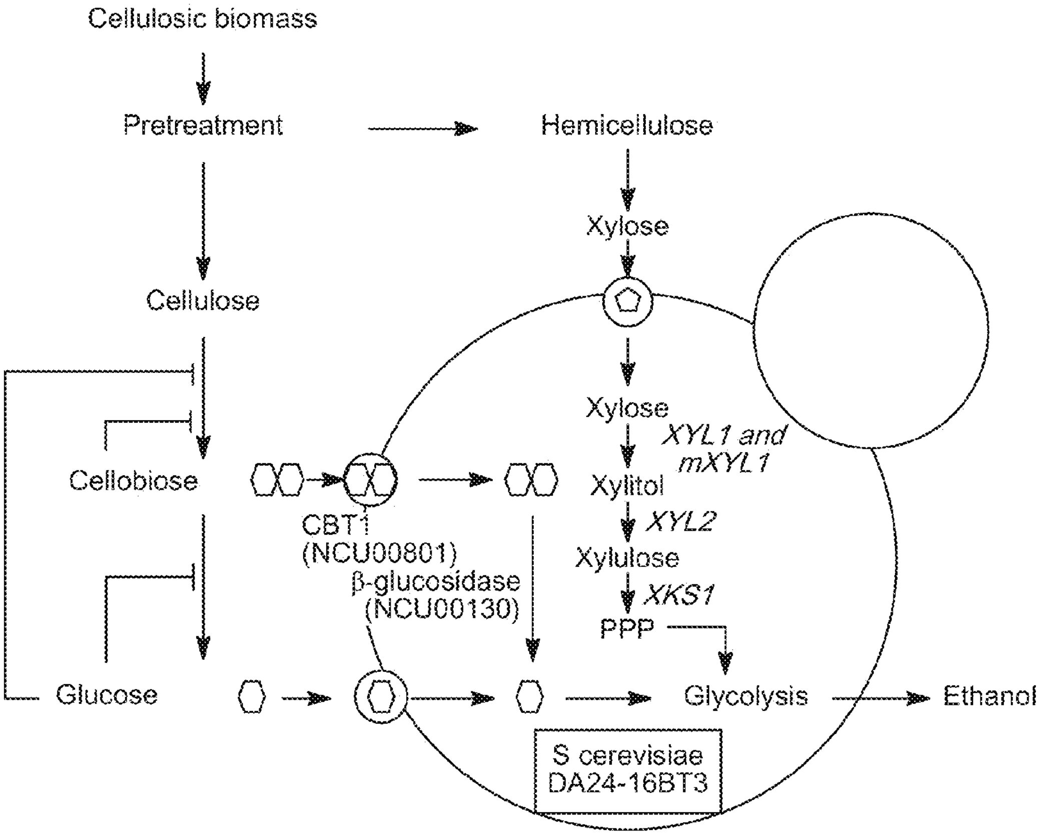
FIG. 63A shows a strain improvement strategy to engineer yeast strain capable of fermenting two non-metabolizable sugars (cellobiose and xylose). The cellodextrin assimilation pathway consists of a cellodextrin transporter (NCU00801) and an intracellular β-glucosidase (NCU00130) from *N. crassa*. The modified xylose metabolic pathway utilizes xylose reductase isozymes (wild-type XR and mutant $XR^{R276H}$), xylitol dehydrogenase (XYL2), and xylulokinase (XKS1).
Figure 63B:
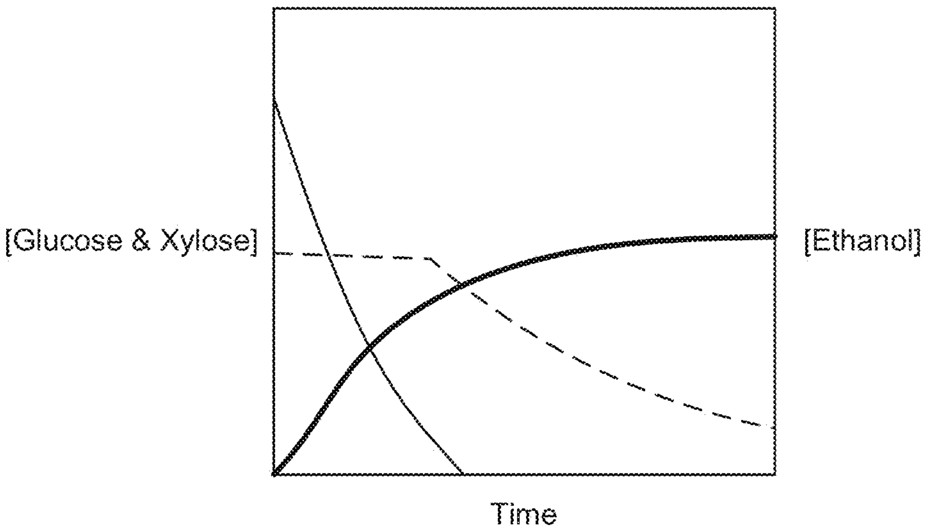
FIG. 63B shows fermentation profile of a sugar mixture containing glucose and xylose by the engineered *S. cerevisiae* developed in this study. Glucose fermentation repressed xylose fermentation completely so that xylose fermentation begins only after glucose depletion.
Figure 63C:
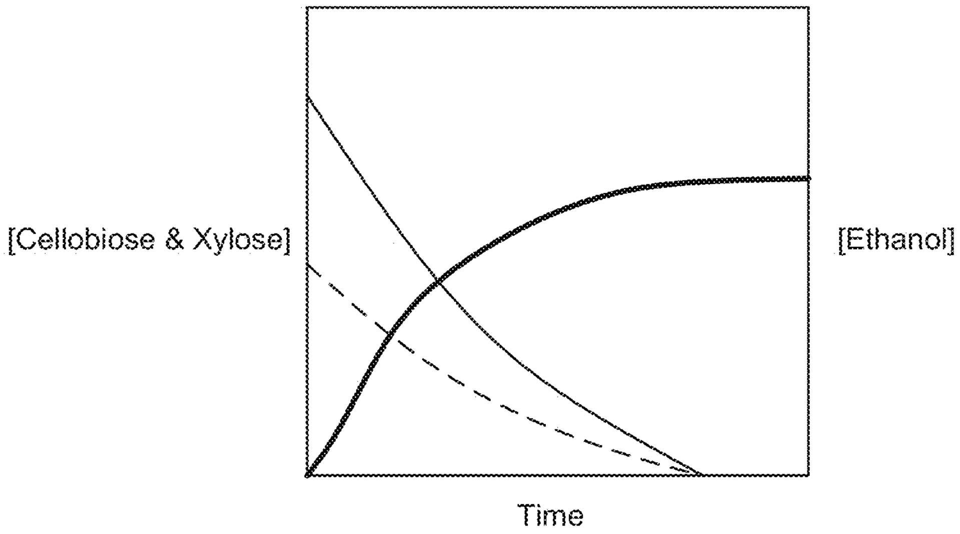
FIG. 63C shows fermentation profile of a sugar mixture containing cellobiose and xylose by the engineered *S. cerevisiae* developed in this study. Cellobiose and xylose are simultaneously utilized, as neither carbon source repressed consumption of the other.

In this example a new strategy was used to overcome glucose repression in which a dimer of glucose, cellobiose, was co-fermented with xylose (a pentose). Cellobiose is an intermediate product from enzymatic hydrolysis of cellulose, which is further converted to glucose by β-glucosidases in the cocktail of cellulases including exocellulases, endocellulases, and β-glucosidases, whereas pentose sugars are the products of dilute acid hydrolysis of hemicellulose. Wild type *S. cerevisiae* cannot assimilate cellobiose because it lacks both a cellobiose transporter and a β-glucosidase capable of hydrolyzing cellobiose into glucose. Hence, the newly discovered cellodextrin transporter genes described in Example 9 and a β-glucosidase gene from *N. crassa* were co-expressed in *S. cerevisiae* and a mixture of xylose and cellobiose was used as carbon source (FIG. 63). Similar approaches have employed either secretion, or cell surface display, of β-glucosidases to allow cellobiose fermentation by *S. cerevisiae* (van Rooyen et al., 2005; Skory et al., 1996; Kotaka et al., 2008; Katahira et al., 2006). In those cases, cellobiose was hydrolyzed into glucose extracellularly before being transported by the endogenous hexose transport system of *S. cerevisiae*. In contrast, in this strategy, cellobiose was hydrolyzed intracellularly following transport.

In the conventional methods for mixed sugar fermentation in *S. cerevisiae*, a mixture of glucose and pentose sugars derived from lignocellulose is used. However, in this new strategy, a mixture of cellobiose and pentose sugars was used. The cellobiose was transported inside yeast cells via the heterologous cellodextrin transporters while pentose sugars were transported inside yeast cells by endogenous hexose transporters, thus removing the direct competition between glucose and pentose sugars for the same transporters, a phenomenon that is partly responsible for glucose repression. Once inside yeast cells, cellobiose was converted to glucose by β-glucosidase and immediately consumed by yeast cells, which resulted in low intracellular glucose concentration, thereby further alleviating glucose repression.

The engineered xylose-utilizing yeast strain L2612 was used as a host to co-express cellodextrin transporter and β-glucosidase genes. In this strain, the D-xylose utilization pathway consisting of xylose reductase, xylitol dehydrogenase, and xylulokinase from *Pichia stipitis* was integrated into the chromosome. The cellodextrin transporters from *Neurospora crassa* including NCU008011, NCU08114, and, NCU00809, and two β-glucosidase genes, one from *Neurospora crassa* and the other from *Aspergillus aculeatus*, were evaluated.

*S. cerevisiae* L2612 (MATa, leu2-3, leu2-112, ura3-52, trp1-298, can1, cyn1, gal+) was cultivated in synthetic dropout media to maintain plasmids (0.17% of Difco yeast nitrogen base without amino acids and ammonium sulfate, 0.5% of ammonium sulfate, 0.05% of amino acid dropout mix). YPA medium (1% yeast extract, 2% peptone, 0.01% adenine hemisulfate) with 2% of sugar was used to grow yeast strains.

To integrate the D-xylose utilization pathway consisting of D-xylose reductase, xylitol dehydrogenase, and xylulokinase from *Pichia stipitis*, the corresponding genes were PCR-amplified and cloned into the pRS416 plasmid using the DNA assembler method (Shao et al., 2009). BamHI and HindIII were used to remove the DNA fragment encoding the D-xylose utilization pathway and then ligated into the pRS406 plasmid digested by the same two restriction enzymes. The resulting plasmid was then linearized by ApaI and integrated into the URA3 locus on the chromosome of L2612.

Figure 64:
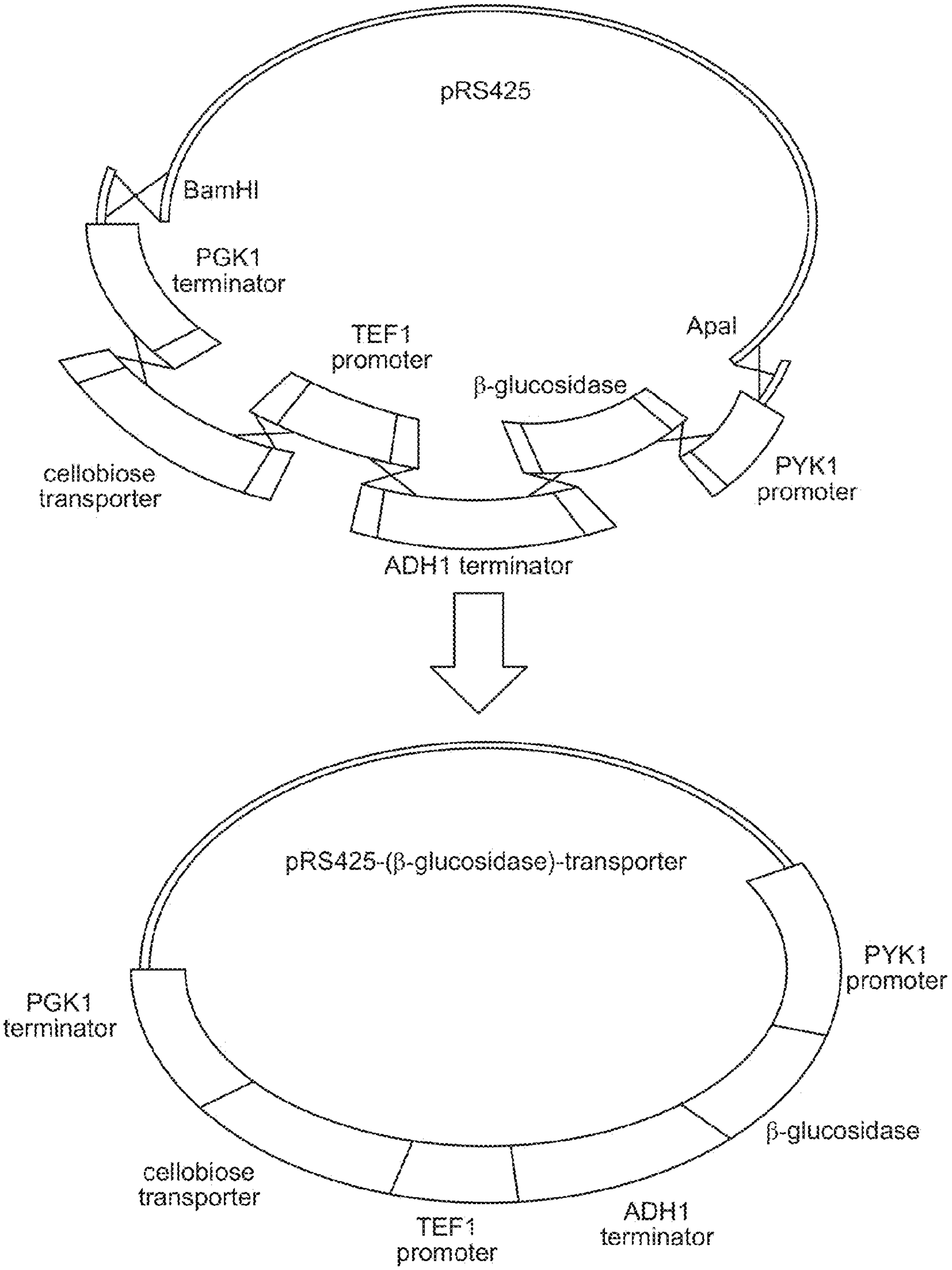
FIG. 64 shows the scheme for plasmid construction. The pRS425 shuttle vector was linearized followed by assembly of the cellobiose transporter and β-glucosidase genes using the DNA assembler method (Shao et al., 2009).

The pRS425 plasmid (New England Biolabs, Ipswich, Mass.) was used to co-express a cellodextrin transporter gene and a β-glucosidase gene. As shown in FIG. 64, the pRS425 plasmid was digested by BamHI and ApaI. The PYK1 promoter and the ADH1 terminator were added to N-terminus and C-terminus of the cellodextrin transporter, respectively, while the TEF1 promoter and the PGK1 terminator were added to the N-terminus and C-terminus of the β-glucosidase, respectively. These DNA fragments were assembled into the linearized pRS425 shuttle vector using the DNA assembler method (Shao et al., 2009). Three cellodextrin transporter genes NCU00801 (XM_958708), NCU08114 (XM_958780), and NCU00809 (XM_959259) from *Neurospora crassa* and two β-glucosidase genes NCU00130 (XM_951090) from *Neurospora crassa* and BGL1 (D64088) from *Aspergillus aculeatus* were used. There were six combinations in total, each with one cellodextrin transporter gene and one β-glucosidase gene.

Yeast plasmids were then transferred into *E. coli* DH5α, which were used for recombinant DNA manipulation. The transformants were plated on Luria broth plates containing 00 mg/L ampicillin. Single colonies of *E. coli* transformants were then inoculated into the liquid Luria broth media (Fisher Scientific, Pittsburgh, Pa.) and grown at 37° C. and 250 rpm. Plasmids were isolated from *E. coli* using the QIAprep Spin Miniprep Kit (QIAGEN). These plasmids were transformed into the L2612 strain individually to yield the following strains: SL01 (contained the plasmid harboring the NCU00801 cellodextrin transporter gene and the NCU00130 β-glucosidase gene from *Neurospora crassa*), SL02 (contained the plasmid harboring the NCU00809 cellodextrin transporter gene and the NCU00130 β-glucosidase gene from *Neurospora crassa*), SL03 (contained the plasmid harboring the NCU08114 cellodextrin transporter gene and the NCU00130 β-glucosidase gene from *Neurospora crassa*), SL04 (contained the plasmid harboring the NCU00801 cellodextrin transporter gene and the BGL1 gene from *Aspergillus aculeatus*), SL05 (contained the plasmid harboring the NCU00809 cellodextrin transporter gene and the BGL1 gene from *Aspergillus aculeatus*), and SL06 (contained the plasmid harboring the NCU08114 cellodextrin transporter gene and the BGL1 gene from *Aspergillus aculeatus*). The empty pRS425 plasmid was transformed into the L2612 strain to yield the SL00 strain, which was used as a negative control. Yeast transformation was carried out using the standard lithium acetate method (Gietz et al., 1995). The resulting transformation mixtures were plated on SC-Ura-Leu medium supplemented with 2% D-glucose.

To confirm the proper construction of plasmids using the DNA assembler method, plasmids were isolated from yeast cells using the Zymoprep Yeast Plasmid Miniprep II kit (Zymo Research, Orange, Calif.) and then transferred into *E. coli* DH5α cells. The resulting cells were spread on LB plates containing 100 mg/L ampicillin. Single *E. coli* colonies were inoculated into the LB liquid media. Plasmids were isolated from *E. coli* using the QIAprep Spin Miniprep Kit (QIAGEN, Valencia, Calif.) and checked by diagnostic PCR or restriction digestion using ClaI and HindIII. All restriction enzymes were obtained from New England Biolabs (Ipswich, Mass.). All chemicals were purchased from Sigma Aldrich or Fisher Scientific.

Figure 65:
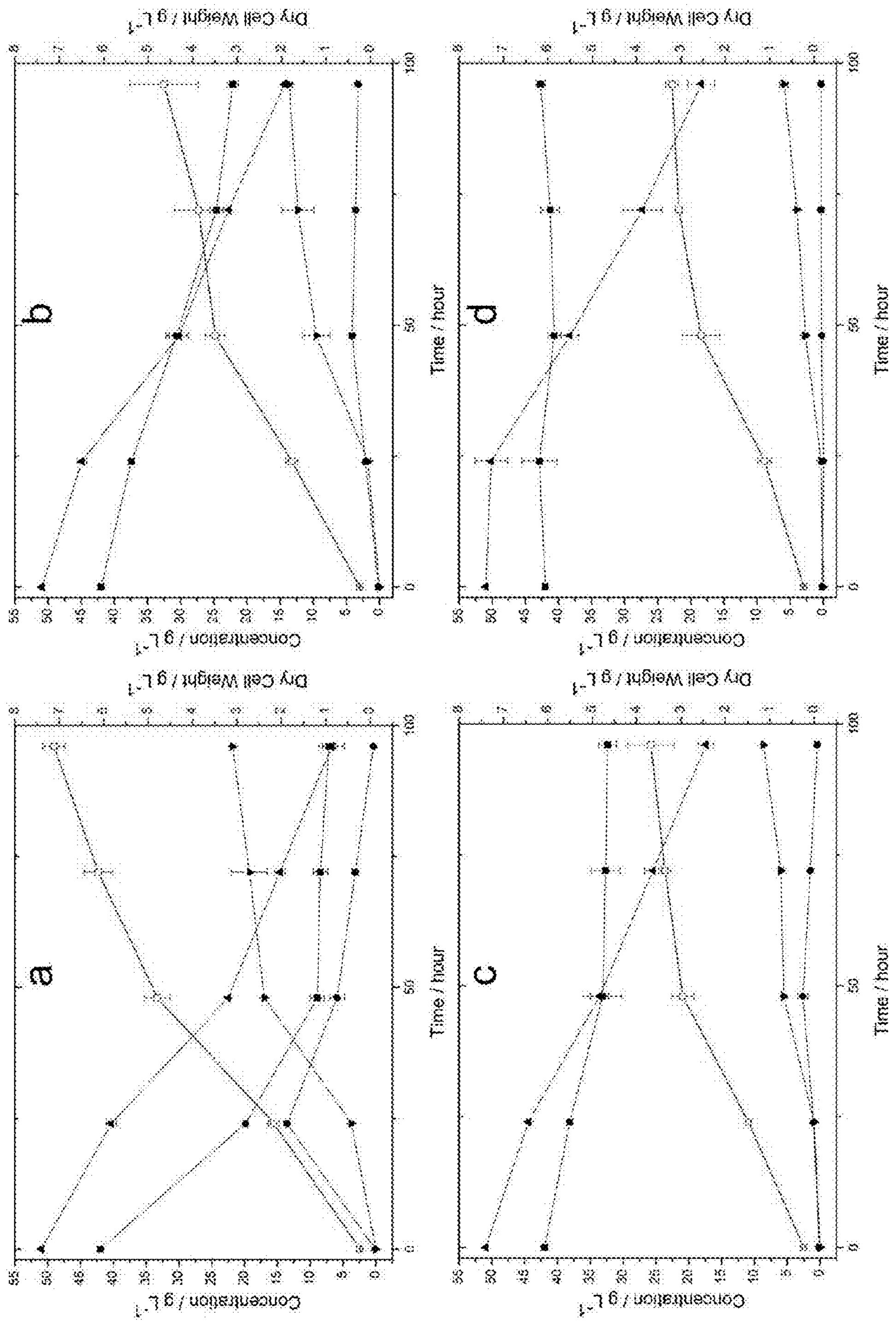
FIG. 65 shows the change in concentrations of cellobiose (■), glucose (●), D-xylose (▲), ethanol (▼), and biomass (□) during co-fermentation of 4% cellobiose and 5% D-xylose by *S. cerevisiae* strains (a) SL01, (b) SL04, (c) SL02, (d) SL05, (e) SL03, (f) SL06, and (g) SL00 as a function of time.
Figure 65:
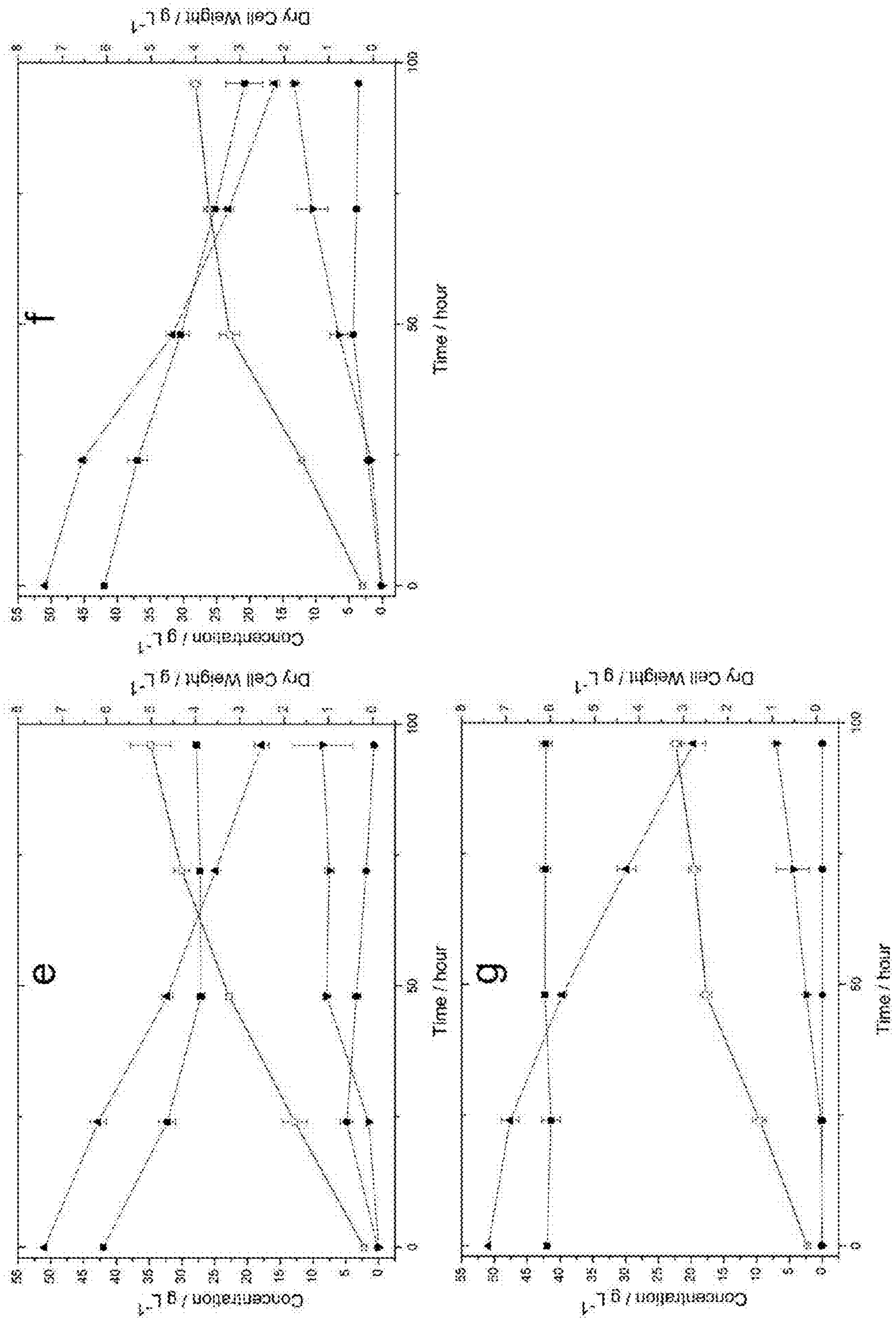

For each yeast strain, single colony was first grown up in 2 mL SC-Ura-Leu medium plus 2% glucose, and then inoculated into 50 mL of the same medium in a 250 mL shake flask to obtain enough cells for mixed sugar fermentation studies. After one day of growth, cells were spun down and inoculated into 50 mL of YPA medium supplemented with 4% cellobiose and 5% D-xylose, or 4% cellobiose, 5% xylose, and 0.5% glucose, or 4% cellobiose, 5% xylose, and 1% glucose in a 250 mL unbaffled shake-flask. Starting from an initial $OD_{600}$~1, cell culture was grown at 30° C. at 100 rpm for fermentation under oxygen limited condition. $OD_{600}$ reading and cell culture sample were taken at various time points. Sugar concentrations were analyzed using HPLC, while ethanol formation was analyzed using the Ethanol Kit (R-biopharm, Darmstadt, Germany). For each data point, triplicate samples were taken. The mixed sugar fermentation results for the strains ranging from SL00 to SL06 are shown in FIG. 65. The best strain SL01 was selected for further characterization.

A total of six different strains, ranging from SL01 to SL06, were constructed by introducing a pRS425 plasmid harboring one of the cellodextrin transporter genes and one of the β-glucosidase genes into the L2612 strain. In each plasmid, the cellodextrin transporter gene and the β-glucosidase gene were added with a yeast promoter and terminator, respectively, and assembled into the pRS425 multi-copy plasmid by the DNA 10 assembler method (Shao et al., 2009) (FIG. 64). The empty pRS425 plasmid was introduced into the L2612 strain to yield the SL00 strain, which was used as a negative control. All strains were cultivated with a mixture of 40 g/L cellobiose and 50 g/L D-xylose in shake-flasks, and their sugar consumption rates, cell growth rates, and ethanol titers were determined (FIG. 65). Amongst all strains, the SL01 strain containing the β-glucosidase from *Neurospora crassa* and the cellodextrin transporter NCU00801 showed the highest sugar consumption rate and ethanol productivity. Thus, this strain was selected for further characterization.

Both SL01 and SL00 were cultivated using a mixture of 40 g/L cellobiose and 50 g/L D-xylose in both shake-flasks and bioreactors (FIG. 66). In the shake-flask cultivation (FIG. 66*a-b*), 83% cellobiose was consumed in 96 hours by SL01, with 41.2% higher average D-xylose consumption rate compared to SL100 (from 0.33 g/L/h to 0.46 g/L/h). Consistent with the enhanced sugar consumption rate, 1.32-fold increased average biomass growth rate was observed (from 0.031 g dry cell weight/L/h to 0.072 g dry cell weight/L/h). The ethanol productivity was increased by more than 2.1-fold, from 0.07 g/L/h to 0.23 g/L/h. The highest ethanol yield of 0.31 g per g sugar was reached in 48 hours, and the average ethanol yield was 0.28 g per g sugar, representing a 23% increase compared to the SL00 strain. In the SL01 cultivation, a faster D-xylose consumption rate was observed, without the lag phase that is the hallmark of glucose repression in co-fermentation of glucose and D-xylose. Moreover, enhanced biomass growth and ethanol production were also observed.

The Multifors system (Infors-HT, Bottmingen, Switzerland) was used for mixed sugar fermentation in bioreactors. Each vessel had a total capacity volume of 750 mL. For each vessel, there was one individual set of $pO_2$ sensor, air sparger, exit gas cooler, temperature sensor, inoculation port, spare port, dip tube, antifoam sensor, pH sensor, drive shaft, heater block, rotameter, and peristaltic pumps system. The whole bioreactor system was equipped with a cooling system, ThermoFlex900 (Thermo Scientific, Waltham, Mass.).

Single colonies of yeast strains were first grown up in 2 mL SC-Ura-Leu medium plus 2% glucose, and then inoculated into 50 mL of the same medium in a 250 mL shake flask to obtain enough cells for mixed sugar fermentation studies. After one day of growth, 10 mL saturated culture were inoculated in 400 mL YPA medium supplemented with 4% cellobiose and 5% D-xylose, or 4% cellobiose, 5% xylose, and 0.5% glucose, or 4% cellobiose, 5% xylose, and 1% glucose. The temperature was maintained at 30° C. and the pH was maintained at 5.5, adjusted by addition of either 2 $NH_2SO4$ or 4 N NaOH. In the first 48 hours, the air flow rate was maintained at 0.5 L/min, with the impeller speed at 250 rpm. Afterwards, the air flow rate was adjusted to 0.2 L/min to achieve high ethanol production under oxygen limited condition. Triplicate samples were taken at various time points and the $OD_{600}$, sugar concentration, and ethanol concentration were determined as described above.

In the bioreactor cultivation (FIG. 66*c-d*), almost all cellobiose and 66% D-xylose were consumed in 48 hours, representing 44% increased D-xylose consumption rate (from 0.47 g/L/h to 0.68 g/L/h) and 1.1-fold increased biomass growth rate (from 0.08 g dry cell weight/L/h to 0.17 g dry cell weight/L/h). The ethanol productivity was increased by more than 4.3-fold (from 0.09 g/L/h to 0.50 g/L/h), and the ethanol yield was 0.39 g per g sugar. Compared to shake-flask cultivations, sugar consumption rates in the first 24 hours were lower, which was due to the low cell density used in the beginning of batch cultivation.

Figure 66A:
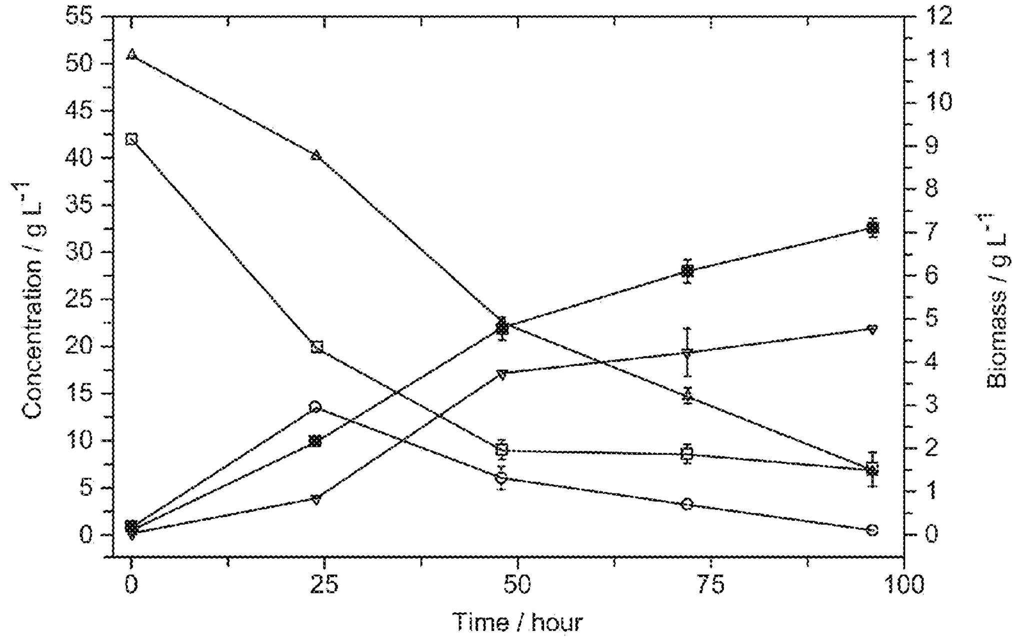
FIG. 66A shows *S. cerevisiae* strain SL01 grown in cellobiose-xylose mixtures in shake-flasks.
Figure 66B:
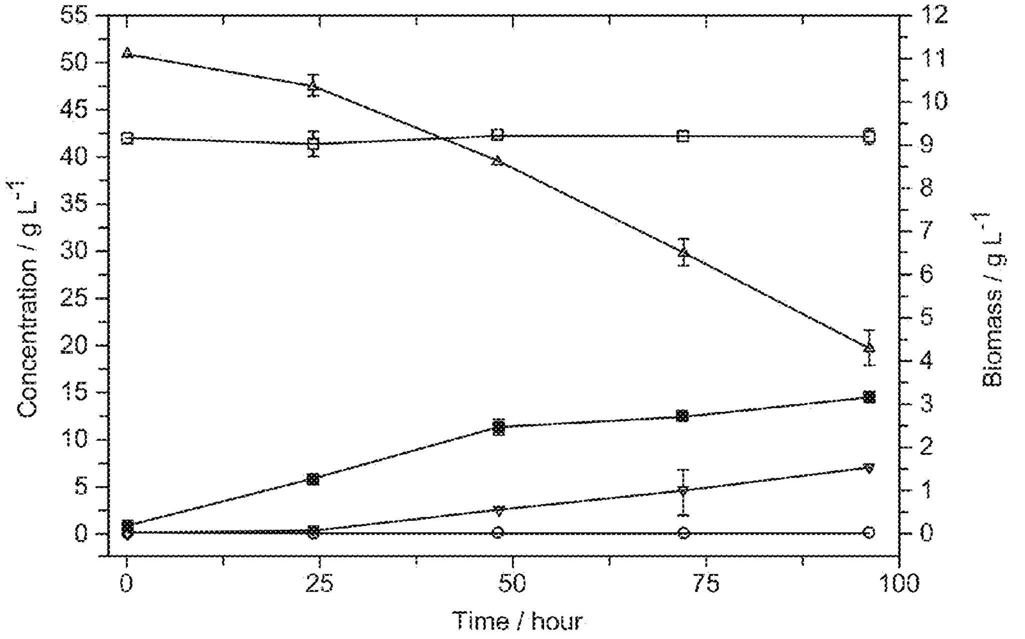
FIG. 66B shows *S. cerevisiae* strain SL00 grown in cellobiose-xylose mixtures in shake-flasks.
Figure 66C:
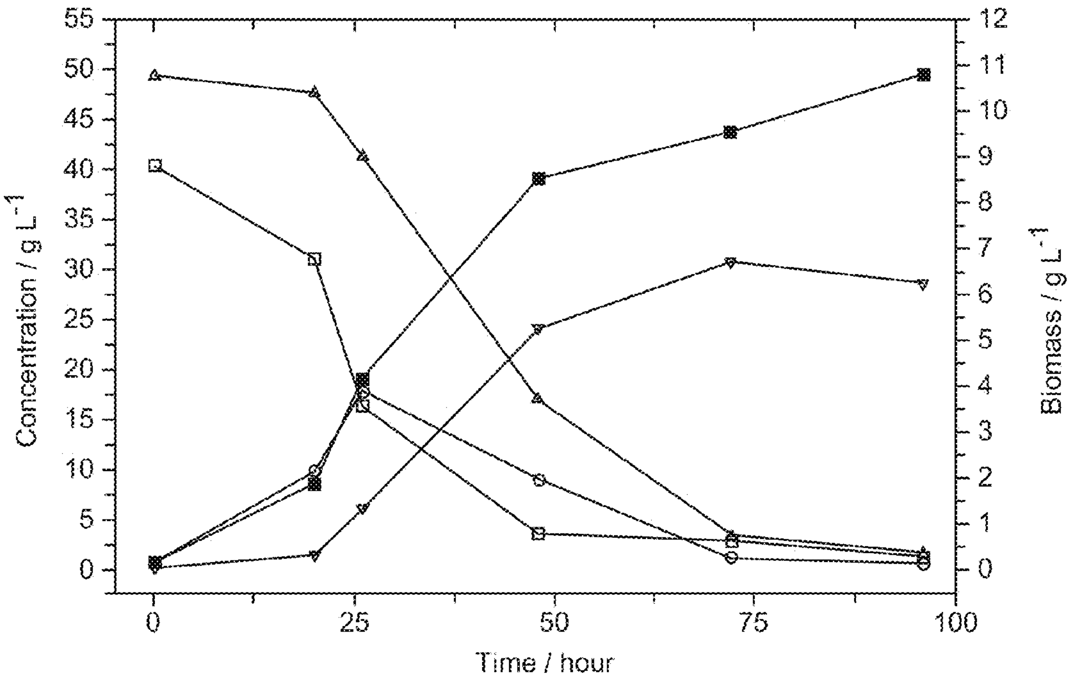
FIG. 66C shows *S. cerevisiae* strain SL01 grown in cellobiose-xylose mixtures in bioreactors.
Figure 66D:
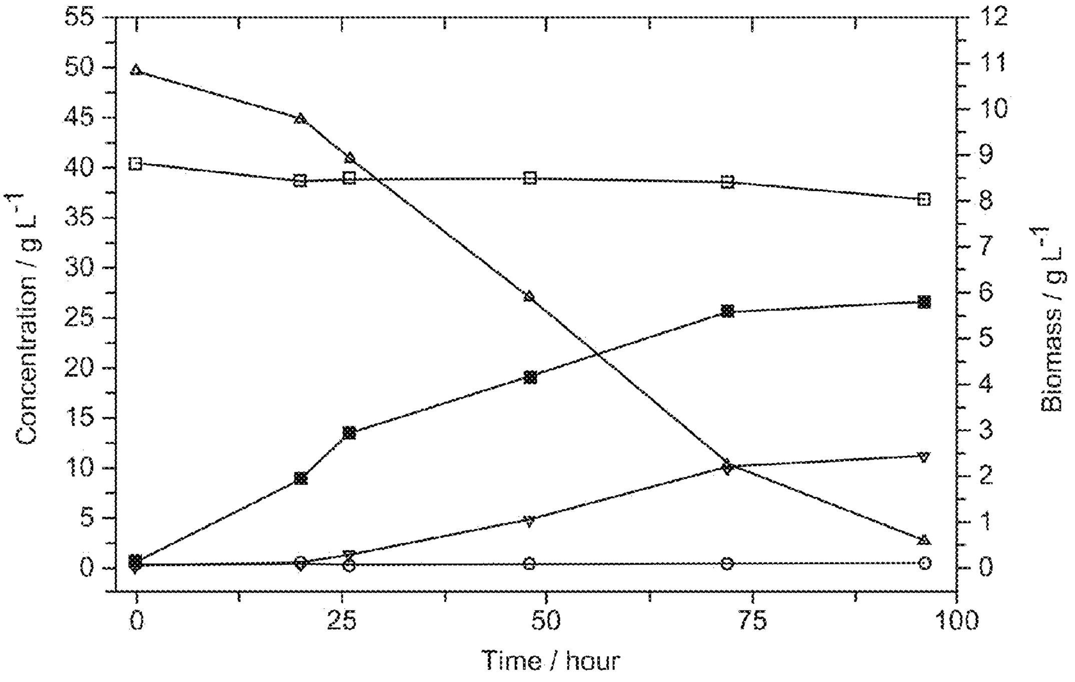
FIG. 66D shows *S. cerevisiae* strain SL00 grown in cellobiose-xylose mixtures in bioreactors.

Unexpectedly, a small amount of glucose was detected even though there was no glucose added in fermentation (FIG. 66*a-b*). The maximum glucose concentration was reached in approximately 24 hours in both shake-flasks (12.1 g/L) and bioreactors (17.5 g/L) and then dropped to a very low level. However, no obvious glucose repression was observed even in the presence of such glucose. Because no glucose was detected in the SL00 strain, the extracellular glucose may result from the slow conversion of β-glucose to its epimer α-glucose, the main form of glucose used in glycolysis. Typically, β6-glucose can be efficiently converted to α-glucose either enzymatically or chemically because of its relatively low concentration in glucose (Bouffard et al., 1994). However, in the engineered SL01 strain, catalyzed by β-glucosidase, an excess amount of β-glucose is produced from cellobiose intracellularly and a small fraction may be secreted outside cells, similar to what was observed with β-galactose (Bouffard et al., 1994).

Figure 67A:
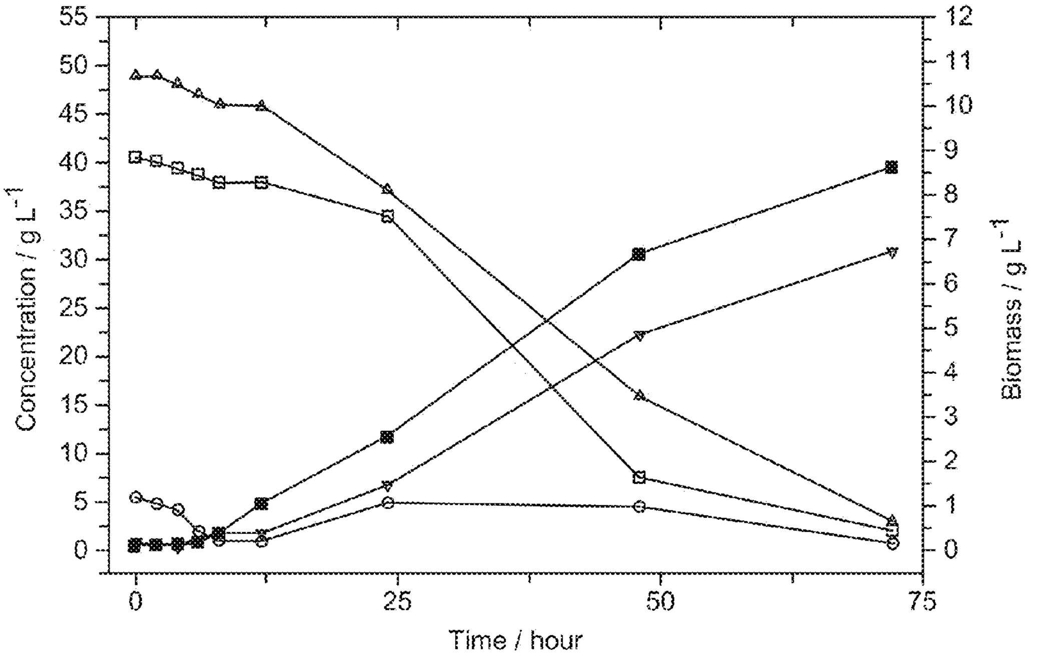
FIG. 67A shows *S. cerevisiae* strain SL01 grown in media containing 5 g/L glucose-40 g/L cellobiose-50 g/L xylose mixture.
Figure 67B:
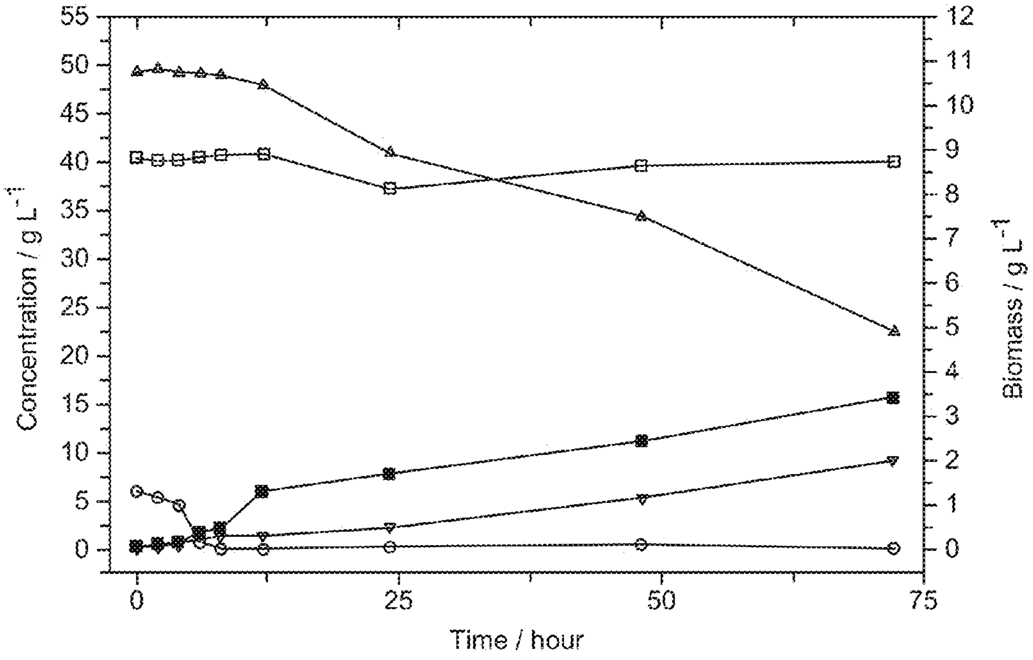
FIG. 67B shows *S. cerevisiae* strains SL00 grown in media containing 5 g/L glucose-40 g/L cellobiose-50 g/L xylose mixture.
Figure 67C:
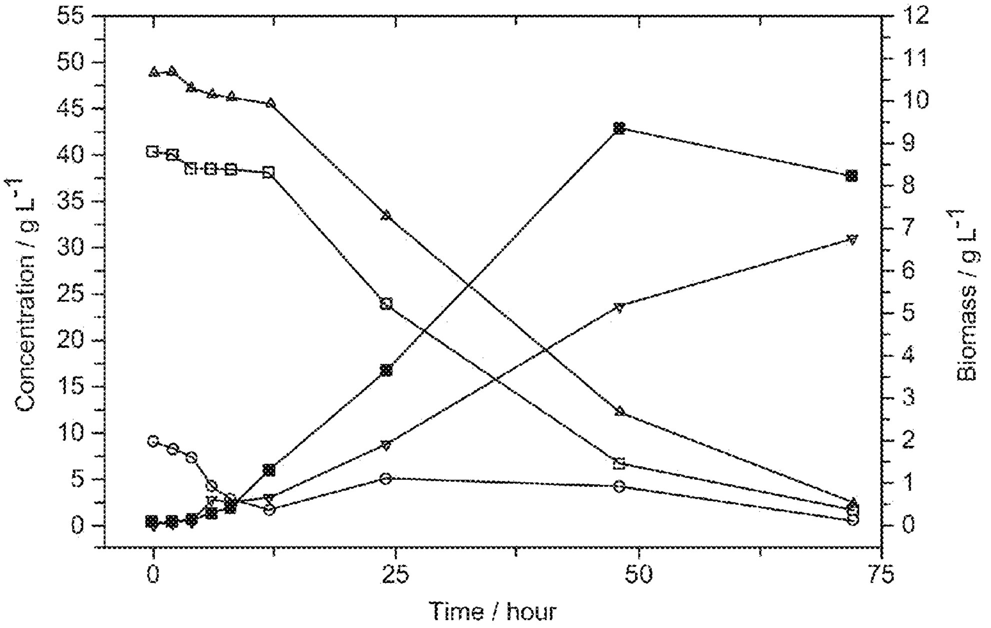
FIG. 67C shows *S. cerevisiae* strain SL01 grown in media containing 10 g/L glucose-40 g/L cellobiose-50 g/L xylose mixture.
Figure 67D:
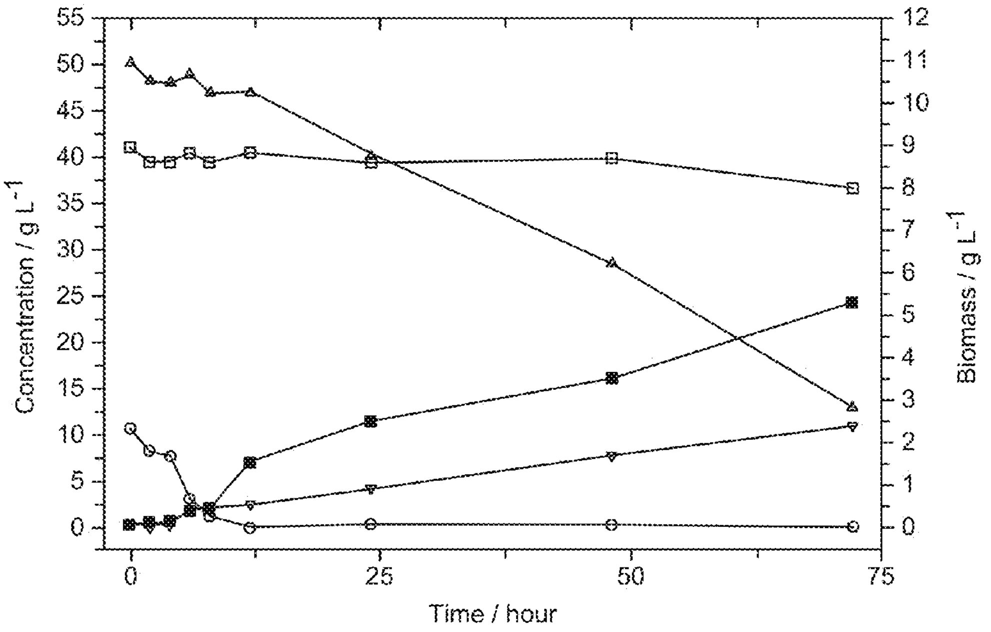
FIG. 67D shows *S. cerevisiae* strains SL00 grown in media containing 10 g/L glucose-40 g/L cellobiose-50 g/L xylose mixture.

Because a small amount of glucose (less than 10% of total sugars) is typically present in lignocellulosic hydrolysates in industrial settings, the fermentation performance of the engineered SL01 strain was also investigated using a mixture of cellobiose, D-xylose, and glucose. Two concentrations of glucose, 5 g/L or 10 g/L, were combined with 40 g/L cellobiose and 50 g/L D-xylose as mixed carbon source in bioreactors. With 5 g/L glucose (FIG. 67*a-b*), 81.7% cellobiose was consumed by SL01, with 67.8% D-xylose consumed at 48 hours in batch cultivation. The D-xylose consumption rate was increased by 1.19-fold, from 0.32 g/L/h to 0.69 g/L/h. The ethanol productivity was increased by 3.3-fold (from 0.11 g/L/h to 0.46 g/L/h) while the ethanol yield was increased from 0.26 g per g sugar to 0.33 g per g sugar. With 10 g/L glucose (FIG. 67*c-d*), 83.8% cellobiose was consumed by SL01, with 74.7% D-xylose consumed at 48 hour in batch cultivation. The D-xylose consumption rate was increased by 68%, from 0.45 g/L/h to 0.76 g/L/h. The ethanol productivity was increased by 2.1-fold (from 0.16 g/L/h to 0.50 g/L/h) and the ethanol yield was increased from 0.30 g per g sugar to 0.33 g per g sugar. As expected, the engineered SL01 strain showed both a higher efficiency of sugar consumption and a higher rate of ethanol production than the SL00 wild type strain. More importantly, there was no significant glucose repression in the co-fermentation of three sugars even with glucose up to 10% of total sugars (FIG. 67*c-d*) suggesting that this approach may be viable for industrial applications.

A similar study was carried out in the *S. cerevisiae* strain D452-2, where the three *N. crassa* cellodextrin transporters NCU00801, NCU08114, and NCU00809 were introduced together with the β-glucosidase NCU00130. The transformants were selected on YSC medium containing 20 g/liter cellobiose expressing an intracellular β-glucosidase (NCU00130). Strains and plasmids used in this work are described in Table 17 (Ex. 12). The primers used are listed in Table 28.

Table 28 shows the synthetic oligonucleotides used in the study.

| Name | Sequences |
|---|---|
| NCU00801-F | ATGGATCCAAAAATGTCGTCTCACGGCTCC SEQ ID NO: 92 |
| NCU00801-R | ATGAATTCCTACAAATCTTCTTCAGAAATCAATTTTT GTTCAGCAACGATAGCTTCGGAC SEQ ID NO: 93 |
| NCU08114-F | ATACTAGTAAAAATGGGCATCTTCAACAAGAAGC SEQ ID NO: 94 |
| NCU08114-R | GCATATCGATCTACAAATCTTCTTCAGAAATCAATTT TTGTTCAGCAACAGACTTGCCCTCATG SEQ ID NO: 95 |
| NCU00130-F | GCATACTAGTAAAAATGTCTCTTCCTAAGGATTTCCT CT SEQ ID NO: 96 |
| NCU00130-R | ATACTGCAGTTAATGATGATGATGATGATGGTCCTTC TTGATCAAAGAGTCA AAG SEQ ID NO: 97 |

Yeast were grown in YP medium containing 20 g/L of glucose or 20 g/L of cellobiose to prepare inoculums for xylose or cellobiose fermentation experiments, respectively. Cells at mid-exponential phase from YP media containing 20 g/L of glucose or cellobiose were harvested and inoculated after washing twice with sterilized water. All of the flask fermentation experiments were performed using 50 mL of YP medium containing 40 g/L or 80 g/L of xylose in 250 mL flask at 30° C. with initial $OD_{600}$ of 1.0 under oxygen limited conditions. Bioreactor fermentations were performed in 400 mL of YP medium containing appropriate amounts of sugars using Sixfors Bioreactors (Appropriate Technical Resources, Inc) at 30° C. with an agitation speed of 200 rpm under oxygen limited 250 conditions. Initial cell densities were adjusted to $OD_{600}$=1.0.

Cell growth was monitored by optical density (OD) at 600 nm using UV-visible Spectrophotometer (Biomate 5, Thermo, N.Y.). Glucose, xylose, xylitol, glycerol, acetate, and ethanol concentrations were determined by high performance liquid chromatography 264 (HPLC, Agilent Technologies 1200 Series) equipped with a refractive index detector using 265 a Rezex ROA-Organic Acid H+ (8%) column (Phenomenex Inc., Torrance, Calif.). The column was eluted with 0.005 N of $H_2SO_4$ at a flow rate of 0.6 mL/min at 50° C.

Figure 68A:
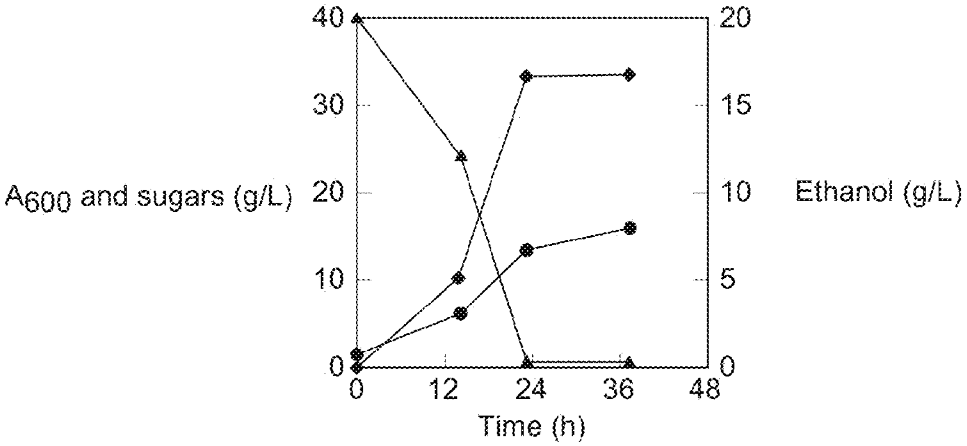
FIG. 68A shows NCU00801.
Figure 68B:
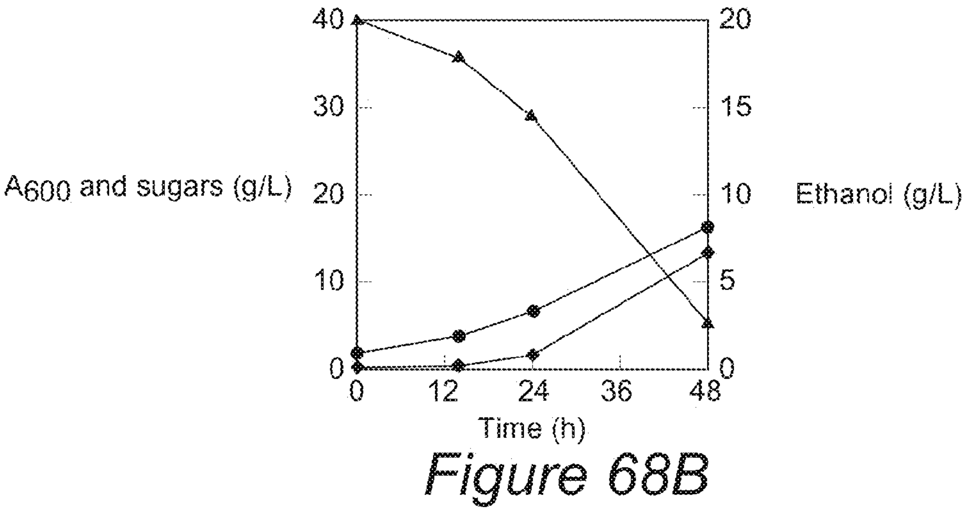
FIG. 68B shows NCU00809.
Figure 68C:
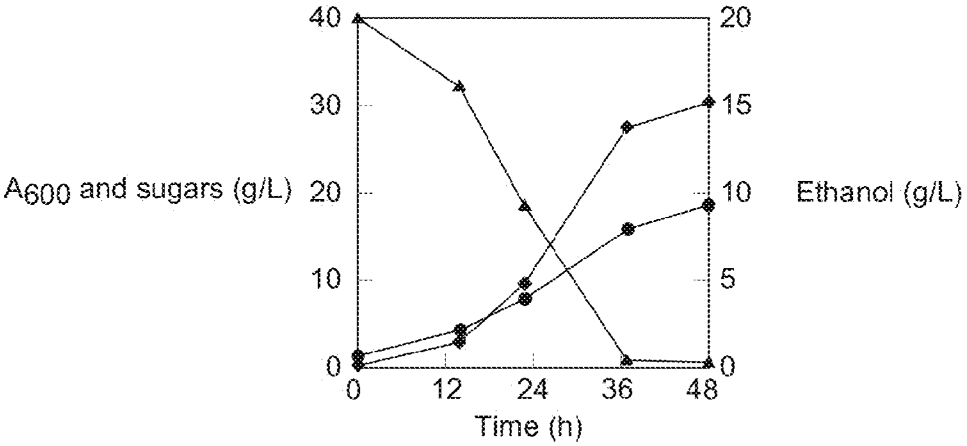
FIG. 68C shows NCU08114.

All three transformants were able to grow and produce ethanol when cellobiose was the sole carbon source (FIG. 68), but the three transformants exhibited different cellobiose fermentation rates (NCU00801>NCU08114>NCU00809). The fastest cellulose-fermenting transformant (D801-130), expressing both NCU00801 and NCU00130, consumed 40 g/L of cellobiose within 4 hours, producing 16.8 g/L of ethanol. The volumetric productivity of cellobiose fermentation ($P_{Ethanol/Cellobiose}$=0.7 g/L/h) was lower than that of glucose fermentation ($P_{Ethanal/Glucose}$=1.2 g/L/h), and ethanol yield from cellobiose ($Y_{Ethanol/Cellobiose}$=0.42 g/g) was about the same as ethanol yield from glucose ($Y_{Ethanal/Glucose}$=0.43 g/g) under the same culture conditions. However, the observed cellobiose consumption rate and ethanol yield by D801-130 were an improvement over *S. cerevisiae* strains engineered to ferment cellobiose through surface display of β-glucosidase (Kotaka et al., 2008; Nakamura et al., 2008). These results suggest that simultaneous expression of NCU00801 and NCU00130 in *S. cerevisiae* can result in efficient cellobiose fermentation.

After developing the efficient xylose fermenting strain DA24-16 (described in Example 13), genes coding cellodextrin transporter and β-glucosidase (NCU00801 and NCU00130) enzyme were introduced into the strain enabling it to consume cellobiose and xylose simultaneously. It was hypothesized that glucose repression of xylose utilization may be alleviated in this strain, due to the intracellular hydrolysis of cellobiose. The NCU00801 gene was integrated into the genome of DA24-16, and NCU00130 was expressed from a multi-copy plasmid. The resulting transformant, DA24-16-BT3, was selected on an agar plate containing cellobiose as the sole carbon source.

Figure 69A:
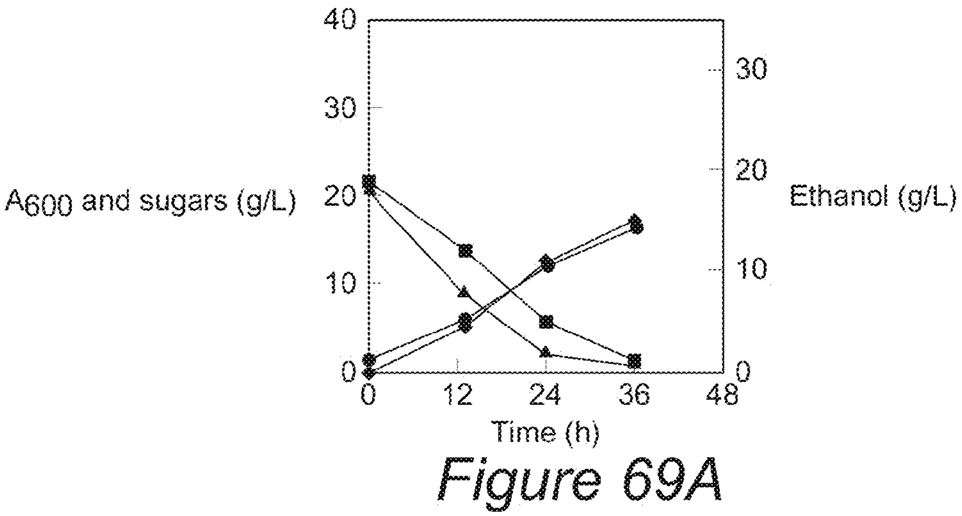
FIG. 69A shows 20 g/L (each) of cellobiose and xylose.
Figure 69B:
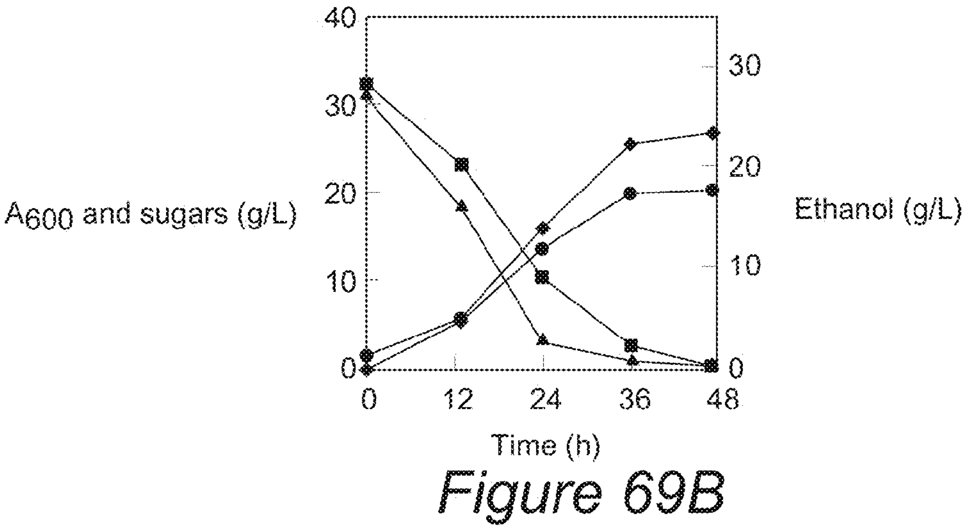
FIG. 69B shows 30 g/L (each) of cellobiose and xylose.
Figure 69C:
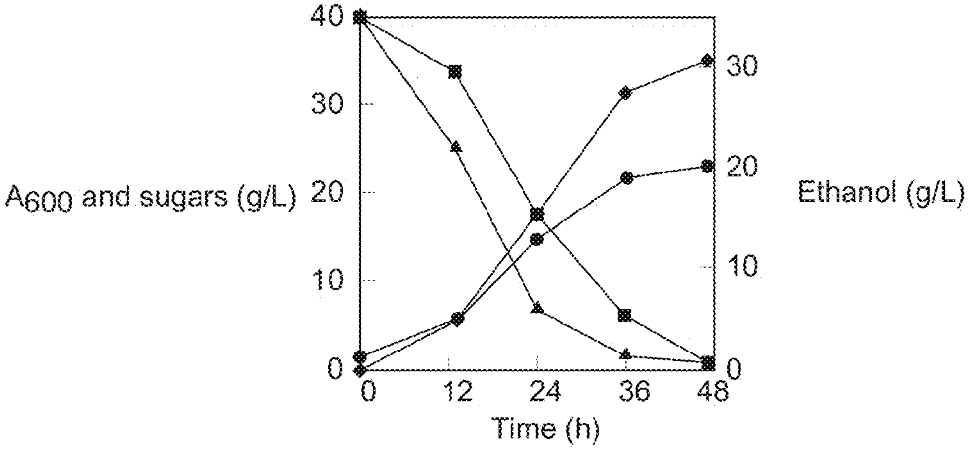
FIG. 69C shows 40 g/L (each) of cellobiose and xylose.
Figure 70A:
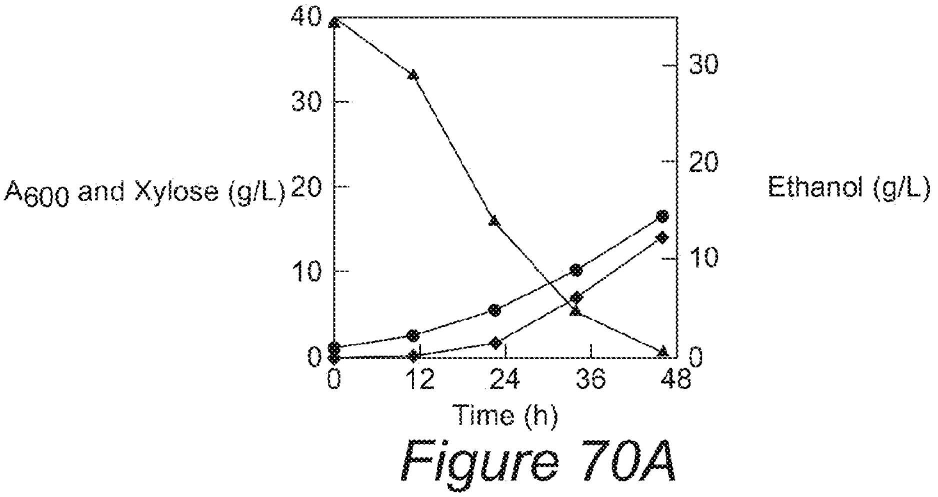
FIG. 70A shows 40 g/L cellobiose.
Figure 70B:
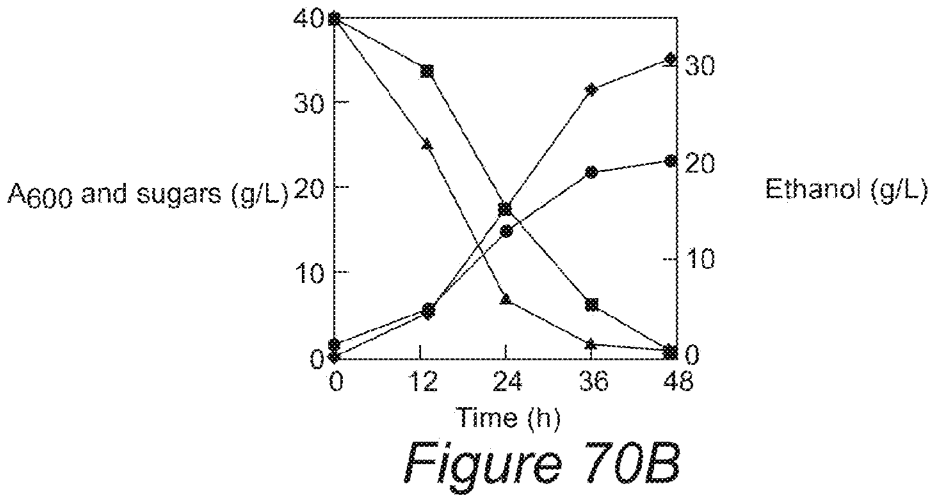
FIG. 70B shows 40 g/L (each) of cellobiose and xylose.
Figure 70C:
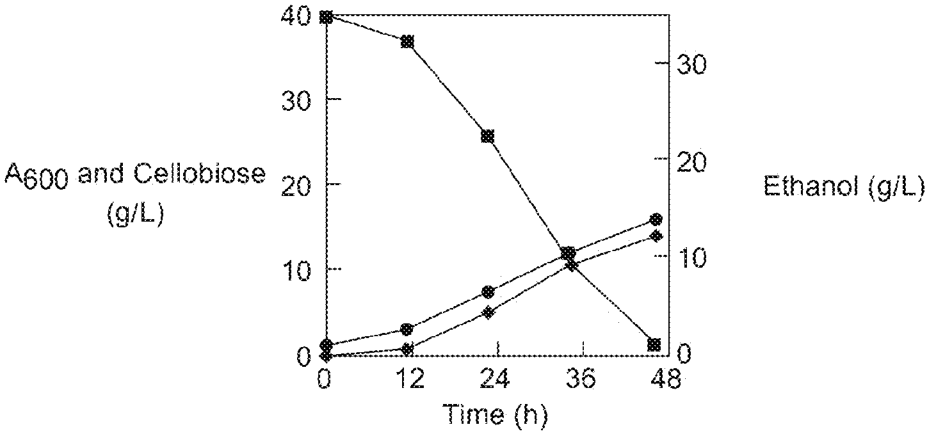
FIG. 70C shows 40 g/L xylose.

The DA24-16-BT3 strain grown in media containing various amounts of cellobiose and xylose co-consumed cellobiose and xylose, and produced ethanol with yields of 0.38-0.39 g/g in all conditions tested (FIG. 69). The potential synergistic effects of co-fermentation were tested by culturing DA2416-BT3 under three different conditions: 40 g/L of cellobiose, 40 g/L of xylose, and 40 g/L of both sugars (total 80 g/L of sugars). Surprisingly, DA24-16BT3 was able to co-consume 80 g/L of a cellobiose/xylose mixture within the same period that was required to consume 40 g/L of cellobiose or 40 g/L xylose separately (FIG. 70). Moreover, DA24-16BT3 produced ethanol with a higher yield (0.39 g/g) from a mixture of cellobiose and xylose as compared to ethanol yields (0.31~0.33 g/g) from single sugar fermentations (cellobiose or xylose). Ethanol productivity also drastically increased from 0.27 g/L/h to 0.65 g/L/h during co-fermentation. These results demonstrated that co-fermentation of cellobiose and xylose can enhance overall ethanol yield and productivity. Fermentation experiments were also done to compare this engineered *S. cerevisiae* strain (DA24-16BT3) to *P. stipitis*, which is capable of co-fermenting cellobiose and xylose efficiently.

A simulated hydrolysate (10 g/L of glucose, 80 g/L of cellobiose, 40 g/L of xylose) based on the composition of energycane was used. The composition of different lignocellulosic plants varies in a broad range. For instance, the US Department of Energy biomass database lists the composition of more than 150 biomass samples (webpage eere.energy.gov/biomass/m/feedstock_databases.html). The cellulose-to-hemicellulose ratios of these samples are between 1.4 and 19, and the average is 2.3. Energy crops typically have higher hemicellulose content than woody biomass. The average cellulose to hemicellulose ratios of sugarcane bagasse, corn stover, sorghum are 2.0, 1.85 and 2.14, respectively. We therefore used a glucan/xylan ratio of 2 in our simulated sugar experiment design. The engineered yeast will likely be used in conjunction with traditional cellulase cocktails that are deficient in β-glucosidase activities for the biofuels production. The biomass hydrolysis process may result in small amounts of glucose in the lignocellulosic hydrolysates as 6-30% glucan-to-glucose conversions with incomplete cellulase cocktails were reported (Medve et al., 1998). Considering all the above factors, a sugar combination of 10 g/L glucose, 80 g/L cellobiose, and 40 g/L xylose was chosen in the simulated sugar experiments.

Figure 71A:
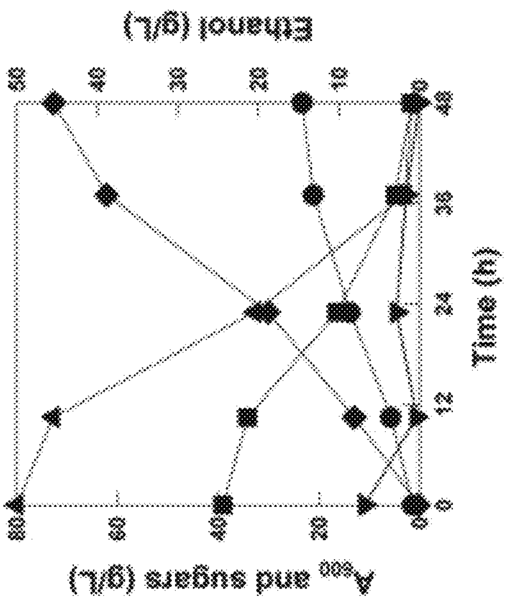
FIG. 71A shows DA24-16BT3.
Figure 71B:
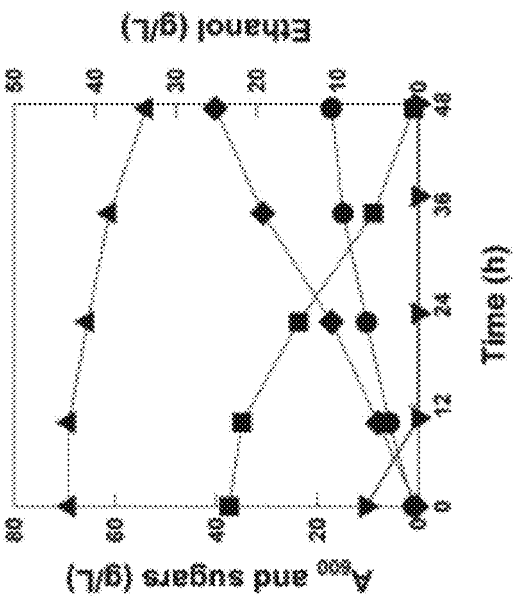
FIG. 71B shows *P. stipitis.*

The DA24-16BT3 consumed glucose first before co-consuming cellobiose and xylose rapidly. A total of 130 g/L of sugars was consumed within 60 hours even though small inoculums were used ($OD_{600}$=1). In contrast, *P. stipitis* could not finish fermenting the sugar mixture within the same period under identical culture conditions (FIG. 71). DA24-16BT3 produced 48 g/L of ethanol within 60 hours ($Y_{Ethanol/Sugars}$=0.37 g/g and $P_{Ethanol/Sugars}$=0.79 g/L/h).

Figure 72:
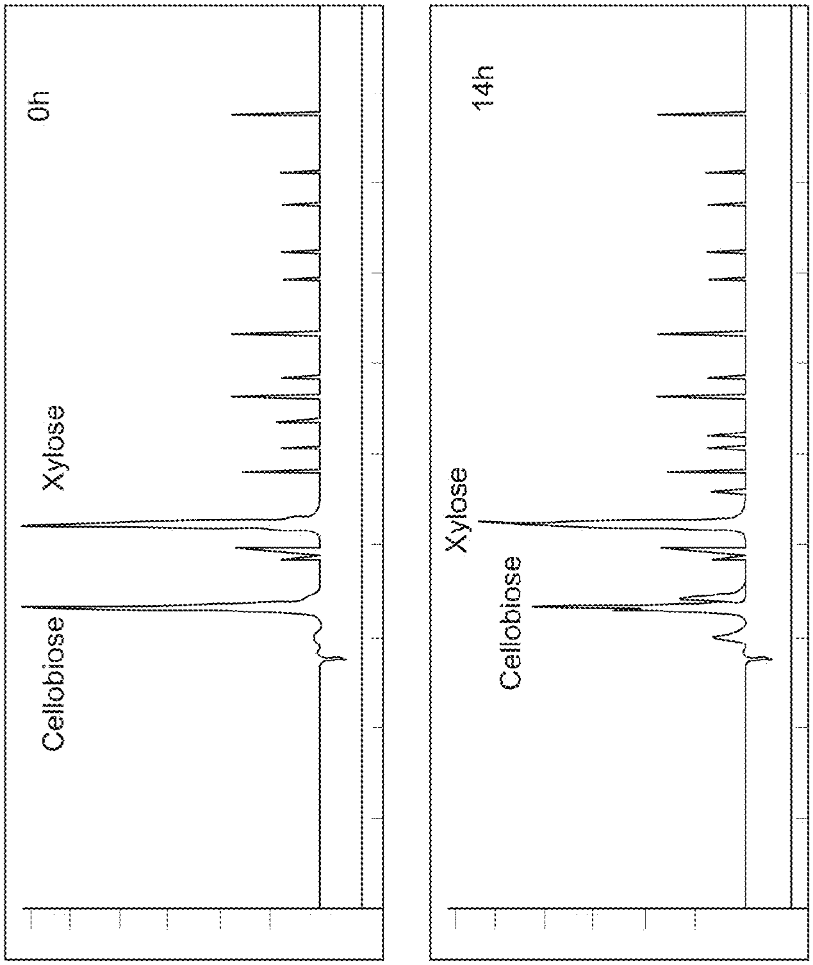
FIG. 72 shows HPLC chromatograms from each time point, suggesting cellotriose and cellotetraose accumulation during c-fermentation of cellobiose and xylose by the *S. cerevisiae* strain DA24-16BT3.
Figure 72:
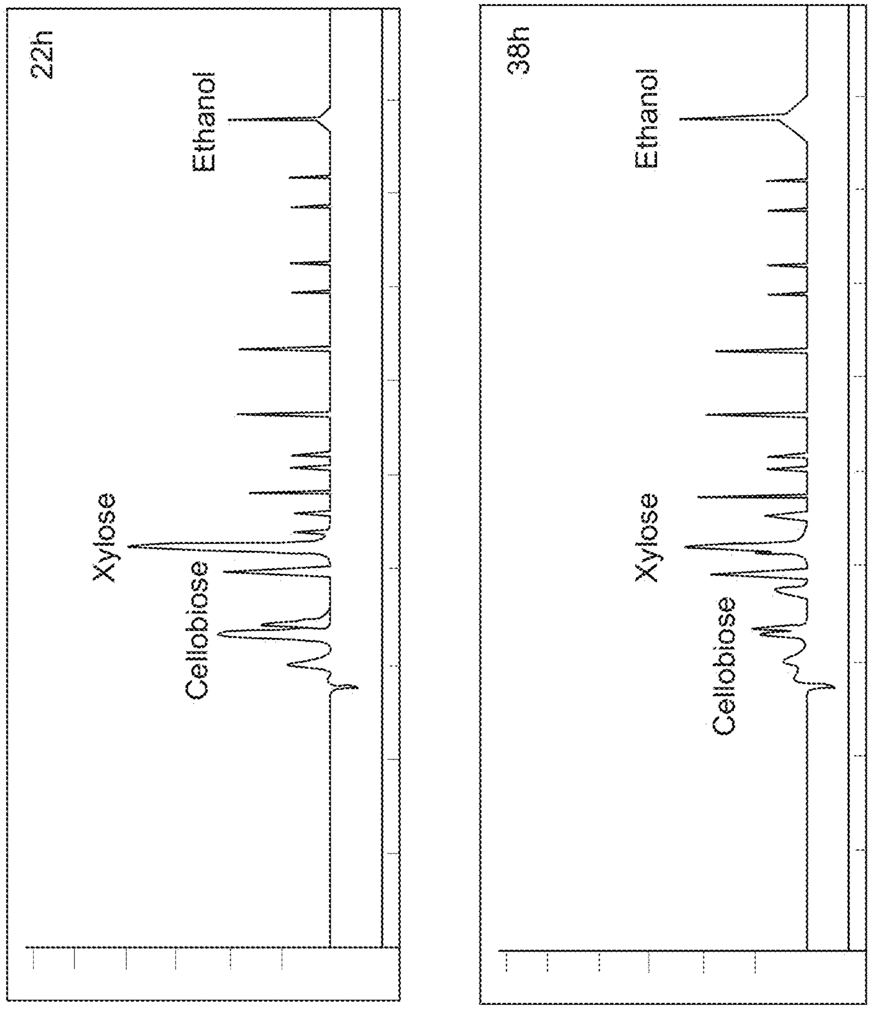
Figure 72:
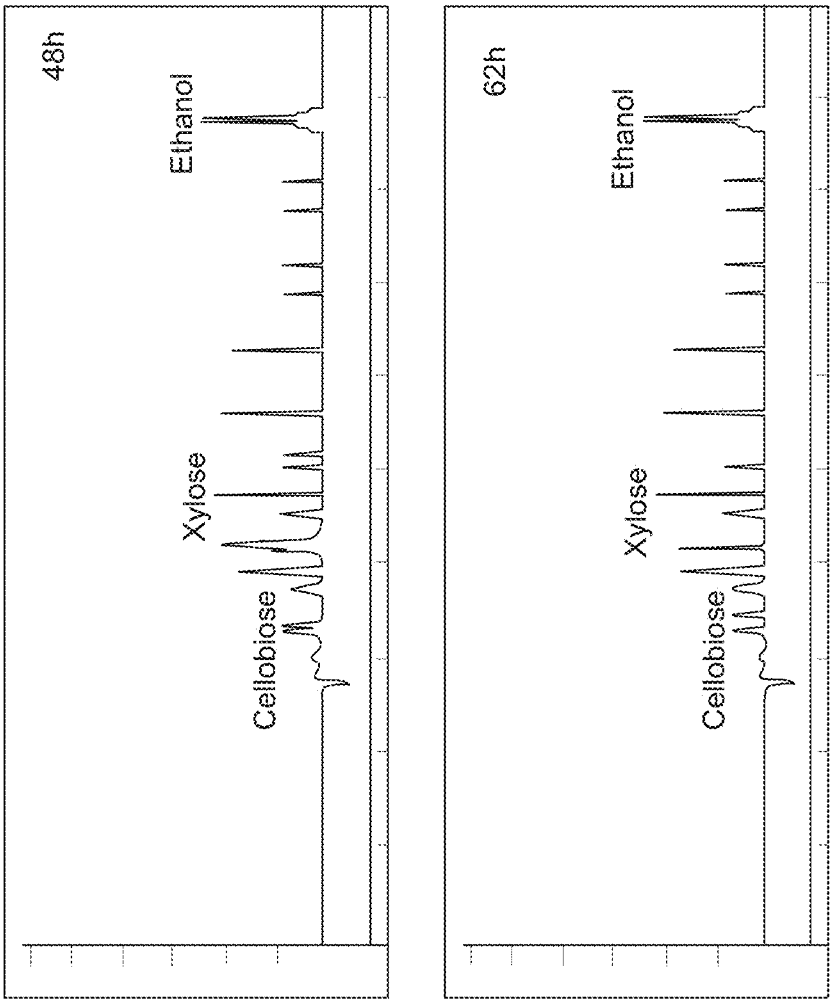
Figure 73:
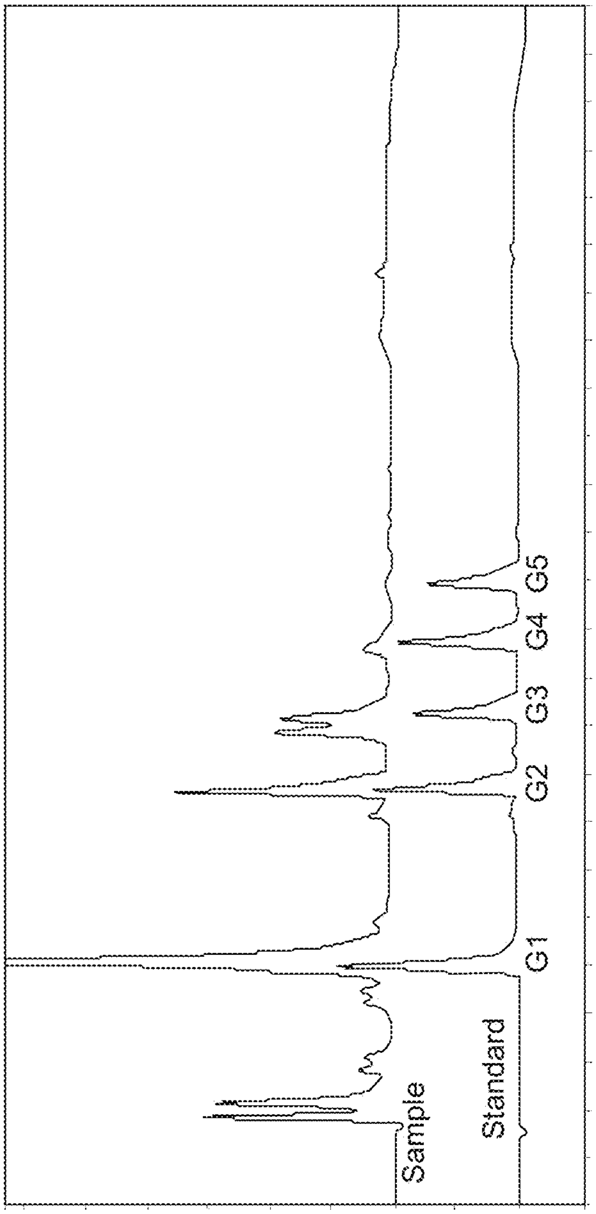
FIG. 73 shows HPAEC analysis demonstrating cellodextrin accumulation in fermentation medium after 22 hours fermentation by the *S. cerevisiae* strain DA24-16BT3 during co-fermentation of cellobiose and xylose. (G1: glucose, G2: cellobiose, G3: cellotriose, G4: cellotetraose, and G5: cellopentaose).

A transient accumulation of cellodextrins in the medium during cellobiose consumption was observed (FIG. 72-73). The accumulated cellotriose and cellotetraose were again consumed after depletion of cellobiose. It is likely that the accumulated cellodextrins were generated by the trans-glycosylation activity (Christakopoulos et al., 1994) of β-glucosidase (NCU00130), and secreted by the cellodextrin transporter (NCU00801), which might facilitate the transport of cellodextrins in both directions (intracellular↔extracellular). This transient cellodextrin accumulation would probably not reduce product yields since the accumulated cellodextrins would eventually be consumed by the engineered yeast. However, it might decrease productivity because the transport rates of cellotriose and cellotetraose might be slower than that of cellobiose.

Figure 74A:
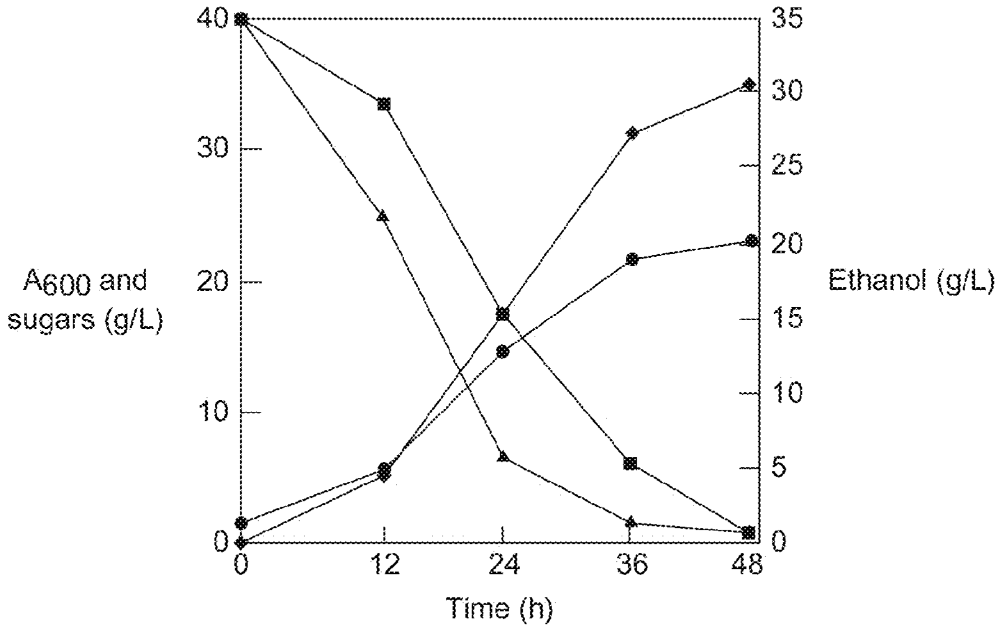
FIG. 74A shows *S. cerevisiae* transformants expressing an integrated copy of NCU00801.
Figure 74B:
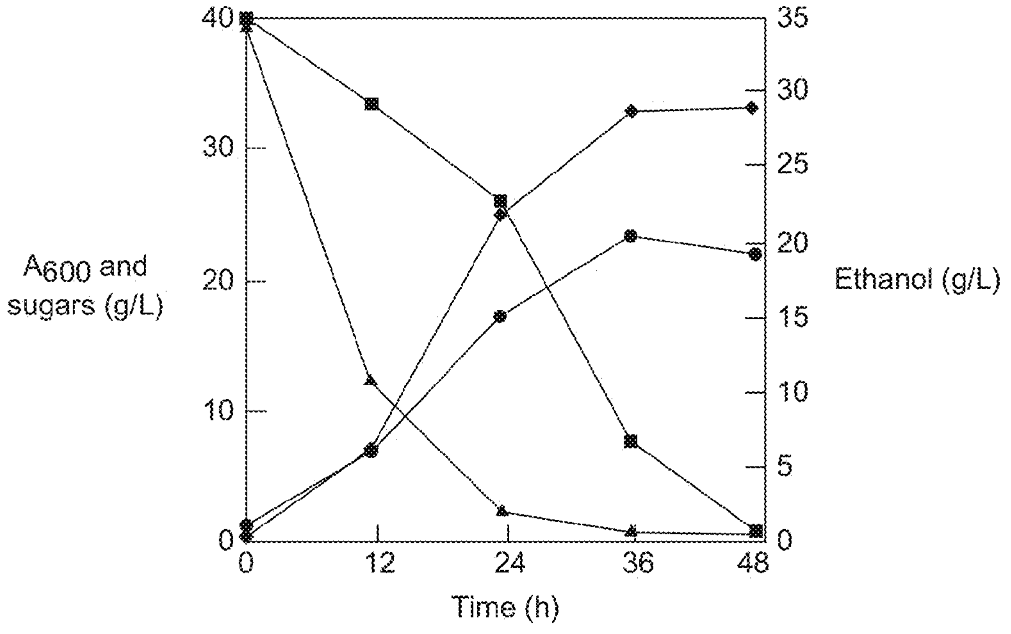
FIG. 74B shows *S. cerevisiae* transformants expressing NCU00801 on a multi-copy plasmid.

Small amounts of glucose were constantly detected in the medium during co-fermentation. Since even low amounts of glucose accumulation can repress xylose fermentation, glucose levels have to be kept at a minimum. It can be hypothesized that the relative expression levels of the cellodextrin transporter and β-glucosidase are likely to affect glucose accumulation. In support of this, it was observed that more glucose was accumulated in the medium when NCU00801 was introduced on a multi-copy plasmid than when NCU00801 was integrated into the yeast genome. The strain (DA24-16-BT). containing both NCU00801 and NCU00130 on multi-copy plasmids, had relatively slower xylose utilization rates than those observed in DA24-16-BT3, a potential reason being glucose repression (FIG. 74). Further adjustments of the cellodextrin transporter and β-glucosidase expression levels, or the identification of β-glucosidases with reduced trans-glycosylation activities, may be able to reduce the accumulation of glucose and cellodextrin during co-fermentation.

Figure 75A:
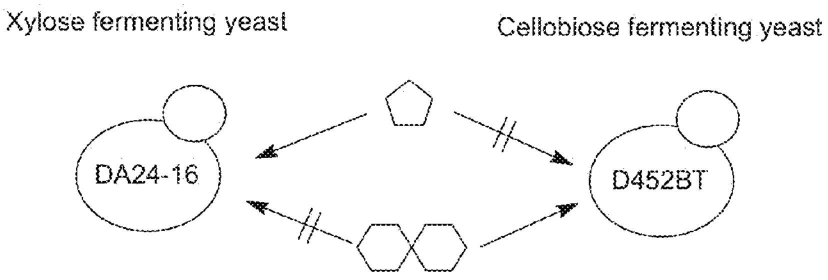
FIG. 75A shows the two different *S. cerevisiae* strains used in study: DA24-16 and D452BT. A xylose molecule is shown as a pentagon and a cellobiose molecule is shown as two hexagons.
Figure 75B:
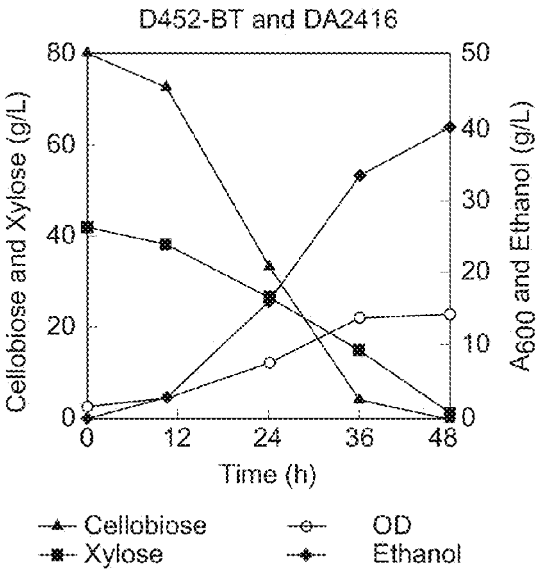
FIG. 75B shows mixed cultures of xylose-fermenting strain and cellobiose-fermenting strain.

Co-fermentation of xylose and cellobiose could also be achieved by mixed cultivation of two different yeast strains: the xylose-fermenting DA24-16 strain and the cellobiose-fermenting DA452BT (FIG. 75). As explained above, the yeast strain DA24-16 expressed the xylose-utilizing enzymes wild type xylose reductase (XYL1), mutant xylose reductase R276H (mXYL1), xylitol dehydrogenase (XYL2), and xylulokinase (XKS1) (Ex. 12; Table 17). D452BT was formed by engineering D452 to express the cellodextrin transporter NCU00801 and the β-glucosidase NCU00130. In the mixed culture, the DA24-16 strain took up xylose (xylose molecule shown as a green pentagon in FIG. 75*a*) and metabolized it using the enzymes XYL1 (wild type and mutant), XYL2, and XYL3, whereas the other strain D452BT was able to take up cellobiose (cellobiose molecule shown as two red hexagons in FIG. 75*a*) using the transporter NCU00801 and convert the cellobiose into glucose using the enzyme NCU00130. Hence, the mixed culture was able to co-ferment both xylose and cellobiose to produce ethanol (FIG. 75*b*).

This study demonstrated a novel strategy to allow co-fermentation of hexose and pentose sugars by *S. cerevisiae*. By combining an efficient xylose utilization pathway with a cellodextrin transport system, the problem caused by glucose repression was over-come. As a result, the engineered yeast co-fermented two non-metabolizable sugars in cellulosic hydrolysates synergistically into ethanol. The new co-fermentation method described herein advances lignocellulosic technologies on both the saccharification and fermentation fronts. Most traditional fungal cellulase cocktails are deficient in β-glucosidase and end the cellulose hydrolysis with cellobiose that is not fermented efficiently by yeast. As a result, extra β-glucosidase enzyme must be added to convert cellobiose into glucose. The cellobiose/xylose co-fermentation yeast makes it possible to use these cellulase cocktails with limited β-glucosidase activities, lowering enzyme usage and cost associated with the cellulose saccharification process. Further, the synergy between cellobiose and xylose co-fermentation significantly increases ethanol productivity, thus improving fermentation economics. The presence of a small amount of glucose from the pre-treatment and hydrolysis of lignocellulosic materials does not affect the capacity of the engineered yeast to convert hexose and pentose sugar mixtures into ethanol.

This study involved measuring the capacity of an engineered *S. cerevisiae* strain to ferment various mixtures of sugars meant to mimic hydrolysates from plant biomass. The ability of this strain to co-ferment cellodextrins and xylose is particularly useful during the simultaneous saccharification and co-fermentation (SSCF) of pre-treated plant biomass. During SSCF, hemicellulose would first be hydrolyzed by acid pre-treatment, resulting in formation of xylose and still-crystalline cellulose. Then, fungal cellulases and the yeast strain described herein would be added, allowing the cellulases to co-convert xylose and cellobiose into ethanol. Because of the limited extracellular glucose production in this scheme, there will be reduced repression of xylose utilization and co-fermentation will proceed rapidly and synergistically.

Although the *S. cerevisiae* strain used in this study was a laboratory strain, the fermentation performance of the engineered strain was very impressive when compared to published results. The key fermentation parameters (yield and productivity) may be further improved by the use of industrial yeast strains as a platform. Applications of this co-fermentation strategy would not be limited to ethanol production. Since it is a foundational technology, the strategy presented here can be combined with any other product diversification technologies to produce commodity chemicals and advanced biofuels.

Example 18

Transcriptome Analysis of *N. crassa* Grown on Xylan

Lignocellulosic biomass is composed of cellulose, hemicellulose, and lignin. Examples 1-3 describe the discovery of genes critical for growth on cellulose through transcriptome and secretome analysis of *N. crassa*. In this example the expression profile of the *N. crassa* genome was examined during growth on xylan to determine which genes are important for utilization of hemicellulose.

Ten day old conidia of WT or ΔxlnR strains were inoculated at $10^6$ conidia/mL on 100 mL 1× Vogel's salts minimal medium (2% sucrose), grown for 16 hours at 25° C. with constant light, and washed with 1× Vogel's only medium. Conidia were then transferred into 100 mL 1× Vogel's salts with 2% sucrose or 2% Beechwood xylan as the sole carbon source in the medium and allowed to grow for 4 hours. Mycelia were harvested by filtration and immediately flash frozen in liquid nitrogen. Total RNA was isolated using TRIzol (Invitrogen) according to the manufacturer's instructions and treated with DNase (Turbo DNA-free kit; Ambion) (Kasuga, Townsend et al., 2005).

For cDNA synthesis and labeling, the Pronto kit (Catalog No. 40076; Corning) was used according to the manufacturer's specifications except that the total RNA used was 10 μg per sample.

Microarray hybridization and data analysis were performed as previously described (Tian, Kasuga et al., 2007). A GenePix 4000B scanner (Axon Instruments) was used to acquire images, and GenePix Pro6 software was used to quantify hybridization signals and collect the raw data. Normalized expression values were analyzed by using the BAGEL (Bayesian analysis of gene expression levels) software program (Townsend and Hartl 2002; Townsend 2004). 354 genes were found to be induced greater than 2-fold in *N. crassa* grown on xylan. The list is shown in FIG. 76.

Example 19

Secretome Analysis of *N. crassa* Grown on Xylan

The secretome of *N. crassa* during growth on xylan was analyzed using a shotgun proteomics approach. Supernatants from xylan cultures were digested with trypsin and analyzed by liquid chromatography nano-electrospray ionization tandem mass spectrometry.

Mass spectrometry samples were prepared as follows. *N. crassa* wild type strain was grown on 2% xylan media for 4 or 7 days. Culture supernatants were isolated by centrifugation, filtered through 0.22 μm filters, and concentrated 10 times with 10 kDa MWCO PES spin concentrators. 3.36 mg of urea, 5 μL of 1M Tris pH 8.5, and 5 μL of 100 mM DTT were then added to 100 μL of concentrated culture supernatant, and the mixture was heated at 60° C. for 1 hour. After heating, 700 μL of 25 mM ammonium bicarbonate and 140 μL of methanol were added to the solution followed by treatment with 50 μL of 100 μg/mL trypsin in 50 mM sodium acetate pH 5.0. The trypsin was left to react overnight at 37° C. with inverting for about 8-9 hours at basal pH. After digestion the volume was reduced to dryness by speedvac and washed with 300 μl MilliQ water three times. The final volume was 1004 TFA was added at 0.1-0.3% v/v. Residual salts in the sample were removed by using OMIX microextraction pipette tips according to the manufacturer's instructions. The acetonitrile was removed by evaporation. The sample solution was an aqueous solution with 0.1%-1% TFA, and the final volume was 10 microliters or greater.

Example 20

Analysis of Xylan-Induced Genes Predicted to Encode Secreted Proteins

Figure 77:
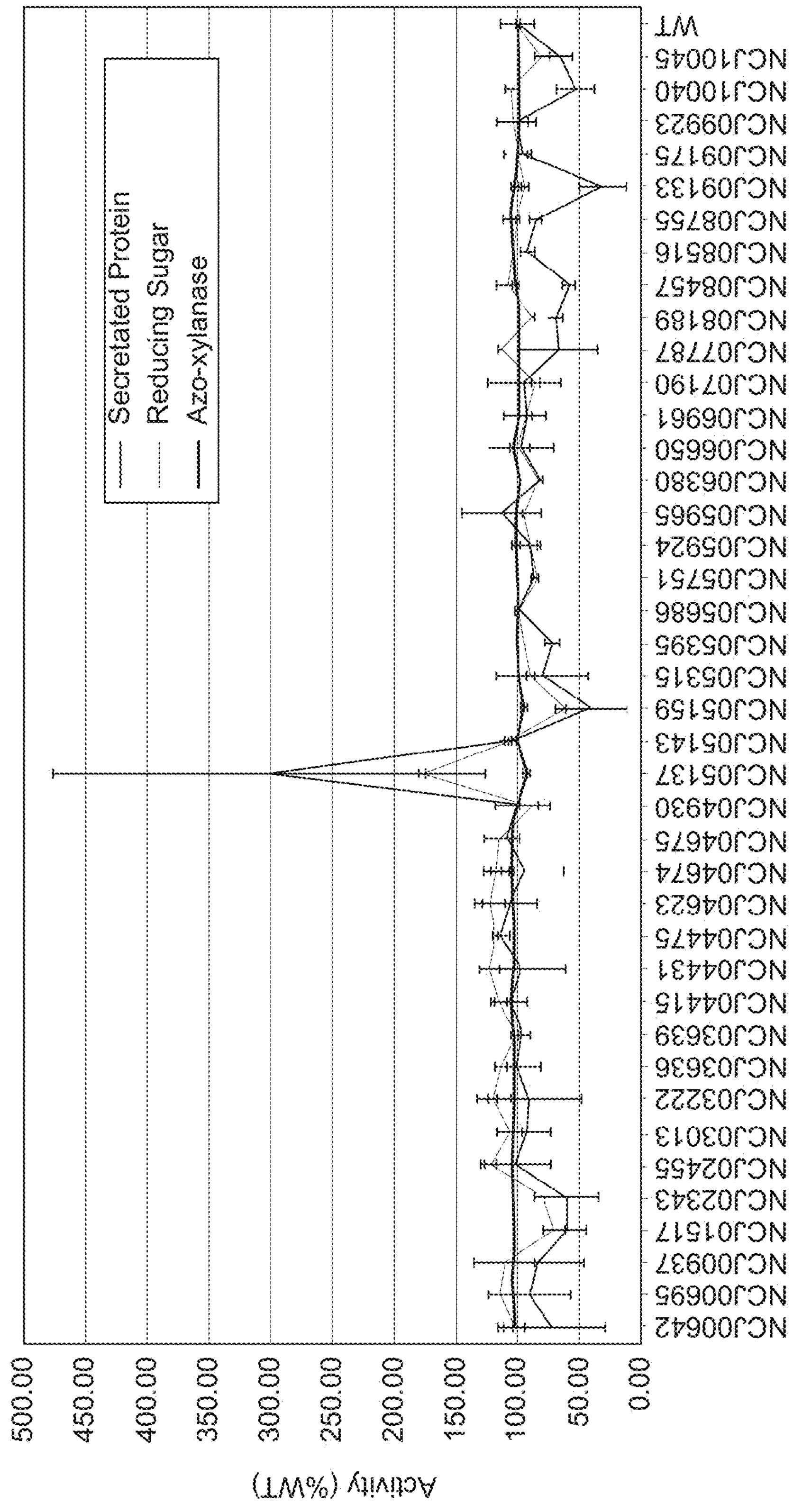
FIG. 77 shows secreted protein levels, reducing sugar, and azo-xylanase activity for various *N. crassa* knock-out strains. Secreted protein levels were relatively constant for all strains.

The transcriptome and secretome analysis results indicated a total of 71 genes, of which 55 were predicted to be secreted. The list of these genes is in Table 29. Deletion strains were available for 46 out of 69 genes. Out of these 46, six of the strains were heterokaryons, thus the remaining 40 deletion strains were analyzed for total secreted protein, amount of xylose present, and azo-endo-xylanase activity. Results are shown in FIG. 77.

Table 29 shows xylan-induced *N. crassa* genes

| Gene Name | Signal P | Data | Annotation |
|---|---|---|---|
| NCU00642 | Y | Transcription | probable beta-galactosidase |
| NCU00695 | Y | Transcription | putative protein |
| NCU00798 | | MS | hypothetical protein |
| NCU00937 | Y | Transcription | conserved hypothetical protein |
| NCU01517 | Y | Transcription | glucan 1,4-alpha-glucosidase |
| NCU02136 | | MS | probable transaldolase |
| NCU02252 | | MS | probable phosphoglyceromutase |
| NCU02343 | Y | Transcription | related to alpha-L-arabinofuranosidase A precursor |
| NCU02455 | Y | Transcription | FK506-binding protein 2 precursor (Peptidyl-prolyl cis-trans isomerase) |
| NCU02583 | Y | Transcription | probable Alpha-glucosidase precursor (Maltase) |
| NCU03013 | Y | Transcription | related to cytosolic Cu/Zn superoxide dismutase |
| NCU03222 | Y | Transcription | putative protein |
| NCU03636 | Y | Transcription | |
| NCU03639 | Y | Transcription | probable triacylglycerol lipase precursor |
| NCU04202 | | MS | nucleoside-diphosphate kinase |
| NCU04265 | Y | Transcription | related to beta-fructofuranosidase |
| NCU04388 | Y | Transcription | probable phosphatidylglycerol/ phosphatidylinositol transfer protein |
| NCU04395 | | MS | beta-1,6-glucanase Neg1 NEG-1 |
| NCU04415 | Y | Transcription | related to brefeldin A resistance protein |
| NCU04431 | Y | MS | related to endo-1,3-beta-glucanase |
| NCU04475 | Y | Transcription | probable lipase B precursor |
| NCU04482 | | MS | hypothetical protein |
| NCU04623 | Y | Transcription | related to beta-galactosidase |
| NCU04674 | Y | Transcription | related to alpha-glucosidase b |
| NCU04675 | Y | Transcription | putative protein |
| NCU04930 | Y | Transcription | related to triacylglycerol lipase |
| NCU05137 | Y | Transcription | conserved hypothetical protein |
| NCU05143 | Y | Transcription | related to Rds1 protein |
| NCU05159 | Y | Transcription | probable acetylxylan esterase precursor |
| NCU05275 | | MS | probable ubiquitin fusion protein (ubiquitin/ribosomal protein) |
| NCU05315 | Y | Transcription | hypothetical protein |
| NCU05395 | Y | Transcription | conserved hypothetical protein |
| NCU05686 | Y | MS | probable cell wall protein UTR2 |
| NCU05751 | Y | Transcription | related to acetylxylan esterase |
| NCU05924 | Y | Transcription | probable endo-beta-1,4-D-xylanase |
| NCU05965 | Y | Transcription | related to putative arabinase |
| NCU05974 | | MS | related to cell wall protein (putative glycosidase) |
| NCU06364 | Y | Transcription | hypothetical protein |
| NCU06380 | Y | Transcription | related to catecholamines up protein |
| NCU06650 | Y | Transcription | conserved hypothetical protein |
| NCU06781 | | MS | probable beta (1-3) glucanosyltransferase |
| NCU06961 | Y | Transcription | probable exopolygalacturonase |
| NCU07067 | | MS | related to class I alpha-mannosidase 1B |
| NCU07143 | Y | Transcription | |
| NCU07190 | Y | Transcription | related to cellulose 1,4-beta-cellobiosidase II precursor |
| NCU07200 | Y | MS | related to metalloprotease MEP1 |
| NCU07225 | Y | Transcription | probable endo-1,4-beta-xylanase B precursor |
| NCU07281 | | MS | probable glucose-6-phosphate isomerase |
| NCU07787 | Y | MS | probable SnodProt1 precursor |
| NCU08131 | Y | Transcription | probable alpha-amylase precursor |
| NCU08171 | Y | MS | conserved hypothetical protein |
| NCU08189 | Y | Transcription | related to endo-1,4-beta-xylanase |
| NCU08384 | | MS | probable D-xylose reductase |

-continued

| Gene Name | Sig-nal P | Data | Annotation |
|---|---|---|---|
| NCU08418 | | MS | related to tripeptidyl-peptidase I |
| NCU08457 | Y | Transcription | hydrophobin Ccg-2 CCG-2 |
| NCU08516 | Y | Transcription | related to aldose 1-epimerase |
| NCU08750 | Y | Transcription | related to isoamyl alcohol oxidase |
| NCU08752 | Y | Transcription | related to esterase |
| NCU08755 | Y | Transcription | hypothetical protein |
| NCU08909 | Y | MS | probable beta (1-3) glucanosyltransferase gel3p |
| NCU08936 | | MS | related to sporulation-specific gene SPS2 |
| NCU09024 | Y | MS | related to choline dehydrogenase |
| NCU09133 | Y | Transcription | putative protein |
| NCU09170 | Y | MS | probable alpha-N-arabinofuranosidase |
| NCU09175 | Y | Transcription | related to glucan 1,3-beta-glucosidase precursor |
| NCU09267 | | MS | related to glyoxal oxidase precursor |
| NCU09491 | | MS | feruloyl esterase B precursor (subclass of the carboxylic acid esterases) |
| NCU09923 | Y | Transcription | related to xylan 1,4-beta-xylosidase |
| NCU09924 | Y | Transcription | conserved hypothetical protein |
| NCU10040 | Y | Transcription | |
| NCU10045 | Y | Transcription | |

Samples were prepared as follows. 10 day old conidia were grown in 100 mL 2% xylan Vogel's media at $10^6$ conidia/mL. Two replicates were prepared for each strain. Cultures were grown at 25° C. with constant light and 220 rpm. Samples were harvested on day 4. Supernatants were isolated by centrifugation and used in assays.

Bradford protein concentrations were measured to determine the total amount of secreted protein. Stocks were prepared with BSA standards: 0 μg/mL, 50 μg/mL, 100 μg/mL, 250 μg/mL, and 500 μg/mL. Bradford solution was diluted 1:4. A multichannel pipette was used to pipette 200 μL of Bradford solution into a 96-well plate. 10 μL of sample and 10 μL of each standard were added. Samples were incubated at room temperature for 10 minutes. The absorbance was read at 595 nm, and the protein concentration was determined.

The assay used to measure xylose was modified from Bailey et al., 1992 (*J Biotech* 23: 257-270). Xylose standards were prepared in $H_2O$. For concentrated 0.8 M xylose (1.2 g in 10 mL), the standards included 0 mM, 8 mM (1:100 dilution; 990 μl+10 μl), 20 mM (1:100 dilution; 975 μl+25 μl), 40 mM (1:100 dilution; 950 μl+50 μl), 80 mM (1:100 dilution; 900 μl+100 μl), and 160 mM (1:100 dilution; 800 μl+200 μl). A multichannel pipette was used to add 900 μL of substrate solution to a deep well 96-well plate. The substrate was allowed to incubate at 50° C. for 10 minutes. One hundred μL of culture supernatant and the standards were added and allowed to incubate at 50° C. for 5 minutes. Samples were centrifuged for 10 minutes at 3,400 rpm. A multichannel pipette was used to pipette 75 μL DNS solution into a 96-well PCR plate. Five μL of solution was removed from the reaction and added to the PCR plate containing DNS solution. The plate was heated at 99° C. in the PCR machine for 5 min. After the samples cooled, they were transferred to clear flat-bottomed plates, and the absorbance was read at 540 nm. Substrate solution (500 mL) contained beechwood xylan (5 g; 10 mg/mL), 3M NaOAc, pH 5.0 (8.33 mL; 50 mM), water (491 mL), and was autoclaved for 20 minutes. DNS solution (100 mL) contained 3,5-dinitrosalicylic acid (707 mg), NaOH (1.32 g), Rochelle salts (Na K tartrate) (20.4 g), Sodium meta-bisulfate (553 mg), phenol (507 μL), and water (94.4 mL).

Azo-endo-xylanase activity was measured with a kit from Megazyme. This assay indirectly measures the amount of endo-xylanase activity in a sample by spectrophotometrically measuring the amount of dye liberated from a xylan chain complexed with the dye. The more enzymes that are present, the more dye will be released. All supernatant samples were diluted 1:10 by adding 50 μL of supernatant to 450 μL of Na Acetate buffer (50 mM, pH 4.5) in separate 15 mL Falcon tubes. Next, Falcon tubes were pre-warmed about 10 minutes. Substrate solution was added for all samples (500 μL/sample) to the tubes. Samples and substrate solutions were added into a 40° C. water bath for 10 minutes to pre-equilibrate them. Five hundred μL substrate solution was added to each 1:10 diluted sample, vortexed for 10 seconds, and incubated at 40° C. for 10 minutes. The reaction was terminated by adding 2.5 mL of precipitant solution (95% ethanol) to each sample and vortexing for 10 seconds. Tubes were allowed to stand at room temperature for 10 minutes. Tubes were vortexed for 10 seconds and then centrifuged at room temperature for 10 minutes at 1,000 g. One mL of supernatant solution from each tube was placed directly into a cuvette, and the absorbance was measured at 590 nm. The blank used for this procedure was the supernatant from 500 μL substrate solution added to 2.5 mL of precipitant solution.

In conclusion, it is anticipated that the modulation of genes identified here that affect the degradation of hemicellulose in *N. crassa* will facilitate engineering strains that have enhanced capacity for plant cell wall breakdown and growth on plant cell wall components such as hemicellulose. Genes of interest include NCU01517, which encodes a predicted glucamylase; NCU02343, which encodes a predicted arabinofuranosidase; NCU05137, which encodes a conserved hypothetical protein; NCU05159, which encodes a predicted acetylxylan esterase precursor; NCU09133, which encodes a conserved hypothetical protein; and NCU10040, which encodes a hypothetical protein.

The growth of a cell on hemicellulose will be increased by providing a host cell that contains a recombinant polynucleotide that encodes a polypeptide encoded by NCU01517, NCU09133, or NCU10040. The host cell will be cultured in a medium that contains hemicellulose such that the recombinant polynucleotide is expressed. The host cell will grow at a faster rate in this medium than a cell that does not contain the recombinant polynucleotide.

Example 21

Further Analysis of the ΔNCU05137 Strain

As described in Examples 1-3 and 18-20, NCU05137 is a predicted secreted protein that was overexpressed during growth of *N. crassa* on any of *Miscanthus*, Avicel, or xylan. A deletion strain of *N. crassa* lacking NCU05137 grown on Avicel showed increased endoglucanase, β-glucosidase, and Avicelase activity. An NCU05137 deletion strain grown on xylan showed increased azo-endo-xylanase activity. As described in this example, the complementation of ΔNCU05137 was performed in order to verify that the phenotypes observed in the ΔNCU05137 strain were due to the loss of the NCU05137 gene.

A plasmid containing NCU05137 with a C-terminal GFP tag under the control of the ccg1 promoter was generated. *N. crassa* conidia were transformed with the NCU05137-GFP construct. Experiments were performed according to standard *Neurospora* procedures (webpage fgsc.net/Neurospora/NeurosporaProtocolGuide.htm).

Figure 78:
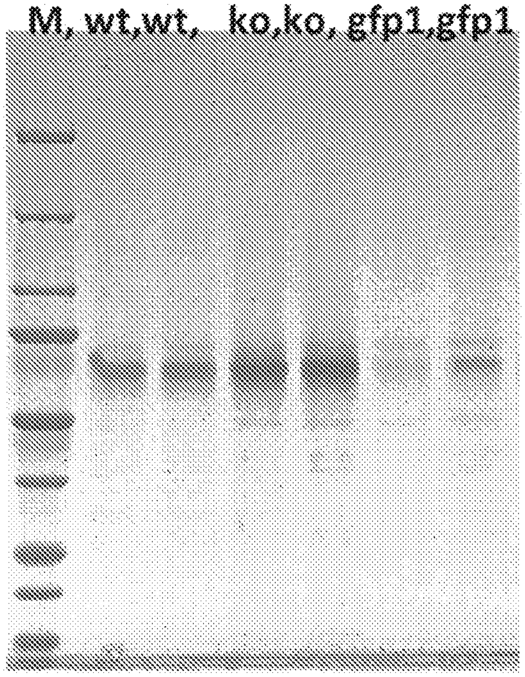
FIG. 78A shows total secreted protein and CMC-activity for wild type, ΔNCU05137, and ΔNCU05137/ΔNCU05137-GFP *Neurospora* strains.
FIG. 78B shows a Coomassie stain of total protein in supernatants from cultures of the three different strains.

The total secreted protein and carboxymethyl cellulase (CMC) activity of wild-type, ΔNCU05137, and ΔNCU05137-NCU05137-GFP strains was measured. Total secreted protein was measured by taking 100 μL of supernatant from a culture of each strain, adding it to 900 μL Bradford Dye, and measuring absorbance at 595 nm. CMC activity was measured with 20× diluted supernatant from each strain culture and an azo-CMC kit (Megazyme SCMCL). ΔNCU05137 knockout strains displayed increased levels of secreted protein and CMC activity. Introduction of the GFP-tagged NCU05137 into ΔNCU05137 strains reduced these levels back to wild-type levels (FIG. 78).

Figure 79:
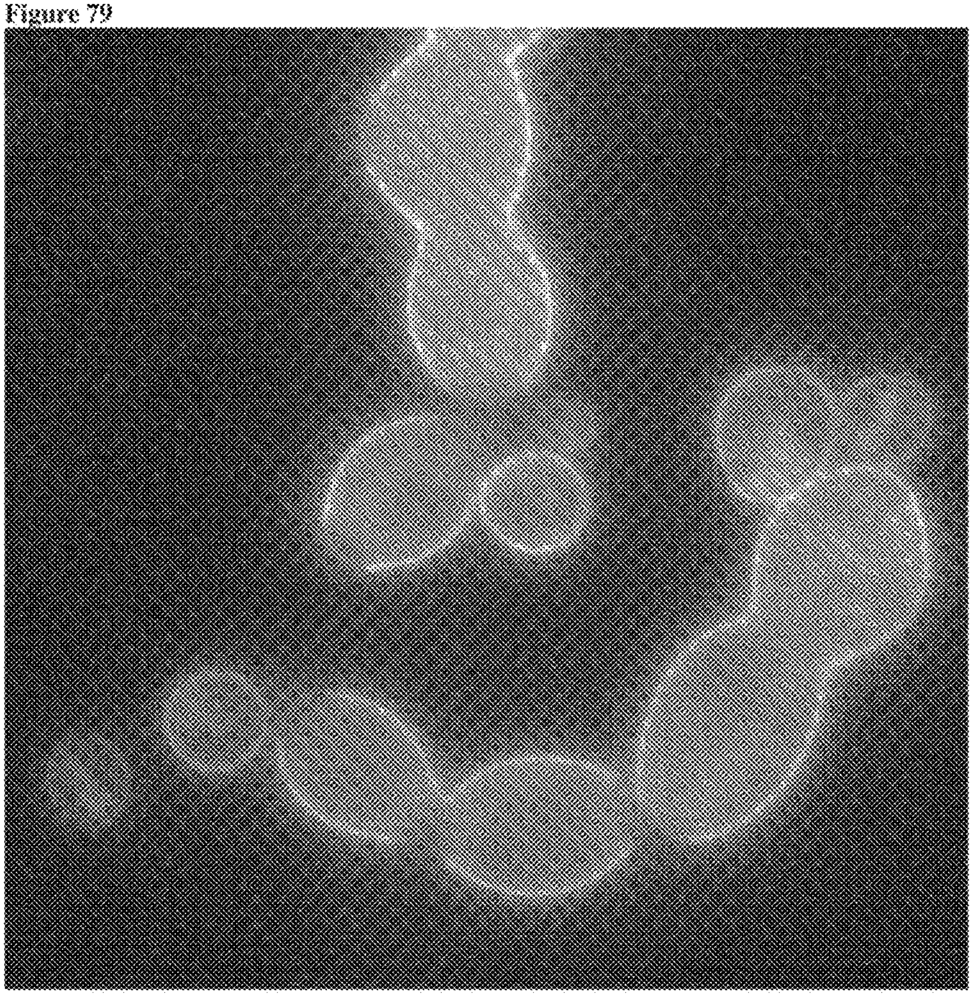
FIG. 79 shows localization of NCU05137-GFP in conidia.
Figure 80:
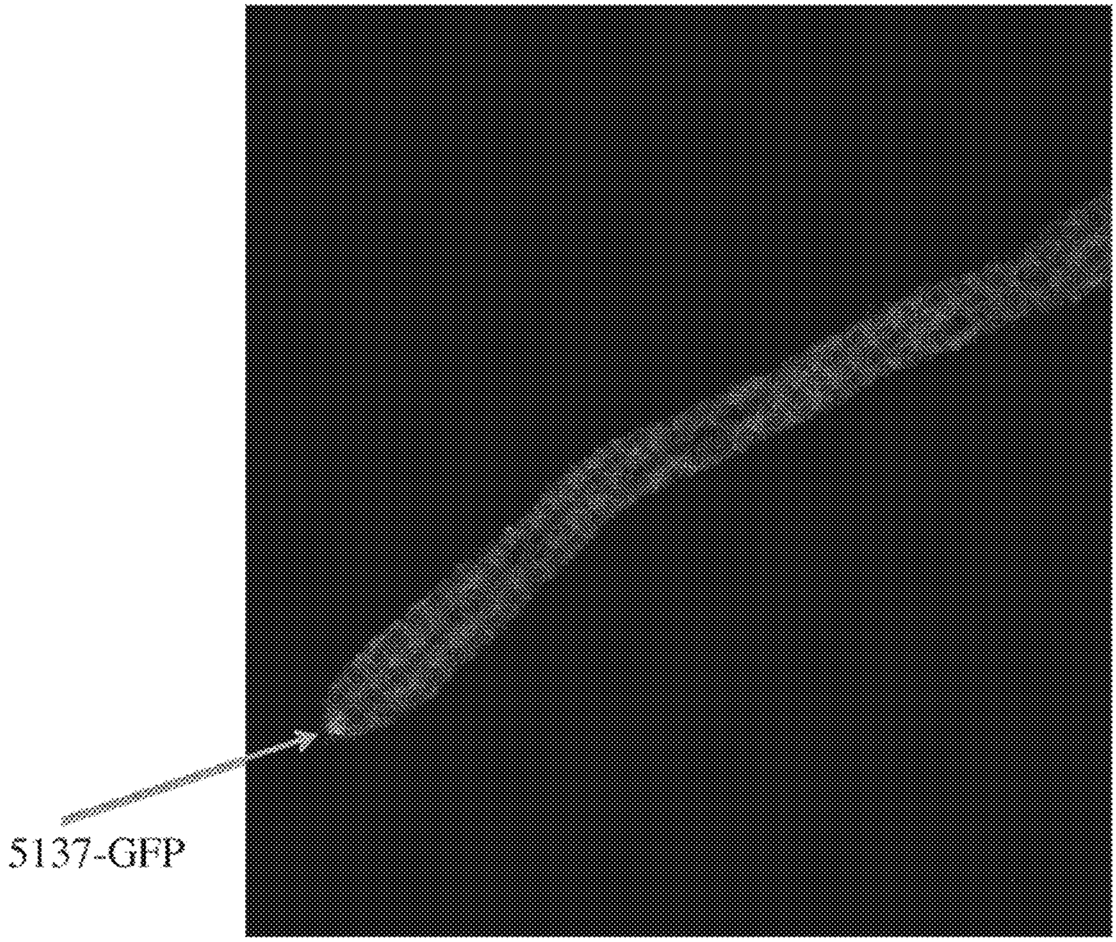
FIG. 80 shows localization of NCU05137-GFP in the hypha tip.

In addition, the localization of NCU05137-GFP in complemented strains was observed. NCU05137-GFP localized to the cell wall of conidia and to the hypha tip (FIG. 79-80). These data indicate that the GFP-tagged NCU05137 protein is fully functional and can be used for purification and experiments addressing the biochemical activity of this protein.

Thus, the normal function of NCU05137 may be to inhibit signaling processes associated with induction of cellulase and hemicellulase gene expression. Reduction of expression of NCU05137 or a homolog of NCU05137 in a cell is likely to increase cellulase and hemicellulase activity in that cell and, consequently, growth of the cell on cellulose or hemicellulose. The growth of a cell on cellulose or hemicellulose will be increased by providing a host cell that contains an endogenous polynucleotide that encodes a polypeptide encoded by NCU05137. The expression of the endogenous polynucleotide will be inhibited, and the cell will be cultured in a medium containing cellulose and/or hemicellulose. The host cell will grow at a faster rate in the medium than a cell in which expression of the endogenous polynucleotide is not inhibited.

Example 22

Further Analysis of NCU07705

Expression of NCU07705 was found to be upregulated during growth of *N. crassa* on cellulose. BLAST analysis of the polypeptide encoded by NCU07705 revealed that the polypeptide has high similarity to many C6 zinc finger domain containing transcription factors (FIG. 1). To further investigate the role of NCU07705 in the utilization of cellulose, the phenotype of a deletion strain lacking NCU07705 was evaluated.

The ΔNCU07705 strain was unable to grow on 2% cellulose (Avicel), PASC, or CMC as a sole carbon source (Table 30) but grew with similar kinetics to wild-type strain on sucrose, xylan, and xylose. In order to determine whether NCU07705 plays a role in regulating expression of cellulases, the expression of cellulase and hemicellulase genes was examined during growth of ΔNCU07705 on cellulose. Ten-day-old conidia from wild-type (FGSC 2489) and ΔNCU07705 strains were inoculated into Vogel's liquid MM (2% sucrose) (Vogel 1956) and grown for 16 hours. Mycelia were centrifuged, washed with 1× Vogel's salts, and then transferred into either Vogel's media with 2% sucrose or 2% Avicel and grown in constant light for 4 hours. They were harvested by filtration and immediately frozen in liquid nitrogen. Total RNA was isolated using TRIzol (Invitrogen, Carlsbad, Calif.) according to the manufacturer's instructions and treated with DNase (Turbo DNA-free kit, Ambion/Applied Biosystems, Foster City, Calif.) (Kasuga et al., 2005). ChipShot™ Indirect Labeling/Clean-Up System (Catalog No. Z4000, Promega, Madison, Wis.) and CyDye Post-Labeling Reactive Dye Pack (Catalog No. RPN5661, GE Healthcare, Piscataway, N.J.) were used to synthesize and label cDNA according to the manufacturer's instructions except the amount of RNA used was 10 μg. The Pronto! Hybridization Kit (Catalog No. 40076, Corning, Lowell, Mass.) was used for microarray hybridization according to the manufacturer's specifications.

Data analyses were performed as previously described (Tian et al., 2007). A GenePix 4000B scanner (Axon Instruments, Union City, Calif.) was used to acquire images, and GenePix Pro6 software was used to quantify hybridization signals and collect the raw data. Normalized expression values were analyzed by using BAGEL (Bayesian Analysis of Gene Expression Levels) (Townsend and Hartl, 2002). None of the predicted cellulase genes were induced in the ΔNCU07705 strain, whereas induction of predicted hemicellulase genes was unaffected (see Table 30 below). Thus, NCU07705 has been named cdr-1, cellulose degradation regulator 1.

Therefore, the growth of a cell on cellulose will be increased by providing a host cell that contains a recombinant polynucleotide that encodes a polypeptide encoded by NCU07705. The host cell will be cultured in a medium that contains cellulose such that the recombinant polynucleotide is expressed. The host cell will grow at a faster rate in this medium than a cell that does not contain the recombinant polynucleotide.

Table 30 shows expression profile of genes in *N. crassa* ΔNCU07705 strain

| 7705-switch[2] | WT-switch[1] | Gene/ locus name | GH Family | Class | up in Avi[3] |
|---|---|---|---|---|---|
| No | 15 | NCU00762 | 5 | endo- | 31.5 |
| No | No | NCU03996 | 6 | CBHII like | |
| No | 168 | NCU07190 | 6 | CBHII like | 119 |
| No | 26 | NCU09680 | 6 | CBHII | 251.3 |
| No | 18 | NCU04854 | 7 | CBHI like | 10.8 |
| No | 3.8 | NCU05057 | 7 | CBHI like | 7.4 |
| No | No | NCU05104 | 7 | CBHI like | |
| No | 93 | NCU07340 | 7 | CBHI | 382.2 |
| No | 2 | NCU05121 | 45 | endo- | 17.2 |
| No | 5.8 | NCU00836 | 61 | endo- | 31 |
| No | 3.7 | NCU01050 | 61 | endo- | 382.1 |
| No | No | NCU01867 | 61 | endo- | |
| No | 49 | NCU02240 | 61 | endo- | 84 |
| No | No | NCU02344 | 61 | endo- | 4.1 |
| No | 6.1 | NCU02916 | 61 | endo- | 17.7 |
| No | No | NCU03000 | 61 | endo- | |
| No | 17 | NCU03328 | 61 | endo- | 23.8 |
| No | No | NCU05969 | 61 | endo- | 12.7 |
| No | No | NCU07520 | 61 | endo- | |
| No | No | NCU07760 | 61 | endo- | |
| No | 103 | NCU07898 | 61 | endo- | 230 |
| No | No | NCU07974 | 61 | endo- | |
| No | 25 | NCU08760 | 61 | endo- | 44.7 |

[1]Expression levels of predicted cellulase genes from an *N. crassa* (NCU07705) culture grown in Vogel's/sucrose for 16 hours, filtered, and resuspended in Vogel's/Avicel for 4 hours prior to RAN extraction.
[2]Expression levels of predicted cellulase gene from an *N. crassa* (wild type FGSC 2489) culture grown in Vogel's/sucrose for 16 hours, filtered, and resuspended in Vogel's/sucrose for 4 hours prior to RNA extraction.
[3]Expression levels derived from microarray analyses of wild type (FGSC 2489) cells grown for 30 hours in Avicel (Tian et al., 2009).

REFERENCES

Arendt, C. S., K. R1, et al. (2007). "Genetic selection for a highly functional cysteine-less membrane protein using site saturation mutagenesis." Anal Biochem 365(2):185-193.

Bai, F. W., W. A. Anderson, and M. Moo-Young (2008). "Ethanol fermentation technologies from sugar and starch feedstocks." Biotechnol Adv 26(1): 89-105.

Bailey, M. J., P. Biely, and K. Poutanen (1992). "Interlaboratory testing of methods for assay of xylanase activity." J Biotechnol 23:257-270.

Bailey, J. E. and D. F. 011 is (1986). Biochemical Engineering Fundamentals, McGraw-Hill Book Company, NY.

Basso, L. C., H. V. de Amorim, et al. (2008). "Yeast selection for fuel ethanol production in Brazil." FEMS Yeast Res 8(7):1155-1163.

Becker, D. M. and V. Lundblad (2001). "Introduction of DNA into yeast cells." Curr Protoc Mol Biol Chapter 13, Unit 13.7.

Bendtsen, J. D., H. Nielsen, et al. (2004). "Improved prediction of signal peptides: SignalP 3.0." J. Mol. Biol 340(4): 783-95.

Bengsston, O., B. Hahn-Hagerdal, and M. F. Gorwa-Grauslund (2009). "Xylose reductase from *Pichia stipitis* with altered coenzyme preference improves ethanolic xylose fermentation by recombinant *Saccharomyces cerevisiae*." Biotechnol Biofuels 2:9.

Bhat, K. M. and R. Maheshwari (1987). "Sporotrichum thermophile Growth, Cellulose Degradation, and Cellulase Activity." Appl Environ Microbiol 53(9):2175-2182.

Bouffard, G. G., K. E. Rudd, and S. L. Adhya (1994). "Dependence of lactose metabolism upon mutarotase encoded in the gal operon in *Escherichia coli*." J Mol Biol 244(3):269-278.

Bouws, H, A. Wattenberg and H. Zorn (2008). "Fungal secretomes—nature's toolbox for white biotechnology." Appl Microbiol Biotechnol 80(3):381-388.

Brat, D., E. Boles, and B. Wiedemann (2009). "Functional Expression of a Bacterial Xylose Isomerase in *Saccharomyces cerevisiae*." Appl Environ Microbiol 75(8):2304-2311.

Canevascini, G. (1988). "Cellobiose dehydrogenase from Sporotrichum thermophile." Method Enzymol 160:443-448.

Cantarel, B. L., P. M. Coutinho, et al. (2009). "The Carbohydrate-Active EnZymes database (CAZy): an expert resource for glycogenomics." Nucleic Acids Res 37(Database issue):D233-238.

Chauve, M., H. Mathis, et al. (2010). "Comparative kinetic analysis of two fungal beta-glucosidases." Biotechnol Biofuels 3(1):3.

Christakopoulos, P., M. K. Bhat, et al. (1994). "Enzymatic synthesis of trisaccharides and alkyl beta-D-glucosides by the transglycosylation reaction of beta-glucosidase from *Fusarium oxysporum*." Int J Biol Macromol 16(6):331-334.

Christianson, T. W., R. S. Sikorskim, et al., (1992). "Multifunctional yeast high-copy number shuttle vectors." Gene, 110(1):119-122.

Chu, B. C. and H. Lee (2007). "Genetic improvement of *Saccharomyces cerevisiae* for xylose fermentation." Biotechnol Adv 25(5):425-441.

Colot, H. V., G. Park, et al. (2006). "A high-throughput gene knockout procedure for *Neurospora* reveals functions for multiple transcription factors." Proc Natl Acad Sci USA 103(27):10352-10357.

Cullen, D., L. J. Wilson, et al. (1987). "Sequence and centromere proximal location of a transformation enhancing fragment ans1 from *Aspergillus nidulans*." Nucleic Acids Res 15(22):9163-9175.

Davies, G. J., A. M. Brzozowski, et al. (2000). "Structure and function of *Humicola insolens* family 6 cellulases: structure of the endoglucanase, Cel6B, at 1.6 A resolution." Biochem J 348 Pt 1:201-207.

Davis, R. H. (2000). "*Neurospora*: Contributions of a model organism." New York, Oxford University Press.

Davis, R. H. and D. D. Perkins (2002). "Timeline: *Neurospora*: a model of model microbes." Nat Rev Genet 3(5): 397-403.

de Groot, M. J., W. Prathumpai, et al. (2005). "Metabolic control analysis of *Aspergillus niger* L-arabinose catabolism." Biotechnol Prog 21(6):1610-1616.

Dementhon K, G. Iyer, and N. L. Glass (2006). "VIB-1 is required for expression of genes necessary for programmed cell death in *Neurospora crassa*." Eukaryot Cell 5(12):2161-2173.

Doran-Peterson, J., A. Jangid, et al. (2009). "Simultaneous saccharification and fermentation and partial saccharification and co-fermentation of lignocellulosic biomass for ethanol production." Methods Mol Biol 581:263-280.

Drissen, R. E. T., R. H. W. Mass, et al. (2009). "Modelling ethanol production from cellulose: separate hydrolysis and fermentation versus simultaneous saccharification and fermentation." Biocatal Biotransfor 27(1):27-35.

Dunlap, J. C., K. A. Borkovich, et al. (2007). "Enabling a Community to Dissect an Organism: Overview of the *Neurospora* Functional Genomics Project." Adv Genet. 57:49-96.

du Preez, J. C., M. Bosch, and B. A. Prior (1986). "The fermentation of hexose and pentose sugars by *Candida shehatae* and *Pichia stipitis*." Appl Microbiol Biotechnol 23(3):228-233.

Eberhart, B. M., R. S. Beck, et al. (1977). "Cellulase of *Neurospora crassa*." J Bacteriol 130(1):181-186.

Ellis, K. J. and J. F. Morrison (1982). "Buffers of constant ionic strength for studying pH-dependent processes." Methods Enzymol 87:405-426.

Espagne, E., O. Lespinet, et al. (2008). "The genome sequence of the model ascomycete fungus *Podospora anserina*." Genome Biol 9(5):R77.

Fonseca, C. R. Romao, et al. (2007). "L-Arabinose transport and catabolism in yeast." FEBS J 274(14):3589-3600.

Freer, S. N. (1991). "Fermentation and aerobic metabolism of cellodextrins by yeasts." Appl Environ Microbiol 57(3): 655-659.

Freer, S, N. and R. V. Greene (1990). "Transport of glucose and cellobiose by *Candida wickerhamii* and *Clavispora lusitaniae*." J Biol Chem 265(22):12864-12868.

Galagan, J. E., S. E. Calvo, et al. (2003). "The genome sequence of the filamentous fungus *Neurospora crassa*." Nature 422(6934):859-868.

Gems, D., I. L. Johnstone, and A. J. Clutterbuck (1991). "An autonomously replicating plasmid transforms *Aspergillus nidulans* at high frequency." Gene 98(1):61-67.

Guindon, S, and O. Gascuel (2003). "A simple, fast, and accurate algorithm to estimate large phylogenies by maximum likelihood." Syst Biol 52(5):696-704.

Hahn-Hägerdal, B., K. Karhumaa, et al. (2007). "Towards industrial pentose-fermenting yeast strains." Appl Microbiol Biotechnol 74(5):937-953.

Hector, R. E., N. Qureshi et al. (2008). "Expression of a heterologous xylose transporter in a *Saccharomyces cerevisiae* strain engineered to utilize xylose improves aerobic xylose consumption." Appl Microbiol Biotechnol 80(4): 675-684.

Himmel, M. E., S. Y. Ding, et al. (2007). "Biomass recalcitrance: engineering plants and enzymes for biofuels production." Science 315(5813):804-807.

Hosaka, K., J. Nikawa, et al., (1992). "A dominant mutation that alters the regulation of INO1 expression in *Saccharomyces cerevisiae*." J Biochem 111(3):352-358.

Jacobson, D. J., A. J. Powell, et al. (2004). "*Neurospora* in temperate forests of western North America." Mycologia 96(1):66-74.

Jeffries, T. W., I. V. Grigoriev, et al. (2007). "Genome sequence of the lignocellulose-bioconverting and xylose-fermenting yeast *Pichia stipitis*." Nat Biotechnol 25(3): 319-326.

Kasuga, T. and N. L. Glass (2008). "Dissecting colony development of *Neurospora crassa* using mRNA profiling and comparative genomics approaches." Eukaryot Cell 7(9): 1549-64.

Kasuga, T., J. P. Townsend, et al. (2005). "Long-oligomer microarray profiling in *Neurospora crassa* reveals the transcriptional program underlying biochemical and physiological events of conidial germination." Nucleic Acids Res 33(20): 6469-85.

Katahira, S., M. Ito, et al. (2008). "Improvement of ethanol productivity during xylose and glucose co-fermentation by xylose-assimilating *S. cerevisiae* via expression of glucose transporter Sut1." Enzyme Microb Tech 43(2):115-119.

Katahira, S., A. Mizuike, et al. (2006). "Ethanol fermentation from lignocellulosic hydrolysates by a recombinant xylose- and cellooligosaccharide-assimilating yeast strain." Appl Microbiol Biotechnol 72(6): 1136-1143.

Korkhin, Y., A. J. Kalb(Gilboa), et al. (1998). "NADP-dependent bacterial alcohol dehydrogenases: crystal structure, cofactor-binding and cofactor specificity of the ADHs of *Clostridium beijerinckii* and *Thermoanaerobacter brockii*." J Mol Biol 278(5):967-981.

Kotaka, A., H. Bando, et al. (2008). "Direct ethanol production from barley beta-glucan by sake yeast displaying *Aspergillus oryzae* beta-glucosidase and endoglucanases." J Biosci Bioeng 105(6):622-627.

Kötter, P. and M. Ciriacy (1993). "Xylose fermentation by *Saccharomyces cerevisiae*." Appl Microbiol Biotechnol 38(6):776-783.

Kubicek, C. P., R. Messner, et al. (1993). "Triggering of cellulase biosynthesis by cellulose in *Trichoderma reesei*. Involvement of a constitutive, sophorose-inducible, glucose-inhibited beta-diglucoside permease." J Biol Chem 268(26):19364-19368.

Kumar, R., S. Singh, and O. V. Singh (2008). "Bioconversion of lignocellulosic biomass: biochemical and molecular perspectives." J Ind Microbiol Biotechnol 35(5):377-391.

Kuyper, M, H. R. Harhangi, et al. (2003). "High-level functional expression of a fungal xylose isomerase: the key to efficient ethanolic fermentation of xylose by *Saccharomyces cerevisiae*? FEMS Yeast Res 4(1):69-78.

Lang, J. M. and V. P. Cirillo (1987). "Glucose transport in a kinaseless *Saccharomyces cerevisiae* mutant." J Bacteriol 169(7):2932-2937.

Leandro, M. J., P. Gonçalves, and I. Spencer-Martins (2006). "Two glucose/xylose transporter genes from the yeast *Candida* intermedia: first molecular characterization of a yeast xylose-H+ symporter." Biochem J 395(3):543-549.

Linder, M. and T. T. Teeri (1996). "The cellulose-binding domain of the major cellobiohydrolase of *Trichoderma reesei* exhibits true reversibility and a high exchange rate on crystalline cellulose." Proc Natl Acad Sci USA 93(22): 12251-12255.

Lynd, L. R., M. S. Laser, et al. (2008). "How biotech can transform biofuels." Nat. Biotechnol. 26(2):169-172.

Lynd, L. R., P. J. Weimer, et al. (2002). "Microbial cellulose utilization: fundamentals and biotechnology." Microbiol Mol Biol Rev 66(3):506-77, table of contents.

Madhavan, A., S. Tamalampudi, et al. (2009). "Xylose isomerase from polycentric fungus orpinomyces: gene sequencing, cloning, and expression in *Saccharomyces cerevisiae* for bioconversion of xylose to ethanol." Appl Microbiol Biotechnol 82(6):1067-1078.

Martin, F., A. Kohler, et al. (2010). "Perigord black truffle genome uncovers evolutionary origins and mechanisms of symbiosis." Nature 464(7291):1033-1038.

Martinez, D., R. M. Berka, et al. (2008). "Genome sequencing and analysis of the biomass-degrading fungus *Trichoderma reesei* (syn. *Hypocrea* jecorina)." Nat Biotechnol 26(5):553-60.

Martinez, D., J. Callacombe, et al. (2009). "Genome, transcriptome, and secretome analysis of wood decay fungus *Postia placenta* supports unique mechanisms of lignocellulose conversion." Proc Natl Acad Sci USA 106(6):1954-1959.

Martinez, D., L. F. Larrondo, et al. (2004). "Genome sequence of the lignocellulose degrading fungus *Phanerochaete* chrysosporium strain RP78." Nat Biotechnol 22(6): 695-700.

Matsushika, A., S. Watanabe, et al. (2008). "Expression of protein engineered NADP+-dependent xylitol dehydrogenase increases ethanol production from xylose in recombinant *Saccharomyces cerevisiae*." Appl Microbiol Biotechnol 81(2):243-255.

Matteucci, M. D. and M. H. Caruthers (1980). Tetrahedron Lett 21:719-722.

McCluskey, K. (2003). "The Fungal Genetics Stock Center: from molds to molecules." Adv Appl Microbiol 52:245-262.

Medve, J., J. Karlsson, et al. (1998). "Hydrolysis of microcrystalline cellulose by cellobiohydrolase I and endoglucanase II from *Trichoderma reesei*: adsorption, sugar production pattern, and synergism of the enzymes." Biotechnol Bioeng 59(5):621-34.

Miyasaka, H. (1999). "The positive relationship between codon usage bias and translation initiation AUG context in *Saccharomyces cerevisiae*." Yeast 15(8):633-637.

Nair, N. and H. Zhao (2007). "Biochemical characterization of an L-Xylulose reductase from *Neurospora crassa*." Appl Environ Microbiol 73(6):2001-2004.

Nakamura, N., R. Yamada, et al. (2008). "Effective xylose/cellobiose co-fermentation and ethanol production by xylose-assimilating *S. cerevisiae* via expression of β-glucosidase on its cell surface." Enzyme Microb Tech 43(3): 233-236.

Noguchi, Y., M. Sano, et al. (2009). "Genes regulated by AoXlnR, the xylanolytic and cellulolytic transcriptional regulator, in *Aspergillus oryzae*." Appl Microbiol Biotechnol 85(1):141-154.

Notredame, C., D. G. Higgins, and J. Hering a (2000). "T-Coffee: A novel method for fast and accurate multiple sequence alignment." J Mol Biol 302(1):205-217.

Pandit, A. and R. Maheshwari (1996). "Life-history of *Neurospora* intermedia in a sugar cane field." J Biosci (Bangalore) 21(1):57-79.

Pauly, T. A., J. L. Ekstrom, et al. (2003). "X-ray crystallographic and kinetic studies of human sorbitol dehydrogenase." Structure 11(9):1071-1085.

Pedelacq, J. D., S. Cabantous, et al. (2006). "Engineering and characterization of a superfolder green fluorescent protein." Nat Biotechnol 24(1):79-88.

Perkins, D. D., B. C. Turner, et al. (1976). "Strains of *Neurospora* collected from nature." Evolution 30: 281-313.

Ramos, J., K. Szkutnicka, and V. P. Cirillo (1988). "Relationship between low- and high-affinity glucose transport systems of *Saccharomyces cerevisiae*." J Bacteriol 170(11): 5375-5377.

Rawat, U. and M. Rao (1997). "Site and significance of cysteine residues in xylose reductase from *Neurospora crassa* as deduced by fluorescence studies." Biochemical and Biophysical Research Communications 239(3): 789-93.

Reifenberger E., E. Boles, and M. Ciriacy (1997). "Kinetic characterization of individual hexose transporters of *Saccharomyces cerevisiae* and their relation to the triggering mechanisms of glucose repression." Eur J Biochem 245(2): 324-333.

Romero, M. D., J. Aguado, et al. (1999). "Cellulase production by *Neurospora crassa* on wheat straw." Enzyme Microb Tech 25: 244-250.

Roy, A., A. Kucukural, and Y. Zhang (2010). "I-TASSER: a unified platform for automated protein structure and function prediction." Nat Protoc 5(4):725-738.

Rubin E. M. (2008). "Genomics of cellulosic biofuels." Nature 454(7206):841-845.

Ruepp, A., A. Zollner, et al. (2004). "The FunCat, a functional annotation scheme for systematic classification of proteins from whole genomes." Nucleic Acids Res 32(18):5539-5545.

Runquist, D., C. Fonseca, et al. (2009). "Expression of the Gxfl transporter from *Candida* intermedia improves fermentation performance in recombinant xylose-utilizing *Saccharomyces cerevisiae*." Appl Microbiol Biotechnol 82(1): 123-130.

Runquist, D., B. Hahn-Hagerdal, and P. Rådström (2010). "Comparison of heterologous xylose transporters in recombinant *Saccharomyces cerevisiae*." Biotechnol Biofuels 3:5.

Saha, B. C. (2003). "Hemicellulose bioconversion." J Ind Microbiol Biotechnol 30:279-291.

Saloheimo, A., J. Rauta, et al. (2007). "Xylose transport studies with xylose-utilizing *Saccharomyces cerevisiae* strains expressing heterologous and homologous permeases." Appl Microbiol Biotechnol 74(5):1041-1052.

Sarkar, G. and S. S. Sommer (1990). "The "megaprimer" method of site-directed mutagenesis." Biotechniques 8(4): 404-407.

Sauer, U. (2001). "Evolutionary engineering of industrially important microbial phenotypes." Adv Biochem Eng Biotechnol 73:129-169.

Scarborough, G. A. (1973). "Transport in *Neurospora*." Int Rev Cytol 34:103-122.

Seiboth B, S. Hakola, et al. (1997). "Role of four major cellulases in triggering of cellulase gene expression by cellulose in *Trichoderma reesei*." J Bacteriol 179(17): 5318-5320.

Seidl, V., C. Gamauf, et al. (2008). "The *Hypocrea* jecorina (*Trichoderma reesei*) hypercellulolytic mutant RUT C30 lacks a 85 kb (29 gene-encoding) region of the wild-type genome." BMC Genomics 9:327.

Shao, Z., H. Zhao, and H. Zhao (2009). "DNA assembler, an in vivo genetic method for rapid construction of biochemical pathways." Nucleic Acids Res. 37(2):e16.

Sikorski, R. S, and P. Hieter (1989). "A system of shuttle vectors and yeast host strains designed for efficient manipulation of DNA in *Saccharomyces cerevisiae*." Genetics 122(1):19-27.

Skory, C. D., S, N. Freer, and R. J. Bothast (1996). "Expression and secretion of the *Candida* wickerhamii extracellular beta-glucosidase gene, bglB, in *Saccharomyces cerevisiae*." Curr Genet 30(5):417-422.

Smith, M. L., O. C. Micali, et al. (2000). "Vegetative incompatibility in the het-6 region of *Neurospora crassa* is mediated by two linked genes." Genetics 155(3):1095-1104.

Stambuk, B. U., M. A. Franden, et al. (2003). "D-Xylose transport by *Candida succiphila* and *Kluyveromyces marxianus*." Appl Biochem Biotechnol 105-108:255-263.

Stephanopoulos, G. (2007). "Challenges in Engineering Microbes for Biofuels Production." Science 315(5813): 801-804.

Stricker A. R., R. L. Mach and L. H. de Graaff (2008). "Regulation of transcription of cellulases- and hemicellulases-encoding genes in *Aspergillus niger* and *Hypocrea jecorina* (*Trichoderma reesei*)." Appl Microbiol Biotechnol 78(2):211-220.

Sullivan, R. and H. Zhao (2007). "Cloning, characterization, and mutational analysis of a highly active and stable L-arabinitol 4-dehydrogenase from *Neurospora crassa*." Appl Microbiol Biotechnol 77(4):845-52.

Sun Y. and J. Cheng (2002). "Hydrolysis of lignocellulosic materials for ethanol production: a review." Bioresource Technol 83(1):1-11.

Suominen P. L., A. L. Mantyla, et al. (1993). "High frequency one-step gene replacement in *Trichoderma reesei*. II. Effects of deletions of individual cellulase genes." Mol Gen Genet 241(5-6):523-530.

Tian, C., W. T. Beeson, et al. (2009). "Systems analysis of plant cell wall degradation by the model filamentous fungus *Neurospora crassa*." Proc Natl Acad Sci USA 106(52): 22157-22162.

Tian, C., T. Kasuga, et al. (2007). "Transcriptional profiling of cross pathway control in *Neurospora crassa* and comparative analysis of the Gcn4 and CPC1 regulons." Eukaryot Cell 6(6): 1018-1029.

Townsend J. P. (2004). "Resolution of large and small differences in gene expression using models for the Bayesian analysis of gene expression levels and spotted DNA microarrays." BMC Bioinformatics 5:54.

Townsend J. P. and D. L. Hartl (2002). "Bayesian analysis of gene expression levels: statistical quantification of relative mRNA level across multiple strains or treatments." Genome Biol 3(12):research0071.1-0071.16.

USDA, The Economic Feasibility of Ethanol Production from Sugar in the United States, United States Department of Agriculture (2006).

van Rooyen, R., B. Hahn-Hägerdal, et al. (2005). "Construction of cellobio se-growing and fermenting *Saccharomyces cerevisiae* strains." J Biotechnol 120(3):284-295.

Vogel, H. J. (1956). "A convenient growth medium for *Neurospora*." Microbiol. Genet. Bull. 13:42-46.

Wagner, S., M. L. Bader, et al. (2006). "Rationalizing membrane protein overexpression." Trends Biotechnol 24(8): 364-371.

Watanabe, S., A. Abu Saleh, et al. (2007). "Ethanol production from xylose by recombinant *Saccharomyces cerevisiae* expressing protein-engineered NADH-preferring xylose reductase from *Pichia stipitis*." Microbiology 153 (Pt 9):3044-3054.

Watanabe, S., T. Kodaki, and K. Makino (2005a). "L-Arabinose 1-dehydrogenase: a novel enzyme involving in bacterial L-arabinose metabolism." Nucleic Acids Symp Ser (Oxf) 49:309-310.

Watanabe, S., T. Kodaki, and K. Makino (2005b). "Complete reversal of coenzyme specificity of xylitol dehydrogenase and increase of thermostability by the introduction of structural zinc." J Biol Chem 280(11):10340-10349.

Wiedemann, B. and E. Boles (2008). "Codon-optimized bacterial genes improve L-arabinose fermentation in recombinant *Saccharomyces cerevisiae*." Appl Environ Microbiol 74(7):2043-2050.

Wisselink, H. W., M. J. Toirkens, et al. (2007). "Engineering of *Saccharomyces cerevisiae* for efficient anaerobic alcoholic fermentation of L-arabinose." Appl Environ Microbiol 73(15):4881-4891.

Wisselink, H. W., M. J. Toirkens, et al. (2009). "Novel Evolutionary Engineering Approach for Accelerated Utilization of Glucose, Xylose, and Arabinose Mixtures by Engineered *Saccharomyces cerevisiae* Strains." Appl Environ Microbiol 75(4):907-914.

Woodyer, R., M. Simurdiak, et al. (2005). "Heterologous expression, purification, and characterization of a highly active xylose reductase from *Neurospora crassa*." Appl Environ Microbiol 71(3): 1642-7.

Wymelenberg, A. V., et al. (2009). "Transcriptome and Secretome Analyses of *Phanerochaete* Chrysosporium Reveal Complex Patterns of Gene Expression." Appl Environ Microbiol 75(12):4058-4068.

Xin, Z, Q. Yinbo, and G. Peiji. (1993). "Acceleration of ethanol production from paper mill waste fiber by supplementation with β-glucosidase." Enzyme Microb Tech 15(1):62.

The invention claimed is:

1. A method of increasing transport of cellodextrin into a cell, comprising:

culturing a host cell which comprises a recombinant polynucleotide encoding a cellodextrin transporter polypeptide in a medium such that the recombinant polynucleotide is expressed, said cellodextrin transporter having the structure of a Major Facilitator Superfamily protein and comprising transmembrane α-helix 1, α-helix 2, α-helix 3, α-helix 4, α-helix 5, α-helix 6, α-helix 7, α-helix 8, α-helix 9, α-helix 10, α-helix 11, α-helix 12, said transmembrane α-helix 2 characterized by:

a tyrosine or phenylalanine at the position corresponding to amino acid 1 of SEQ ID NO:2;

a glycine at the position corresponding to amino acid 4 of SEQ ID NO:2;

a proline, valine, or phenylalanine at the position corresponding to amino acid 10 of SEQ ID NO:2; and an aspartate or glutamine at the position corresponding to amino acid 17 of SEQ ID NO:2, wherein expression of the recombinant polynucleotide results in increased transport of cellodextrin into the cell compared with a cell that does not comprise the recombinant polynucleotide.

2. The method of claim 1 wherein the polypeptide comprises an amino acid sequence having at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% amino acid identity to NCU00801 or NCU08114.

3. The method of claim 1 wherein the host cell further comprises a second recombinant polynucleotide encoding at least a catalytic domain of a β-glucosidase.

4. The method of claim 3 wherein the β-glucosidase is from *Neurospora crassa.*

5. The method of claim 4 wherein the β-glucosidase is encoded by NCU00130.

6. The method of claim 1 wherein the host cell further comprises one or more recombinant polynucleotides wherein the one or more polynucleotides encode one or more enzymes selected from one or more of the group consisting of L-arabinose isomerase, L-ribulokinase, L-ribulose-5-P 4 epimerase, xylose isomerase, xylulokinase, aldose reductase, L-arabinitol 4-dehydrogenase, L-xylulose reductase, and xylitol dehydrogenase.

7. The method of claim 1, wherein the host cell further comprises a second recombinant polynucleotide wherein the second recombinant polynucleotide encodes a pentose transporter.

8. The method of claim 7, wherein the pentose transporter is selected from the group consisting of NCU00821, NCU04963, NCU06138, STL12/XUT6, SUT2, SUT3, XUT1, and XUT3.

9. The method of claim 1 wherein the medium comprises a cellulase-containing enzyme mixture from an altered organism, wherein the cellulase-containing mixture has reduced β-glucosidase activity compared to a cellulase-containing mixture from an unaltered organism.

10. The method of claim 1, wherein the host cell is selected from the group consisting of *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Kluyveromyces* sp., *Kluyveromyces marxiamus, Kluyveromyces lactis, Kluyveromyces fragilis, Pichia stipitis, Sporotrichum thermophile, Candida shehatae, Candida tropicalis, Neurospora crassa, Zymomonas mobilis, Clostridium* sp., *Clostridium phytofermentans, Clostridium thermocellum, Clostridium beijerinckii, Clostridium acetobutylicum, Moorella thermoacetica, Escherichia coli, Klebsiella oxytoca, Thermoanaerobacterium saccharolyticum*, and *Bacillus subtilis.*

11. The method of claim 1 wherein the cellodextrin is selected from one or more of the group consisting of cellobiose, cellotriose, and cellotetraose.

12. The method of claim 2, wherein the polypeptide comprises an amino acid sequence having at least 85% amino acid identity to NCU00801.

13. The method of claim 2, wherein the polypeptide comprises an amino acid sequence having at least 85% amino acid identity to NCU08114.

14. The method of claim 2, wherein the polypeptide comprises an amino acid sequence having at least 90% amino acid identity to NCU00801.

15. The method of claim 2, wherein the polypeptide comprises an amino acid sequence having at least 90% amino acid identity to NCU08114.

16. The method of claim 2, wherein the polypeptide comprises an amino acid sequence having at least 95% amino acid identity to NCU00801.

17. The method of claim 2, wherein the polypeptide comprises an amino acid sequence having at least 95% amino acid identity to NCU08114.

* * * * *

UNITED STATES PATENT AND TRADEMARK OFFICE

CERTIFICATE OF CORRECTION

PATENT NO. : 8,765,410 B2
APPLICATION NO. : 13/802533
DATED : July 1, 2014
INVENTOR(S) : N. Louise Glass et al.

It is certified that error appears in the above-identified patent and that said Letters Patent is hereby corrected as shown below:

On the Title Page, Item 56

On first page, under OTHER PUBLICATIONS, in column 2, line 1 delete "recieved" and insert --received--, therefor.

On second page, under OTHER PUBLICATIONS, in column 1, line 14 delete "Mediatied" and insert --Mediated--, therefor.

On second page, under OTHER PUBLICATIONS, in column 1, line 14 delete "Inducibile" and insert --Inducible--, therefor.

On third page, under OTHER PUBLICATIONS, in column 1, line 15 delete "recieved" and insert --received--, therefor.

On third page, under OTHER PUBLICATIONS, in column 1, line 17 delete "recieved" and insert --received--, therefor.

On third page, under OTHER PUBLICATIONS, in column 1, line 20 delete "recieved" and insert --received--, therefor.

On third page, under OTHER PUBLICATIONS, in column 1, line 23 delete "recieved" and insert --received--, therefor.

On third page, under OTHER PUBLICATIONS, in column 1, line 25 delete "recieved" and insert --received--, therefor.

On third page, under OTHER PUBLICATIONS, in column 1, line 30 delete "Techniques" and insert --Technologies--, therefor.

Signed and Sealed this
Thirty-first Day of March, 2015

Michelle K. Lee
*Director of the United States Patent and Trademark Office*

On fourth page, under OTHER PUBLICATIONS, in column 1, line 6 delete "Eningineered" and insert --Engineered--, therefor.

On fourth page, under OTHER PUBLICATIONS, in column 1, line 33 delete "Microbial" and insert --Microbiol--, therefor.

On fourth page, under OTHER PUBLICATIONS, in column 1, line 43 delete "Microbial" and insert --Microbiol--, therefor.

On fourth page, under OTHER PUBLICATIONS, in column 1, line 57 delete "Genomic," and insert --Genomics,--, therefor.

On fourth page, under OTHER PUBLICATIONS, in column 2, line 59 delete "Conventional," and insert --Convenient--, therefor.

On fourth page, under OTHER PUBLICATIONS, in column 2, line 72 delete "Metabilism"," and insert --Metabolism",--, therefor.

On fifth page, under OTHER PUBLICATIONS, in column 2, line 12 delete "Waster" and insert --Waste--, therefor.

On fifth page, under OTHER PUBLICATIONS, in column 2, line 13 delete "Micro." and insert --Microb.--, therefor.

In the Specification

At column 26, line number 41, delete "plasmid" and insert --plasmid.--, therefor.

At column 48, line number 17, delete "011 is" and insert --Ollis--, therefor.

At column 58, line numbers 5-6, delete "may by" and insert --may be--, therefor.

At column 63, line number 55, delete "6ND," and insert --$^{6}$ND,--, therefor.

At column 63, line number 56, delete "7NC," and insert --$^{7}$NC,--, therefor.

At column 74, line numbers 66-67, delete "T of" and insert --Tof--, therefor.

At column 97, line number 64, delete "(SEQ ID NO: 13)" and insert --(SEQ ID NO: 13).--, therefor.

At column 117, line number 28, delete "NAD" and insert --NAD+--, therefor.

At column 118, line number 43, delete "1214" and insert --I214--, therefor.

At column 118, line number 44, delete "1225" and insert --I225--, therefor.

At column 118, line number 44, delete "1213" and insert --I213--, therefor.

At column 119, line number 25, delete "1225R" and insert --I225R--, therefor.

At column 119, line number 26, delete "1214R" and insert --I214R--, therefor.

At column 119, line number 29, delete "NAD" and insert --NAD+--, therefor.

At column 121, line number 34, delete “NAD” and insert --NAD+--, therefor.

At column 137, line number 4, delete “011 is” and insert --Ollis--, therefor.

At column 140, line number 50, delete “Hering a” and insert --Heringa--, therefor.

At column 142, line number 44, delete “cellobio se” and insert --cellobiose--, therefor.

SEQUENCE LISTING

```
<160> NUMBER OF SEQ ID NOS: 97

<210> SEQ ID NO 1
<211> LENGTH: 18
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 1
<223> OTHER INFORMATION: Xaa = Leu or Ile or Val or Met
<221> NAME/KEY: VARIANT
<222> LOCATION: 3
<223> OTHER INFORMATION: Xaa = Phe or Leu
<221> NAME/KEY: VARIANT
<222> LOCATION: 4, 5, 6, 7, 8, 9, 10, 11, 12, 13, 14, 15, 16
<223> OTHER INFORMATION: Xaa = Any Amino Acid
<221> NAME/KEY: VARIANT
<222> LOCATION: 17
<223> OTHER INFORMATION: Xaa = Tyr or Phe

<400> SEQUENCE: 1

Xaa Tyr Xaa Xaa Xaa Xaa Xaa Xaa Xaa Xaa Xaa Xaa Xaa Xaa Xaa Xaa
 1               5                  10                  15

Xaa Asp


<210> SEQ ID NO 2
<211> LENGTH: 17
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 1
<223> OTHER INFORMATION: Xaa = Tyr or Phe
<221> NAME/KEY: VARIANT
<222> LOCATION: 2, 3, 5, 6, 7, 8, 9, 11, 12, 13, 14, 15, 16
<223> OTHER INFORMATION: Xaa = Any Amino Acid
<221> NAME/KEY: VARIANT
<222> LOCATION: 10
<223> OTHER INFORMATION: Xaa = Pro or Val or Phe
<221> NAME/KEY: VARIANT
<222> LOCATION: 17
<223> OTHER INFORMATION: Xaa = Asp or Gln

<400> SEQUENCE: 2

Xaa Xaa Xaa Gly Xaa Xaa Xaa Xaa Xaa Xaa Xaa Xaa Xaa Xaa Xaa Xaa
 1               5                  10                  15

Xaa


<210> SEQ ID NO 3
<211> LENGTH: 3
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 3
```

<223> OTHER INFORMATION: Xaa = Arg or Lys

<400> SEQUENCE: 3

Gly Arg Xaa
 1

<210> SEQ ID NO 4
<211> LENGTH: 9
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 2, 3, 4, 5, 6, 7
<223> OTHER INFORMATION: Xaa = Any Amino Acid
<221> NAME/KEY: VARIANT
<222> LOCATION: 8
<223> OTHER INFORMATION: Xaa = Tyr or Phe

<400> SEQUENCE: 4

Arg Xaa Xaa Xaa Xaa Xaa Xaa Xaa Asn
 1               5

<210> SEQ ID NO 5
<211> LENGTH: 8
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 3
<223> OTHER INFORMATION: Xaa = Ile or Val or Leu or Ala
<221> NAME/KEY: VARIANT
<222> LOCATION: 5, 6, 7
<223> OTHER INFORMATION: Xaa = Any Amino Acid

<400> SEQUENCE: 5

Trp Arg Xaa Pro Xaa Xaa Xaa Gln
 1               5

<210> SEQ ID NO 6
<211> LENGTH: 24
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 6, 8, 9, 10, 11, 12, 13, 14, 15, 17, 18, 19, 21, 22
<223> OTHER INFORMATION: Xaa = Any Amino Acid

<400> SEQUENCE: 6

Pro Glu Ser Pro Arg Xaa Leu Xaa Xaa Xaa Xaa Xaa Xaa Xaa Xaa Ala
 1               5                  10                  15

Xaa Xaa Xaa Leu Xaa Xaa Tyr His
            20

<210> SEQ ID NO 7
<211> LENGTH: 9
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 2
<223> OTHER INFORMATION: Xaa = Gly or Ser or Thr
<221> NAME/KEY: VARIANT
<222> LOCATION: 4, 8
<223> OTHER INFORMATION: Xaa = Any Amino Acid
<221> NAME/KEY: VARIANT
<222> LOCATION: 9

<223> OTHER INFORMATION: Xaa = Leu or Ile or Val

<400> SEQUENCE: 7

Phe Xaa Gln Xaa Ser Gly Asn Xaa Xaa
 1               5

<210> SEQ ID NO 8
<211> LENGTH: 18
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 2, 3, 4, 6, 7, 9, 11, 12, 13, 14
<223> OTHER INFORMATION: Xaa = Any Amino Acid
<221> NAME/KEY: VARIANT
<222> LOCATION: 5
<223> OTHER INFORMATION: Xaa = Tyr or Ile or Val
<221> NAME/KEY: VARIANT
<222> LOCATION: 16
<223> OTHER INFORMATION: Xaa = Gly or Ala

<400> SEQUENCE: 8

Leu Xaa Xaa Xaa Xaa Xaa Xaa Glu Xaa Leu Xaa Xaa Xaa Xaa Arg Xaa
 1               5                   10                  15

Lys Gly

<210> SEQ ID NO 9
<211> LENGTH: 5
<212> TYPE: PRT
<213> ORGANISM: Artificial Sequence
<220> FEATURE:
<223> OTHER INFORMATION: Transmembrane helix

<400> SEQUENCE: 9

Pro Glu Ser Pro Arg
 1               5

<210> SEQ ID NO 10
<211> LENGTH: 4
<212> TYPE: PRT
<213> ORGANISM: Artificial Sequence
<220> FEATURE:
<223> OTHER INFORMATION: Transmembrane helix

<400> SEQUENCE: 10

Pro Glu Thr Lys
 1

<210> SEQ ID NO 11
<211> LENGTH: 18
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 1
<223> OTHER INFORMATION: Xaa = Leu or Ile or Val or Met or Ser or Thr or
      Ala or Gly
<221> NAME/KEY: VARIANT
<222> LOCATION: 2
<223> OTHER INFORMATION: Xaa = Leu or Ile or Val or Met or Phe or Ser or
      Ala or Gly
<221> NAME/KEY: VARIANT
<222> LOCATION: 3
<223> OTHER INFORMATION: Xaa = Any Amino Acid But Ser or His
<221> NAME/KEY: VARIANT
<222> LOCATION: 4
<223> OTHER INFORMATION: Xaa = Any Amino Acid But Arg or Asp or Glu
<221> NAME/KEY: VARIANT
<222> LOCATION: 5
<223> OTHER INFORMATION: Xaa = Leu or Ile or Val or Met or Ser or Ala
<221> NAME/KEY: VARIANT
<222> LOCATION: 6
<223> OTHER INFORMATION: Xaa = Asp or Glu
<221> NAME/KEY: VARIANT
<222> LOCATION: 7
<223> OTHER INFORMATION: Xaa = Any Amino Acid But Thr or Asp
<221> NAME/KEY: VARIANT
<222> LOCATION: 8
<223> OTHER INFORMATION: Xaa = Leu or Ile or Val or Met or Phe or Tyr or Trp or Ala
<221> NAME/KEY: VARIANT
<222> LOCATION: 11
<223> OTHER INFORMATION: Xaa = Arg or Lys
<221> NAME/KEY: VARIANT
<222> LOCATION: 12, 13, 14, 15, 16, 17
<223> OTHER INFORMATION: Xaa = Any Amino Acid and up to two of them can be present or absent
<221> NAME/KEY: VARIANT
<222> LOCATION: 18
<223> OTHER INFORMATION: Xaa = Gly or Ser or Thr or Ala

<400> SEQUENCE: 11

```
Xaa Xaa Xaa Xaa Xaa Xaa Xaa Xaa Gly Arg Xaa Xaa Xaa Xaa Xaa Xaa
 1               5                  10                  15

Xaa Xaa
```

<210> SEQ ID NO 12
<211> LENGTH: 26
<212> TYPE: PRT
<213> ORGANISM: Artificial Sequence
<220> FEATURE:
<223> OTHER INFORMATION: Sequence motif
<221> NAME/KEY: VARIANT
<222> LOCATION: 1
<223> OTHER INFORMATION: Xaa = Leu or Ile or Val or Met or Phe
<221> NAME/KEY: VARIANT
<222> LOCATION: 2, 6, 9, 10, 11, 12, 13, 14, 15, 17, 18, 20, 21, 22, 23, 24, 25
<223> OTHER INFORMATION: Xaa = Any Amino Acid
<221> NAME/KEY: VARIANT
<222> LOCATION: 4
<223> OTHER INFORMATION: Xaa = Leu or Ile or Val or Met or Phe or Ala
<221> NAME/KEY: VARIANT
<222> LOCATION: 5
<223> OTHER INFORMATION: Xaa = Any Amino Acid But Val
<221> NAME/KEY: VARIANT
<222> LOCATION: 8
<223> OTHER INFORMATION: Xaa = Any Amino Acid But Lys or Pro
<221> NAME/KEY: VARIANT
<222> LOCATION: 16
<223> OTHER INFORMATION: Xaa = Leu or Ile or Phe or Tyr
<221> NAME/KEY: VARIANT
<222> LOCATION: 19
<223> OTHER INFORMATION: Xaa = Glu or Gln
<221> NAME/KEY: VARIANT
<222> LOCATION: 26
<223> OTHER INFORMATION: Xaa = Arg or Lys

<400> SEQUENCE: 12

```
Xaa Xaa Gly Xaa Xaa Xaa Gly Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25
```

<210> SEQ ID NO 13
<211> LENGTH: 8
<212> TYPE: PRT
<213> ORGANISM: Artificial Sequence
<220> FEATURE:
<223> OTHER INFORMATION: Synthesized Construct
<221> NAME/KEY: VARIANT
<222> LOCATION: 1
<223> OTHER INFORMATION: Xaa = Ala or Cys
<221> NAME/KEY: VARIANT
<222> LOCATION: 2, 4, 5, 6, 7
<223> OTHER INFORMATION: Xaa = Any Amino Acid
<221> NAME/KEY: VARIANT
<222> LOCATION: 8
<223> OTHER INFORMATION: Xaa = Any Amino Acid But Glu or Asp

<400> SEQUENCE: 13

Xaa Xaa Val Xaa Xaa Xaa Xaa Xaa
1 5

<210> SEQ ID NO 14
<211> LENGTH: 9
<212> TYPE: PRT
<213> ORGANISM: Artificial Sequence
<220> FEATURE:
<223> OTHER INFORMATION: Sequence motif
<220> FEATURE:
<221> NAME/KEY: VARIANT
<222> LOCATION: 1
<223> OTHER INFORMATION: Xaa = Leu or Ile or Val or Met or Phe or Ser or Thr or Cys
<220> FEATURE:
<221> NAME/KEY: VARIANT
<222> LOCATION: 2
<223> OTHER INFORMATION: Xaa = Leu or Ile or Val or Phe or Tyr or Ser
<220> FEATURE:
<221> NAME/KEY: VARIANT
<222> LOCATION: 3
<223> OTHER INFORMATION: Xaa = Leu or Ile or Val
<220> FEATURE:
<221> NAME/KEY: VARIANT
<222> LOCATION: 4
<223> OTHER INFORMATION: Xaa = Leu or Ile or Val or Met or Ser or Thr
<220> FEATURE:
<221> NAME/KEY: VARIANT
<222> LOCATION: 8
<223> OTHER INFORMATION: Xaa = Leu or Ile or Val or Met or Phe or Ala or Arg
<220> FEATURE:
<221> NAME/KEY: VARIANT
<222> LOCATION: 9
<223> OTHER INFORMATION: Xaa = Cys or Ser or Ala or Gly or Asn

<400> SEQUENCE: 14

Xaa Xaa Xaa Xaa Glu Asn Gly Xaa Xaa
1 5

<210> SEQ ID NO 15
<211> LENGTH: 18
<212> TYPE: PRT
<213> ORGANISM: Artificial Sequence
<220> FEATURE:
<223> OTHER INFORMATION: Sequence motif
<220> FEATURE:
<221> NAME/KEY: VARIANT
<222> LOCATION: 1, 2
<223> OTHER INFORMATION: Xaa = Leu or Ile or Val or Met
<220> FEATURE:
<221> NAME/KEY: VARIANT
<222> LOCATION: 3
<223> OTHER INFORMATION: Xaa = Lys or Arg
<220> FEATURE:
<221> NAME/KEY: VARIANT
<222> LOCATION: 4, 6, 7, 8, 9, 16, 17
<223> OTHER INFORMATION: Xaa = Any Amino Acid
<220> FEATURE:
<221> NAME/KEY: VARIANT
<222> LOCATION: 5
<223> OTHER INFORMATION: Xaa = Glu or Gln or Lys or Arg or Asp
<220> FEATURE:
<221> NAME/KEY: VARIANT
<222> LOCATION: 11

<223> OTHER INFORMATION: Xaa = Leu or Ile or Val or Met or Phe or Thr or Cys
<220> FEATURE:
<221> NAME/KEY: VARIANT
<222> LOCATION: 12
<223> OTHER INFORMATION: Xaa = Leu or Ile or Val or Thr
<220> FEATURE:
<221> NAME/KEY: VARIANT
<222> LOCATION: 13
<223> OTHER INFORMATION: Xaa = Leu or Ile or Val or Met or Phe
<220> FEATURE:
<221> NAME/KEY: VARIANT
<222> LOCATION: 14
<223> OTHER INFORMATION: Xaa = Ser or Thr
<220> FEATURE:
<221> NAME/KEY: VARIANT
<222> LOCATION: 18
<223> OTHER INFORMATION: Xaa = Ser or Gly or Ala or Asp or Asn or Ile or Thr

<400> SEQUENCE: 15

```
Xaa Xaa Xaa Xaa Xaa Xaa Xaa Xaa Xaa Gly Xaa Xaa Xaa Xaa Asp Xaa
 1               5                  10                  15

Xaa Xaa
```

<210> SEQ ID NO 16
<211> LENGTH: 19
<212> TYPE: DNA
<213> ORGANISM: Artificial Sequence
<220> FEATURE:
<223> OTHER INFORMATION: Synthesized Construct

<400> SEQUENCE: 16
atctgggaag cgaacaaag 19

<210> SEQ ID NO 17
<211> LENGTH: 18
<212> TYPE: DNA
<213> ORGANISM: Artificial Sequence
<220> FEATURE:
<223> OTHER INFORMATION: Synthesized Construct

<400> SEQUENCE: 17
tagcggtcgt cggaatag 18

<210> SEQ ID NO 18
<211> LENGTH: 18
<212> TYPE: DNA
<213> ORGANISM: Artificial Sequence
<220> FEATURE:
<223> OTHER INFORMATION: Synthesized Construct

<400> SEQUENCE: 18
cccatcacca ctactacc 18

<210> SEQ ID NO 19
<211> LENGTH: 18
<212> TYPE: DNA
<213> ORGANISM: Artificial Sequence
<220> FEATURE:
<223> OTHER INFORMATION: Synthesized Construct

<400> SEQUENCE: 19
ccagccctga acaccaag 18

<210> SEQ ID NO 20
<211> LENGTH: 18
<212> TYPE: DNA

<213> ORGANISM: Artificial Sequence
<220> FEATURE:
<223> OTHER INFORMATION: Synthesized Construct

<400> SEQUENCE: 20
tgatcttacc gactacct 18

<210> SEQ ID NO 21
<211> LENGTH: 18
<212> TYPE: DNA
<213> ORGANISM: Artificial Sequence
<220> FEATURE:
<223> OTHER INFORMATION: Synthesized Construct

<400> SEQUENCE: 21
cagagcttct ccttgatg 18

<210> SEQ ID NO 22
<211> LENGTH: 533
<212> TYPE: PRT
<213> ORGANISM: Sporotrichum thermophile

<400> SEQUENCE: 22

```
Met Gly Leu Ser Thr Lys Ile Leu Gln Lys Ile Val Arg Asn Glu Ala
 1               5                  10                  15

Met Ala Ser Asp Pro Pro Glu Ile Tyr Gly Trp Arg Val Tyr Leu Leu
            20                  25                  30

Ala Cys Ser Ala Cys Phe Gly Ala Met Ser Phe Gly Trp Asp Ser Ser
        35                  40                  45

Val Ile Gly Gly Val Ile Val Leu Pro Pro Phe Ile Arg Asp Phe Asn
    50                  55                  60

Leu Gly Asp Pro Lys Ser Gln Ala Ser Ala Asn Leu Ser Ala Asn Ile
65                  70                  75                  80

Val Ser Thr Leu Gln Ala Gly Cys Phe Leu Gly Ala Leu Val Ala Ser
                85                  90                  95

Pro Met Thr Asp Arg Phe Gly Arg Lys Trp Cys Leu Ile Gly Val Ser
            100                 105                 110

Leu Ile Ile Ile Ile Gly Ile Ile Met Gln Ala Ala Ala Ser Gly Asn
        115                 120                 125

Leu Gly Pro Met Tyr Ala Gly Arg Phe Ile Ala Gly Ala Gly Val Gly
    130                 135                 140

Ala Ala Ser Thr Ile Asn Pro Ile Tyr Val Ser Glu Asn Ala Pro Arg
145                 150                 155                 160

Ala Ile Arg Gly Leu Leu Thr Gly Leu Tyr Gln Leu Phe Ile Val Thr
                165                 170                 175

Gly Gly Met Ile Ala Phe Trp Ile Asn Tyr Ser Val Ser Ile His Phe
            180                 185                 190

Pro Glu Thr Lys Ile Met Tyr Val Phe Pro Leu Ala Ile Gln Ala Leu
        195                 200                 205

Pro Ala Ala Leu Leu Cys Leu Cys Met Leu Leu Cys Gln Glu Ser Pro
    210                 215                 220

Arg Trp Leu Ala Arg Arg Asp Arg Trp Glu Asp Thr Lys Arg Val Leu
225                 230                 235                 240

Ser Arg Ile Arg Asn Leu Pro Pro Asp His Pro Tyr Ile Gln Asp Glu
                245                 250                 255

Phe Gln Glu Ile Val Ala Gln Leu Glu His Glu Arg Arg Leu Ile Gly
            260                 265                 270
```

-continued

```
Asp Ala Ser Phe Trp Asn Leu Gln Arg Glu Met Trp Thr Ile Ala Gly
        275                 280                 285

Asn Arg Arg Arg Val Leu Ile Ser Ile Ile Leu Met Ile Cys Gln Gln
    290                 295                 300

Met Thr Gly Thr Asn Ala Ile Asn Thr Tyr Ala Pro Thr Ile Phe Lys
305                 310                 315                 320

Asn Leu Gly Leu Thr Gly Thr Ser Thr Ser Leu Phe Ser Thr Gly Val
                325                 330                 335

Tyr Gly Ile Val Lys Val Thr Ser Cys Ile Ile Phe Leu Leu Phe Met
            340                 345                 350

Ala Asp Ser Leu Gly Arg Arg Arg Ser Leu Leu Trp Thr Ser Ile Ala
        355                 360                 365

Gln Gly Leu Ala Met Phe Tyr Ile Gly Leu Tyr Val Arg Ile Ala Pro
    370                 375                 380

Pro Lys Glu Gly Glu Ser Val Pro Pro Ala Gly Tyr Phe Ala Leu Val
385                 390                 395                 400

Cys Ile Phe Leu Phe Ala Ala Phe Phe Gln Phe Gly Trp Gly Pro Ala
                405                 410                 415

Cys Trp Ile Tyr Ala Ser Glu Ile Pro Ala Ala Arg Leu Arg Ser Leu
            420                 425                 430

Asn Val Ala Tyr Ala Ala Ala Thr Gln Trp Leu Phe Asn Phe Val Val
        435                 440                 445

Ala Arg Thr Val Pro Val Met Ile Val Thr Met Gly Glu Gly Gly Tyr
    450                 455                 460

Gly Thr Tyr Leu Leu Phe Gly Ser Phe Cys Phe Ser Met Phe Val Phe
465                 470                 475                 480

Val Trp Phe Phe Val Pro Glu Thr Lys Gly Val Ser Leu Glu Ala Met
                485                 490                 495

Asp Lys Leu Phe Gly Val Thr Asp Glu Ser Ser Lys Ser Leu Thr Val
            500                 505                 510

Asp Glu Asp Ala Lys Glu Lys Glu Lys Asp Gly Pro His Ala Arg Gln
        515                 520                 525

Thr Glu Val Val Ala
    530


<210> SEQ ID NO 23
<211> LENGTH: 512
<212> TYPE: PRT
<213> ORGANISM: Sporotrichum thermophile

<400> SEQUENCE: 23

Met Lys Lys Phe Leu Gly Leu Arg Gly Gln Ala Leu Asn Leu Ala Val
 1               5                  10                  15

Gly Thr Ile Ala Gly Cys Asp Phe Leu Leu Phe Gly Tyr Asp Gln Gly
            20                  25                  30

Val Met Gly Gly Ile Leu Thr Leu Lys Val Phe Leu Asp Ala Phe Pro
        35                  40                  45

Met Ile Asn Pro Glu Ala Ala Gly Leu Ser His Asp Glu Ser Ser Thr
    50                  55                  60

Arg Ser Thr Tyr Gln Gly Ile Ala Val Ala Ser Tyr Asn Leu Gly Cys
65                  70                  75                  80

Phe Leu Gly Ala Ile Ile Thr Ile Phe Ile Gly Asn Pro Leu Gly Arg
                85                  90                  95

Lys Arg Val Ile Met Leu Gly Thr Ser Val Met Val Ile Gly Ala Ile
            100                 105                 110
```

```
Leu Gln Ala Ser Ser Thr Thr Leu Pro Gln Phe Ile Val Gly Arg Ile
        115                 120                 125

Ile Thr Gly Leu Gly Asn Gly Gly Asn Thr Ser Thr Val Pro Thr Trp
    130                 135                 140

Gln Ser Glu Thr Ser Lys Ala His Lys Arg Gly Lys Met Ile Phe Phe
145                 150                 155                 160

Cys Ala Ile Ile Leu Ala Phe Ile Pro Phe Leu Pro Glu Ser Pro Arg
                165                 170                 175

Trp Leu Ile Leu Lys Gly Arg Glu Asp Glu Ala Arg Glu Val Ile Ala
            180                 185                 190

Ala Leu Glu Asp Thr Asp Thr Ser Asp Arg Ile Val Glu Asn Glu Phe
        195                 200                 205

Leu Ala Ile Lys Glu Thr Val Leu Glu Met Ser Lys Gly Thr Phe Arg
    210                 215                 220

Asp Leu Phe Thr Met Asp Lys Asn Arg Asn Leu His Arg Thr Leu Leu
225                 230                 235                 240

Ala Tyr Phe Asn Gln Val Phe Gln Gln Ile Ser Gly Ile Asn Leu Ile
                245                 250                 255

Thr Tyr Tyr Ala Ala Val Ile Tyr Lys Gly Leu Gly Met Ser Asp Phe
            260                 265                 270

Leu Ser Arg Leu Leu Ala Ala Leu Asn Gly Thr Glu Tyr Phe Leu Ala
        275                 280                 285

Ser Trp Pro Ala Val Phe Leu Val Glu Arg Val Gly Arg Arg Asn Leu
    290                 295                 300

Met Leu Phe Gly Ala Val Gly Gln Ala Ala Thr Met Ala Ile Leu Ala
305                 310                 315                 320

Gly Val Asn Ser Arg Gln Glu Thr Gly Phe Gln Ile Ala Gly Ile Val
                325                 330                 335

Phe Leu Phe Val Phe Asn Thr Phe Phe Ala Val Gly Trp Leu Gly Met
            340                 345                 350

Thr Trp Leu Tyr Pro Ala Glu Ile Val Pro Leu Arg Ile Arg Ala Pro
        355                 360                 365

Ala Asn Ala Leu Ser Thr Ser Ala Asn Trp Ile Phe Asn Phe Leu Val
    370                 375                 380

Val Met Ile Thr Pro Val Ala Phe Asn Asn Ile Gly Tyr Gln Thr Tyr
385                 390                 395                 400

Ile Ile Phe Ala Val Ile Asn Ala Phe Met Val Pro Cys Val Tyr Phe
                405                 410                 415

Phe Tyr Pro Glu Thr Ala Tyr Arg Ser Leu Glu Glu Met Asp Asn Ile
            420                 425                 430

Phe His Lys Val Ala Asp Gly Trp Lys Gly Val Phe Thr Val Val His
        435                 440                 445

Gln Ala Lys Val Glu Pro Arg Trp Tyr Gly Lys Asn Gly Glu Leu Leu
    450                 455                 460

Val Asp Tyr Gln Gln Thr Glu Glu His Arg Arg His Leu Gln Gln Gln
465                 470                 475                 480

Glu Gly Ala Val Thr Ala Ser Glu Lys Arg Ser Val Glu Gly Ala Gly
                485                 490                 495

Ser Gly Ser Gly Ser Gly Asp Val Lys Gln Asp Glu Tyr Lys Asp Cys
            500                 505                 510
```

<210> SEQ ID NO 24
<211> LENGTH: 519

<212> TYPE: PRT
<213> ORGANISM: Sporotrichum thermophile

<400> SEQUENCE: 24

```
Met Glu Ser Thr His Glu Pro Ala Asp Pro Ile Ala Lys Gly Val Leu
 1               5                  10                  15

Ala Thr Ala Lys Gln Ser Trp His Asp Leu Phe Ile Phe Lys Gln Arg
            20                  25                  30

Val Val Val Thr Asn Glu Leu Gly Glu Thr Ser Thr Glu Trp Ala Arg
        35                  40                  45

Pro Val Pro Leu Arg Asn Pro Ile Ser Leu Leu Ala Gln Leu Ser Ala
    50                  55                  60

Arg Asn Trp Leu Phe Phe Ile Val Gly Phe Leu Ala Trp Val Ala Asp
65                  70                  75                  80

Ala Tyr Asp Phe His Ala Leu Ser Ile Gln Gln Val Lys Leu Ala Glu
                85                  90                  95

Phe Tyr Asn Thr Thr Lys Thr Asn Ile Ser Thr Ala Ile Thr Leu Thr
            100                 105                 110

Leu Leu Leu Arg Ser Val Gly Ala Ala Phe Phe Gly Leu Ala Gly Asp
        115                 120                 125

Lys Trp Gly Arg Lys Trp Pro Met Val Ala Asn Met Ile Val Leu Gly
    130                 135                 140

Val Leu Gln Ile Gly Thr Ile Tyr Ser Val Thr Phe Ser Asp Phe Leu
145                 150                 155                 160

Ala Val Arg Ala Leu Phe Gly Leu Phe Met Gly Gly Val Tyr Gly Asn
                165                 170                 175

Ala Ile Ala Met Ala Leu Glu Asn Ser Pro Pro Asp Ala Arg Gly Leu
            180                 185                 190

Met Ser Gly Ile Leu Gln Gln Gly Tyr Ser Leu Gly Tyr Val Ile Ala
        195                 200                 205

Ala Cys Ala Asn Leu Gly Val Gly Gly Gly Asp Asn Ser Trp Lys Thr
    210                 215                 220

Val Phe Trp Ile Gly Ala Gly Leu Ser Ile Gly Val Gly Leu Val Arg
225                 230                 235                 240

Cys Phe Phe Pro Glu Ser Gln Gln Phe Leu Glu Ala Arg Ala Ala Gly
                245                 250                 255

Lys Gly Gln Ala Ser Ala Ser Ala Phe Trp Lys Glu Thr Lys Met Met
            260                 265                 270

Leu Ala Gln Glu Trp Lys Met Cys Val Tyr Cys Ile Ile Leu Met Thr
        275                 280                 285

Trp Phe Asn Tyr Tyr Ser His Thr Ser Gln Asp Ser Tyr Thr Thr Phe
    290                 295                 300

Met Leu Thr Gln Lys Glu Leu Asp Asn Asp Gly Ala Ser Arg Ala Ser
305                 310                 315                 320

Ile Leu Met Lys Val Gly Ala Cys Val Gly Gly Thr Ile Ile Gly Tyr
                325                 330                 335

Ile Ser Gln Trp Phe Gly Arg Arg Arg Thr Ile Ile Val Ala Ala Leu
            340                 345                 350

Ile Ser Gly Leu Ile Ile Pro Ala Trp Ile Leu Pro Glu Gly Glu Arg
        355                 360                 365

Ser Leu Ser Val Thr Gly Phe Phe Met Gln Phe Phe Val Gln Gly Ala
    370                 375                 380

Trp Gly Val Ile Pro Ile His Leu Asn Glu Leu Ser Pro Pro Ala Phe
385                 390                 395                 400
```

Arg Ser Ser Phe Pro Gly Leu Thr Tyr Gln Leu Gly Asn Met Ile Ser
405 410 415

Ser Pro Ser Ala Gln Ile Val Asn Ala Ile Ala Glu Ser His Ser Val
420 425 430

Thr Ser Lys Ser Gly Lys Ser Val Asn Ala Tyr Gly Pro Thr Met Gly
435 440 445

Ile Ala Thr Ala Ile Ile Ala Thr Gly Ile Ala Val Thr Thr Ala Leu
450 455 460

Gly Pro Glu Lys Arg Gly Arg Glu Phe Glu Lys Thr Leu Pro Ala Gly
465 470 475 480

Met Asn Ile Ile Gln Gly Gly Lys Ala Val Asp Asp Leu Glu Lys Gly
485 490 495

Asp Ser Arg Asp Glu Lys Pro Val Val Gly Glu Val Glu Gly Gly Asn
500 505 510

Asp Gly Ser Gly Glu Lys Lys
515

<210> SEQ ID NO 25
<211> LENGTH: 488
<212> TYPE: PRT
<213> ORGANISM: Sporotrichum thermophile

<400> SEQUENCE: 25

Met Ala Asp Glu Lys Arg Met Gly Ser Ser Asp Ser Asp Lys Ala Ala
1 5 10 15

Val Gln His Ser Glu Thr Leu Pro Gly Val Ser Ser Thr Ala Ala Glu
20 25 30

Arg Gly Phe Ala Ala Thr Asp Gln Asn Gly Gln Pro Ile Val Gln Phe
35 40 45

Asp Leu Lys Ala Glu Ala Arg Leu Arg Arg Lys Leu Asp Leu Phe Ile
50 55 60

Val Pro Thr Val Ser Leu Leu Tyr Leu Phe Cys Phe Ile Asp Arg Ala
65 70 75 80

Asn Ile Gly Asn Ala Arg Ile Ala Gly Leu Glu Lys Asp Leu Asn Leu
85 90 95

Thr Gly Tyr Asp Tyr Asn Ala Leu Leu Ser Val Phe Tyr Ile Ser Tyr
100 105 110

Ile Val Phe Glu Ile Pro Ser Asn Ile Ala Cys Lys Trp Ile Gly Pro
115 120 125

Gly Trp Phe Ile Pro Ala Ile Ser Leu Gly Phe Gly Val Val Ser Leu
130 135 140

Ala Thr Ala Phe Val Asp Asn Phe Ala Gln Ala Ala Gly Val Arg Phe
145 150 155 160

Leu Leu Gly Val Phe Glu Ala Gly Met Met Pro Gly Ile Ala Tyr Tyr
165 170 175

Leu Ser Arg Trp Tyr Arg Arg Ala Glu Leu Thr Phe Arg Leu Ser Leu
180 185 190

Tyr Ile Val Met Ala Pro Met Ala Gly Ala Phe Gly Gly Leu Leu Ala
195 200 205

Ser Gly Ile Leu Ser Leu Asp His Val Gly Gly Val Thr Gly Trp Arg
210 215 220

Met Ile Phe Val Val Glu Gly Ile Ile Thr Ile Gly Leu Ser Val Ile
225 230 235 240

Ser Phe Ile Thr Leu Thr Asp Arg Pro Glu Thr Ala Arg Trp Leu Thr

```
                245                 250                 255

Gln Glu Glu Lys Asp Leu Ala Ile Ala Arg Val Lys Ser Glu Arg Val
            260                 265                 270

Ala Thr Thr Glu Val Leu Asp Arg Met Asp Thr Lys Lys Leu Ile Gln
        275                 280                 285

Gly Ile Leu Ser Pro Val Thr Leu Ala Thr Ser Phe Met Phe Leu Leu
    290                 295                 300

Asn Asn Ile Thr Gln Leu Phe Thr Val Pro Pro Tyr Val Val Gly Gly
305                 310                 315                 320

Phe Phe Thr Leu Ala Leu Pro Leu Leu Ser Trp Tyr Leu Asp Arg Arg
                325                 330                 335

Gln Ile Ile Ile Leu Leu Ser Thr Pro Leu Val Ile Val Gly Tyr Ser
            340                 345                 350

Met Phe Leu Gly Thr Thr Asn Pro Ser Ala Arg Tyr Gly Ala Thr Phe
        355                 360                 365

Leu Leu Ser Ser Ser Leu Phe Ala Val Gly Ala Leu Ser Asn Ser Gln
    370                 375                 380

Val Ser Ala Asn Val Val Ser Asp Thr Ala Arg Ser Ser Ala Ile Gly
385                 390                 395                 400

Leu Asn Val Met Met Gly Asn Val Gly Gly Leu Ile Ala Thr Trp Ser
                405                 410                 415

Tyr Leu Pro Trp Asp Gly Pro Asn Tyr Lys Ile Gly Asn Gly Leu Asn
            420                 425                 430

Leu Ala Ala Cys Cys Thr Val Leu Ile Leu Ser Ala Val Thr Leu Leu
        435                 440                 445

Trp Met Lys Trp Asp Asn Arg Arg Arg Glu Gly Arg Asn Ala Glu Glu
    450                 455                 460

Glu Leu Ala Gly Met Ser Arg Gln Glu Ile Gln Asp Leu Asp Trp Lys
465                 470                 475                 480

His Pro Ala Phe Arg Trp Arg Pro
                485


<210> SEQ ID NO 26
<211> LENGTH: 546
<212> TYPE: PRT
<213> ORGANISM: Sporotrichum thermophile

<400> SEQUENCE: 26

Met Pro Lys Ala Arg Ser Arg Val Pro Val Lys Val Asn Val Gly Thr
 1               5                  10                  15

Ser Ala Asp Pro Ile Val Thr Arg Leu Val Gln Glu Asp Lys Ile Pro
            20                  25                  30

Trp Tyr Lys Lys Pro Asn Leu Arg Arg Met Tyr Ile Phe Leu Phe Leu
        35                  40                  45

Cys Cys Met Gly Val Glu Met Thr Ser Gly Phe Asp Ser Gln Leu Ile
    50                  55                  60

Asn Thr Leu Gln Tyr Ala Glu Thr Phe His Lys Tyr Leu Gly Asn Gly
65                  70                  75                  80

Arg Lys Asp Glu Asp Gly Asn Tyr Ala Ile Glu Pro Gly Leu Leu Gly
                85                  90                  95

Phe Val Asn Ser Cys Tyr Gln Leu Gly Ser Ile Phe Ala Val Pro Ile
            100                 105                 110

Ala Pro Trp Phe Ala Gln Arg Phe Gly Arg Arg Trp Ser Ile Met Leu
        115                 120                 125
```

-continued

```
Gly Ser Leu Ile Met Val Gly Gly Ala Ile Ile Gln Gly Phe Ala Gln
    130                 135                 140

His Val Ala Met Tyr Ile Ile Ala Arg Met Ile Leu Gly Met Gly Ile
145                 150                 155                 160

Leu Phe Cys Ile Ile Ser Gly Ala Ala Leu Ile Gly Glu Leu Gly His
                165                 170                 175

Pro Lys Glu Arg Ala Val Leu Thr Ser Leu Phe Asn Ser Ser Tyr Phe
            180                 185                 190

Ile Gly Gln Ile Leu Ala Ser Ala Ile Thr Ile Gly Thr Thr Glu Met
        195                 200                 205

Lys Thr Asn Trp Ala Trp Arg Leu Pro Ser Leu Leu Gln Ile Cys Pro
    210                 215                 220

Ser Leu Leu Gln Ile Val Thr Val Phe Phe Leu Pro Glu Ser Pro Arg
225                 230                 235                 240

Phe Leu Ile Ser Lys Asp Arg Asp Asp Asp Ala Lys Glu Val Leu Ile
                245                 250                 255

Lys Tyr His Ala Glu Gly Asp Ala Ser Ser Leu Leu Val Gln Ala Glu
            260                 265                 270

Ile Val Gln Ile Arg Glu Thr Ile Arg Thr Glu Met Glu Val Ser Asn
        275                 280                 285

Gln Ser Trp Met Glu Leu Val Ser Thr Tyr Gly Met Arg Arg Arg Leu
    290                 295                 300

Val Ile Thr Leu Phe Ile Gly Leu Phe Thr Gln Leu Ser Gly Asn Thr
305                 310                 315                 320

Leu Leu Ser Tyr Tyr Ser Gly Lys Leu Phe Glu Met Met Gly Tyr Thr
                325                 330                 335

Glu Ala Ser Val Lys Thr Arg Ile Asn Val Ala Asn Ala Cys Trp Ser
            340                 345                 350

Leu Leu Asn Ala Thr Thr Ile Ala Phe Leu Val Pro Tyr Phe Lys Arg
        355                 360                 365

Arg His Met Phe Met Thr Ser Ala Leu Ser Met Cys Ala Val Phe Ile
    370                 375                 380

Ala Ile Thr Val Ser Leu Glu Arg Thr Gln Ala Ala Gln Asp Ala Gly
385                 390                 395                 400

Phe Lys Asn Thr Ala Ala Gly Ile Ser Gly Leu Phe Trp Tyr Phe Ala
                405                 410                 415

Phe Ala Pro Cys Tyr Asn Met Gly Asn Asn Ala Leu Thr Tyr Thr Tyr
            420                 425                 430

Leu Val Glu Leu Trp Pro Tyr Ser His Arg Ser Arg Gly Ile Gly Val
        435                 440                 445

Gln Gln Ile Phe Gly Lys Leu Gly Gly Phe Phe Ser Thr Asn Val Asn
    450                 455                 460

Ser Ile Ala Leu Asp Ala Ile Arg Trp Lys Tyr Met Ala Ile Tyr Cys
465                 470                 475                 480

Gly Trp Ile Phe Phe Glu Phe Leu Ile Val Phe Phe Leu Tyr Pro Glu
                485                 490                 495

Thr Ser Gly Arg Thr Leu Glu Glu Leu Ala Phe Leu Phe Glu Asp Ala
            500                 505                 510

Ser Leu Asn Glu Lys Ala Ala Ala Ala Val Glu Lys Gln Ile His Tyr
        515                 520                 525

Gly Asp Glu Lys Val Val His Glu Glu Gly Gln Pro Ala Ala Lys Ser
    530                 535                 540

Val Val
```

545

<210> SEQ ID NO 27
<211> LENGTH: 481
<212> TYPE: PRT
<213> ORGANISM: Sporotrichum thermophile

<400> SEQUENCE: 27

```
Met Leu Ser Ser Gly Phe Trp Lys Arg Arg Ser Leu Arg Val Pro Asp
 1               5                  10                  15

Asn Gln Arg Thr Lys Ala Ala Glu Leu Thr Leu Arg Glu Ser Leu Tyr
            20                  25                  30

Pro Leu Ser Leu Val Thr Ile Leu Phe Phe Leu Trp Gly Phe Ser Tyr
        35                  40                  45

Gly Leu Leu Asp Thr Leu Asn Lys His Phe Gln Asn Thr Leu Gly Ile
    50                  55                  60

Thr Lys Thr Arg Ser Ser Gly Leu Gln Ala Ala Tyr Phe Gly Ala Tyr
65                  70                  75                  80

Pro Leu Ala Ser Leu Gly His Ala Ala Trp Ile Leu Arg His Tyr Gly
                85                  90                  95

Tyr Arg Ala Val Phe Ile Trp Gly Leu Phe Leu Tyr Gly Leu Gly Ala
            100                 105                 110

Leu Leu Ala Ile Pro Ser Ile Met His His Ser Phe Ala Gly Phe Cys
        115                 120                 125

Val Cys Ile Phe Ile Ile Gly Asn Gly Leu Gly Ser Leu Glu Thr Ala
    130                 135                 140

Ala Asn Pro Tyr Ile Thr Val Cys Gly Pro Pro Lys Phe Ser Glu Ile
145                 150                 155                 160

Arg Ile Asn Val Ala Gln Ala Phe Asn Gly Ile Gly Thr Val Val Ala
                165                 170                 175

Pro Val Leu Gly Ser Tyr Val Phe Phe Thr Phe Asp Asp Gln Thr Ala
            180                 185                 190

Leu Arg Asn Val Gln Trp Val Tyr Leu Ala Ile Ala Cys Phe Val Phe
        195                 200                 205

Leu Leu Ala Gly Val Phe Phe Leu Ser Val Ile Pro Glu Ile Thr Asp
    210                 215                 220

Ala Asp Met Ala Phe Gln Ala Ala Glu Thr His Ala Gly Ala Asp Asp
225                 230                 235                 240

Arg Pro Phe His Thr Gln Tyr Arg Leu Phe His Ala Ala Phe Ala Gln
                245                 250                 255

Phe Cys Tyr Thr Gly Ala Gln Val Ala Ile Ala Gly Tyr Phe Ile Asn
            260                 265                 270

Tyr Ala Thr Glu Thr Arg Pro Asn Thr Asp Ser Ser Leu Gly Ser Lys
        275                 280                 285

Phe Leu Ala Gly Ser Gln Ala Gly Phe Ala Val Gly Arg Phe Gly Gly
    290                 295                 300

Ala Ala Met Met Gln Phe Ile Lys Pro Arg Lys Val Phe Ala Leu Phe
305                 310                 315                 320

Met Thr Met Cys Ile Val Phe Ser Ala Pro Ala Ile Thr Gln Arg Gly
                325                 330                 335

Asn Ala Gly Leu Ser Met Leu Tyr Leu Val Met Phe Phe Glu Ser Ile
            340                 345                 350

Cys Phe Pro Thr Ile Ile Ala Leu Gly Met Arg Gly Leu Gly Arg His
        355                 360                 365
```

```
Thr Lys Arg Gly Ser Gly Trp Ile Val Ala Gly Val Leu Gly Gly Ala
    370                 375                 380

Cys Val Pro Pro Leu Met Gly Ala Ala Ala Asp Ala Arg Gly Thr Gly
385                 390                 395                 400

Phe Ser Met Leu Val Pro Leu Cys Phe Phe Val Ala Ala Trp Thr Tyr
                405                 410                 415

Ala Leu Ala Val Asn Phe Ala Pro Pro Tyr Arg Ser Val Val Asp Ala
            420                 425                 430

Phe Ser Thr Thr Asp Val Gly Leu Arg Glu Lys Gln Arg Glu Asp Val
        435                 440                 445

Gly Ala Glu Lys Gly Gly Glu Ala Gly Gly Lys Gly Gly Val Thr Gly
    450                 455                 460

Pro Glu Asp Ala Ser Glu Asp Lys Pro Asp Val Val Asn Ser Glu Lys
465                 470                 475                 480

Val


<210> SEQ ID NO 28
<211> LENGTH: 419
<212> TYPE: PRT
<213> ORGANISM: Sporotrichum thermophile

<400> SEQUENCE: 28

Met Leu Ser Ser Leu Arg Ile Ala Ser Arg Arg Ala Ala Val Ala Arg
 1               5                  10                  15

Asn Phe Ser Ala Val Arg Ala Ala Ser Thr Trp Ala Asn Val Pro Gln
            20                  25                  30

Gly Pro Pro Val Cys Ile Thr Glu Ala Phe Lys Ala Asp Pro Phe Glu
        35                  40                  45

Lys Lys Ile Asn Leu Gly Val Gly Ala Tyr Arg Asp Asp Lys Gly Lys
    50                  55                  60

Pro Tyr Val Leu Pro Ser Val Arg Lys Ala Glu Glu Lys Val Ile Ala
65                  70                  75                  80

Ser Arg Leu Asn Lys Glu Tyr Ala Gly Ile Thr Gly Val Pro Glu Phe
                85                  90                  95

Thr Lys Ala Ala Ala Val Leu Ala Tyr Gly Lys Asp Ser Ser Ala Leu
            100                 105                 110

Asp Arg Leu Ala Ile Thr Gln Ser Ile Ser Gly Thr Gly Ala Leu Arg
        115                 120                 125

Ile Gly Ala Ala Phe Leu Ser Arg Phe Tyr Pro Gly Ala Lys Thr Ile
    130                 135                 140

Tyr Ile Pro Thr Pro Ser Trp Ala Asn His Ala Ala Val Phe Lys Asp
145                 150                 155                 160

Ser Gly Leu Gln Val Glu Lys Tyr Ala Tyr Tyr Asn Lys Asp Thr Ile
                165                 170                 175

Arg Leu Asp Phe Glu Gly Met Ile Ala Asp Ile Asn Lys Ala Pro Asn
            180                 185                 190

Gly Ser Ile Phe Leu Phe His Ala Cys Ala His Asn Pro Thr Gly Val
        195                 200                 205

Asp Pro Thr Gln Glu Gln Trp Lys Glu Ile Glu Ala Ala Val Lys Ala
    210                 215                 220

Lys Gly His Phe Ala Phe Phe Asp Met Ala Tyr Gln Gly Phe Ala Ser
225                 230                 235                 240

Gly Asp Ile His Arg Asp Ala Phe Ala Val Arg Tyr Phe Val Glu Lys
                245                 250                 255
```

-continued

```
Gly His Asn Ile Cys Leu Ala Gln Ser Phe Ala Lys Asn Met Gly Leu
            260                 265                 270

Tyr Gly Glu Arg Thr Gly Ala Phe Ser Ile Val Cys Ala Asp Ala Glu
        275                 280                 285

Glu Arg Lys Arg Val Asp Ser Gln Ile Lys Ile Leu Val Arg Pro Met
    290                 295                 300

Tyr Ser Asn Pro Pro Ile His Gly Ala Arg Ile Ala Ala Glu Ile Leu
305                 310                 315                 320

Asn Thr Pro Glu Leu Tyr Asp Gln Trp Leu Val Glu Val Lys Glu Met
                325                 330                 335

Ala Asn Arg Ile Ile Thr Met Arg Ala Leu Leu Lys Glu Asn Leu Glu
            340                 345                 350

Lys Leu Gly Ser Lys His Asp Trp Ser His Ile Thr Ser Gln Ile Gly
        355                 360                 365

Met Phe Ala Tyr Thr Gly Leu Thr Pro Glu Gln Met Glu Lys Leu Ala
    370                 375                 380

Lys Glu His Ser Val Tyr Ala Thr Arg Asp Gly Arg Ile Ser Val Ala
385                 390                 395                 400

Gly Ile Thr Thr Asp Asn Val Gly Arg Leu Ala Glu Ala Ile Phe Lys
                405                 410                 415

Val Lys Gly


<210> SEQ ID NO 29
<211> LENGTH: 522
<212> TYPE: PRT
<213> ORGANISM: Sporotrichum thermophile

<400> SEQUENCE: 29

Met Gly Ile Phe Ala Phe Asn Lys Gln Lys Pro Asn Ala Glu Ala Thr
 1               5                  10                  15

Ala Val Ala Gln Glu Glu Ala Pro Gln Phe Glu Arg Val Asp Trp Lys
            20                  25                  30

Arg Asp Pro Gly Leu Arg Lys Leu Tyr Phe Tyr Ala Phe Val Leu Cys
        35                  40                  45

Ile Ala Ser Ala Thr Thr Gly Tyr Asp Gly Met Phe Phe Asn Ser Val
    50                  55                  60

Gln Asn Phe Glu Thr Trp Glu Asn Tyr Phe Asn His Pro Thr Gly Ser
65                  70                  75                  80

Lys Leu Gly Val Leu Gly Ala Leu Tyr Gln Ile Gly Ser Leu Ala Ser
                85                  90                  95

Ile Pro Leu Val Pro Ile Ile Ala Asp Arg Val Gly Arg Lys Ile Pro
            100                 105                 110

Ile Ala Ile Gly Cys Val Ile Met Ile Val Gly Ala Val Leu Gln Ala
        115                 120                 125

Ala Cys Arg Asn Leu Gly Thr Phe Met Gly Gly Arg Phe Leu Leu Gly
    130                 135                 140

Phe Gly Asn Ser Leu Ala Gln Leu Cys Ser Pro Met Leu Leu Thr Glu
145                 150                 155                 160

Leu Ala His Pro Gln His Arg Gly Arg Leu Thr Thr Val Tyr Asn Cys
                165                 170                 175

Leu Trp Asn Val Gly Ala Leu Val Val Ala Trp Val Ser Phe Gly Thr
            180                 185                 190

Asp Tyr Leu Lys Ser Asp Trp Ser Trp Arg Ile Pro Ala Leu Ile Gln
        195                 200                 205
```

-continued

Ala Phe Pro Ser Val Ile Gln Leu Leu Phe Ile Phe Trp Val Pro Glu
    210                 215                 220

Ser Pro Arg Tyr Leu Met Ala Lys Asp Lys His Glu Arg Ala Leu Ala
225                 230                 235                 240

Ile Leu Ala Lys Tyr His Ala Asn Gly Asp Ala Asn His Pro Thr Val
                245                 250                 255

Gln Phe Glu Tyr Arg Glu Ile Lys Glu Thr Leu Arg Leu Glu Phe Glu
            260                 265                 270

Ala Ser Lys Ser Ser Ser Tyr Leu Asp Phe Val Arg Thr Arg Gly Asn
        275                 280                 285

Arg Tyr Arg Leu Ala Val Leu Ile Ser Leu Gly Ile Phe Ser Gln Trp
    290                 295                 300

Ser Gly Asn Ala Ile Ile Ser Asn Tyr Ser Ser Lys Leu Tyr Asp Thr
305                 310                 315                 320

Ala Gly Val Thr Gly Ser Thr Gln Lys Leu Gly Leu Ser Ala Gly Gln
                325                 330                 335

Thr Gly Leu Ser Leu Ile Ile Ser Val Thr Met Ala Leu Leu Val Asp
            340                 345                 350

Lys Phe Gly Arg Arg Pro Met Phe Leu Thr Ser Thr Ala Gly Met Phe
        355                 360                 365

Cys Thr Phe Ile Phe Trp Thr Leu Thr Ser Gly Leu Tyr Glu Glu His
    370                 375                 380

Asn Ala Asp Gly Ala Arg Tyr Ala Met Ile Leu Phe Ile Trp Ile His
385                 390                 395                 400

Gly Ile Phe Tyr Ser Ile Ser Trp Ser Gly Leu Leu Val Gly Tyr Ala
                405                 410                 415

Ile Glu Val Leu Pro Tyr Lys Leu Arg Ala Lys Gly Leu Met Ile Met
            420                 425                 430

Asn Leu Thr Val Gln Ala Ala Leu Thr Leu Asn Thr Tyr Ala Asn Pro
        435                 440                 445

Val Ala Phe Asp Ala Phe Glu Gly His Ser Trp Lys Leu Tyr Ile Ile
    450                 455                 460

Tyr Thr Ile Trp Ile Phe Leu Glu Leu Cys Phe Val Trp Lys Met Tyr
465                 470                 475                 480

Ile Glu Thr Lys Gly Pro Thr Leu Glu Glu Leu Ala Lys Ile Ile Asp
                485                 490                 495

Gly Asp Glu Ala Ala Val Ala His Val Asp Ile Lys Gln Val Glu Lys
            500                 505                 510

Glu Thr His Ile Asn Glu Glu Lys Ser Val
        515                 520

<210> SEQ ID NO 30
<211> LENGTH: 554
<212> TYPE: PRT
<213> ORGANISM: Sporotrichum thermophile

<400> SEQUENCE: 30

Met Ser Ser Ser Glu Lys Glu Ala Thr Gly Pro Val Ala Ala His Val
1               5                   10                  15

Gly Asn Leu Ala Thr Thr Gln Asp Val Glu Lys Ile Glu Ala Pro Val
            20                  25                  30

Thr Trp Lys Ala Tyr Leu Ile Cys Ala Phe Ala Ser Phe Gly Gly Ile
        35                  40                  45

Phe Phe Gly Tyr Asp Ser Gly Tyr Ile Asn Gly Val Leu Ala Ser Lys
    50                  55                  60

-continued

```
Leu Phe Ile Asn Ala Val Glu Gly Ala Gly Lys Asp Ala Ile Ser Glu
65                  70                  75                  80

Ser His Ser Ser Leu Ile Val Ser Ile Leu Ser Cys Gly Thr Phe Phe
                85                  90                  95

Gly Ala Leu Ile Ala Gly Asp Leu Ala Asp Phe Ile Gly Arg Lys Tyr
            100                 105                 110

Thr Val Ile Leu Gly Cys Leu Ile Tyr Ile Ile Gly Cys Val Ile Gln
        115                 120                 125

Ile Ile Thr Gly Leu Gly Asn Ala Leu Gly Ala Ile Val Ala Gly Arg
    130                 135                 140

Leu Ile Ala Gly Ile Gly Val Gly Phe Glu Ser Ala Ile Val Ile Leu
145                 150                 155                 160

Tyr Met Ser Glu Ile Cys Pro Arg Lys Val Arg Gly Ala Leu Val Ala
                165                 170                 175

Gly Tyr Gln Phe Cys Ile Thr Ile Gly Leu Met Leu Ala Ser Cys Val
            180                 185                 190

Val Tyr Gly Thr Gln Asn Arg Gln Asp Thr Gly Gln Tyr Arg Ile Pro
        195                 200                 205

Ile Gly Ile Gln Phe Ile Trp Ala Leu Ile Leu Gly Gly Gly Leu Leu
    210                 215                 220

Cys Leu Pro Asp Ser Pro Arg Tyr Phe Val Lys Arg Gly Arg Leu Ala
225                 230                 235                 240

Asp Ala Thr Ser Ala Leu Ser Arg Leu Arg Gly Gln Pro Glu Asp Ser
                245                 250                 255

Glu Tyr Ile Gln Val Glu Leu Ala Glu Ile Val Ala Asn Glu Glu Tyr
            260                 265                 270

Glu Arg Gln Leu Ile Pro Ser Thr Thr Trp Phe Gly Ser Trp Ala Asn
        275                 280                 285

Cys Phe Lys Gly Ser Leu Phe Lys Ala Asn Ser Asn Leu Arg Lys Thr
    290                 295                 300

Ile Leu Gly Thr Ser Leu Gln Met Met Gln Gln Trp Thr Gly Val Asn
305                 310                 315                 320

Phe Ile Phe Tyr Tyr Ser Thr Pro Phe Leu Lys Ser Thr Gly Ala Ile
                325                 330                 335

Asp Asp Pro Phe Leu Met Ser Met Val Phe Thr Ile Ile Asn Val Phe
            340                 345                 350

Ser Thr Pro Ile Ser Phe Tyr Thr Val Glu Arg Phe Gly Arg Arg Thr
        355                 360                 365

Ile Leu Phe Trp Gly Ala Leu Gly Met Leu Ile Cys Gln Phe Leu Val
    370                 375                 380

Ala Ile Val Gly Val Thr Val Gly Phe Asn His Thr His Pro Ala Pro
385                 390                 395                 400

Thr Ala Asp Asp Pro Glu Ala Thr Leu Ala Asn Asn Ile Ser Ala Val
                405                 410                 415

Asn Ala Gln Ile Ala Phe Ile Ala Ile Phe Ile Phe Phe Phe Ala Ser
            420                 425                 430

Thr Trp Gly Pro Gly Ala Trp Ile Val Ile Gly Glu Ile Phe Pro Leu
        435                 440                 445

Pro Ile Arg Ser Arg Gly Val Gly Leu Ser Thr Ala Ser Asn Trp Leu
    450                 455                 460

Trp Asn Thr Ile Ile Ala Val Ile Thr Pro Tyr Met Val Gly Glu Asp
465                 470                 475                 480
```

```
Arg Gly Asn Met Lys Ser Ser Val Phe Phe Val Trp Gly Gly Leu Cys
                485                 490                 495

Thr Cys Ala Phe Val Tyr Thr Tyr Phe Leu Val Pro Glu Thr Lys Gly
            500                 505                 510

Leu Ser Leu Glu Gln Val Asp Lys Met Met Glu Glu Thr Thr Pro Arg
        515                 520                 525

Thr Ser Ala Lys Trp Lys Pro Thr Thr Thr Phe Ala Ala Ser His Pro
    530                 535                 540

Thr Asp Leu Lys Gln Gly Glu Ala Ala Val
545                 550


<210> SEQ ID NO 31
<211> LENGTH: 537
<212> TYPE: PRT
<213> ORGANISM: Sporotrichum thermophile

<400> SEQUENCE: 31

Met Gly Thr Ser Arg Asp Glu Lys Glu Thr Val Val Ala Asp His Ala
 1               5                  10                  15

Asp Asp Asp Ala Leu Arg Glu Ala Asp Leu Ala Val Gln Val Ala His
            20                  25                  30

Asp Ala Asp Gly Thr Val Tyr Ser Pro Trp Ser Leu Arg Met Ile Arg
        35                  40                  45

Leu Tyr Leu Val Leu Ser Leu Ser Tyr Leu Cys Gly Cys Leu Asn Gly
    50                  55                  60

Tyr Asp Gly Ser Leu Met Gly Gly Leu Asn Gly Met Thr Ser Tyr Gln
65                  70                  75                  80

Arg Tyr Phe His Met Ser Thr Ala Gly Ser Thr Thr Gly Leu Ile Phe
                85                  90                  95

Ala Met Tyr Asn Ile Gly Ser Val Ala Ala Val Phe Phe Thr Gly Pro
            100                 105                 110

Val Asn Asp Tyr Phe Gly Arg Arg Trp Gly Met Phe Val Gly Ala Leu
        115                 120                 125

Leu Val Ile Val Gly Thr Cys Val Gln Ala Pro Cys Thr Thr Arg Gly
    130                 135                 140

Gln Phe Leu Ala Gly Arg Phe Val Leu Gly Phe Gly Val Ser Phe Cys
145                 150                 155                 160

Cys Val Ser Ala Pro Cys Tyr Val Ser Glu Met Ala His Pro Lys Trp
                165                 170                 175

Arg Gly Thr Leu Thr Gly Leu Tyr Asn Cys Thr Trp Tyr Ile Gly Ser
            180                 185                 190

Ile Val Ala Ser Trp Val Val Tyr Gly Cys Ser Tyr Ile Asp Thr Leu
        195                 200                 205

Asp Ala Trp Arg Ile Pro Ile Trp Cys Gln Met Val Thr Ser Gly Leu
    210                 215                 220

Val Cys Leu Gly Val Phe Trp Leu Pro Glu Ser Pro Arg Trp Leu Met
225                 230                 235                 240

Ala Gln Asp Arg His Asp Asp Ala Ala Arg Val Leu Ala Thr Tyr His
                245                 250                 255

Gly Glu Gly Arg Ala Asp His Pro Leu Val Lys Leu Gln Met Gln Glu
            260                 265                 270

Met Met Asn Gln Ile Ser Thr Glu Ala Ser Asp Lys Lys Trp Tyr Asp
        275                 280                 285

Tyr His Glu Leu Trp Asn Thr His Ser Ala Arg Arg Arg Leu Ile Cys
    290                 295                 300
```

```
Val Ile Gly Met Ala Val Phe Gly Gln Ile Ser Gly Asn Ser Leu Ser
305                 310                 315                 320

Ser Tyr Tyr Leu Val Asn Met Leu Lys Ser Ala Gly Ile Thr Glu Glu
                325                 330                 335

Arg Arg Val Leu Ala Leu Asn Gly Val Asn Pro Ala Leu Ser Phe Leu
            340                 345                 350

Gly Ala Ile Leu Gly Ala Arg Met Thr Asp Val Val Gly Arg Arg Pro
        355                 360                 365

Leu Leu Leu Tyr Thr Ile Val Phe Ala Ser Val Cys Phe Ala Val Ile
    370                 375                 380

Thr Gly Thr Ser Lys Met Ala Thr Asp Asp Pro Thr Arg Thr Ala Ala
385                 390                 395                 400

Ala Asn Ala Thr Ile Ala Phe Ile Phe Ile Phe Gly Ile Val Phe Ser
                405                 410                 415

Phe Gly Trp Thr Pro Leu Gln Ser Met Tyr Ile Ala Glu Thr Leu Pro
            420                 425                 430

Thr Ala Thr Arg Ala Lys Gly Thr Ala Val Gly Asn Phe Ser Ser Ser
        435                 440                 445

Val Ala Ser Thr Ile Leu Gln Tyr Ala Ser Gly Pro Ala Phe Glu Gly
    450                 455                 460

Ile Gly Tyr Tyr Phe Tyr Leu Val Phe Val Phe Trp Asp Leu Ile Glu
465                 470                 475                 480

Gly Ala Ile Met Tyr Phe Tyr Phe Pro Glu Thr Lys Asp Arg Thr Leu
                485                 490                 495

Glu Glu Leu Glu Glu Val Phe Ser Ala Pro Asn Pro Val Lys Lys Ser
            500                 505                 510

Leu Glu Lys Arg Ser Ala Gln Thr Val Leu Asn Thr Val Gly Ala Ala
        515                 520                 525

Gln Asn Glu Lys Leu Ala Arg Asp Val
    530                 535


<210> SEQ ID NO 32
<211> LENGTH: 566
<212> TYPE: PRT
<213> ORGANISM: Sporotrichum thermophile

<400> SEQUENCE: 32

Met Ala Val Phe Ala Met Gly Trp Gln Lys Pro Asp Asn Val Ala Gly
 1               5                  10                  15

Ser Ser Ala Pro Ala Ile Met Val Gly Leu Phe Val Ala Thr Gly Gly
            20                  25                  30

Leu Leu Phe Gly Tyr Asp Thr Gly Ala Ile Asn Gly Ile Leu Ala Met
        35                  40                  45

Asp Thr Phe Lys Glu Asp Phe Thr Thr Gly Tyr Thr Asp Lys Gln Gly
    50                  55                  60

Lys Pro Gly Leu Tyr Ala Ser Glu Val Ser Leu Ile Val Ala Met Leu
65                  70                  75                  80

Ser Ala Gly Thr Ala Thr Gly Ala Leu Leu Ser Ala Pro Met Gly Asp
                85                  90                  95

Arg Trp Gly Arg Arg Leu Ser Leu Ile Val Ala Ile Gly Val Phe Cys
            100                 105                 110

Val Gly Ala Ile Ile Gln Val Cys Ala Thr Asn Val Ala Met Leu Val
        115                 120                 125

Val Gly Arg Thr Leu Ala Gly Ile Gly Val Gly Val Val Ser Val Leu
```

-continued

```
        130                 135                 140

Val Pro Leu Tyr Gln Ser Glu Met Ala Pro Lys Trp Ile Arg Gly Thr
145                 150                 155                 160

Leu Val Cys Ala Tyr Gln Leu Ser Ile Thr Ala Gly Leu Leu Ala Ala
                165                 170                 175

Ala Thr Val Asn Ile Leu Thr Tyr Lys Leu Lys Ser Ala Ala Ala Tyr
            180                 185                 190

Arg Ile Pro Ile Gly Leu Gln Leu Thr Trp Ala Leu Val Leu Ala Leu
        195                 200                 205

Gly Leu Val Ile Leu Pro Glu Thr Pro Arg Tyr Leu Val Lys Arg Gly
    210                 215                 220

Leu Lys Glu Ala Ala Ala Leu Ser Leu Ser Arg Leu Arg Arg Leu Asp
225                 230                 235                 240

Ile Thr His Pro Ala Leu Ile Glu Glu Leu Ala Glu Ile Glu Ala Asn
                245                 250                 255

His Glu Tyr Glu Met Ala Leu Gly Pro Asp Thr Tyr Lys Asp Ile Ile
            260                 265                 270

Phe Gly Glu Pro His Leu Gly Arg Arg Thr Leu Thr Gly Cys Gly Leu
        275                 280                 285

Gln Met Leu Gln Gln Leu Thr Gly Val Asn Phe Ile Met Tyr Tyr Gly
    290                 295                 300

Thr Thr Phe Phe Tyr Gly Ala Gly Ile Gly Asn Ala Phe Thr Val Ser
305                 310                 315                 320

Leu Ile Met Gln Val Ile Asn Leu Val Ser Thr Phe Pro Gly Leu Phe
                325                 330                 335

Val Val Glu Ser Trp Gly Arg Arg Lys Leu Leu Ile Val Gly Ser Val
            340                 345                 350

Gly Met Ala Ile Cys Gln Leu Leu Ile Ala Ser Phe Ala Thr Ala Ser
        355                 360                 365

Gly Asn Asp Asn Lys Pro Thr Gln Asn Gln Ile Leu Ile Ile Phe Val
    370                 375                 380

Ala Ile Tyr Ile Phe Phe Phe Ala Ala Ser Trp Gly Pro Val Val Trp
385                 390                 395                 400

Val Val Thr Ser Glu Ile Tyr Pro Leu Lys Val Arg Ala Lys Ser Met
                405                 410                 415

Ser Ile Ser Thr Ala Ser Asn Trp Val Leu Asn Phe Gly Ile Ala Tyr
            420                 425                 430

Gly Thr Pro Tyr Leu Val Asp Thr Ser Asp Gly Ser Pro Asp Leu Gly
        435                 440                 445

Ser Arg Val Phe Phe Val Trp Gly Ala Phe Cys Ile Leu Ser Ile Ala
    450                 455                 460

Phe Val Trp Tyr Met Val Tyr Glu Thr Ser Lys Ile Ser Leu Glu Gln
465                 470                 475                 480

Ile Asp Glu Met Tyr Glu Arg Val Ala His Ala Trp Asn Ser Arg Ser
                485                 490                 495

Phe Glu Pro Ser Trp Ser Phe Gln Gln Met Arg Asp Phe Gly Phe Ser
            500                 505                 510

Asp Ser Gly Ile Pro Pro Ala Glu Pro Gln Leu Glu Leu Gln Gln Ser
        515                 520                 525

Asn Ala Ser Thr Ser Gln Ser Asp Thr Gly Gly Ser Ser Ala Thr His
    530                 535                 540

Ala Thr Ala Ala Asn Pro Gln Asp Ala Lys Met Val Ser Gln Leu Ala
545                 550                 555                 560
```

Asn Ile Asp Leu Ser Tyr
565

<210> SEQ ID NO 33
<211> LENGTH: 1404
<212> TYPE: DNA
<213> ORGANISM: Pichia stipitis

<400> SEQUENCE: 33
atgaagtatt ttcaaatctg gaaatcaggc aaacaagtaa gctacgctgt tacattcact 60
tgtgaattgg catttattct ttttggtatt gaacagggta ttattggtaa tcttattaac 120
aaccaggact tcctaaacac ttttggaaac cccaccggta gttatttagg tattatcgtt 180
tctatctata ccttagggtg tttttttggt tgtgttatga acttcttcat tggtgatcga 240
atgggcagaa gaagcaaaat tgcttcctca atgacagtta tcacaattgg tgttgctctt 300
caatgtagtt ccttttcagt tgaacaattg atgattggaa gatttatcac tgggcttgga 360
actggttggg aaacttctac ttgtccaatg tatcaggcag aactttcacc tccaaaagtt 420
agaggacgtt tggtgtgctc agaagcattg tttgttggag ttggtttaat ctatgcatat 480
tggtttgatt atgctctttc tttcacttct ggtcctattg catggagact tcctcttgcc 540
tctcagattg tgttcgcctt tgttgttttc tgtttcactt tcacaatacc cgaatcccct 600
agatacatgt tttacaaagg agagaaagaa gaagccaaaa gaattttatc ttatgtcttt 660
ggaaagccag gagatcatcc tgacattctt aaggaatgga atgatattaa tgatgctgtt 720
attttggaaa cttcagaagg agctttctcg tgggcaaaac ttttcaagcc cgataaggca 780
agaactggat acagagtctt cttggcatac atgagcatgt ttgcgcaaca gttgagtggt 840
gttaatgtag ttaattacta tattacattt gttttgatta acagtgttgg catcgaagac 900
aacttggccc taattcttgg tggtgttgcc gtcatctgtt tcactgttgg ttcattagtt 960
cctactttct ttgctgatag gatgggaaga agattgcctt cagcagttgg agcttttggc 1020
tgtggtgttt gtatgatgct aatttcaatc ttattaagtt ttcaagacaa tccaaagttg 1080
aagaagagca gtggagctgg tgctgtggct ttctttttcg ttttccaact tgtcttcggc 1140
tccactggta attgtattcc atggctgatg atttcagagc ttatcccccct tcatgcacgt 1200 gctaaaggat cttcattagc tacatcaagt aactggcttt ggaatttctt tgttgttgag 1260
atcactccaa ctatcattga aaagttgaag tggaaagcat atttgatctt tatgtgctgc 1320
aacttctcct tcgtaccaat gttttacttt ttctttcccg agacaaagaa ccttacttta 1380
gaagccattg acgatttgtt ctca 1404

<210> SEQ ID NO 34
<211> LENGTH: 1653
<212> TYPE: DNA
<213> ORGANISM: Pichia stipitis

<400> SEQUENCE: 34
atgtcctcac aagatttacc ctcgggtgct caaaccccaa tcgatggttc ttccatcctc 60
gaagataaag ttgagcaaag ttcgtcctca aatagccaaa gtgatttagc ttccattcca 120
gcaacaggta tcaaagccta tctcttggtt tgtttcttct gcatgttggt tgcctttggt 180
ggcttcgtat tcggtttcga taccggtaca atttccggtt tccttaatat gtctgatttc 240
ctttccagat ttggtcaaga tggttctgaa ggaaaatatt tgtctgatat cagagtcggt 300
ttgattgttt ccatttttaa cattggttgt gcaattggtg gtattttcct ttctaagata 360

-continued ggagatgttt acggtagaag aattggtatc atttcagcta tggttgtcta cgtcgtcggt 420
attatcatcc agatctcgtc ccaagacaag tggtaccaac ttacaattgg acgtggagtt 480
acaggattag ctgttggtac tgtttcagtg ttgtctccaa tgttcattag tgaaagtgct 540
ccaaagcatt tgagaggtac tttggtatac tgttaccaat tatgtatcac cttaggtatt 600
ttcattggtt actgtgtcac ttatggaacc aaagatttaa atgattcaag acaatggaga 660
gttcctttgg gcttatgctt cctttgggct attttcttag ttgtcggtat gttggctatg 720
ccagaatccc caagattctt aattgaaaag aagagaatcg aagaagccaa gaagtccctt 780
gcaagatcca acaagttatc tccggaagat ccaggtgtct acactgaact tcaattgatt 840
caggctggta ttgacagaga agctgctgca ggttctgctt cgtggatgga attgatcact 900
ggtaagccag ctattttcag aagagttatc atgggaatta tcttgcagtc tttgcaacaa 960
ttaactggtg tcaactattt cttctattac ggaactacaa tcttccaagc tgttggtttg 1020
caagattcct tccagacttc catcatctta ggtacagtca actttctttc tacatttgtt 1080
ggtatttggg ccattgaaag atttggaaga agacaatgtt tgttagtcgg ttctgctggt 1140
atgttcgttt gtttcatcat ttactccgtt attggtacaa ctcatttgtt cattgatgga 1200
gtagtagata acgacaacac ccgtcaactg tctggtaatg ctatgatctt tatcacttgt 1260
ttgttcatct tcttctttgc ctgtacatgg gctggaggtg tttttaccat catttccgaa 1320
tcatatccat tgagaatcag atccaaggca atgtctattg ctactgctgc taactggatg 1380
tggggcttct tgatttcctt ctgcactcca ttcattgtta atgccatcaa cttcaagttc 1440
ggctttgtgt ttactggttg tttactcttt tcgttcttct atgtctactt ctttgtcagc 1500
gaaaccaaag gtttgtcgtt ggaagaagtt gatgagttgt acgctgaagg tattgcacca 1560
tggaagtctg gtgcatgggt tcctccttct gcccaacaac aaatgcaaaa ctccacttat 1620
ggtgccgaag caaaagagca agagcaagtt tag 1653

<210> SEQ ID NO 35
<211> LENGTH: 2025
<212> TYPE: DNA
<213> ORGANISM: Neurospora crassa

<400> SEQUENCE: 35
atggcgtcga acccaacgaa caccgcggcc cctacgggtg gccttaccga gaagaagcat 60
gaccgccgtt caacatcgtc cgaatccgtc tcgggaaccg ggtttgcgga acatgcagac 120
cgcaccggca cttttaacca gaacgctcga ctagaggctt caaaaaagat agcgaatcct 180
ttggccggtc taagccctca gcgtctcgag gccatgggag aagaatatgc aatgatggcc 240
ggtctcacca gcgaggagga catcagggcc tttcgactcg gagccagaat cgccggcgat 300
gagagcaact acgacctcat cccggagctt actgaacggg agaaagaggt gttggtgcgc 360
gaaacaactc acaagtggtc taacccaccc atgctttact gggttgttgt catttgctct 420
ctatgcgccg ccgtccaagg aatggacgag acggtcgtca acggcgccca gctcttctac 480
aaggacaagt ttggcattgg tactgatagc cagagagaca cttggcttct gggtctcgtc 540
aactcagcgc cctacctttg ctgtgccttt atcggctgct ggctcactga accgatgaac 600
agaatctttg gcagacgagg caccatcttt gtttcttgca tcatctcagc cgtagcttgc 660
ttccaccagg cctttaccaa cacgtggtgg cacatgttca tcgcccgttt ctacctcggc 720
cttggcatcg gtcccaagtc agccaccacc cccatcttcg ccgccgaatg ctcccctccc 780

```
aagctccgcg gtgcgctggt catgcaatgg cagatgtgga ccgccttcgg tatcatggtc    840
ggctacattg ccgatctcgc tttctacttc gttcccgatc acggcatcgg cttgggtctg    900
aactggcgtc tgatgatggg ctccgccatg attcccgccg tcatcgtcgt ctgcctcgcc    960
ttcctctgcc cggagtcgcc ccgttggtac ctcagcaagg gccgacacca agacgccttc   1020
ggggcgctct gccgcctgcg tttcgaaaag gtccaagccg cccgcgacct cttctacacc   1080
cacaccctcc tagaagccga gaagcaagcc atgtcgggcg tcaagaaggg taaccgcttt   1140
aaggagctct tcaccgtgcg tcgtaaccgc aacgcggtca ttgcctcgtc gggactcatg   1200
ttcatgcagc agttctgcgg cgtcaacatc atcgcctact actcctcggc ggtcttccga   1260
gacgccggct tcagcgacgt ctcagcactg gccgcctcgc tcgggtttgg cgtcgtcaac   1320
tggctgtttg ccatcccggc catgtacacc atcgacactt tcggccggcg caacctgctg   1380
ctgaccacct tcccgctcat gtccctcttc ctcttcttca ccggcttcag cttttggatc   1440
cccgaggact ccaaagccca catcggctgc atcgcgctag gcatttactt gttcggcatg   1500
gtctactccc ccggtgaagg gccggtgccg tttacttact cggccgaggc ctacccgctg   1560
tacatccggc caatcggcat gtccctcgcc acggcgacta cctggttctt caatttcatt   1620
ctttccatca cctggcctag gatggtcacg gccttcaagc cgcagggcgc gtttggctgg   1680
tatgcagggt ggaatatcat tgggtttctc tttaccctgt tcttggtccc cgagaccaag   1740
ggcaagacgc tggaggagct cgatcacgtg tttgacgtgc cgttgaagaa gttggtcaga   1800
tacggggcgg atcagagctt gtggtttttc cacaggggaa agaatggaaa tggaatgagg   1860
ccgacggcgc ctagtgcgga gatgtatcat ggggatgcgg agcggatgaa cgaggtggtt   1920
agcgggcagc agcttgggga gggtgagagg gagaagaggt ggaacaagga acaagagagg   1980
gaaggggga ttatgggacg aggggatgct gctgggaagg tgtag                    2025
```

<210> SEQ ID NO 36
<211> LENGTH: 1458
<212> TYPE: DNA
<213> ORGANISM: Neurospora crassa

<400> SEQUENCE: 36

```
atgtccgcca tcgtcgtgac cgaccaatac ctcacctact tcaacaaccc ccatgatatc     60
atccaaggag ccatcggctc tgcccttgct gctggctccg tcgtcggttc cgccatcgcc    120
ggtcctcttt ccgacaagat cggtcgtcgt gactccatct tttcgcctg cttcttctgg     180
ctcattggta cctccgtcca ggttgcctgc aagaactatg gccagctcat cgccggccgt    240
gtgctcaacg gctttaccgt cggcatcact tcctcccagg ttcccgtgta ccttgccgag    300
atcgccaagg cagagaagcg tggttccttg gtcatcatcc agcaactcgc catcgagttt    360
ggtatcttga tcatgtactt tatcggctac ggctgtgcgt cgatcgaggg ccctgcttcg    420
ttccggaccg cttggggcat tcagtttatc ccttgctttt tcctcatggt cggtcttccc    480
ttcttgccta ggtcgcccag atggctggcc aaggtcggta gggaccagga ggccattgct    540
gtcctggcta acatccaggc tgatggcaac gttgatgacc cgagagtcgt tgctgagtgg    600
gaggagattg tcaccgttat gaacgccgag cgtgaggccg gtaagggatg gaggaagttt    660
gtcaagaacg gcatgtggaa gcgaaccatg gctggcatga ctgtacaggc ttggcagcaa    720
ctcgccggcg ccaacgtaat cgtctactac ctaacctaca tcgcccaaat ggccggactc    780
acaggcaacg tcgccatggt gacctcgggc atccaatacg ccgttttcat catcttcacc    840
ggcgtcatgt ggctcttcat cgacaagacc ggtcgtcgca cccttttagt ttacggcgcc    900
```

```
ttgggaatgg ccttctgcca ctttgtcgtc ggcggcgtca tgggcgcgca ccacgacaac     960

gttccggacg gcgtcggcgg caacgccaac attgtcatta gcgtgcacaa gggcgcgccc    1020

gccaacacgg tcatcctgtt ctcgtacctg ctcattgtcg tctacgcctt gacgctcgct    1080

cccgtctgct ggatctacgc cgccgaggtc tggtcgttgg gcactcgcgc tacgggcatg    1140

tccatggctg ccatgtccaa ctgggtgttc aactttgcgc tgggcatgtt cacgccgccg    1200

gcgtttgtca atattacgtg gaagctgttt atcattttcg ggtgctttg cgtcacggcg     1260

gcggtctggt tctggttgtt ttacccggag acgtgtggta agacgctgga ggagattgag    1320

atcctgtttg gtgatcaggg tcctaagccg tggaagacaa agaagggcga gtcgagactt    1380

acggcggaga ttgaggctgt caaggcgagg aagacggtgg agcacgagat tgaggtgcat    1440

gagcatgaga aggtttag                                                  1458


<210> SEQ ID NO 37
<211> LENGTH: 1407
<212> TYPE: DNA
<213> ORGANISM: Pichia stipitis

<400> SEQUENCE: 37

atgaagtatt ttcaaatctg gaaatcaggc aaacaagtaa gctacgctgt tacattcact      60

tgtgaattgg catttattct tttggtattt gaacagggta ttattggtaa tcttattaac     120

aaccaggact tcctaaacac ttttggaaac cccaccggta gttatttagg tattatcgtt     180

tctatctata ccttagggtg tttttttggt tgtgttatga acttcttcat tggtgatcga     240

atgggcagaa gaagcaaaat tgcttcctca atgacagtta tcacaattgg tgttgctctt     300

caatgtagtt ccttttcagt tgaacaattg atgattggaa gatttatcac tgggcttgga     360

actggttggg aaacttctac ttgtccaatg tatcaggcag aactttcacc tccaaaagtt     420

agaggacgtt tggtgtgctc agaagcattg tttgttggag ttggtttaat ctatgcatat     480

tggtttgatt atgctctttc tttcacttct ggtcctattg catggagact tcctcttgcc     540

tctcagattg tgttcgcctt tgttgttttc tgtttcactt tcacaatacc cgaatcccct     600

agatacatgt tttacaaagg agagaaagaa gaagccaaaa gaattttatc ttatgtcttt     660

ggaaagccag gagatcatcc tgacattctt aaggaatgga atgatattaa tgatgctgtt     720

attttggaaa cttcagaagg agctttctcg tgggcaaaac ttttcaagcc cgataaggca     780

agaactggat acagagtctt cttggcatac atgagcatgt ttgcgcaaca gttgagtggt     840

gttaatgtag ttaattacta tattacattt gttttgatta acagtgttgg catcgaagac     900

aacttggccc taattcttgg tggtgttgcc gtcatctgtt tcactgttgg ttcattagtt     960

cctactttct ttgctgatag gatgggaaga agattgcctt cagcagttgg agcttttggc    1020

tgtggtgttt gtatgatgct aatttcaatc ttattaagtt ttcaagacaa tccaaagttg    1080

aagaagagca gtggagctgg tgctgtggct ttctttttcg ttttccaact tgtcttcggc    1140

tccactggta attgtattcc atggctgatg atttcagagc ttatccccct tcatgcacgt    1200

gctaaaggat cttcattagc tacatcaagt aactggcttt ggaatttctt tgttgttgag    1260

atcactccaa ctatcattga aaagttgaag tggaaagcat atttgatctt tatgtgctgc    1320

aacttctcct tcgtaccaat gttttacttt ttctttcccg agacaaagaa ccttacttta    1380

gaagccattg acgatttgtt ctcataa                                        1407


<210> SEQ ID NO 38
```

<211> LENGTH: 1653
<212> TYPE: DNA
<213> ORGANISM: Pichia stipitis

<400> SEQUENCE: 38
atgtcctcac aagatttacc ctcgggtgct caaaccccaa tcgatggttc ttccatcctc 60
gaagataaag ttgagcaaag ttcgtcctca aatagccaaa gtgatttagc ttccattcca 120
gcaacaggta tcaaagccta tctcttggtt tgtttcttct gcatgttggt tgcctttggt 180
ggattcgtat tcggtttcga taccggtaca atttccggtt tccttaatat gtctgatttc 240
ctttccagat ttggtcaaga tggttctgaa ggaaaatatt tgtctgatat cagagtcggt 300
ttgattgttt ccatttttaa cattggttgt gcaattggtg gtattttcct ttctaagata 360
ggagatgttt acggtagaag aattggtatc atttcagcta tggttgtcta cgtcgtcggt 420
attatcatcc agatctcgtc ccaagacaag tggtaccaac ttacaattgg acgtggagtt 480
acaggattag ctgttggtac tgtttcagtg ttgtctccaa tgttcattag tgaaagtgct 540
ccaaagcatt tgagaggtac tttggtatac tgttaccaat tatgtatcac cttaggtatt 600
ttcattggtt actgtgtcac ttatggaacc aaagatttaa atgattcaag acaatggaga 660
gttcctttgg gtttatgttt cctttgggct attttcttag ttgtcggtat gttggctatg 720
cctgaatccc caagattctt aattgaaaag aagagaatcg aagaagccaa gaagtccctt 780
gcaagatcca acaagttatc tccagaagat ccaggtgtct acactgaagt tcaattgatt 840
caggctggta ttgacagaga agctgctgca ggttctgctt catggatgga attgatcact 900
ggtaagccag ctattttcag aagagttatc atgggaatta tcttacagtc tttgcaacaa 960
ttaactggtg tcaactattt cttctattac ggaactacaa tcttccaagc tgttggtttg 1020
caagattcct tccagacttc catcatctta ggtacagtca actttctttc tacatttgtt 1080
ggtatttggg ccattgaaag atttggaaga agacaatgtt tgttagtcgg ttctgctggt 1140
atgttcgttt gtttcatcat ttactccatt attggtacaa ctcatttgtt cattgatgga 1200
gtagtagata acgacaacac ccgtcaactg tctggtaatg ctatgatctt tatcacttgt 1260
ttgttcatct tcttctttgc ctgtacatgg gctggaggtg tttttaccat catttccgaa 1320
tcatatccat tgagaatcag atccaaggca atgtctattg ctactgctgc taactggatg 1380
tggggcttct tgatttcctt ctgcactcca ttcattgtta atgccatcaa cttcaagttc 1440
ggctttgtgt ttactggttg tttactcttt tcgttcttct atgtctactt ctttgtcagc 1500
gaaaccaaag gtttgtcgtt ggaagaagtt gatgagttgt acgctgaagg tattgcacca 1560
tggaagtctg gtgcatgggt tcctccttct gcccaacaac aaatgcaaaa ctccacttat 1620
ggtgccgaag caaaagagca agagcaagtt tag 1653

<210> SEQ ID NO 39
<211> LENGTH: 1641
<212> TYPE: DNA
<213> ORGANISM: Pichia stipitis

<400> SEQUENCE: 39
atggaattct ccagtgttga aaaaagtgct gaaactgctt cctatacgtc gcaggtcagc 60
gcaagcggct ctgcaaagac caacagctac cttggcctca gaggccacaa acttaatttt 120
gctgtctctt gttttgctgg tgttggtttc ttacttttcg gttacgatca aggtgtcatg 180
ggttcattgt tgaccttgcc atccttcgaa aacactttcc cggccatgaa ggctagcaac 240
aacgctacct tacaaggcgc cgttattgca ctttatgaaa tcggttgtat gtcttcttct 300

-continued ttagcaacca tttaccttgg tgacagattg ggtagattga agatcatgtt tattggctgt 360
gtaattgtct gtattggtgc tgctttgcaa gcttctgctt tcactattgc tcacttgact 420
gttgctagaa ttatcactgg tttaggtaca ggtttcatca cttctactgt tccagtttac 480
caatcggagt gctctccagc caagaaaaga ggacagttga tcatgatgga aggttctctt 540
atcgcccttg gcattgccat ctcatactgg attgactttg gattttactt tttgagaaac 600
gatggtttgc actcctcggc ttcttggaga gcacctatcg cgcttcaatg tgtcttcgct 660
gtcttgttga tttccacagt cttcttcttc ccagaatctc caagatggtt gctcaacaaa 720
ggtaggaccg aagaagctag agaagttttt tctgctcttt acgacttgcc agccgactct 780
gaaaagattt ctattcaaat tgaagaaatt caagctgcta tagatttaga aagacaagcc 840
ggagaaggtt tcgtacttaa ggaattgttc actcagggcc cagccagaaa cttgcagcgt 900
gtggccttgt catgttggtc tcaaataatg caacaaatca ctggtattaa cattattacg 960
tactatgctg gtactatttt tgaatcatac attggtatga gtccatttat gtcaagaatc 1020
ttggctgcct tgaacggtac tgaatatttc cttgtctctc ttattgcttt ctacaccgtc 1080
gaaagattag gtagaagatt ccttttgttc tggggtgcca tcgccatggc tcttgtcatg 1140
gctggtttaa ctgttaccgt taaacttgcc ggtgaaggca acacccatgc tggtgtcggt 1200
gctgctgttc ttttgtttgc attcaactca ttcttcggcg tctcctggtt aggtggatcc 1260
tggttgttac cacctgaatt gttgtctttg aaattgagag ctcctggtgc tgctttgtcg 1320
accgcttcta actgggcttt taacttcatg gttgtcatga tcactcctgt cggtttccaa 1380
agtattggtt cctacaccta ccttatcttt gctgccatca atttgttgat ggctccggtc 1440
atctacttct tgtatcccga aaccaagggt agatcgttgg aagaaatgga tatcattttc 1500
aaccaatgtc ctgtttggga gccatggaag gttgtccaaa ttgccagaga cctccctatt 1560
atgcactcag aagttcttga ccacgaaaag aatgtcatta ttaaaaaatc tagaatagag 1620
catgtcgaaa acatcagcta a 1641

<210> SEQ ID NO 40
<211> LENGTH: 1701
<212> TYPE: DNA
<213> ORGANISM: Pichia stipitis

<400> SEQUENCE: 40
atgcacggtg gtggtgacgg taacgatatc acagaaatta ttgcagccag acgtctccag 60
atcgctggta agtctggtgt ggctggttta gtcgcaaact caagatcttt cttcatcgca 120
gtctttgcat ctcttggtgg attggtctac ggttacaatc aaggtatgtt cggtcaaatt 180
tccggtatgt actcattctc caaagctatt ggtgttgaaa agattcaaga caatcctact 240
ttgcaaggtt tgttgacttc tattcttgaa cttggtgcct gggttggtgt cttgatgaac 300
ggttacattg ctgatagatt gggtcgtaag aagtcagttg ttgtcggtgt tttcttcttc 360
ttcatcggtg tcattgtaca agctgttgct cgtggtggta actacgacta catcttaggt 420
ggtagatttg tcgtcggtat tggtgtgggt attctttcta tggttgtgcc attgtacaat 480
gctgaaattt ctccaccaga aattcgtggt tctttggttg ctttgcaaca attggctatt 540
actttcggta ttatgatttc ttactggatt acctacggta ccaactacat tggtggtact 600
ggctctggtc aaagtaaagc ttcttggttg gttcctattt gtatccaatt ggttccagct 660
ttgctcttgg gtgttggtat cttcttcatg cctgagtctc caagatggtt gatgaacgaa 720

-continued

```
gacagagaag acgaatgttt gtccgttctt tccaacttgc gttccttgag taaggaagat    780
actcttgttc aaatggaatt ccttgaaatg aaggcacaaa agttgttcga aagagaactt    840
tctgcaaagt acttccctca cctccaagac ggttctgcca agagcaactt cttgattggt    900
ttcaaccaat acaagtccat gattactcac tacccaacct tcaagcgtgt tgcagttgcc    960
tgtttaatta tgaccttcca acaatggact ggtgttaact tcatcttgta ctatgctcca   1020
ttcatcttca gttctttagg tttgtctgga aacaccattt ctcttttagc ttctggtgtt   1080
gtcggtatcg tcatgttcct tgctaccatt ccagctgttc tttgggtcga cagacttggt   1140
agaaagccag ttttgatttc cggtgccatt atcatgggta tttgtcactt tgttgtggct   1200
gcaatcttag gtcagttcgg tggtaacttt gtcaaccact ccggtgctgg ttgggttgct   1260
gttgtcttcg tttggatttt cgctatcggt ttcggttact cttggggtcc atgtgcttgg   1320
gtccttgttg ccgaagtctt cccattgggt ttgcgtgcta agggtgtttc tatcggtgcc   1380
tcttctaact ggttgaacaa cttcgctgtc gccatgtcta ccccagattt tgttgctaag   1440
gctaagttcg gtgcttacat ttcttaggt ttgatgtgta ttttcggtgc cgcatacgtt   1500
caattcttct gtccagaaac taagggtcgt accttggaag aaattgatga acttttcggt   1560
gacacctctg gtacttccaa gatggaaaag gaaatccatg agcaaaagct taaggaagtt   1620
ggtttgcttc aattgctcgg tgaagaaaat gcttctgaat ccgaaaacag caaggctgat   1680
gtctaccacg ttgaaaaata a                                              1701
```

<210> SEQ ID NO 41
<211> LENGTH: 1656
<212> TYPE: DNA
<213> ORGANISM: Pichia stipitis

<400> SEQUENCE: 41

```
atgagagaag ttggtattct tgatgttgcc catggcaacg ttgtaactat aatgatgaaa     60
gatccagtag tattttggt gattttattt gcatcccttg gaggtttgct ttttggttat    120
gatcaagggg ttattagtgg cattgtcaca atggaatctt ttggtgcaaa attccccaga    180
atttttatgg atgccgatta caagggttgg tttgtgtcta ctttttgct atgcgcatgg     240
tttggctcta ttattaatac tccaattgtt gataggtttg gaagacgtga ttctatcaca    300
atctcttgtg ttatttttgt cattggttct gcgttccaat gtgctggcat taatacaagt    360
atgttatttg gtgggcgtgc tgttgctggt cttgcagtcg gtcaattaac catggtagtt    420
ccaatgtaca tgtcggaatt ggctcctcca tcggtgagag gtgggttggt tgtaattcag    480
caactttcga ttacaattgg tatcatgatt tcctattggt tggattatgg cactcatttt    540
attggaggta ctagatgtgc tcctagtcac ccataccaag gtgaaacttt taaccctaat    600
gtggatgttc ctccaggtgg ctgctatggt caaagtgatg ccagttggag aattcctttt    660
ggtgttcaga ttgctccagc agtgttgttg ggtattggaa tgatattttt cccaagatct    720
cccagatggt tactctctaa aggtcgcgac gaagaagctt ggagctcttt gaaatatctc    780
agaagaaaga gtcatgagga tcaagtcgaa agagagtttg ctgaaattaa ggcagaggtc    840
gtttatgaag acaagtacaa ggaaaagaga ttccctggta agactggagt tgctttaaca    900
cttactggat actgggatat tcttactact aaatctcact tcaagagagt tttattgga    960
tcagctgtca tgttcttcca acaattcatt ggctgcaatg caataattta ttacgcacct   1020
acaattttca cacaattggg aatgaactct acaactactt ccttgcttgg tactggtctt   1080
tatggtattg ttaattgtct ttccaccctt ccagcagtgt tcttgatcga tagatgtgga   1140
```

-continued agaaagactt tgttaatggc aggtgctatt ggaactttta tttccttggt tattgtcggc 1200
gcaatcgttg gcaagtatgg cgatcgttta tctgaattca agacagcagg gagaactgca 1260
attgctttca ttttcattta tgatgtgaat ttctcgtaca gttgggctcc aattggatgg 1320
gttttaccct cagagatttt cccaatcggc atcagatcca atgccatctc cataactacc 1380
tcatctactt ggatgaataa ttttattatt ggcttggtca ctccacatat gttagaaaca 1440
atgaagtggg gcacttacat ttttttgca gcgtttgcta ttattgcgtt ctttttcact 1500
tggcttatca tcccggaaac caagggagtt ccattggaag aaatggatgc cgtgtttggc 1560
gatactgcag cattgcagga aaagaatttg gttaccatta cgtcagtttc tgaatctgac 1620
gccaaggatc gcaactcgat tgaaatgtca gaataa 1656

<210> SEQ ID NO 42
<211> LENGTH: 1590
<212> TYPE: DNA
<213> ORGANISM: Pichia stipitis

<400> SEQUENCE: 42
atggcatatc ttgattggtt aacagctaga accaacactt tcgggttgag gggcaagaag 60
ttgagagcct tcatcactgt agtggctgtc actggtttct cattattcgg atatgatcaa 120
gggttgatgt ccggaattat tactgctgat caattcaact ctgagtttcc cgccactaga 180
aataacagta ctatccaagg tgccgtcacc tcctgttacg agcttggttg tttctttggt 240
gctgtgtttg ccttgttaag aggtgaaaga attggaagaa gacctcttgt gctttgtggc 300
tcgcttatta tcatcttggg aacagttatt tctgtaaccg ccttccatcc acactggtca 360
ttaggtcagt ttgttattgg tagagttatc actggtattg gtaatggtat gaatactgcc 420
accattccag tttggcaatc ggaaatgtca agagctgaaa acagaggaag attggtcaac 480
ttggaaggtt ccgttgtcgc tgtgggtaca tgtattgcct actggttgga tttcggtttg 540
tcttatgtcg acaattcagt ttcctggaga tttccagttg ctttccaaat agtgtttgct 600
tccgttttat ttgtgggaat gttgcaattg cccgactctc caagatggtt ggttgctaac 660
cacagaagag cagaggctct tcaagtgttg tctgctttga aagacttgcc cgaagacgac 720
gaagaaattc ttaatgaagc tgaagttatt caggaaagtg tagacaagtt tgctggacat 780
gcttccgtca aggaagtgtt tactggtggt aagacccagc actggcaaag aatggttatt 840
ggatccagca cccaattctt tcagcagttc actggttgta acgctgccat ttactattcc 900
actgtcttgt ttcaagacac tattggttta gaaagaagaa tggcattgat tatcggtggt 960
gttttcgcaa ctgtctacgc cattttcaca attccttcct tcttcttggt cgatactctt 1020
ggacgtagaa acttgttctt gattggtgct atgggacaag gtattgcatt cactatcacc 1080
tttgcctgtt tgattgacga tactgaaaac aacgccaagg gtgccgcagt tggtttattc 1140
ttgtttattt gtttcttcgc cttcaccatc ttgccattgc catgggtata cccaccagaa 1200
atcaatcctt tgagaactag aactatagct tctgcaattt ccacttgtac caactggatc 1260
tgtaactttg ctgttgttat gttcacccct gtctttgtca ctaacaccag atggggagcc 1320
tatcttttct ttgctgtgat gaacttcctt ttcgttccta ttattttctt cttctaccca 1380
gaaacagctg gaagatcgtt ggaagaaatc gatatcatct ttgcgaaggc attcgttgac 1440
aaaagacagc catggagagt tgctgcaacc atgccaaagt tgtccaacca cgaaattgaa 1500
gacgaagcca acagattggg cttgtttgac gatggtacat tcgacaagga agcatttgaa 1560

-continued

```
accaaagaaa acgcatccag cagctcttaa                                  1590


<210> SEQ ID NO 43
<211> LENGTH: 1689
<212> TYPE: DNA
<213> ORGANISM: Neurospora crassa

<400> SEQUENCE: 43

atggcgcctc caaagttcct gggcctctca ggccgaccgc tctctctagc tgtctcgact     60

gtagccacca cgggcttcct tctcttcggc tatgaccaag gtgtcatgag cggcatcatt    120

accgcccccg ctttcaacaa cttcttcaca ccaaccaaag acaactcgac catgcagggt    180

ctcatcactg ccatctacga aattggatgc ttgattggtg ccatgttcgt cctctggacc    240

ggcgatttgt tgggtagacg caggaacatc atggtgggcg ccttcattat ggctctcggt    300

gtcattattc aggttacctg tcaggctgga tccaaccctt ttgctcagct gttcgtcggc    360

agagtcgtca tgggtattgg caacggcatg aacacttcga ccattcccac ttatcaagcc    420

gaatgctcaa agacatcgaa ccgcggtctt ttgatctgca ttgaaggcgg tgtcattgcc    480

tttggtactt tgattgctta ttggatcgac tatggtgcat cttacggtcc cgatgacctc    540

gtttggcgct tccccatcgc tttccagctt ctcttcgcca tcttcatctg cgtccccatg    600

ttttaccttc ccgagtcgcc cagatggctc ctcagccatg gccggaccca agaagctgac    660

aaggtcattg ctgccctccg tggctacgag atcgatggtc ccgagaccat ccaagagcgc    720

aacctcattg ttgactccct gcgtgcctct ggaggtttcg gccaaaagag cactcccttc    780

aaggccctct tcactggcgg caagacccag catttccgtc gtctcttgct cggttccagc    840

tcccagttca tgcagcaagt tggtggttgc aacgccgtca tctactactt ccccattctg    900

ttccaggatt ctattggcga gtcccacaac atgtccatgt tgctgggcgg tatcaacatg    960

atcgtctact ccatcttcgc taccgtttcc tggttcgcca ttgagcgtgt cggtcgtcgt   1020

cgtctgttct tgatcggcac cgttggccag atgctctcca tggtcatcgt cttcgcctgc   1080

ttgatccccg acgaccctat gaaggcccgc ggtgccgcgg tcggtctctt cacttacatt   1140

gcctttttcg gtgccacttg gcttcccctc ccctggctct accccgccga ggttaacccc   1200

atccgcacac gtggaaaggc taacgccgtc tccacctgct ccaactggat gttcaacttc   1260

ctcatcgtca tggtcacccc catcatggtc gacaagattg gctggggaac ttacctcttc   1320

ttcgcggtca tgaacggctg cttccttccc atcatttact tcttctaccc cgagactgcg   1380

aaccgctcgc tcgaggagat cgacatcatc ttcgccaagg gcttcgtcga gaacatgtcg   1440

tacgtcactg ccgccaagga gctgcctcac ctcactgccg aggagatcga gtcctatgcc   1500

aacaagtatg gcctcgtcga ccgcgattcc aacggcgagg gcggcaaccg ccatgacgag   1560

gagaagacgc gcgaccgccc cgaccagagt gacagcgact cccccgctca cgtcgagatt   1620

gatgttgtcg acgagcacgg tgtcgagtcc ggcttcggtg atggtattaa caccaaggaa   1680

acacgttaa                                                         1689


<210> SEQ ID NO 44
<211> LENGTH: 1626
<212> TYPE: DNA
<213> ORGANISM: Neurospora crassa

<400> SEQUENCE: 44

atggaattcg agcacgatca ctccgcctcc gacattgaga aggaggccgt cactgtggcc     60

cggccacagg gcgatgtcac ccgcgttgag gctcccgtta ccctcaaggc gtacatgatg    120
```

-continued tgcgtctttg ccgctttcgg cggtatcttc tttggctacg attcaggtta catctctggt 180
gtcatgggca tgaagtactt tatcgaaacc atcaacggac ccggcgccac cttcctgcca 240
tccaaggaaa agtcgctcat cacctccatt ctctctgccg gaaccttctt tggcgccctc 300
atgggcggtg atctcgctga ctgggttggc cgtcgtccta ccatcatctt cggctgcctc 360
gtcttcatcg tcggtgttgt tctccagact gcctcccaga gcttgggtct cattgtggcc 420
ggccgtctcg tcgctggttt cggtgtcggt ttcgtctcgg ccattatcat cctgtacatg 480
tctgagatcg cgccccgcaa ggtccgcggt gctatggtgt cgggctacca gttctgcatc 540
tgcctgggtc tgctcctggc ctcgtgcgtt gactacggca cccagaaccg caccgacagc 600
ggctcttaca gaatcccgat tggtctccag atggcctggg ccctcattct tgctactggt 660
atctttttcc ttcctgaatc ccctcgcttc ttcgtcaaga agggcaagct cgacaaggcc 720
gccggcgtgc tctcccgcct gcgcgaccag ccgctcgatt ccgactacgt cagggacgaa 780
cttgccgaga tcgttgccaa ccacgaattc gaaatgaccg tcgtccccta cggcaactac 840
ttccagcagt gggccaactg cttccgcggc tccatctggc agggtggttc ttacctccgc 900
cgcaccattc tcggcacttc gatgcagatg atgcagcagt ggacgggaat caactttatc 960
ttttactttg gaaccacctt cttccagcag ctcggcacca ttgacaaccc cttcctgatg 1020
tctctggtca ctactcttgt caacgtctgc tccacccca tctccttcta caccatggag 1080
aagctcggcc gtcgtaccct cctcatctgg ggcgctctcg gcatgctgat ctgcgagttt 1140
atcgtcgcca tcgttggtac ctgcaggccg gatgatacca tggccatcaa ggccatgctc 1200
gccttcatct gcatctacat cttcttcttt gctaccacct ggggccctgc ttcctgggtc 1260
gtcatcggcg aggttttccc tcttcccatt cgtgccaagg gtgttgccct ttccaccgcc 1320
tccaactggc tctgtaactg catcatcgcc gtcatcactc cctacatggt cgacgaggac 1380
aagggcaacc tgggccccaa ggtgttctac atctggggtg gcctctgcac ctgctgcttc 1440
atctacgcct acctgcttgt gcccgagacc aagggcctca cgctcgagca ggtcgaccaa 1500
atgctttccg agtctacccc ccgcacctcg accaagtgga agcctcacac cacttatgct 1560
gctgagatgg gcatgaccga gaagactgtt gctggccacg ctgagaaccg cagcgatagc 1620
gagtaa 1626

<210> SEQ ID NO 45
<211> LENGTH: 1614
<212> TYPE: DNA
<213> ORGANISM: Neurospora crassa

<400> SEQUENCE: 45
atgggtcttt cgataggaaa taggatcctc cggaaaattg tcaaaaatga ggccatggca 60
gaagatcccc cagagatcta tggctggcgt gtctatctcc tagcgtgctc tgcctgcttc 120
ggcgccatgt ctttcggctg ggattcctcc gtcatcggcg gcgtcatcga actcgaaccc 180
tttaaacacg actttggctt catcggcaac gataaagcca aggccaacct gggcgccaat 240
atcgtctcta ccctccaagc cggctgcttc ctcggtgcgc tgatcgcctc acctataacc 300
gatcgcttcg gccgcaagtg gtgtctcatc gctgtctccc tggtcgtcat catcggtatc 360
atcatgcaag ccgccgcctc aggcaacctc gcacccatgt acattggccg tttcgtcgcc 420
ggcgtgggcg tcggcgccgc cagctgcatc aaccccgtct ttgtgtctga gaacgctccc 480
cgctcgatcc gcggtctgtt gacgggcctc taccaactct tcattgtcac cggcggcatg 540

-continued

```
atcgcatttt ggatcaacta ctccgtctct ctgcacttca agggcaaatc catgtacatc    600
ttcccgctcg ccatccaagg tcttcccgcc ggccttttgt gcgtctgcat gctcctctgc    660
cacgaaagcc cgcgctggct ggcccgtcgt gaccgatggg aagaatgcaa gtctgtgctg    720
gcgcgcatcc gcaacctccc cccagaccac ccgtacatcg tcgacgagtt ccgcgagatc    780
caggaccagc tcgaacagga gcgtcgtctc cagggcgacg ccacttactg ggacttgacc    840
cgcgatatgt ggaccgtcgc cggcaaccgc aagcgcgccc tgattagtat tttcttgatg    900
atctgccagc aaatgacggg caccaacgcc atcaacacgt acgcgcctac catcttcaag    960
aacttgggta tcaccggcac gtcgactagc ttgtttagta ccggcatcta tggtattgtc   1020
aaggtcgtta gctgcgtcat tttcttgctg ttcttggccg actcgctggg tcgtagacgt   1080
tcgctgctgt ggacgtcgat tgcgcagggt cttgctatgt tttatattgg cctttatgtc   1140
cgcatctcgc cgccgattga tggccagccg gtgccgcctg cgggttatgt agcgttggtg   1200
tgcatctttc tgtttgccgc tttcttccaa tttggctggg gtcctgcctg ctggatctac   1260
gcctcggaaa tccccgccgc ccgcctgcgc tccctcaacg tgtcctacgc cgccgcgacg   1320
cagtggctgt tcaatttcgt cgtggcccgc gccgtgccta ctatgctggt cacggtcggc   1380
ccccacggtt acggcaccta cctcatcttt ggcagcttct gcctcagcat gtttgtcttt   1440
gtctggttct tcgtgcccga gacaaagggt atctcgcttg agcacatgga tgagctgttt   1500
ggcgttactg atgggcctgc cgctgagaag tcgtcggtgc atggtggaga tgatgtcggg   1560
tcggagatgg ggaaggggga tcagaagtcg aagcatgtgg aggtttatgt ttaa         1614
```

```
<210> SEQ ID NO 46
<211> LENGTH: 1587
<212> TYPE: DNA
<213> ORGANISM: Pichia stipitis

<400> SEQUENCE: 46
```

```
atgtcttcgt tattgactaa cgaatacttc aaagactact accacaaccc gactcctgtt     60
gaagtgggta ctatgattgc tatcttagag atcggcgcac ttttttcctc cttcatagct    120
ggaagagtag gtgacatcgt tggcagaaga agaaccatta gatacgggtc tttcattttt    180
gtagtaggcg gtcttgtaca agctacttcg gtcaatattg tcaatctctc actaggaaga    240
ttgattgccg gtattgccat tggctttttg acaaccatca tcccatgcta ccagtctgaa    300
atcagccccc cagacgatag aggtttctat gcctgtttgg agttcaccgg aaatatcatt    360
ggatatgcta gtagtatttg ggtagactac gggttttcat ttttagacaa tgatttcagc    420
tggaggagcc cattgtatgt tcaggttgtt attggctcca tgttatttat tggttcattc    480
cttattgtag aaacccctag atggctcttg gatcacaacc atgatatcga aggcatgatt    540
gtcatttctg acttgtatgc agatggtgat gtggaagacg atgatgctat tgctgagtac    600
agaaacataa aggaaagtgt cttgatagcc agagttgaag gcggagagag atcgtaccag    660
tatttgttca ccaaatatac caagagactt tctgtggcat gcttttcgca aatgtttgcc    720
cagatgaatg gtataaacat ggtatcttac tatgctccta tgatcttcga atctgctggc    780
tgggttggta gacaagctat cttgatgact ggtatcaact ccattatcta catctttagt    840
accattcctc catggtactt agttgattct tggggcagaa aacctttgct tttatctgga    900
tctgtgctca tgggtgttcc gctcttaacc attgcttgtt cgttattctt aaacaacaca    960
tacacacccg ggttgtggt tggcagtgta atcgtattca atgctgcttt tggatacagt   1020
tggggtccaa ttccttggct catgagcgaa gtgttcccta actcagttag atcaaaaggt   1080
```

```
gctgccatgt ctactgcaac caactggctc tttaacttta ttgttggaga gatgacacct    1140

attttgttgg atacaattac ctggagaact tacttgatcc cggcaacttc gtgtgtatta    1200

tcgtttttg ctgttggatt tttatttcca gagaccaagg gtttagcatt ggaggatatg    1260

ggctccgtat tcgatgataa ttcgtcaata ttttcatatc actcaacttc ttccactggg    1320

tatggtgcga ccgagtctaa cagtaatgcc aggagagcaa gtgtcatctc ttcagaaaac    1380

taccaggata gtttgcatca gacagcggct tcattggcta gaaatccttc aagcatgagg    1440

cctgattacg atggcataat cacaggagct gctacccttt cgccagtacc accattaaaa    1500

ccaataaaca tttccagcaa tattccgcag gaaattgaac caccaacctt tgatgaaatc    1560

tttaagtaca agttgaatga gatggaa                                        1587

<210> SEQ ID NO 47
<211> LENGTH: 1257
<212> TYPE: DNA
<213> ORGANISM: Pichia stipitis

<400> SEQUENCE: 47

atgacttttg cagttaactt gtatgtgttt gcagttggta gagtgctttc tggggtgggt      60

gtaggagttc tatcgactat ggtgccgtcc tatcaatgcg aaattagtcc cagcgaagaa     120

agaggcaagt tggtgtgtgg agagttcacg ggaaatatca ctggttatgc tctcagtgta     180

tgggccgatt acttctgcta ctttattcaa gatataggtg atgcaaggga gaagcctcat     240

agcttctttg cccacttgtc ctggcgattg cctctattca tccaggtggt gatagcggct     300

gttctctttg ttgggggatt ttttattgtc gagtcacctc gttggttatt agatgtagac     360

caggaccaac aaggattcca tgtattagcg ttgctctatg attcacatct agatgataac     420

aaaccacgtg aagagttctt tatgatcaaa aactccatct tgttagaaag agaaactaca     480

cctaagagcg aacgaacttg gaaacatatg ttcaagaact acatgacccg agtgcttata     540

gcttgttcag cacttggctt tgcacagttc aacggcataa atatcatttc gtactatgcc     600

cccatggtat ttgaagaagc aggcttcaac aactccaagg ctttacttat gacaggcatc     660

aactctatag tatattggtt cagtacgatt cctccgtggt ttctcgtgga tcattggggt     720

agaaagccaa ttttgatatc cgggggttta tctatgggaa tatgtattgg tttgattgcg     780

gtggtaattc tactagacaa gtcgttcaca ccgtctatgg ttgcggtatt ggtgataatc     840

tacaatgcat cttttggcta cagttggggt cctatcggat tcttgatccc gccggaggtg     900

atgccattgg cagttagatc gaaaggtgtt tctatttcta cggctacaaa ctggtttgcc     960

aattttgttg tgggtcagat gacgccaatt ctacagcaga gattgggctg gggaacttat    1020

ctattcccgg ctggtagttg tatcatctcg gtgatagtgg tgattttctt ctatccagag    1080

acaaagggtg cagagctaga ggatatggac tctgtgttcg agagctttta caactacaag    1140

tctccgttca agatttcacg aaagagacac cagaatgatg ccaggcgta ccaaagggta    1200

gagaacgata tccgccacaa cgatgtagaa atggacgatt tggacgattt ggactaa       1257

<210> SEQ ID NO 48
<211> LENGTH: 1757
<212> TYPE: DNA
<213> ORGANISM: Neurospora crassa

<400> SEQUENCE: 48

atggaattcg gtggcggagg cggctccggc gcagctggtt tttatgatgc ggctcttcag      60
```

```
aggcgtgagg cagtgatggg gaagagtggc cctgcagcac ttgtcaagaa cttccgggtc    120
ttttctattg catgcttcgc atgtatcggt ggtgtgctct atgggtacaa ccaagggatg    180
ttttcgggtg tcctcgccat gccagccttt cagaaacaca tgggcgaata cgatccgata    240
gacgagaacg cgagtcagac aaagaagggc tggctaaccg caattcttga gctcggtgct    300
tggcttggta cgcttctgtc tgggttcatg gcagaggttc tctcgagaaa gtacggtgtg    360
ctagtggcgt gcttggtttt catgctgggt gtggtcatcc aagccacgtc tatctctgga    420
ggacatgaga ccattcttgc cggacggttt atcacgggta tgggtgtcgg atccttagcc    480
atgatcattc ccatttacaa ctcggaagtt gcaccacctg aggtccgtgg agctcttgtt    540
gctctccagc agttggctat ctgcttcggt atcatggtca gcttctggat tgactacgga    600
accaactata tcggcggcac caagctcgag acccaatccg acgccgcctg gcttgtaccc    660
gtctgcctgc aactcgcccc tgctctcatt ctgtttttcg gcatgatgtt catgcccttc    720
tccccacgct ggctcatcca ccatggccgc gaggcggaag ctcgaaagat cctctccacc    780
cttcgcggtc taccccaaga ccacgagctt gtcgagctcg agttcctcga aataaaggct    840
cagtctctct tcgaaaaacg cagcattgcc gagttgtttc ccgaattgcg cgagcagact    900
gcctggaata cctttaagct ccagtttgtc gccatagaga agcttttccg gacaaaggca    960
atgttccgac gcgttgtcgt ggcaaccgta accatgttct tccagcagtg gtccggcatc   1020
aatgcgattc tctactacgc cccgcaaatc ttcaagcagc ttggactgag cggtaacaca   1080
acctcactcc tggctacggg tgtagtaggc atcgtcatgt tcatcgcaac ggttcctgcc   1140
gtgctgtgga tcgaccgtgt tggtcgcaag cccgtgctta ctatcggtgc cctcgggatg   1200
gctacctgcc atatcatcat cgctgtcatt gttgccaaga acgtggacca atgggagact   1260
cataaggctg ctggatgggc tgctgtagcc atggtctggc tattcgtcat tcactttgga   1320
tattcatggg gtccatgtgc ctggatcatt gttgctgaga tctggccgtt gagtacgagg   1380
ccatatggtg tctctctagg agcttcgagc aactggatga acaactttat cgtcggtcag   1440
gtcacgccgg atatgttaaa ggcgatcccg tacggaacgt atatcatctt cgggttgttg   1500
actatatggg tgccgccttt atttggttct ttgtgccgga aacgaagaga ttaaccttgg   1560
aagagatgga catgatcttc ggatccgaag gcactgcaca agccgacaat gagcgcatgg   1620
aggagatcaa tgctgagatt ggtcttaccc gattcctgca aggtggtagt ggtgcaaacc   1680
aaggtgctgc tgatggaagc gatactggtt atgatgcgga gaagggcaag agcgaacact   1740
attctcagca tgtctaa                                                  1757
```

<210> SEQ ID NO 49
<211> LENGTH: 1584
<212> TYPE: DNA
<213> ORGANISM: Neurospora crassa

<400> SEQUENCE: 49

```
atgggcttgt cactcaagaa gcctgaaggt gtgccgggca agtcatggcc cgccattgtc     60
attggcttgt ttgtcgcctt tggtggtgta ctctttgggt atgacactgg cactattggc    120
ggtatccttg ctatgcccta ttggcaagat ttgttttcga caggttacag aaacccagag    180
catcacttgg acgttaccgc gtcgcagtct gccactatcg tctccattct gtctgctgga    240
accttctttg gcgctcttgg tgccgctccc cttgccgact gggctggacg acgcttgggc    300
cttattctgt cgtcgtttgt gtttatcttc ggtgtcatcc tgcagaccgc agccgtcagc    360
attcctcttt ttctggctgg ccgattcttt gctggattgg gagttggtct catatcggca    420
```

accatccccc tctatcaatc cgagactgcc ccgaaatgga ttcgtggtgt catcgtcggg 480
tcctatcagc tagccattac catcggtctt cttcttgcct ccattgtcaa caatgccacg 540
cataacatgc agaacaccgg ctgctatcgc atccccatag ctgtccaatt tgcatgggcg 600
atcatcctga tcgttggcat gatcattctt cccgaaactc cacgctttca tatcaagaga 660
gacaatctcc cagccgccac taggtctcta gctatcctcc gccgtctgga gcagaaccat 720
ccagcgatca tcgaagagct ttccgagatc caagccaatc atgaatttga gaagagcctc 780
gggaaggcga cctacttgga ctgcctcaag ggcaatttac tcaagcggct ccttactggc 840
tgttttctcc agagcctgca gcagttgact ggcatcaact ttatcttcta ctacggcaca 900
cagttcttca aaaactccgg attctcagac tcgtttctga tatccttgat cactaatctt 960
gtcaatgtcg tgtcgaccct tcccggactc tacgccatcg acaaatgggg ccggaggcct 1020
gttttactct ggggagctgt tgggatgtgt gtctgccagt tcatcgttgc tattcttggg 1080
acaacaacga caagtcaaga tgcaagcgga atgatcattg tgcataatct cgccgcacag 1140
aaagcagcta ttgcattcat ctgcttctac atctttttct tcgctgcatc ttggggtcca 1200
gttgcctggg tcgttacagg cgagatcttc cccttaaag tccgcgccaa gtcgctctcc 1260
ataactacag cgtcgaattg gctgctcaac tgggccattg cttacagcac accttacctt 1320
gtcaactacg gccctggcaa tgcgaacctg cagtccaaga tcttcttcgt ctggggcgga 1380
tgctgcttca tctgcatcgc attcgtttac ttcatgatct atgagacaaa aggtctcaca 1440
ctggagcagg ttgacgagct atatgaagag gtctcggatg ccaggaagag tattggttgg 1500
gtgccgacca tcactttccg ggagatccgg gaggaaaaga aagtaaggga tccagttgtt 1560
gatatcactg aagaggcagc ttga 1584

<210> SEQ ID NO 50
<211> LENGTH: 1968
<212> TYPE: DNA
<213> ORGANISM: Neurospora crassa

<400> SEQUENCE: 50
atgggccaca atccagacct ggacagtagc ggcactgccg gagaacccaa aggtgtcacc 60
ggctcgcaca ttgaacaaac ctcgtccaac ctcgaagcca acatcaacct cgaagccaag 120
ctcaagaacc cgctcgacgg cctttcccgc gtcgagctcc tgtcacgcgt cgagaccttt 180
tgcgccgaaa agaacctaac cgagcacctc cctcttttcc gtaagggagc actcatcgcc 240
cagtccccgg acagctatgc gtccatctcg ggcccggaag ccttggacga tgaggagaag 300
gcagtacttt tgaaggaggt cgaacacaag tggcggctgc cggcaagact gttcctgacg 360
attgctactt gctcgatcgg tgctgctgtc caaggttggg atcagacggg cacgaatggc 420
gcgaatatct tctttcccaa ctattacggt atcggaggcg acactgcgag ggagaagttg 480
cttgtcggat tgatcaatgc tgggccctat attgggagcg cattcatcgg ttgctggctt 540
tctgatccca tcaacaactg gattggtcgt cgtggtgtta tctttgtctc tgctcacttc 600
tgtatctggc ccgtcatcgg ttctgctttc tgtcacacat ggccccagca actggcctgc 660
cgtctgctga tgggtatcgg tatgggtgtg aaggcatcaa cggtgccgat ctatgccgcg 720
gaaaactcgc ctgcttctat tcgaggtgcg ctggtcatgt catggcagat gtggacagcc 780
ttcggcatct tcttgggcac tgcctttaac cttgccgtct tccacgccag ctccaacgtt 840
aactggcgcc tcatgctcgg tgccccttc attcccgccg taccccctgct tctgctcatc 900

-continued

```
tatctttgcc ccgagtcccc gcgctggtac atgaagaagg gccgctaccc agaagcctgg    960

aaatccatgg tcaagctgcg caaccacccc atccaagttg cccgcgacat gttctacatc   1020

cactcgcaat tggaagtcga gcaccagctc ctcgccggct ccaactatgc caagcgcttc   1080

gtcgagctct tcaccgtccc tcgtgttcgc cgcgccaccc tcgccgcttt caccgtcatg   1140

attgcccagc agatgtgcgg aatcaacatc atcgcctttt acagcaccac catcttcaag   1200

gattccggct ccaccgaatt ccaagccctg ctttcctcct tcggcttcgg tctagtcaat   1260

tggctctttg ccttccccgc cttctggact atcgacactt ttggccggcg ctctctgctt   1320

ctttttacct tcccgcaaat gatgtggacc ctgctagcag ccggcctctt caccttgctc   1380

gacatgggtc ccgcccggac cgggctcgtc gccttattcg tcttcctctt cgccgcgttc   1440

tactcacccg gtgaaggtcc tgtccccttc acctactcgg ccgaagtctt ccccctctct   1500

cacagagaag taggcatggg cttcgccgtc gccacctgcc tcttctgggc atctgttttg   1560

ggtattacct tcccttcttt gcttgactct ctcggcaccg tcggcgcctt tggtctgtac   1620

gcgggcttca acctagtggc gtttattgcc atcttcttgg tcgtgccgga gacgaagcag   1680

aagacgctcg aggagttgga ttatgtcttt gctgtgaaga cgagcaagtt catgtcgtat   1740

cagtgcacca aggcgctgcc gtggttcatc aagaggtggg tgttttggca gaggaatgca   1800

aagctggagc cactgtatga gtttgatcgg atcaaggagg cggagaagga gaggagagca   1860

gaggaggaga gaagggcaaa ggagacggga acgatcacct ctactgctac aggagctgag   1920

ttggatgaga agaagggact gagtcatgtt aatgctccta attcttag                1968
```

<210> SEQ ID NO 51
<211> LENGTH: 1725
<212> TYPE: DNA
<213> ORGANISM: Saccharomyces cerevisiae

<400> SEQUENCE: 51

```
atggcagttg aggagaacaa tatgcctgtt gtttcacagc aaccccaagc tggtgaagac     60

gtgatctctt cactcagtaa agattcccat ttaagcgcac aatctcaaaa gtattctaat    120

gatgaattga aagccggtga gtcagggtct gaaggctccc aaagtgttcc tatagagata    180

cccaagaagc ccatgtctga atatgttacc gtttccttgc tttgtttgtg tgttgccttc    240

ggcggcttca tgtttggctg ggataccggt actatttctg ggtttgttgt ccaaacagac    300

tttttgagaa ggtttggtat gaaacataag gatggtaccc actatttgtc aaacgtcaga    360

acaggtttaa tcgtcgccat tttcaatatt ggctgtgcct ttggtggtat tatactttcc    420

aaaggtggag atatgtatgg ccgtaaaaag ggtctttcga ttgtcgtctc ggtttatata    480

gttggtatta tcattcaaat tgcctctatc aacaagtggt accaatattt cattggtaga    540

atcatatctg gtttgggtgt cggcggcatc gccgtcttat gtcctatgtt gatctctgaa    600

attgctccaa agcacttgag aggcacacta gtttcttgtt atcagctgat gattactgca    660

ggtatctttt tgggctactg tactaattac ggtacaaaga gctattcgaa ctcagttcaa    720

tggagagttc cattagggct atgtttcgct tggtcattat ttatgattgg cgctttgacg    780

ttagttcctg aatccccacg ttatttatgt gaggtgaata aggtagaaga cgccaagcgt    840

tccattgcta agtctaacaa ggtgtcacca gaggatcctg ccgtccaggc agagttagat    900

ctgatcatgg ccggtataga agctgaaaaa ctggctggca atgcgtcctg gggggaatta    960

ttttccacca agaccaaagt atttcaacgt ttgttgatgg gtgtgtttgt tcaaatgttc   1020

caacaattaa ccggtaacaa ttattttttc tactacggta ccgttatttt caagtcagtt   1080
```

ggcctggatg attcctttga aacatccatt gtcattggtg tagtcaactt tgcctccact 1140
ttctttagtt tgtggactgt cgaaaacttg ggacatcgta aatgtttact tttgggcgct 1200
gccactatga tggcttgtat ggtcatctac gcctctgttg gtgttactag attatatcct 1260
cacggtaaaa gccagccatc ttctaaaggt gccggtaact gtatgattgt ctttacctgt 1320
ttttatattt tctgttatgc cacaacctgg gcgccagttg cctgggtcat cacagcagaa 1380
tcattcccac tgagagtcaa gtcgaaatgt atggcgttgg cctctgcttc caattgggta 1440
tgggggttct tgattgcatt tttcacccca ttcatcacat ctgccattaa cttctactac 1500
ggttatgtct tcatgggctg tttggttgcc atgttttttt atgtcttttt ctttgttcca 1560
gaaactaaag gcctatcgtt agaagaaatt caagaattat gggaagaagg tgttttacct 1620
tggaaatctg aaggctggat tccttcatcc agaagaggta ataattacga tttagaggat 1680
ttacaacatg acgacaaacc gtggtacaag gccatgctag aataa 1725

<210> SEQ ID NO 52
<211> LENGTH: 1908
<212> TYPE: DNA
<213> ORGANISM: Pichia stipitis

<400> SEQUENCE: 52
atgagtgctg acgaaaaagt cgctgctgcc ggccaggacg gcttgtttga acacaacagt 60
tccacttcga gcatcgagga caagaagccc tccaagagct ccgatgtcga ttccgtgaac 120
tcgcaattag tagacaactc ggtagagggc aacatcttgt cccagtacac cgaaagtcag 180
gtgatgcaga tgggtagaag ctatgccacc aagcacggct tggacccaga attgttcgcc 240
aaggcagctg ctgttgccag aactcctctt ggtttcaact ccatgccctt cttgacagag 300
gaagagaagg ttggtttgaa tgccgaagcc actaataagt ggcacattcc acccagattg 360
atcggggtta ttgccttggg ttctatggcc gctgctgtgc agggtatgga cgaatcggtc 420
attaacggtg ccaacttgtt ctaccccaag gctttcggag tcgacaccat gcacaattcg 480
gacttgattg aaggtttgat caatggtgct ccttaccttt gctgtggtat tctttcctgt 540
tggttgtctg acgcttgtaa ccgtcgtctt ggtagaaaat ggaccatttt ctggtgttgt 600
gtcatttctg ccatcacctg tgtctggcaa ggtcttgtca acaactggta ccatttgttc 660
attgctcgtt tcttccttgg atttggtgtt ggtatcaagt ccgccactgt tcctgcctac 720
tctgccgaat gtactcctaa acacatcaga ggttcgttag tcatgttgtg gcaattcttc 780
acagctgttg gtattatgtt tggttatgtt gcttccttgg ctttctacaa tgtcggagat 840
agaggaatcc attacgggtt gaactggaga ttgatgcttg gttcggccgc tattcctgct 900
gtcatcatct tgttccaaat tcctttcgct cctgaatctc cacgttggtt aatgggtaag 960
gacagacacc ttgaagcctt tgagtccttg aagcaattga gatacgaaga acttgctgct 1020
gctcgtgact gtttctacca gtacgtcttg ttagctgaag aaggttctta caagatccca 1080
accctcacca gatttaagga aatgttcacc aagagaagaa acagaaacgg tgccatcggt 1140
gcatttattg tcatgttcat gcaacagttc tgtggtatca acgtcattgc ttactactct 1200
tcgtctatct ttgtccaatc tggtttctct caaacttctg ctttgatcgc ttcttggggt 1260
ttcggtatgc ttaacttcac ctttgccatt cctgccttct tcacaatcga tcgtttcggt 1320
agaagatcct tattgttggt taccttcccc ttgatggcta ttttcttatt gattgccggt 1380
ttcggtttct tgataaacga agaaacaaac tccaagggaa gattgggaat gatcatcatc 1440

-continued

```
ggtatctata tgttcaccat ctgttactct tccggtgaag gtccagttcc tttcacctac   1500

tctgccgaag ccttcccatt gtacatcaga gacttgggta tgtcttttgc tactgccacc   1560

tgttggactt tcaacttcat cttggccttc acctggaaca gattggtcaa tgcattcaca   1620

tctactggtg ccttcggctt ctacgctgct tggaacatca ttggtttctt cttggtctta   1680

tggttcttgc cagaaaccaa gggcttgacc ttggaagaat tggacgaagt cttcgccgtt   1740

tccgccgtcc aacacgccaa gtaccaaacc aagagtttga tcaacttcat ccaaagatac   1800

gttttacgtt ccaaggtggc tccattgcct ccattgtacg accaccagag attggctgtc   1860

accaacccag aatggaacga caagccagaa gtctcttatg tcgagtag                1908
```

<210> SEQ ID NO 53
<211> LENGTH: 40
<212> TYPE: DNA
<213> ORGANISM: Artificial Sequence
<220> FEATURE:
<223> OTHER INFORMATION: Synthesized Construct

<400> SEQUENCE: 53
atatatgagc tcgtgagtaa ggaaagagtg aggaactatc 40

<210> SEQ ID NO 54
<211> LENGTH: 50
<212> TYPE: DNA
<213> ORGANISM: Artificial Sequence
<220> FEATURE:
<223> OTHER INFORMATION: Synthesized Construct

<400> SEQUENCE: 54
atatatacta gttgttttat atttgttgta aaaagtagat aattacttcc 50

<210> SEQ ID NO 55
<211> LENGTH: 30
<212> TYPE: DNA
<213> ORGANISM: Artificial Sequence
<220> FEATURE:
<223> OTHER INFORMATION: Synthesized Construct

<400> SEQUENCE: 55
atggatccaa aaatgtcgtc tcacggctcc 30

<210> SEQ ID NO 56
<211> LENGTH: 60
<212> TYPE: DNA
<213> ORGANISM: Artificial Sequence
<220> FEATURE:
<223> OTHER INFORMATION: Synthesized Construct

<400> SEQUENCE: 56
atgaattcct acaaatcttc ttcagaaatc aatttttgtt cagcaacgat agcttcggac 60

<210> SEQ ID NO 57
<211> LENGTH: 34
<212> TYPE: DNA
<213> ORGANISM: Artificial Sequence
<220> FEATURE:
<223> OTHER INFORMATION: Synthesized Construct

<400> SEQUENCE: 57
atactagtaa aaatgggcat cttcaacaag aagc 34

<210> SEQ ID NO 58
<211> LENGTH: 64

<212> TYPE: DNA
<213> ORGANISM: Artificial Sequence
<220> FEATURE:
<223> OTHER INFORMATION: Synthesized Construct

<400> SEQUENCE: 58
gcatatcgat ctacaaatct tcttcagaaa tcaatttttg ttcagcaaca gacttgccct 60
catg 64

<210> SEQ ID NO 59
<211> LENGTH: 42
<212> TYPE: DNA
<213> ORGANISM: Artificial Sequence
<220> FEATURE:
<223> OTHER INFORMATION: Synthesized Construct

<400> SEQUENCE: 59
tattaaatcg atggtagtgg tagtgtgagc aagggcgagg ag 42

<210> SEQ ID NO 60
<211> LENGTH: 36
<212> TYPE: DNA
<213> ORGANISM: Artificial Sequence
<220> FEATURE:
<223> OTHER INFORMATION: Synthesized Construct

<400> SEQUENCE: 60
tattaagtcg acctacttgt acagctcgtc catgcc 36

<210> SEQ ID NO 61
<211> LENGTH: 28
<212> TYPE: DNA
<213> ORGANISM: Artificial Sequence
<220> FEATURE:
<223> OTHER INFORMATION: Synthesized Construct

<400> SEQUENCE: 61
gcatggatcc atgtcgtctc acggctcc 28

<210> SEQ ID NO 62
<211> LENGTH: 31
<212> TYPE: DNA
<213> ORGANISM: Artificial Sequence
<220> FEATURE:
<223> OTHER INFORMATION: Synthesized Construct

<400> SEQUENCE: 62
tataatgaat tcagcaacga tagcttcgga c 31

<210> SEQ ID NO 63
<211> LENGTH: 34
<212> TYPE: DNA
<213> ORGANISM: Artificial Sequence
<220> FEATURE:
<223> OTHER INFORMATION: Synthesized Construct

<400> SEQUENCE: 63
tattaaacta gtatgggcat cttcaacaag aagc 34

<210> SEQ ID NO 64
<211> LENGTH: 33
<212> TYPE: DNA
<213> ORGANISM: Artificial Sequence
<220> FEATURE:
<223> OTHER INFORMATION: Synthesized Construct

<400> SEQUENCE: 64
ttataagaat tcagcaacag acttgccctc atg 33

<210> SEQ ID NO 65
<211> LENGTH: 39
<212> TYPE: DNA
<213> ORGANISM: Artificial Sequence
<220> FEATURE:
<223> OTHER INFORMATION: Synthesized Construct

<400> SEQUENCE: 65
gcatactagt aaaaatgtct cttcctaagg atttcctct 39

<210> SEQ ID NO 66
<211> LENGTH: 55
<212> TYPE: DNA
<213> ORGANISM: Artificial Sequence
<220> FEATURE:
<223> OTHER INFORMATION: Synthesized Construct

<400> SEQUENCE: 66
atactgcagt taatgatgat gatgatgatg gtccttcttg atcaaagagt caaag 55

<210> SEQ ID NO 67
<211> LENGTH: 6
<212> TYPE: PRT
<213> ORGANISM: Artificial Sequence
<220> FEATURE:
<223> OTHER INFORMATION: Synthesized Construct

<400> SEQUENCE: 67

Pro Glu Ser Pro Arg Phe
1 5

<210> SEQ ID NO 68
<211> LENGTH: 4
<212> TYPE: PRT
<213> ORGANISM: Artificial Sequence
<220> FEATURE:
<223> OTHER INFORMATION: Synthesized Construct

<400> SEQUENCE: 68

Pro Glu Ser Pro
1

<210> SEQ ID NO 69
<211> LENGTH: 4
<212> TYPE: PRT
<213> ORGANISM: Artificial Sequence
<220> FEATURE:
<223> OTHER INFORMATION: Synthesized Construct

<400> SEQUENCE: 69

Pro Glu Ser Pro
1

<210> SEQ ID NO 70
<211> LENGTH: 10
<212> TYPE: PRT
<213> ORGANISM: Artificial Sequence
<220> FEATURE:
<223> OTHER INFORMATION: GS-linker

<400> SEQUENCE: 70

Gly Gly Gly Gly Ser Gly Gly Gly Gly Ser
1 5 10

<210> SEQ ID NO 71
<211> LENGTH: 29
<212> TYPE: DNA
<213> ORGANISM: Artificial Sequence
<220> FEATURE:
<223> OTHER INFORMATION: Synthesized Construct

<400> SEQUENCE: 71
gacatcgatg acatatgcgc taccgcaac 29

<210> SEQ ID NO 72
<211> LENGTH: 24
<212> TYPE: DNA
<213> ORGANISM: Artificial Sequence
<220> FEATURE:
<223> OTHER INFORMATION: Synthesized Construct

<400> SEQUENCE: 72
gtgcacgtcg gacccgcaga ttcc 24

<210> SEQ ID NO 73
<211> LENGTH: 24
<212> TYPE: DNA
<213> ORGANISM: Artificial Sequence
<220> FEATURE:
<223> OTHER INFORMATION: Synthesized Construct

<400> SEQUENCE: 73
ggaatctgcg ggtccgacgt gcac 24

<210> SEQ ID NO 74
<211> LENGTH: 28
<212> TYPE: DNA
<213> ORGANISM: Artificial Sequence
<220> FEATURE:
<223> OTHER INFORMATION: Synthesized Construct

<400> SEQUENCE: 74
cagaagattt aaggatcctg aacgtaga 28

<210> SEQ ID NO 75
<211> LENGTH: 26
<212> TYPE: DNA
<213> ORGANISM: Artificial Sequence
<220> FEATURE:
<223> OTHER INFORMATION: Synthesized Construct

<400> SEQUENCE: 75
gacatcagtg acatatgtcg ccttcc 26

<210> SEQ ID NO 76
<211> LENGTH: 26
<212> TYPE: DNA
<213> ORGANISM: Artificial Sequence
<220> FEATURE:
<223> OTHER INFORMATION: Synthesized Construct

<400> SEQUENCE: 76
cctggattga ggatcctgaa cgtata 26

<210> SEQ ID NO 77
<211> LENGTH: 28
<212> TYPE: DNA
<213> ORGANISM: Artificial Sequence
<220> FEATURE:

<223> OTHER INFORMATION: Synthesized Construct

<400> SEQUENCE: 77
gacatcgatg acatatggct tccgcaac 28

<210> SEQ ID NO 78
<211> LENGTH: 29
<212> TYPE: DNA
<213> ORGANISM: Artificial Sequence
<220> FEATURE:
<223> OTHER INFORMATION: Synthesized Construct

<400> SEQUENCE: 78
ccagaagtat tgagaattct gaacgtaga 29

<210> SEQ ID NO 79
<211> LENGTH: 27
<212> TYPE: DNA
<213> ORGANISM: Artificial Sequence
<220> FEATURE:
<223> OTHER INFORMATION: Synthesized Construct

<400> SEQUENCE: 79
gacatcgatg acatatggcg actctgc 27

<210> SEQ ID NO 80
<211> LENGTH: 29
<212> TYPE: DNA
<213> ORGANISM: Artificial Sequence
<220> FEATURE:
<223> OTHER INFORMATION: Synthesized Construct

<400> SEQUENCE: 80
ggatacagaa tgaggatcct gaacgtaga 29

<210> SEQ ID NO 81
<211> LENGTH: 20
<212> TYPE: DNA
<213> ORGANISM: Artificial Sequence
<220> FEATURE:
<223> OTHER INFORMATION: Synthesized Construct

<400> SEQUENCE: 81
taatacgact cactataggg 20

<210> SEQ ID NO 82
<211> LENGTH: 19
<212> TYPE: DNA
<213> ORGANISM: Artificial Sequence
<220> FEATURE:
<223> OTHER INFORMATION: Synthesized Construct

<400> SEQUENCE: 82
gctagttatt gctcagcgg 19

<210> SEQ ID NO 83
<211> LENGTH: 36
<212> TYPE: DNA
<213> ORGANISM: Artificial Sequence
<220> FEATURE:
<223> OTHER INFORMATION: Synthesized Construct

<400> SEQUENCE: 83
cctatcgtca ttacctcacg tgacgagggg cggctg 36

<210> SEQ ID NO 84
<211> LENGTH: 36
<212> TYPE: DNA
<213> ORGANISM: Artificial Sequence
<220> FEATURE:
<223> OTHER INFORMATION: Synthesized Construct

<400> SEQUENCE: 84
cagccgcccc tcgtcacgtg aggtaatgac gatagg 36

<210> SEQ ID NO 85
<211> LENGTH: 29
<212> TYPE: DNA
<213> ORGANISM: Artificial Sequence
<220> FEATURE:
<223> OTHER INFORMATION: Synthesized Construct

<400> SEQUENCE: 85
ccttcgaaac ggctacaaac cccaagacg 29

<210> SEQ ID NO 86
<211> LENGTH: 34
<212> TYPE: DNA
<213> ORGANISM: Artificial Sequence
<220> FEATURE:
<223> OTHER INFORMATION: Synthesized Construct

<400> SEQUENCE: 86
gcttgtcatc acatcacgtt cagagagccg tctg 34

<210> SEQ ID NO 87
<211> LENGTH: 34
<212> TYPE: DNA
<213> ORGANISM: Artificial Sequence
<220> FEATURE:
<223> OTHER INFORMATION: Synthesized Construct

<400> SEQUENCE: 87
cagacggctc tctgaacgtg atgtgatgac aagc 34

<210> SEQ ID NO 88
<211> LENGTH: 30
<212> TYPE: DNA
<213> ORGANISM: Artificial Sequence
<220> FEATURE:
<223> OTHER INFORMATION: Synthesized Construct

<400> SEQUENCE: 88
gcatttgaga cgtcaacaga tcccaagagc 30

<210> SEQ ID NO 89
<211> LENGTH: 36
<212> TYPE: DNA
<213> ORGANISM: Artificial Sequence
<220> FEATURE:
<223> OTHER INFORMATION: Synthesized Construct

<400> SEQUENCE: 89
cctattgtca tcacttcacg tgacgagggc cgcttg 36

<210> SEQ ID NO 90
<211> LENGTH: 36
<212> TYPE: DNA
<213> ORGANISM: Artificial Sequence
<220> FEATURE:
<223> OTHER INFORMATION: Synthesized Construct

<400> SEQUENCE: 90
caagcggccc tcgtcacgtg aagtgatgac aatagg 36

<210> SEQ ID NO 91
<211> LENGTH: 33
<212> TYPE: DNA
<213> ORGANISM: Artificial Sequence
<220> FEATURE:
<223> OTHER INFORMATION: Synthesized Construct

<400> SEQUENCE: 91
cctttgagac tgccacaaac cctaagaccg gtg 33

<210> SEQ ID NO 92
<211> LENGTH: 30
<212> TYPE: DNA
<213> ORGANISM: Artificial Sequence
<220> FEATURE:
<223> OTHER INFORMATION: Synthesized Construct

<400> SEQUENCE: 92
atggatccaa aaatgtcgtc tcacggctcc 30

<210> SEQ ID NO 93
<211> LENGTH: 60
<212> TYPE: DNA
<213> ORGANISM: Artificial Sequence
<220> FEATURE:
<223> OTHER INFORMATION: Synthesized Construct

<400> SEQUENCE: 93
atgaattcct acaaatcttc ttcagaaatc aatttttgtt cagcaacgat agcttcggac 60

<210> SEQ ID NO 94
<211> LENGTH: 34
<212> TYPE: DNA
<213> ORGANISM: Artificial Sequence
<220> FEATURE:
<223> OTHER INFORMATION: Synthesized Construct

<400> SEQUENCE: 94
atactagtaa aaatgggcat cttcaacaag aagc 34

<210> SEQ ID NO 95
<211> LENGTH: 64
<212> TYPE: DNA
<213> ORGANISM: Artificial Sequence
<220> FEATURE:
<223> OTHER INFORMATION: Synthesized Construct

<400> SEQUENCE: 95
gcatatcgat ctacaaatct tcttcagaaa tcaatttttg ttcagcaaca gacttgccct 60
catg 64

<210> SEQ ID NO 96
<211> LENGTH: 39
<212> TYPE: DNA
<213> ORGANISM: Artificial Sequence
<220> FEATURE:
<223> OTHER INFORMATION: Synthesized Construct

<400> SEQUENCE: 96
gcatactagt aaaaatgtct cttcctaagg atttcctct 39

-continued

<210> SEQ ID NO 97
<211> LENGTH: 55
<212> TYPE: DNA
<213> ORGANISM: Artificial Sequence
<220> FEATURE:
<223> OTHER INFORMATION: Synthesized Construct

<400> SEQUENCE: 97
atactgcagt taatgatgat gatgatgatg gtccttcttg atcaaagagt caaag 55